(12) United States Patent
Nonoshita et al.

(10) Patent No.: US 7,728,025 B2
(45) Date of Patent: Jun. 1, 2010

(54) 2-HETEROARYL-SUBSTITUTED BENZIMIDAZOLE DERIVATIVE

(75) Inventors: Katsumasa Nonoshita, Ibaraki (JP); Makoto Ishikawa, Ibaraki (JP); Hiroshi Nakashima, Ibaraki (JP); Daisuke Tsukahara, Ibaraki (JP); Yoshio Ogino, Ibaraki (JP); Fumiko Sakai, Ibaraki (JP); Yoshikazu Nagae, Ibaraki (JP); Keisuke Arakawa, Ibaraki (JP); Teruyuki Nishimura, Ibaraki (JP)

(73) Assignee: Banyu Pharmaceutical Co., Ltd., Tokyo (JP)

( * ) Notice: Subject to any disclaimer, the term of this patent is extended or adjusted under 35 U.S.C. 154(b) by 333 days.

(21) Appl. No.: 10/582,564

(22) PCT Filed: Dec. 28, 2004

(86) PCT No.: PCT/JP2004/019843

§ 371 (c)(1),
(2), (4) Date: Mar. 26, 2007

(87) PCT Pub. No.: WO2005/063738

PCT Pub. Date: Jul. 14, 2005

(65) Prior Publication Data

US 2008/0070928 A1 Mar. 20, 2008

(30) Foreign Application Priority Data

Dec. 29, 2003 (JP) .............................. 2003-436992
Aug. 13, 2004 (JP) .............................. 2004-235696

(51) Int. Cl.
*A01N 43/50* (2006.01)

(52) U.S. Cl. ................. 514/394; 548/304.7; 548/146; 548/215; 548/240; 548/131; 548/207; 540/215; 514/398; 514/399; 514/256; 514/364; 514/277; 514/406; 544/224; 544/295

(58) Field of Classification Search ............... 514/394, 514/397; 548/304.7
See application file for complete search history.

(56) References Cited

U.S. PATENT DOCUMENTS

| | | | |
|---|---|---|---|
| 3,370,957 A | 2/1968 | Wagner et al. | |
| 3,536,809 A | 10/1970 | Applezweig | |
| 3,598,123 A | 8/1971 | Zaffaroni | |
| 3,845,770 A | 11/1974 | Theeuwes et al. | |
| 3,916,899 A | 11/1975 | Theeuwes et al. | |
| 4,008,719 A | 2/1977 | Theeuwes et al. | |
| 6,040,449 A | 3/2000 | Tsuchiya et al. | |
| 6,239,152 B1 | 5/2001 | Gordeev et al. | |
| 7,064,215 B2 * | 6/2006 | Renhowe et al. | 548/125 |
| 2005/0272740 A1 | 12/2005 | Dorsch et al. | |
| 2006/0167053 A1 | 7/2006 | Iino et al. | |
| 2006/0258701 A1 | 11/2006 | Mitsuya et al. | |
| 2007/0088071 A1 | 4/2007 | Kim et al. | |
| 2008/0085926 A1 | 4/2008 | Stelmach et al. | |
| 2008/0125429 A1 | 5/2008 | Hashimoto et al. | |

FOREIGN PATENT DOCUMENTS

| | | | |
|---|---|---|---|
| DE | 1237731 | * | 5/1964 |
| EP | 0 726 260 A1 | | 8/1996 |
| JP | 2000 26430 | | 1/2000 |

OTHER PUBLICATIONS

Dörwald, F. Zaragoza. Side Reactions in Organic Synthesis: A Guide to Successful Synthesis Design, Weinheim: WILEY-VCH Verlag GmbH & Co. KGaA, 2005, Preface.*

(Continued)

*Primary Examiner*—Kamal A Saeed
*Assistant Examiner*—Valerie Rodriguez-Garcia
(74) *Attorney, Agent, or Firm*—Richard C. Billups; John C. Todaro

(57) ABSTRACT

A glucokinase activator is provided; and a remedy and/or a preventive for diabetes, or a remedy and/or a preventive for diabetes such as retinopathy, nephropathy, neurosis, ischemic cardiopathy, arteriosclerosis, and further a remedy and/or a preventive for obesity are provided.

A glucokinase activator characterized by containing a 2-heteroaryl-substituted benzimidazole derivative of a general formula (I-0) or its pharmaceutically-acceptable salt:

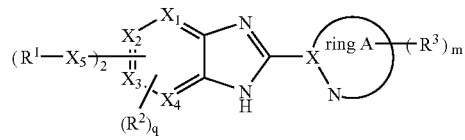

(I-0)

[in the formula, X represents a carbon atom or a nitrogen atom;
$X_1$, $X_2$, $X_3$ and $X_4$ each independently represent a carbon atom or a nitrogen atom; the ring A represents a 5- or 6-membered nitrogen-containing aromatic hetero ring of a formula (II):

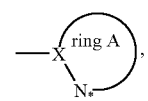

(II)

(in the formula, X represents a carbon atom or a nitrogen atom); $R^1$ represents an aryl, etc.; $R^2$ represents a hydroxy, etc.; $R^3$ represents a —$C_{1-6}$ alkyl, etc.; $R^4$ represents a —$C_{1-6}$ alkyl, etc.; $X_5$ represents —O—, etc.; a indicates an integer of 1, 2 or 3; q indicates an integer of from 0 to 2; m indicates an integer of from 0 to 2].

11 Claims, No Drawings

OTHER PUBLICATIONS

Jordan, V. C. Nature Reviews: Drug Discovery, 2, 2003, pp. 205-213.*

Grupe, A. et al., "Transgenic Knockouts Reveal a Critical Requirement for Pancreatic B Cell Glucokinase in Maintaining Glucose Homeostasis", Cell, vol. 83, pp. 69-78, 1995.

Mitsunobu, O., "The Use of Diethyl Azodicarboxylate and Triphenylphosphine in Synthesis and Transformation of Natural Products", Synthesis, vol. 1, pp. 1-28, 1981.

Tani, Junichi, et al., "Studies on biologically Active Halogenated Compounds IV Synthesis and Antibaterial Activity of Fluorinated Quinoline Derivatives", Chemical and Parmaceutical Bulletin, vol. 30, pp. 3530-3543, 1982.

Tasneem, et al., "Ammonium Nickel Sulphate Mediated Nitration of Aromatic Compounds with Nitric Acid", Synthetic Communications, vol. 31 (7), pp. 1123-1127, 2001.

Fonseca, T. et al., "A short synthesis of phenanthrol[2,3-d]imidazoles from dehydroabietic acid. Application of the methodology as a convenient route to benzimidazoles" Tetrahedron, vol. 57, pp. 1793-1799, 2001.

Singh, M.P. et al., "Synthetic Utility of Catalytic Fe(III)/Fe(II) Redox Cycling Towards Fused Heterocycles: A Facile Access to Substituted Benzimidazole, Bis-benzimidazole and Imidazopyridine Derivatives" Synthesis, vol. 10, pp. 1380-1390, 2000.

Singh, S.P. et al., "Reaction of 2-hydrazinobenzhnidazole with B-diketones: A structural reinvestigation" Indian Journal of Chemistry, vol. 32, pp. 262-265, 1993.

Ferre, T. et al., "Correction of diabetic alterations by glucokinase", Proc. Natl. Acad. Sci, vol. 93, pp. 7225-7230, 1996.

Glaser, B. et al., "Familial Hyperinsulinism Caused by an Activating Glucokinase Mutation" The new England Journal of Medicine, vol. 338, pp. 226-230, 1998.

Dolle, F. et al., "Synthesis and Nicotinic Acetylcholine Receptor in Vivo Binding Properties of 2-Fluoro-3-[2(S)-2-azetidinylmethoxy]pyridine: A New Positron Emission Tomography Ligand for Nicotinic Receptors" J. Med. Chem, vol. 42, pp. 2251-2259, 1999.

Sitzmann, M. E. et al., "Fluronitroanilines Reaction Control via Hydrogen Bonding", J. Org. Chem, vol. 43, (6), pp. 1241-1243, 1978.

Vionnet, N. et al., "Nonsense mutation in the glucokinase gene causes early-onset non-insulin-dependent diabetes mellitus" Nature, vol. 356, pp. 721-722, 1992.

* cited by examiner

2-HETEROARYL-SUBSTITUTED BENZIMIDAZOLE DERIVATIVE

CROSS REFERENCE TO RELATED APPLICATIONS

This application is the National Stage of International Application No. PCT/JP2004/019843, filed 28 Dec. 2004, which claims the benefit of JP 2003-436992 filed in Japan on Dec. 29, 2003 and JP 2004-235696 filed in Japan on Aug. 13, 2004, priority of which is claimed hereunder.

TECHNICAL FIELD

The present invention relates to a glucokinase activator comprising, as the active ingredient thereof, a 2-heteroaryl-substituted benzimidazole derivative and useful in the field of medicines. Further, it relates to a novel 2-heteroaryl-substituted benzimidazole derivative.

BACKGROUND ART

Glucokinase (GK) (ATP: D-hexose 6-phosphotransferase, EC 2.7.1.1) is one (hexokinase IV) of four mammal hexokinases. Hexokinase is a first-stage enzyme in glycolysis and catalyzes a reaction from glucose to glucose hexaphosphate. In its expression, glucokinase is limited essentially in liver and pancreas beta cells, and it controls the rate-limiting step of glucose metabolism in these cells thereby playing an important role in systemic saccharometabolism. Glucokinase in liver beta cells and that in pancreas beta cells differ from each other in point of the N-terminal 15-amino acid sequence owing to the difference in splicing therebetween, but they are the same in point of the enzymatic property. The enzymatic activity of the other three hexokinases (I, II, III) except glucokinase is saturated at a glucose concentration of at most 1 mM, but Km of glucokinase to glucose is 8 mM and is near to a physiological blood-sugar level. Therefore, in accordance with the blood-sugar level change from a normal blood-sugar level (5 mM) to an increased blood-sugar level after meals (10 to 15 mM), intercellular glucose metabolism is accelerated via glucokinase.

Since ten years ago, a hypothesis that glucokinase may act as a glucose sensor in pancreas beta cells and liver has been proposed [for example, see Garfinkel D. et al., Computer modeling identifies glucokinase as glucose sensor of pancreatic beta-cells; American Journal Physiology, Vol. 247 (3Pt2), 1984, pp. 527-536].

A result of recent glucokinase gene-manipulated mice has confirmed that glucokinase actually plays an important role in systemic glucose homeostasis. Mice in which the glucokinase gene was disrupted die soon after their birth [for example, see Grupe A. et al., Transgenic knockouts reveal a critical requirement for pancreatic beta cell glucokinase in maintaining glucose homeostasis; Cell, Vol. 83, 1995, pp. 69-78]; but on the other hand, normal or diabetic mice in which glucokinase was excessively expressed have a lowered blood-sugar level [for example, see Ferre T. et al., Correction of diabetic alterations by glucokinase; Proceedings of the National Academy of Sciences of the U.S.A., Vol. 93, 1996, pp. 7225-7230].

With the increase in glucose concentration therein, the reaction of pancreas beta cells and that of liver cells are both toward the reduction in a blood-sugar level, though differing from each other. Pancreas beta cells come to secrete more insulin, and liver takes up sugar to store it as glycogen therein and simultaneously reduces sugar release.

To that effect, the change in the enzymatic activity of glucokinase plays an important role in mammal glucose homeostasis via liver and pancreas beta cells. In a juvenile diabetic case that is referred to as MODY2 (maturity-onset diabetes of the young), mutation of a glucokinase gene has been found, and the glucokinase activity reduction causes the blood-sugar level increase [for example, see Vionnet N. et al., Nonsense mutation in the glucokinase gene causes early-onset non-insulin-dependent diabetes mellitus; Nature Genetics, Vol. 356, 1992, pp. 721-722].

On the other hand, a pedigree having mutation of increasing glucokinase activity has been found, and those of the family line show low blood-sugar level symptoms [for example, see Glaser B. et al., Familial hyperinsulinism caused by an activating glucokinase mutation; New England Journal Medicine, Vol. 338, 1998, pp. 226-230].

From these, glucokinase acts as a glucose sensor and plays an important role in glucose homeostasis also in humans. On the other hand, blood-sugar level control by utilizing a glucokinase sensor system may be possible in many type-II diabetes patients. A glucokinase-activating substance may be expected to have an insulin secretion promoting effect in pancreas beta cells and have a sugar take-up accelerating and sugar release inhibiting activity in liver, and therefore it may be useful as a remedy for type-II diabetes patients.

Recently, it has become clarified that pancreas beta cell-type glucokinase is limitedly expressed locally in rat brains, especially in ventromedial hypothalamus (VMH) thereof. About 20% neurocytes in VMH are referred to as glucose-responsive neutrons, and heretofore it has been considered they may play an important role in body weight control. When glucose is administered to a rat brain, then it reduces the amount of ingestion; but when glucose metabolism is retarded through intracerebral administration of glucosamine, a glucose analogue, then it causes hyperphagia. From an electrophysiological experiment, it is admitted that glucose-responsive neurons are activated in accordance with a physiological glucose concentration change (5 to 20 mM), but when glucose metabolisms is inhibited by glucosamine or the like, then their activity is retarded. In the glucose concentration-sensitive system in VMH, a glucose-mediated mechanism is anticipated like the insulin secretion in pancreas beta cells. Accordingly, there may be a possibility that a substance for glucokinase activation in VMH, in addition to liver and pancreas beta cells, may be effective not only for blood-sugar level correction but also for solution of obesity that is problematic in many type-II diabetes patients.

From the above description, a compound having a glucokinase activation effect is useful for remedies and/or preventives for diabetes, or for remedies and/or preventives for chronic complications of diabetes such as retinopathy, nephropathy, neurosis, ischemic cardiopathy, arteriosclerosis, and further for remedies and/or preventives for obesity.

For benzimidazole derivatives, for example, a compound of the following formula is described [for example, see JP-A2000-026430]:

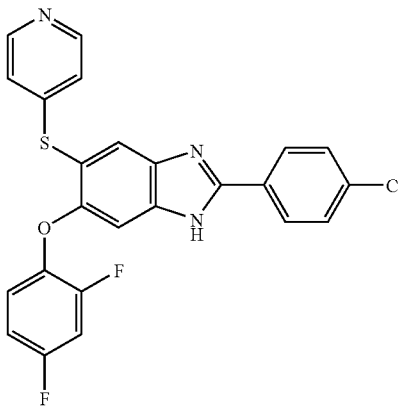

The compound of the above formula has a substituent at the 2-position of the benzimidazole skeleton thereof, but the substituent is 4-chlorophenyl and differs from the ring A in the present invention.

Further, the use of the compound is for an interleukin production inhibitor, and there is given neither description indicating that the compound may be useful for remedy and/or prevention of diabetes nor description suggesting it.

For benzimidazole compounds, for example, also described is a compound of the following formula (for example, see WO2004017963):

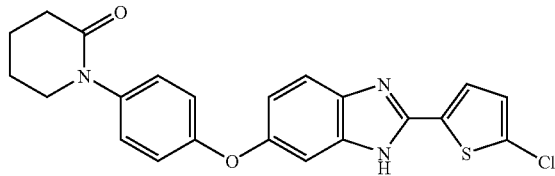

The compound of the above formula has only one substituent on the benzene ring of the benzimidazole skeleton thereof, and though it has a substituent at the 2-position of the benzimidazole skeleton, the substituent is 5-chlorothienyl and differs from the ring A in the present invention.

Further, the use of the compound is for a factor Xa and factor VIIa inhibitor, and there is given neither description indicating that the compound may be useful for remedy and/or prevention of diabetes nor description suggesting it.

DISCLOSURE OF THE INVENTION

Problems that the Invention is to Solve

An object of the present invention is to provide a novel 2-heteroaryl-substituted imidazole derivative and a glucokinase activator comprising it, especially providing a remedy and/or a preventive for diabetes and obesity.

We, the present inventors have assiduously studied so as to develop a novel medicine for diabetes, which has a pharmaceutical potency over that of the above-mentioned already-existing medicines for diabetes owing to its effect different from that of the already-existing medicines and which has an additional pharmaceutical potency, and, as a result, have found that a novel 2-heteroaryl-substituted benzimidazole derivative has a glucokinase-activating effect and have completed the present invention.

Specifically, the invention relates to:
(1) a compound of a formula (I-0):

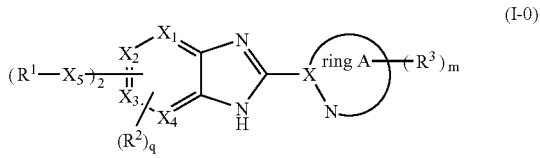

wherein:

X represents a carbon atom or a nitrogen atom;

$X_1$, $X_2$, $X_3$ and $X_4$ each independently represent a carbon atom or a nitrogen atom;

the ring A represents a 5- or 6-membered nitrogen-containing aromatic hetero ring of a formula (II), optionally having, in the ring, from 1 to 3 hetero atoms selected from a group consisting of a nitrogen atom, a sulfur atom and an oxygen atom but excepting the nitrogen atom of N* in formula II:

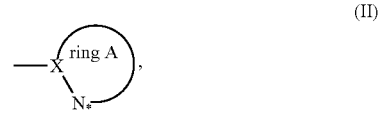

or represents a twin-ring of the nitrogen-containing aromatic hetero ring condensed with a phenyl or a pyridyl;

$R^1$ represents an aryl, or represents a 4- to 10-membered, monocyclic or twin-cyclic hetero ring having, in the ring, from 1 to 4 hetero atoms selected from a group consisting of a nitrogen atom, a sulfur atom and an oxygen atom and $R^1$ may be independently substituted with from 1 to 3 $R^4$'s, and when the hetero ring is an aliphatic hetero ring, then it may have 1 or 2 double bonds;

$R^2$ independently represents a hydroxy, a formyl, —$CH_{3-a}F_a$, —$OCH_{3-a}F_a$, an amino, CN, a halogen, a $C_{1-6}$ alkyl or —$(CH_2)_{1-4}OH$;

$R^3$ represents a —$C_{1-6}$ alkyl, —$(CH_2)_{1-6}$—OH, a —C(O)—$OC_{1-6}$ alkyl, a —$(CH_2)_{1-6}$—$OC_{1-6}$ alkyl, —$(CH_2)_1$—$NH_2$, a cyano, a —C(O)—$C_{1-6}$ alkyl, a halogen, a —$C_{2-6}$ alkenyl, a —$OC_{1-6}$ alkyl, —COOH, —OH or an oxo;

$R^4$ independently represents a —$C_{1-6}$ alkyl optionally substituted with the same or different, from 1 to 3 hydroxyls, halogens, —OC(O)—$C_{1-6}$ alkyls optionally substituted with from 1 to 3 halogens, or —$OC_{1-6}$ alkyls, a —$C_{3-7}$ cycloalkyl, a —$C_{2-4}$ alkenyl,

—C(O)—N($R^{51}$)$R^{52}$,

—S(O)$_2$—N($R^{51}$)$R^{52}$, an —O—$C_{1-6}$ alkyl optionally substituted with a halogen or N($R^{51}$)$R^{52}$, an —S(O)$_{0-2}$—$C_{1-6}$ alkyl, a —C(O)—$C_{1-6}$ alkyl optionally substituted with a halogen, an amino, CN, a hydroxy, an —O—$C_{1-6}$ alkyl, —$CH_{3-a}F_a$, an —OC(O)—$C_{1-6}$ alkyl, an —N($C_{1-6}$ alkyl)C(O)O—$C_{1-6}$ alkyl, an —NH—C(O)O—$C_{1-6}$ alkyl, a phenyl, —N($R^{51}$)$R^{52}$, an —NH—C(O)—$C_{1-6}$ alkyl, an —N($C_{1-6}$ alkyl)-C(O)—$C_{1-6}$ alkyl or an —NH—S(O)$_{0-22}$—$C_{1-6}$ alkyl), a —C(S)—$C_{3-7}$ cycloalkyl, a —C(S)—$C_{1-6}$ alkyl, a —C(O)—O—$C_{1-6}$ alkyl,

—$(CH_2)_{0-4}$—N($R^{53}$)—C(O)—$R^{54}$,

—N($R^{53}$)—C(O)—O—$R^{54}$, a —C(O)-aryl optionally substituted with a halogen, a —C(O)-aromatic hetero ring, a —C(O)-aliphatic hetero ring, a hetero ring optionally substituted with a —$C_{1-6}$ alkyl (the —$C_{1-6}$ alkyl may be substituted with a halogen or an —O—$C_{1-6}$ alkyl)), a phenyl optionally substituted with a halogen, a —$C_{1-6}$ alkyl, an —O—$C_{1-6}$ alkyl, a halogen, CN, a formyl, COOH, an amino, an oxo, a hydroxy, a hydroxyamidino or a nitro;

$R^{51}$ and $R^{52}$ each independently represent a hydrogen atom, a —$C_{1-6}$ alkyl; or the nitrogen atom, $R^{51}$ and $R^{52}$ together form a 4- to 7-membered hetero ring;

$R^{53}$ represents a hydrogen atom or a —$C_{1-6}$ alkyl, $R^{54}$ represents a —$C_{1-6}$ alkyl, or the alkyls for $R^{53}$ and $R^{54}$ and —N—C(O)— together form a 4- to 7-membered nitrogen-containing aliphatic hetero ring, or the alkyls for $R^{53}$ and $R^{54}$ and —N—C(O)—O— together form a 4- to 7-membered nitrogen-containing aliphatic hetero ring (the aliphatic hetero ring may be substituted with an oxo, or the aliphatic hetero ring may have 1 or 2 double bonds in the ring);

$X_5$ represents —O—, —S—, —S(O)—, —S(O)$_2$—, a single bond or an —O—$C_{1-6}$-alkyl;

a independently indicates an integer of 1, 2 or 3;

q indicates an integer of from 0 to 2;

m indicates an integer of from 0 to 2, but excepting a case where one of $X_5$'s is —O—, —S—, —S(O)— or —S(O)$_2$—, and the other of $X_5$'s is a single bond, and $R^1$ is an aryl, or a nitrogen-containing aromatic hetero ring having from 1 to 4 hetero atoms selected from a group consisting of a nitrogen atom, a sulfur atom and an oxygen atom and the aryl may be substituted with from 1 to 3 $R^4$'s, a case where $X_5$'s are both single bonds, or a case where $R^1$'s are both aliphatic hetero rings, or its pharmaceutically-acceptable salt.

The invention also relates to:

(2) A compound or a pharmaceutically acceptable salt of above (1), wherein in formula (I-0), $X_1$ to $X_4$ are all carbon atoms; and (3) A compound or a pharmaceutically acceptable salt of above (1), wherein in formula (I-0), $X_5$ is —O—, —S—, —S(O)—, —S(O)$_2$— or a single bond.

The invention also relates to:

(4) A compound or a pharmaceutically acceptable salt of above (1), wherein the compound of formula (I-0) is represented by a formula (I-1):

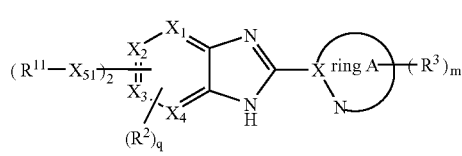

(I-1)

wherein:

$R^{11}$ represents a phenyl optionally substituted with from 1 to 3 $R^4$'s, or represents a 5- or 6-membered nitrogen-containing aromatic hetero ring having from 1 to 4 hetero atoms selected from a group consisting of a nitrogen atom, a sulfur atom and an oxygen atom and the nitrogen-containing aromatic hetero ring may be substituted with from 1 to 3 $R^4$'s; and $X_{51}$ represents —O—, —S—, —S(O)— or —S(O)$_2$—; and the other symbols have the same meanings as above.

The invention also relates to:

(5) A compound or a pharmaceutically acceptable salt of above (4), wherein in formula (I-1), $R^{11}$'s are both phenyls optionally substituted with from 1 to 3 $R^4$'s;

(6) A compound or a pharmaceutically acceptable salt of above (4), wherein in formula (I-1), $R^{11}$'s are both 5- or 6-membered nitrogen-containing aromatic hetero rings having from 1 to 4 hetero atoms selected from a group consisting of a nitrogen atom, a sulfur atom and an oxygen atom and the nitrogen-containing aromatic hetero ring may be substituted with from 1 to 3 $R^4$'s; and (7) A compound or a pharmaceutically acceptable salt of above (4), wherein in formula (I-1), one of $R^{11}$'s is a phenyl optionally substituted with from 1 to 3 $R^4$'s, and the other of $R^{11}$'s is a 5- or 6-membered nitrogen-containing aromatic hetero ring having from 1 to 4 hetero atoms selected from a group consisting of a nitrogen atom, a sulfur atom and an oxygen atom and the nitrogen-containing aromatic hetero ring may be substituted with from 1 to 3 $R^4$'s.

The invention also relates to:

(8) A compound or a pharmaceutically acceptable salt of formula (I-0), which is represented by a formula (I-2):

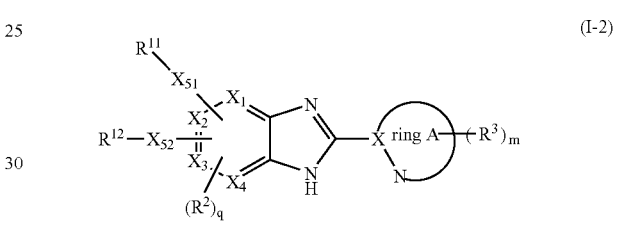

(I-2)

wherein:

$R^{11}$ represents a phenyl optionally substituted with from 1 to 3 $R^4$'s, or represents a 5- or 6-membered nitrogen-containing aromatic hetero ring having from 1 to 4 hetero atoms selected from a group consisting of a nitrogen atom, a sulfur atom and an oxygen atom and the nitrogen-containing aromatic hetero ring may be substituted with from 1 to 3 $R^4$'s; and $R^{12}$ represents a 4- to 7-membered nitrogen-containing hetero ring having, as the hetero atom constituting the hetero ring, at least one nitrogen atom and optionally having, as the other hetero atoms, from 1 to 4 hetero atoms selected from a group consisting of a nitrogen atom, a sulfur atom and an oxygen atom and $R^{12}$ may be substituted with from 1 to 3 $R^4$'s, and when the hetero ring is an aliphatic hetero ring, then it may have 1 or 2 double bonds);

$X_{51}$ represents —O—, —S—, —S(O)— or —S(O)$_2$—;

$X_{52}$ represents —O—, —S—, —S(O)—, —S(O)$_2$— or a single bond; and the other symbols have the same meanings as above.

The invention also relates to:

(9) A compound or a pharmaceutically acceptable salt of above (8), wherein in formula (I-2), $R^{12}$ represents a 4- to 7-membered saturated nitrogen-containing aliphatic hetero ring having, as the hetero atom constituting the hetero ring, at least one nitrogen atom and optionally having, as the other hetero atoms, 1 or 2 hetero atoms selected from a group consisting of a nitrogen atom, a sulfur atom and an oxygen atom and the nitrogen-containing aliphatic hetero ring may be substituted with from 1 to 3 $R^4$'s, and $X_{52}$ is a single bond; or $R^{12}$ represents a 5- to 7-membered nitrogen-containing aliphatic hetero ring having, as the atom constituting the hetero ring, at least one nitrogen atom and optionally having, as the other hetero atoms, 1 or 2 hetero atoms selected from a group consisting of a nitrogen atom, a sulfur atom and an oxygen atom, and having, in the ring, 1 or 2 double bonds and the 5- to 7-membered hetero ring may be substituted with from 1 to 3 $R^4$'s, and $X_{52}$ is —O—, —S—, —S(O)— or —S(O)$_2$—;

(10) A compound or a pharmaceutically acceptable salt of above (8), wherein in formula (I-2), $R^{12}$ represents a 4- to 7-membered saturated nitrogen-containing aliphatic hetero ring having, as the hetero atom constituting the hetero ring, at least one nitrogen atom and optionally having, as the other hetero atoms, 1 or 2 hetero atoms selected from a group consisting of a nitrogen atom, a sulfur atom and an oxygen atom and the nitrogen-containing aliphatic hetero ring may be substituted with from 1 to 3 $R^4$'s), and $X_{52}$ is a single bond;

(11) A compound or a pharmaceutically acceptable salt of above (8), wherein in formula (I-2), $R^{12}$ represents a 5- to 7-membered nitrogen-containing aliphatic hetero ring having, as the atom constituting the hetero ring, at least one nitrogen atom and optionally having, as the other hetero atoms, 1 or 2 hetero atoms selected from a group consisting of a nitrogen atom, a sulfur atom and an oxygen atom, and having, in the ring, 1 or 2 double bonds and the 5- to 7-membered hetero ring may be substituted with from 1 to 3 $R^4$'s, and $X_{52}$ is —O—, —S—, —S(O)— or —S(O)$_2$—; and

(12) A compound or a pharmaceutically acceptable salt of above (8), wherein in formula (I-2), $R^{12}$ represents a 5- to 7-membered nitrogen-containing aliphatic hetero ring having, as the hetero atom constituting the hetero ring, at least one nitrogen atom and optionally having, as the other hetero atoms, 1 or 2 hetero atoms selected from a group consisting of a nitrogen atom, a sulfur atom and an oxygen atom, and having, in the ring, 1 or 2 double bonds and the nitrogen-containing aliphatic hetero ring may be substituted with from 1 to 3 $R^4$'s, and $X_{52}$ is —O—.

The invention also relates to:

(13) A compound or a pharmaceutically acceptable salt of formula (I-1), which is represented by a formula (I-11):

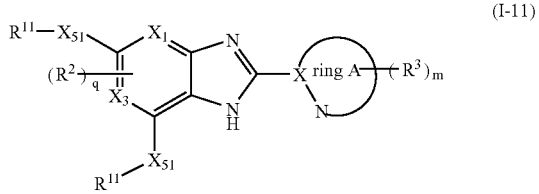

(I-11)

wherein:

the symbols have the same meanings as above;

(14) A compound or a pharmaceutically acceptable salt of formula (13), which is represented by a formula (I-12) wherein $X_{51}$'s are both —O—;

(15) A compound or a pharmaceutically acceptable salt of formula (I-1), which is represented by a formula (I-12):

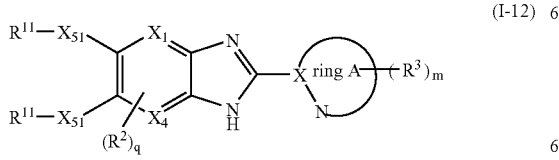

(I-12)

wherein:

the symbols have the same meanings as above; and

(16) A compound or a pharmaceutically acceptable salt of above (15), wherein in formula (I-12), $X_{51}$'s are both —O—.

The invention also relates to:

(17) A compound or a pharmaceutically acceptable salt of above (10), wherein in formula (I-2), $R^{12}$ is represented by a formula (III-1):

(III-1)

or a formula (III-2):

(III-2)

wherein n indicates an integer of from 1 to 3; $R^{41}$ has the same meaning as that of $R^4$.

The invention also relates to:

(18) A compound or a pharmaceutically acceptable salt of any one of above (1) to (17), wherein the ring A is a thiazolyl, an imidazolyl, an isothiazolyl, a thiadiazolyl, an oxadiazolyl, a triazolyl, an oxazolyl, an isoxazolyl, a pyrazinyl, a pyridyl, a pyridazinyl, a pyrazolyl or a pyrimidinyl, which may be substituted with from 1 to 3 $R^4$'s.

The invention also relates to:

(19) A compound of formula (I-0), which is the following compound:

5-(4-methanesulfonyl-phenoxy)-2-pyrazin-2-yl-6-(2-carbamoyl-phenoxy)-1H-benzimidazole,
5-(2-carbamoyl-phenoxy)-2-pyridin-2-yl-6-(6-(methanesulfonyl-pyridin-3-yloxy)-1H-benzimidazole,
5-(2-carbamoyl-phenoxy)-2-pyrazin-2-yl-6-(6-methanesulfonyl-pyridin-3-yloxy)-1H-benzimidazole,
5-(2-fluoro-phenoxy)-2-pyridin-2-yl-6-(6-methanesulfonyl-pyridin-3-yloxy)-1H-benzimidazole,
5-(2-difluoromethoxy-pyridin-3-yloxy)-6-(6-methanesulfonyl-pyridin-3-yloxy)-2-pyridin-2-yl-1H-benzimidazole,
5-(2-difluoromethoxy-pyridin-3-yloxy)-6-(6-methanesulfonyl-pyridin-3-yloxy)-2-pyrazin-2-yl-1H-benzimidazole,
5-(2-difluoromethoxy-pyridin-3-yloxy)-6-(6-methanesulfonyl-pyridin-3-yloxy)-2-(1-methyl-1H-pyrazol-3-yl)-1H-benzimidazole,
5-(2-cyano-phenoxy)-2-pyridin-2-yl-6-(6-ethanesulfonyl-pyridin-3-yloxy)-1H-benzimidazole,
5-(2-fluoro-phenoxy)-2-pyridin-2-yl-6-(6-ethanesulfonyl-pyridin-3-yloxy)-1H-benzimidazole,
5-(2-fluoro-phenoxy)-2-(1H-pyrazol-3-yl)-6-(6-ethanesulfonyl-pyridin-3-yloxy)-1H-benzimidazole,
5-(2,3-difluoro-phenoxy)-2-(1-methyl-1H-pyrazol-3-yl)-6-(6-ethanesulfonyl-pyridin-3-yloxy)-1H-benzimidazole,
5-(2,4-difluoro-phenoxy)-2-pyrazin-2-yl-6-(6-ethanesulfonyl-pyridin-3-yloxy)-1H-benzimidazole,
5-(2,5-difluoro-phenoxy)-2-pyridin-2-yl-6-(6-ethanesulfonyl-pyridin-3-yloxy)-1H-benzimidazole, 5-(2,6-difluoro-phenoxy)-2-pyrazin-2-yl-6-(6-ethanesulfonyl-pyridin-3-yloxy)-1H-benzimidazole,
5-(2,6-difluoro-phenoxy)-2-(1-methyl-1H-pyrazol-3-yl)-6-(6-ethanesulfonyl-pyridin-3-yloxy)-1H-benzimidazole,
5-(2-fluoropyridin-3-yloxy)-6-(6-ethanesulfonylpyridin-3H-yloxy)-2-pyridin-2-yl-1H-benzimidazole,
5-(2-fluoropyridin-3-yloxy)-6-(6-ethanesulfonylpyridin-3-yloxy)-2-pyrazin-2-yl-1H-benzimidazole,
5-(2-chloropyridin-3-yloxy)-6-(6-ethanesulfonylpyridin-3-yloxy)-2-pyridin-2-yl-1H-benzimidazole,
5-(2-chloropyridin-3-yloxy)-6-(6-ethanesulfonylpyridin-3-yloxy)-2-pyrazin-2-yl-1H-benzimidazole,
5-(2-cyanopyridin-3-yloxy)-6-(6-ethanesulfonylpyridin-3-yloxy)-2-pyridin-2-yl-1H-benzimidazole,
5-(2-difluoromethoxy-pyridin-3-yloxy)-6-(6-ethanesulfonyl-pyridin-3-yloxy)-2-pyridin-2-yl-1H-benzimidazole,
5-(2-difluoromethoxy-pyridin-3-yloxy)-6-(6-ethanesulfonyl-pyridin-3-yloxy)-2-pyrazin-2-yl-1H-benzimidazole,
5-(2-difluoromethoxy-pyridin-3-yloxy)-6-(4-ethanesulfonyl-phenoxy)-2-pyridin-2-yl-1H-benzimidazole,
5-(2-difluoromethoxy-pyridin-3-yloxy)-6-(4-ethanesulfonyl-phenoxy)-2-pyrazin-2-yl-1H-benzimidazole,
5-(2,6-difluoro-phenoxy)-2-pyridin-2-yl-6-(6-methanesulfonyl-pyridin-3-yloxy)-1H-benzimidazole,
5-(2-carbamoyl-phenoxy)-2-pyridin-2-yl-6-(6-ethanesulfonyl-pyridin-3-yloxy)-1H-benzimidazole,
5-(2-fluoro-6-cyano-phenoxy)-2-pyridin-2-yl-6-(6-ethanesulfonyl-pyridin-3-yloxy)-1H-benzimidazole,
5-(2-fluoro-6-carbamoyl-phenoxy)-2-pyridin-2-yl-6-(6-ethanesulfonyl-pyridin-3-yloxy)-1H-benzimidazole,
5-(2-fluoro-6-carbamoyl-phenoxy)-2-pyrazin-2-yl-6-(4-ethanesulfonyl-phenoxy)-1H-benzimidazole,
5-(2-fluoro-6-cyano-phenoxy)-2-pyrazin-2-yl-6-(6-ethanesulfonyl-pyridin-3-yloxy)-1H-benzimidazole,
5-(2-fluoro-6-(tetrazol-5-yl)-phenoxy)-2-pyrazin-2-yl-6-(6-ethanesulfonyl-pyridin-3-yloxy)-1H-benzimidazole,
5-(2-difluoromethoxypyridin-3-yloxy)-6-(3-chloro-4-methanesulfonyl-phenoxy)-2-pyridin-2-yl-1H-benzimidazole,
4-(2-fluoro-phenoxy)-2-(pyridin-2-yl)-6-(4-methanesulfonyl-phenoxy)-1H-benzimidazole,
4-(2,6-difluoro-phenoxy)-6-(6-methanesulfonyl-pyridin-3-yloxy)-2-pyrazin-2-yl-1H-benzimidazole,
4-(2,6-difluoro-phenoxy)-6-(6-methanesulfonyl-pyridin-3-yloxy)-2-pyridin-2-yl-1H-benzimidazole,
4-(2,6-difluoro-phenoxy)-6-(6-ethanesulfonyl-pyridin-3-yloxy)-2-pyrazin-2-yl-1H-benzimidazole,
4-(2,6-difluoro-phenoxy)-6-(6-ethanesulfonyl-pyridin-3-yloxy)-2-pyridin-2-yl-1H-benzimidazole,
4-(1-methyl-2-oxo-1,2-dihydro-pyridin-3-yloxy)-6-(4-ethanesulfonyl-phenoxy)-2-pyridin-2-yl-1H-benzimidazole,
4-(2,6-difluoro-phenoxy)-6-(6-ethanesulfonyl-pyridin-3-yloxy)-2-(1H-pyrazol-3-yl)-1H-benzimidazole,
4-(2-fluoro-phenoxy)-6-(6-ethanesulfonyl-pyridin-3-yloxy)-2-pyrazin-2-yl-1H-benzimidazole,
4-(2,3-difluoro-phenoxy)-6-(6-ethanesulfonyl-pyridin-3-yloxy)-2-pyridin-2-yl-1H-benzimidazole,
4-(2,5-difluoro-phenoxy)-6-(6-ethanesulfonyl-pyridin-3-yloxy)-2-pyridin-2-yl-1H-benzimidazole,
4-(2-cyano-6-fluoro-phenoxy)-6-(6-ethanesulfonyl-pyridin-3-yloxy)-2-pyrazin-2-yl-1H-benzimidazole,
4-(2-cyano-6-fluoro-phenoxy)-6-(6-methanesulfonyl-pyridin-3-yloxy)-2-pyridin-2-yl-1H-benzimidazole,
4-(2-cyano-6-fluoro-phenoxy)-6-(6-methanesulfonyl-pyridin-3-yloxy)-2-pyrazin-2-yl-1H-benzimidazole,
1-(2-(6-(5-bromo-pyridin-2-yloxy)-2-pyridin-2-yl-3H-benzimidazol-5-yl)-pyrrolidin-1-yl)-ethanone,
1-(2-(6-(6-methanesulfonyl-pyridin-3-yloxy)-2-pyridin-2-yl-3H-benzimidazol-5-yl)-pyrrolidin-1-yl)-ethanone,
1-(2-(6-(4-hydroxymethyl-phenoxy)-2-pyridin-2-yl-3H-benzimidazol-5-yl)-pyrrolidin-1-yl)-ethanone,
1-(2-(6-(4-methanesulfonyl-phenoxy)-2-pyridin-2-yl-3H-benzimidazol-5-yl)-pyrrolidin-1-yl)-ethanone,
2-(6-(4-methanesulfonyl-phenoxy)-2-pyridin-2-yl-3H-benzimidazol-5-yl)-pyrrolidine-1-carboxamide,
2-hydroxy-1-(2-(6-(4-methanesulfonyl-1-phenoxy)-2-pyridin-2-yl-3H-benzimidazol-5-yl)-pyrrolidin-1-yl)-ethanone,
1-(2-(6-(6-ethanesulfonyl-pyridin-3-yloxy)-2-pyridin-2-yl-3H-benzimidazol-5-yl)-pyrrolidin-1-yl)-ethanone,
1-(2-(6-(4-methanesulfonyl-phenoxy)-2-pyrazin-2-yl-3H-benzimidazol-5-yl)-pyrrolidin-1-yl)-ethanone,
2-fluoro-1-(6-(4-methanesulfonyl-phenoxy)-2-pyridin-2-yl-3H-benzimidazol-5-yl)-pyrrolidin-1-yl)-ethanone,
5-(6-(1-acetyl-pyrrolidin-2-yl)-2-pyridin-2-yl-1H-benzimidazole-5-yloxy)pyridine-2-carbonitrile,
1-(2-(6-(4-methanesulfonyl)-phenoxy)-2-pyridin-2-yl-3H-benzimidazol-5-yl)-pyrrolidin-1-yl)-2-methylamino-ethanone,
1-(2-(6-(4-methanesulfonyl-phenoxy)-2-(1H-pyrazol-3-yl)-3H-benzimidazol-5-yl)-pyrrolidin-1-yl)-ethanone,
1-(4-fluoro-2-(6-(4-methanesulfonyl-phenoxy)-2-pyridin-2-yl-3H-benzimidazol-5-yl)-pyrrolidin-1-yl)-ethanone,
N-(5-(6-(1-acetyl-pyrrolidin-2-yl)-2-pyridin-2-yl-1H-benzimidazol-5-yloxy)-pyridin-2-yl)-acetamide,
1-(2-(2-(5-bromo-pyridin-2-yl)-6-(4-methanesulfonyl-phenoxy)-3H-benzimidazol-5-yl)-pyrrolidin-1-yl)-ethanone,
N-(2-(2-(6-(4-methanesulfonyl-phenoxy)-2-pyridin-2-yl-3H-benzimidazol-5-yl)pyrrolidin-1-yl)-2-oxo-ethyl)-acetamide,
6-(1-acetylpyrrolidin-2-yl)-5-(4-(methoxymethyl)phenoxy)-2-pyridin-2-yl-1H-benzimidazol monotrifluoroacetate,
1-(4-((6-(1-acetylpyrrolidin-2-yl)-2-pyridin-2-yl-1H-benzimidazol-5-yl)oxy)phenyl)pyridin-2(1H)-one,
6-(1-acetylpyrrolidin-2-yl)-5-((6-(5-methyl-[1,2,4]-oxadiazol-3-yl)pyridin-3-yl)oxy)-2-pyridin-2-yl-1H-benzimidazole,
(2-(2-(5-((2'-fluorobiphenyl-4-yl)oxy)-2-pyridin-2-yl-1H-benzimidazol-6-yl)pyrrolidin-1-yl)-2-oxoethyl)methylamine,
6-(1-acetylpyrrolidin-2-yl)-5-((6-([1,2,4]-oxadiazol-3-yl)pyridin-3-yl)oxy)-2-pyridin-2-yl-1H-benzimidazole,
6-(1-(4-(2-methyl-2H-tetrazol-5-yl)phenoxy)-2-pyrazin-2-yl-1H-benzimidazole,
5-(1-acetyl-3-fluoropyrrolidin-2-yl)-6-(4-(methanesulfonyl)phenoxy)-2-pyridin-2-yl-1H-benzimidazole,
6-(1-acetylpyrrolidin-2-yl)-5-((6-(2-methyl-2H-tetrazol-5-yl)pyridin-3-yl)oxy)-2-pyridin-2-yl-1H-benzimidazole,
6-(1-acetylpyrrolidin-2-yl)-5-(4-(2-methyl-2H-tetrazol-5-yl)phenoxy)-2-pyridin-2-yl-1H-benzimidazole,
5-(1-acetyl-5-methylpyrrolidin-2-yl)-6-(4-(methanesulfonyl)phenoxy)-2-pyridin-2-yl-1H-benzimidazole,
6-(1-acetylpyrrolidin-2-yl)-5-((6-(2-methyl-2H-tetrazol-5-yl)pyridin-3-yl)oxy)-2-pyrazin-2-yl-1H-benzimidazole,
6-(1-acetylpyrrolidin-2-yl)-5-(6-methoxymethylpyridin-3-yl)oxy)-2-pyridin-2-yl-1H-benzimidazole,
2-(2-(5-(4-(2-methyl-2H-tetrazol-5-yl)phenoxy)-2-pyridin-2-yl-1H-benzimidazol-6-yl)pyrrolidin-1-yl)-2-oxoethanol,
2-(5-(4-(2-methyl-2H-tetrazol-5-yl)phenoxy)-2-pyridin-2-yl-1H-benzimidazol-6-yl)pyrrolidine-1-carboxamide,
5'-((6-(1-acetylpyrrolidin-2-yl)-2-pyridin-2-yl-1H-benzimidazol-5-yl)oxy)-2H-1,2'-bipyridin-2-one, 3-(4-((6-(1-acetylpyrrolidin-2-yl)-2-pyridin-2-yl-1H-benzimidazol-5-yl)oxy)phenyl)-1,3-oxazolidin-2-one,
6-(1-acetylpyrrolidin-2-yl)-5-((6-methylpyridin-3-yl)oxy)-2-pyridin-2-yl-1H-benzimidazole,
6-(1-acetylpyrrolidin-2-yl)-5-((6-pyrazin-2-ylpyridin-3-yl)oxy)-2-pyridin-2-yl-1H-benzimidazole,
6-(1-acetyl-3-fluoropyrrolidin-2-yl)-5-((2'-fluorobiphenyl-4-yl)oxy)-2-pyridin-2-yl-1H-benzimidazole,
3-(4-((6-(1-acetylpyrrolidin-2-yl)-2-pyrazin-2-yl-1H-benzimidazol-5-yl)oxy)phenyl)-1,3-oxazolidine-2-one,
6-(1-acetylpyrrolidin-2-yl)-2-pyrazin-2-yl-5-((6-pyrazin-2-ylpyridin-3-yl)oxy)-1H-benzimidazole,
6-(1-acetylpyrrolidin-2-yl)-5-((6-(5-methyl-[1,2,4]-oxadiazol-3-yl)pyridin-3-yl)oxy)-2-pyrazin-2-yl-1H-benzimidazole,
1-(4-((6-(1-acetylpyrrolidin-2-yl)-2-pyrazin-2-yl-1H-benzimidazol-5-yl)oxy)phenyl)ethanone,
6-(1-acetylpyrrolidin-2-yl)-5-(4-(5-methyl-[1,2,4]-oxadiazol-3-yl)phenoxy)-2-pyrazin-2-yl-1H-benzimidazole,
6-(1-acetyl-5-methylpyrrolidin-2-yl)-5-(4-methanesulfonylphenoxy)-2-pyrazin-2-yl-1H-benzimidazole,
N-methyl-2-(2-(5-(4-(2-methyl-2H-tetrazol-5-yl)phenoxy)-2-pyridin-2-yl-1H-benzimidazol-6-yl)pyrrolidin-1-yl)-2-oxoethanamine,
6-(1-acetyl-6-methylpyrrolidin-2-yl)-5-((6-(methoxymethyl)pyridin-3-yl)oxy)-2-pyrazin-2-yl-1H-benzimidazole,
1-(1-(6-(4-methanesulfonyl-phenoxy)-2-pyridin-2-yl-3H-benzimidazol-5-yl)-pyrrolidin-2-yl)-ethanone,
1-(1-(6-(6-methanesulfonyl-pyridin-3-yloxy)-2-pyridin-2-yl-3H-benzimidazol-5-yl)pyrrolidin-2-yl)-ethanone,
1-(1-(6-(6-ethanesulfonyl-pyridin-3-yloxy)-2-pyrazin-2-yl-3H-benzimidazol-5-yl)pyrrolidin-2-yl)ethanone, or
1-(1-(6-(6-ethanesulfonyl-pyridin-3-yloxy)-2-pyrazin-2-yl-3H-benzimidazol-5-yl)-4-fluoro-pyrrolidin-2-yl)-ethanone, or their pharmaceutically-acceptable salts.

The invention also relates to:

(20) a pharmaceutical composition comprising the following (1) to (3), which is used for remedy, prevention and/or retardation of onset of type-II diabetes:

(1) a compound described in any one of above (1) to (19), (2) one or more compounds selected from the following groups (a) to (h):
  (a) any other glucokinase activator,
  (b) a bis-guanide,
  (c) a PPAR agonist,
  (d) an insulin,
  (e) a somatostatin,
  (f) an α-glucosidase inhibitor,
  (g) an insulin, and
  (h) a DPP-IV (dipeptidyl peptidase IV) inhibitor, (3) a pharmaceutically acceptable carrier;

(21) a glucokinase activator comprising a compound or its pharmaceutically acceptable salt described in any one of above (1) to (19), as the active ingredient thereof;

(22) a medicine for remedy and/or prevention of diabetes, comprising a compound or its pharmaceutically-acceptable salt described in any one of above (1) to (20), as the active ingredient thereof; and

(23) a remedy and/or a preventive for obesity, comprising a compound or its pharmaceutically-acceptable salt described in any one of above (1) to (20), as the active ingredient thereof.

BEST MODE FOR CARRYING OUT THE INVENTION

The meanings of the terms used in this description are described below, and the compounds of the invention are described in more detail hereinunder.

Unless otherwise specifically indicated in this description, the following groups have the meanings described below.

"Aryl" means preferably a hydrocarbon aromatic ring having from 6 to 14 carbon atoms, including, for example, phenyl, naphthyl, biphenyl, anthryl. Of those, preferred are phenyl and naphthyl; and more preferred is phenyl.

"$C_{1-6}$ alkyl" means a linear or branched alkyl having from 1 to 6 carbon atoms, including, for example, methyl, ethyl, propyl, isopropyl, butyl, isobutyl, sec-butyl, tert-butyl, pentyl, isoamyl, neopentyl, isopentyl, 1,1-dimethylpropyl, 1-methylbutyl, 2-methylbutyl, 1,2-dimethylpropyl, hexyl, isohexyl, 1-methylpentyl, 2-methylpentyl, 3-methylpentyl, 1,1-dimethylbutyl, 1,2-dimethylbutyl, 2,2-dimethylbutyl, 1,3-dimethylbutyl, 2,3-dimethylbutyl, 3,3-dimethylbutyl, 1-ethylbutyl, 2-ethylbutyl, 1,2,2-trimethylpropyl, 1-ethyl-2-methylpropyl.

"$C_{2-6}$ alkenyl" means a linear or branched alkenyl having from 2 to 6 carbon atoms, including, for example, allyl, 2-propenyl, 1-butenyl, 2-butenyl, 2-methyl-2-butenyl, 1-pentenyl.

"$C_{3-7}$ cycloalkyl" concretely includes, for example, cyclopropyl, cyclobutyl, cyclopentyl, cyclohexyl, cycloheptyl.

"Halogen" means fluorine, chlorine, bromine or iodine.

"—$(CH_2)_{1-6}$—OH" includes, for example, hydroxymethylene, hydroxyethylene.

"—O—$C_{1-6}$ alkyl" includes, for example, methoxy, ethoxy, propoxy or tert-butoxy.

"—$(CH_2)_{1-6}$—$OC_{1-6}$ alkyl" includes, for example, methoxymethyl, methoxyethyl, propyloxymethyl, isopropyloxymethyl.

"—C(O)—$_{1-6}$ alkyl" includes, for example, acetyl, ethylcarbonyl, isopropylcarbonyl, propylcarbonyl.

"—C(O)O$C_{1-6}$ alkyl" includes, for example, methoxycarbonyl, ethoxycarbonyl or tert-butoxycarbonyl.

"—$(CH_2)_{1-6}$—$NH_2$" includes, for example, aminomethyl, aminoethyl, aminopropyl.

"—NH—$C_{1-6}$ alkyl" includes, for example, methylamino, ethylamino, propylamino or 2-methylbutyl-amino.

"—N-di-($C_{1-6}$ alkyl)" means a group of the same or different, above-defined "$C_{1-6}$ alkyls" combined with N, and includes, for example, dimethylamino, ethylpropylamino, 2-methylbutyl-1-methylamino. In "—N-di-($C_{1-6}$ alkyl)", the same or different $C_{1-4}$ alkyls may form a ring together with the nitrogen atom. Examples of the ring are piperidine, pyrrolidine.

"—$CH_{3-a}F_a$" means a group derived from methyl by substituting from 1 to 3 hydrogen atoms therein with fluorine atoms, and includes, for example, trifluoromethyl, difluoromethyl or fluoromethyl.

"—$OCH_{3-a}F_a$" means a group of the above-defined "—$CH_{3-a}F_a$" combined with an oxygen atom, and includes, for example, trifluoromethoxy, difluoromethoxy or fluoromethoxy.

a indicates an integer of from 1 to 3.

For more concretely disclosing the compounds of the invention, symbols used in formula (I-0), (I-1), (I-2), (I-11) or (1-12) are described with reference to its concrete examples.

Compounds of formula (I-0) of the invention are described.

$$(R^1-X_5)_{\overline{2}} \begin{array}{c} X_1 \\ X_2 \\ X_3 \\ X_4 \end{array} \begin{array}{c} N \\ \\ N \\ H \end{array} X \text{ ring A} (R^3)_m \quad (I-0)$$

$(R^2)_q$ $X_5$ represents —O—, —S—, —S(O)—, —S(O)$_2$—, a single bond or a —O—$C_{1-6}$-alkyl.

$R^1$ represents an aryl, or represents a 4- to 10-membered, monocyclic or twin-cyclic hetero ring having, in the ring, from 1 to 4 hetero atoms selected from a group consisting of a nitrogen atom, a sulfur atom and an oxygen atom.

"Aryl" for $R^1$ may be the same as the above-defined aryl, preferably phenyl, naphthyl or biphenyl, more preferably phenyl.

"4- to 7-membered monocyclic or 9- or 10-membered condensed hetero ring having, in the ring, from 1 to 4 hetero atoms selected from a group consisting of a nitrogen atom, a sulfur atom and an oxygen atom" represented by $R^1$ means a 4- to 7-membered monocyclic or 9- or 10-membered twin-cyclic aliphatic hetero ring or aromatic hetero ring as a whole of the ring, in which from 1 to 4 ring-constituting atoms of the hetero ring are hetero atoms selected from a nitrogen atom, a sulfur atom and an oxygen atom and the other atoms of the hetero ring-constituting atoms are carbon atoms.

In case where the hetero ring has a nitrogen atom in the ring, then the nitrogen atom may form an N-oxide.

In case where the hetero ring has 2 or 3 hetero atoms in the ring, then the hetero atoms may be the same or different.

In case where the hetero ring is an aliphatic hetero ring, then it may have 1 or 2 double bonds in the ring.

In case where the hetero ring is an aliphatic hetero ring, then the methylene in the hetero ring may be substituted with a nitrogen atom, a sulfur atom or an oxygen atom, and further, the sulfur atom may be oxidized to be a sulfenyl or sulfonyl.

The hetero ring includes, for example, azetidinyl, thiazolidinyl, pyrrolidinyl, pyrrolinyl, 2-pyrrolidonyl, azepanyl, 2,5-dioxopyrrolidinyl, 2-benzoxolinonyl, 1,1-dioxotetrahydrothienyl, 2,4-dioxoimidazolidinyl, 2-oxo-[1,3,4]-(4-triazolinyl), 2-oxazolidinonyl, 5,6-dihydrouracylyl, 1,3-benzodioxolyl, [1,2,4]-oxadiazolinyl, 2-azabicyclo[2.2.1]heptyl, 4-thiazolidonyl, morpholinyl, 2-oxotetrahydrofuranyl, tetrahydrofuranyl, 2,3-dihydrobenzofuranyl, benzothienyl, isoxazolyl, tetrahydropyranyl, piperidyl, 1-oxo-1,3-dihydroisoindolyl, piperazinyl, thiomorpholino, 1,1-dioxothiomorpholino, tetrahydropyranyl, 1,3-dioxolanyl, homopiperazinyl, thienyl, isoxazolyl, imidazolyl, pyrrolyl, thiazolyl, thiadiazolyl, isothiazolyl, [1,2,4]-triazolyl, [1,2,3]-triazolyl, pyranyl, indolyl, pyrimidinyl, thiazinyl, pyrazinyl, pyridazinyl, pyridyl, 4-pyridonyl, quinolyl or isoquinolyl.

Of those, the 4- to 7-membered monocyclic hetero ring concretely includes, for example, azetidinyl, isoxazolyl, pyrrolidinyl, 2-pyrrolidonyl, 2,5-dioxopyrrolidinyl, morpholino, tetrahydrofuranyl, azepanyl, piperidyl, piperazinyl, thiomorpholino, tetrahydropyranyl, imidazolyl, triazolyl, oxadiazolyl, tetrazolyl, pyrazolyl, indolyl, thiazolyl, thiadiazolyl, pyrazinyl, pyridazinyl or pyridyl.

Of those, the 4- to 7-membered monocyclic aliphatic hetero ring concretely includes, for example, azetidinyl, pyrrolidinyl, piperidino, piperidinyl, azepanyl, piperazinyl, morpholino, thiomorpholino, homopiperazinyl, imidazolidinyl, pyrazolidinyl.

Of those, the 5- or 6-membered monocyclic aromatic hetero ring concretely includes, for example, pyrrolyl, furyl, thienyl, pyrazolyl, isoxazolyl, isothiazolyl, imidazolyl, oxazolyl, thiazolyl, triazolyl, oxadiazolyl, thiadiazolyl, tetrazolyl, pyridyl, pyrazinyl, pyrimidinyl, pyridazinyl.

Of those, the 9- or 10-membered condensed hetero ring concretely includes, for example, benzofuranyl, benzimidazolyl, benzothiophenyl, benzothiazolyl, benzisothiazolyl, benzoxazolyl, benzisoxazolyl, pyridoimidazolyl, quinolyl, isoquinolyl, quinoxalinyl, quinazolinyl, phthalazinyl, cinnolinyl, indolyl, indazolyl, purinyl, indolidinyl, isoindolyl, pteridinyl or naphthyridinyl.

The hetero ring is preferably a 4- to 7-membered monocyclic aliphatic hetero ring or a 5- or 6-membered aromatic hetero ring in which at least one hetero ring-constituting atom is a nitrogen atom.

$R^1$ may be substituted with from 1 to 3 $R^4$'s.

$R^4$ independently represents a —$C_{1-6}$ alkyl (the alkyl may be substituted with the same or different, from 1 to 3 hydroxyls, halogens, —OC(O)—$C_{1-6}$ alkyls (the alkyl may be substituted with from 1 to 3 halogens) or —O$C_{1-6}$ alkyls), a —$C_{3-8}$ cycloalkyl, a —$C_{2-6}$ alkenyl,

—C(O)—N(R$^{51}$)R$^{52}$,

—S(O)$_2$—N(R$^{51}$)R$^{52}$, an —O—$C_{1-6}$ alkyl (the $C_{1-6}$ alkyl may be substituted with a halogen or N(R$^5$)R$^{52}$), an —S(O)$_{0-2}$—$C_{1-6}$ alkyl, a —C(O)—$C_{1-6}$ alkyl (the $C_{1-6}$ alkyl may be substituted with a halogen, an amino, CN, a hydroxy, an —O—$C_{1-6}$ alkyl, —CH$_{3-a}$F$_a$, an —OC(O)—$C_{1-6}$ alkyl, an —N(C$_{1-6}$ alkyl)C(O)O—$C_{1-6}$ alkyl, a phenyl, —N(R$^{15}$)R$^{52}$, an —NH—C(O)—$C_{1-6}$ alkyl, an —N(C$_{1-6}$ alkyl)-C(O)—$C_{1-6}$ alkyl or an —NH—S(O)$_{0-2}$—$C_{1-6}$ alkyl), a —C(O)—$C_{3-8}$ cycloalkyl, a —C(S)—$C_{1-6}$ alkyl, a —C(O)—O—$C_{1-6}$ alkyl,

—(CH$_2$)$_{0-4}$—N(R$^{53}$)C(O)—R$^{54}$,

—N(R$^{53}$)—C(O)—O—R$^{54}$, a —C(O)-aryl (the aryl may be substituted with a halogen), a —C(O)-aromatic hetero ring, a —C(O)-aliphatic hetero ring, a hetero ring (the hetero ring may be substituted with a —$C_{1-6}$ alkyl (the —$C_{1-6}$ alkyl may be substituted with a halogen or an —O—$C_{1-6}$ alkyl)), a phenyl, (the phenyl may be substituted with a halogen, a —$C_{1-6}$ alkyl, an —O—$C_{1-6}$ alkyl), a halogen, CN, a formyl, COOH, an amino, an oxo, a hydroxy, a hydroxyamidino or a nitro;

"Halogen" for $R^4$ means the same as the above-defined group.

"—$C_{1-6}$ alkyl" for $R^4$ means a linear or branched alkyl having from 1 to 6 carbon atoms, including, for example, methyl, ethyl, propyl, isopropyl, butyl, isobutyl, sec-butyl, tert-butyl, pentyl, isoamyl, neopentyl, isopentyl, 1,1-dimethylpropyl, 1-methylbutyl, 2-methylbutyl, 1,2-dimethylpropyl, hexyl, isohexyl, 1-methylpentyl, 2-methylpentyl, 3-methylpentyl, 1,1-dimethylbutyl, 1,2-dimethylbutyl, 2,2-dimethylbutyl, 1,3-dimethylbutyl, 2,3-dimethylbutyl, 3,3-dimethylbutyl, 1-ethylbutyl, 2-ethylbutyl, 1,2,2-trimethylpropyl, 1-ethyl-2-methylpropyl.

"—$C_{1-6}$ alkyl" may be substituted with from 1 to 3 hydroxyl, halogens, —OC(O)—$C_{1-6}$ alkyls (the alkyl may be substituted with from 1 to 3 halogens) or —O—$C_{1-6}$ alkyls.

In case where "—$C_{1-6}$ alkyl" has 2 or 3 of the above-mentioned substituents, they may be the same or different.

The halogen for the substituent includes the same as those for the above-defined halogen.

The —OC(O)—$C_{1-6}$ alkyl for the substituent includes, for example, methylcarbonyloxy, ethylcarbonyloxy, isopropylcarbonyloxy.

The —OC(O)—$C_{1-6}$ alkyl for the substituent may be substituted with from 1 to 3 of the above-defined halogen atoms.

The —O—$C_{1-6}$ alkyl for the substituent includes, for example, methoxy, ethoxy, propoxy, isopropoxy.

"—$S(O)_{0-2}$—$C_{1-6}$ alkyl" for $R^4$ means a group of —$S(O)_{0-2}$— combined with the above-defined —$C_{1-6}$ alkyl, including, for example, —S-ethyl, —S-methyl, —S-isopropyl, —S-propyl, —$S(O)_2$—methyl, —$S(O)_2$-ethyl.

The —$C_{1-6}$ alkyl in "—$S(O)_{0-2}$—$C_{1-6}$ alkyl" may be substituted with a hydroxy.

"—$C_{3-8}$ cycloalkyl" for $R^4$ includes the same as those of the above-defined group.

"—$C_{2-6}$ alkenyl" for $R^4$ includes the same as those of the above-defined group.

"—$C(O)N(R^{51})R^{52}$" for $R^4$ means a substituted or unsubstituted carbamoyl group, or means a 4- to 7-membered aliphatic hetero ring formed together by N, $R^{51}$ and $R^{52}$ and combined with the carbonyl.

Of "$C(O)N(R^5)R^{52}$" for $R^4$, the substituted or unsubstituted carbamoyl includes, for example, carbamoyl, methylcarbamoyl, ethylcarbamoyl, isopropylcarbamoyl, propylcarbamoyl, ethylmethylcarbamoyl, dimethylcarbamoyl, isopropylmethylcarbamoyl, diisopropylcarbamoyl, diethylcarbamoyl.

Of "$C(O)N(R^{51})R^{52}$" for $R^4$, the 4- to 7-membered aliphatic hetero ring formed together by N, $R^{51}$ and $R^{52}$ concretely includes, for example, azetidinyl, pyrrolidinyl, piperidino, piperazinyl, morpholino. Accordingly, $C(O)N(R^{51})R^{52}$ includes azetidine-1-carbonyl, pyrrolidine-1-carbonyl, piperidine-1-carbonyl, piperazine-1-carbonyl, morpholine-1-carbonyl.

"—C(O)—O—$C_{1-6}$ alkyl" for $R^4$ may be the same as the above-defined "—C(O)—O—$C_{1-6}$ alkyl".

"—O—$C_{1-6}$ alkyl" for $R^4$ may be the same as the above-defined "—O—$C_{1-6}$ alkyl".

The —O—$C_{1-6}$ alkyl may be substituted with a halogen or $N(R^{51})R^{52}$.

"—C(O)—$C_{1-6}$ alkyl" for $R^4$ may be the same as the above-defined "—C(O)—$C_{1-6}$ alkyl".

The "—C(O)—$C_{1-6}$ alkyl" may be substituted with a halogen, an amino, —$CH_{3-a}F_a$, CN, a hydroxy, an —O—$C_{1-6}$ alkyl, an —O—C(O)—$C_{1-6}$ alkyl, an —N—($C_{1-6}$ alkyl)-C(O)O—$C_{1-6}$ alkyl, an —NH—C(O)O—$C_{1-6}$ alkyl, a phenyl, —$N(R^{51})R^{52}$, an —NH—C(O)—$C_{1-6}$ alkyl, an —N—($C_{1-6}$ alkyl)-C(O)—$C_{1-6}$ alkyl or an —NH—$S(O)_{0-2}$—$C_{1-6}$ alkyl.

"Halogen" for the substituent may be the same as the above-defined halogen.

"—$CH_{3-a}F_a$" for the substituent may be the same as the above-defined "—$CH_{3-a}F_a$".

"—O—$C_{1-6}$ alkyl" for the substituent may be the same as the above-defined "—O—$C_{1-6}$ alkyl".

"—O—C(O)—$C_{1-6}$ alkyl" for the substituent may be the same as the above-defined "—O—C(O)—$C_{1-6}$ alkyl".

"—N—($C_{1-6}$ alkyl)-C(O)O—$C_{1-6}$ alkyl" for the substituent means a group of —N—($C_{1-6}$ alkyl)- as combined with the above-mentioned —C(O)O—$C_{1-6}$ alkyl, and concretely includes, for example, —N(Me)—C(O)O-tert-butyl.

"—NH—C(O)O—$C_{1-6}$ alkyl" for the substituent means a group of —NH— as combined with the above-mentioned —C(O)O—$C_{1-6}$ alkyl, and concretely includes, —NH—C(O)O-methyl, —NH—C(O)O-ethyl, —NH—C(O)O-isopropyl, —NH—C(O)-propyl.

"—$N(R^{51})R^{52}$" for the substituent may be the same as the above-defined "—$N(R^{51})R^{52}$".

"—NH—C(O)—$C_{1-6}$ alkyl" for the substituent means a group of —NH—C(O)— as combined with the above-defined) —$C_{1-6}$ alkyl, and concretely includes, for example, —NH—C(O)-methyl, —NH—C(O)-ethyl, —NH—C(O)-isopropyl, —NH—C(O)-propyl.

"—N—($C_{1-6}$ alkyl)-C(O)—$C_{1-6}$ alkyl" for the substituent means a group of —N—($C_{1-6}$ alkyl)-C(O)— as combined with the above-defined) —$C_{1-6}$ alkyl, and concretely includes, for example, —N(methyl)-C(O)-methyl, —N(methyl)-C(O)-ethyl, —N(ethyl)-C(O)-isopropyl, —N(methyl)-C(O)-isopropyl, —N(isopropyl)-C(O)-methyl.

The —NH—$S(O)_{0-2}$—$C_{1-6}$ alkyl for the substituent means a group of —NH— as combined the above-mentioned —$S(O)_{0-2}$—$C_{1-6}$ alkyl, and concretely includes, for example, —NH—$S(O)_2$-methyl, —NH—$S(O)_2$-ethyl, —NH—$S(O)_2$-isopropyl.

"—C(O)—$C_{1-6}$ alkyl" optionally having the above-mentioned substituent on the $C_{1-6}$ alkyl concretely includes, for example, fluoromethylcarbonyl, 2,2,2-trifluoroethylcarbonyl, cyanomethylcarbonyl, hydroxymethylcarbonyl, 2-hydroxyethylcarbonyl, methoxymethylcarbonyl, aminomethylcarbonyl, N-methylaminocarbonyl, 2-phenylethylcarbonyl.

"—C(S)—$C_{1-6}$ alkyl" for $R^4$ means a group of —C(S)— as combined with the above-defined "—$C_{1-6}$ alkyl", and concretely includes, for example, —C(S)-methyl, —C(S)-ethyl, —C(S)-isopropyl, —C(S)-propyl.

In "—$(CH_2)_{0-4}$—$N(R^{53})$—C(O)—$R^{54}$" for $R^4$, $R^{53}$ means a hydrogen atom or a —$C_{1-6}$ alkyl; and $R^{54}$ means a —$C_{1-6}$ alkyl; or in —$N(R^{53})$—C(O)—$R^{54}$ in "$(CH_2)_{0-4}$—$N(R^{53})$—C(O)—$R^{54}$", —N—C(O)— and $R^{53}$ and $R^{54}$ may together form a 4- to 7-membered nitrogen-containing aliphatic hetero ring (the hetero ring may be substituted with an oxo, and may have 1 or 2 double bonds in the ring).

"—$(CH_2)_{0-4}$—$N(R^{53})$—C(O)—$R^{54}$" in which $R^{53}$ is a hydrogen atom or a —$C_{1-6}$ alkyl and $R^{54}$ is a —$C_{1-6}$ alkyl concretely includes, for example, —$CH_2$—NH—C(O)-methyl, —$CH_2$—NH—C(O)-ethyl, —$CH_2$—NH—C(O)-isopropyl, —$CH_2$—NH—C(O)-propyl, —$CH_2$—N(methyl)-C(O)-methyl, —$CH_2$—N(ethyl)-C(O)-methyl, —NH—C(O)-methyl, —NH—C(O)-ethyl, —NH—C(O)-isopropyl, —NH—C(O)-propyl, —N(methyl)-C(O)-methyl, —N(ethyl)-C(O)-methyl.

In case where —N—C(O)— and the $C_{1-6}$-alkyls for $R^{53}$ and $R^{54}$ together form a 4- to 7-membered nitrogen-containing aliphatic hetero ring (the hetero ring may be substituted with an oxo, and may have 1 or 2 double bonds in the ring), "—$(CH_2)_{0-4}$—$N(R^{53})$—C(O)—$R^{54}$" concretely includes, for example, groups of the following formula (IV):

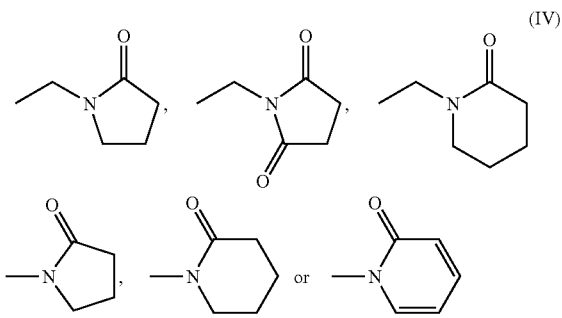

(IV)

In "—N(R$^{55}$)—C(O)—O—R$^{56}$" for R$^4$, R$^{55}$ represents a hydrogen atom or a —C$_{1-6}$ alkyl; and R$^{56}$ represents a —C$_{1-6}$ alkyl; or in —N(R$^{55}$)—C(O)—O—R$^{56}$ in "—N(R$^{55}$)—C(O)—O—R$^{56}$", —N—C(O)—O— and the alkyls for R$^{55}$ and R$^{56}$ together form a 4- to 7-membered nitrogen-containing aliphatic hetero ring.

In case where R$^{55}$ represents a hydrogen atom or a —C$_{1-6}$ alkyl, and R$^{56}$ represents a —C$_{1-6}$ alkyl, "—N(R$^{55}$)—C(O)—O—R$^{56}$" concretely includes, for example, —NH—C(O)—O-methyl, —NH—C(O)—O-ethyl, —NH—C(O)—O-isopropyl, —NH—C(O)—O-propyl, —N(methyl)-C(O)—O-methyl, —N(ethyl)-C(O)—O-methyl.

In case where —N—C(O)—O— and the C$_{1-6}$-alkyls for R$^{55}$ and R$^{56}$ together form a 4- to 7-membered nitrogen-containing aliphatic hetero ring, "—N(R$^{53}$)—C(O)—R$^{54}$" concretely includes, for example, groups of the following formula (V):

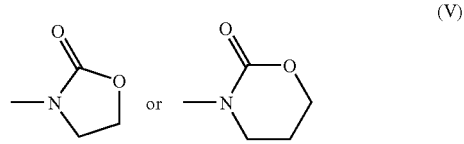

(V)

"—C(O)-aryl" for R$^4$ means a group of a carbonyl as combined with the above-defined aryl, and concretely includes, for example, benzoyl, naphthylcarbonyl.

The aryl in the "—C(O)-aryl" may be substituted with from 1 to 3 of the above-defined halogen atoms.

In case where the group has 2 or 3 halogens for the substituents, then they may be the same or different.

"—C(O)-aromatic hetero ring" for R$^4$ means a group of a carbonyl as combined with the above-defined, 5- or 6-membered monocyclic aromatic hetero ring or 9- or 10-membered twin-cyclic aromatic hetero ring, and concretely includes, for example, —C(O)-pyrrolyl, —C(O)-furyl, —C(O)-thienyl, —C(O)—, —C(O)-pyrazolyl, —C(O)-isoxazolyl, —C(O)-isothiazolyl, —C(O)-imidazolyl, —C(O)-oxazolyl, —C(O)-thiazolyl, —C(O)-triazolyl, —C(O)-oxadiazolyl, —C(O)-thiadiazolyl, —C(O)-tetrazolyl, —C(O)-pyridyl, —C(O)-pyrazinyl, —C(O)-pyrimidinyl, —C(O)-pyridazinyl.

"—C(O)-aromatic hetero ring" for R$^4$ means a group of a carbonyl as combined with the above-defined, 4- to 7-membered monocyclic aliphatic hetero ring, and concretely includes, for example, —C(O)-azetidinyl, —C(O)-pyrrolidinyl, —C(O)-piperidino, —C(O)-piperidinyl, —C(O)-azepanyl, —C(O)-piperazinyl, —C(O)-morpholino, —C(O)-thiomorpholino, —C(O)-homopiperazinyl, —C(O)-imidazolidinyl, —C(O)-pyrazolidinyl.

"Hetero ring" for R$^4$ may be the same as those of the "hetero ring" for R$^1$.

The hetero ring may be substituted with from 1 to 3-C$_{1-6}$-alkyls, halogens or —O—C$_{1-6}$-alkyls.

In case where the ring is substituted with 2 or 3 such substituents, then they may be the same or different.

The —C$_{1-6}$-alkyl, halogen and —O—C$_{1-6}$-alkyl for the substituents may be the same as those mentioned hereinabove for the groups.

"Halogen" for R$^4$ may be the same as the above-defined "halogen".

"Phenyl" for R$^4$ may be substituted with a halogen, a —C$_{1-6}$ alkyl or an —O—C$_{1-6}$ alkyl.

In case where R$^1$ has 2 or 3 R$^4$'s, then the same or different two R$^4$'s may together form a 4- to 6-membered ring, which concretely includes, for example, groups of the following formula (VI):

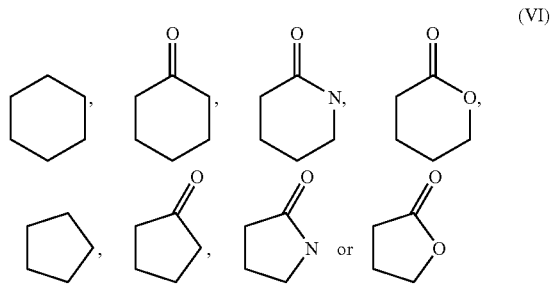

(VI)

—X$_5$— represents —O—, —S—, —S(O)—, —S(O)$_2$—, a single bond or an —O—C$_{1-6}$ alkyl.

Preferably, —X$_5$— is —O—, —S—, —S(O)—, —S(O)$_2$— or a single bond.

R$^1$—X$_5$— (R$^1$ may be substituted with from 1 to 3 R$^4$'s) concretely includes, for example, phenylsulfanyl, phenoxy, benzyloxy, phenethyloxy, 2-cyanophenoxy, 3-cyanophenoxy, 4-cyanophenoxy, 2-cyano-6-fluorophenoxy, 2-carbamoylphenoxy, 3-carbamoylphenoxy, 4-carbamoylphenoxy, 2-fluoro-6-carbamoylphenoxy, 2-methylcarbamoylphenoxy, 3-methylcarbamoylphenoxy, 4-methylcarbamoylphenoxy, 2-dimethylcarbamoylphenoxy, 3-dimethylcarbamoylphenoxy, 4-dimethylcarbamoylphenoxy, 2-methoxy-phenoxy, 3-methoxyphenoxy, 4-methoxyphenoxy, 4-methoxymethylphenoxy, 2-isopropylphenoxy, 3-isopropylphenoxy, 4-isopropylphenoxy-2-methylphenoxy, 3-methylphenoxy, 4-methylphenoxy, 2-ethylphenoxy, 3-ethylphenoxy, 4-ethylphenoxy, 2-acetylphenoxy, 3-acetylphenoxy, 4-acetylphenoxy, 2-methanesulfonyl-phenoxy, 3-methanesulfonylphenoxy, 3-chloro-4-methanesulfonylphenoxy, 4-methanesulfonylphenoxy, 2-ethanesulfonylphenoxy, 3-ethanesulfonylphenoxy, 4-ethanesulfonylphenoxy, 2-methoxycarbonylphenoxy, 3-methoxycarbonylphenoxy, 4-methoxycarbonylphenoxy, 2-ethoxycarbonylphenoxy, 3-ethoxycarbonylphenoxy, 4-ethoxycarbonylphenoxy, 2-hydroxyphenoxy, 3-hydroxyphenoxy, 4-hydroxyphenoxy, 2-hydroxymethylphenoxy, 3-hydroxymethylphenoxy, 4-hydroxymethylphenoxy, 2-hydroxyethylphenoxy, 3-hydroxyethylphenoxy, 4-hydroxyethylphenoxy, 2-formylphenoxy, 3-formylphenoxy, 4-formylphenoxy, 2-(1-hydroxyethyl)phenoxy, 3-(1-hydroxyethyl)phenoxy, 4-(1-hydroxyethyl)phenoxy, 2,3-difluorophenoxy, 2,5-difluorophenoxy, 2,4-difluorophenoxy, 2,6-difluorophenoxy, 2-fluorophenoxy, 3-fluorophenoxy, 4-fluorophenoxy, 2-di-fluoromethoxyphenoxy, 3-difluoromethoxyphenoxy, 4-difluoromethoxyphenoxy, 2-trifluoromethoxyphenoxy, 3-trifluoromethoxyphenoxy, 4-trifluoromethoxyphenoxy, 2-(1H-tetrazol-5-yl)phenoxy, 3-(1H-tetrazol-5-yl)phenoxy, 4-(1H-tetrazol-5-yl)phenoxy, 4-(2-methyl-2H-tetrazol-5-yl)phenoxy, 2-(oxadiazol-3-yl)phenoxy, 3-(oxadiazol-3-yl)phenoxy, 4-(oxadiazol-3-yl)phenoxy, 2-(5-methyloxadiazol-3-yl)phenoxy, 3-(5-methyloxadiazol-3-yl)phenoxy, 4-(5-methyloxadiazol-3-yl)phenoxy, 2-methoxyphenylsulfanyl, 3-methoxyphenylsulfanyl, 4-methoxyphenylsulfanyl, 2-methoxyphenylmethylsulfanyl, 3-methoxyphenylmethylsulfanyl, 4-methoxyphenylmethylsulfanyl, 2-(5-oxo-4,5-dihydro[1,2,4]oxadiazol-3-yl)phenoxy, 3-(5-oxo-4,5-dihydro-[1,2,4]oxadiazol-3-yl)phenoxy, 4-(5-oxo-4,5-dihydro-[1,2,4]oxadiazol-3-yl)phenoxy, 2-(N-hydroxyamidino)phenoxy, 3-(N-hydroxyamidino)phenoxy, 4-(N-hydroxyamidino)phenoxy, 2'-fluorobiphenyl-4-yloxy, pyridin-2-ylsulfanyl, pyridin-3-ylsulfanyl, pyridin-4-ylsulfanyl, pyridin-4-ylsulfonylaminopyridiyl-2-yloxy, pyridin-2-yloxy, pyridin-3-yloxy, pyridin-4-yloxy, 2-methoxypyridin-3-yloxy, 2-methoxypyridin-4-yloxy, 6-methoxypyridin-3-yloxy, 6-methoxypyridin-2-yloxy, 3-methoxypyridin-2-yloxy, 4-methoxypyridin-2-yloxy, 5-methoxypyridin-2-yloxy, 6-methoxymethylpyridin-3-yloxy, 2-difluoromethoxypyridin-3-yloxy, 4-difluoromethoxypyridin-3-yloxy, 6-methylpyridin-2-ylsulfanyl, 5-methylpyridin-2-ylsulfanyl, 4-methylpyridin-2-ylsulfanyl, 3-methylpyridin-2-ylsulfanyl, 4-cyano-pyridin-3-yloxy, 6-cyano-pyridin-3-yloxy, 4-dimethylcarbamoyl-pyridin-3-yloxy, 6-methanesulfonyl-pyridin-3-yloxy, 6-ethanesulfonyl-pyridin-3-yloxy, 4-methanesulfonyl-pyridin-3-yloxy, 2-cyano-pyridin-3-yloxy, 2-dimethylcarbamoyl-pyridin-3-yloxy, 2-methanesulfonyl-pyridin-3-yloxy, 2-methylpyridin-3-ylsulfanyl, 2-chloropyridin-3-yloxy, 6-acetylamino-pyridin-3-yloxy, 2-oxo-2H-[1,3']bipyridin-6'-yloxy, 4-methylpyridin-3-ylsulfanyl, 5-methylpyridin-3-ylsulfanyl, 6-methylpyridin-3-ylsulfanyl, 2-methylpyridin-4-ylsulfanyl, 3-methylpyridin-4-ylsulfanyl, 4-methylpyridin-3-ylsulfonyl, 5-methylpyridin-3-ylsulfonyl, 6-methylpyridin-3-ylsulfonyl, 2-methylpyridin-3-ylsulfonyl, 3-methylpyridin-2-ylsulfonyl, 4-methylpyridin-2-ylsulfonyl, 5-methylpyridin-2-ylsulfonyl, 6-methylpyridin-2-ylsulfonyl, 2-oxo-1,2-dihydropyridin-3-yloxy, 1-methyl-2-oxo-1,2-dihydropyridin-3-yloxy, 1-ethyl-2-oxo-1,2-dihydropyridin-3-yloxy, 5-bromopyridin-2-yloxy, 6-(5-methyl-[1,2,4]oxadiazol-3-yl-pyridin)-3-yloxy, 6-([1,2,4]oxadiazol-3-yl-pyridin)-3-yloxy, 1H-imidazol-2-ylsulfanyl, 1-methyl-1H-imidazol-2-ylsulfanyl, 4H-[1,2,4]triazol-3-ylsulfanyl, 4-methyl-4H-[1,2,4]triazol-3-ylsulfanyl, 6-(2-methyl-2H-tetrazol-5-yl)pyridin-3-yloxy, 5-(2-oxo-oxadiazolidin-3-yl)pyridin-2-yloxy, 6-pyrazin-2-yl-pyridin-3-yloxy, 1-acetylpyrrolidin-2-yl, 2-acetylpyrrolidin-1-yl, 1-acetyl-3-fluoro-pyrrolidin-2-yl, 1-acetyl-5-methyl-pyrrolidin-2-yl, 1-acetylpiperidin-2-yl, 1-ethylcarbonyl-pyrrolidin-2-yl, 2-ethylcarbonyl-pyrrolidin-1-yl, 1-ethylcarbonyl-piperidin-2-yl, 1-n-propylcarbonyl-pyrrolidin-2-yl, 2-n-propylcarbonyl-pyrrolidin-2-yl, 1-n-propylcarbonyl-piperidin-2-yl, 1-isopropyl-pyrrolidin-2-yl, 2-isopropyl-pyrrolidin-1-yl, 1-isopropyl-piperidin-2-yl, 1-hydroxyethylcarbonyl-pyrrolidin-2-yl, 2-hydroxyethylcarbonyl-pyrrolidin-1-yl, 1-hydroxyethylcarbonyl-piperidin-2-yl, 1-hydroxymethylcarbonyl-pyrrolidin-2-yl, 2-hydroxymethylcarbonyl-pyrrolidin-1-yl, 1-hydroxymethylcarbonyl-piperidin-2-yl, 1-methoxymethylcarbonyl-pyrrolidin-2-yl, 2-methoxymethylcarbonyl-pyrrolidin-1-yl, 1-methoxymethylcarbonyl-piperidin-2-yl, 1-ethoxymethylcarbonyl-pyrrolidin-2-yl, 2-ethoxymethylcarbonyl-pyrrolidin-1-yl, 1-ethoxymethylcarbonyl-piperidin-2-yl, 1-methylpyrrolidin-2-yl, 2-methylpyrrolidin-1-yl, 1-methylpiperidin-2-yl, 1-ethylpyrrolidin-2-yl, 2-ethylpyrrolidin-1-yl, 1-ethylpiperidin-2-yl, 1-phenylcarbonyl-pyrrolidin-2-yl, 2-phenylcarbonyl-pyrrolidin-1-yl, 1-phenylcarbonyl-piperidin-2-yl, 1-phenethylcarbonyl-pyrrolidin-2-yl, 2-phenethylcarbonyl-pyrrolidin-1-yl, 1-phenethylcarbonyl-piperidin-2-yl, 1-benzylcarbonyl-pyrrolidin-2-yl, 2-benzylcarbonyl-pyrrolidin-1-yl, 1-benzylcarbonyl-piperidin-2-yl, 1-dimethylaminomethylcarbonyl-pyrrolidin-2-yl, 2-dimethylaminomethylcarbonyl-pyrrolidin-1-yl, 1-dimethylaminomethylcarbonyl-piperidin-2-yl, 1-methylaminomethylcarbonyl-pyrrolidin-2-yl, 2-methylaminomethylcarbonyl-pyrrolidin-1-yl, 1-methylaminomethylcarbonyl-piperidin-2-yl, 1-cyclohexylcarbonyl-pyrrolidin-2-yl, 2-cyclohexylcarbonyl-pyrrolidin-1-yl, 1-ylpiperidin-2-yl, 1-cyclopentylcarbonyl-pyrrolidin-2-yl, 2-cyclopentylcarbonyl-pyrrolidin-1-yl, 1-cyclopentylcarbonyl-piperidin-2-yl, 1-(1-methyl-3-oxobutylcarbonyl)-pyrrolidin-2-yl, 2-(1-methyl-3-oxobutylcarbonyl)pyrrolidin-1-yl, 1-(1-methyl-3-oxobutylcarbonyl)piperidin-2-yl, 1-methanesulfonyl-pyrrolidin-2-yl, 2-methanesulfonyl-pyrrolidin-1-yl, 1-methanesulfonyl-piperidin-2-yl, 1-ethanesulfonyl-pyrrolidin-2-yl, 2-ethanesulfonyl-pyrrolidin-1-yl, 1-ethanesulfonyl-piperidin-2-yl, 1-isopropylsulfonyl-pyrrolidin-2-yl, 2-isopropylsulfonyl-pyrrolidin-1-yl, 1-isopropylsulfonyl-piperidin-2-yl, 1-carbamoyl-pyrrolidin-2-yl, 2-carbamoyl-pyrrolidin-1-yl, 1-carbamoyl-piperidin-2-yl, 1-carbamoylmethyl-pyrrolidin-2-yl, 2-carbamoylmethyl-pyrrolidin-1-yl, 1-carbamoylmethyl-piperidin-2-yl, 1-carbamoylethyl-pyrrolidin-2-yl, 2-carbamoylethyl-pyrrolidin-1-yl, 1-carbamoylethyl-piperidin-2-yl, 1-(pyrrolidin-2-ylcarbonyl)pyrrolidin-2-yl, 2-(pyrrolidin-2-ylcarbonyl)pyrrolidin-1-yl, 1-(pyrrolidin-2-ylcarbonyl)-piperidin-2-yl, 1-(pyrimidinyl-2-yl)pyrrolidin-2-yl, 2-(pyrimidinyl-2-yl)pyrrolidin-1-yl, 1-(pyrimidinyl-2-yl)piperidin-2-yl, 1-(pyrazinyl-2-yl)pyrrolidin-2-yl, 2-(pyrazinyl-2-yl)pyrrolidin-1-yl, 1-(pyrazinyl-2-yl)piperidin-2-yl, 1-(pyridyl-2-yl)pyrrolidin-2-yl, 2-(pyridyl-2-yl)pyrrolidin-1-yl, 1-(pyridyl-2-yl)piperidin-2-yl, 1-(pyridyl-3-yl)pyrrolidin-2-yl, 2-(pyridyl-3-yl)pyrrolidin-1-yl, 1-(pyridyl-3-yl)piperidin-2-yl, 1-trifluoromethylcarbonyl-pyridin-2-yl, 2-trifluoromethylcarbonyl-pyrrolidin-1-yl, 1-trifluoromethylcarbonyl-piperidin-2-yl, 1-(2-hydroxyacetyl)pyrrolidin-2-yl, 2-(2-hydroxyacetyl)pyrrolidin-1-yl, 1-(2-hydroxyacetyl)piperidin-2-yl, 1-(2-methylaminoacetyl)pyrrolidin-2-yl, 2-(2-methylaminoacetyl)pyrrolidin-1-yl, 1-(2-methylaminoacetyl)piperidin-2-yl, 1-(2-dimethylaminoacetyl)pyrrolidin-2-yl, 2-(2-dimethylaminoacetyl)pyrrolidin-1-yl, 1-(2-dimethylaminoacetyl)piperidin-2-yl, 1-n-propylaminoacetyl-pyrrolidin-2-yl, 2-n-propylaminoacetyl-pyrrolidin-1-yl, 1-n-propylaminoacetyl-piperidin-2-yl, 1-isopropylaminoacetyl-pyrrolidin-2-yl, 2-isopropylaminoacetyl-pyrrolidin-1-yl, 1-isopropylaminoacetyl-piperidin-2-yl.

The ring A represents a 5- or 6-membered nitrogen-containing aromatic hetero ring of a formula (II), optionally having, in the ring, from 1 to 3 hetero atoms selected from a group consisting of a nitrogen atom, a sulfur atom and an oxygen atom (excepting the nitrogen atom of N* in formula II):

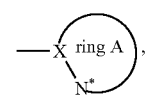

(II)

or represents a group of the 5- or 6-membered aromatic hetero ring condensed with a phenyl or a pyridyl.

X represents a carbon atom or a nitrogen atom.

More concretely, the 5- or 6-membered nitrogen-containing aromatic hetero ring for the ring A includes, for example, thiazolyl, imidazolyl, isothiazolyl, thiadiazolyl, triazolyl, oxazolyl, oxadiazolyl, isoxazolyl, pyrazinyl, pyridyl, pyridazinyl, pyrazolyl, pyrimidinyl. Of those, preferred is thiazolyl, thiadiazolyl, isoxazolyl, pyrazinyl, pyridyl, pyridazinyl, triazolyl or pyrazolyl; and more preferred is pyridyl, pyrazinyl, thiazolyl, thiadiazolyl, isoxazolyl or pyrazolyl.

More concretely, the twin ring of the 5- or 6-membered nitrogen-containing aromatic ring condensed with a phenyl or a pyridyl for the ring A includes, for example, indolyl, benzimidazolyl, benzoxazolyl, pyridothiazolyl, benzothiazolyl.

The ring A is preferably a 5- or 6-membered nitrogen-containing aromatic hetero ring.

The ring A may have, in the ring, 1 or 2 substituents mentioned hereinabove for $R^3$. In case where the ring A has two such substituents, they may be the same or different.

Concretely, $R^3$ includes, for example, methyl, ethoxy, hydroxymethyl, methoxycarbonyl, methoxymethyl, aminomethyl, cyano, acetyl, fluorine, chlorine, bromine and difluoromethyl.

From the above, the ring A (the ring A may be substituted with from 1 to 3 $R^3$'s) more concretely includes, for example, 3H-imidazol-4-yl, 1H-imidazol-2-yl, [1,2,4]triazol-3-yl, [1,2,3]triazol-4-yl, pyrazol-3-yl, pyrazol-1-yl, pyridin-2-yl, pyrazin-2-yl, oxazol-2-yl, oxazol-4-yl, [1,2,4]thiadiazol-5-yl, [1,2,4]thiadiazol-3-yl, thiazol-2-yl, thiazol-4-yl, [1,2,5]thiadiazol-3-yl, pyrrol-2-yl, isothiazol-3-yl, isoxazol-3-yl, 4-methyl-thiazol-2-yl, 4-hydroxymethyl-thiazol-2-yl, 4-methoxycarbonyl-thiazol-2-yl, 4-methoxymethyl-thiazol-2-yl, 4-aminomethyl-thiazol-2-yl, 4-cyano-thiazol-2-yl, 4-cyano-thiazol-2-yl, 4-fluoro-thiazol-2-yl, imidazol-2-yl, 4-methyl-imidazol-2-yl, 4-methoxycarbonyl-imidazol-2-yl, isothiazol-3-yl, 4-hydroxymethyl-isothiazol-3-yl, [1,3,4]thiadiazol-2-yl, 5-acetyl-[1,3,4]thiadiazol-2-yl, [1,2,4]triazol-2-yl, 5-hydroxymethyl-[1,2,4]triazol-3-yl, 4-methyl-pyridin-2-yl, 4-methoxymethyl-imidazol-2-yl, 4-acetyl-imidazol-2-yl, 5-hydroxymethyl-imidazol-2-yl, 5-methyl-[1,3,4]thiadiazol-2-yl, 5-fluoro[1,3,4]thiadiazol-2-yl, 5-methyl-[1,2,4]triazol-2-yl, 5-acetyl-[1,2,4]triazol-3-yl, 4-methoxymethyl-isoxazol-2-yl, 5-methyl-isoxazol-3-yl, 5-hydroxymethyl-isoxazol-3-yl, 1-oxy-pyrazin-2-yl, 1-oxy-pyridin-2-yl, 5-methoxymethyl-isoxazol-3-yl, 5-methylcarbonyl-isoxazol-3-yl, 5-chloro-isoxazol-3-yl, 5-aminomethyl-isoxazol-3-yl, 4-methyl-1H-pyrazol-3-yl, pyrimidin-2-yl, pyrimidin-4-yl, pyridazin-3-yl, 6-methyl-pyridazin-3-yl, 2-methyl-thiazol-4-yl, thiazolo[5,4-b]pyridin-2-yl, 3-methyl [1,2,4]thiadiazolyl-5-yl, 1-methyl-1H-pyrazol-3-yl.

$R^2$ means a hydroxy, a formyl, $-CH_{3-a}F_a$, $-OCH_{3-a}F_a$, an amino, CN, a halogen, a $C_{1-6}$ alkyl or $-(CH_2)_{1-4}OH$.

$R^2$ is preferably a hydroxy, a formyl, $-CH_{3-a}F_a$ (preferably trifluoromethyl), $-OCH_{3-a}F_a$, a halogen, a $C_{1-6}$ alkyl, an amino, CN, $-(CH_2)_{1-4}OH$; more preferably a hydroxy, a formyl, $-CH_{3-a}F_a$ (preferably, trifluoromethyl), $-OCH_{3-a}F_a$ (preferably, trifluoromethoxy), an amino, a halogen, a $-C_{1-6}$ alkyl, CN or $-(CH_2)_{1-4}OH$, even more preferably a hydroxy, a formyl, an amino, a halogen (preferably, fluorine, chlorine), a $-C_{1-6}$ alkyl or $-(CH_2)_{1-4}OH$.

q indicates an integer of from 0 to 2.

When q is 2, then $R^2$'s may be the same or different.

Of the compounds of formula (I-0), however, those where one $X_5$ is an oxygen atom or a sulfur atom and the other $X_5$ is a single bond, and those where both $X_5$'s are single bonds, and $R^1$ is an aryl, or a 4- to 10-membered monocyclic or twin-cyclic hetero ring having, in the ring, from 1 to 4 hetero atoms selected from a group consisting of a nitrogen atom, a sulfur atom and an oxygen atom ($R^1$ may be substituted independently with from 1 to 3 $R^1$'s; and when the hetero ring is an aliphatic hetero ring, then it may have 1 or 2 double bonds) are excluded from the compounds of the invention.

Of the above-mentioned formula (I), a group of the partial structure represented by the following formula (VII) is described.

(VII)

In formula (VII), $X_1$ to $X_4$ each are a carbon atom or a nitrogen atom; and of $X_1$ to $X_4$, at least two are carbon atoms.

More preferably, all of $X_1$ to $X_4$ in formula (VII) are carbon atoms.

In a preferred embodiment of the invention, the compounds of formula (I-0) are those represented by the following formula (I-1):

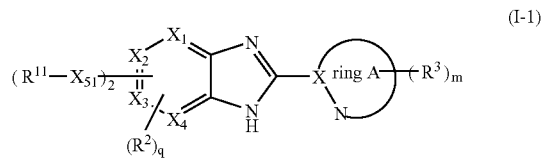

(I-1)

[In the formula, $R^{11}$ represents a phenyl optionally substituted with from 1 to 3 $R^4$'s, or represents a 5- or 6-membered nitrogen-containing aromatic hetero ring having, in the ring, from 1 to 4 hetero atoms selected from a group consisting of a nitrogen atom, a sulfur atom and an oxygen atom (the nitrogen-containing aromatic hetero atom may be substituted with from 1 to 3 $R^4$'s); and $X_{51}$ represents $-O-$, $-S-$, $-S(O)-$ or $-S(O)_2-$; and the other symbols have the same meanings as above].

"Phenyl optionally substituted with from 1 to 3 $R^4$'s" for $R^{11}$ is a phenyl that may be substituted with 1 to 3 of the above-mentioned $R^4$'s.

"5- or 6-membered nitrogen-containing aromatic hetero ring having, in the ring, from 1 to 4 hetero atoms selected from a group consisting of a nitrogen atom, a sulfur atom and an oxygen atom" for $R^{11}$ means a 5- or 6-membered monocyclic aromatic hetero ring mentioned hereinabove for $R^1$, which has at least one nitrogen atom in the ring as the hetero ring-constitutive atom, and it concretely includes, for example, pyrrolyl, pyrazolyl, isoxazolyl, isothiazolyl, imidazolyl, oxazolyl, thiazolyl, triazolyl, oxadiazolyl, thiadiazolyl, tetrazolyl, pyridyl, pyrazinyl, pyrimidinyl, pyridazinyl.

$X_1$, $X_2$, $X_3$ and $X_4$ in formula (I-1) have the same meanings as those in formula (I-0); and preferably, all of $X_1$, $X_2$, $X_3$ and $X_4$ are carbon atoms.

$R^4$ in formula (I-1) has the same meaning as that of $R^4$ in formula (I-0).

$X_{51}$ represents $-O-$, $-S-$, $-S(O)-$ or $-S(O)_2-$, preferably $-O-$ or $-S-$, more preferably $-O-$.

Formula (I-1) has two groups each represented by $-X_{51}-R^{11}$, and these may be the same or different.

$R^{11}$—$X_{51}$— in formula (I-1) ($R^{11}$ may be substituted with from 1 to 3 $R^4$'s) concretely includes, for example, phenylsulfanyl, phenoxy, benzyloxy, 2-cyanophenoxy, 3-cyanophenoxy, 4-cyanophenoxy, 2-carbamoylphenoxy, 3-carbamoylphenoxy, 4-carbamoylphenoxy, 2-methylcarbamoylphenoxy, 3-methylcarbamoylphenoxy, 4-methylcarbamoylphenoxy, 2-dimethylcarbamoylphenoxy, 3-dimethylcarbamoylphenoxy, 4-dimethylcarbamoylphenoxy, 2-(pyrrolidin-1-carbonyl)-phenoxy, 3-(pyrrolidin-1-carbonyl)-phenoxy, 4-(pyrrolidin-1-carbonyl)-phenoxy, 2-methoxy-phenoxy, 3-methoxyphenoxy, 4-methoxyphenoxy, 2-isopropylphenoxy, 3-isopropylphenoxy, 4-isopropylphenoxy, 2-methylphenoxy, 3-methylphenoxy, 4-methylphenoxy, 2-ethylphenoxy, 3-ethylphenoxy, 4-ethylphenoxy, 2-acetylphenoxy, 3-acetylphenoxy, 4-acetylphenoxy, 2-methanesulfonyl-phenoxy, 3-methanesulfonylphenoxy, 4-methanesulfonylphenoxy, 2-methoxycarbonylphenoxy, 3-methoxycarbonylphenoxy, 4-methoxycarbonylphenoxy, 2-ethoxycarbonylphenoxy, 3-ethoxycarbonylphenoxy, 4-ethoxycarbonylphenoxy, 2-hydroxyphenoxy, 3-hydroxyphenoxy, 4-hydroxyphenoxy, 2-hydroxymethylphenoxy, 3-hydroxymethylphenoxy, 4-hydroxymethylphenoxy, 2-hydroxyethylphenoxy, 3-hydroxyethylphenoxy, 4-hydroxyethylphenoxy, 2-formylphenoxy, 3-formylphenoxy, 4-formylphenoxy, 2-(1-hydroxyethyl)phenoxy, 3-(1-hydroxyethyl)phenoxy, 4-(1-hydroxyethyl)phenoxy, 2,5-difluorophenoxy, 2,4-difluorophenoxy, 2,3-difluorophenoxy, 2,6-difluorophenoxy, 2-fluorophenoxy, 3-fluorophenoxy, 4-fluorophenoxy, 2-fluoro-6-carbamoylphenoxy, 2-do-fluoromethoxyphenoxy, 3-difluoromethoxyphenoxy, 4-difluoromethoxyphenoxy, 2-trifluoromethoxyphenoxy, 3-trifluoromethoxyphenoxy, 4-trifluoromethoxyphenoxy, 2-cyano-6-fluorophenoxy, 2-(1H-tetrazol-5-yl)phenoxy, 3-(1H-tetrazol-5-yl)phenoxy, 4-(1H-tetrazol-5-yl)phenoxy, 2-(oxadiazol-3-yl)phenoxy, 3-(oxadiazol-3-yl)phenoxy, 4-(oxadiazol-3-yl)phenoxy, 2-(5-methyloxadiazol-3-yl)phenoxy, 3-(5-methyloxadiazol-3-yl)phenoxy, 4-(5-methyloxadiazol-3-yl)phenoxy, 2-methoxyphenylsulfanyl, 3-methoxyphenylsulfanyl, 4-methoxyphenylsulfanyl, 2-methoxyphenylmethylsulfanyl, 3-methoxyphenylmethylsulfanyl, 4-methoxyphenylmethylsulfanyl, 2-(5-oxo-4,5-dihydro-[1,2,4]oxadiazol-3-yl)phenoxy, 3-(5-oxo-4,5-dihydro-[1,2,4]oxadiazol-3-yl)phenoxy, 4-(5-oxo-4,5-dihydro-[1,2,4]oxadiazol-3-yl)phenoxy, 2-(N-hydroxyamidino)phenoxy, 3-(N-hydroxyamidino)phenoxy, 4-(N-hydroxyamidino)phenoxy, pyridin-2-ylsulfanyl, pyridin-3-ylsulfanyl, pyridin-4-ylsulfanyl, pyridin-2-yloxy, pyridin-3-yloxy, pyridin-4-yloxy, 2-methoxypyridin-3-yloxy, 2-methoxypyridin-4-yloxy, 6-methoxypyridin-3-yloxy, 6-methoxypyridin-2-yloxy, 3-methoxypyridin-2-yloxy, 4-methoxypyridin-2-yloxy, 5-methoxypyridin-2-yloxy, 2-difluoromethoxypyridin-3-yloxy, 6-methylpyridin-2-ylsulfanyl, 5-methylpyridin-2-ylsulfanyl, 4-methylpyridin-2-ylsulfanyl, 3-methylpyridin-2-ylsulfanyl, 4-cyano-pyridin-3-yloxy, 4-dimethylcarbamoyl-pyridin-3-yloxy, 4-methanesulfonyl-pyridin-3-yloxy, 2-cyano-pyridin-3-yloxy, 2-dimethylcarbamoyl-pyridin-3-yloxy, 2-methanesulfonyl-pyridin-3-yloxy, 2-methylpyridin-3-ylsulfanyl, 4-methylpyridin-3-ylsulfanyl, 5-methylpyridin-3-ylsulfanyl, 6-methylpyridin-3-ylsulfanyl, 2-methylpyridin-4-ylsulfanyl, 3-methylpyridin-4-ylsulfanyl, 4-methylpyridin-3-ylsulfonyl, 5-methylpyridin-3-ylsulfonyl, 6-methylpyridin-3-ylsulfonyl, 2-methylpyridin-3-ylsulfonyl, 3-methylpyridin-2-ylsulfonyl, 4-methylpyridin-2-ylsulfonyl, 5-methylpyridin-2-ylsulfonyl, 6-methylpyridin-2-ylsulfonyl, 2-oxo-1,2-dihydropyridin-3-yloxy, 1-methyl-2-oxo-1,2-dihydropyridin-3-yloxy, 1-ethyl-2-oxo-1,2-dihydropyridin-3-yloxy, 1H-imidazol-2-ylsulfanyl, 1-methyl-1H-imidazol-2-ylsulfanyl, 4H-[1,2,4]triazol-3-ylsulfanyl or 4-methyl-4H-[1,2,4]triazol-3-ylsulfanyl.

In a preferred embodiment of the compounds of the invention, both $R^{11}$'s in formula (I-1) are phenyls optionally substituted with from 1 to 3 $R^4$'s.

In another preferred embodiment of the compounds of the invention, both $R^{11}$'s in formula (I-1) are 5- or 6-membered monocyclic nitrogen-containing aromatic hetero rings each having, in the ring, from 1 to 4 hetero atoms selected from a group consisting of a nitrogen atom, a sulfur atom and an oxygen atom (the nitrogen-containing hetero-aromatic ring may be substituted with from 1 to 3 $R^4$'s).

In still another preferred embodiment of the compounds of the invention, one $R^{11}$ in formula (I-1) is a phenyl optionally substituted with from 1 to 3 $R^4$'s, and the other $R^{11}$ is a 5- or 6-membered monocyclic nitrogen-containing aromatic hetero ring having, in the ring, from 1 to 4 hetero atoms selected from a group consisting of a nitrogen atom, a sulfur atom and an oxygen atom (the nitrogen-containing aromatic hetero ring may be substituted with from 1 to 3 $R^4$'s).

In another preferred embodiment of the invention, the compounds of formula (I-0) are those represented by the following formula (I-2):

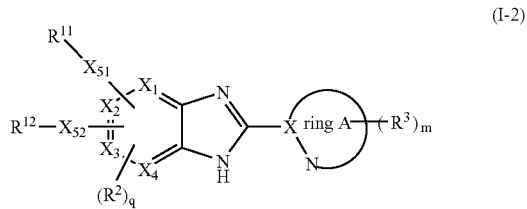

(I-2)

[In the formula, $R^{12}$ represents a 5- to 7-membered nitrogen-containing hetero ring having, as the atom constituting the hetero ring, at least one nitrogen atom and optionally having, as the other hetero atoms, from 1 to 4 hetero atoms selected from a group consisting of a nitrogen atom, a sulfur atom and an oxygen atom ($R^{12}$ may be substituted with from 1 to 3 $R^4$'s, and when $R^{12}$ is an aliphatic hetero ring, then it may have 1 or 2 double bonds in the ring); $X_{52}$ represents —O—, —S—, —S(O)—, —S(O)$_2$— or a single bond; and the other symbols have the same meanings as above].

"4- to 7-membered nitrogen-containing hetero ring having, as the atom constituting the hetero ring, at least one nitrogen atom and optionally having, as the other hetero atoms, from 1 to 4 hetero atoms selected from a group consisting of a nitrogen atom, a sulfur atom and an oxygen atom" for $R^{12}$ may be the 4- to 7-membered monocyclic hetero ring for $R^1$, which has at least one nitrogen atom in the hetero ring, and it concretely includes, for example, azetidinyl, pyrrolidinyl, piperidinyl, azepanyl, piperazinyl, morpholino, thiomorpholino, homopiperazinyl, imidazolidinyl, pyrazolidinyl, pyrrolyl, pyrazolyl, isoxazolyl, isothiazolyl, imidazolyl, oxazolyl, thiazolyl, triazolyl, oxadiazolyl, thiadiazolyl, tetrazolyl, pyridyl, pyrazinyl, pyrimidinyl or pyridazinyl.

$R^{12}$ may have from 1 to 3 $R^4$'s as the substituents.

When $R^{12}$ has 2 or 3 $R^4$'s as the substituents, then they may be the same or different.

Of the groups mentioned hereinabove for $R^4$, those preferred for the substituents for $R^{12}$ are a —C(O)—$C_{1-6}$ alkyl (the $C_{1-6}$ alkyl may be substituted with a halogen, a hydroxy, —N($R^5$)$R^{52}$, an —O—$C_{1-6}$ alkyl or phenyl), —C(O)-phenyl, a —C(O)—$C_{3-7}$ cycloalkyl, a —C(O)—O—$C_{1-6}$ alkyl, —C(O)—N(R$^5$)R$^{52}$, a —C$_{1-6}$ alkyl, an aromatic hetero ring, —S(O)$_2$—N(R$^{51}$)R$^{52}$ or an —S(O)$_2$—C$_{1-6}$ alkyl.

The substituents for R$^{12}$ concretely include, for example, acetyl, ethylcarbonyl, propylcarbonyl, isopropylcarbonyl, hydroxyethylcarbonyl, hydroxymethylcarbonyl, methoxymethylcarbonyl, ethoxymethylcarbonyl, methyl, ethyl, phenylcarbonyl, phenethylcarbonyl, benzylcarbonyl, dimethylaminomethylcarbonyl, methylaminomethylcarbonyl, cyclohexylcarbonyl, cyclopentylcarbonyl, 1-methyl-3-oxobutylcarbonyl, methanesulfonyl, ethanesulfonyl, isopropylsulfonyl, carbamoyl, carbamoylmethyl, carbamoylethyl, pyrrolidin-2-carbonyl, pyrimidinyl, pyrazinyl, pyridyl, trifluoromethylcarbonyl, 2-hydroxyacetyl, 2-methylaminoacetyl, 2-dimethylaminoacetyl, 2-ethylaminoacetyl, n-propylaminoacetyl, isopropylaminoacetyl, oxo, methyl, ethyl, isopropyl.

X$_{51}$ in formula (I-2) is preferably —O— or —S— of those mentioned hereinabove for X$_{51}$, more preferably —O—.

X$_{52}$ in formula (I-2) represents —O—, —S—, —S(O)—, —S(O)$_2$— or a single bond.

In case where R$^{12}$ is a 4- to 7-membered saturated nitrogen-containing aliphatic hetero ring having, as the atom constituting the hetero ring, at least one nitrogen atom and optionally having, as the other hetero atoms, 1 or 2 hetero atoms selected from a group consisting of a nitrogen atom, a sulfur atom and an oxygen atom (the nitrogen-containing aliphatic hetero ring may be substituted with from 1 to 3 R$^{4'}$s), then X$_{52}$ is preferably a single bond.

In case where R$^{12}$ is a 5- to 7-membered nitrogen-containing aliphatic hetero ring having, as the atom constituting the hetero ring, at least one nitrogen atom and optionally having, as the other hetero atoms, 1 or 2 hetero atoms selected from a group consisting of a nitrogen atom, a sulfur atom and an oxygen atom, and having, in the ring, 1 or 2 double bonds (the 5- to 7-membered hetero ring may be substituted with from 1 to 3 R$^{4'}$s), then X$_{52}$ is preferably —O—, —S—, —S(O)— or —S(O)$_2$—, more preferably —O—.

"4- to 7-membered saturated nitrogen-containing aliphatic hetero ring having, as the atom constituting the hetero ring, at least one nitrogen atom and optionally having, as the other hetero atoms, 1 or 2 hetero atoms selected from a group consisting of a nitrogen atom, a sulfur atom and an oxygen atom" for R$^{12}$ concretely includes, for example, azetidinyl, pyrrolidinyl, piperidino, piperidinyl, homopiperidinyl, azepanyl, piperazinyl, morpholino, thiomorpholino, homopiperazinyl, imidazolidinyl, pyrazolidinyl. Of those, preferred is azetidinyl, pyrrolidinyl or piperidinyl; also preferred is pyrrolidinyl, piperidinyl, homopiperidinyl; and more preferred is a group of a formula (III-1):

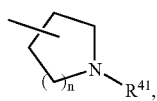
(III-1)

or a formula (III-2):

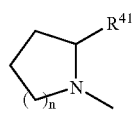
(III-2)

[in the formulae, n indicates an integer of from 1 to 3; and R$^{41}$ has the same meaning as R$^4$]; and even more preferred is a group of a formula (III-3):

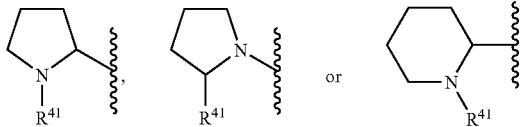
(III-3)

[in the formulae, R$^4$ has the same meaning as defined above, and the following formula (VIII):

(VIII)

indicates a bonding site at which the group bonds to X$^{53}$].

"4- to 7-membered saturated nitrogen-containing aliphatic hetero ring having, as the atom constituting the hetero ring, at least one nitrogen atom and optionally having, as the other hetero atoms, 1 or 2 hetero atoms selected from a group consisting of a nitrogen atom, a sulfur atom and an oxygen atom (the nitrogen-containing aliphatic hetero ring may be substituted with from 1 to 3 R$^{4'}$s)" for R$^{12}$ includes concretely, for example, 1-acetylpyrrolidin-2-yl, 2-acetylpyrrolidin-1-yl, 1-acetyl-3-fluoropyrrolidin-2-yl, 1-acetyl-5-methyl-pyrrolidin-2-yl, 1-acetylpiperidin-2-yl, 1-ethylcarbonyl-pyrrolidin-2-yl, 2-ethylcarbonylpyrrolidin-1-yl, 1-ethylcarbonyl-piperidin-2-yl, 1-n-propylcarbonyl-pyrrolidin-2-yl, 2-n-propylcarbonyl-pyrrolidin-2-yl, 1-n-propylcarbonyl-piperidin-2-yl, 1-isopropyl-pyrrolidin-2-yl, 2-isopropyl-pyrrolidin-1-yl, 1-isopropyl-piperidin-2-yl, 1-hydroxyethylcarbonyl-pyrrolidin-2-yl, 2-hydroxyethylcarbonyl-pyrrolidin-1-yl, 1-hydroxyethylcarbonyl-piperidin-2-yl, 1-hydroxymethylcarbonyl-pyrrolidin-2-yl, 2-hydroxymethylcarbonyl-pyrrolidin-1-yl, 1-hydroxymethylcarbonyl-piperidin-2-yl, 1-methoxymethylcarbonyl-pyrrolidin-2-yl, 2-methoxymethylcarbonyl-pyrrolidin-1-yl, 1-methoxymethylcarbonyl-piperidin-2-yl, 1-ethoxymethylcarbonyl-pyrrolidin-2-yl, 2-ethoxymethylcarbonyl-pyrrolidin-1-yl, 1-ethoxymethylcarbonyl-piperidin-2-yl, 1-methylpyrrolidin-2-yl, 2-methylpyrrolidin-1-yl, 1-methylpiperidin-2-yl, 1-ethylpyrrolidin-2-yl, 2-ethylpyrrolidin-1-yl, 1-ethylpiperidin-2-yl, 1-phenylcarbonyl-pyrrolidin-2-yl, 2-phenylcarbonyl-pyrrolidin-1-yl, 1-phenylcarbonyl-piperidin-2-yl, 1-phenethylcarbonyl-pyrrolidin-2-yl, 2-phenethylcarbonyl-pyrrolidin-1-yl, 1-phenethylcarbonyl-piperidin-2-yl, 1-benzylcarbonyl-pyrrolidin-2-yl, 2-benzylcarbonyl-pyrrolidin-1-yl, 1-benzylcarbonyl-piperidin-2-yl, 1-dimethylaminomethylcarbonyl-pyrrolidin-2-yl, 2-dimethylaminomethylcarbonyl-pyrrolidin-1-yl, 1-dimethylaminomethylcarbonyl-piperidin-2-yl, 1-methylaminomethylcarbonyl-pyrrolidin-2-yl, 2-methylaminomethylcarbonyl-pyrrolidin-1-yl, 1-yl-piperidin-2-yl, 1-cyclohexylcarbonyl-pyrrolidin-2-yl, 2-cyclohexylcarbonyl-pyrrolidin-1-yl, 1-cyclohexylcarbonyl-piperidin-2-yl, 1-cyclopentylcarbonyl-pyrrolidin-2-yl, 2-cyclopentylcarbonyl-pyrrolidin-1-yl, 1-cyclopentylcarbonyl-piperidin-2-yl, 1-(1-methyl-3-oxobutylcarbonyl)-pyrrolidin-2-yl, 2-(1-methyl-3-oxobutylcarbonyl)pyrrolidin-1-yl, 1-(1-methyl-3-oxobutylcarbonyl)piperidin-2-yl, 1-methanesulfonyl-pyrrolidin-2-yl, 2-methanesulfonyl-pyrrolidin-1-yl, 1-methanesulfonyl-piperidin-2-yl, 1-ethanesulfonyl-pyrrolidin-2-yl, 2-ethanesulfonyl-pyrrolidin-1-yl, 1-ethanesulfonyl-piperidin-2-yl, 1-isopropylsulfonyl-pyrrolidin-2-yl, 2-isopropylsulfonyl-pyrrolidin-1-yl, 1-isopropylsulfonyl-piperidin-2-yl, 1-carbamoyl-pyrrolidin-2-yl, 2-carbamoyl-pyrrolidin-1-yl, 1-carbamoyl-piperidin-2-yl, 1-carbamoylmethyl-pyrrolidin-2-yl, 2-carbamoylmethyl-pyrrolidin-1-yl, 1-carbamoylmethyl-piperidin-2-yl, 1-carbamoylethyl-pyrrolidin-2-yl, 2-carbamoylethyl-pyrrolidin-1-yl, 1-carbamoylethyl-piperidin-2-yl, 1-(pyrrolidin-2-ylcarbonyl)pyrrolidin-2-yl, 2-(pyrrolidin-2-ylcarbonyl)pyrrolidin-1-yl, 1-(pyrrolidin-2-ylcarbonyl)-piperidin-2-yl, 1-(pyrimidinyl-2-yl)pyrrolidin-2-yl, 2-(pyrimidinyl-2-yl)pyrrolidin-1-yl, 1-(pyrimidinyl-2-yl)piperidin-2-yl, 1-(pyrazinyl-2-yl)pyrrolidin-2-yl, 2-(pyrazinyl-2-yl)pyrrolidin-1-yl, 1-(pyrazinyl-2-yl)piperidin-2-yl, 1-(pyridyl-2-yl)pyrrolidin-2-yl, 2-(pyridyl-2-yl)pyrrolidin-1-yl, 1-(pyridyl-2-yl)piperidin-2-yl, 1-(pyridyl-3-yl)pyrrolidin-2-yl, 2-(pyridyl-3-yl)pyrrolidin-1-yl, 1-(pyridyl-3-yl)piperidin-2-yl, 1-trifluoromethylcarbonyl-pyridin-2-yl, 2-trifluoromethylcarbonyl-pyrrolidin-1-yl, 1-trifluoromethylcarbonyl-piperidin-2-yl, 1-(2-hydroxyacetyl)pyrrolidin-2-yl, 2-(2-hydroxyacetyl)pyrrolidin-1-yl, 1-(2-hydroxyacetyl)piperidin-2-yl, 1-(2-methylaminoacetyl)pyrrolidin-2-yl, 2-(2-methylaminoacetyl)pyrrolidin-1-yl, 1-(2-methylaminoacetyl)piperidin-2-yl, 1-(2-dimethylaminoacetyl)pyrrolidin-2-yl, 2-(2-dimethylaminoacetyl)pyrrolidin-1-yl, 1-(2-dimethylaminoacetyl)piperidin-2-yl, 1-n-propylaminoacetyl-pyrrolidin-2-yl, 2-n-propylaminoacetyl-pyrrolidin-1-yl, 1-n-propylaminoacetyl-piperidin-2-yl, 1-isopropylaminoacetyl-pyrrolidin-2-yl, 2-isopropylaminoacetyl-pyrrolidin-1-yl, 1-isopropylaminoacetyl-piperidin-2-yl.

"5- to 7-membered nitrogen-containing aliphatic hetero ring having, as the atom constituting the hetero ring, at least one nitrogen atom and optionally having, as the other hetero atoms, 1 or 2 hetero atoms selected from a group consisting of a nitrogen atom, a sulfur atom and an oxygen atom, and having, in the ring, 1 or 2 double bonds" for $R^{12}$ includes concretely, for example, groups of a formula (IX):

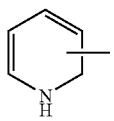

(IX)

"5- to 7-membered nitrogen-containing aliphatic hetero ring having, as the atom constituting the hetero ring, at least one nitrogen atom and optionally having, as the other hetero atoms, 1 or 2 hetero atoms selected from a group consisting of a nitrogen atom, a sulfur atom and an oxygen atom, and having, in the ring, 1 or 2 double bonds (the nitrogen-containing aliphatic hetero ring may be substituted with from 1 to 3 $R^{4}$'s)" for $R^{12}$ includes concretely, for example, 1-methyl-2-oxo-1,2-dihydropyridyl, 2-oxo-1,2-dihydropyridyl, 1-ethyl-2-oxo-1,2-dihydropyridyl, 1-isopropyl-2-oxo-1,2-dihydropyridyl, 1-propyl-2-oxo-1,2-dihydropyridyl.

$R^{11}$—$X_{51}$— ($R^{11}$ may be substituted with from 1 to 3 $R^{4}$'s) in formula (I-2) may be the same as those in formula (I-1). Of those, concretely preferred are, for example, 5-bromopyridin-2-yloxy, 6-methanesulfonyl-pyridin-3-yloxy, 2-chloropyridin-3-yloxy, 4-hydroxymethoxymethyl-phenoxy, 4-methanesulfonylphenoxy, 6-ethanesulfonyl-pyridin-3-yloxy, 6-cyanopyridin-3-yloxy, 6-acetylamino-pyridin-3-yloxy, 4-methoxymethyl-phenoxy, 4-(2-oxo-2H-pyridin-1-yl)phenoxy, 6-(5-methyl-[1,2,4]-oxadiazol-3-yl)pyridin-3-yloxy, 2'-fluorobiphenyl-4-yloxy, 6-([1,2,4]-oxadiazol-3-yl)pyridin-3-yloxy, 6-(2-methyl-2H-tetrazol-5-yl)-pyridin-3-yloxy, 4-(2-methyl-2H-tetrazol-5-yl)phenoxy), 6-methoxymethyl-pyridin-3-yloxy, 2-oxo-2H-[1,3']bipyridin-6'-yloxy, 5-(2-oxo-oxazolidinon-3-yl)pyridin-2-yloxy, 6-methylpyridin-3-yloxy, 6-pyrazin-2-ylpyridin-3-yloxy, 4-acetylphenoxy.

In a preferred embodiment of the invention, the compounds of formula (I-1) are those represented by the following formula (I-11):

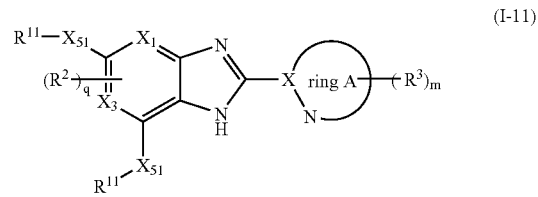

(I-11)

[in the formula, the symbols have the same meanings as above].

In formula (I-11), $R^{11}$ ($R^{11}$ may be substituted with from 1 to 3 $R^{4}$'s) may be the same as $R^{11}$ in formula (I-1).

In formula (I-11), Xs, is preferably —O— or —S—, more preferably —O—.

In formula (I-11), $X_1$ and $X_3$ each independently represent a carbon atom or a nitrogen atom, but preferably both $X_1$ and $X_3$ are carbon atoms.

In formula (I-11), $R^{11}$—$X_{51}$— ($R^{11}$ may be substituted with from 1 to 3 $R^{4}$'s) includes concretely, for example, methanesulfonylphenoxy, 3-methanesulfonylphenoxy, 2-methoxyphenoxy, 3-methoxyphenoxy, 2-acetylphenoxy, 3-acetylphenoxy, 2-carbamoylphenoxy, 3-carbamoylphenoxy, phenoxy, 2-cyano-6-fluorophenoxy, 2-methylphenoxy, 3-methylphenoxy, 2-fluorophenoxy, 3-fluorophenoxy, 2,3-difluorophenoxy, 2,4-difluorophenoxy, 2,5-difluorophenoxy, 2,6-difluorophenoxy, pyridin-2-yloxy, pyridin-3-yloxy, 2-methoxypyridin-3-yloxy, 2-difluoromethoxypyridin-3-yloxy. Of those, preferred are 2-methanesulfonylphenoxy, 2-methoxyphenoxy, 2-acetylphenoxy, 2-carbamoylphenoxy, phenoxy, 2-cyano-6-fluorophenoxy, 2-methylphenoxy, 2-fluorophenoxy, 2,3-difluorophenoxy, 2,6-difluorophenoxy, pyridin-3-yloxy, 2-methoxypyridin-3-yloxy, 2-difluoromethoxypyridin-3-yloxy.

In another preferred embodiment of the invention, the compounds of formula (I-1) are those represented by the following formula (I-12):

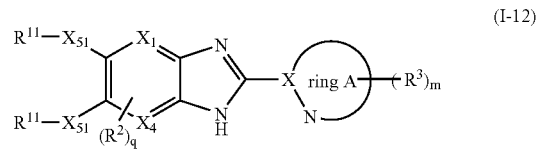

(I-12)

[in the formula, the symbols have the same meanings as above].

In formula (I-12), $R^{11}$ ($R^{11}$ may be substituted with from 1 to 3 $R^{4}$'s) may be the same as $R^{11}$ in formula (I-1).

In formula (I-12), $X_{51}$ is preferably —O— or —S—, more preferably —O—.

In formula (I-12), $X_1$ and $X_3$ each independently represent a carbon atom or a nitrogen atom, but preferably both $X_1$ and $X_3$ are carbon atoms.

In formula (I-12), $R^{11}$—$X_{51}$— ($R^{11}$ may be substituted with from 1 to 3 $R^4$'s) includes concretely, 2-carbamoylphenoxy, 3-carbamoylphenoxy, 4-carbamoylphenoxy, 2-cyanophenoxy, 3-cyanophenoxy, 4-cyanophenoxy, 2-methoxyphenoxy, 3-methoxyphenoxy, 4-methoxyphenoxy, 2-methanesulfonylphenoxy, 3-methanesulfonylphenoxy, 4-methanesulfonylphenoxy, 2-(pyrrolidin-1-carbonyl)-phenoxy, 3-(pyrrolidin-1-carbonyl)-phenoxy, 4-(pyrrolidin-1-carbonyl)-phenoxy, pyridin-2-yloxy, pyridin-3-yloxy, pyridin-4-yloxy, 2-methylcarbamoylphenoxy, 3-methylcarbamoylphenoxy, 4-methylcarbamoylphenoxy, 2-dimethylcarbamoylphenoxy, 3-dimethylcarbamoylphenoxy, 4-dimethylcarbamoylphenoxy, 2-(oxadiazol-3-yl)phenoxy, 2-methoxycarbonylphenoxy, 3-methoxycarbonylphenoxy, 4-methoxycarbonylphenoxy, 2-acetylphenoxy, 3-acetylphenoxy, 4-acetylphenoxy, 2-ethoxycarbonylphenoxy, 3-ethoxycarbonylphenoxy, 4-ethoxycarbonylphenoxy, 2-N-hydroxyamidino-phenoxy, 3-N-hydroxyamidino-phenoxy, 4-N-hydroxyamidino-phenoxy, 2-hydroxymethyl-phenoxy, 3-hydroxymethyl-phenoxy, 4-hydroxymethyl-phenoxy, 2-(2H-tetrazol-5-yl)phenoxy, 3-(2H-tetrazol-5-yl)phenoxy, 4-(2H-tetrazol-5-yl)phenoxy, 2-cyano-pyridin-3-yloxy, 4-cyano-pyridin-3-yloxy, 2-carbamoyl-pyridin-3-yl, 2-difluoromethoxy-pyridin-3-yloxy, 4-carbamoyl-pyridin-3-yl, 2-(5-4,5-dihydro-[1,2,4]oxadiazol-3-yl)phenoxy, 3-(5-oxo-4,5-dihydro-[1,2,4]oxadiazol-3-yl)phenoxy, 4-(5-oxo-4,5-dihydro-[1,2,4]oxadiazol-3-yl)phenoxy, 2-formylphenoxy, 3-formylphenoxy, 4-formylphenoxy.

Of those, for example, one $R^{11}$—$X_{51}$— is preferably 2-carbamoylphenoxy, 4-carbamoylphenoxy, 2-cyanophenoxy, 4-cyanophenoxy, 2-methoxyphenoxy, 4-methoxyphenoxy, 2-methanesulfonylphenoxy, 4-methanesulfonylphenoxy, pyridin-2-yloxy, pyridin-3-yloxy, pyridin-4-yloxy, 2-cyano-pyridin-3-yloxy, 2-difluoromethoxy-pyridin-3-yloxy, 4-cyano-pyridin-3-yloxy, 2-carbamoyl-pyridin-3-yloxy, 4-carbamoyl-pyridin-3-yloxy, 5-cyano-pyridin-3-yloxy, 4-cyano-pyridin-3-yloxy, 5-carbamoyl-pyridin-3-yloxy, 4-carbamoyl-pyridin-3-yloxy, 2-methylcarbamoylphenoxyoxy, 4-methylcarbamoylphenoxyoxy, 2-dimethylcarbamoylphenoxyoxy, 4-dimethylcarbamoylphenoxy, 2-(oxadiazol-3-yl)phenoxy, 2-methoxycarbonylphenoxy, 4-methoxycarbonylphenoxy, 2-acetylphenoxy, 4-acetylphenoxy, 2-ethoxycarbonylphenoxy, 4-ethoxycarbonylphenoxy, 2-N-hydroxydiamidino-phenoxy, 4-N-hydroxyamidino-phenoxy, 2-hydroxymethyl-phenoxy, 4-hydroxymethyl-phenoxy, 2-difluoromethoxy-pyridin-3-yloxy, 2-(2H-tetrazol-5-yl)phenoxy, 4-(2H-tetrazol-5-yl)phenoxy, 2-(5-oxo-4,5-dihydro-[1,2,4]oxadiazol-3-yl)phenoxy, 4-(5-oxo-4,5-dihydro-[1,2,4]oxadiazol-3-yl)phenoxy, 2-formylphenoxy, 4-formylphenoxy; more preferably 2-carbamoylphenoxy, 2-cyanophenoxy, 2-methoxyphenoxy, 2-methanesulfonylphenoxy, pyridin-3-yloxy, 2-difluoromethoxy-pyridin-3-yloxy, 2-methylcarbamoylphenoxy, 2-dimethylcarbamoylphenoxy, 2-(oxadiazol-3-yl)phenoxy, 2-methoxycarbonylphenoxy, 2-acetylphenoxy, 2-ethoxycarbonylphenoxy, 2-N-hydroxyamidino-phenoxy, 2-cyano-pyridin-3-yloxy, 2-difluoromethoxy-pyridin-3-yloxy, 2-carbamoyl-pyridin-3-yloxy, 2-hydroxymethyl-phenoxy, 2-(2H-tetrazol-5-yl)phenoxy, 2-difluoromethoxy-pyridin-3-yloxy, 2-(5-oxo-4,5-dihydro-[1,2,4]oxadiazol-3-yl)phenoxy, 2-formylphenoxy.

For example, the other $R^{11}$—$X_{51}$— is preferably 3-carbamoylphenoxy, 4-carbamoylphenoxy, 3-cyanophenoxy, 4-cyanophenoxy, 3-methoxyphenoxy, 4-methoxyphenoxy, 3-(pyrrolidin-1-carbonyl)-phenoxy, 4-(pyrrolidin-1-carbonyl)-phenoxy, 3-methanesulfonylphenoxy, 4-methanesulfonylphenoxy, pyridin-2-yloxy, pyridin-3-yloxy, pyridin-4-yloxy, 2-difluoromethoxy-pyridin-3-yloxy, 3-methylcarbamoylphenoxy, 4-methylcarbamoylphenoxy, 5-cyano-pyridin-3-yloxy, 4-cyano-pyridin-3-yloxy, 5-carbamoyl-pyridin-3-yloxy, 4-carbamoyl-pyridin-3-yloxy, 3-dimethylcarbamoylphenoxy, 4-dimethylcarbamoylphenoxy, 4-(oxadiazol-3-yl)phenoxy, 3-methoxycarbonylphenoxy, 4-methoxycarbonylphenoxy, 3-acetylphenoxy, 4-acetylphenoxy, 3-ethoxycarbonylphenoxy, 4-ethoxycarbonylphenoxy, 3-N-hydroxyamidino-phenoxy, 4-N-hydroxyamidino-phenoxy, 3-hydroxymethyl-phenoxy, 4-hydroxymethyl-phenoxy, 3-(2H-tetrazol-5-yl)phenoxy, 4-(2H-tetrazol-5-yl)phenoxy, 3-(5-oxo-4,5-dihydro-[1,2,4]oxadiazol-3-yl)phenoxy, 4-(5-oxo-4,5-dihydro-[1,2,4]oxadiazol-3-yl)phenoxy, 3-formylphenoxy, 4-formylphenoxy; more preferably 4-carbamoylphenoxy, 4-cyanophenoxy, 4-methoxyphenoxy, 4-methanesulfonylphenoxy, pyridin-3-yloxy, 4-methylcarbamoylphenoxy, 4-dimethylcarbamoylphenoxy, 4-(oxadiazol-3-yl)phenoxy, 4-methoxycarbonylphenoxy, 4-acetylphenoxy, 4-ethoxycarbonylphenoxy, 4-N-hydroxyamidino-phenoxy, 4-hydroxymethyl-phenoxy, 4-cyano-pyridin-3-yloxy, 2-difluoromethoxy-pyridin-3-yloxy, 4-carbamoyl-pyridin-3-yloxy, 4-(2H-tetrazol-5-yl)phenoxy, 4-(5-oxo-4,5-dihydro-[1,2,4]oxadiazol-3-yl)phenoxy, 4-formylphenoxy.

In still another preferred embodiment of the compounds of the invention, one $R^1$ in formula (I-0) is a phenyl optionally substituted with from 1 to 3 $R^4$'s, or is a 5- or 6-membered nitrogen-containing aromatic hetero ring having from 1 to 4 hetero atoms selected from a group consisting of a nitrogen atom, a sulfur atom and an oxygen atom (the nitrogen-containing aromatic hetero ring may be substituted with from 1 to 3 $R^4$'s), and the other $R^1$ is a 5- to 7-membered nitrogen-containing hetero ring having, as the hetero atom constituting the hetero ring, at least one nitrogen atom and optionally having, as the other hetero atoms, from 1 to 4 hetero atoms selected from a nitrogen atom, a sulfur atom and an oxygen atom.

The 5- to 7-membered nitrogen-containing hetero ring may be a 5- or 6-membered nitrogen-containing aromatic hetero ring, or a 5- to 7-membered nitrogen-containing aliphatic hetero ring.

The 5- or 6-membered nitrogen-containing aromatic hetero ring includes concretely, for example, pyrrolyl, furyl, thienyl, pyrazolyl, isoxazolyl, isothiazolyl, imidazolyl, oxazolyl, thiazolyl, triazolyl, oxadiazolyl, thiadiazolyl, tetrazolyl, pyridyl, pyrazinyl, pyrimidinyl, pyridazinyl.

The 5- to 7-membered nitrogen-containing aliphatic hetero ring includes concretely, for example, azetidinyl, pyrrolidinyl, piperidino, piperidinyl, azepanyl, piperazinyl, morpholino, thiomorpholino, homopiperazinyl, imidazolidinyl, pyrazolidinyl.

The hetero ring may be substituted with from 1 to 3 $R^4$'s; and when the hetero ring is an aliphatic hetero ring, it may have 1 or 2 double bonds.

In still another preferred embodiment of the invention, the compounds of the invention are represented by formula (I-0), and one $R^1$ is a phenyl optionally substituted with from 1 to 3 $R^4$'s, or is a 5- or 6-membered nitrogen-containing aromatic hetero ring having from 1 to 4 hetero atoms selected from a group consisting of a nitrogen atom, a sulfur atom and an oxygen atom (the nitrogen-containing aromatic hetero ring may be substituted with from 1 to 3 $R^4$'s), and the other $R^1$ is a 5- or 6-membered nitrogen-containing hetero-aromatic ring having, as the hetero atom constituting the hetero ring, at least one nitrogen atom and optionally having, as the other hetero atoms, from 1 to 4 hetero atoms selected from a nitrogen atom, a sulfur atom and an oxygen atom.

The 5- or 6-membered nitrogen-containing aromatic hetero ring having from 1 to 4 hetero atoms selected from a group consisting of a nitrogen atom, a sulfur atom and an oxygen atom may be the same as those mentioned hereinabove.

In still another preferred embodiment of the invention, the compounds of the invention are represented by formula (I-0), and one $R^1$ is a phenyl optionally substituted with from 1 to 3 $R^4$'s, or is a 5- or 6-membered nitrogen-containing aromatic hetero ring having from 1 to 4 hetero atoms selected from a group consisting of a nitrogen atom, a sulfur atom and an oxygen atom (the nitrogen-containing aromatic hetero ring may be substituted with from 1 to 3 $R^4$'s), and the other $R^1$ is a 5- to 7-membered nitrogen-containing aliphatic hetero ring having, as the hetero atom constituting the hetero ring, at least one nitrogen atom and optionally having, as the other hetero atoms, 1 or 2 hetero atoms selected from a nitrogen atom, a sulfur atom and an oxygen atom (the nitrogen-containing aliphatic hetero ring may be substituted with from 1 to 3 $R^4$'s, and may have, in the ring, 1 or 2 double bonds).

Of the compounds of formula (I-0), concretely preferred are, for example:

5-(4-methanesulfonyl-phenoxy)-2-pyrazin-2-yl-6-(2-carbamoyl-phenoxy)-1H-benzimidazole,
5-(2-carbamoyl-phenoxy)-2-pyridin-2-yl-6-(6-(methanesulfonyl-pyridin-3-yloxy)-1H-benzimidazole,
5-(2-carbamoyl-phenoxy)-2-pyrazin-2-yl-6-(6-methanesulfonyl-pyridin-3-yloxy)-1H-benzimidazole,
5-(2-fluoro-phenoxy)-2-pyridin-2-yl-6-(6-methanesulfonyl-pyridin-3-yloxy)-1H-benzimidazole,
5-(2-difluoromethoxy-pyridin-3-yloxy)-6-(6-methanesulfonyl-pyridin-3-yloxy)-2-pyridin-2-yl-1H-benzimidazole,
5-(2-difluoromethoxy-pyridin-3-yloxy)-6-(6-methanesulfonyl-pyridin-3-yloxy)-2-pyrazin-2-yl-1H-benzimidazole,
5-(2-difluoromethoxy-pyridin-3-yloxy)-6-(6-methanesulfonyl-pyridin-3-yloxy)-2-(1-methyl-1H-pyrazol-3-yl)-1H-benzimidazole,
5-(2-cyano-phenoxy)-2-pyridin-2-yl-6-(6-ethanesulfonyl-pyridin-3-yloxy)-1H-benzimidazole,
5-(2-fluoro-phenoxy)-2-pyridin-2-yl-6-(6-ethanesulfonyl-pyridin-3-yloxy)-1H-benzimidazole,
5-(2-fluoro-phenoxy)-2-(1H-pyrazol-3-yl)-6-(6-ethanesulfonyl-pyridin-3-yloxy)-1H-benzimidazole,
5-(2,3-difluoro-phenoxy)-2-(1-methyl-1H-pyrazol-3-yl)-6-(6-yloxy-pyridin-3-yloxy)-1H-benzimidazole,
5-(2,4-difluoro-phenoxy)-2-pyrazin-2-yl-6-(6-ethanesulfonyl-pyridin-3-yloxy)-1H-benzimidazole,
5-(2,5-difluoro-phenoxy)-2-pyridin-2-yl-6-(6-ethanesulfonyl-pyridin-3-yloxy)-1H-benzimidazole,
5-(2,6-difluoro-phenoxy)-2-pyrazin-2-yl-6-(6-ethanesulfonyl-pyridin-3-yloxy)-1H-benzimidazole,
5-(2,6-difluoro-phenoxy)-2-(1-methyl-1H-pyrazol-3-yl)-6-(6-ethanesulfonyl-pyridin-3-yloxy)-1H-benzimidazole,
5-(2-fluoropyridin-3-yloxy)-6-(6-ethanesulfonylpyridin-3-yloxy)-2-pyridin-2-yl-1H-benzimidazole,
5-(2-fluoropyridin-3-yloxy)-6-(6-ethanesulfonylpyridin-3-yloxy)-2-pyrazin-2-yl-1H-benzimidazole,
5-(2-chloropyridin-3-yloxy)-6-(6-ethanesulfonylpyridin-3-yloxy)-2-pyridin-2-yl-1H-benzimidazole,
5-(2-chloropyridin-3-yloxy)-6-(6-ethanesulfonylpyridin-3-yloxy)-2-pyrazin-2-yl-1H-benzimidazole,
5-(2-cyanopyridin-3-yloxy)-6-(6-ethanesulfonylpyridin-3-yloxy)-2-pyridin-2-yl-1H-benzimidazole,
5-(2-difluoromethoxy-pyridin-3-yloxy)-6-(6-ethanesulfonyl-pyridin-3-yloxy)-2-pyridin-2-yl-1H-benzimidazole,
5-(2-difluoromethoxy-pyridin-3-yloxy)-6-(6-ethanesulfonyl-pyridin-3-yloxy)-2-pyrazin-2-yl-1H-benzimidazole,
5-(2-difluoromethoxy-pyridin-3-yloxy)-6-(4-ethanesulfonyl-phenoxy)-2-pyridin-2-yl-1H-benzimidazole,
5-(2-difluoromethoxy-pyridin-3-yloxy)-6-(4-ethanesulfonyl-phenoxy)-2-pyrazin-2-yl-1H-benzimidazole,
5-(2,6-difluoro-phenoxy)-2-pyridin-2-yl-6-(6-methanesulfonyl-pyridin-3-yloxy)-1H-benzimidazole;
5-(2-carbamoyl-phenoxy)-2-pyridin-2-yl-6-(6-ethanesulfonyl-pyridin-3-yloxy)-1H-benzimidazole,
5-(2-fluoro-6-cyano-phenoxy)-2-pyridin-2-yl-6-(6-ethanesulfonyl-pyridin-3-yloxy)-1H-benzimidazole,
5-(2-fluoro-6-carbamoyl-phenoxy)-2-pyridin-2-yl-6-(6-ethanesulfonyl-pyridin-3-yloxy)-1H-benzimidazole,
5-(2-fluoro-6-carbamoyl-phenoxy)-2-pyrazin-2-yl-6-(4-ethanesulfonyl-phenoxy)-1H-benzimidazole,
5-(2-fluoro-6-cyano-phenoxy)-2-pyrazin-2-yl-6-(6-ethanesulfonyl-pyridin-3-yloxy)-1H-benzimidazole,
5-(2-fluoro-6-(tetrazol-5-yl)-phenoxy)-2-pyrazin-2-yl-6-(6-ethanesulfonyl-pyridin-3-yloxy)-1H-benzimidazole,
5-(2-difluoromethoxypyridin-3-yloxy)-6-(3-chloro-4-methanesulfonyl-phenoxy)-2-pyridin-2-yl-1H-benzimidazole,
4-(2-fluoro-phenoxy)-2-(pyridin-2-yl)-6-(4-methanesulfonyl-phenoxy)-1H-benzimidazole,
4-(2,6-difluoro-phenoxy)-6-(6-methanesulfonyl-pyridin-3-yloxy)-2-pyrazin-2-yl-1H-benzimidazole,
4-(2,6-difluoro-phenoxy)-6-(6-methanesulfonyl-pyridin-3-yloxy)-2-pyridin-2-yl-1H-benzimidazole,
4-(2,6-difluoro-phenoxy)-6-(6-ethanesulfonyl-pyridin-3-yloxy)-2-pyrazin-2-yl-1H-benzimidazole,
4-(2,6-difluoro-phenoxy)-6-(6-ethanesulfonyl-pyridin-3-yloxy)-2-pyridin-2-yl-1H-benzimidazole,
4-(1-methyl-2-oxo-1,2-dihydro-pyridin-3-yloxy)-6-(4-ethanesulfonyl-phenoxy)-2-pyridin-2-yl-1H-benzimidazole,
4-(2,6-difluoro-phenoxy)-6-(6-ethanesulfonyl-pyridin-3-yloxy)-2-(1H-pyrazol-3-yl)-1H-benzimidazole,
4-(2-fluoro-phenoxy)-6-(6-ethanesulfonyl-pyridin-3-yloxy)-2-pyrazin-2-yl-1H-benzimidazole,
4-(2,3-difluoro-phenoxy)-6-(6-ethanesulfonyl-pyridin-3-yloxy)-2-pyrazin-2-yl-1H-benzimidazole,
4-(2,5-difluoro-phenoxy)-6-(6-ethane sulfonyl-pyridin-3-yloxy)-2-pyridin-2-yl-1H-benzimidazole,
4-(2-cyano-6-fluoro-phenoxy)-6-(6-ethanesulfonyl-pyridin-3-yloxy)-2-pyrazin-2-yl-1H-benzimidazole,
4-(2-cyano-6-fluoro-phenoxy)-6-(6-methanesulfonyl-pyridin-3-yloxy)-2-pyridin-2-yl-1H-benzimidazole,
4-(2-cyano-6-fluoro-phenoxy)-6-(6-methanesulfonyl-pyridin-3-yloxy)-2-pyrazin-2-yl-1H-benzimidazole,
1-(2-(6-(5-bromo-pyridin-2-yloxy)-2-pyridin-2-yl-3H-benzimidazol-5-yl)-pyrrolidin-1-yl)-ethanone,
1-(2-(6-(6-methanesulfonyl-pyridin-3-yloxy)-2-pyridin-2-yl-3H-benzimidazol-5-yl)-pyrrolidin-1-yl)-ethanone,
1-(2-(6-(4-hydroxymethyl-phenoxy)-2-pyridin-2-yl-3H-benzimidazol-1-yl)-pyrrolidin-1-yl)-ethanone,
1-(2-(6-(4-methanesulfonyl-phenoxy)-2-pyridin-2-yl-3H-benzimidazol-5-yl)-pyrrolidin-1-yl)-ethanone,
2-(6-(4-methanesulfonyl-phenoxy)-2-pyridin-2-yl-3H-benzimidazol-5-yl)-pyrrolidin-1-carboxamide,
2-hydroxy-1-(2-(6-(4-methanesulfonyl-1-phenoxy)-2-pyridin-2-yl-3H-benzimidazol-5-yl)-pyrrolidin-1-yl)-ethanone,
1-(2-(6-(6-ethanesulfonyl-pyridin-3-yloxy)-2-pyridin-2-yl-3H-benzimidazol-5-yl)-pyrrolidin-1-yl)-ethanone,
1-(2-(6-(4-methanesulfonyl-phenoxy)-2-pyrazin-2-yl-3H-benzimidazol-5-yl)-pyrrolidin-1-yl)-ethanone, 2-fluoro-1-(2-(6-(4-methanesulfonyl-phenoxy)-2-pyridin-2-yl-3H-benzimidazol-5-yl)-pyrrolidin-1-yl)-ethanone,
5-(6-(1-acetyl-pyrrolidin-2-yl)-2-pyridin-2-yl-1H-benzimidazole-5-yloxy)pyridine-2-carbonitrile,
1-(2-(6-(4-methanesulfonyl-phenoxy)-2-pyridin-2-yl-3H-benzimidazol-5-yl)-pyrrolidin-1-yl)-2-methylaminoethanone,
1-(2-(6-(4-methanesulfonyl-phenoxy)-2-(1H-pyrazol-3-yl)-3H-benzimidazol-5-yl)-pyrrolidin-1-yl)-ethanone,
1-(4-fluoro-2-(6-(4-methanesulfonyl-phenoxy)-2-pyridin-2-yl-3H-benzimidazol-5-yl)-pyrrolidin-1-yl)-ethanone,
N-(5-(6-(1-acetyl-pyrrolidin-2-yl)-2-pyridin-2-yl-1H-benzimidazol-5-yloxy)-pyridin-2-yl)-acetamide,
1-(2-(2-(5-bromo-pyridin-2-yl)-6-(4-methanesulfonyl-phenoxy)-3H-benzimidazol-5-yl)-pyrrolidin-1-yl)-ethanone,
N-(2-(2-(6-(4-methanesulfonyl-phenoxy)-2-pyridin)-2-yl-3H-benzimidazol-5-yl)pyrrolidin-1-yl)-2-oxo-ethyl)-acetamide,
6-(1-acetylpyrrolidin-2-yl)-5-(4-(methoxymethyl)phenoxy)-2-pyridin-2-yl-1H-benzimidazol monotrifluoroacetate,
1-(4-((6-(1-acetylpyrrolidin-2-yl)-2-pyridin-2-yl-1H-benzimidazol-5-yl)oxy)phenyl)pyridin-2(1H)-one,
6-(1-acetylpyrrolidin-2-yl)-5-((6-(5-methyl-[1,2,4]-oxadiazol-3-yl)pyridin-3-yl)oxy)-2-pyridin-2-yl-1H-benzimidazole,
(2-(2-(5-((2'-fluorobiphenyl-4-yl)oxy)-2-pyridin-2-yl-1H-benzimidazol-6-yl)pyrrolidin-1-yl)-2-oxoethyl)methylamine,
6-(1-acetylpyrrolidin-2-yl)-5-((6-([1,2,4]-oxadiazol-3-yl)pyridin-3-yl)oxy)-2-pyridin-2-yl-1H-benzimidazole,
6-(1-acetylpyrrolidin-2-yl)-5-(4-(2-methyl-2H-tetrazol-5-yl)phenoxy)-2-pyrazin-2-yl-1H-benzimidazole,
5-(1-acetyl-3-fluoropyrrolidin-2-yl)-6-(4-(methanesulfonyl)phenoxy)-2-pyridin-2-yl-1H-benzimidazole,
6-(1-acetylpyrrolidin-2-yl)-5-((6-(2-methyl-2H-tetrazol-5-yl)pyridin-3-yl)oxy)-2-pyridin-2-yl-1H-benzimidazole,
6-(1-acetylpyrrolidin-2-yl)-5-(4-(2-methyl-2H-tetrazol-5-yl)phenoxy)-2-pyridin-2-yl-1H-benzimidazole,
5-(1-acetyl-5-methylpyrrolidin-2-yl)-6-(4-(methanesulfonyl)phenoxy)-2-pyridin-2-yl-1H-benzimidazole,
6-(1-acetylpyrrolidin-2-yl)-5-((6-(2-methyl-2H-tetrazol-5-yl)pyridin-3-yl)oxy)-2-pyrazin-2-yl-1H-benzimidazole,
6-(1-acetylpyrrolidin-2-yl)-5-(6-methoxymethylpyridin-3-yl)oxy)-2-pyridin-2-yl-1H-benzimidazole,
2-(2-(5-(4-(2-methyl-2H-tetrazol-5-yl)phenoxy)-2-pyridin-2-yl-1H-benzimidazol-6-yl)pyrrolidin-1-yl)-2-oxoethanol,
2-(5-(4-(2-methyl-2H-tetrazol-5-yl)phenoxy)-2-pyridin-2-yl-1H-benzimidazol-6-yl)pyrrolidine-1-carboxamide,
5'-((6-(1-acetylpyrrolidin-2-yl)-2-pyridin-2-yl-1H-benzimidazol-5-yl)oxy)-2H-1,2'-bipyridin-2-one,
3-(4-((6-(1-acetylpyrrolidin-2-yl)-2-pyridin-2-yl-1H-benzimidazol-5-yl)oxy)phenyl)-1,3-oxazolidin-2-one,
6-(1-acetylpyrrolidin-2-yl)-5-((6-methylpyridin-3-yl)oxy)-2-pyridin-2-yl-1H-benzimidazole,
6-(1-acetylpyrrolidin-2-yl)-5-((6-pyrazin-2-ylpyridin-3-yl)oxy)-2-pyridin-2-yl-1H-benzimidazole,
6-(1-acetyl-3-fluoropyrrolidin-2-yl)-5-((2'-fluorobiphenyl-4-yl)oxy-2-pyridin-2-yl-1H-benzimidazole,
3-(4-((6-(1-acetylpyrrolidin-2-yl)-2-pyrazin-2-yl-1H-benzimidazol-5-yl)oxy)phenyl)-1,3-oxazolidine-2-one,
6-(1-acetylpyrrolidin-2-yl)-2-pyrazin-2-yl-5-((6-pyrazin-2-ylpyridin-3-yl)oxy)-1H-benzimidazole,
6-(1-acetylpyrrolidin-2-yl)-5-((6-(5-methyl-[1,2,4]-oxadiazol-3-yl)pyridin-3-yl)oxy)-2-pyrazin-2-yl-1H-benzimidazole,
1-(4-((6-(1-acetylpyrrolidin-2-yl)-2-pyrazin-2-yl-1H-benzimidazol-5-yl)oxy)phenyl)ethanone,
6-(1-acetylpyrrolidin-2-yl)-5-(4-(5-methyl-[1,2,4]-oxadiazol-3-yl)phenoxy)-2-pyrazin-2-yl-1H-benzimidazole,
6-(1-(4-methanesulfonyl-phenoxy)-2-pyrazin-2-yl-1H-benzimidazole,
N-methyl-2-(2-(5-(4-(2-methyl-2H-tetrazol-5-yl)phenoxy)-2-pyridin-2-yl-1H-benzimidazol-6-yl)pyrrolidin-1-yl)-2-oxoethanamine,
((6-(methoxymethyl)pyridin-3-yl)oxy)-2-pyrazin-2-yl-1H-benzimidazole,
1-(1-(6-(4-methanesulfonyl-phenoxy)-2-pyridin-2-yl-3H-benzimidazol-5-yl)-pyrrolidin-2-yl)-ethanone,
1-(1-(6-(6-methanesulfonyl-pyridin-3-yloxy)-2-pyridin-2-yl-3H-benzimidazol-5-yl)pyrrolidin-2-yl)-ethanone,
1-(1-(6-(6-ethanesulfonyl-pyridin-3-yloxy)-2-pyrazin-2-yl-3H-benzimidazol-5-yl)pyrrolidin-2-yl)ethanone, or
1-(1-(6-(6-ethanesulfonyl-pyridin-3-yloxy)-2-pyrazin-2-yl-3H-benzimidazol-1-yl)-4-fluoro-pyrrolidin-2-yl)-ethanone, or their pharmaceutically-acceptable salts.

The novel 2-heteroaryl-substituted benzimidazole derivatives of the invention may be in the form of their pharmaceutically-acceptable salts. The salts include acid-addition salts and base-addition salts.

Depending on the type of the substituents therein, the compounds of the invention include stereoisomers and tautomers such as optical isomers, diastereomeric isomers and geometrical isomers. Needless-to-say, the compounds of the invention include all these isomers. Further needless-to-say, the compounds of the invention include all mixtures of such isomers.

Since the compounds of the invention have a glucokinase-activating effect, they are useful as remedies and/or preventives for diabetes and further as remedies and/or preventives for complications of diabetes.

Complications of diabetes as referred to herein are meant to indicate diseases complicated by diabetes, including, for example, diabetic nephropathy, diabetic retinopathy, diabetic neuropathy, diabetic arteriosclerosis.

The compounds of the invention are applicable to both types of diabetes, insulin-dependent diabetes mellitus (IDDM) and non-insulin-dependent diabetes mellitus (NIDDM).

Insulin-dependent diabetes mellitus (IDDM) is developed by predispositions to genetic insulin secretion reduction and insulin resistance in skeletal muscle, as promoted by obesity-caused insulin resistance, and is essentially considered as adult-onset diabetes.

The compounds of the invention are considered useful not only for type I insulin-dependent diabetes mellitus but also for type II diabetes for which conventional medicines are ineffective for sufficiently lowering the blood-sugar level.

In type II diabetics, the degree of high blood-sugar level after meals lasts remarkably longer than that in healthy persons, but the compounds and their pharmaceutically-acceptable salts of the invention are useful also for type II diabetes.

In addition, the compounds and their pharmaceutically-acceptable salts of the invention are useful for remedy and/or prevention of obesity.

The compounds of the following formula (I-0) of the invention:

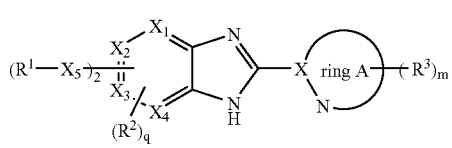

[in the formula, the symbols have the same meanings as above] may be produced, for example, according to the following method:

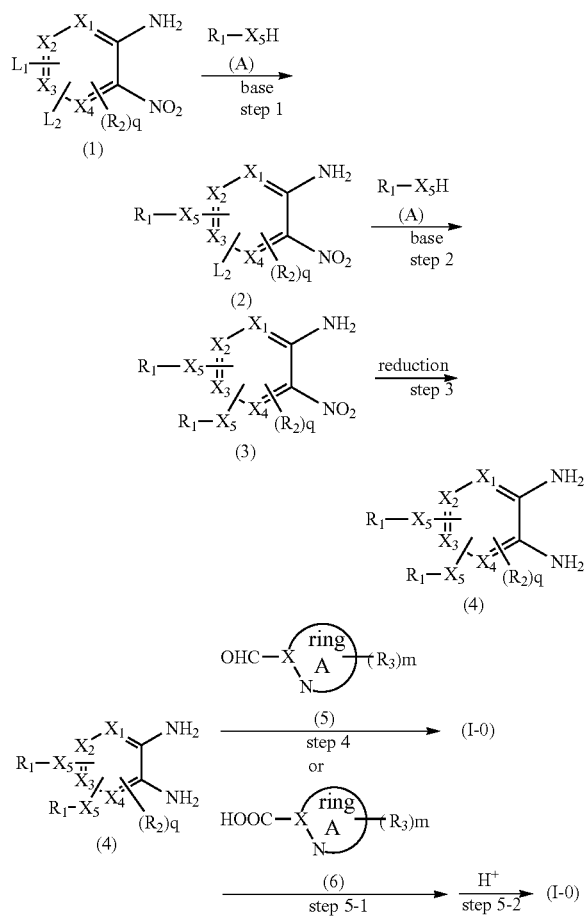

[In the formulae, $L^1$ and $L^2$ each represent a leaving group such as a halogen. The other symbols have the same meanings as defined hereinabove.]

(Step 1)

This step is a process for reacting a compound (1) with a compound (A) represented by $R^1$—$X_5H$ in the presence of a base to produce a compound (2).

$L^1$ and $L^2$ more concretely include, for example, halogens such as fluorine, chlorine, bromide. $L^1$ and $L^2$ may be the same or different.

The compound (1) for use in this step includes, for example, 3,5-difluoro-2-nitroaniline, 3,5-dichloro-2-nitroaniline, 3,5-dibromo-2-nitroaniline, 4-bromo-5-fluoro-2-nitroaniline, 4,5-difluoro-2-nitroaniline.

The amount of the compound (A) to be used varies depending on the type of the compound and the solvent used and on the other reaction conditions, but may be generally from 0.1 to 20 equivalents, preferably from 0.5 to 5 equivalents relative to one equivalent of the compound (1).

The amount of the base to be used also varies depending on the type of the compound and the solvent used and on the other reaction conditions, but may be generally from 0.1 to 20 equivalents, preferably from 0.5 to 5 equivalents.

The base to be used may be any one capable of producing a compound (2) through the reaction of the compound (1) with $R^5$—$X_5H$ in this step, including, for example, sodium hydride, cesium carbonate, sodium carbonate, potassium carbonate, potassium phosphate, potassium acetate, potassium tert-butyrate, triethylamine. When $R^5$—$X_5H$ is a primary or secondary amine, then the base may not be used.

The reaction solvent to be used may be an inert solvent, not specifically defined so far as it does not interfere with the reaction. Concretely, for example, it includes pyridine, toluene, tetrahydrofuran, 1,4-dioxane, N,N-dimethylformamide, N,N-dimethylacetamide, dimethylsulfoxide, 1-methyl-2-pyrrolidinone.

The reaction temperature in this step may be generally from 0 to 250° C., preferably from 0 to 150° C.

The reaction time in this step may be generally from 0.1 to 72 hours, preferably from 0.5 to 5 hours.

The compound (2) thus obtained may be subjected to the next step, after isolated and purified in any known manner for isolation and purification, for example, through concentration, concentration under reduced pressure, crystallization, solvent extraction, reprecipitation, chromatography, or not after isolated and purified.

(Step 2)

This step is a process for producing a compound (3) by reacting the compound (2) obtained in the previous step 1 with a compound (A) which is the same as or different from that in the step 1, in the presence of a base.

This step may be carried out in the same manner as in the step 1 or in accordance with the method of the step 1 or by combining it with an ordinary method.

(Step 3)

This step is a process for producing a compound (4) by reducing the nitro group in the compound (3) obtained in the previous step 2.

For the reduction in this step, employable is any method well known by those skilled in the art. The reduction in this step concretely includes, for example, catalytic reduction using hydrogen, formic acid, ammonium formate, hydrazine hydrate and a palladium, platinum, nickel catalyst; reduction using hydrochloric acid, ammonium chloride and iron; and reduction using methanol and tin chloride.

The amount of the reducing agent to be used for the reduction varies depending on the type of the compound and the solvent used and on the other reaction conditions, but may be generally from 1 to 50 equivalents, preferably from 2 to 20 equivalents relative to one equivalent of the compound (3).

The reaction solvent to be used is not specifically defined so far as it does not interfere with the reaction. For it, for example, herein employable are methanol, N,N-dimethylformamide, ethyl acetate, tetrahydrofuran and their mixed solvents.

The reaction temperature and the reaction time are not specifically defined. At a reaction temperature of from −10 to 100° C. or so, preferably from 0 to 50° C. or so, the reaction may be effected for 1 to 20 hours or so, preferably for 1 to 5 hours or so.

The compound (4) thus obtained may be subjected to the next step, after isolated and purified in any known manner for isolation and purification, for example, through concentration, concentration under reduced pressure, solvent extraction, crystallization, reprecipitation, chromatography, or not after isolated and purified.

(Step 4)

This step is a process for producing a compound (I) by reacting the compound (4) obtained in the previous step 3 with a compound (5).

The cyclization in this step may be effected in any method described in references (for example, Synthesis, 2000, Vol. 10, pp. 1380-1390), or in accordance with it, or by combining it with an ordinary method.

The compound (5) to be used includes, for example, pyridinecarboxaldehyde, pyrazinecarboxaldehyde, 1H-pyrazole-3-carboxyaldehyde.

The amount of the compound (5) to be used may be generally from 0.1 to 100 equivalents, preferably from 0.1 to 3 equivalents.

The reaction solvent to be used in this step is not specifically defined so far as it does not interfere with the reaction. For it, for example, herein employable are nitrobenzene, methanol, tetrahydrofuran, N,N-dimethylformamide, toluene, and mixtures of those solvents.

The reaction temperature may be generally from 0° C. to the reflux temperature of the reaction solvent used, preferably from room temperature to the reflux temperature of the reaction solvent.

The reaction time may be generally from 0.1 to 72 hours, preferably from 0.1 to 24 hours.

The compound (I) of the invention thus obtained may be isolated and purified in any known manner for isolation and purification, for example, through concentration, concentration under reduced pressure, solvent extraction, crystallization, reprecipitation, chromatography.

(Step 5-1)

This step is a process for producing a condensed product by reacting the compound (4) obtained in the step 3 with a compound (6).

The amidation in this step may be carried out, using a carboxylic acid or its reactive derivative for the compound (6), and the compound (4)

The amount of the compound (6) or its reactive derivative to be used may be generally from 0.1 to 100 equivalents, preferably from 0.1 to 3 equivalents.

The "reactive derivative" of the compound (6) includes, for example, mixed acid anhydrides, active esters, active amides, and these may be obtained, for example, according to the method described in WO98/05641.

In the above reaction, when a carboxylic acid for the compound (6) is used, then the reaction is preferably effected in the presence of a condensing agent, for example, carbonyldiimidazole, N,N'-dicyclohexylcarbodiimide, 1-ethyl-3-(3-dimethylaminopropyl)carbodiimide, diphenylphosphorylamide, dipyridyl disulfide-triphenyl phosphine, preferably carbonyldiimidazole.

Not strictly limited, the amount of the condensing agent to be used may be generally from 0.1 to 100 equivalents, preferably from 0.1 to 10 equivalents relative to the compound (6).

The reaction may be effected generally in an inert solvent. The inert solvent includes, for example, tetrahydrofuran, N,N-dimethylformamide, 1,4-dioxane, benzene, toluene, methylene chloride, chloroform, carbon tetrachloride, 1,2-dichloroethane, pyridine, or mixtures of those solvents.

The reaction temperature may be generally from 0° C. to the reflux temperature of the reaction solvent used, preferably from room temperature to the reflux temperature of the reaction solvent.

The reaction time may be generally from 0.1 to 72 hours, preferably from 0.5 to 24 hours.

In order to smoothly promote it, the reaction may be effected in the presence of a base and a condensation promoter.

The base includes 4-dimethylaminopyridine, triethylamine.

The amount of the base to be used may be generally from 0.1 to 100 equivalents, preferably from 0.1 to 1 equivalent relative to one mol of the carboxylic acid or its reactive derivative for the compound (6).

The condensation promoter includes N-hydroxybenzotriazole hydrate, N-hydroxysuccinimide.

The amount of the condensation promoter to be used may be generally from 1 to 100 equivalents, preferably from 1 to 5 equivalents relative to one mol of the carboxylic acid or its reactive derivative for the compound (6).

In the reaction, when an amino group or an imino group not participating in the reaction exists in the reactants, it is desirable that the amino group or the imino group is suitably protected with a protective group for the amino group or the imino group, then the reaction is carried out, and the protective group is removed after the reaction.

Thus obtained, the condensation product may be subjected to the next step, after isolated and purified in any known manner for isolation and purification, for example, through concentration, concentration under reduced pressure, solvent extraction, crystallization, reprecipitation, chromatography, or not after isolated and purified.

(Step 5-2)

This step is a process for producing a compound (I-0) through cyclization of the condensation product obtained in the previous step 5-1.

The cyclization in this step may be effected in any method described in references (for example, the method described in Tetrahedron, 2001, Vol. 57, No. 9, pp. 1793-1800), or in accordance with it, or by combining it with an ordinary method.

When p-toluenesulfonic acid is used in the cyclization, then the amount of p-toluenesulfonic acid to be used may be generally from 0.1 to 100 equivalents, preferably from 0.1 to 1 equivalent.

The reaction solvent to be used in this step is not specifically defined so far as it does not interfere with the reaction. For it, for example, herein employable are toluene, N,N-dimethylformamide, 1,4-dioxane, N-methylpyrrolidinone, or mixtures of those solvents.

The reaction temperature may be generally from 0 to 200° C., preferably from room temperature to the reflux temperature of the reaction solvent used.

The reaction time may be generally from 0.1 to 72 hours, preferably from 0.5 to 12 hours.

The compound (I-0) of the invention thus obtained may be isolated and purified in any known manner for isolation and purification, for example, through concentration, concentration under reduced pressure, solvent extraction, crystallization, reprecipitation, chromatography.

The compounds (I-11) of the invention may also be produced according to the following method:

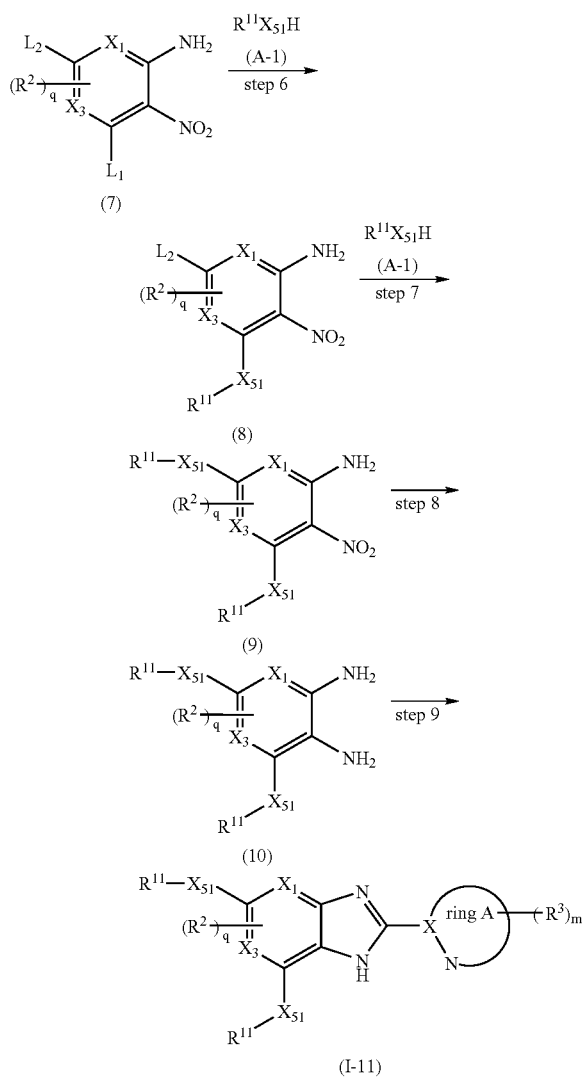

[In the formulae, $L^1$ and $L^2$ each represent a leaving group such as a halogen. The other symbols have the same meanings as defined hereinabove.]

(Step 6)

This step is a process for reacting a compound (7) with a compound (A-1) in the presence of a base to produce a compound (8).

$L^1$ and $L^2$ more concretely include, for example, halogens such as fluorine, chlorine, bromide.

The amount of the compound (A-1) to be used varies depending on the type of the compound and the solvent used and on the other reaction conditions, but may be generally from 0.1 to 20 equivalents, preferably from 0.5 to 5 equivalents relative to one equivalent of the compound (7).

The amount of the base to be used also varies depending on the type of the compound and the solvent used and on the other reaction conditions, but may be generally from 0.1 to 20 equivalents, preferably from 0.5 to 5 equivalents.

The base to be used may be any one capable of producing a compound (8) through the reaction of the compound (7) with the compound (A-1) in this step, including, for example, sodium hydride, cesium carbonate, sodium carbonate, potassium carbonate, potassium phosphate, potassium acetate, potassium tert-butyrate, triethylamine.

The reaction solvent to be used may be an inert solvent, not specifically defined so far as it does not interfere with the reaction. Concretely, for example, it includes pyridine, toluene, tetrahydrofuran, 1,4-dioxane, N,N-dimethylformamide, N,N-dimethylacetamide, dimethylsulfoxide, 1-methyl-2-pyrrolidinone.

The reaction temperature in this step may be generally from 0° C. to the reflux temperature of the reaction solvent used, preferably from 0 to 250° C.

The reaction time in this step may be generally from 0.1 to 72 hours, preferably from 0.1 to 5 hours.

The compound (8) thus obtained may be subjected to the next step, after isolated and purified in any known manner for isolation and purification, for example, through concentration, concentration under reduced pressure, crystallization, solvent extraction, reprecipitation, chromatography, or not after isolated and purified.

(Step 7)

This step is a process for producing a compound (9) by reacting the compound (8) with the same compound (A-1) as in the previous step 1, in the presence of a base.

This step may be carried out in the same manner as in the step 6 or in accordance with the method of the step 1 or by combining it with an ordinary method.

The compound (9) thus obtained may be subjected to the next step, after isolated and purified in any known manner for isolation and purification, for example, through concentration, concentration under reduced pressure, solvent extraction, crystallization, reprecipitation, chromatography, or not after isolated and purified.

(Step 8)

This step is a process for producing a compound (10) by reducing the nitro group in the compound (9).

This step may be effected in the same manner as in the step 3, or in accordance with it, or by combining it with an ordinary method.

The compound (10) thus obtained may be subjected to the next step, after isolated and purified in any known manner for isolation and purification, for example, through concentration, concentration under reduced pressure, crystallization, solvent extraction, reprecipitation, chromatography, or not after isolated and purified.

(Step 9)

This step is a process for producing a compound (I-11) of the invention by reacting the compound (10) with the above-mentioned compound (5) or (6).

The reaction of the compound (10) with the compound (5) may be effected in the same manner as in the step 4, or in accordance with it, or by combining it with an ordinary method.

The reaction of the compound (10) with the compound (6) may be effected in the same manner as in the step 5-1 or 5-2, or in accordance with it, or by combining it with an ordinary method.

The compound (I-11) of the invention thus obtained may be isolated and purified in any known manner for isolation and purification, for example, through concentration, concentration under reduced pressure, crystallization, solvent extraction, reprecipitation, chromatography.

The compounds (I-11) of the invention may also be produced according to the following method:

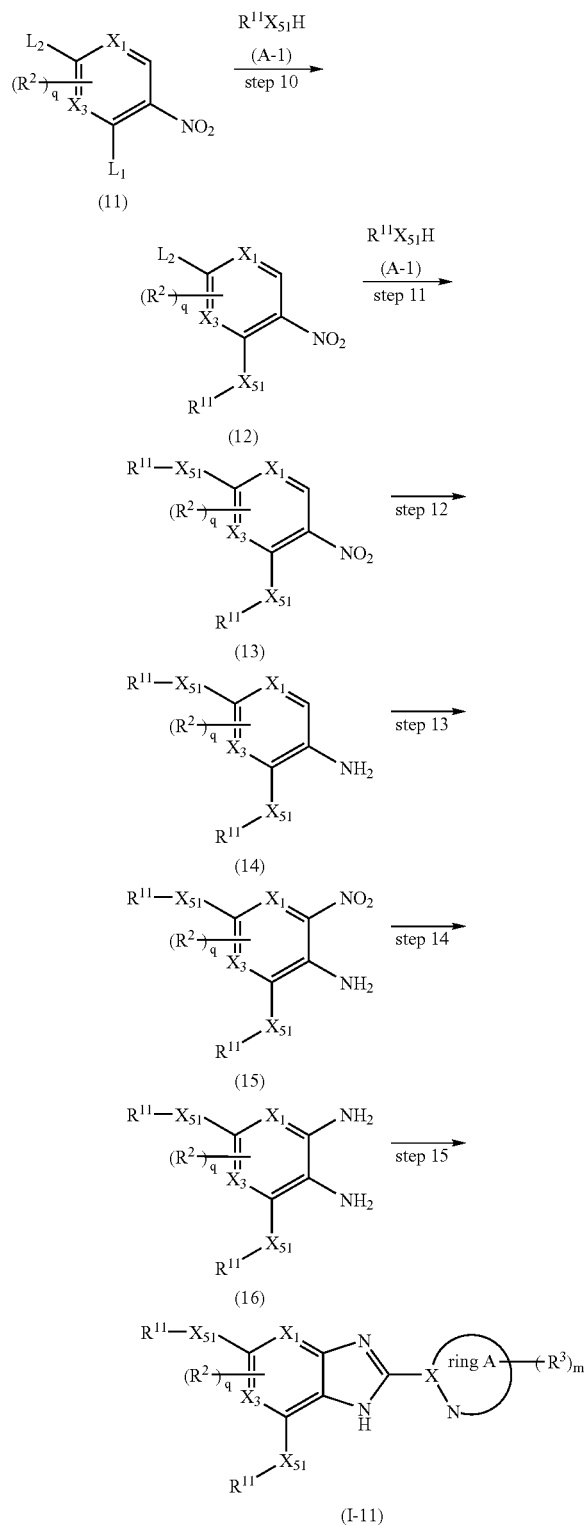

[In the formulae, $L^1$ and $L^2$ each represent a leaving group such as a halogen. The other symbols have the same meanings as defined hereinabove.]

(Step 10)

This step is a process for reacting a compound (11) with the above-mentioned compound (A-1) to produce a compound (12).

This step may be carried out in the same manner as in the step 6, or in accordance with it, or by combining it with an ordinary method.

The compound (12) thus obtained may be subjected to the next step, after isolated and purified in any known manner for isolation and purification, for example, through concentration, concentration under reduced pressure, solvent extraction, crystallization, reprecipitation, chromatography, or not after isolated and purified.

(Step 11)

This step is a process for producing a compound (13) by reacting the compound (12) with the above-mentioned compound (A-1).

This step may be carried out in the same manner as in the step 6, or in accordance with it, or by combining it with an ordinary method.

The compound (13) thus obtained may be subjected to the next step, after isolated and purified in any known manner for isolation and purification, for example, through concentration, concentration under reduced pressure, solvent extraction, crystallization, reprecipitation, chromatography, or not after isolated and purified.

(Step 12)

This step is a process for producing a compound (14) by reducing the nitro group in the compound (13).

This step may be effected in the same manner as in the step 3, or in accordance with it, or by combining it with an ordinary method.

The compound (14) thus obtained may be subjected to the next step, after isolated and purified in any known manner for isolation and purification, for example, through concentration, concentration under reduced pressure, solvent extraction, crystallization, reprecipitation, chromatography, or not after isolated and purified.

(Step 13)

This step is a process for producing a compound (15) by introducing a nitro group into the compound (14) obtained in the previous step.

The nitration in this step may be effected in any method described in references (for example, Synthetic Communication, 2001, Vol. 31, No. 7, pp. 1123-1128), or in accordance with it, or by combining it with an ordinary method. If necessary, the nitration may be effected after protection of the amino group in the compound (14).

When potassium nitrate is used for the nitration, the amount of potassium nitrate to be used may be generally from 0.1 to 100 equivalents, preferably from 0.1 to 2 equivalents.

The reaction solvent to be used in this step is not specifically defined so far as it does not interfere with the reaction. For it, for example, herein employable are trifluoroacetic acid, trifluoroacetic acid anhydride, hydrochloric acid, sulfuric acid, nitric acid.

The reaction temperature may be generally from 0° C. to the reflux temperature of the reaction solvent used, preferably from room temperature to 70° C.

The reaction time may be generally from 0.1 to 72 hours, preferably from 0.5 to 12 hours.

The compound (15) thus obtained may be subjected to the next step, after isolated and purified in any known manner for isolation and purification, for example, through concentration, concentration under reduced pressure, solvent extraction, crystallization, reprecipitation, chromatography, or not after isolated and purified.

(Step 14)

This step is a process for producing a compound (16) by reducing the nitro group in the compound (15).

This step may be effected in the same manner as in the step 3, or in accordance with it, or by combining it with an ordinary method.

The compound (16) thus obtained may be subjected to the next step, after isolated and purified in any known manner for isolation and purification, for example, through concentration, concentration under reduced pressure, solvent extraction, crystallization, reprecipitation, chromatography, or not after isolated and purified.

(Step 15)

This step is a process for producing a compound (I-11) of the invention by reacting the compound (16) with the abovementioned compound (5) or (6).

The reaction of the compound (16) with the compound (5) may be effected in the same manner as in the step 4, or in accordance with it, or by combining it with an ordinary method.

The reaction of the compound (16) with the compound (6) may be effected in the same manner as in the step 5-1 or 5-2, or in accordance with it, or by combining it with an ordinary method.

The compounds (I-11) of the invention may also be produced in a different process in which, after the compounds (14) and (6) are reacted, a nitro group is introduced into the reaction product, and finally the nitro group is reduced to an amino group simultaneously with cyclization of the resulting compound, or, if desired, the compound is separately cyclized.

The amidation of the compound (14) and the compound (6), the nitration, the reduction from the nitro group into an amino group, and the cyclization may be effected in the same manner as in the step 5-1, the step 13, the step 3 and the step 5-1, respectively, or in accordance with it, or by combining it with an ordinary method.

The compound (I-11) of the invention thus obtained may be isolated and purified in any known manner for isolation and purification, for example, through concentration, concentration under reduced pressure, crystallization, solvent extraction, reprecipitation, chromatography.

The compounds (I-11-0) of the invention may also be produced according to the following method:

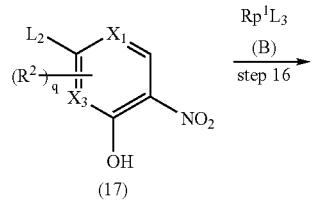

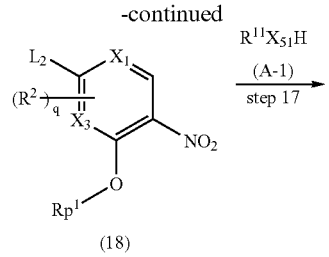

-continued

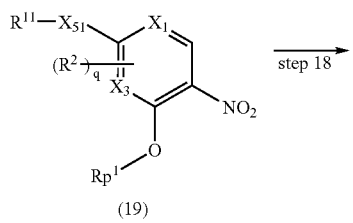

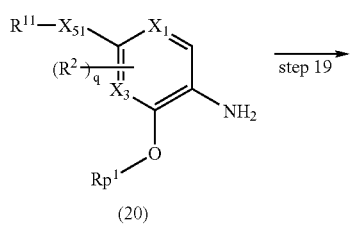

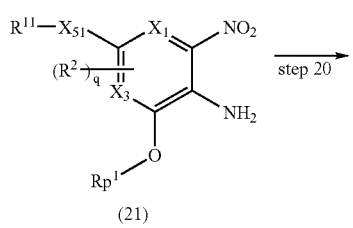

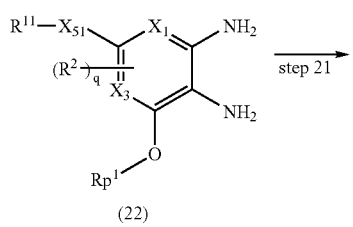

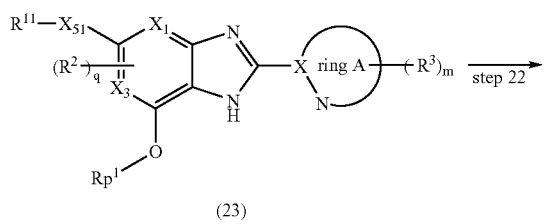

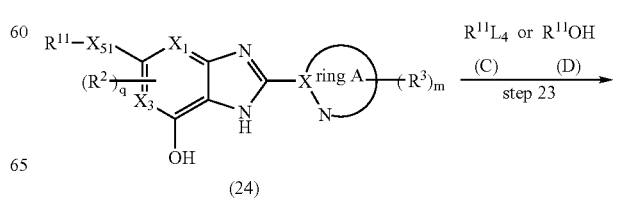

-continued

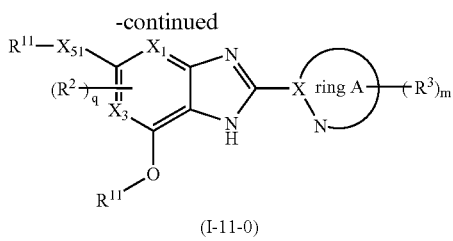

(I-11-0)

[In the formulae, $L^1$, $L^2$, $L^3$ and $L^4$ each represent a leaving group such as a halogen. $Rp^1$ represents a hydroxy-protective group. The other symbols have the same meanings as above.]

(Step 16)

This step is for reaction of introducing a protective group into a compound (17). The introduction of a hydroxy-protective group $Rp^1$ into the compound (17) in this step may be effected in any method described in references (for example, Protective Groups in Organic Synthesis, by T. W. Green, 2nd Ed., John Wiley & Sons, 1991), or in accordance with it, or by combining it with an ordinary method.

$Rp^1$ includes more concretely, for example, methoxymethyl, methyl, benzyl, 4-methoxybenzyl, 2-(trimethoxysilyl)ethoxymethyl, 2-(trimethylsilyl)ethyl, tert-butyldimethylsilyl, tert-butylcarbonyl.

The amount of the compound (B) to be used varies, depending on the type of the compound and the solvent used and on the other reaction conditions, but may be generally from 0.1 to 20 equivalents, preferably from 0.5 to 5 equivalents relative to one equivalent of the compound (17).

The amount of the base to be used also varies, depending on the type of the compound and the solvent used and on the other reaction conditions, but may be generally from 0.1 to 20 equivalents, preferably from 0.5 to 5 equivalents.

The base to be used may be any one capable of producing a compound (18) through the reaction of the compound (17) with the compound (B) in this step, including, for example, cesium carbonate, sodium carbonate, potassium carbonate, potassium phosphate, potassium acetate, potassium tert-butyrate, triethylamine, imidazole.

The reaction temperature may be generally from 0° C. to the reflux temperature of the reaction solvent used, but preferably from 0 to 80° C.

The reaction time may be generally from 0.1 to 72 hours, preferably from 0.5 to 12 hours.

The reaction solvent to be used may be an inert solvent, not specifically defined so far as it does not interfere with the reaction. Concretely, for example, it includes pyridine, toluene, 1,4-dioxane, N,N-dimethylformamide, N,N-dimethylacetamide, dimethylsulfoxide, 1-methyl-2-pyrrolidinone.

The compound (18) thus obtained may be subjected to the next step, after isolated and purified in any known manner for isolation and purification, for example, through concentration, concentration under reduced pressure, solvent extraction, crystallization, reprecipitation, chromatography, or not after isolated and purified.

(Step 17)

This step is a process for reacting a compound (18) with the above-mentioned compound (A-1) to produce a compound (19).

This step may be carried out in the same manner as in the step 10, or in accordance with it, or by combining it with an ordinary method.

The compound (19) thus obtained may be subjected to the next step, after isolated and purified in any known manner for isolation and purification, for example, through concentration, concentration under reduced pressure, solvent extraction, crystallization, reprecipitation, chromatography, or not after isolated and purified.

(Step 18)

This step is a process for producing a compound (20) by reducing the nitro group in the compound (19).

This step may be carried out in the same manner as in the step 12, or in accordance with it, or by combining it with an ordinary method.

The compound (20) thus obtained may be subjected to the next step, after isolated and purified in any known manner for isolation and purification, for example, through concentration, concentration under reduced pressure, crystallization, solvent extraction, reprecipitation, chromatography, or not after isolated and purified.

(Step 19)

This step is a process for producing a compound (21) by introducing a nitro group into the compound (20).

This step may be carried out in the same manner as in the step 13, or in accordance with it, or by combining it with an ordinary method.

The compound (21) thus obtained may be subjected to the next step, after isolated and purified in any known manner for isolation and purification, for example, through concentration, concentration under reduced pressure, solvent extraction, crystallization, reprecipitation, chromatography, or not after isolated and purified.

(Step 20)

This step is a process for producing a compound (22) by reducing the nitro group in the compound (21).

This step may be effected in the same manner as in the step 14, or in accordance with it, or by combining it with an ordinary method.

The compound (22) thus obtained may be subjected to the next step, after isolated and purified in any known manner for isolation and purification, for example, through concentration, concentration under reduced pressure, crystallization, solvent extraction, reprecipitation, chromatography, or not after isolated and purified.

(Step 21)

This step is a process for producing a compound (23) by reacting the compound (22) with the above-mentioned compound (5) or (6).

The reaction of the compound (22) with the compound (5) may be effected in the same manner as in the step 4, or in accordance with it, or by combining it with an ordinary method.

The reaction of the compound (22) with the compound (6) may be effected in the same manner as in the step 5-1 or 5-2, or in accordance with it, or by combining it with an ordinary method.

The compound (23) thus obtained may be subjected to the next step, after isolated and purified in any known manner for isolation and purification, for example, through concentration, concentration under reduced pressure, crystallization, solvent extraction, reprecipitation, chromatography, or not after isolated and purified.

(Step 22)

This step is a process for producing a compound (24) by removing the hydroxy-protective group in the compound (23).

The removal of the protective group in this step may be effected in any method described in references (for example, Protective Groups in Organic Synthesis, by T. W. Green, 2nd Ed., John Wiley & Sons, 1991), or in accordance with it, or by combining it with an ordinary method. When $Rp^1$ is a benzyl, then the removal of the protective group may be attained, for example, through catalytic hydrogenation with a palladium-carbon catalyst.

In case where a palladium hydroxide-carbon catalyst is used for the removal of $Rp^1$, then the amount of the catalyst to be used may be generally from 0.01 to 1000 equivalents, preferably from 0.1 to 10 equivalents.

The reaction solvent to be used in this step is not specifically defined so far as it does not interfere with the reaction. For it, for example, herein employable are methanol, ethanol.

The reaction temperature may be generally from room temperature to the reflux temperature of the reaction solvent used, preferably from room temperature to 100° C.

The reaction time may be generally from 0.1 to 72 hours, preferably from 0.5 to 12 hours.

The compound (24) thus obtained may be subjected to the next step, after isolated and purified in any known manner for isolation and purification, for example, through concentration, concentration under reduced pressure, solvent extraction, crystallization, reprecipitation, chromatography, or not after isolated and purified.

(Step 23)

This step is a process for producing a compound (I-2) of the invention according to a step (step 23-1) of reacting the compound (24) with a compound (C) or according to a step (step 23-2) of reacting the compound (24) with a compound (D).

(Step 23-1)

$L_4$ in the compound (C) is concretely, for example, a halogen such as chlorine, bromine, iodine.

The amount of the compound (C) to be used varies, depending on the type of the compound and the solvent used and on the other reaction conditions, but may be generally from 0.1 to 20 equivalents, preferably from 0.5 to 5 equivalents relative to one equivalent of the compound (24).

The reaction in this step may be effected in the presence of a base.

The amount of the base to be used varies, depending on the type of the compound and the solvent used and on the other reaction conditions, but may be generally from 0.1 to 20 equivalents, preferably from 0.5 to 5 equivalents relative to one equivalent of the compound (24).

The base to be used may be any one capable of producing a compound (I-2) through the reaction of the compound (24) with the compound (C), including, for example, sodium hydride, cesium carbonate, sodium carbonate, potassium carbonate, potassium phosphate, potassium acetate, potassium tert-butyrate, triethylamine.

The reaction solvent to be used may be an inert solvent, not specifically defined so far as it does not interfere with the reaction. Concretely, for example, it includes pyridine, toluene, tetrahydrofuran, 1,4-dioxane, N,N-dimethylformamide, N,N-dimethylacetamide, dimethylsulfoxide, 1-methyl-2-pyrrolidinone.

The reaction temperature in this step may be generally from 0° C. to the reflux temperature of the reaction solvent used, preferably from 0 to 150° C.

The reaction time in this step may be generally from 0.1 to 72 hours, preferably from 0.5 to 5 hours.

The compound (I-2) of the invention thus obtained may be isolated and purified in any known manner for isolation and purification, for example, through concentration, concentration under reduced pressure, crystallization, solvent extraction, reprecipitation, chromatography.

(Step 23-2)

This step is a process for producing a compound (I-2) of the invention by reacting the compound (24) obtained in the previous step 24 with a compound (D) and then optionally protecting and deprotecting the product.

The reaction of the compound (24) with the compound (D) is so-called Mitsunobu reaction, which may be effected in the presence of a phosphine compound and an azo compound, according to a method described in references (for example, "The use of diethyl azodicarboxylate and triphenylphosphine in synthesis and transformation of natural products", by Mitsunobu O.; Synthesis, Vol. 1, 1981, pp. 1-28), or in accordance with it, or by combining it with an ordinary method.

The amount of the alcohol compound (D) to be used in this step may be generally from 0.5 to 10 equivalents, preferably from 1 to 3 equivalents, relative to 1 equivalent of the compound (24).

The phosphine compound to be used in this step may be generally triphenyl phosphine or triethyl phosphine.

The amount of the phosphine compound to be used may be generally from 0.5 to 10 equivalents, preferably from 1 to 3 equivalents, relative to 1 equivalent of the compound (24).

The azo compound to be used may be, for example, diethyl azodicarboxylate, diisopropyl azodicarboxylate.

The amount of the azo compound to be used may be generally from 0.5 to 10 equivalents, preferably from 1 to 3 equivalents, relative to 1 equivalent of the compound (24).

The reaction time in this step may be generally from 1 to 48 hours, preferably from 4 to 12 hours.

The reaction temperature in this step may be generally from 0° C. to the reflux temperature of the reaction solvent used, preferably from 15 to 30° C.

The reaction solvent to be used in this step is not specifically defined so far as it does not interfere with the reaction. Concretely, for example, herein employable are tetrahydrofuran, toluene.

The compounds (I-11-0) of the invention may also be produced in a different process in which, after the compounds (20) and (6) are reacted, a nitro group is introduced into the reaction product, and finally the nitro group is reduced to an amino group simultaneously with cyclization of the resulting compound, or, if desired, the compound is separately cyclized.

The amidation of the compound (20) and the compound (6), the nitration, the reduction from the nitro group into an amino group, and the cyclization may be effected in the same manner as in the step 5-1, the step 13, the step 3 and the step 5-1, respectively, or in accordance with it, or by combining it with an ordinary method.

The compound (I-11-0) of the invention thus obtained may be isolated and purified in any known manner for isolation and purification, for example, through concentration, concentration under reduced pressure, crystallization, solvent extraction, reprecipitation, chromatography.

Of the compounds (I) of the invention, the compounds (I-4) where X is a nitrogen atom may also be produced according to the following method:

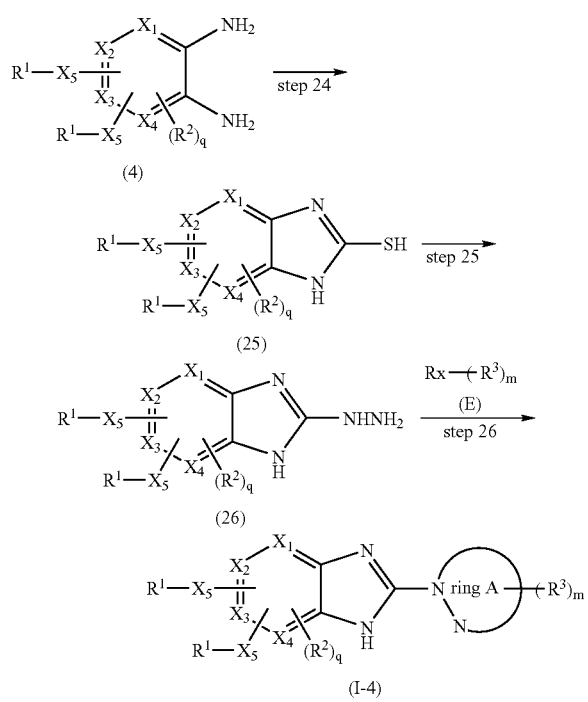

[In these formulae, Rx represents a $C_{1-6}$ alkyl having 2 substituents of halogens, aldehydes, esters, CN or their homologues; and the other symbols have the same meanings as above.]

(Step 24)

This step is a process for producing a compound (25) from the compound (4).

This reaction may be effected in the presence of a base in any method described in references (for example, Indian J. Chem. Sect. B; 32; 2; 1993; 262-265), or in accordance with it, or by combining it with an ordinary method.

For example, when the reaction is carried out by the use of sulfur dioxide, the amount of the sulfur dioxide to be used may be generally from 0.1 to 500 equivalents, preferably from 0.5 to 10 equivalents.

The base to be used may be any one capable of producing a compound (25) through the reaction with the compound (4), including, for example, sodium hydroxide, sodium hydride, cesium carbonate, sodium carbonate, potassium carbonate, potassium phosphate, potassium acetate, potassium tert-butyrate, triethylamine.

The reaction time in this step may be generally from 1 to 48 hours, preferably from 4 to 12 hours.

The reaction temperature in this step may be generally from 0° C. to the reflux temperature of the reaction solvent used, preferably from 0° C. to the reflux temperature of the solvent.

The reaction solvent to be used in this step is not specifically defined so far as it does not interfere with the reaction. Concretely, for example, herein employable are ethanol, water, toluene, tetrahydrofuran, 1,4-dioxane, N,N-dimethylformamide, N,N-dimethylacetamide, dimethylsulfoxide, 1-methyl-2-pyrrolidinone.

The compound (25) thus obtained may be subjected to the next step, after isolated and purified in any known manner for isolation and purification, for example, through concentration, concentration under reduced pressure, solvent extraction, crystallization, reprecipitation, chromatography, or not after isolated and purified.

(Step 25)

This step is a process for producing a compound (26) from the compound (25). Using hydrazine monohydrate, the reaction in this step may be effected in any method described in references (for example, Indian J. Chem. Sect. B; EN; 32; 2; 1993; 262-265), or in accordance with it, or by combining it with an ordinary method.

The amount of hydrazine monohydrate to be used may be generally from 0.1 to 1000 equivalents, preferably from 1 to 100 equivalents.

The reaction time in this step may be generally from 1 to 48 hours, preferably from 4 to 24 hours.

The reaction temperature in this step may be generally from 0° C. to the reflux temperature of the reaction solvent used, preferably from 0° C. to the reflux temperature of the solvent.

Preferably, the reaction in this step is effected in the absence of a solvent, but a reaction solvent may be used for it so far as it does not interfere with the reaction. The usable reaction solvent includes, for example, ethanol, water, toluene, tetrahydrofuran, 1,4-dioxane, N,N-dimethylformamide, N,N-dimethylacetamide, dimethylsulfoxide, 1-methyl-2-pyrrolidinone.

The compound (26) thus obtained may be subjected to the next step, after isolated and purified in any known manner for isolation and purification, for example, through concentration, concentration under reduced pressure, solvent extraction, crystallization, reprecipitation, chromatography, or not after isolated and purified.

(Step 26)

This step is a process for producing a compound (I-4) of the invention by reacting the compound (26) with a compound (E).

This reaction may be effected in any method described in references (for example, Indian J. Chem. Sect. B; EN; 32; 2; 1993; 262-265), or in accordance with it, or by combining it with an ordinary method.

For example, when a pyrazole is constructed, it may be synthesized through the reaction with tetramethoxypropane.

The amount of tetramethoxypropane to be used may be generally from 0.1 to 500 equivalents, preferably from 0.5 to 100 equivalents.

The reaction time in this step may be generally from 1 to 48 hours, preferably from 4 to 12 hours.

The reaction temperature in this step may be generally from 0° C. to the reflux temperature of the reaction solvent used, preferably from 0° C. to the reflux temperature of the solvent.

The reaction solvent to be used in this step is not specifically defined so far as it does not interfere with the reaction. Concretely, for example, herein employable are ethanol, water, toluene, tetrahydrofuran, 1,4-dioxane, N,N-dimethylformamide, N,N-dimethylacetamide, dimethylsulfoxide, 1-methyl-2-pyrrolidinone.

The compound (I-4) of the invention thus obtained may be isolated and purified in any known manner for isolation and purification, for example, through concentration, concentration under reduced pressure, crystallization, solvent extraction, reprecipitation, chromatography.

Compounds (I-12) of the invention:

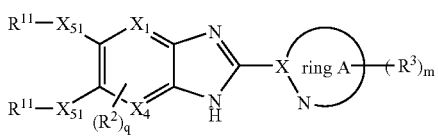

[in the formula, the symbols have the same meanings as above] may also be produced, for example, according to the following method:

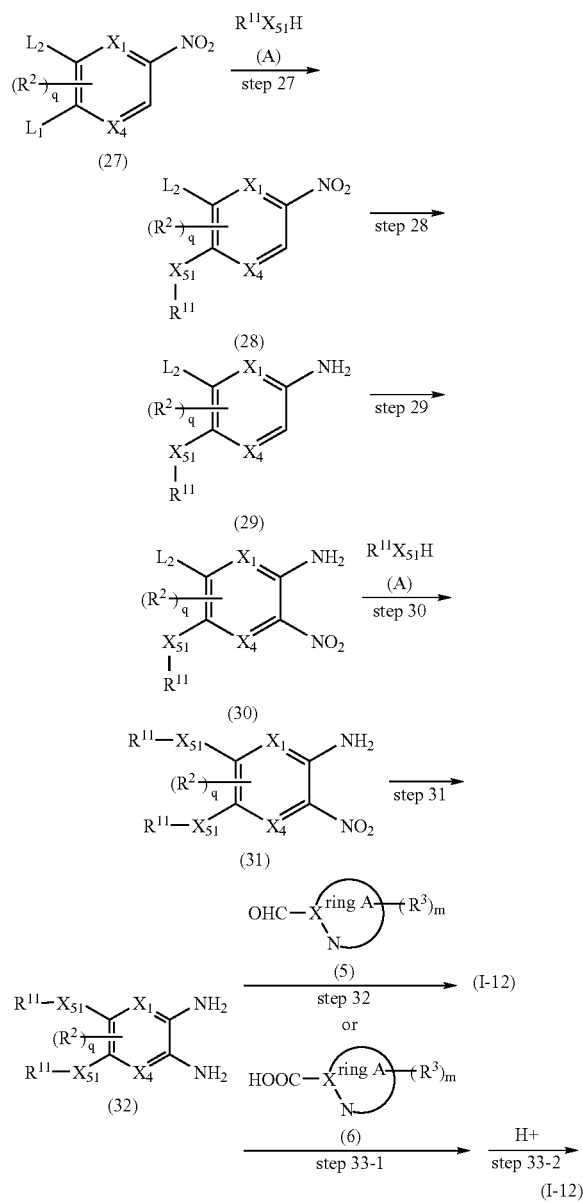

[In the formulae, $L^1$ and $L^2$ each represent a leaving group such as a halogen; and the other symbols have the same meanings as defined hereinabove.]

(Step 27)

This step is a process for reacting a compound (27) with the above-mentioned compound (A-1) in the presence of a base to produce a compound (28).

$L^1$ and $L^2$ more concretely include, for example, halogens such as fluorine, chlorine, bromide.

The amount of the compound (A-1) to be used varies depending on the type of the compound and the solvent used and on the other reaction conditions, but may be generally from 0.1 to 20 equivalents, preferably from 0.5 to 5 equivalents relative to one equivalent of the compound (27).

The amount of the base to be used also varies depending on the type of the compound and the solvent used and on the other reaction conditions, but may be generally from 0.1 to 20 equivalents, preferably from 0.5 to 5 equivalents.

The base to be used may be any one capable of producing a compound (28) through the reaction of the compound (27) with the compound (A-1) in this step, including, for example, sodium hydride, cesium carbonate, sodium carbonate, potassium carbonate, potassium phosphate, potassium acetate, potassium tert-butyrate, triethylamine.

The reaction solvent to be used may be an inert solvent, not specifically defined so far as it does not interfere with the reaction. Concretely, for example, it includes pyridine, toluene, tetrahydrofuran, 1,4-dioxane, N,N-dimethylformamide, N,N-dimethylacetamide, dimethylsulfoxide, 1-methyl-2-pyrrolidinone.

The reaction temperature in this step may be generally from 0° C. to the reflux temperature of the reaction solvent used, preferably from room temperature to 150° C.

The reaction time in this step may be generally from 0.1 to 72 hours, preferably from 0.5 to 5 hours.

The compound (28) thus obtained may be subjected to the next step, after isolated and purified in any known manner for isolation and purification, for example, through concentration, concentration under reduced pressure, crystallization, solvent extraction, reprecipitation, chromatography, or not after isolated and purified.

(Step 28)

This step is a process for producing a compound (29) by reducing the nitro group in the compound (28) obtained in the previous step.

For the reduction in this step, employable is any method well known by those skilled in the art. The reduction in this step concretely includes, for example, catalytic reduction using hydrogen, formic acid, ammonium formate, hydrazine hydrate and a palladium, platinum, nickel catalyst; reduction using hydrochloric acid, ammonium chloride and iron; and reduction using methanol and tin chloride.

In case where a 10% palladium-carbon catalyst is used for the reduction of the nitro group, the amount of the 10% palladium-carbon catalyst to be used may be generally from 0.01 to 10 equivalents, preferably from 0.1 to 1 equivalent.

The reaction solvent to be used in this step is not specifically defined so far as it does not interfere with the reaction. For it, for example, herein employable are methanol, ethanol, tetrahydrofuran, N,N-dimethylformamide.

The reaction temperature may be generally from 0° C. to the reflux temperature of the reaction solvent used, preferably from room temperature to the reflux temperature of the reaction solvent.

The reaction time may be generally from 0.1 to 72 hours, preferably from 0.5 to 12 hours.

The compound (29) thus obtained may be subjected to the next step, after isolated and purified in any known manner for isolation and purification, for example, through concentration, concentration under reduced pressure, solvent extraction, crystallization, reprecipitation, chromatography, or not after isolated and purified.

(Step 29)

This step is a process for producing a compound (30) by introducing a nitro group into the compound (29) obtained in the previous step.

The nitration in this step may be effected, after optionally protected at aniline, in any method described in references (for example, Synthetic Communication, 2001, Vol. 31, No. 7, pp. 1123-1128), or in accordance with it, or by combining it with an ordinary method.

When potassium nitrate is used for the nitration, the amount of potassium nitrate to be used may be generally from 0.1 to 100 equivalents, preferably from 0.1 to 1 equivalent.

The reaction solvent to be used in this step is not specifically defined so far as it does not interfere with the reaction. For it, for example, herein employable are trifluoroacetic acid, trifluoroacetic acid anhydride, hydrochloric acid, sulfuric acid, nitric acid.

The reaction temperature may be generally from 0° C. to the reflux temperature of the reaction solvent used, preferably from room temperature to the reflux temperature of the reaction solvent.

The reaction time may be generally from 0.1 to 72 hours, preferably from 0.5 to 12 hours.

The compound (30) thus obtained may be subjected to the next step, after isolated and purified in any known manner for isolation and purification, for example, through concentration, concentration under reduced pressure, solvent extraction, crystallization, reprecipitation, chromatography, or not after isolated and purified.

(Step 30)

This step is a process for producing a compound (31) by reducing the compound (30) obtained in the previous step with the above-mentioned compound (A-1).

This step may be effected, after optionally protected at aniline, in the same manner as in the step 27, or in accordance with it, or by combining it with an ordinary method.

The compound (31) thus obtained may be subjected to the next step, after isolated and purified in any known manner for isolation and purification, for example, through concentration, concentration under reduced pressure, solvent extraction, crystallization, reprecipitation, chromatography, or not after isolated and purified.

(Step 31)

This step is a process for producing a compound (32) by reducing the nitro group in the compound (31) obtained in the previous step 30.

The reaction in this step may be effected in the same manner as in the step 8, or in accordance with it, or by combining it with an ordinary method.

The compound (32) thus obtained may be subjected to the next step, after isolated and purified in any known manner for isolation and purification, for example, through concentration, concentration under reduced pressure, crystallization, solvent extraction, reprecipitation, chromatography, or not after isolated and purified.

(Step 32)

This step is a process for producing a compound (I-2) of the invention by reacting the compound (32) obtained in the previous step with a compound (5).

The reaction in this step may be effected in the same manner as in the step 4, or in accordance with it, or by combining it with an ordinary method.

The compound (I-2) of the invention thus obtained may be isolated and purified in any known manner for isolation and purification, for example, through concentration, concentration under reduced pressure, solvent extraction, crystallization, reprecipitation, chromatography.

(Step 33-1)

This step is a process for producing a condensed product by reacting the compound (32) obtained in the previous step 31 with a compound (6).

The reaction in this step may be carried out in the same manner as in the step 5-1, or in accordance with it, or by combining it with an ordinary method.

Thus obtained, the condensation product may be subjected to the next step, after isolated and purified in any known manner for isolation and purification, for example, through concentration, concentration under reduced pressure, crystallization, solvent extraction, reprecipitation, chromatography, or not after isolated and purified.

(Step 33-2)

This step is a process for producing a compound (I-12) through cyclization of the condensation product obtained in the previous step 33-1.

The cyclization in this step may be effected in the same manner as in the step 5-2, or in accordance with it, or by combining it with an ordinary method.

The compounds (I-11) of the invention may also be produced in a different process in which, after the compounds (29) and (6) are reacted, a nitro group is introduced into the reaction product, and finally the nitro group is reduced to an amino group simultaneously with cyclization of the resulting compound, or, if desired, the compound is separately cyclized, or after the cyclization or before the cyclization, the compound is reacted with a compound (A).

The amidation of the compound (29) and the compound (6), the nitration, the reduction from the nitro group into an amino group, the reaction with the compound (A) and the cyclization may be effected in the same manner as in the step 5-1, the step 13, the step 3, step 30 and the step 5-1, respectively, or in accordance with it, or by combining it with an ordinary method.

The compound (I-12) of the invention thus obtained may be isolated and purified in any known manner for isolation and purification, for example, through concentration, concentration under reduced pressure, crystallization, solvent extraction, reprecipitation, chromatography.

The compounds (I-12) of the invention may also be produced from a compound (31) that is prepared according to the following method:

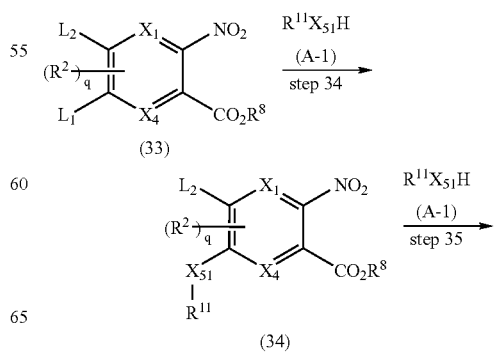

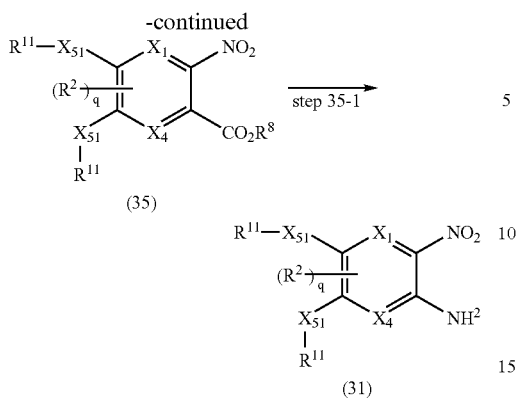

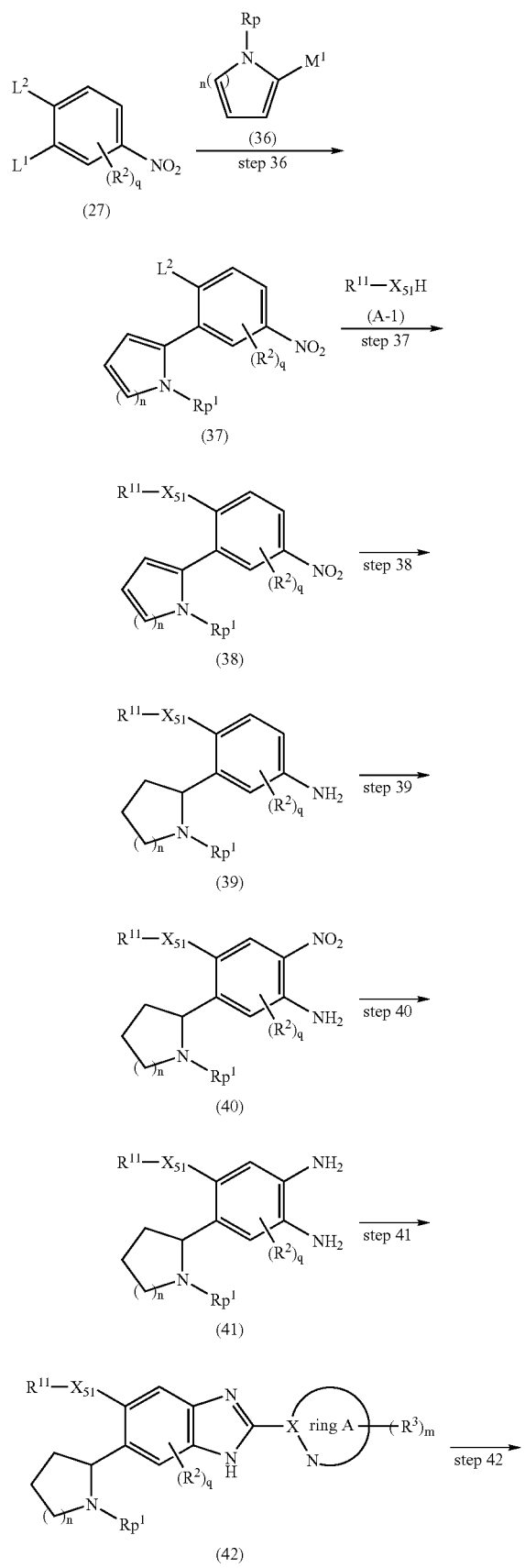

[In these formulae, the symbols have the same meanings as above.]

(Step 34)

This step is a process for producing a compound (34) by reacting a compound (33) with the above-mentioned compound (A-1). The reaction in this step may be carried out in the same manner as in the step 27, or in accordance with it, or by combining it with an ordinary method.

The compound (34) thus obtained may be subjected to the next step, after isolated and purified in any known manner for isolation and purification, for example, through concentration, concentration under reduced pressure, solvent extraction, crystallization, reprecipitation, chromatography, or not after isolated and purified.

(Step 35)

This step is a process for producing a compound (35) by reacting the compound (34) with the above-mentioned compound (A-1). The reaction in this step may be carried out in the same manner as in the step 30, or in accordance with it, or by combining it with an ordinary method.

The compound (35) thus obtained may be subjected to the next step, after isolated and purified in any known manner for isolation and purification, for example, through concentration, concentration under reduced pressure, solvent extraction, crystallization, reprecipitation, chromatography, or not after isolated and purified.

(Step 33-1)

This step is a process for producing a compound (31) by converting —C(O)OR$^8$ in the compound (35) obtained in the previous step 35, into an amino group, and, for example, this is so-called Curtius transition reaction. The reaction in this step may be carried out in the same manner as in the step 48 to be described hereinunder, or in accordance with it, or by combining it with an ordinary method.

The compound (31) thus obtained may be isolated and purified in any known manner for isolation and purification, for example, through concentration, concentration under reduced pressure, crystallization, solvent extraction, reprecipitation, chromatography.

Using the thus-obtained compound (31) in accordance with the process of the above-mentioned step 31, 32, 33-1 or 33-2, the compounds (I-12) of the invention may be produced.

The compounds (I-31) of the invention may also be produced according to the following method:

-continued

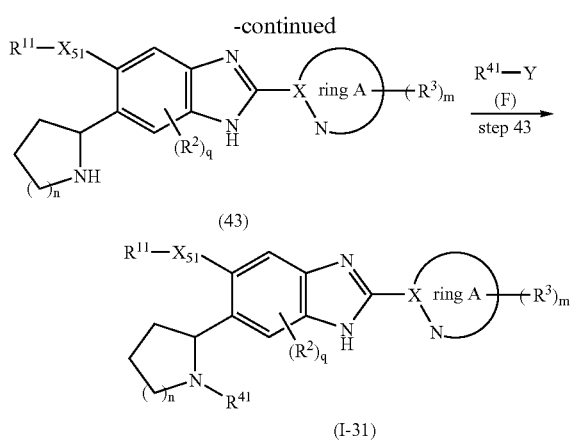

[In the formulae, n indicates 1 or 2; Y represents a leaving group; and the other symbols have the same meanings as above.]

(Step 36)

This step is a process for producing a compound (37) by reacting the compound (27) with a compound (36) in the presence of a base and a metal catalyst.

$L^1$ and $L^2$ more concretely include, for example, halogens such as fluorine, chlorine, bromide.

$M^1$ may be any one capable of producing the compound (37) through the reaction of the compound (27) with the compound (36). Concretely, for example, it includes trialkyltin, boronic acid, boronate. More concretely, the compound (36) includes, for example, trimethyl-(pyridin-2-yl)tin or 1-(tert-butoxycarbonyl)pyrrole-2-boronic acid.

In case where trimethyl-(pyridin-2-yl)tin is used as the compound (36), for example, the reaction may be so-called Stille reaction In case where 1-(tert-butoxycarbonyl)pyrrole-2-boronic acid is used as the compound (36), for example, the reaction may be so-called Suzuki reaction.

The amount of the compound (36) to be used varies, depending on the type of the compound and the solvent used and on the other reaction conditions, but may be generally from 0.1 to 50 equivalents, preferably from 0.2 to 10 equivalents relative to one equivalent of the compound (27).

The amount of the base to be used also varies, depending on the type of the compound and the solvent used and on the other reaction conditions, but may be generally from 0.1 to 20 equivalents, preferably from 0.5 to 5 equivalents.

The base to be used may be any one capable of producing the compound (37) through the reaction of the compound (27) with the compound (36) in this step, including, for example, sodium hydride, cesium carbonate, sodium carbonate, potassium carbonate, potassium phosphate, potassium acetate, potassium tert-butoxide, triethylamine.

The amount of the metal catalyst to be used also varies, depending on the type of the compound and the solvent used and on the other reaction conditions, but may be generally from 0.01 to 10 equivalents, preferably from 0.05 to 5 equivalents.

The metal catalyst to be used may be any one capable of producing the compound (37) through the reaction of the compound (27) with the compound (36) in this step, including, for example, tetrakistriphenylphosphine palladium, dichlorobistriphenylphosphine palladium, dichloro(1,1'-bis (diphenylphosphino)ferrocene)palladium.

The reaction solvent to be used in this step is not specifically defined so far as it does not interfere with the reaction. For it, for example, herein employable are ethylene glycol dimethyl ether, water, toluene, tetrahydrofuran, N,N-dimethylformamide, 1,4-dioxane, benzene, acetone.

The reaction temperature in this step may be generally from 0° C. to the reflux temperature of the reaction solvent used, preferably from room temperature to 150° C.

The reaction time in this step may be generally from 0.1 to 72 hours, preferably from 0.5 to 12 hours.

The compound (37) thus obtained may be subjected to the next step, after isolated and purified in any known manner for isolation and purification, for example, through concentration, concentration under reduced pressure, crystallization, solvent extraction, reprecipitation, chromatography, or not after isolated and purified.

(Step 37)

This step is a process for producing a compound (38) by reacting the compound (37) with the above-mentioned compound (A-1).

The reaction in this step may be carried out in the same manner as in the step 27, or in accordance with it, or by combining it with an ordinary method.

The compound (38) thus obtained may be subjected to the next step, after isolated and purified in any known manner for isolation and purification, for example, through concentration, concentration under reduced pressure, crystallization, solvent extraction, reprecipitation, chromatography, or not after isolated and purified.

(Step 38)

This step is a process for producing a compound (39) by reducing the hetero-aromatic ring and the nitro group in the compound (38) with a metal catalyst in a hydrogen atmosphere and optionally introducing a protective group into the reaction product.

The amount of the reducing agent to be used may be generally from 0.01 to 10 equivalents, preferably from 0.1 to 1 equivalent.

The reducing agent to be used may be any one capable of producing the compound (39) from the compound (38) in this step. For it, for example, herein usable is 10% platinum-carbon or platinum-black.

The reaction solvent to be used in this step is not specifically defined so far as it does not interfere with the reaction. For it, for example, herein employable are methanol, ethanol, tetrahydrofuran, 1,4-dioxane, ethyl acetate.

The reaction temperature in this step may be generally from 0° C. to the reflux temperature of the reaction solvent used, preferably from room temperature to 150° C.

The reaction time in this step may be generally from 0.1 to 72 hours, preferably from 0.5 to 12 hours.

The reaction pressure in this step may be generally from normal pressure to 100 atmospheres, preferably from normal pressure to 20 atmospheres.

The compound (39) thus obtained may be subjected to the next step, after isolated and purified in any known manner for isolation and purification, for example, through concentration, concentration under reduced pressure, crystallization, solvent extraction, reprecipitation, chromatography, or not after isolated and purified.

(Step 39)

This step is a process for producing a compound (40) by introducing a nitro group into the compound (39). The reaction in this step may be carried out in the same manner as in the step 29, or in accordance with it, or by combining it with an ordinary method. If desired, $Rp^1$ may be converted.

The compound (40) thus obtained may be subjected to the next step, after isolated and purified in any known manner for isolation and purification, for example, through concentration, concentration under reduced pressure, crystallization, solvent extraction, reprecipitation, chromatography, or not after isolated and purified.

(Step 40)

This step is a process for producing a compound (41) by reducing the nitro group in the compound (40). The reaction in this step may be carried out in the same manner as in the step 31, or in accordance with it, or by combining it with an ordinary method.

The compound (41) thus obtained may be subjected to the next step, after isolated and purified in any known manner for isolation and purification, for example, through concentration, concentration under reduced pressure, crystallization, solvent extraction, reprecipitation, chromatography, or not after isolated and purified.

(Step 41)

This step is a process for producing a compound (42) by reacting the compound (41) with the above-mentioned compound (5), or by reacting the compound (41) with the above-mentioned compound (6), and then cyclizing the resulting product.

The reaction of the compound (41) with the compound (5) may be carried out in the same manner as in the step 32, or in accordance with it, or by combining it with an ordinary method.

The reaction of the compound (41) with the compound (6) followed by cyclization may be carried out in the same manner as in the above-mentioned step 33-1 and 33-2, or in accordance with it, or by combining it with an ordinary method.

The compound (42) thus obtained may be subjected to the next step, after isolated and purified in any known manner for isolation and purification, for example, through concentration, concentration under reduced pressure, crystallization, solvent extraction, reprecipitation, chromatography, or not after isolated and purified.

(Step 42)

This step is a process for producing a compound (43) by removing the amino-protective group $Rp^1$ in the resulting compound (42).

The removal of the amino-protective group $Rp^1$ may be attained in the same manner as in the method described in references (for example, Protective Groups in Organic Synthesis, by T. W. Green, 2nd Ed., John Wiley & Sons, 1991), or in accordance with it, or by combining it with an ordinary method.

The compound (43) thus obtained may be subjected to the next step, after isolated and purified in any known manner for isolation and purification, for example, through concentration, concentration under reduced pressure, crystallization, solvent extraction, reprecipitation, chromatography, or not after isolated and purified.

(Step 43)

This step is a process for producing a compound (I-3) of the invention by reacting the compound (43) with a compound (F). The introduction of the amino-protective group $R^4$ in this step may be attained in the same manner as in the method described in references (for example, Protective Groups in Organic Synthesis, by T. W. Green, 2nd Ed., John Wiley & Sons, 1991), or in accordance with it, or by combining it with an ordinary method.

More concretely, $R^4$ includes an alkyl, an alkylamide, a carbamoyl, an alkylcarbamoyl, an alkyl carbamate.

The compound (F) includes concretely, for example, acetic anhydride, trifluoroacetic anhydride, propionic acid, chloroacetic acid, ethyl acrylate, methanesulfonyl chloride, benzyl chloride.

The amount of the compound (F) to be used varies, depending on the type of the compound and the solvent used and on the other reaction conditions, but may be generally from 0.1 to 20 equivalents, preferably from 0.5 to 5 equivalents relative to one equivalent of the compound (43).

The reaction solvent to be used in this step is not specifically defined so far as it does not interfere with the reaction. For it, for example, herein employable are dichloromethane, chloroform, tetrahydrofuran, acetonitrile, dimethylformamide, benzene, acetone, ethanol, 2-propanol.

The reaction temperature in this step may be generally from 0° C. to the reflux temperature of the reaction solvent used, preferably from room temperature to 150° C.

The reaction time in this step may be generally from 0.1 to 72 hours, preferably from 0.5 to 12 hours.

The compound (I-31) of the invention may also produced in a different process, in which after the compounds (39) and (6) are reacted, a nitro group is introduced into the resulting product, and finally the nitro group is reduced to an amino group simultaneously with cyclization of the resulting compound, or, if desired, the compound is separately cyclized.

The amidation of the compound (39) and the compound (6), the nitration, the reduction from the nitro group into an amino group, and the cyclization may be effected in the same manner as in the step 5-1, the step 13, the step 3 and the step 5-1, respectively, or in accordance with it, or by combining it with an ordinary method.

The compound (I-31) of the invention thus obtained may be isolated and purified in any known manner for isolation and purification, for example, through concentration, concentration under reduced pressure, solvent extraction, crystallization, reprecipitation, chromatography.

In case where the amino-protective group $Rp^1$ in the compound (42) corresponds to the desired $R^4$, then the subsequent steps 42 and 43 are unnecessary, or that is, the compound (42) may be directly a compound of the invention.

In case where the compound (43) is a desired compound, then the step 43 is unnecessary, or that is, the compound (43) may be directly a compound of the invention.

The compounds (I-31) of the invention may also be produced according to the following method:

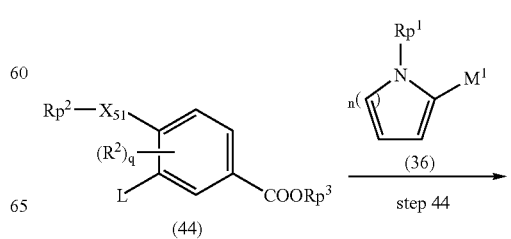

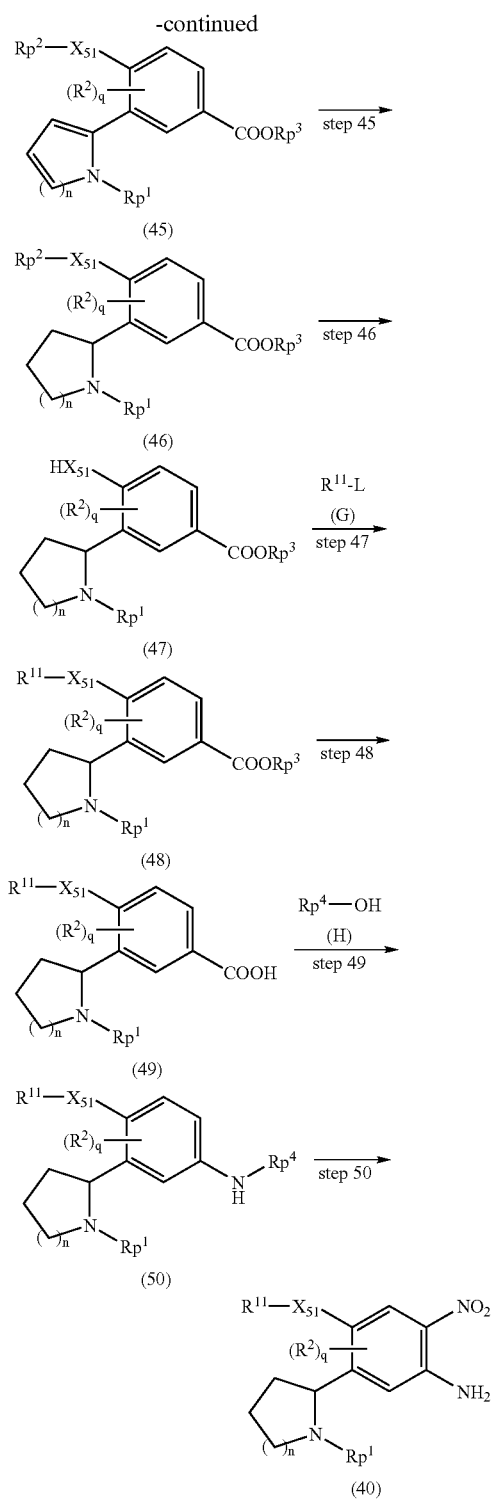

[In the formulae, $Rp^2$, $Rp^3$ and $Rp^4$ each represent a protective group; L represents a leaving group; and the other symbols have the same meanings as above.]

(Step 44)

This step is a process for producing a compound (45) by reacting a compound (44) with the above-mentioned compound (36). $Rp^2$ is an $X_{51}$-protective group, concretely including, for example, methoxymethyl, methyl, benzyl, 4-methoxy-benzyl, 2-(trimethylsilyl)ethoxymethyl, 2-(trimethylsilyl)ethyl, tert-butyldimethylsilyl, tert-butylcarbonyl. $Rp^3$ is a carboxyl-protective group, concretely including, for example, methoxymethyl, methyl, ethyl, tert-butyl, benzyl, 4-methoxy-benzyl, 2-(trimethylsilyl)ethyl, tert-butyldimethylsilyl. $Rp^4$ is an inert alkyl group, concretely including, for example, methyl, ethyl, tert-butyl, benzyl, 4-methoxy-benzyl, 2-(trimethylsilyl)ethyl. The reaction in this step may be carried out in the same manner as in the step 36, or in accordance with it, or by combining it with an ordinary method. The compound (45) thus obtained may be subjected to the next step, after isolated and purified in any known manner for isolation and purification, for example, through concentration, concentration under reduced pressure, crystallization, solvent extraction, reprecipitation, chromatography, or not after isolated and purified.

(Step 45)

This step is a process for producing a compound (46) by reducing the hetero-aromatic ring in the compound (45) obtained in the previous step, with a metal catalyst in a hydrogen atmosphere.

The amount of the reducing agent to be used may be generally from 0.01 to 10 equivalents, preferably from 0.05 to 1 equivalent.

The reducing agent to be used may be any one capable of producing the compound (46) from the compound (45) in this step. For it, for example, herein usable is 10% platinum-carbon or platinum-black.

The reaction solvent to be used in this step is not specifically defined so far as it does not interfere with the reaction. For it, for example, herein employable are methanol, ethanol, tetrahydrofuran, N,N-dimethylformamide, 1,4-dioxane, ethyl acetate.

The reaction temperature in this step may be generally from 0° C. to the reflux temperature of the reaction solvent used, preferably from room temperature to 150° C.

The reaction time in this step may be generally from 0.1 to 72 hours, preferably from 0.5 to 12 hours.

The reaction pressure in this step may be generally from normal pressure to 100 atmospheres, preferably from normal pressure to 20 atmospheres.

The compound (46) thus obtained may be subjected to the next step, after isolated and purified in any known manner for isolation and purification, for example, through concentration, concentration under reduced pressure, crystallization, solvent extraction, reprecipitation, chromatography, or not after isolated and purified.

(Step 46)

This step is a process for producing a compound (47) by removing the protective group $Rp^2$ in the compound (46). The removal of the protective group in this step may be effected in any method described in references (for example, Protective Groups in Organic Synthesis, by T. W. Green, 2nd Ed., John Wiley & Sons, 1991), or in accordance with it, or by combining it with an ordinary method. When $Rp^2$ is a methoxymethyl, then the removal of the protective group may be attained, for example, by the use of trifluoroacetic acid.

In case where trifluoroacetic acid is used for the removal of $Rp^1$, then the amount of the catalyst to be used may be generally from 0.01 to 1000 equivalents, preferably from 0.1 to 10 equivalents.

The reaction solvent to be used in this step is not specifically defined so far as it does not interfere with the reaction. For it, for example, herein employable is chloroform.

The reaction temperature may be generally from room temperature to the reflux temperature of the reaction solvent used, preferably from room temperature to 100° C.

The reaction time may be generally from 0.1 to 72 hours, preferably from 0.5 to 12 hours.

The compound (47) thus obtained may be subjected to the next step, after isolated and purified in any known manner for isolation and purification, for example, through concentration, concentration under reduced pressure, solvent extraction, crystallization, reprecipitation, chromatography, or not after isolated and purified. If desired, $Rp^1$ may be converted.

(Step 47)

This step is a process for producing a compound (48) by reacting the compound (47) with a compound (G). L represents a leaving group, and may be the same as the above-mentioned $L_1$ and $L_2$.

The compound (G) concretely includes, for example, benzyl bromide, 4-fluoro-benzonitrile, 4-fluoro-benzaldehyde. The reaction in this step may be carried out in the same manner as in the step 27, or in accordance with it, or by combining it with an ordinary method. The compound (48) thus obtained may be subjected to the next step, after isolated and purified in any known manner for isolation and purification, for example, through concentration, concentration under reduced pressure, crystallization, solvent extraction, reprecipitation, chromatography, or not after isolated and purified.

(Step 48)

This step is a process for producing a compound (49) by removing the carboxyl-protective group $Rp^3$ in the compound (48). The carboxyl-protective group in the compound (48) may be any one capable of acting as a protective group for carboxyl in the previous steps 44 to 47 and capable of being readily removed in the step 48. For example, it includes a linear or branched lower alkyl such as methyl, ethyl, tert-butyl; a halogeno-lower alkyl such as 2-iodomethyl, 2,2,2-trichloroethyl; a lower alkenyl such as allyl, 2-propenyl, 2-methyl-2-propenyl; and an aralkyl such as benzyl, para-methoxy-benzyl.

The introduction and the removal of the carboxyl-protective group $Rp^3$ may be effected in any method described in references (for example, Protective Groups in Organic Synthesis, by T. W. Green, 2nd Ed., John Wiley & Sons, 1991), or in accordance with it, or by combining it with an ordinary method.

The compound (49) thus obtained may be subjected to the next step, after isolated and purified in any known manner for isolation and purification, for example, through concentration, concentration under reduced pressure, solvent extraction, crystallization, reprecipitation, chromatography, or not after isolated and purified. If desired, $Rp^1$ may be converted.

(Step 49)

This step is a process for producing a compound (50) by reacting the compound (49) with a compound (H), and, for example, this is so-called Curtius transition reaction. Briefly, using a phosphoric acid azide compound and an alcoholic compound (17-1) in the presence of a base, the reaction may be effected in any method described in references (for example, Tetrahedron, Vol. 31, 1974, pp. 2151-2157), or in accordance with it, or by combining it with an ordinary method.

The amount of the alcoholic compound (H) to be used varies, depending on the type of the compound and the solvent used and on the other reaction conditions, but may be generally from 0.1 to 20 equivalents, preferably from 0.5 to 5 equivalents relative to one equivalent of the compound (49).

The amount of the base to be used also varies, depending on the type of the compound and the solvent used and on the other reaction conditions, but may be generally from 0.1 to 20 equivalents, preferably from 0.5 to 5 equivalents.

The phosphoric acid azide compound to be used may be any one capable of producing the compound (50) through the reaction of the compound (49) with the compound (H) in this step. For example, it includes diethylphosphoric acid azide, diphenylphosphoric acid azide.

The base to be used may be any one capable of producing the compound (50) through the reaction of the compound (49) with the compound (H) in this step. For example, it includes sodium hydride, cesium carbonate, sodium carbonate, potassium carbonate, potassium phosphate, potassium acetate, potassium tert-butoxide, triethylamine.

The reaction solvent to be used in this step is not specifically defined so far as it does not interfere with the reaction. For example, it includes toluene, tetrahydrofuran, methylene chloride, chloroform, 1,4-dioxane, benzene.

The reaction temperature in this step may be generally from 0° C. to the reflux temperature of the reaction solvent used, preferably from room temperature to 150° C.

The reaction time in this step may be generally from 0.1 to 72 hours, preferably from 0.5 to 12 hours.

The compound (50) thus obtained may be subjected to the next step, after isolated and purified in any known manner for isolation and purification, for example, through concentration, concentration under reduced pressure, crystallization, solvent extraction, reprecipitation, chromatography, or not after isolated and purified.

(Step 50)

This step is a process for producing the compound (40) by introducing a nitro group into the compound (50). The reaction in this step may be carried out in the same manner as in the step 29, or in accordance with it, or by combining it with an ordinary method.

After or not after isolated and purified in any known manner for isolation and purification, for example, through concentration, concentration under reduced pressure, crystallization, solvent extraction, reprecipitation, chromatography, the compound (40) thus obtained may be processed according to the above-mentioned steps 40 to 43 to thereby produce a compound (I-3) of the invention.

The compounds (I-31) of the invention may also be produced in a different process in which, after $Rp^4$ is removed from the compound (50) to give the aniline derivative and after the aniline derivative is reacted with the compound (6), a nitro group is introduced into the reaction product, and finally the nitro group is reduced to an amino group simultaneously with cyclization of the resulting compound, or, if desired, the compound is separately cyclized.

The amidation of the compound (50) and the compound (6), the nitration, the reduction from the nitro group into an amino group, and the cyclization may be effected in the same manner as in the step 5-1, the step 13, the step 3 and the step 5-1, respectively, or in accordance with it, or by combining it with an ordinary method. The removal of $Rp^4$ may be effected in the same manner as in the above-mentioned method (Protective Groups in Organic Synthesis, by T. W. Green, 2nd Ed., John Wiley & Sons, 1991), or in accordance with it, or by combining it with an ordinary method.

The novel 2-heteroaryl-substituted benzimidazole derivatives that the invention provides may be in the form of their pharmaceutically-acceptable salts. The salts may be produced in any ordinary method from the compounds (I-0) of the invention and from the compounds of the above-mentioned formulae (I-1), (I-11), (I-12), (I-2), (I-11-0), (I-31) and (I-4) that are within the scope of the compounds (I-0).

Concretely, when the compounds (I-0), (I-1), (I-11), (I-12), (I-2), (I-11-0), (I-31) and (I-4) have a basic group derived from, for example, an amino group or a pyridyl group in the molecule, then the compounds may be processed with acid so as to convert them into the corresponding pharmaceutically-acceptable salts.

The acid-addition salts include, for example, hydrohalides such as hydrochlorides, hydrofluorides, hydrobromides, hydroiodides; inorganic acid salts such as nitrates, perchlorates, sulfates, phosphates, carbonates; lower alkylsulfonates such as methanesulfonates, trifluoromethanesulfonates, ethanesulfonates; arylsulfonates such as benzenesulfonates, p-toluenesulfonates; organic acid salts such as fumarates, succinates, citrates, tartrates, oxalates, maleates; other organic acid-addition salts with amino acid such as glutamates, aspartates. When the compounds of the invention have an acid group in the molecule, for example, when they have a carboxyl group, then the compounds may be processed with a base so as to convert them into the corresponding pharmaceutically-acceptable salts. The base-addition salts include, for example, alkali metal salts with sodium or potassium; alkaline earth metal salts with calcium or magnesium; ammonium salts; organic base-addition salts with guanidine, triethylamine, dicyclohexylamine, etc. In addition, the compounds of the invention may also be in any other form of hydrates or solvates of their free compounds or their salts.

In producing medicines for prevention and remedy of type II diabetes or diseases or symptoms associated with it, the compounds of formula (I) of the invention may be combined with carrier substances.

The dose of the compounds of formula (I) of the invention for prevention or remedy of diseases naturally varies, depending on the property of the symptom to be treated, the specific compound selected for it and the administration route.

In addition, the dose also varies depending on the age, the body weight and the sensitivity of patients. In general, the daily dose for one-time or plural-times administration may be from about 0.001 mg/kg-body weight to about 100 mg/kg-body weight, preferably from about 0.01 mg/kg-body weight to about 50 mg/kg-body weight, even more preferably from about 0.1 mg/kg-body weight to about 10 mg/kg-body weight. As the case may be, administration of a dose over the range may be necessary.

An example of a suitable dose for oral administration is described. The daily dose for one-time or two- to four-times administration may be at least from about 0.01 mg to at most 2.0 g. Preferably, the daily administration frequency is once or twice a day, and the daily dose is from about 1.0 mg to about 200 mg. More preferably, the daily dose is from about 10 mg to 100 mg for one-time administration a day.

For intravenous administration or oral administration, a typical dose of the compound (I) may be from about 0.001 mg/day/g-body weight to about 100 mg/day/g-body weight (preferably from 0.01 mg/day/g-body weight to about 10 mg/day/g-body weight), more preferably from about 0.1 mg/day/g-body weight to 10 mg/day/g-body weight.

As so mentioned hereinabove, the pharmaceutical composition of the invention comprises a compound of formula (I) and a pharmaceutically-acceptable carrier. The term "composition" is meant to contain not only a product produced by directly or indirectly combining, hybridizing or aggregating 2 or more any ingredients, a product produced as a result of dissociation of one or more ingredients, or a compound produced as a result of reaction or interaction of different types of ingredients, but also an active and inactive ingredient of constituting a carrier (pharmaceutically-acceptable vehicle).

As combined with a pharmaceutically-acceptable carrier, the composition of the invention preferably contains a compound of formula (I) in an amount effective for remedy and prevention of type II diabetes and for retardation of the onset of the disease.

For administering the effective dose of the compound of the invention to mammals, especially to humans, employable is any suitable administration route. For example, the route may be oral administration, rectal administration, local administration, intravenous administration, ophthalmic administration, lung administration or nasal administration. Examples of the administration forms are tablets, troches, powders, suspensions, solutions, capsules, creams, aerosols. Preferred are oral tablets.

In preparing oral compositions, usable are any ordinary pharmaceutical media. Their examples are water, glycol, oil alcohol, fragrant additives, preservatives, colorants. In preparing liquid compositions for oral administration, for example, mentioned are suspensions, elixirs and solutions. Their carriers are, for example, starch, sugar, microcrystalline cellulose, diluent, granulating promoter, lubricant, binder, disintegrator. In preparing solid compositions for oral administrations, for example, mentioned are powders, capsules and tablets. Above all, such solid compositions for oral administration are preferred.

In view of the easiness in their administration, tablets and capsules are the most advantageous forms for oral administration. If desired, the tablets may be coated according to standard aqueous or non-aqueous coating techniques.

In addition to the above-mentioned ordinary administration modes for them, the compounds of formula (I) may also be administered according to controlled release systems and/or controlled delivery systems, for example, as in U.S. Pat. Nos. 3,845,770, 3,916,899, 3,536,809, 3,598,123, 3,630,200 and 4,008,719.

The pharmaceutical composition of the invention suitable for oral administration includes capsules, cashews and tablets that contain a predetermined amount of the active ingredient in the form of powders or granules thereof, or in the form of water-soluble liquids, water-insoluble liquids, oil-in-water emulsions or water-in-oil emulsions thereof. These compositions may be prepared in any pharmaceutical methods, and all the methods include a process of combining the active ingredient with a carrier of one or more necessary ingredients.

In general, the active ingredient is uniformly and fully mixed with a liquid carrier, or a well-separated solid carrier or with both the two, and then, if desired, the product is shaped into suitable forms to prepare the composition. For example, tablets are produced through compression and shaping, optionally along with one or more side components. Using a suitable machine, compressed tablets may be produced by mixing the active ingredient optionally with binder, lubricant, inert vehicle, surfactant or dispersant and compressing the resulting mix in any desired manner into powder or granules.

The shaped tablets are prepared by shaping the mixture of the powdery wet compound and an inert liquid diluent, using a suitable machine.

Preferably, the tablets each contain from about 1 mg to 1 g of the active ingredient; and the cashews and the capsules each contain from about 1 mg to 500 mg of the active ingredient.

Examples of the administration modes of the compounds of formula (I) for pharmaceutical use are as follows:

TABLE 1

Suspension for Injection (I.M.)

|  | mg/ml |
|---|---|
| compound of formula (I) | 10 |
| methyl cellulose | 5.0 |
| Tween 80 | 0.5 |
| benzyl alcohol | 9.0 |
| benzalkonium chloride | 1.0 | water for injection is added to make 1.0 ml.

TABLE 2

Tablets

|  | mg/tablet |
|---|---|
| compound of formula (I) | 25 |
| methyl cellulose | 415 |
| Tween 80 | 14.0 |
| benzyl alcohol | 43.5 |
| magnesium stearate | 2.5 |
| total | 500 mg |

TABLE 3

Capsules

|  | mg/capsule |
|---|---|
| compound of formula (I) | 25 |
| lactose powder | 573.5 |
| magnesium stearate | 1.5 |
| total | 600 mg |

TABLE 4

Aerosol

|  | per one container |
|---|---|
| compound of formula (I) | 24 mg |
| lecithin, NF Liq. Conc. | 1.2 mg |
| trichlorofluoromethane, NF | 4.025 g |
| dichlorodifluoromethane, NF | 12.15 g |

The compounds of formula (I) may be used, as combined with any other medicines usable not only for type II diabetes-associated diseases or symptoms but also for remedy/prevention/retardation of the onset of type II diabetes. The additional medicines may be administered in any administration route and dose generally employed in the art, simultaneously with or separately from the compound of formula (I).

In case where the compound of formula (I) is used along with one or more other medicines, then a pharmaceutical composition comprising the compound of formula (I) and the additional medicines is preferred. Accordingly, the pharmaceutical composition of the invention may comprise not only the compound of formula (I) but also one or more such active ingredients. Examples of the active ingredients that may be combined with the compounds of formula (I) are mentioned below, which, however, are not limitative. These may be separately administered or may be administered simultaneously as contained in the same pharmaceutical composition.

(a) bis-guanides (e.g., buformin, metoformin, fenformin,),
(b) PPAR agonists (e.g., triglytazon, pioglytazon, nosiglytazon),
(c) insulin,
(d) somatostatin,
(e) α-glucosidase inhibitors (e.g., boglybose, miglytol, acarbose),
(f) insulin secretion promoters (e.g., acetohexamide, calbutamide, chlorpropamide, lgybomlide, glycrazide, glymerpide, glypidide, glyquidine, glysoxepide, glyburide, glyhexamide, glypinamide, fenbutamide, trazamide, tolbutamide, tolcyclamide, nateglynide, repaglynide), and
(g) DPP-IV (dipeptidyl peptidase IV) inhibitors.

The weight ratio of the compound of formula (I) to the second active ingredient may vary within a broad range, and depends on the effective amount of the individual active ingredients. Accordingly, for example, when the compound of formula (I) is combined with a PPAR agonist, then the weight ratio of the compound of formula (I) to the PPAR agonist may be generally from about 1000/1 to 1/1000, preferably from about 200/1 to 1/200. The combination of the compound of formula (I) and the other active ingredient may be within the above-mentioned range. In any case, an effective amount of the individual ingredients should be in the combination.

The glucokinase-activating potency of the compounds of formula (I) of the invention and a test method for it are described below.

The excellent glucokinase-activating effect of the compounds of formula (I) may be determined by a method described in references (for example, Diabetes, Vol. 45, pp. 1671-1677, 1996), or in accordance with it.

The glucokinase activity may be determined not by directly measuring glucose-6-phosphate but by measuring the level of Thio-NADH, which is produced when a reporter enzyme, glucose-6-phosphate dehydrogenase produces phosphogluconolactone from glucose-6-phosphate, and based on the level, the degree of glucokinase activity of the compound tested may be determined.

In this assay, used was a recombinant human liver GK, which was expressed by $E.\ coli$ as a FLAG fusion protein therein and was purified by ANTIFLAG M2 AFFINITY GEL (Sigma).

Using a 96-well plate, the assay was carried out at 30° C. 69 μl of an assay buffer (25 mM Hepes Buffer/pH=7.2, 2 mM $MgCl_2$, 1 mM ATP, 0.5 mM TNAD, 1 mM dithiothreitol) was put into the plate, and 1 μl of a DMSO solution of the compound or DMSO alone as a control was added thereto. Next, 20 μl of an enzyme mixture (FLAG-GK, 20 U/ml G6PDH) cooled in ice was added to it, and 10 μl of a substrate, 25 mM glucose was added to it, and the reaction was initiated (final glucose concentration=2.5 mM).

After the start of the reaction, the increase in the absorbance at 405 nm was measured for 10 minutes at intervals of 30 seconds, and the increase for the first 5 minutes was used for evaluating the compound tested. FLAG-GK was added so that the absorbance increase after 5 minutes in the presence of 1% DMSO could be from 0.05 to 1.0.

The OD level of the DMSO control was set as 100%; and the OD level of the test compound at different concentrations was determined. From the OD level at each concentration, Emax (%) and EC50 (μM) were computed and used as the index of the GK-activating potency of the compound.

The GK-activating potency of the compounds of the invention was measured according to the method as above, and the results are shown in Table 1 below.

TABLE 5

(GK-Activating Potency of Compounds of the Invention)

| Compound No. | Emax (%) | EC50 (μM) |
|---|---|---|
| Example 67 | 832 | 1.4 |
| Example 26 | 768 | 2.3 |
| Example 122 | 664 | 1.9 |

As shown in Table 1 above, the compounds of the invention have an excellent GK-activating potency indicated by Emax and EC50.

EXAMPLES

The invention is described more concretely with reference to the following Examples, by which, however, the invention should not be limited at all.

Preparation Example 1

10 parts of the compound of Production Example 1, 15 parts of heavy magnesium oxide and 75 parts of lactose are uniformly mixed to give a powdery or particulate preparation of at most 350 μm in size. The preparation is encapsulated to prepare capsules.

Preparation Example 2

45 parts of the compound of Production Example 1, 15 parts of starch, 16 parts of lactose, 21 parts of crystalline cellulose, 3 parts of polyvinyl alcohol and 30 parts of distilled water are uniformly mixed, then ground, granulated and dried, and thereafter sieved to prepare granules having a size of from 1410 to 177 μm in diameter.

Preparation Example 3

Granules are prepared in the same manner as in Preparation Example 2. 3 parts of calcium stearate is added to 96 parts of the granules, and shaped under compression to give tablets having a diameter of 10 mm.

Preparation Example 4

10 parts of crystalline cellulose and 3 parts of calcium stearate are added to 90 parts of the granules obtained according to the method of Preparation Example 2, and shaped under compression to give tablets having a diameter of 8 mm. These are coated with a mixture suspension of syrup gelatin and precipitated calcium carbonate to prepare sugar-coated tablets.

In the following, the invention is described more concretely with reference to Preparation Examples, Production Examples and Reference Examples, by which, however, the invention should not be limited at all.

In the thin-layer chromatography in Examples, Silicagel 60F$_{245}$ (Merck) was used for the plate, and a UV detector was used for detection. For the column silica gel, used was Wakogel™ C-300 (Wako Pure Chemical); and for the reversed-phase column silica gel, used was LC-SORBT SP-B-ODS (Chemco) or YMC-GELT ODS-AQ 120-S50 (Yamamura Chemical Laboratory).

The meanings of the abbreviations in the following Examples are shown below.

i-Bu: isobutyl
n-Bu: n-butyl
t-Bu: t-butyl
Me: methyl
Et: ethyl
Ph: phenyl
i-Pr: isopropyl
n-Pr: n-propyl
CDCl$_3$: heavy chloroform
CD$_3$OD: heavy methanol
DMSO-d$_6$: heavy dimethylsulfoxide The meanings of the abbreviations in the following nuclear magnetic resonance spectra are shown below.

s: singlet
d: doublet
dd: double-doublet
t: triplet
m: multiplet
br: broad
q: quartet
J: coupling constant
Hz: hertz Example 1

2-Pyridin-2-yl-5,6-bis(pyridin-3-yloxy)-1H-benzimidazole (Step 1) Production of 3-(2-fluoro-4-nitro-phenoxy)-pyridine 2.09 g of 3-hydroxypyridine and 5.52 g of potassium carbonate were added to a dimethylformamide (20 ml) solution of 3.18 g of 3,4-difluoronitrobenzene, and the reaction liquid was stirred at 90° C. for 1 hour. The reaction liquid was diluted with ethyl acetate, washed with water and saturated saline in order, and dried with anhydrous magnesium sulfate. The solvent was evaporated away under reduced pressure, and the resulting residue was purified through silica gel column chromatography (developing solvent: hexane/ethyl acetate=9/1) to obtain the entitled compound.

(Step 2) Production of 5-fluoro-2-nitro-4-(pyridin-3-yloxy)-phenylamine 1.0 g of 20% palladium hydroxide-carbon catalyst was added to a methanol (30 ml) solution of 4.72 g of 3-(2-fluoro-4-nitro-phenoxy)-pyridine, and the reaction liquid was stirred in a hydrogen atmosphere for 5 hours. The catalyst was removed through filtration, and the solvent was evaporated away under reduced pressure to obtain a crude product. 1.88 g of potassium nitrate was added to a trifluoroacetic acid (40 ml) solution of the resulting crude product, and the reaction liquid was stirred overnight at room temperature. Then, the solvent was evaporated away under reduced pressure. The residue was diluted with ethyl acetate, washed with saturated sodium bicarbonate solution and saturated saline in order, and then dried with anhydrous magnesium sulfate. The solvent was evaporated away under reduced pressure, and the resulting residue was purified through silica gel column chromatography (developing solvent: hexane/ethyl acetate=4/1) to obtain the entitled compound.

(Step 3) Production of 4,5-bis(pyridin-3-yloxy)-benzene-1,2-diamine 285 mg of 3-hydroxypyridine and 829 mg of potassium carbonate were added to a dimethylformamide (8 ml) solution of 680 mg of 3-(2-fluoro-4-nitro-phenoxy)-pyridine, and the reaction liquid was stirred at 90° C. for 2 hours. The reaction liquid was diluted with ethyl acetate, washed with water and saturated saline in order, and then dried with anhydrous magnesium sulfate. The solvent was evaporated away under reduced pressure, and the resulting residue was purified through silica gel column chromatography (developing solvent: hexane/ethyl acetate=1/1 to ethyl acetate) to obtain a crude product. 500 mg of a developed Raney-nickel catalyst was added to an ethanol (10 ml) solution of the resulting crude product, and the reaction liquid was stirred in a hydrogen atmosphere for 2 hours. The catalyst was removed through filtration, and the solvent was evaporated away under reduced pressure to obtain the entitled compound.

(Step 4) Production of 2-pyridin-2-yl-5,6-bis(pyridin-3-yloxy)-1H-benzimidazole 0.01 ml of pyridine-2-carboxaldehyde was added to a nitrobenzene (0.3 ml) solution of 30 mg of 4,5-bis(pyridin-3-yloxy)-benzene-1,2-diamine at 120° C., and the reaction liquid was stirred at the same temperature for 2 hours. The reaction mixture was purified through reversed-phase middle-pressure liquid chromatography [ODS-AS-360-CC (by YMC), mobile phase: water-acetonitrile-0.1% trifluoroacetic acid]. The solvent of the resulting fraction was evaporated away under reduced pressure, and this was purified through partitioning thin-layer chromatography (Kieselgel™ 60F$_{254}$, Art 5744 (by Merck), chloroform/methanol=20/1) to obtain the entitled compound as a yellow oily substance.

$^1$HNMR (CDCl$_3$) δ: 7.10-7.40 (4H, m), 7.28 (1H, s), 7.38 (1H, ddd, J=1.2 Hz, 4.8 Hz, 7.6 Hz), 7.62 (1H, s), 7.87 (1H, td, J=7.6 Hz, 1.2 Hz), 8.12-8.40 (4H, m), 8.38 (1H, d, J=7.6 Hz), 8.63 (1H, d, J=4.8 Hz), 10.8 (1H, brs)

ESI-MS (m/e): 382 [M+H]

Example 2

5-(2-Hydroxymethyl-phenoxy)-2-pyridin-2-yl-6-(pyridin-3-yloxy)-1H-benzimidazole

The entitled compound was obtained as a colorless solid in the same method as in Example 1 or in accordance with the method or by combining it with an ordinary method but using 5-fluoro-2-nitro-4-(pyridin-3-yloxy)-phenylamine obtained in Example 1 (step 2) and 2-hydroxymethyl-phenol.

$^1$HNMR (CDCl$_3$) δ: 4.45 (2H, s), 6.76 (1H, d, J=8.0 Hz), 7.04 (1H, t, J=6.8 Hz), 7.08-7.30 (5H, m), 7.30-7.43 (2H, m), 7.86 (1H, td, J=8.0 Hz, 2.4 Hz), 8.18-8.32 (1H, m), 8.22 (1H, s), 7.36 (1H, d, J=7.6 Hz), 8.62 (1H, d, J=8.4 Hz), 10.54 (1H, brs)

ESI-MS (m/e): 411 [M+H]

Example 3

5-(2-(1-Hydroxy-ethyl)-phenoxy)-2-pyridin-2-yl-6-(pyridin-3-yloxy)-1H-benzimidazole The entitled compound was obtained as a colorless solid in the same method as in Example 2 or in accordance with the method or by combining it with an ordinary method but using 2-(1-hydroxy-ethyl)-phenol.

$^1$HNMR (CDCl$_3$) δ: 1.25-1.34 (6H, m), 4.80-4.96 (1H, m), 7.76 (1H, dd, J=4.4 Hz, 8.0 Hz), 7.02-7.34 (6H, m), 7.38 (1H, t, J=6.4 Hz), 7.42-7.60 (1H, m), 7.87 (1H, td, J=7.6 Hz, 1.6 Hz), 8.20-8.34 (2H, m), 8.39 (1H, d, J=7.6 Hz), 8.60-8.64 (1H, m), 10.72 (1H, brs)

ESI-MS (m/e): 425 [M+H]

Example 4

5-(2-Acetyl-phenoxy)-2-pyridin-2-yl-6-(pyridin-3-yloxy)-1H-benzimidazole

The entitled compound was obtained as a colorless solid in the same method as in Example 2 or in accordance with the method or by combining it with an ordinary method but using 2-acetyl-phenol.

$^1$HNMR (CDCl$_3$) δ: 2.22-2.50 (3H, m), 6.81 (1H, d, J=8.4 Hz), 7.00-7.45 (4H, m), 7.45-7.95 (5H, m), 8.20-8.35 (2H, m), 8.37 (1H, d, J=7.6 Hz), 8.60-8.70 (1H, m), 10.49 (1H, brs)

ESI-MS (m/e): 423 [M+H]

Example 5

5-(2-Cyano-phenoxy)-2-pyridin-2-yl-6-(pyridin-3-yloxy)-1H-benzimidazole

The entitled compound was obtained as a pale yellow solid in the same method as in Example 2 or in accordance with the method or by combining it with an ordinary method but using 2-hydroxy-benzonitrile.

$^1$HNMR (CDCl$_3$) δ: 6.80 (1H, t, J=8.0 Hz), 7.06 (1H, t, J=7.6 Hz), 7.25-7.35 (2H, m), 7.35-7.747 (1H, m), 7.56 (1H, d, J=7.6 Hz), 7.58-7.70 (1H, m), 7.87 (1H, t, J=7.6 Hz), 8.12-8.25 (1H, m), 8.31 (1H, brs), 8.38 (1H, d, J=8.0 Hz), 8.58-8.68 (1H, m), 10.80-11.08 (1H, m)

ESI-MS (m/e): 406 [M+H]

Example 6

5-(3-Cyano-phenoxy)-2-pyridin-2-yl-6-(pyridin-3-yloxy)-1H-benzimidazole

The entitled compound was obtained in the same method as in Example 2 or in accordance with the method or by combining it with an ordinary method but using 3-hydroxy-benzonitrile.

$^1$HNMR (CDCl$_3$) δ: 7.02-7.08 (2H, m), 7.14 (1H, d, J=7.5 Hz), 7.20 (1H, dd, J=4.4 Hz, 7.5 Hz), 7.28-7.36 (3H, m), 7.39 (1H, t, J=5.9 Hz), 7.42-7.52 (1H, m), 7.88 (1H, dt, J=1.6 Hz, 7.9 Hz), 8.22 (1H, d, J=3.6 Hz), 8.30 (1H, d, J=3.6 Hz), 8.39 (1H, d, J=7.9 Hz), 8.62 (1H, d, J=5.9 Hz)

ESI-MS (m/e): 406 [M+H]

Example 7

5-(4-Cyano-phenoxy)-2-pyridin-2-yl-6-(pyridin-3-yloxy)-1H-benzimidazole

The entitled compound was obtained in the same method as in Example 2 or in accordance with the method or by combining it with an ordinary method but using 4-hydroxy-benzonitrile.

$^1$HNMR (CDCl$_3$) δ: 6.84 (2H, d, J=7.0 Hz), 7.04-7.12 (1H, m), 7.12-7.26 (1H, m), 7.26-7.43 (1H, m), 7.30-7.43 (1H, m), 7.51 (2H, d, J=7.0 Hz), 7.44-7.76 (1H, m), 7.78-7.90 (1H, m), 8.12-8.21 (1H, m), 8.21-8.30 (1H, m), 8.30-8.40 (1H, m), 8.43-8.65 (1H, m), 10.88 (1H, brs)

ESI-MS (m/e): 406 [M+H]

Example 8

5-(4-Dimethylcarbamoyl-phenoxy)-2-pyridin-2-yl-6-(pyridin-3-yloxy)-1H-benzimidazole The entitled compound was obtained in the same method as in Example 2 or in accordance with the method or by combining it with an ordinary method but using 4-hydroxy-benzoic acid dimethylamide.

$^1$HNMR (CDCl$_3$) δ: 3.00 (3H, brs), 3.08 (3H, brs), 6.83 (1H, d, J=8.8 Hz), 6.86 (1H, d, J=8.8 Hz), 7.18-7.23 (2H, m), 7.26-7.36 (3H, m), 7.38-7.42 (1H, m), 7.61 (1H, d, J=2.5 Hz), 7.89 (1H, dd, J=7.7, 7.7 Hz), 8.19-8.38 (2H, m), 8.36 (1H, d, J=7.7 Hz), 8.63 (1H, d, J=4.8 Hz)

ESI-MS (m/e): 452 [M+H]

Example 9

5-(4-Methanesulfonyl-phenoxy)-2-pyridin-2-yl-6-(pyridin-3-yloxy)-1H-benzimidazole The entitled compound was obtained in the same method as in Example 2 or in accordance with the method or by combining it with an ordinary method but using 4-methanesulfonyl-phenol.

$^1$HNMR (CDCl$_3$) δ: 3.40 (3H, s), 6.96 (2H, d, J=8.8 Hz), 7.10-7.16 (1H, m), 7.17-7.25 (1H, m), 7.32 (½H, s), 7.38 (½H, s), 7.39-7.43 (1H, m), 7.65 (½H, s), 7.70 (½H, s), 7.83 (2H, dd, J=8.8, 3.1 Hz), 7.90 (1H, ddd, J=7.8, 7.8, 1.7 Hz), 8.23 (1H, brs), 8.32 (1H, brs), 8.39 (1H, d, J=7.8 Hz), 8.65 (1H, d, J=4.7 Hz), 10.84 (1H, brs)

ESI-MS (m/e): 459 [M+H]

Example 10

5-(4-Methoxycarbonyl-phenoxy)-2-pyridin-2-yl-6-(pyridin-3-yloxy-1H-benzimidazole The entitled compound was obtained in the same method as in Example 2 or in accordance with the method or by combining it with an ordinary method but using methyl 4-hydroxybenzoate.

$^1$HNMR (CDCl$_3$) δ: 3.88 (3H, s), 6.82 (2H, d, J=8.8 Hz), 7.12 (1H, ddd, J=8.6, 2.9, 1.5 Hz), 7.18 (1H, dd, J=8.6, 4.8 Hz), 7.28 (1H, brs), 7.32 (1H, brs), 7.87 (1H, ddd, J=7.7, 7.7, 1.8 Hz), 7.92 (2H, d, J=8.8 Hz), 8.20 (1H, d, J=2.9 Hz), 8.27 (1H, d, J=4.8 Hz), 8.37 (1H, dd, J=7.7, 1.1 Hz), 8.61 (1H, dd, J=5.1, 1.8 Hz), 10.80 (1H, brs)

ESI-MS (m/e): 439 [M+H]

Example 11

5-(2-Formyl-phenoxy)-2-pyridin-2-yl-6-(pyridin-3-yloxy)-1H-benzimidazole

The entitled compound was obtained as a pale yellow solid in the same method as in Example 2 or in accordance with the method or by combining it with an ordinary method but using 2-hydroxy-benzaldehyde.

$^1$HNMR (CDCl$_3$) δ: 6.80 (1H, d, J=8.4 Hz), 6.92-7.58 (6H, m), 7.83 (1H, d, J=8.0 Hz), 7.87 (1H, td, J=7.6 Hz, 1.2 Hz), 8.12-8.34 (3H, m), 8.39 (1H, d, J=8.4 Hz), 8.55-8.67 (1H, m), 10.06 (1H, s)

ESI-MS (m/e): 409 [M+H]

Example 12

5-(2-Carboxy-phenoxy)-2-pyridin-2-yl-6-(pyridin-3-yloxy)-1H-benzimidazole

The entitled compound was obtained in the same method as in Example 2 or in accordance with the method or by combining it with an ordinary method but using 2-hydroxybenzoic acid.

$^1$HNMR (CD$_3$OD) δ: 6.83 (2H, d, J=8.8 Hz), 7.31 (1H, ddd, J=8.6, 2.9, 1.5 Hz), 7.34 (1H, ddd, J=8.6, 4.8, 0.7 Hz), 7.48 (1H, dd, J=7.7, 4.8 Hz), 7.54 (1H, s), 7.56 (1H, s), 7.92 (2H, d, J=8.8 Hz), 7.96 (1H, ddd, J=7.7, 7.7, 1.5 Hz), 8.09 (1H, dd, J=2.9, 0.7 Hz), 8.20 (1H, dd, J=4.8, 1.5 Hz), 8.27 (1H, d, J=7.7 Hz), 8.72 (1H, d, J=4.8 Hz)

ESI-MS (m/e): 425 [M+H]

Example 13

5-(2-Methyl-pyridin-5-ylsulfanyl)-2-pyridin-2-yl-6-(pyridin-3-yloxy)-1H-benzimidazole The entitled compound was obtained in the same method as in Example 2 or in accordance with the method or by combining it with an ordinary method but using 6-methyl-pyridine-3-thiol.

$^1$HNMR (CDCl$_3$) δ: 2.53 (3H, s), 7.05 (1H, d, J=7.6 Hz), 7.05, 7.36 (tautomer, 1H, s), 7.12-7.24 (2H, m), 7.32-7.36 (1H, m), 7.44, 7.76 (tautomer, 1H, s), 7.50-7.56 (1H, m), 7.83 (1H, t, J=8.0 Hz), 8.26-8.36 (3H, m), 8.45 (1H, s), 8.56 (1H, d, J=4.4 Hz), 11.28-11.40, 11.40-11.50 (tautomer, 1H, brs)

ESI-MS (m/e): 412 [M+H]

Example 14

5-(2-Ethoxycarbonyl-phenoxy)-6-(4-methanesulfonyl-phenoxy)-2-pyridin-2-yl-1H-benzimidazole The entitled compound was obtained in the same method as in Example 1 or in accordance with the method or by combining it with an ordinary method but using 4-methanesulfonyl-phenol and ethyl 2-hydroxybenzoate in order.

$^1$HNMR (CDCl$_3$) δ: 1.19 (3H, t, J=7.0 Hz), 3.03 (3H, s), 4.14 (2H, q, J=7.0 Hz), 6.87 (1H, dd, J=7.4, 6.3 Hz), 7.00 (2H, dd, J=9.0, 2.2 Hz), 7.10-7.17 (1H, m), 7.14 (½H, brs), 7.32 (½H, brs), 7.37-7.43 (2H, m), 7.49 (½H, brs), 7.67 (½H, brs), 7.81 (2H, dd, J=9.0, 2.2 Hz), 7.82-7.90 (2H, m), 8.36-8.40 (1H, m), 8.62-8.64 (1H, m), 10.85 (1H, brs)

ESI-MS (m/e): 530 [M+H]

Example 15

5-(2-Dimethylcarbamoyl-phenoxy)-6-(4-methanesulfonyl-phenoxy)-2-pyridin-2-yl-1H-benzimidazole The entitled compound was obtained in the same method as in Example 14 or in accordance with the method or by combining it with an ordinary method but using 4-fluoro-5-(4-methanesulfonyl-phenoxy)-2-nitro-phenylamine obtained in Example 14 and 2-hydroxybenzoic acid dimethylamide in order.

$^1$HNMR (CDCl$_3$) δ: 2.58-3.06 (9H, m), 6.83 (⅓H, d, J=8.6 Hz), 6.86 (⅔H, d, J=8.4 Hz), 7.02-7.11 (3H, m), 7.12-7.18

(2H, m), 7.12-7.18 (½H, m), 7.23-7.33 (1H, m), 7.23-7.33 (½H, m), 7.36-7.40 (1H, m), 7.58 (⅓H, s), 7.64 (⅔H, s), 7.83-7.90 (3H, m), 8.34-8.38 (1H, m), 8.62-8.64 (1H, m), 10.58 (⅔H, brs), 10.61 (⅓H, brs)
ESI-MS (m/e): 529 [M+H]

Example 16

5-(2-Methoxy-phenoxy)-6-(4-methanesulfonyl-phenoxy)-2-pyridin-2-yl-1H-benzimidazole The entitled compound was obtained in the same method as in Example 15 or in accordance with the method or by combining it with an ordinary method but using 2-methoxy-phenol.
$^1$HNMR (CDCl$_3$) δ: 3.03 (3H, s), 3.69 (3H, s), 6.87-6.95 (3H, m), 7.00 (½H, s), 7.08 (2H, dd, J=8.9, 2.8 Hz), 7.08-7.38 (1H, m), 7.31 (½H, s), 7.35 (½H, s), 7.35-7.38 (1H, m), 7.64 (½H, s), 7.83 (2H, dd, J=8.9, 2.8 Hz), 7.87 (1H, dd, J=7.8, 1.6 Hz), 8.33-8.38 (1H, m), 8.60-8.62 (1H, m), 10.62 (½H, brs), 10.73 (½H, brs)
ESI-MS (m/e): 488 [M+H]

Example 17

5-(2-Cyano-phenoxy)-2-pyridin-2-yl-6-(4-methanesulfonyl-phenoxy)-1H-benzimidazole The entitled compound was obtained as a colorless solid in the same method as in Example 15 or in accordance with the method or by combining it with an ordinary method but using 2-hydroxy-benzonitrile.
$^1$HNMR (CDCl$_3$) δ: 6.78 (1H, d, J=8.4 Hz), 6.86 (2H, t, J=9.6 Hz), 7.09 (1H, dd, J=8.4 Hz, 12.8 Hz), 7.37-7.55 (4H, m), 7.62-7.92 (4H, m), 8.40 (1H, d, J=8.4 Hz), 8.64 (1H, d, J=4.0 Hz)
ESI-MS (m/e): 483 [M+H]

Example 18

5-(4-Dimethylcarbamoyl-phenoxy)-6-phenoxy-2-pyridin-2-yl-1H-benzimidazole

The entitled compound was obtained as a colorless solid in the same method as in Example 1 or in accordance with the method or by combining it with an ordinary method but using 4-hydroxybenzoic acid dimethylamine and phenol in order.
$^1$HNMR (CDCl$_3$) δ: 2.99 (3H, brs), 3.07 (3H, brs), 6.85-6.88 (4H, m), 6.97-7.14 (1H, m), 7.21-7.27 (3H, m), 7.31-7.37 (3H, m), 7.55 (½H, brs), 7.61 (½H, brs), 7.84 (1H, ddd, J=7.7, 7.7, 1.5 Hz), 8.35 (1H, d, J=7.7 Hz), 8.61 (1H, brs), 10.48 (½H, brs), 10.51 (½H, brs)
ESI-MS (m/e): 451 [M+H]

Example 19

5-(4-Dimethylcarbamoyl-phenoxy)-6-(4-methylsulfanyl-phenoxy)-2-pyridin-2-yl-1H-benzimidazole The entitled compound was obtained in the same method as in Example 1 or in accordance with the method or by combining it with an ordinary method but using 4-fluoro-5-(4-dimethylcarbamoyl-phenoxy)-2-nitro-phenylamine obtained in Example 18 and 4-methylmercapto-phenol.
$^1$HNMR (CDCl$_3$) δ: 2.44 (3H, s), 2.99 (3H, brs), 3.07 (3H, brs), 6.81 (2H, d, J=8.4 Hz), 6.87 (2H, d, J=8.4 Hz), 7.18 (2H, d, J=8.4 Hz), 7.10-7.28 (1H, m), 7.32-7.35 (1H, m), 7.33 (2H, d, J=8.4 Hz), 7.54 (½H, brs), 7.60 (½H, brs), 7.84 (1H, dd, J=7.7, 7.7 Hz), 8.34 (1H, d, J=7.7 Hz), 8.59-8.61 (1H, m), 10.55 (½H, brs), 10.60 (½H, brs)
ESI-MS (m/e): 497 [M+H]

Example 20

5-(4-Dimethylcarbamoyl-phenoxy)-6-(2-methanesulfonyl-phenoxy)-2-pyridin-2-yl-1H-benzimidazole The entitled compound was obtained in the same method as in Example 19 or in accordance with the method or by combining it with an ordinary method but using 2-methanesulfonyl-phenol.
$^1$HNMR (CDCl$_3$) δ: 2.94 (3/2H, s), 2.99 (3H, brs), 3.03 (3/2H, brs), 3.08 (3H, brs), 6.88-6.93 (3H, m), 7.15-7.22 (1H, m), 7.24 (½H, s), 7.34-7.42 (3H, m), 7.39 (½H, s), 7.45-7.52 (1H, m), 7.64 (½H, s), 7.70 (½H, s), 7.86-7.90 (1H, m), 8.00 (1H, d, J=7.8 Hz), 8.38 (1H, d, J=7.8 Hz), 8.65 (1H, d, J=3.9 Hz), 10.72 (1H, brs)
ESI-MS (m/e): 529 [M+H]

Example 21

5-(4-Dimethylcarbamoyl-phenoxy-6-(4-methanesulfonylphenoxy)-2-pyridin-2-yl-1H-benzimidazole The entitled compound was obtained in the same method as in Example 19 or in accordance with the method or by combining it with an ordinary method but using 4-methanesulfonyl-phenol.
$^1$HNMR (CDCl$_3$) δ: 3.00 (3H, brs), 3.03 (3H, s), 3.08 (3H, brs), 6.81 (2H, d, J=8.1 Hz), 6.95 (2H, d, J=8.4 Hz), 7.26 (½H, brs), 7.32 (2H, d, J=8.1 Hz), 7.39 (1H, dd, J=7.7, 4.9 Hz), 7.64 (½H, brs), 7.66 (½H, brs), 7.79 (2H, d, J=8.4 Hz), 7.87 (1H, ddd, J=7.7, 7.7, 1.8 Hz), 8.37 (1H, d, J=7.7 Hz), 8.63 (1H, d, J=4.9 Hz), 10.77 (1H, brs)
ESI-MS (m/e): 529 [M+H]

Example 22

5-(4-Dimethylcarbamoyl-phenoxy)-6-(4-methoxy-phenoxy)-2-pyridin-2-yl-1H-benzimidazole The entitled compound was obtained in the same method as in Example 19 or in accordance with the method or by combining it with an ordinary method but using 4-methoxy-phenol.
$^1$HNMR (CDCl$_3$) δ: 3.00-3.07 (6H, m), 3.76 (3/2H, s), 3.77 (3/2H, s), 6.74-6.86 (4H, m), 6.91 (2H, d, J=8.4 Hz), 7.05 (½H, brs), 7.19 (½H, brs), 7.32-7.36 (1H, m), 7.35 (2H, d, J=8.4 Hz), 7.43 (½H, brs), 7.58 (½H, brs), 7.83 (1H, dd, J=7.7, 7.7 Hz), 8.33 (1H, dd, J=7.7, 3.7 Hz), 8.58-8.61 (1H, m), 10.58 (½H, brs), 10.79 (½H, brs)
ESI-MS (m/e): 481 [M+H]

Example 23

5-(4-Dimethylcarbamoyl-phenoxy)-2-pyridin-2-yl-6-(pyridin-2-yloxy)-1H-benzimidazole-ditrifluoroacetate The entitled compound was obtained as a yellow solid in the same method as in Example 19 or in accordance with the method or by combining it with an ordinary method but using 2-hydroxypyridine.

¹HNMR (CD₃OD) δ: 6.93-7.13 (4H, m), 7.37-7.45 (2H, m), 7.41 (1H×½, s), 7.56 (1H×½, s), 7.64 (1H×½, s), 7.67-7.75 (1H, m), 7.77-7.84 (1H, m), 7.81 (1H×½, s), 8.02-8.06 (1H, m), 8.12-8.20 (1H, m), 8.27-8.33 (1H, m), 8.82-8.87 (1H, m)
ESI-MS (m/e): 452 [M+H]

Example 24

5-(4-Dimethylcarbamoyl-phenoxy)-6-(2-ethoxycarbonyl-phenoxy)-2-pyridin-2-yl-1H-benzimidazole The entitled compound was obtained in the same method as in Example 19 or in accordance with the method or by combining it with an ordinary method but using ethyl 2-hydroxy-benzoate.
¹HNMR (CDCl₃) δ: 1.20 (3H, t, J=7.0 Hz), 3.01 (3H, brs), 3.07 (3H, brs), 4.17 (2H, q, J=7.0 Hz), 6.80-6.91 (3H, m), 7.08-7.14 (1H, m), 7.12 (½H, brs), 7.18 (½H, brs), 7.26-7.41 (4H, m), 7.49 (½H, brs), 7.61 (½H, brs), 7.84-7.87 (2H, m), 8.34-8.38 (1H, m), 8.61-8.62 (1H, m), 10.85 (½H, brs), 10.95 (½H, brs)
ESI-MS (m/e): 523 [M+H]

Example 25

5-(2-Dimethylcarbamoyl-phenoxy)-6-(4-dimethylcarbamoyl-phenoxy)-2-pyridin-2-yl-1H-benzimidazole The entitled compound was obtained as a pale yellow solid in the same method as in Example 19 or in accordance with the method or by combining it with an ordinary method but using 2-hydroxybenzoic acid dimethylamide.
¹HNMR (CDCl₃) δ: 2.64-3.08 (12H, m), 6.81 (½H, s), 6.85 (½H, s), 6.94 (1H, dd, J=8.8, 2.7 Hz), 7.08 (½H, s), 7.12 (½H, s), 7.21 (½H, s), 7.24 (½H, s), 7.25-7.29 (2H, m), 7.30-7.34 (1H, m), 7.35-7.53 (2H, m), 7.59 (1H, d, J=3.1 Hz), 7.83-7.88 (1H, m), 8.33-8.38 (1H, m), 8.63 (1H, d, J=4.9 Hz), 10.52 (1H, brs)
ESI-MS (m/e): 522 [M+H]

Example 26

5-(2-Acetyl-phenoxy)-6-(4-dimethylcarbamoyl-phenoxy)-2-pyridin-2-yl-1H-benzimidazole The entitled compound was obtained in the same method as in Example 19 or in accordance with the method or by combining it with an ordinary method but using 2-acetyl-phenol.
¹HNMR (CDCl₃) δ: 2.36 (³⁄₂H, s), 2.40 (³⁄₂H, s), 3.00 (3H, brs), 3.08 (3H, brs), 6.76-6.84 (3H, m), 7.05-7.11 (1H, m), 7.15-7.25 (1H, m), 7.26-7.28 (1H, m), 7.32-7.35 (2H, m), 7.38-7.42 (1H, m), 7.63 (½H, s), 7.68 (½H, s), 7.78 (1H, d, J=7.4 Hz), 7.86-7.90 (1H, m), 8.39 (1H, d, J=7.0 Hz), 8.65 (1H, s), 10.73 (1H×½, brs), 10.88 (1H×½, brs)
ESI-MS (m/e): 493 [M+H]

Example 27

5-(4-Acetyl-phenoxy)-6-(4-dimethylcarbamoyl-phenoxy)-2-pyridin-2-yl-1H-benzimidazole The entitled compound was obtained in the same method as in Example 19 or in accordance with the method or by combining it with an ordinary method but using 4-acetyl-phenol.
¹HNMR (CDCl₃) δ: 2.55 (3H, s), 2.98 (3H, brs), 3.09 (3H, brs), 6.70-6.90 (4H, m), 7.23 (½H, s), 7.34 (½H, s), 7.26 (½H, s), 7.33-7.35 (2H, m), 7.38-7.42 (1H, m), 7.65 (½H, s), 7.68 (½H, s), 7.86-7.91 (3H, m), 8.40 (1H, d, J=7.8 Hz), 8.65 (1H, d, J=3.5 Hz), 10.85 (½H, brs), 10.95 (½H, brs)
ESI-MS (m/e): 493 [M+H]

Example 28

5-(2-Cyano-phenoxy)-2-pyridin-2-yl-6-(4-cyano-phenoxy)-1H-benzimidazole

The entitled compound was obtained as a colorless solid in the same method as in Example 1 or in accordance with the method or by combining it with an ordinary method but using 2-hydroxy-benzonitrile and 4-hydroxy-benzonitrile in order.
¹HNMR (CDCl₃) δ: 6.80 (1H, t, J=8.8 Hz), 6.86 (1H, d, J=8.8 Hz), 6.89 (1H, d, J=8.8 Hz), 7.08 (1H, td, J=7.6 Hz, 74 Hz), 7.34-7.47 (3H, m), 7.47-7.58 (3H, m), 7.67 (1H, d, J=5.2 Hz), 7.88 (1H, t, J=7.6 Hz), 8.38 (1H, d, J=7.6 Hz), 8.65 (1H, d, J=4.0 Hz), 10.58 (1H, brs)
ESI-MS (m/e): 430 [M+H]

Example 29

5-(2-Cyano-phenoxy)-2-pyridin-2-yl-6-(3-cyano-phenoxy)-1H-benzimidazole

The entitled compound was obtained as a brown solid in the same method as in Example 28 or in accordance with the method or by combining it with an ordinary method but using 4-fluoro-5-(2-cyano-phenoxy)-2-nitro-phenylamine obtained in Example 28 and 3-hydroxy-benzonitrile.
¹HNMR (CDCl₃) δ: 6.93-6.84 (1H, m), 6.96-7.12 (3H, m), 7.27-7.38 (3H, m), 7.38-7.48 (2H, m), 7.54 (1H, dd, J=1.6 Hz, 7.6 Hz), 7.68 (1H, d, J=13.2 Hz), 7.89 (1H, t, J=7.6 Hz,), 8.42 (1H, d, J=7.6 Hz), 8.65 (1H, s)
ESI-MS (m/e): 430 [M+H]

Example 30

5-(2-Cyano-phenoxy)-2-pyridin-2-yl-6-(4-(2-hydroxyethyl)-phenoxy)-1H-benzimidazole-monotrifluoroacetate The entitled compound was obtained as a brown solid in the same method as in Example 29 or in accordance with the method or by combining it with an ordinary method but using 4-hydroxyethyl-phenol.
¹HNMR (CD₃OD) δ: 2.78 (2H, t, J=7.0 Hz), 3.72 (2H, t, J=7.0 Hz), 6.83 (2H, d, J=8.6 Hz), 6.94 (1H, d, J=8.6 Hz), 7.19-7.21 (3H, m), 7.41 (1H, s), 7.56 (1H, t, J=8.6 Hz), 7.63-7.73 (3H, m), 8.11 (1H, t, J=7.8 Hz), 8.26 (1H, d, J=7.8 Hz), 8.85 (1H, d, J=4.7 Hz)
ESI-MS (m/e): 449 [M+H]

Example 31

5-(4-Cyano-phenoxy)-2-pyridin-2-yl-6-(1-oxy-pyridin-3-yloxy)-1H-benzimidazole

The entitled compound was obtained in the same method as in Example 1 or in accordance with the method or by combining it with an ordinary method but using 1-oxy-pyridin-3-yl and 4-cyano-phenol.
¹HNMR (CDCl₃) δ: 6.86-6.90 (2H, m), 7.11 (½H, ddd, J=7.3, 2.8, 1.5 Hz), 7.13 (½H, ddd, J=7.3, 2.8, 1.5 Hz), 7.18

(½H, dd, J=7.3, 4.8 Hz), 7.20 (½H, dd, J=7.3, 4.8 Hz), 7.36-7.41 (1H, m), 7.37 (½H, s), 7.44 (½H, s), 7.48-7.57 (3H, m), 7.60 (½H, s), 7.66 (½H, s), 8.20 (½H, d, J=2.8 Hz), 8.21 (½H, d, J=2.8 Hz), 8.30 (½H, dd, J=4.8, 1.5 Hz), 8.32 (½H, dd, J=4.8, 1.5 Hz), 8.37 (1H, d, J=7.0 Hz), 8.65-8.70 (1H, m)
ESI-MS (m/e): 422 [M+H]

Example 32

Production of 2-pyrazin-2-yl-5,6-bis(pyridin-3-yloxy)-1H-benzimidazole 7.7 mg of pyrazine-2-carboxylic acid and 20 mg of 1-(3-dimethylaminopropyl)-3-ethylcarbodiimide monohydrochloride were added to a pyridine (1 ml) solution of 15 mg of 4,5-bis(pyridin-3-yloxy)-benzene-1,2-diamine obtained in Example 1 (step 3), and the reaction liquid was stirred overnight at room temperature. The reaction liquid was diluted with ethyl acetate, washed with saturated sodium bicarbonate solution, water and saturated saline in order, and dried with anhydrous sodium sulfate. The solvent was evaporated away under reduced pressure, and the resulting residue was suspended in 1 ml of phosphorus oxychloride, and the reaction liquid was stirred overnight at 100° C. Phosphorus oxychloride was evaporated away under reduced pressure, and this was diluted with ethyl acetate, washed with saturated sodium bicarbonate solution and saturated saline in order, and dried with anhydrous sodium sulfate. The solvent was evaporated away under reduced pressure, and the residue was purified through partitioning thin-layer chromatography (Kieselgel™ 60F$_{254}$, Art 5744 (by Merck), chloroform/methanol=15/1+ 0.1% aqueous ammonia) to obtain the entitled compound as a yellow solid.
$^1$HNMR (CD$_3$OD) δ: 7.20-7.82 (6H, m), 8.11 (2H, s), 8.20-8.28 (2H, m), 8.67 (1H, s), 8.75 (1H, s), 9.47 (1H, s)
ESI-MS (m/e): 383 [M+H]

Example 33

5-(4-Methanesulfonyl-phenoxy)-2-pyrazin-2-yl-6-(pyridin-3-yloxy)-1H-benzimidazole The entitled compound was obtained in the same method as in Example 32 or in accordance with the method or by combining it with an ordinary method but using 4-(4-methanesulfonyl-phenoxy)-5-(pyridin-3-yloxy)-benzene-1,2-diamine obtained in Example 9.
$^1$HNMR (CDCl$_3$) δ: 2.91 (3H, s), 3.04 (3H, d, J=1.6 Hz), 6.96 (2H, d, J=9.0 Hz), 7.14-7.18 (1H, m), 7.19-7.25 (1H, m), 7.35 (½H, s), 7.41 (½H, s), 7.68 (½H, s), 7.73 (½H, s), 7.84 (2H, dd, J=9.0, 1.6 Hz), 8.24 (1H, dd, J=7.1, 2.7 Hz), 8.32-8.35 (1H, m), 8.59-8.62 (1H, m), 8.69 (1H, d, J=2.5 Hz), 9.63-9.64 (1H, m), 10.91 (1H×½, brs), 10.8 (1H×½, brs)
ESI-MS (m/e): 460 [M+H]

Example 34

5-(4-Dimethylcarbamoyl-phenoxy)-6-(2-methanesulfonyl-phenoxy)-2-pyrazin-2-yl-1H-benzimidazole The entitled compound was obtained in the same method as in Example 32 or in accordance with the method or by combining it with an ordinary method but using 4-(4-dimethylcarbamoyl-phenoxy)-5-(2-methanesulfonyl-phenoxy)-benzene-1,2-diamine obtained in Example 20.
$^1$HNMR (CDCl$_3$) δ: 2.95 (³⁄₂H, s), 2.99 (3H, brs), 3.05 (³⁄₂H, brs), 3.08 (3H, brs), 6.80-6.91 (3H, m), 6.89-6.95 (3H, s), 7.17-7.24 (1H, m), 7.20 (½H, s), 7.35-7.39 (2H, m), 7.35-7.39 (½H, m), 7.46-7.54 (1H, m), 7.66 (½H, s), 7.70 (½H, s), 8.02 (1H, d, J=7.8 Hz), 8.60 (1H, d, J=2.4 Hz), 8.67 (1H, dd, J=2.4, 2.0 Hz), 9.61 (1H, d, J=2.0 Hz), 10.65 (½H, brs), 10.74 (½H, brs)
ESI-MS (m/e): 530 [M+H]

Example 35

5-(2-Cyano-phenoxy)-2-pyrazin-2-yl-6-(4-methanesulfonyl-phenoxy)-1H-benzimidazole The entitled compound was obtained as a brown solid in the same method as in Example 32 or in accordance with the method or by combining it with an ordinary method but using 4-(2-cyano-phenoxy)-5-(4-methanesulfonyl-phenoxy)-benzene-1,2-diamine obtained in Example 17.
$^1$HNMR (CD$_3$OD) δ: 3.09 (3H, s), 6.91 (1H, d, J=7.8 Hz), 6.96-7.00 (2H, m), 7.15 (1H, td, J=7.6 Hz, 1.0 Hz), 7.54-7.58 (1H, m), 7.64 (1H, dd, J=1.6 Hz, 7.8 Hz), 7.72 (2H, d, J=3.5 Hz), 7.87 (2H, d, J=8.6 Hz), 8.77 (1H, d, J=2.7 Hz), 8.81-8.85 (1H, dd, J=1.6 Hz, 2.7 Hz), 8.52 (1H, d, J=1.6 Hz)
ESI-MS (m/e): 484 [M+H]

Example 36

5-(2-Methoxy-phenoxy)-6-(4-methanesulfonyl-phenoxy)-2-pyrazin-2-yl-1H-benzimidazole The entitled compound was obtained in the same method as in Example 32 or in accordance with the method or by combining it with an ordinary method but using 4-(2-methoxy-phenoxy)-5-(4-methanesulfonyl-phenoxy)-benzene-1,2-diamine obtained in Example 16.
$^1$HNMR (CDCl$_3$) δ: 3.04 (3H, s), 3.71 (3H, d, J=3.1 Hz), 6.86-6.97 (3H, m), 7.00 (½H, s), 7.06-7.14 (3H, m), 7.34 (½H, s), 7.36 (½H, s), 7.68 (½H, s), 7.85 (2H, dd, J=9.0, 3.1 Hz), 8.56-8.59 (1H, m), 8.65 (1H, dd, J=4.3, 2.7 Hz), 9.57-9.61 (1H, m), 10.24 (1H×½, brs), 10.34 (1H×½, brs)
ESI-MS (m/e): 489 [M+H]

Example 37

5-(4-Dimethylcarbamoyl-phenoxy)-6-(2-methanesulfonyl-phenoxy)-2-thiazol-2-yl-1H-benzimidazole The entitled compound was obtained in the same method as in Example 1 (step 4) or in accordance with the method or by combining it with an ordinary method but using 4-(4-dimethylcarbamoyl-phenoxy)-5-(2-methanesulfonyl-phenoxy)-benzene-1,2-diamine obtained in Example 20 and thiazol-2-carboxaldehyde.
$^1$HNMR (CDCl$_3$) δ: 2.94 (³⁄₂H, s), 2.96 (3H, brs), 3.05 (³⁄₂H, brs), 3.08 (3H, brs), 6.87-6.93 (3H, m), 7.13 (½H, brs), 7.16-7.23 (1H, m), 7.34-7.38 (2H, m), 7.45-7.53 (1H, m), 7.51 (½H, brs), 7.54-7.56 (1H, m), 7.62 (½H, s), 7.66 (½H, s), 7.94 (1H, d, J=3.1 Hz), 8.01 (1H, dd, J=7.8, 1.6 Hz)
ESI-MS (m/e): 535 [M+H]

Example 38

5-(2-Cyano-phenoxy)-2-pyridazin-3-yl-6-(4-methanesulfonyl-phenoxy)-1H-benzimidazole 3.3 mg of pyridazine-3-carboxylic acid, 15 mg of 1-hydroxybenzotriazole and 15 mg of 1-(3-dimethylaminopropyl)-3-ethylcarbodiimide monohydride were added in order to an N-methylpyrrolidone (0.3 ml) solution of 15 mg of 4-(2-cyano-phenoxy)-5-(4-methanesulfonyl-phenoxy)-benzene-1,2-diamine obtained in Example 17, and the reaction liquid was stirred overnight at room temperature. The reaction liquid was diluted with ethyl acetate, and washed with saturated sodium bicarbonate solution, and the solvent was evaporated away under reduced pressure. The resulting residue was dissolved in 0.2 ml of N-methylpyrrolidone, and 5 mg of ytterbium trifluoromethanesulfonate was added to it, and the reaction liquid was stirred overnight at 140° C. The reaction mixture was purified through reversed-phase middle-pressure liquid chromatography [ODS-AS-360-CC (by YMC), mobile phase: water-acetonitrile-0.1% trifluoroacetic acid]. The solvent of the resulting fraction was evaporated away under reduced pressure to obtain the entitled compound as a brown solid.

$^1$HNMR (CD$_3$OD) δ: 3.10 (3H, s), 6.92 (1H, d, J=7.6 Hz), 6.99 (2H, d, J=8.6 Hz), 7.20 (1H, t, J=7.6 Hz), 7.58 (1H, t, J=7.6 Hz), 7.64 (1H, d, J=7.6 Hz), 7.70-7.80 (2H, m), 7.87 (2H, d, J=8.6 Hz), 7.96-8.02 (1H, m), 8.58 (1H, brs), 9.36 (1H, brs)

ESI-MS (m/e): 484 [M+H]

Example 39

5-(2-Cyano-phenoxy)-2-[1,2,5]-thiadiazol-3-yl-6-(4-methanesulfonyl-phenoxy-1H-benzimidazole The entitled compound was obtained as a brown solid in the same method as in Example 38 or in accordance with the method or by combining it with an ordinary method but using [1,2,5]-thiadiazole-3-carboxylic acid.

$^1$HNMR (CD$_3$OD) δ: 3.09 (3H, s), 6.90 (1H, d, J=7.8 Hz), 6.98 (2H, d, J=8.6 Hz), 7.19 (1H, t, J=7.7 Hz), 7.56 (1H, t, J=7.8 Hz), 7.64 (1H, d, J=7.8 Hz), 7.72 (1H, s), 7.73 (1H, s), 7.87 (2H, d, J=8.6 Hz), 9.39 (1H, s)

ESI-MS (m/e): 490 [M+H]

Example 40

5-(2-Cyano-phenoxy)-2-(2H-[1,2,3]-triazol-4-yl)-6-(4-methanesulfonyl-phenoxy)-1H-benzimidazole The entitled compound was obtained as a brown solid in the same method as in Example 38 or in accordance with the method or by combining it with an ordinary method but using 2H-[1,2,3]-triazole-4-carboxylic acid.

$^1$HNMR (CD$_3$OD) δ: 3.12 (3H, s), 6.91 (1H, d, J=7.6 Hz), 6.98 (2H, d, J=8.6 Hz), 7.20 (1H, t, J=7.6 Hz), 7.56 (1H, t, J=7.6 Hz), 7.64 (1H, d, J=7.6 Hz), 7.70 (1H, d, J=2.7 Hz), 7.87 (2H, d, J=8.6 Hz), 8.52 (1H, brs)

ESI-MS (m/e): 473 [M+H]

Example 41

5-(2-Cyano-phenoxy)-2-furazan-3-yl-6-(4-methanesulfonyl-phenoxy)-1H-benzimidazole The entitled compound was obtained as a brown solid in the same method as in Example 38 or in accordance with the method or by combining it with an ordinary method but using furazane-3-carboxylic acid.

$^1$HNMR (CD$_3$OD) δ: 3.06 (3H, s), 6.84 (1H, d, J=7.8 Hz), 6.92 (2H, d, J=8.6 Hz), 7.15 (1H, t, J=7.8 Hz), 7.52 (1H, t, J=7.8 Hz), 7.57-7.62 (2H, m), 7.82 (2H, d, J=8.6 Hz)

ESI-MS (m/e): 474 [M+H]

Example 42

5-(2-Cyano-phenoxy)-2-(4H-[1,2,4]-triazol-3-yl)-6-(4-methanesulfonyl-phenoxy)-1H-benzimidazole The entitled compound was obtained as a pale yellow solid in the same method as in Example 38 or in accordance with the method or by combining it with an ordinary method but using [1,2,4]-triazole-3-carboxylic acid.

$^1$HNMR (CD$_3$OD) δ: 3.07 (3H, s), 6.92 (1H, d, J=7.8 Hz), 6.98 (2H, d, J=8.6 Hz), 7.19 (1H, t, J=7.8 Hz), 7.55 (1H, t, J=7.8 Hz), 7.63 (1H, d, J=7.8 Hz), 7.74 (2H, d, J=6.3 Hz), 7.85 (2H, d, J=8.6 Hz), 8.73 (1H, s)

ESI-MS (m/e): 473 [M+H]

Example 43

5-(2-Carbamoyl-phenoxy)-2-pyridin-2-yl-6-(pyridin-3-yloxy)-1H-benzimidazole

A 80% sulfuric acid solution of 3.5 mg of 5-(2-cyanophenoxy)-2-pyridin-2-yl-6-(pyridin-3-yloxy)-1H-benzimidazole obtained in Example 5 was stirred overnight at 50° C. The reaction mixture was purified through reversed-phase middle-pressure liquid chromatography [ODS-AS-360-CC (by YMC), mobile phase: water-acetonitrile-0.1% trifluoroacetic acid]. The solvent of the resulting fraction was evaporated away under reduced pressure to obtain the entitled compound as a colorless solid.

$^1$HNMR (CDCl$_3$) δ: 5.59 (1H, brs), 6.80 (1H, dd, J=8.4 Hz, 0.8 Hz), 7.01-7.48 (7H, m), 7.88 (1H, td, J=8.0 Hz, 2.0 Hz), 8.16 (1H, dd, J=8.4 Hz, 2.0 Hz), 8.21 (1H, s), 8.27-8.85 (1H, m), 8.38 (1H, d, J=8.0 Hz), 8.63 (1H, d, J=8.4 Hz)

ESI-MS (m/e): 424 [M+H]

Example 44

5-(4-Carbamoyl-phenoxy)-2-pyridin-2-yl-6-(pyridin-3-yloxy)-1H-benzimidazole

The entitled compound was obtained as a pale yellow solid in the same method as in Example 43 or in accordance with the method or by combining it with an ordinary method but using 5-(4-cyano-phenoxy)-2-pyridin-2-yl-6-(pyridin-3-yloxy)-1H-benzimidazole obtained in Example 7.

$^1$HNMR (CDCl$_3$) δ: 6.82 (2H, d, J=8.8 Hz), 7.13 (1H, ddd, J=8.4, 2.6, 1.5 Hz), 7.17 (1H, dd, J=8.4, 4.8 Hz), 7.13-7.20 (1H, m), 7.30-7.37 (1H, m), 7.38 (1H, ddd, J=7.7, 4.4, 1.1 Hz), 7.71 (2H, d, J=8.8 Hz), 7.87 (1H, ddd, J=7.7, 7.7, 1.8 Hz), 8.16 (1H, dd, J=2.6, 0.7 Hz), 8.25 (1H, dd, J=4.8, 1.5 Hz), 8.39 (1H, ddd, J=7.7, 1.1, 0.7 Hz), 8.61 (1H, ddd, J=4.4, 1.8, 0.7 Hz)

ESI-MS (m/e): 424 [M+H]

Example 45

5-(4-Carbamoyl-phenoxy)-6-(pyridin-3-yloxy)-2-thiazol-2-yl-1H-benzimidazole

The entitled compound was obtained in the same method as in Example 37 and Example 43 or in accordance with the method or by combining it with an ordinary method but using 4-(4,5-diamino-2-(pyridin-3-yloxy)-phenoxy)-benzonitrile obtained in Example 7.

$^1$HNMR (CDCl$_3$) δ: 6.01 (2H, brs), 6.82-6.86 (2H, m), 7.13 (1H, ddd, J=8.4, 2.9, 1.5 Hz), 7.18 (1H, dd, J=8.4, 4.6 Hz), 7.29 (½H, s), 7.30 (½H, s), 7.52-7.54 (1H, m), 7.92 (2H, d, J=8.8 Hz), 7.61 (½H, s), 7.64 (½H, s), 7.70-7.75 (2H, m), 7.92 (1H, d, J=2.9 Hz), 8.21 (1H, d, J=2.9 Hz), 8.29 (1H, dd, J=4.6, 1.5 Hz)

ESI-MS (m/e): 430 [M+H]

Example 46

5-(4-Carbamoyl-phenoxy)-2-pyridin-2-yl-6-(2-carbamoyl-phenoxy)-1H-benzimidazole

The entitled compound was obtained as a colorless solid in the same method as in Example 43 or in accordance with the method or by combining it with an ordinary method but using 5-(2-cyano-phenoxy)-2-pyridin-2-yl-6-(4-cyano-phenoxy)-1H-benzimidazole obtained in Example 28.

$^1$HNMR (CD$_3$OD) δ: 7.86 (2H, d, J=8.8 Hz), 7.13 (1H, t, J=7.6 Hz), 7.39 (1H, t, J=7.6 Hz), 7.45-7.74 (4H, m), 7.78 (2H, d, J=8.8 Hz), 7.91 (1H, d, J=7.6 Hz), 7.99 (1H, t, J=7.6 Hz), 8.30 (1H, d, J=7.6 Hz), 8.74 (1H, s)

ESI-MS (m/e): 466 [M+H]

Example 47

5-(3-Carbamoyl-phenoxy)-2-pyridin-2-yl-6-(2-carbamoyl-phenoxy)-1H-benzimidazole monotrifluoroacetate The entitled compound was obtained as a colorless solid in the same method as in Example 43 or in accordance with the method or by combining it with an ordinary method but using 5-(2-cyano-phenoxy)-2-pyridin-2-yl-6-(3-cyano-phenoxy)-1H-benzimidazole obtained in Example 29.

$^1$HNMR (CD$_3$OD) δ: 6.78-6.96 (1H, m), 6.96-7.08 (1H, m), 7.08-7.20 (1H, m), 7.30-7.70 (7H, m), 7.88-8.08 (2H, m), 8.29 (1H, d, J=7.6 Hz), 8.73 (1H, s)

ESI-MS (m/e): 466 [M+H]

Example 48

5-(4-Methanesulfonyl-phenoxy)-2-pyridin-2-yl-6-(2-carbamoyl-phenoxy)-1H-benzimidazole The entitled compound was obtained as a pale yellow solid in the same method as in Example 43 or in accordance with the method or by combining it with an ordinary method but using 5-(2-cyano-phenoxy)-2-pyridin-2-yl-6-(4-methanesulfonyl-phenoxy)-1H-benzimidazole obtained in Example 17.

$^1$HNMR (CD$_3$OD) δ: 3.12 (3H, s), 6.85 (1H, d, J=7.8 Hz), 6.98 (2H, d, J=8.6 Hz), 7.15 (1H, t, J=7.8 Hz), 7.42 (1H, t, J=7.8 Hz), 7.52 (1H, dd, J=4.3 Hz, 7.0 Hz), 7.64 (2H, brs), 7.83 (2H, d, J=8.6 Hz), 7.91 (1H, d, J=7.8 Hz), 8.01 (1H, dd, J=7.0 Hz, 7.8 Hz), 8.32 (1H, d, J=7.8 Hz), 8.76 (1H, d, J=4.3 Hz)

ESI-MS (m/e): 501 [M+H]

Example 49

5-(4-Methanesulfonyl-phenoxy)-2-pyrazin-2-yl-6-(2-carbamoyl-phenoxy)-1H-benzimidazole The entitled compound was obtained as a colorless solid in the same method as in Example 43 or in accordance with the method or by combining it with an ordinary method but using 5-(2-cyano-phenoxy)-2-pyrazin-2-yl-6-(4-methanesulfonyl-phenoxy)-1H-benzimidazole obtained in Example 35.

$^1$HNMR (CD$_3$OD) δ: 3.05 (3H, s), 5.80 (1H, brs), 6.82 (1H, d, J=7.8 Hz), 6.95-7.00 (3H, m), 7.17 (2H, q, J=8.2 Hz), 7.36-7.39 (2H, m), 7.76 (1H, d, J=7.8 Hz), 7.81-7.85 (2H, m), 8.15 (1H, d, J=7.8 Hz), 8.63 (1H, s), 8.72 (1H, s), 9.66 (1H, s), 10.80 (1H, brs)

ESI-MS (m/e): 502 [M+H]

Example 50

5-(4-Carbamoyl-phenoxy)-2-pyridin-2-yl-6-(1-oxy-pyridin-3-yloxy)-1H-benzimidazole The entitled compound was obtained in the same method as in Example 43 or in accordance with the method or by combining it with an ordinary method but using 5-(4-cyano-phenoxy)-2-pyridin-2-yl-6-(1-oxy-pyridin-3-yloxy)-1H-benzimidazole obtained in Example 31.

$^1$HNMR (CDCl$_3$) δ: 6.82-6.86 (2H, m), 7.15-7.26 (2H, m), 7.38-7.42 (1H, m), 7.41 (½H, s), 7.44 (½H, s), 7.54-7.58 (1H, m), 7.62 (½H, s), 7.65 (½H, s), 7.71-7.75 (2H, m), 8.12-8.16 (1H, m), 8.22-8.27 (1H, m), 8.37 (1H, d, J=7.0 Hz), 8.64-8.67 (1H, m),

ESI-MS (m/e): 440 [M+H]

Example 51

5-(3-Carbamoyl-phenoxy)-2-pyridin-2-yl-6-(pyridin-3-yloxy)-1H-benzimidazole

The entitled compound was obtained in the same method as in Example 43 or in accordance with the method or by combining it with an ordinary method but using 5-(3-cyano-phenoxy)-2-pyridin-2-yl-6-(pyridin-3-yloxy)-1H-benzimidazole obtained in Example 6.

$^1$HNMR (CDCl$_3$) δ: 7.07 (1H, ddd, J=0.8, 3.4, 10.3 Hz), 7.36 (1H, dd, J=1.9, 3.4 Hz), 7.40 (1H, t, J=10.3 Hz), 7.56 (1H, s), 7.57-7.62 (2H, m), 7.69 (1H, dd, J=7.2, 10.3 Hz), 7.73 (1H, s), 7.78 (1H, ddd, J=0.8, 3.8, 11.4 Hz), 8.16 (1H, dt, J=3.0, 11.0 Hz), 8.29 (1H, dt, J=0.4, 11.0 Hz), 8.37-8.41 (2H, m), 8.80 (1H, dt, J=0.4, 3.8 Hz)

ESI-MS (m/e): 424 [M+H]$^+$

Example 52

5-(2-Carbamoyl-phenoxy)-6-(4-dimethylcarbamoyl-phenoxy)-2-pyridin-2-yl-1H-benzimidazole The entitled compound was obtained in the same method as in Example 1 and Example 43 or in accordance with the method or by combining it with an ordinary method but using 4-fluoro-5-(2-cyano-phenoxy)-2-nitro-phenylamine obtained in Example 28 and 4-hydroxybenzoic acid dimethylamide.

$^1$HNMR (CDCl$_3$) δ: 2.98 (3H, brs), 3.07 (3H, brs), 5.72 (1H, brs), 6.76-6.83 (3H, m), 6.97 (½H, brs), 7.09 (½H, dd, J=7.7, 7.7 Hz), 7.11 (½H, dd, J=7.7, 7.7 Hz), 7.14 (½H, s), 7.30-7.35 (3H, m), 7.37-7.40 (1H, m), 7.67 (1H, d, J=7.7 Hz), 7.86 (1H, ddd, J=7.7, 7.7, 1.5 Hz), 8.12 (1H, dd, J=7.7, 1.8 Hz), 8.14 (1H, dd, J=7.7, 1.8 Hz), 8.38 (1H, d, J=7.7 Hz), 8.61-8.62 (1H, m), 10.99 (1H, brs)

ESI-MS (m/e): 494 [M+H]

Example 53

5-(2-Carbamoyl-phenoxy)-6-(4-dimethylcarbamoyl-henoxy)-2-pyridin-2-yl-1H-benzimidazole The entitled compound was obtained in the same method as in Example 37 and Example 43 or in accordance with the method or by combining it with an ordinary method but using 4-(2-cyano-phenoxy)-5-bis-(4-dimethylcarbamoyl-phenoxy)-benzene-1,2-diamine obtained in Example 52.

¹HNMR (CDCl₃) δ: 2.97 (3H, brs), 3.08 (3H, brs), 5.91 (½H, brs), 6.00 (½H, brs), 6.75-6.82 (3H, m), 6.93 (½H, brs), 7.07-7.13 (1H, m), 7.17 (1H, brs), 7.25 (½H, brs), 7.32 (2H, d, J=8.8 Hz), 7.53 (1H, d, J=2.9 Hz), 7.65 (2H, d, J=8.8 Hz), 7.37-7.40 (1H, m), 7.65 (1H, d, J=7.0 Hz), 7.92-7.93 (1H, m), 8.11 (½H, d, J=6.6 Hz), 8.13 (½H, d, J=6.6 Hz)

ESI-MS (m/e): 500 [M+H]

Example 54

5-(2-Carbamoyl-phenoxy)-2-pyridin-2-yl-6-(4-(2-(2,2,2-trifluoro-acetoxy)-ethyl)-phenoxy)-1H-benzimidazole monotrifluoroacetate In the same method as in Example 43 or in accordance with the method or by combining it with an ordinary method but using 5-(2-cyano-phenoxy)-2-pyridin-2-yl-6-(4-(2-hydroxyethyl)-phenoxy)-1H-benzimidazole obtained in Example 30, the reaction mixture was purified through reversed-phase middle-pressure liquid chromatography [ODS-AS-360-CC (by YMC), mobile phase: water-acetonitrile-0.1% trifluoroacetic acid]. The solvent of the resulting fraction was evaporated away under reduced pressure to obtain the entitled compound as a colorless solid.

¹HNMR (CD₃OD) δ: 2.94 (2H, t, J=6.7 Hz), 4.17 (2H, t, J=6.7 Hz), 6.84 (2H, d, J=8.6 Hz), 6.90 (1H, d, J=8.6 Hz), 7.19 (1H, d, J=8.6 Hz), 7.25 (1H, d, J=8.6 Hz), 7.41 (1H, s), 7.42-7.48 (1H, m), 7.58 (1H, s), 7.61-7.66 (1H, m), 8.09 (1H, t, J=7.8 Hz), 8.25 (1H, d, J=7.8 Hz), 8.83 (1H, d, J=4.7 Hz)

ESI-MS (m/e): 563 [M+H]

Example 55

5-(4-Carbamoyl-phenoxy)-6-(4-dimethylcarbamoyl-phenoxy)-2-pyridin-2-yl-1H-benzimidazole The entitled compound was obtained in the same method as in Example 1 and Example 43 or in accordance with the method or by combining it with an ordinary method but using 4-fluoro-5-(4-dimethylcarbamoyl-phenoxy)-2-nitro-phenylamine obtained in Example 18 and 4-hydroxy-benzonitrile.

¹HNMR (CDCl₃) δ: 2.97 (3H, brs), 3.08 (3H, brs), 6.80-6.86 (4H, m), 7.26-7.29 (2H, m), 7.31 (½H, s), 7.35 (½H, s), 7.38-7.41 (1H, m), 7.66-7.70 (3H, m), 7.86-7.91 (1H, m), 8.40 (1H, d, J=7.8 Hz), 8.65 (1H, d, J=4.7 Hz), 10.89 (1H, brs)

ESI-MS (m/e): 494 [M+H]

Example 56

5-(4-Methylcarbamoyl-phenoxy)-2-pyridin-2-yl-6-(pyridin-3-yloxy)-1H-benzimidazole 0.05 ml of a 40% methylamine/methanol solution was added to a methanol (1 ml) solution of 3.0 mg of 5-(4-methoxycarbonyl-2-pyridin-2-yl-6-(pyridin-3-yloxy)-1H-benzimidazole obtained in Example 10, and the reaction liquid was stirred overnight at room temperature. The solvent was evaporated away under reduced pressure, and this was purified through partitioning thin-layer chromatography (Kieselgel™ 60F₂₅₄, Art 5744 (by Merck), chloroform/methanol=20/1) to obtain the entitled compound.

¹HNMR (CDCl₃) δ: 2.96 (³⁄₂H, s), 2.97 (³⁄₂H, s), 6.80 (1H, d, J=8.4 Hz), 7.14-7.23 (2H, m), 7.36 (1H, brs), 7.40 (1H, dd, J=7.7, 4.7 Hz), 7.62 (1H, brs), 7.66 (2H, d, J=8.4 Hz), 7.90 (1H, dd, J=7.7, 7.7 Hz), 8.10 (1H, brs), 8.20 (1H, brs), 8.37 (1H, d, J=7.7 Hz), 8.63 (1H, d, J=4.7 Hz)

ESI-MS (m/e): 438 [M+H]

Example 57

5-(4-Methane-sulfonyl-phenoxy)-6-(2-methylcarbamoyl-phenoxy)-2-pyridin-2-yl-1H-benzimidazole The entitled compound was obtained in the same method as in Example 56 or in accordance with the method or by combining it with an ordinary method but using 5-(2-ethoxycarbonyl-phenoxy)-6-(4-methanesulfonyl-phenoxy)-2-pyridin-2-yl-1H-benzimidazole obtained in Example 14.

¹HNMR (CDCl₃) δ: 2.73 (³⁄₂H, s), 2.74 (³⁄₂H, s), 3.03 (3H, s), 6.74-6.79 (1H, m), 6.89-76.96 (2H, m), 7.01 (½H, brs), 7.09-7.15 (1H, m), 7.17 (½H, brs), 7.30 (½H, brs), 7.40 (½H, brs), 7.40-7.44 (1H, m), 7.72 (1H, s), 7.82 (2H, dd, J=8.2, 6.7 Hz), 7.88-7.93 (1H, m), 8.10-8.15 (1H, m), 8.41 (1H, d, J=6.8 Hz), 8.66 (1H, s), 11.09 (½H, brs), 11.12 (½H, brs)

ESI-MS (m/e): 515 [M+H]

Example 58

5-(4-Dimethylcarbamoyl-phenoxy)-6-(2-methylcarbamoyl-phenoxy)-2-pyridin-2-yl-1H-benzimidazole The entitled compound was obtained in the same method as in Example 56 or in accordance with the method or by combining it with an ordinary method but using 5-(2-ethoxycarbonyl-phenoxy)-6-(4-dimethylcarbamoyl-phenoxy)-2-pyridin-2-yl-1H-benzimidazole obtained in Example 24.

¹HNMR (CDCl₃) δ: 2.77 (3H, d, J=3.5 Hz), 2.99 (3H, brs), 3.08 (3H, brs), 6.75-6.86 (3H, m), 7.00-7.14 (1H, m), 7.15-7.27 (½H, m), 7.27-7.32 (2H, m), 7.27-7.32 (½H, m), 7.35-7.42 (2H, m), 7.69 (1H, s), 7.87-7.91 (1H, m), 8.11-8.17 (1H, m), 8.40 (1H, d, J=7.4 Hz), 8.66 (1H, s), 11.01 (1H, brs)

ESI-MS (m/e): 508 [M+H]

Example 59

5-(2-Methylcarbamoyl-phenoxy)-2-pyridin-2-yl-6-pyridin-3-yloxy)-1H-benzimidazole The entitled compound was obtained as a brown solid in the same method as in Example 1 and Example 56 or in accordance with the method or by combining it with an ordinary method but using 3-(2-fluoro-4-nitro-phenoxy)-pyridin obtained in Example 1 (step 2) and methyl 2-hydroxybenzoate.

¹HNMR (CDCl₃) δ: 2.70-8.80 (3H, m), 6.77 (1H, d, J=7.6 Hz), 7.25-7.44 (7H, m), 7.67 (1H, s), 7.82 (1H, t, J=7.6 Hz), 8.15 (1H, t, J=7.6 Hz), 8.18-8.26 (1H, m), 8.26-8.36 (1H, m), 8.38 (1H, d, J=7.6 Hz), 8.64 (1H, d, J=2.4 Hz), 10.6 (1H, brs)

ESI-MS (m/e): 438 [M+H]

Example 60

5-(4-Methanesulfonyl-phenoxy)-2-pyridin-2-yl-6-(2-(2H-tetrazol-5-yl)-phenoxy)-1H-benzimidazole monotrifluoroacetate 30 mg of sodium azide and 32 mg of magnesium chloride were added to a dimethylformamide (1 ml) solution of 30 mg of 5-(4-methanesulfonyl-phenoxy)-2-pyridin-2-yl-6-(2-cyano-phenoxy)-1H-benzimidazole obtained in Example 17, and the reaction liquid was stirred at 170° C. for 24 hours. The reaction mixture was purified through reversed-phase middle-pressure liquid chromatography [ODS-AS-360-CC (by YMC), mobile phase: water-acetonitrile-0.1% trifluoroacetic acid], and the solvent of the resulting fraction was evaporated away under reduced pressure to obtain the entitled compound as a yellow solid.

$^1$HNMR (CD$_3$OD) δ: 3.11 (3H, s), 6.75 (2H, d, J=8.6 Hz), 6.96 (1H, d, J=7.6 Hz), 7.29 (1H, t, J=7.6 Hz), 7.51 (1H, t, J=7.6 Hz), 7.62 (2H, d, J=8.6 Hz), 7.58-7.69 (1H, m), 7.73 (1H, s), 7.93 (1H, s), 8.13 (1H, d, J=7.6 Hz), 8.08-8.16 (1H, m), 8.33-8.38 (1H, m), 8.84-8.88 (1H, m)

ESI-MS (m/e): 526 [M+H]

Example 61

5-(4-Methanesulfonyl-phenoxy)-2-pyridin-2-yl-6-(2-(2-(N-hydroxycarbaminidoyl)-phenoxy)-1H-benzimidazole 0.1 ml of an aqueous 50% hydroxylamine solution was added to an ethanol (2 ml) solution of 25 mg of 5-(4-methanesulfonyl-phenoxy)-2-pyridin-2-yl-6-(2-cyano-phenoxy)-1H-benzimidazole obtained in Example 17, and the reaction liquid was stirred overnight at 50° C. The solvent was evaporated away under reduced pressure, and the resulting residue was purified through partitioning thin-layer chromatography (Kieselgel™ 60F$_{254}$, Art 5744 (by Merck), chloroform/methanol=5/1) to obtain the entitled compound as a colorless solid.

$^1$HNMR (CDCl$_3$) δ: 3.06 (3H, s), 5.12 (2H, s), 6.52 (1H, s), 6.80 (1H, d, J=7.6 Hz), 7.11 (2H, d, J=8.6 Hz), 7.28 (1H, t, J=7.6 Hz), 7.47 (1H, dd, J=7.8 Hz, 4.3 Hz), 7.66 (1H, d, J=7.6 Hz), 7.66 (1H, s), 7.89 (2H, d, J=8.6 Hz), 7.96 (1H, t, J=7.8 Hz), 8.55 (1H, d, J=7.8 Hz), 8.65 (1H, d, J=4.3 Hz)

ESI-MS (m/e): 516 [M+H]

Example 62

5-(4-Methanesulfonyl-phenoxy)-2-pyridin-2-yl-6-(2-(2-oxo-4,5-dihydro-[1,2,4]-oxadiazol-3-yl)-phenoxy)-1H-benzimidazole 10 mg of 1,1'-carbonyldiimidazole was added to an N-methylpyrrolidinone (0.25 ml) solution of 8 mg of 5-(2-(N-hydroxycarbaminidoyl)-phenoxy)-2-pyridin-2-yl-6-(4-methanesulfonyl-phenoxy)-1H-benzimidazole obtained in Example 61, and the reaction liquid was stirred at 70° C. for 4 hours. The reaction mixture was purified through reversed-phase middle-pressure liquid chromatography [ODS-AS-360-CC (by YMC), mobile phase: water-acetonitrile-0.1% trifluoroacetic acid], and the resulting fraction was diluted with ethyl acetate, washed with saturated sodium bicarbonate solution and saturated saline in order, and then dried with anhydrous sodium sulfate. The solvent was evaporated away under reduced pressure to obtain the entitled compound as a colorless solid.

$^1$HNMR (CDCl$_3$) δ: 3.12 (3H, s), 6.84 (2H, d, J=8.6 Hz), 6.82-6.88 (1H, m), 7.19 (1H, t, J=7.2 Hz), 7.41-7.47 (2H, m), 7.82 (2H, d, J=8.6 Hz), 7.91-7.97 (2H, m), 8.44 (1H, d, J=7.8 Hz), 8.69 (1H, d, J=4.3 Hz)

ESI-MS (m/e): 542 [M+H]

Example 63

5-(4-Methanesulfonyl-phenoxy)-2-pyridin-2-yl-6-(2-[1,2,4]-oxadiazol-3-yl-phenoxy)-1H-benzimidazole 0.5 ml of ethyl orthoformate was added to an N-methylpyrrolidinone (0.25 ml) solution of 8 mg of 5-(2-(N-hydroxycarbaminidoyl)-phenoxy)-2-pyridin-2-yl-6-(4-methanesulfonyl-phenoxy)-1H-benzimidazole obtained in Example 61, and the reaction liquid was stirred at 100° C. for 3 hours. The reaction mixture was purified through reversed-phase middle-pressure liquid chromatography [ODS-AS-360-CC (by YMC), mobile phase: water-acetonitrile-0.1% trifluoroacetic acid], and the solvent of the resulting fraction was evaporated away under reduced pressure, and this was purified through partitioning thin-layer chromatography (Kieselgel™ 60F$_{254}$, Art 5744 (by Merck), chloroform/methanol 10/1) to obtain the entitled compound as a yellow solid.

$^1$HNMR (CDCl$_3$) δ: 3.03 (3H, s), 6.85-6.97 (3H, m), 7.23 (1H, t, J=7.8 Hz), 7.40-7.45 (3H, m), 7.68-7.74 (3H, m), 7.91 (1H, t, J=7.8 Hz), 8.03 (1H, d, J=7.8 Hz), 8.42 (1H, d, J=7.8 Hz), 8.65-8.68 (2H, m)

ESI-MS (m/e): 526 [M+H]

Example 64

5-(Pyridin-3-yloxy)-2-pyridin-2-yl-6-(2-(5-methyl-[1,2,4]-oxadiazol-3-yl)-phenoxy)-1H-benzimidazole 0.3 ml of acetic anhydride was added to a pyridine (0.5 ml) solution of 20 mg of 5-(2-(N-hydroxycarbaminidoyl)-phenoxy)-2-pyridin-2-yl-6-(pyridin-3-yloxy)-1H-benzimidazole obtained in the same manner as in Example 61 but using 5-(2-cyano-phenoxy)-2-pyridin-2-yl-6-(pyridin-3-yloxy)-1H-benzimidazole obtained in Example 5, and the reaction liquid was stirred overnight at 60° C. The solvent was evaporated away under reduced pressure, and this was purified through partitioning thin-layer chromatography (Kieselgel™ 60F$_{254}$, Art 5744 (by Merck), chloroform/methanol=10/1) to obtain the entitled compound as a pale yellow solid.

$^1$HNMR (CDCl$_3$) δ: 6.80-7.00 (1H, m), 7.00-7.30 (4H, m), 7.30-7.44 (2H, m), 7.44-7.68 (1H, m), 7.86 (1H, td, J=7.6 Hz, 2.0 Hz), 7.97 (1H, dd, J=2.0 Hz, 7.6 Hz), 8.38 (1H, d, J=7.6 Hz), 8.60 (1H, d, J=4.8 Hz)

ESI-MS (m/e): 463 [M+H]

Example 65

5-(4-Methyl-pyridine-3-sulfonyl)-2-pyridin-2-yl-6-(pyridin-3-yloxy)-1H-benzimidazole 92 mg of OXONE and 0.1 ml of water were added to a tetrahydrofuran (1.5 ml) solution of 42 mg of 5-(2-methyl-pyridin-5-ylsulfanyl)-2-pyridin-2-yl-6-(pyridin-3-yloxy)-1H-benzimidazole obtained in Example 13, and the reaction liquid was stirred overnight at room temperature. The solvent was evaporated away under reduced pressure, and the resulting residue was purified through reversed-phase middle-pressure liquid chromatography [ODS-AS-360-CC (by YMC), mobile phase: water-acetonitrile-0.1% trifluoroacetic acid]. An aqueous solution of saturated sodium hydrogencarbonate was added to the resulting fraction, and this was extracted with chloroform, and dried with anhydrous magnesium sulfate. The solvent was evaporated away under reduced pressure to obtain the entitled compound.

$^1$HNMR (CDCl$_3$) δ: 2.63 (3H, s), 7.23 (1H, s), 7.32 (1H, d, J=7.6 Hz), 7.44-7.50 (3H, m), 7.93 (1H, t, J=7.6 Hz), 8.09-8.14 (1H, m), 8.28 (1H, d, J=2.8 Hz), 8.36-8.41 (2H, m), 8.60, 8.61 (tautomer, 1H, s), 8.68 (1H, d, J=4.8 Hz), 8.93, 8.95 (tautomer, 1H, d, J=2.0 Hz)

ESI-MS (m/e): 444 [M+H]

Example 66

5-(4-Methanesulfonyl-phenoxy)-2-(1-oxo-pyridin-2-yl)-6-(2-carbamoyl-phenoxy)-1H-benzimidazole 15 mg of metachloroperbenzoic acid was added to a chloroform (2 ml) solution of 8.0 mg of 5-(4-methanesulfonyl-phenoxy)-2-pyridin-2-yl-6-(2-carbamoyl-phenoxy)-1H-benzimidazole obtained in Example 48, and the reaction liquid was stirred at room temperature for 1 hour. The reaction solvent was evaporated away under reduced pressure, and the resulting residue was purified through reversed-phase middle-pressure liquid chromatography [ODS-AS-360-CC (by YMC), mobile phase: water-acetonitrile-0.1% trifluoroacetic acid]. The solvent of the resulting fraction was evaporated away under reduced pressure to obtain the entitled compound as a yellow solid.

$^1$HNMR (CD$_3$OD) δ: 3.12 (3H, s), 6.87 (1H, d, J=7.8 Hz), 7.00 (2H, d, J=7.8 Hz), 7.18 (1H, t, J=7.8 Hz), 7.43 (1H, t, J=7.8 Hz), 7.69-7.76 (2H, m), 7.84-7.86 (3H, m), 7.92 (1H, d, J=7.8 Hz), 8.52 (1H, d, J=7.0 Hz), 8.64 (1H, d, J=7.8 Hz)

ESI-MS (m/e): 517 [M+H]

Example 67

4-(2-Methoxy-phenoxy)-2-pyridin-2-yl-6-(pyridin-3-yloxy)-1H-benzimidazole (Step 1) Production of 5-fluoro-3-(2-methoxyphenoxy)-2-nitroaniline 528 mg of sodium hydride was added to a tetrahydrofuran (30 ml) solution of 1.64 g of 2-methoxyphenol with cooling with ice, and the reaction liquid was stirred for 30 minutes at the same temperature. Next, 1.91 g of 3,5-difluoro-2-nitroaniline, which had been produced according to the method described in Journal of Organic Chemistry, 1978, Vol. 43, No. 6, pp. 1241-1243, was added to it, and the reaction liquid was stirred for 2 days at room temperature. The reaction liquid was poured into water, extracted with ethyl acetate, and dried with anhydrous magnesium sulfate. The solvent was evaporated away under reduced pressure, and the resulting residue was purified through silica gel column chromatography (developing solvent: hexane/ethyl acetate=5/1 to 4/1) to obtain the entitled compound as an orange solid.

(Step 2) Production of 3-(2-methoxyphenoxy)-2-nitro-5-(pyridin-3-yloxy)-aniline 1.24 g of 3-hydroxypyridine and 5.42 g of potassium carbonate were added to a dimethylformamide (30 ml) solution of 3.03 g of 5-fluoro-3-(2-methoxyphenoxy)-2-nitroaniline, and the reaction liquid was stirred overnight at 90° C. The reaction liquid was diluted with ethyl acetate, washed with water and saturated saline in order, and then dried with anhydrous magnesium sulfate. The solvent was evaporated away under reduced pressure, and the resulting residue was purified through silica gel column chromatography (developing solvent: hexane/ethyl acetate=2/1 to 1/1 to 1/2) to obtain the entitled compound as an orange solid.

(Step 3) Production of 3-(2-methoxyphenoxy)-5-(pyridin-3-yloxy)-benzene-1,2-diamine 1 g of 20% palladium hydroxide-carbon catalyst was added to a methanol (20 ml) solution of 1.33 g of 3-(2-methoxyphenoxy)-2-nitro-5-(pyridin-3-yloxy)-aniline, and the reaction liquid was stirred for 4 hours in a hydrogen atmosphere. The catalyst was removed through filtration, the solvent was evaporated away under reduced pressure, and the resulting residue was purified through silica gel column chromatography (developing solvent: hexane/ethyl acetate=1/2 to ethyl acetate) to obtain the entitled compound as a pale orange oily substance.

(Step 4) Production of 4-(2-methoxy-phenoxy)-2-pyridin-2-yl-6-(pyridin-3-yloxy)-1H-benzimidazole 0.026 ml of pyridin-2-carboxaldehyde was added to a nitrobenzene (0.5 ml) solution of 59 mg of 3-(2-methoxyphenoxy)-5-(pyridin-3-yloxy)-benzene-1,2-diamine at 120° C., and the reaction liquid was stirred for 1 hour at the same temperature. The reaction mixture was purified through silica gel column chromatography (developing solvent: hexane/ethyl acetate=1/1 to ethyl acetate to chloroform/methanol=20/1). The solvent of the resulting fraction was evaporated away under reduced pressure, and the resulting residue was purified through partitioning thin-layer chromatography (Kieselgel™ 60F$_{254}$, Art 5744 (by Merck), chloroform/methanol=20/1) to obtain the entitled compound as a pale yellow solid.

$^1$HNMR(CDCl$_3$) δ: 3.79 and 3.83 (total 3H, each s), 6.20-7.40 (9H, m), 7.80-7.88 (1H, m), 8.24-8.65 (4H, m), 10.68-10.94 (1H, m)

ESI-MS (m/e): 411 [M+H]

Example 68

4-(4-Fluoro-phenoxy)-2-pyridin-2-yl-6-(pyridin-3-yloxy)-1H-benzimidazole 18.6 mg of pyrazine-2-carboxylic acid and 57.5 mg of 1-ethyl-3-(3'-dimethylaminopropyl)-carbodiimide hydrochloride were added to a pyridine (2 ml) solution of 46.7 mg of 3-(4-fluorophenoxy)-5-(pyridin-3-yloxy)-benzene-1,2-diamine produced in the same manner as in Example 67 but using 4-fluorophenol and 3-hydroxypyridine, and the reaction liquid was stirred overnight, and then pyridine was evaporated away under reduced pressure. The residue was diluted with ethyl acetate, washed with water, and dried with anhydrous magnesium sulfate. The solvent was evaporated away under reduced pressure to obtain a mixture of amides as a yellow oily substance. The resulting mixture of amides was dissolved in 3 ml of toluene, and 28 mg of p-toluenesulfonic acid monohydrate was added to it, and the reaction liquid was stirred overnight at 120° C. The reaction liquid was diluted with ethyl acetate, washed with aqueous saturated sodium bicarbonate, and dried with anhydrous magnesium sulfate. The solvent was evaporated away under reduced pressure, and the resulting residue was purified through partitioning thin-layer chromatography (Kieselgel™ 60F$_{254}$, Art 5744 (by Merck), chloroform/methanol=20/1) to obtain the entitled compound as a yellow solid.

$^1$HNMR (CDCl$_3$) δ: 6.35 and 6.53 (total 1H, each d, J=2.0 Hz), 6.77-7.31 (7H, m), 8.32-8.40 (2H, m), 8.54 and 8.56 (total 1H, each d, J=1.8 Hz), 8.61 and 8.64 (total 1H, each d, J=2.6 Hz), 9.59 and 9.69 (total 1H, each d, J=1.5 Hz), 10.60 (1H, brs)

ESI-MS (m/e): 400 [M+H]

Example 69

6-(4-Methoxy-phenoxy-4-(1-methyl-1H-imidazol-2-ylsulfanyl)-2-pyridin-2-yl-1H-benzimidazole The entitled compound was obtained as a pale brown solid in the same method as in Example 67 or in accordance with the method or by combining it with an ordinary method but using 1-methyl-1H-imidazole-2-thiol and 4-methoxyphenol in order.
$^1$HNMR (CDCl$_3$) δ: 3.73 and 3.74 (total 3H, each s), 3.81 (3H, s), 6.31-7.39 (9H, m), 7.78-7.88 (1H, m), 8.30 and 8.41 (total 1H, each d, J=7.8 Hz), 8.59 and 8.73 (total 1H, each d, J=4.5 Hz)
ESI-MS (m/e): 430 [M+H]

Example 70

6-(4-Methoxy-phenoxy)-2-pyridin-2-yl-4-(pyridin-2-ylsulfanyl)-1H-benzimidazole

The entitled compound was obtained as a pale yellow solid in the same method as in Example 67 or in accordance with the method or by combining it with an ordinary method but using pyridine-2-thiol and 4-methoxyphenol in order.
$^1$HNMR (CDCl$_3$) δ: 3.80 and 3.81 (total 3H, each s), 6.86-7.50 (10H, m), 7.75-7.88 (1H, m), 8.32-8.62 (3H, m)
ESI-MS (m/e): 427 [M+H]

Example 71

6-(3-Methoxy-phenoxy)-4-(2-methoxy-phenoxy)-2-pyridin-2-yl-1H-benzimidazole

The entitled compound was obtained as a white solid in the same method as in Example 67 or in accordance with the method or by combining it with an ordinary method but using 3-(2-methoxyphenoxy)-2-nitro-5-(pyridin-3-yloxy)-aniline obtained in Example 67 (step 2) and 3-methoxyphenol.
$^1$HNMR (CDCl$_3$) δ: 3.75 (3H, s), 3.79 and 3.84 (total 3H, each s), 6.24-7.23 (10H, m), 7.29-7.39 (1H, m), 7.79-7.89 (1H, m), 8.37 and 8.53 (total 1H, each d, J=7.5 Hz), 8.56-8.65 (1H, m), 10.53-10.83 (1H, m)
ESI-MS (m/e): 440 [M+H]

Example 72

4-(2-Methoxy-phenoxy)-6-(pyridin-3-yloxy)-2-thiazol-2-yl-1H-benzimidazole

The entitled compound was obtained as a yellow solid in the same method as in Example 67 or in accordance with the method or by combining it with an ordinary method but using 3-(2-methoxyphenoxy)-5-(pyridin-3-yloxy)-benzene-1,2-diamine obtained in Example 67 (step 3) and 2-thiazolecarboxaldehyde.
$^1$HNMR (CDCl$_3$) δ: 3.78 and 3.82 (total 3H, each s), 6.20 and 6.44 (total 1H, each s), 6.68-7.28 (7H, m), 7.43-7.53 (1H, m), 7.88-7.98 (1H, m), 8.29-8.41 (2H, m), 10.90-11.10 (1H, m)
ESI-MS (m/e): 417 [M+H]

Example 73

4-(2-Fluoro-phenoxy)-2-pyridin-2-yl-6-(pyridin-3-yloxy)-1H-benzimidazole

The entitled compound was obtained in the same method as in Example 67 or in accordance with the method or by combining it with an ordinary method but using 2-fluorophenol.
$^1$HNMR (CDCl$_3$) δ: 6.18-6.78 (2H, m), 6.98-7.42 (8H, m), 7.72-7.90 (1H, m), 8.22-8.66 (3H, m), 11.3 (1H, brs)
ESI-MS (m/e): 399 [M+H]

Example 74

4-(4-Fluoro-phenoxy)-2-pyridin-2-yl-6-(pyridin-3-yloxy)-1H-benzimidazole

The entitled compound was obtained in the same method as in Example 67 or in accordance with the method or by combining it with an ordinary method but using 4-fluorophenol.
$^1$HNMR (CDCl$_3$) δ: 6.39 (1H, d, J=2.1 Hz), 6.84 (1H, d, J=2.1 Hz) 7.17-7.25 (4H, m), 7.39 (1H, dd, J=8.4, 4.7 Hz), 7.45 (1H, ddd, J=8.4, 2.8, 1.5 Hz), 7.50 (1H, dd, J=7.7, 4.9 Hz), 7.96 (1H, ddd, J=7.7, 7.7, 1.8 Hz), 8.22 (1H, d, J=7.7 Hz), 8.33 (1H, dd, J=4.7, 1.5 Hz), 8.38 (1H, d, J=2.8 Hz), 8.69 (1H, ddd, J=4.9, 1.8, 1.1 Hz)
ESI-MS (m/e): 399 [M+H]

Example 75

4-(3-Fluoro-phenoxy)-2-pyridin-2-yl-6-(pyridin-3-yloxy)-1H-benzimidazole

The entitled compound was obtained as a pale brown solid in the same method as in Example 67 or in accordance with the method or by combining it with an ordinary method but using 3-fluorophenol.
$^1$HNMR (CDCl$_3$) δ: 6.47-6.98 (5H, m), 7.19-7.39 (4H, m), 7.78-7.89 (1H, m), 8.29-8.48 (3H, m), 8.58 (1H, s)
ESI-MS (m/e): 399 [M+H]

Example 76

2-Pyridin-2-yl-4,6-bis(pyridin-3-yloxy)-1H-benzimidazole

The entitled compound was obtained in the same method as in Example 67 or in accordance with the method or by combining it with an ordinary method but using 3-hydroxypyridine.
$^1$HNMR (CD$_3$OD) δ: 7.07 (1H, d, J=2.0 Hz), 7.30 (1H, d, J=2.0 Hz), 7.54 (1H, ddd, J=7.6 Hz, 4.8 Hz, 1.2 Hz), 7.85-7.95 (2H, m), 7.98 (1H, td, J=7.6 Hz, 2.0 Hz), 8.10-8.40 (2H, m), 8.22 (1H, d, J=8.8 Hz), 8.48-8.60 (2H, m), 8.66 (1H, d, J=0.2 Hz), 8.70-8.82 (2H, m)
ESI-MS (m/e): 382 [M+H]

Example 77

4-(2-Cyano-phenoxy)-2-pyridin-2-yl-6-(pyridin-2-yloxy)-1H-benzimidazole

The entitled compound was obtained in the same method as in Example 67 or in accordance with the method or by combining it with an ordinary method but using 2-cyanophenol and 2-hydroxypyridine in order.
$^1$HNMR (CDCl$_3$) δ: 6.60-7.40 (3H, m), 6.92 (1H, d, J=8.0 Hz), 6.99 (1H, dd, J=6.4 Hz, 5.2 Hz), 7.15 (1H, t, J=8.0 Hz), 7.46 (1H, dd, J=8.0 Hz, 2.4 Hz), 7.58-7.70 (2H, m), 7.70-7.90 (1H, m), 8.18 (1H, dd, J=4.8 Hz, 1.2 Hz), 8.38 (1H, d, J=8.0 Hz), 8.60 (1H, d, J=4.0 Hz), 10.40-11.00 (1H, m)
ESI-MS (m/e): 406 [M+H]

Example 78

4-(2-Cyano-phenoxy)-2-pyridin-2-yl-6-(pyridin-3-yloxy)-1H-benzimidazole

The entitled compound was obtained in the same method as in Example 67 or in accordance with the method or by combining it with an ordinary method but using 2-cyanophenol.

$^1$HNMR (CDCl$_3$) δ: 6.55 (½H, s), 6.69 (½H, s), 6.70-7.55 (8H, m), 7.58-7.72 (1H, m), 7.76-7.80 (1H, m), 8.26-8.48 (3H, m), 8.55-8.64 (1H, m), 10.8-11.4 (1H, m)

ESI-MS (m/e): 406 [M+H]

Example 79

4-(2-Methoxycarbonyl-phenoxy)-2-pyridin-2-yl-6-(pyridin-3-yloxy)-1H-benzimidazole ditrifluoroacetate The entitled compound was obtained in the same method as in Example 67 or in accordance with the method or by combining it with an ordinary method but using methyl 2-hydroxybenzoate.

$^1$HNMR (CD$_3$OD) δ: 3.70 (3H, s), 6.38 (1H, s), 7.14 (1H, s), 7.34 (1H, dJ=7.6 Hz), 7.39 (1H, t, J=7.6 Hz), 7.50-7.75 (3H, m), 7.75-7.88 (1H, m), 7.99 (1H, dd, J=7.6 Hz, 1.2 Hz), 8.07 (1H, t, J=7.6 Hz), 8.27-8.58 (3H, m), 8.72-8.88 (1H, m)

ESI-MS (m/e): 439 [M+H]

Example 80

4-(2-Acetyl-phenoxy)-2-(pyridin-2-yl)-6-(pyridin-3-yloxy)-1H-benzimidazole

The entitled compound was obtained in the same method as in Example 67 or in accordance with the method or by combining it with an ordinary method but using methyl 2-hydroxyacetophenone.

$^1$HNMR (CDCl$_3$) δ: 2.68 (3H, s), 6.58 (1H, d, J=2.3 Hz), 7.19 (1H, dd, J=1.2, 8.2 Hz), 7.31 (1H, dd, J=1.2, 7.5 Hz), 7.35 (1H, dd, J=1.0, 7.5 Hz), 7.53-7.62 (2H, m), 7.69 (1H, dd, J=4.7, 7.8 Hz), 7.76-7.82 (1H, m), 7.87 (1H, dd, J=1.0, 8.2 Hz), 8.10 (1H, t, J=7.8 Hz), 8.50-8.52 (1H, m), 8.54 (1H, d, J=2.3 Hz), 8.62 (1H, d, J=7.0 Hz), 8.74 (1H, d, J=4.7 Hz)

ESI-MS (m/e): 423 [M+H]

Example 81

4-(1-Methyl-2-oxo-1,2-dihydro-pyridin-3-yloxy)-2-pyridin-2-yl-6-(pyridin-3-yloxy)-1H-benzimidazole The entitled compound was obtained as a pale yellow solid in the same method as in Example 67 or in accordance with the method or by combining it with an ordinary method but using 3-hydroxy-1-methyl-1H-pyridin-2-one.

$^1$HNMR (CDCl$_3$) δ: 3.62 (3H, s), 6.02-7.40 (8H, m), 7.84 (1H, t, J=7.2 Hz), 8.33 (1H, d, J=4.4 Hz), 8.33-8.50 (2H, m), 8.52-8.70 (1H, m)

ESI-MS (m/e): 412 [M+H]

Example 82

6-(4-Dimethylcarbamoyl-phenoxy)-4-(1-methyl-2-oxo-1,2-dihydro-pyridin-3-yloxy)-2-pyridin-2-yl-1H-benzimidazole The entitled compound was obtained as a white solid in the same method as in Example 67 or in accordance with the method or by combining it with an ordinary method but using 3-hydroxy-1-methyl-1H-pyridin-2-one and 4-hydroxy-N,N-dimethylbenzamide in order.

$^1$HNMR (CDCl$_3$) δ: 3.03 and 3.09 (total 6H, each s), 3.60 and 3.64 (total 3H, each s), 6.08-6.15 (1H, m), 6.42 and 6.64 (total 1H, each s), 6.82-7.41 (8H, m), 7.80-7.88 (1H, m), 8.36 and 8.45 (total 1H, each d, J=8.2 Hz), 8.59 and 8.64 (total 1H, each d, J=4.5 Hz)

ESI-MS (m/e): 482 [M+H]

Example 83

4-(2-Difluoromethoxy-pyridin-3-yloxy)-6-(4-dimethylcarbamoyl-phenoxy)-2-pyridin-2-yl-1H-benzimidazole The entitled compound was obtained as a pale yellow solid in the same method as in Example 67 or in accordance with the method or by combining it with an ordinary method but using 2-difluoromethoxy-3-hydroxypyridine and 4-hydroxy-N,N-dimethylbenzamide in order.

$^1$HNMR (CDCl$_3$) δ: 3.02 and 3.09 (total 6H, each s), 6.36 and 6.48 (total 1H, each s), 6.84-7.67 (9H, m), 7.83 and 7.88 (total 1H, each t, J=7.8 Hz), 7.99 and 8.00 (total 1H, each d, J=5.0 Hz), 8.40 and 8.42 (total 1H, each d, J=8.4 Hz), 8.61 and 8.64 (total 1H, each d, J=4.3 Hz)

ESI-MS (m/e): 518 [M+H]

Example 84

6-(2-Methyl-pyridin-5-ylsulfanyl)-2-(pyridin-2-yl)-4-(pyridin-3-yloxy)-1H-benzimidazole The entitled compound was obtained in the same method as in Example 67 or in accordance with the method or by combining it with an ordinary method but using 3-hydroxypyridine and 6-methylpyridine-3-thiol in order.

$^1$HNMR (CDCl$_3$) δ: 2.52 (3H, s), 6.66-6.80 (1H, brs), 7.05 (1H, d, J=8.0 Hz), 7.20-7.28 (3H, m), 7.32 (1H, m), 7.49 (1H, dd, J=2.0 Hz, 8.0 Hz), 7.81 (1H, t, J=7.6 Hz), 8.32-8.40 (3H, m), 8.44 (1H, d, J=2.0 Hz), 8.52 (1H, d, J=4.8 Hz), 11.70-12.0 (1H, brs)

ESI-MS (m/e): 412 [M+H]

Example 85

4-(2-Cyano-phenoxy)-2-(pyridin-2-yl)-6-(4-dimethylcarbamoyl-phenoxy)-1H-benzimidazole The entitled compound was obtained in the same method as in Example 67 or in accordance with the method or by combining it with an ordinary method but using 2-cyanophenol and 4-hydroxy-N,N-dimethylbenzamide in order.

$^1$HNMR (CDCl$_3$) δ: 3.05 (3H, s), 3.18 (3H, s), 6.62 (1H, s), 6.92-7.08 (3H, m), 7.00 (2H, d, J=8.8 Hz), 7.10-7.20 (2H, m), 7.36-7.50 (4H, m), 7.40 (2H, d, J=8.8 Hz), 7.63 (1H, d, J=6.3 Hz), 7.89 (1H, t, J=7.8 Hz), 8.44 (1H, d, J=7.8 Hz), 8.61 (1H, d, J=3.9 Hz)

ESI-MS (m/e): 476 [M+H]

Example 86

4-(2-Fluoro-phenoxy)-2-(pyridin-2-yl)-6-(4-dimethylcarbamoyl-phenoxy)-1H-benzimidazole The entitled compound was obtained in the same method as in Example 67 or in accordance with the method or by combining it with an ordinary method but using 2-fluorophenol and 4-hydroxy-N,N-dimethylbenzamide in order.

$^1$HNMR (CDCl$_3$) δ: 3.02 (3H, s), 3.10 (3H, s), 6.39 (1H, s), 6.92-7.00 (3H, m), 6.96 (2H, d, J=9.0 Hz), 7.10-7.24 (4H, m), 7.36-7.42 (3H, m), 7.39 (2H, d, J=9.0 Hz), 7.88 (1H, d, J=7.7 Hz), 8.51 (1H, d, J=8.0 Hz), 8.63 (1H, d, J=7.7 Hz)

ESI-MS (m/e): 469 [M+H]

Example 87

4-(2-Fluoro-phenoxy)-2-(pyridin-2-yl)-6-(4-methanesulfonyl-phenoxy)-1H-benzimidazole The entitled compound was obtained in the same method as in Example 67 or in accordance with the method or by combining it with an ordinary method but using 2-fluorophenol and 4-(methanesulfonyl)-phenol in order.

$^1$HNMR (CDCl$_3$) δ: 3.08 (3H, s), 6.44 (1H, s), 7.08 (2H, d, J=9.0 Hz), 7.18-7.57 (5H, m), 7.59 (1H, dd, J=3.1, 8.2 Hz), 7.90 (2H, d, J=9.0 Hz), 8.06 (1H, t, J=7.6 Hz), 8.64 (1H, d, J=8.2 Hz), 8.71 (1H, d, J=7.6 Hz)

ESI-MS (m/e): 476 [M+H]

Example 88

4-(2-(1-Hydroxy-ethyl-phenoxy)-2-(pyridin-2-yl)-6-(4-dimethylcarbamoyl-phenoxy)-1H-benzimidazole The entitled compound was obtained in the same method as in Example 67 or in accordance with the method or by combining it with an ordinary method but using 2-(1-hydroxy-ethyl)-phenol and 4-hydroxy-N,N-dimethylbenzamide in order.

$^1$HNMR (CDCl$_3$) δ: 1.48 (3H, d, J=6.4 Hz), 3.05 (3H, s), 3.10 (3H, s), 5.26 (1H, q, J=6.4 Hz), 6.34 (1H, s), 7.04 (2H, d, J=9.0 Hz), 7.05-7.10 (2H, m), 7.29-7.33 (2H, m), 7.44 (2H, d, J=9.0 Hz), 7.57 (1H, dd, J=4.7, 7.6 Hz), 7.68 (1H, dd, J=2.0, 7.4 Hz), 8.04 (1H, dt, J=1.6, 7.8 Hz), 8.37 (1H, d, J=7.8 Hz), 8.80 (1H, d. J=4.7 Hz)

ESI-MS (m/e): 495 [M+H]

Example 89

4-(2-Methanesulfonyl-phenoxy)-2-(pyridin-2-yl)-6-(4-dimethylcarbamoyl-phenoxy)-1H-benzimidazole The entitled compound was obtained in the same method as in Example 67 or in accordance with the method or by combining it with an ordinary method but using 2-(methanesulfonyl)-phenol and 4-hydroxy-N,N-dimethylbenzamide in order.

$^1$HNMR (CDCl$_3$) δ: 3.06 (3H, s), 3.14 (3H, s), 3.49 (3H, s), 7.03 (1H, d, J=2.0 Hz), 7.11 (2H, d, J=8.8 Hz), 7.22 (1H, d, J=8.0 Hz), 7.32-7.40 (2H, m), 7.42 (1H, d, J=2.0 Hz), 7.48 (2H, d, J=9.0 Hz), 7.57 (1H, dd, J=4.9, 7.8 Hz), 7.63 (1H, dd, J=1.8, 7.9 Hz), 8.00 (1H, dt, J=1.6, 7.8 Hz), 8.14 (1H, dd, J=1.8, 8.0 Hz), 8.52 (1H, d. J=8.0 Hz), 8.75 (1H, d, J=4.9 Hz)

ESI-MS (m/e): 529 [M+H]

Example 90

4-(2-Acetyl-phenoxy)-2-(pyridin-2-yl)-6-(4-dimethylcarbamoyl-phenoxy)-1H-benzimidazole The entitled compound was obtained in the same method as in Example 67 or in accordance with the method or by combining it with an ordinary method but using 2-hydroxy-acetophenone and 4-hydroxy-N,N-dimethylbenzamide in order.

$^1$HNMR (CDCl$_3$) δ: 2.68 (3H, s), 3.10 (3H, s), 3.20 (3H, s), 6.67 (1H, s), 7.05 (2H, d, J=8.2 Hz), 7.15-7.22 (2H, m), 7.35 (1H, t, J=7.0 Hz), 7.45 (2H, d, J=8.2 Hz), 7.55 (1H, t, J=7.0 Hz), 7.60-7.64 (1H, m), 7.86 (1H, d, J=7.4 Hz), 8.08-8.14 (1H, m), 8.64 (1H, d, J=7.4 Hz), 8.75-8.77 (1H, m)

ESI-MS (m/e): 493 [M+H]

Example 91

4-(2-Dimethylcarbamoyl-phenoxy)-2-(pyridin-2-yl)-6-(4-dimethylcarbamoyl-phenoxy)-1H-benzimidazole The entitled compound was obtained in the same method as in Example 67 or in accordance with the method or by combining it with an ordinary method but using 2-hydroxy-N,N-dimethylbenzamide and 4-hydroxy-N,N-dimethylbenzamide in order.

$^1$HNMR (CDCl$_3$) δ: 2.99 (3H, s), 3.06 (6H, s), 3.17 (3H, s), 6.91-6.94 (1H, m), 7.04 (2H, d, J=8.6 Hz), 7.06-7.10 (1H, m), 7.17 (1H, t, J=7.4 Hz), 7.28-7.39 (4H, m), 7.42 (2H, d, J=8.6 Hz), 7.84 (1H, t, J=7.8 Hz), 8.41 (1H, d, J=7.8 Hz), 8.68 (1H, d, J=3.9 Hz)

ESI-MS (m/e): 522 [M+H]

Example 92

4-(2,5-Difluoro-phenoxy)-2-(pyridin-2-yl)-6-(4-dimethylcarbamoyl-phenoxy)-1H-benzimidazole The entitled compound was obtained in the same method as in Example 67 or in accordance with the method or by combining it with an ordinary method but using 2,5-difluorophenol and 4-hydroxy-N,N-dimethylbenzamide in order.

$^1$HNMR (CDCl$_3$) δ: 3.02 (3H, s), 3.14 (3H, s), 6.52-6.55 (1H, m), 6.90-6.99 (2H, m), 7.02 (2H, d, J=8.2 Hz), 7.10 (1H, d, J=2.0 Hz), 7.16-7.24 (1H, m), 7.42 (2H, d, J=8.2 Hz), 7.54-7.60 (1H, m), 8.06 (1H, dt, J=1.6, 7.8 Hz), 8.61 (1H, d, J=7.8 Hz), 8.72 (1H, d, J=4.7 Hz)

ESI-MS (m/e): 487 [M+H]

Example 93

4-(2,4-Difluoro-phenoxy)-2-(pyridin-2-yl)-6-(4-dimethylcarbamoyl-phenoxy)-1H-benzimidazole The entitled compound was obtained in the same method as in Example 67 or in accordance with the method or by combining it with an ordinary method but using 2,4-difluorophenol and 4-hydroxy-N,N-dimethylbenzamide in order.

$^1$HNMR (CDCl$_3$) δ: 3.00 (3H, s), 3.09 (3H, s), 6.31 (1H, s), 6.99 (1H, s), 7.02 (2H, d, J=8.6 Hz), 7.10-7.25 (2H, m), 7.28-7.40 (1H, m), 7.43 (2H, d, J=8.6 Hz), 7.49-7.52 (1H, m), 7.98 (1H, d, J=7.8 Hz), 8.34 (1H, d, J=7.9 Hz), 8.74 (1H, d, J=3.9 Hz)

ESI-MS (m/e): 487 [M+H]

Example 94

4-(2,6-Difluoro-phenoxy-2-(pyridin-2-yl)-6-(4-dimethylcarbamoyl-phenoxy)-1H-benzimidazole The entitled compound was obtained in the same method as in Example 67 or in accordance with the method or by combining it with an ordinary method but using 2,6-difluorophenol and 4-hydroxy-N,N-dimethylbenzamide in order.

$^1$HNMR (CDCl$_3$) δ: 3.02 (3H, s), 3.14 (3H, s), 6.39 (1H, s), 7.00 (2H, d, J=8.6 Hz), 7.06-7.18 (3H, m), 7.20-7.25 (1H, m), 7.41 (2H, d, J=8.6 Hz), 7.48-7.51 (1H, m), 7.99 (1H, dt, J=1.6, 7.8 Hz), 8.59 (1H, d, J=8.2 Hz), 8.70 (1H, d, J=4.3 Hz)

ESI-MS (m/e): 487 [M+H]

Example 95

4-(2-Methoxy-phenoxy)-2-(pyridin-2-yl)-6-(4-methanesulfonyl-phenoxy)-1H-benzimidazole The entitled compound was obtained in the same method as in Example 71 or in accordance with the method or by combining it with an ordinary method but using 4-(methanesulfonyl)phenol.

$^1$HNMR (CDCl$_3$) δ: 3.03 (3H, s), 3.79 (3H, s), 6.32 (1H, s), 6.92-6.99 (1H, m), 7.00 (1H, s), 7.06 (2H, d, J=8.6 Hz), 7.10-7.22 (3H, m), 7.38-7.43 (1H, m), 7.83 (2H, d, J=8.6 Hz), 7.90 (1H, t, J=7.8 Hz), 8.50 (1H, d, J=7.8 Hz), 8.64 (1H, d, J=4.7 Hz)

ESI-MS (m/e): 488 [M+H]

Example 96

6-(4-Dimethylcarbamoyl-phenoxy)-4-(1-ethyl-2-oxo-1,2-dihydro-pyridin-3-yloxy)-2-pyridin-2-yl-1H-benzimidazole The entitled compound was obtained as a pale yellow solid in the same method as in Example 67 or in accordance with the method or by combining it with an ordinary method but using 1-ethyl-3-hydroxy-1H-pyridin-2-one and 4-hydroxy-N,N-dimethylbenzamide in order.

$^1$HNMR (CDCl$_3$) δ: 1.38 (3H, t, J=6.8 Hz), 3.02 and 3.09 (total 6H, each s), 4.06 (2H, q, J=6.8 Hz), 6.15 (1H, t, J=7.0 Hz), 6.40-7.42 (9H, m), 7.78-7.86 (1H, m), 8.32-8.42 (1H, m), 8.57-8.66 (1H, m)

ESI-MS (m/e): 496 [M+H]

Example 97

6-(6-Methyl-pyridin-3-ylphenyl)-4-(4-methyl-4H-[1,2,4]triazol-3-ylsulfanyl-2-(pyridin-2-yl)-1H-benzimidazole The entitled compound was obtained in the same method as in Example 67 or in accordance with the method or by combining it with an ordinary method but using 4-methyl-4H-[1,2,4]triazole-3-thiol and 6-methyl-pyridine-3-thiol in order.

$^1$HNMR (CDCl$_3$) δ: 2.55 (3H, s), 3.71 (3H, s), 7.17 (1H, d, J=8.0 Hz), 7.20-7.24 (1H, brs), 7.42-7.46 (1H, m), 7.59 (1H, dd, J=2.4 Hz, 8.0 Hz), 7.66-7.68 (1H, brs), 7.91 (1H, t, J=8.0 Hz), 8.32-8.38 (3H, m), 8.70 (1H, d, J=4.8 Hz)

ESI-MS (m/e): 432 [M+H]

Example 98

4-(4-Fluoro-phenoxy)-2-(5-methyl-isoxazol-3-yl)-6-(pyridin-3-yloxy)-1H-benzimidazole The entitled compound was obtained as a white solid in the same method as in Example 68 or in accordance with the method or by combining it with an ordinary method but using 5-methylisoxazole-3-carboxylic acid.

$^1$HNMR (DMSO-d6) δ: 2.50 (3H, s), 6.40 (1H, s), 6.80 (1H, s), 6.82 (1H, brs), 7.14-7.24 (4H, m), 7.38 (1H, dd, J=8.2, 4.7 Hz), 7.44 (1H, d, J=7.7 Hz), 8.32 (1H, d, J=4.7 Hz), 8.36 (1H, d, J=2.5 Hz)

ESI-MS (m/e): 403 [M+H]

Example 99

4-(4-Fluoro-phenoxy)-2-(1-methyl-1H-imidazol-4-yl)-6-(pyridin-3-yloxy)-1H-benzimidazole The entitled compound was obtained as a pale yellow solid in the same method as in Example 68 or in accordance with the method or by combining it with an ordinary method but using 1-methyl-1H-imidazole-4-carboxylic acid.

$^1$HNMR (DMSO-d6) δ: 3.72 (3H, s), 6.38 (1H, d, J=1.8 Hz), 6.81 (1H, d, J=1.8 Hz), 7.05-7.13 (2H, m), 7.17 (2H, t, J=8.8 Hz), 7.36-7.43 (2H, m), 7.75 (1H, s), 7.78 (1H, d, J=1.1 Hz), 8.28 (1H, s), 8.35 (1H, d, J=2.2 Hz)

ESI-MS (m/e): 402 [M+H]

Example 100

4-(4-Fluoro-phenoxy)-2-(3-methyl-[1,2,4]thiadiazol-5-yl)-6-(pyridin-3-yloxy)-1H-benzimidazole monotrifluoroacetate The entitled compound was obtained as a brown solid in the same method as in Example 68 or in accordance with the method or by combining it with an ordinary method but using 3-methyl[1,2,4]thiadiazole-5-carboxylic acid produced according to the method of EP 0726260 or by combining it with an ordinary method.

$^1$HNMR (DMSO-d6) δ: 2.70 (3H, s), 6.44 (1H, d, J=2.2 Hz), 6.87 (1H, s), 7.15-7.27 (4H, m), 8.39 (1H, dd, J=4.5, 1.5 Hz), 8.44 (1H, d, J=2.5 Hz)

ESI-MS (m/e): 420 [M+H]

Example 101

4-(4-Fluoro-phenoxy)-2-isoxazol-3-yl-6-(pyridin-3-yloxy)-1H-benzimidazole

The entitled compound was obtained in the same method as in Example 68 or in accordance with the method or by combining it with an ordinary method but using isoxazole-3-carboxylic acid.

$^1$HNMR (CD$_3$OD) δ: 6.41 (1H, d, J=2.4 Hz), 7.01 (1H, d, J=2.4 Hz), 7.02-7.20 (5H, m), 7.51 (1H, dd, J=4.4 Hz, 8.4 Hz), 7.59 (1H, dd, J=2.4 Hz, 8.4 Hz), 8.32 (1H, d, J=4.4 Hz), 8.35 (1H, d, J=2.4 Hz), 8.84 (1H, d, J=2.4 Hz)

ESI-MS (m/e): 389 [M+H]

Example 102

4-(4-Fluoro-phenoxy)-2-pyrimidin-4-yl-6-(pyridin-3-yloxy)-1H-benzimidazole

The entitled compound was obtained in the same method as in Example 68 or in accordance with the method or by combining it with an ordinary method but using pyrimidine-4-carboxylic acid.

$^1$HNMR (CDCl$_3$) δ: 2.60 (3H, s), 6.98-7.40 (8H, m), 8.30-8.50 (2H, m), 8.63 (1H, s), 10.40-11.00 (1H, m)
ESI-MS (m/e): 400 [M+H]

Example 103

4-(4-Fluoro-phenoxy-2-pyrimidin-2-yl-6-(pyridin-3-yloxy)-1H-benzimidazole

The entitled compound was obtained in the same method as in Example 68 or in accordance with the method or by combining it with an ordinary method but using pyrimidine-2-carboxylic acid.

$^1$HNMR (CD$_3$OD) δ: 6.42 (1H, s), 6.98 (1H, s), 7.10-7.30 (5H, m), 7.36-7.60 (2H, m), 8.22-8.42 (2H, m), 8.90-9.10 (1H, m), 9.20 (1H, s)
ESI-MS (m/e): 400 [M+H]

Example 104

4-(4-Fluoro-phenoxy)-2-(1H-imidazol-2-yl)-6-(pyridin-3-yloxy)-1H-benzimidazole

The entitled compound was obtained in the same method as in Example 68 or in accordance with the method or by combining it with an ordinary method but using 1H-imidazole-2-carboxylic acid.

$^1$HNMR (CD$_3$OD) δ: 6.44 (1H, d, J=2.0 Hz), 7.00 (1H, d, J=2.0 Hz), 7.05-7.18 (4H, m), 7.25 (2H, s), 7.39 (1H, dd, J=3.2 Hz, 8.4 Hz), 7.42-7.50 (1H, m), 8.26 (1H, dd, J=1.6 Hz, 4.4 Hz), 8.29 (1H, d, J=3.2 Hz)
ESI-MS (m/e): 388 [M+H]

Example 105

4-(4-Fluoro-phenoxy)-2-(1-methyl-1H-imidazol-2-yl)-6-(pyridin-3-yloxy)-1H-benzimidazole The entitled compound was obtained in the same method as in Example 68 or in accordance with the method or by combining it with an ordinary method but using 1-methyl-1H-imidazole-2-carboxylic acid.

$^1$HNMR (CDCl$_3$) δ: 3.98-4.38 (3H, m), 6.38-6.60 (1H, m), 6.60-6.80 (1H, m), 6.80-7.40 (8H, m), 8.20-8.44 (2H, m)
ESI-MS (m/e): 402 [M+H]

Example 106

4-(4-Fluoro-phenoxy)-6-(pyridin-3-yloxy)-2-[1,2,4]thiadiazol-5-yl-1H-benzimidazole The entitled compound was obtained as a pale yellow oily substance in the same method as in Example 68 or in accordance with the method or by combining it with an ordinary method but using [1,2,4]thiadiazole-5-carboxylic acid produced in the method of Reference Example 1.

$^1$HNMR (CD$_3$OD) δ: 6.42 (1H, s), 6.90-7.23 (5H, m), 7.39-7.50 (2H, m), 8.25-8.32 (2H, m), 8.86 (1H, s)
ESI-MS (m/e): 406 [M+H]

Example 107

4-(2,6-Difluoro phenoxy)-2-(pyrazin-2-yl)-6-(4-methanesulfonyl-phenoxy)-1H-benzimidazole The entitled compound was obtained in the same method as in Example 68 or in accordance with the method or by combining it with an ordinary method but using 2,6-difluorophenol and 4-(methanesulfonyl)phenol in order.

$^1$HNMR (CDCl$_3$) δ: 3.03 (3H, s), 6.28 (1H, s), 7.08 (1H, s), 7.17 (2H, d, J=9.4 Hz), 7.19-7.24 (2H, m), 7.30-7.40 (1H, m), 7.93 (2H, d, J=9.4 Hz), 8.70-8.75 (1H, m), 8.77-8.82 (1H, m), 9.55-9.60 (1H, m)
ESI-MS (m/e): 495 [M+H]

Examples 108-1, 108-2

4-(2-Oxo-1,2-dihydro-pyridin-3-yloxy)-2-pyridin-2-yl-6-(pyridin-3-yloxy)-1H-benzimidazole, and 4-(2-methoxy-pyridin-3-yloxy)-2-pyridin-2-yl-6-(pyridin-3-yloxy)-1H-benzimidazole The entitled compounds were obtained in the same method as in Example 68 or in accordance with the method or by combining it with an ordinary method but using 3-hydroxy-2-methoxypyridine, 3-hydroxypyridine and picolinic acid in order.

4-(2-Oxo-1,2-dihydro-pyridin-3-yloxy)-2-pyridin-2-yl-6-(pyridin-3-yloxy)-1H-benzimidazole $^1$HNMR (CDCl$_3$) δ: 6.10-7.35 (8H, m), 7.77-7.84 (1H, m), 8.30-8.41 (3H, m), 8.53 (1H, d, J=4.4 Hz)
ESI-MS (m/e): 398 [M+H]

4-(2-Methoxy-pyridin-3-yloxy)-2-pyridin-2-yl-6-(pyridin-3-yloxy)-1H-benzimidazole $^1$HNMR (CDCl$_3$) δ: 3.95 and 3.99 (total 3H, each s), 6.25 and 6.45 (total 1H, each s), 6.80-7.45 (6H, m), 7.79-7.90 (1H, m), 8.00 (1H, d, J=1.5 Hz), 8.30-8.63 (4H, m)
ESI-MS (m/e): 412 [M+H]

Examples 109, 109-2

6-(4-Dimethylcarbamoyl-phenoxy)-4-(2-methoxy-pyridin-3-yloxy)-2-pyridin-2-yl-1H-benzimidazole, and 6-(4-dimethylcarbamoyl-phenoxy)-4-(2-oxo-1,2-dihydro-pyridin-3-yloxy)-2-pyridin-2-yl-1H-benzimidazole The entitled compounds were obtained in the same method as in Examples 108-1 and 108-2 or in accordance with the method or by combining it with an ordinary method but using 3-hydroxy-2-methoxypyridine, 4-hydroxy-N,N-dimethylbenzamide and picolinic acid in order.

6-(4-Dimethylcarbamoyl-phenoxy)-4-(2-methoxy-pyridin-3-yloxy)-2-pyridin-2-yl-1H-benzimidazole $^1$HNMR (CDCl$_3$) δ: 3.03 and 3.08 (total 6H, each s), 3.95 and 4.00 (total 3H, each s), 6.27 and 6.47 (total 1H, each d, J=1.8 Hz), 6.80-7.45 (8H, m), 7.80-7.91 (1H, m), 7.98-8.03

(1H, m), 8.38 and 8.48 (total 1H, each d, J=7.8 Hz), 8.61 and 8.64 (total 11H, each d, J=4.8 Hz)
ESI-MS (m/e): 482 [M+H]

6-(4-Dimethylcarbamoyl-phenoxy)-4-(2-oxo-1,2-dihydro-pyridin-3-yloxy)-2-pyridin-2-yl-1H-benzimidazole $^1$HNMR (CDCl$_3$) δ: 3.03 and 3.08 (total 6H, each s), 6.18 and 6.23 (total 1H, each t, J=7.0 Hz), 6.52 and 6.73 (total 1H, each d, J=1.8 Hz), 6.80-7.42 (8H, m), 7.79 and 7.84 (total 1H, each t, J=7.8 Hz), 8.37 and 8.40 (total 1H, each d, J=7.8 Hz), 8.56 and 8.57 (total 1H, each d, J=5.0 Hz)
ESI-MS (m/e): 468 [M+H]

Example 110

4-(2-Carbamoyl-phenoxy)-2-pyridin-2-yl-6-(pyridin-3-yloxy)-1H-benzimidazole ditrifluoroacetate The entitled compound was obtained in the same method as in Example 43 or in accordance with the method or by combining it with an ordinary method but using 4-(2-cyano-phenoxy)-2-pyridin-2-yl-6-(pyridin-3-yloxy)-1H-benzimidazole obtained in Example 78.
$^1$HNMR (CD$_3$OD) δ: 6.61 (1H, d, J=2.0 Hz), 7.19 (1H, d, J=8.0 Hz), 7.22 (1H, s), 7.31 (1H, td, J=7.6 Hz, 1.2 Hz), 7.48-7.60 (2H, m), 7.72-7.80 (1H, m), 7.83 (1H, dd, J=7.6 Hz, 1.2 Hz), 7.87-7.95 (1H, m), 8.03 (1H, td, J=8.0 Hz, 1.2 Hz), 8.01 (1H, dd, J=7.6 Hz, 1.2 Hz), 8.45 (1H, d, J=5.2 Hz), 8.48-8.54 (1H, m), 8.76-8.84 (1H, m)
ESI-MS (m/e): 424 [M+H]

Example 111

4-(2-Carbamoyl-phenoxy)-2-(pyridin-2-yl)-6-(4-dimethylcarbamoyl-phenoxy)-1H-benzimidazole The entitled compound was obtained in the same method as in Example 110 or in accordance with the method or by combining it with an ordinary method but using 4-(2-cyano-phenoxy)-2-(pyridin-2-yl)-6-(4-dimethylcarbamoyl-phenoxy)-1H-benzimidazole obtained in Example 85.
$^1$HNMR (CDCl$_3$) δ: 2.99 (3H, s), 3.08 (3H, s), 6.56 (1H, s), 6.86-6.92 (1H, m), 6.95 (2H, J=8.9 Hz), 7.04-7.08 (2H, m), 7.30-7.38 (4H, m), 7.36 (2H, d, J=8.9 Hz), 7.52 (1H, d, J=7.6 Hz), 7.80 (1H, t, J=7.9 Hz), 8.36 (1H, d, J=7.9 Hz), 8.52 (1H, d, J=3.7 Hz)
ESI-MS (m/e): 494 [M+H]

Example 112

4-(2-(N-hydroxycarbamimidoyl)-phenoxy)-2-(pyridin-2-yl)-6-(4-dimethylcarbamoyl-phenoxy)-1H-benzimidazole The entitled compound was obtained in the same method as in Example 61 or in accordance with the method or by combining it with an ordinary method but using 4-(2-cyano-phenoxy)-2-(pyridin-2-yl)-6-(4-dimethylcarbamoyl-phenoxy)-1H-benzimidazole obtained in Example 85.
$^1$HNMR (CDCl$_3$) δ: 3.02 (3H, s), 3.16 (3H, s), 6.61 (1H, d, J=2.0 Hz), 6.95 (1H, d, J=2.0 Hz), 6.97 (2H, d, J=8.6 Hz), 7.14-7.22 (2H, m), 7.38 (2H, d, J=8.6 Hz), 7.52 (1H, dd, J=4.9, 7.6 Hz), 7.56-7.62 (1H, m), 7.63-7.67 (1H, m), 7.97 (1H, dt, J=1.6, 7.8 Hz), 8.48 (1H, d, J=7.8 Hz), 8.68 (1H, d, J=4.9 Hz)
ESI-MS (m/e): 509 [M+H]

Example 113

4-(2-(5-Methyl-[1,2,4]-oxadiazol-3-yl)-phenoxy)-2-(pyridin-2-yl)-6-(4-dimethylcarbamoyl-phenoxy)-1H-benzimidazole The entitled compound was obtained in the same method as in Example 64 or in accordance with the method or by combining it with an ordinary method but using 4-(2-(N-hydroxycarbamimidoyl)-phenoxy)-2-(pyridin-2-yl)-6-(4-dimethylcarbamoyl-phenoxy)-1H-benzimidazole obtained in Example 112.
$^1$HNMR (CDCl$_3$) δ: 2.70 (3H, s), 3.02 (3H, s), 3.15 (3H, s), 6.91 (1H, s), 7.04 (2H, d, J=8.6 Hz), 7.30-7.38 (3H, m), 7.44 (2H, d, J=8.6 Hz), 7.50-7.58 (2H, m), 7.95 (1H, d, J=7.8 Hz), 8.02 (1H, t, J=7.8 Hz), 8.63 (1H, d, J=8.6 Hz), 8.71 (1H, d, J=4.7 Hz)
ESI-MS (m/e): 533 [M+H]

Example 114

4-(2-(5-Oxo-4,5-dihydro-[1,2,4]-oxadiazol-3-yl)-phenoxy)-2-(pyridin-2-yl)-6-(4-dimethylcarbamoyl-phenoxy)-1H-benzimidazole The entitled compound was obtained in the same method as in Example 62 or in accordance with the method or by combining it with an ordinary method but using 4-(2-(N-hydroxycarbamimidoyl)-phenoxy)-2-(pyridin-2-yl)-6-(4-dimethylcarbamoyl-phenoxy)-1H-benzimidazole obtained in Example 112.
$^1$HNMR (CDCl$_3$) δ: 3.04 (3H, s), 3.15 (3H, s), 6.74 (1H, s), 6.99 (2H, d, J=8.6 Hz), 7.10 (1H, s), 7.28-7.36 (2H, m), 7.44 (2H, d, J=8.6 Hz), 7.50-7.58 (2H, m), 7.89 (1H, d, J=7.8 Hz), 8.00-8.07 (1H, m), 8.56-8.64 (2H, m)
ESI-MS (m/e): 535 [M+H]

Example 115

4-(4-Fluoro-phenoxy)-2-(pyrazol-1-yl)-6-(pyridin-3-yloxy)-1H-benzimidazole (Step 1) Production of 4-(4-fluoro-phenoxy)-6-(pyridin-3-yloxy)-1H-benzimidazole-2-thiol 0.06 ml of carbon disulfide and 54 mg of potassium hydroxide were added to an ethanol (2.0 ml) solution of 273 mg of 3-(4-fluoro-phenoxy)-5-(pyridin-3-yloxy)-benzene-1,2-diamine obtained in Example 68, and the reaction liquid was stirred overnight at 80° C. The reaction liquid was diluted with ethyl acetate, washed with water and saturated saline in order, and dried with anhydrous magnesium sulfate. The solvent was evaporated away under reduced pressure to obtain the entitled compound.

(Step 2) Production of (4-(4-fluoro-phenoxy)-6-(pyridin-3-yloxy)-1H-benzimidazol-2-yl)-hydrazine 1.0 ml of hydrazine monohydrate was added to 130 mg of 4-(4-fluoro-phenoxy)-6-(pyridin-3-yloxy)-1H-benzimidazole-2-thiol, and the reaction liquid was stirred overnight at 130° C. The reaction liquid was diluted with ethyl acetate, washed with water and saturated saline in order, and dried with anhydrous magnesium sulfate. The solvent was evaporated away under reduced pressure, and the resulting residue was purified through partitioning thin-layer chromatography (Kieselgel™ 60F$_{254}$, Art 5744 (by Merck), hexane/ethyl acetate=1/1) to obtain the entitled compound.

(Step 3) Production of 4-(4-fluoro-phenoxy)-2-(pyrazol-1-yl)-6-(pyridin-3-yloxy)-1H-benzimidazole 0.012 ml of tetramethoxypropane was added to an ethanol (0.3 ml) solution of 8.3 mg of (4-(4-fluoro-phenoxy)-6-(pyridin-3-yloxy)-1H-benzimidazol-2-yl)-hydrazine, and the reaction liquid was stirred overnight at 80° C. The reaction solvent was evaporated away under reduced pressure, and the resulting residue was purified through partitioning thin-layer chromatography (Kieselgel™ 60F$_{254}$, Art 5744 (by Merck), chloroform/methanol=9/1) to obtain the entitled compound.

$^1$HNMR (CDCl$_3$) δ: 6.36 (1H, d, J=2.6 Hz), 6.48-6.51 (2H, m), 6.77 (1H, d, J=2.6 Hz), 7.05 (2H, d, J=6.9 Hz), 7.11-7.18 (1H, m), 7.22-7.28 (2H, m), 7.72-7.75 (1H, m), 8.30-8.38 (2H, m), 8.48 (1H, d, J=3.8 Hz)

ESI-MS (m/e): 388 [M+H]

Example 116

4-(4-Fluoro-phenoxy)-6-(pyridin-3-yloxy)-2-[1,2,4]triazol-1-yl-1H-benzimidazole (Step 1) Production of 4-(4-fluoro-phenoxy)-2-methylsulfanyl-6-(pyridin-3-yloxy)-1H-benzimidazole 30 mg of potassium carbonate and 0.014 ml of methyl iodide were added to a dimethylformamide (1.0 ml) solution of 78 mg of 4-(4-fluoro-phenoxy)-6-(pyridin-3-yloxy)-1H-benzimidazole-2-thiol produced in Example 115, and the reaction liquid was stirred at 0° C. for 30 minutes. The reaction liquid was diluted with ethyl acetate, washed with water and saturated saline in order, and dried with anhydrous magnesium sulfate. The solvent was evaporated away under reduced pressure to obtain the entitled compound.

(Step 2) Production of 4-(4-fluoro-phenoxy)-2-methanesulfonyl-6-(pyridin-3-yloxy)-1H-benzimidazole 84 mg of metachloroperbenzoic acid was added to a chloroform (1.0 ml) solution of 80 mg of 4-(4-fluoro-phenoxy)-2-methylsulfanyl-6-(pyridin-3-yloxy)-1H-benzimidazole, and the reaction liquid was stirred at 0° C. for 30 minutes. The reaction liquid was diluted with ethyl acetate, washed with water and saturated saline in order, and dried with anhydrous magnesium sulfate. The solvent was evaporated away under reduced pressure, and the resulting residue was purified through partitioning thin-layer chromatography (Kieselgel™ 60F$_{254}$, Art 5744 (by Merck), ethyl acetate) to obtain the entitled compound.

(Step 3) Production of 4-(4-fluoro-phenoxy)-6-(pyridin-3-yloxy)-2-[1,2,4]triazol-1-yl-1H-benzimidazole 5.0 mg of sodium hydride was added to a dimethylformamide (0.5 ml) solution of 16 mg of 4-(4-fluoro-phenoxy)-2-methanesulfonyl-6-(pyridin-3-yloxy)-1H-benzimidazole, and then 10.4 mg of [1,2,4]triazole was added to it, and the reaction liquid was stirred overnight at 160° C. The reaction liquid was diluted with ethyl acetate, washed with water and saturated saline in order, and dried with anhydrous magnesium sulfate. The solvent was evaporated away under reduced pressure, and the resulting residue was purified through partitioning thin-layer chromatography (Kieselgel™ 60F$_{254}$, Art 5744 (by Merck), ethyl acetate) to obtain the entitled compound.

$^1$HNMR (CDCl$_3$) δ: 6.42 (1H, s), 7.03-7.15 (3H, m), 7.19 (1H, s), 7.27-7.32 (3H, m), 8.12 (1H, s), 8.32-8.38 (2H, m), 9.15 (1H, s)

ESI-MS (m/e): 389 [M+H]

Example 117

5-Chloro-2-pyridin-2-yl-4,6-bis-(pyridin-3-yloxy)-1H-benzimidazole (Step 1) Production of 3-chloro-2,4-bis(pyridin-3-yloxy)-nitrobenzene 628 mg of 3-hydroxypyridine and 1.82 g of potassium carbonate were added to a dimethylformamide (8 ml) solution of 679 mg of [1,2,3]-trichloro-4-nitrobenzene, and the reaction liquid was stirred at 100° C. for 2 hours. The reaction liquid was diluted with ethyl acetate, washed with water and saturated saline, and dried with anhydrous magnesium sulfate. The solvent was evaporated away under reduced pressure, and the resulting residue was purified through silica gel column chromatography (developing solvent: hexane/ethyl acetate=1/1 to ethyl acetate) to obtain the entitled compound as a pale yellow oily substance.

(Step 2) Production of 3-chloro-2,4-bis(pyridin-3-yloxy)aniline 963 mg of ammonium chloride and 503 mg of iron powder were added to a suspension of 1.2 g of 3-chloro-2,4-bis(pyridin-3-yloxy)-nitrobenzene in 15 ml of methanol and 7.5 ml of water, and the reaction liquid was heated under reflux for 3 hours. The reaction liquid was filtered, and the solvent was evaporated away under reduced pressure. The residue was diluted with ethyl acetate, washed with water, and dried with anhydrous magnesium sulfate. The solvent was evaporated away under reduced pressure, and the resulting residue was purified with silica gel column chromatography (developing solvent: hexane/ethyl acetate=1/1 to ethyl acetate) to obtain the entitled compound as a pale yellow oily substance.

(Step 3) Production of 3-chloro-2,4-bis(pyridin-3-yloxy)-6-nitroaniline 315 mg of potassium nitrate was added to a trifluoroacetic acid (20 ml) solution of 891 mg of 3-chloro-2,4-bis(pyridin-3-yloxy)aniline, and the reaction liquid was stirred overnight at room temperature, and then the solvent was evaporated away under reduced pressure. The residue was diluted with ethyl acetate, washed with aqueous saturated sodium bicarbonate and saturated saline in order, and dried with anhydrous magnesium sulfate. The solvent was evaporated away under reduced pressure, and the resulting residue was purified with silica gel column chromatography (developing solvent: hexane/ethyl acetate=1/1 to ethyl acetate) to obtain the entitled compound as an orange solid.

(Step 4) Production of 4-chloro-3,5-bis(pyridin-3-yloxy)-benzene-1,2-diamine 128 mg of ammonium chloride and 67 mg of iron powder were added to a suspension of 143 mg of 3-chloro-2,4-bis(pyridin-3-yloxy)-6-nitroaniline in 8 ml of methanol and 4 ml of water, and the reaction liquid was heated under reflux for 2 hours. The reaction liquid was filtered, and the solvent was evaporated away under reduced pressure. The residue was diluted with ethyl acetate, washed with water, and dried with anhydrous magnesium sulfate. The solvent was evaporated away to obtain the entitled compound as a pale brown solid.

(Step 5) Production of 5-chloro-2-pyridin-2-yl-4,6-bis(pyridin-3-yloxy)-1H-benzimidazole In the same manner as in Example 68 but using 4-chloro-3,5-bis(pyridin-3-yloxy)-benzene-1,2-diamine and picolinic acid, the entitled compound was obtained as a pale yellow solid.
$^1$HNMR (DMSO-d6) δ: 7.18-7.62 (6H, m), 7.92 and 7.99 (total 1H, each dt, J=8.0, 1.8 Hz), 8.10-8.44 (5H, m), 8.66-8.72 (1H, m)
ESI-MS (m/e): 416,418 [M+H]

Example 118

5-Methyl-2-pyridin-2-yl-4,6-bis-(pyridin-3-yloxy-1H-benzimidazole

The entitled compound was obtained as a pale yellow solid in the same method as in Example 117 or in accordance with the method or by combining it with an ordinary method but using 2,4-difluoro-3-methylnitrobenzene produced according to the method described in Chemical and Pharmaceutical Bulletin, 1982, Vol. 30, No. 10, pp. 3530-3543.
$^1$HNMR (DMSO-d6) δ: 2.03 and 2.10 (total 3H, each s), 7.01-7.50 (6H, m), 7.88 and 7.87 (total 1H, each dt, J=7.7, 1.6 Hz), 8.06-8.41 (5H, m), 8.63-8.70 (1H, m)
ESI-MS (m/e): 396 [M+H]

Example 119

5-Fluoro-2-pyridin-2-yl-4,6-bis-(pyridin-3-yloxy)-1H-benzimidazole

The entitled compound was obtained as a pale yellow solid in the same method as in Example 117 or in accordance with the method or by combining it with an ordinary method but using [1,2,3]-trifluoro-4-nitrobenzene.
$^1$HNMR (DMSO-d6) δ: 7.21-7.63 (6H, m), 7.90-8.01 (1H, m), 8.12-8.39 (3H, m), 8.43-8.50 (2H, m), 8.63-8.73 (1H, m)
ESI-MS (m/e): 400 [M+H]

Example 120

4-(2-Cyano-phenoxy)-6-(4-N,N-dimethylcarbamoyl-phenylsulfonyl)-2-pyridin-2-yl-1H-benzimidazole (Step 1) Production of 5-(4-carboxy-phenylsulfanyl)-3-(2-cyanophenoxy)-2-nitro-phenylamine 31 mg of 4-mercaptobenzoic acid and 55 mg of potassium carbonate were added to a dimethylformamide (2 ml) solution of 47 mg of 3-(2-cyanophenoxy)-5-fluoro-2-nitro-phenylamine obtained in Example 78, and the reaction liquid was stirred at 60° C. for 2 hours. The reaction liquid was concentrated, and 1 ml of trifluoroacetic acid was added to the residue, and the solvent was evaporated away under reduced pressure. The resulting residue was purified through partitioning thin-layer chromatography (Kieselgel™ 60F$_{254}$, Art 5744 (by Merck), chloroform/methanol=10/1) to obtain the entitled compound as an orange solid.

(Step 2) Production of 3-(2-cyanophenoxy)-5-(4-N,N-dimethylcarbamoyl-phenylsulfanyl)-2-nitro-phenylamine 0.059 ml of dimethylamine (2.0 M tetrahydrofuran solution), 28 mg of 1-ethyl-3-(3'-dimethylaminopropyl)-carbodiimide hydrochloride and 20 mg of N-hydroxybenzotriazole hydrate were added to a dichloromethane (2 ml) solution of 40 mg of 5-(4-carboxy-phenylsulfanyl)-3-(2-cyanophenoxy)-2-nitro-phenylamine, and the reaction liquid was stirred at room temperature for 1.5 hours. The reaction liquid was diluted with chloroform, washed with aqueous saturated sodium bicarbonate and saturated saline in order, and then dried with anhydrous sodium sulfate. The solvent was evaporated away under reduced pressure, and the resulting residue was purified through partitioning thin-layer chromatography (Kieselgel™ 60F$_{254}$, Art 5744 (by Merck), chloroform/methanol=15/1) to obtain the entitled compound as a yellow powder.

(Step 3) Production of 3-(2-cyanophenoxy)-5-(4-N,N-dimethylcarbamoyl-phenylsulfanyl)-benzene-1,2-diamine 19 mg of electrolytic powder and 0.2 ml of aqueous saturated ammonium chloride solution were added to an isopropyl alcohol (2 ml) solution of 32 mg of 3-(2-cyanophenoxy)-5-(4-N,N-dimethylcarbamoyl-phenylsulfanyl)-2-nitro-phenylamine, and the reaction liquid was heated under reflux for 2 hours. The catalyst was removed through filtration, and the solvent was evaporated away under reduced pressure, and the resulting residue was purified through partitioning thin-layer chromatography (Kieselgel™ 60F$_{254}$, Art 5744 (by Merck), chloroform/methanol=10/1) to obtain the entitled compound as a white solid.

(Step 4) Production of 3-(2-cyanophenoxy)-5-(4-N,N-dimethylcarbamoyl-phenylsulfonyl)-benzene-1,2-diamine 38 mg of metachloroperbenzoic acid was added to a dichloromethane (2 ml) solution of 25 mg of 3-(2-cyanophenoxy)-5-(4-N,N-dimethylaminocarbamoyl-phenylsulfanyl)-benzene-1,2-diamine, and the reaction liquid was stirred at room temperature for 15 minutes. The reaction liquid was diluted with chloroform, washed with aqueous saturated sodium bicarbonate and saturated saline, and dried with anhydrous sodium sulfate. The solvent was evaporated away under reduced pressure, and the resulting residue was purified through partitioning thin-layer chromatography (Kieselgel™ 60F$_{254}$, Art 5744 (by Merck), chloroform/methanol=10/1) to obtain the entitled compound as a yellow powder.

(Step 5) Production of 4-(2-cyano-phenoxy)-6-(4-N,N-dimethylaminocarbonyl-phenylsulfonyl)-2-(pyridin-2-yl)-1H-benzimidazole The entitled compound was obtained as a brown solid in the same method as in Example 67 (step 4) or in accordance with the method or by combining it with an ordinary method but using 3-(2-cyanophenoxy)-5-(4-N,N-dimethylaminocarbamoyl-phenylsulfonyl)-benzene-1,2-diamine.
$^1$HNMR (CDCl$_3$) δ: 2.91 and 2.92 (total 3H, each s), 3.10 (3H, s), 6.99 (1H, m), 7.23-7.30 (1H, m), 7.39-7.46 (2H, m), 7.50-7.58 (3H, m), 7.68-7.78 (1H, m), 7.75 and 8.33 (total 1H, each s), 7.85 and 7.92 (total 1H, each t, J=8.4 Hz), 7.95-8.20 (2H, m), 8.39 and 8.42 (total 1H, each d, J=8.4 Hz), 8.63-8.67 (1H, m)
ESI-MS (m/e): 524 [M+H]

Example 121

1-(2-(6-(4-Oxazol-5-yl-phenoxy)-2-pyridin-2-yl-3H-benzimidazol-5-yl)-pyrrolidin-1-yl)-ethanone (Step 1) Production of ethyl 3-bromo-4-methoxymethoxybenzoate 5.5 g of sodium hydride was added to a tetrahydrofuran (300 ml) solution of 20.5 g of ethyl 3-bromo-4-hydroxybenzoate produced according to the method described in Monatsh. Chem.; 22; 1901; 437, with cooling with ice, and the reaction liquid was stirred for 30 minutes, and then, at the same temperature, 10 ml of chloromethyl methyl ether was added to the reaction liquid, and the reaction liquid was stirred overnight at room temperature. The reaction liquid was diluted with ethyl acetate, and washed with water, and the aqueous layer was extracted with ethyl acetate, and dried with anhydrous magnesium sulfate. The solvent was evaporated away under reduced pressure, and the resulting solid was suspended in hexane and then taken out through filtration to obtain the entitled compound as a white solid.

(Step 2) Production of t-butyl 2-(5-ethoxycarbonyl-2-methoxymethoxy-phenyl)-pyrrole-1-carboxylate 21 g of 1-(t-butoxycarbonyl)pyrrole-2-boronic acid, 4.2 g of tetrakistriphenylphosphine palladium and 153 ml of aqueous sodium carbonate solution (2 M) were added in order to a dimethoxyethane (350 ml) solution of 21 g of ethyl 3-bromo-4-methoxymethoxybenzoate, and the reaction liquid was heated overnight under reflux in a nitrogen atmosphere. After cooled, the reaction liquid was diluted with water, extracted with chloroform, and dried with anhydrous magnesium sulfate. The solvent was evaporated away under reduced pressure, and the resulting residue was purified through silica gel column chromatography (developing solvent: hexane/ethyl acetate=12/1 to 10/1) to obtain the entitled compound as a white solid.

(Step 3) Production of t-butyl 2-(5-ethoxycarbonyl-2-methoxymethoxy-phenyl)-pyrrolidine-1-carboxylate 8.2 g of 5% platinum-carbon catalyst was added to an ethanol (400 ml) solution of 28.4 g of t-butyl 2-(5-ethoxycarbonyl-2-methoxymethoxy-phenyl)-pyrrole-1-carboxylate, and the reaction liquid was stirred for 3 days in a hydrogen atmosphere. The catalyst was removed through filtration through Celite, and the solvent was evaporated away under reduced pressure, and the resulting residue was purified through silica gel column chromatography (developing solvent: hexane/ethyl acetate=1/6.5 to 1/6) to obtain the entitled compound as a colorless oily substance.

(Step 4) Production of ethyl 3-(1-acetyl-pyrrolidin-2-yl)-4-hydroxybenzoate 13 g of p-toluenesulfonic acid monohydrate was added to a solution of 26 g of t-butyl 2-(5-ethoxycarbonyl-2-methoxymethoxy-phenyl)-pyrrolidine-1-carboxylate in a mixture of 250 ml of ethanol and 50 ml of water, and the reaction liquid was heated under reflux for 2 days. After cooled, the reaction liquid was diluted with water, neutralized with aqueous sodium bicarbonate, extracted with a mixed solvent of chloroform/methanol (10/1), and dried with anhydrous magnesium sulfate. The solvent was evaporated away under reduced pressure to obtain a crude product. 13 ml of acetic anhydride was added to a pyridine (200 ml) solution of the resulting crude product, and stirred. After 1 hour, 6 ml of acetic anhydride was added to it. Further after 1 hour, 150 ml of pyridine was added to it, and further after 40 minutes, 5 ml of triethylamine was added thereto. Further after 30 minutes, 3 ml of acetic anhydride was added to it, and the reaction liquid was stirred for 30 minutes. The reaction liquid was diluted with ethyl acetate, and washed with aqueous saturated sodium bicarbonate, and the aqueous layer was extracted with ethyl acetate. The combined organic layers were dried with anhydrous magnesium sulfate, and the solvent was evaporated away under reduced pressure to obtain a crude product. 10 g of potassium carbonate was added to a methanol (200 ml) solution of the resulting crude product, and the reaction liquid was stirred for 4 hours at room temperature. The reaction liquid was distilled under reduced pressure, and the resulting residue was diluted with aqueous saturated ammonium chloride solution, and extracted with ethyl acetate. This was dried with anhydrous magnesium sulfate, then the solvent was evaporated away under reduced pressure, and the resulting solid was taken out through filtration with ethyl acetate to obtain the entitled compound as a white solid.

(Step 5) Production of ethyl 3-(1-acetyl-pyrrolidin-2-yl)-4-benzyloxybenzoate 15 g of potassium carbonate and 6.4 ml of benzyl bromide were added to a dimethylformamide (100 ml) solution of 12.4 g of ethyl 3-(1-acetyl-pyrrolidin-2-yl)-4-hydroxybenzoate, and the reaction liquid was stirred at 50° C. for 1 hour. The reaction liquid was cooled, diluted with aqueous saturated ammonium chloride solution, and extracted with ethyl acetate. The organic layer was washed with water, and dried with anhydrous magnesium sulfate. The solvent was evaporated away under reduced pressure, and the resulting residue was purified through silica gel column chromatography (developing solvent: hexane/ethyl acetate=10/1 to 1/2 to 1/3) to obtain the entitled compound as a yellow oily substance.

(Step 6) Production of 3-(1-acetyl-pyrrolidin-2-yl)-4-benzyloxybenzoic acid 23 ml of aqueous 4 N sodium hydroxide solution was added to an ethanol (200 ml) solution of 18.7 g of ethyl 3-(1-acetyl-pyrrolidin-2-yl)-4-benzyloxybenzoate, and the reaction liquid was stirred overnight at room temperature. 15 ml of aqueous 4 N sodium hydroxide solution was added to the reaction liquid, and the reaction liquid was stirred for 7 hours. The reaction solvent was evaporated away under reduced pressure, and the resulting residue was diluted with water, and washed with ether. The aqueous layer was acidified with 6 N hydrochloric acid added thereto, then extracted with chloroform, and dried with anhydrous magnesium sulfate. The solvent was evaporated away under reduced pressure to obtain the entitled compound as a white solid.

(Step 7) Production of t-butyl (3-(1-acetyl-pyrrolidin-2-yl)-4-benzyloxy-phenyl)-carbamate 3.0 ml of diisopropylethylamine and 3.8 ml of diphenylphosphoryl azide were added in order to a solution of 5 g of 3-(1-acetyl-pyrrolidin-2-yl)-4-benzyloxybenzoic acid in a mixture of 15 ml of toluene and 15 ml of 2-methyl-2-propanol, and the reaction liquid was heated overnight under reflux. After cooled, saturated saline and aqueous saturated sodium bicarbonate were added to the reaction liquid, and this was extracted with ethyl acetate, and dried with anhydrous magnesium sulfate. The solvent was evaporated away under reduced pressure, and the resulting residue was purified through silica gel column chromatography (developing solvent: hexane/ethyl acetate=1/0 to 1/1 to 0/1) to obtain the entitled compound as a colorless amorphous substance.

(Step 8) Production of 1-(2-(4,5-diamino-2-benzyloxy-phenyl)-pyrrolidin-1-yl-ethanone 1.1 g of potassium nitrate was added to a trifluoroacetic acid (50 ml) solution of 4.1 g of t-butyl (3-(1-acetyl-pyrrolidin-2-yl)-4-benzyloxy-phenyl)-carbamate, and the reaction liquid was stirred overnight at room temperature. The reaction solvent was evaporated away under reduced pressure, and water with ice was added to the resulting residue. Then, this was neutralized with aqueous ammonia, and diluted with ethyl acetate. The deposit was taken out through filtration to obtain a crude product as a brown solid. The filtrate was diluted with aqueous saturated sodium chloride solution, extracted with ethyl acetate and dried with anhydrous magnesium sulfate. The solvent was evaporated away under reduced pressure, the resulting residue was purified through silica gel column chromatography (developing solvent: ethyl acetate), and the resulting solid was suspended in ethyl acetate and taken out through filtration to obtain a crude product as a brown solid. 1.5 ml of hydrazine monohydrate and 1 g of developed Raney-nickel catalyst were added in order to an ethanol (100 ml) solution of 2.8 g of the resulting crude product, and the reaction liquid was stirred at room temperature for 3 hours. The catalyst was removed through filtration through Celite, and the solvent was evaporated away under reduced pressure. The resulting residue was diluted with aqueous saturated sodium bicarbonate, extracted with ethyl acetate, and dried with anhydrous magnesium sulfate. The solvent was evaporated away under reduced pressure, and the resulting residue was purified through silica gel column chromatography (developing solvent: chloroform/methanol=100/0 to 99/1 to 98/2 to 97/3 to 96/4 to 93/7) to obtain the entitled compound as a green amorphous substance.

(Step 9) Production of 1-(2-(6-benzyloxy-2-pyridin-2-yl-3-(2-trimethylsilanyl-ethoxymethyl)-3H-benzimidazol-5-yl)-pyrrolidin-1-yl)-ethanone 3 ml of a toluene solution of 460 mg of pyridine-2-carboxaldehyde was added to a toluene (43 ml) solution of 1.39 g of 1-(2-(4,5-diamino-2-benzyloxy-phenyl)-pyrrolidin-1-yl-ethanone, and the reaction liquid was stirred at room temperature. After 2 hours, 46 mg of pyridine-2-carboxaldehyde was added to it, and the reaction liquid was stirred at 90° C. for 2 hours. Further, 46 mg of pyridin-2-carboxaldehyde was added to it, and the reaction liquid was stirred at 90° C. for 10 hours. After cooled, the precipitated solid was taken out through filtration to obtain a crude product as a brown solid. 144 mg of sodium hydride and 667 mg of 2-(chloromethoxy) ethyltrimethylsilane were added to a tetrahydrofuran (20 ml) solution of 1.1 g of the resulting crude product, and the reaction liquid was stirred at room temperature for 2.5 hours. Aqueous saturated sodium bicarbonate was added to the reaction liquid, and this was extracted with ethyl acetate and dried with anhydrous magnesium sulfate. The solvent was evaporated away under reduced pressure, and the resulting residue was purified through silica gel column chromatography (developing solvent: ethyl acetate) to obtain the entitled compound as a brown amorphous substance.

(Step 10) Production of 1-(2-(6-hydroxy-2-pyridin-2-yl-3-(2-trimethylsilanyl-ethoxymethyl)-3H-benzimidazol-5-yl)-pyrrolidin-1-yl)-ethanone 713 mg of ammonium formate and 119 mg of 20% palladium hydroxide-carbon catalyst were added to an ethanol (20 ml) solution of 1.18 g of 1-(2-(6-benzyloxy-2-pyridin-2-yl-3-(2-trimethylsilanyl-ethoxymethyl)-3H-benzimidazol-5-yl)-pyrrolidin-1-yl)-ethanone, and the reaction liquid was heated under reflux for 5 hours. 157 mg of ammonium formate and 56 mg of 20% palladium hydroxide-carbon catalyst were added to the reaction liquid, and the reaction liquid was further heated under reflux for 1 hour. After cooled, the catalyst was removed through filtration through Celite, and the solvent was evaporated away under reduced pressure. The resulting residue was diluted with 1 N hydrochloric acid, extracted with ethyl acetate, and dried with anhydrous magnesium sulfate. The solvent was evaporated away under reduced pressure, and the resulting residue was purified through silica gel column chromatography (developing solvent: chloroform/methanol=100/0 to 99/1 to 98/2) to obtain the entitled compound as a brown amorphous substance.

(Step 11) Production of 1-(2-(6-(4-oxazol-5-yl-phenoxy)-2-pyridin-2-yl-3-(2-trimethylsilanyl-ethoxymethyl)-3H-benzimidazol-5-yl)-pyrrolidin-1-yl)-ethanone 30 mg of 5-(4-bromo-phenyl)-oxazole, 56 mg of cesium carbonate and 15 mg of copper(II) oxide were added to a pyridine (1 ml) solution of 29 mg of 1-(2-(6-hydroxy-2-pyridin-2-yl-3-(2-trimethylsilanyl-ethoxymethyl)-3H-benzimidazol-5-yl)pyrrolidin-1-yl)-ethanone, and the reaction liquid was stirred overnight in a sealed tube at 120° C. After cooled, aqueous saturated ammonium chloride solution and saturated saline were added in order to the reaction liquid, and this was extracted with ethyl acetate and dried with anhydrous magnesium sulfate. The solvent was evaporated away under reduced pressure, and the resulting residue was purified through partitioning thin-layer chromatography (Kieselgel™ 60F$_{254}$, Art 5744 (by Merck), chloroform/methanol=12/1) to obtain the entitled compound as a yellow oily substance.

(Step 12) Production of 1-(2-(6-(4-oxazol-5-yl-phenoxy)-2-pyridin-2-yl-3H-benzimidazol-5-yl)-pyrrolidin-1-yl)-ethanone 24 mg of 1-(2-(6-(4-oxazol-5-yl-phenoxy)-2-pyridin-2-yl-3-(2-trimethylsilanyl-ethoxymethyl)-3H-benzimidazol-5-yl)-pyrrolidin-1-yl)-ethanone was dissolved in 1 ml of trifluoroacetic acid, and the reaction liquid was stirred at room temperature for 2 hours. The solvent was evaporated away under reduced pressure, and the resulting residue was purified through reversed-phase middle-pressure liquid chromatography (ODS-AS-360-CC (by YMC), mobile phase: water-acetonitrile-0.1% trifluoroacetic acid) to obtain the entitled compound as a yellow oily substance.

$^1$HNMR (CDCl$_3$) δ: 1.73-2.69 (7H, m), 3.54-3.91 (2H, m), 5.21-5.48 (1H, m), 6.91-7.98, 8.30-8.51, 8.57-8.73 (13H, each m)

ESI-MS (m/e): 466 [M+H]

Example 122

3-(6-(1-Acetyl-pyrrolidin-2-yl)-2-pyridin-2-yl-1H-benzimidazol-5-yloxy)-benzonitrile The entitled compound was obtained as an oily substance in the same method as in Example 121 (step 11), (step 12) or in accordance with the method or by combining it with an ordinary method but using 1-(2-(6-hydroxy-2-pyridin-2-yl-3-(2-trimethylsilanyl-ethoxymethyl)-3H-benzimidazol-5-yl)-pyrrolidin-1-yl)-ethanone obtained in Example 121 (step 10) and 3-cyanobromobenzene.

$^1$HNMR (CDCl$_3$) δ: 1.80-2.42 (7H, m), 3.56-3.93 (2H, m), 5.14-5.45 (1H, m), 6.91-7.73 (7H, m), 7.80-7.96 (1H, m), 8.30-8.43 (1H, m), 8.58-8.70 (1H, m), 10.58-10.82 (1H, m)

ESI-MS (m/e): 424 [M+H]

Example 123

3-(6-(1-Acetyl-pyrrolidin-2-yl)-2-pyridin-2-yl-1H-benzimidazol-5-yloxy)-benzamide The entitled compound was obtained in the same method as in Example 43 or in accordance with the method or by combining it with an ordinary method but using 3-(6-(1-acetyl-pyrrolidin-2-yl)-2-pyridin-2-yl-1H-benzimidazol-5-yloxy)-benzonitrile obtained in Example 122.

$^1$HNMR (CDCl$_3$) δ: 1.70-2.39 (7H, m), 3.39-3.89 (2H, m), 5.17-6.24 (3H, m), 6.97-7.92 (8H, m), 8.26-8.42 (1H, m), 8.52-8.67 (1H, m), 10.42-10.72 (1H, m)

ESI-MS (m/e): 442 [M+H]

Example 124

5-(6-(1-Acetyl-pyrrolidin-2-yl)-2-pyridin-2-yl-1H-benzimidazol-5-yloxy)-pyridine-2-carbonitrile The entitled compound was obtained in the same method as in Example 122 or in accordance with the method or by combining it with an ordinary method but using 5-bromo-pyridine-2-carbonitrile.

$^1$HNMR (CDCl$_3$) δ: 1.50-2.42 (7H, m), 3.56-3.88 (2H, m), 5.09-5.40 (1H, m), 6.89-7.92 (6H, m), 8.26-8.70 (3H, m), 10.63-11.05 (1H, m)

ESI-MS (m/e): 425 [M+H]

Example 125

5-(6-(1-Acetyl-pyrrolidin-2-yl)-2-pyridin-2-yl-1H-benzimidazol-5-yloxy)-pyridine-2-carboxylic acid amide The entitled compound was obtained as an oily substance in the same method as in Example 43 or in accordance with the method or by combining it with an ordinary method but using 5-(6-(1-acetyl-pyrrolidin-2-yl)-2-pyridin-2-yl-1H-benzimidazol-5-yloxy)-pyridine-2-carbonitrile obtained in Example 124.

$^1$HNMR (CDCl$_3$) δ: 0.60-2.42 (7H, m), 3.42-3.90 (2H, m), 4.99-5.80 (2H, m), 6.74-8.67 (10H, m), 10.42-10.10.85 (1H, m)

ESI-MS (m/e): 443 [M+H]

Examples 126-1, 126-2

1-(2-(6-(5-Bromo-pyridin-2-yloxy)-2-pyridin-2-yl-3H-benzimidazol-5-yl-pyrrolidin-1-yl)-ethanone 1-(2-(6-(6-Methanesulfonyl-pyridin-3-yloxy)-2-pyridin-2-yl-3H-benzimidazol-5-yl)-pyrrolidin-1-yl)-ethanone The entitled compounds were obtained in the same method as in Example 122 or in accordance with the method or by combining it with an ordinary method but using 5-bromo-2-methanesulfonyl-pyridine.

1-(2-(6-(5-Bromo-pyridin-2-yloxy)-2-pyridin-2-yl-3H-benzimidazol-5-yl)-pyrrolidin-1-yl)-ethanone $^1$HNMR (CDCl$_3$) δ: 1.50-2.40 (7H, m), 3.50-3.87 (2H, m), 5.03-5.14, 5.31-5.42 (1H, each m), 6.71-7.88, 10.48-11.15 (7H, each m), 8.08-8.40 (2H, m), 8.50-8.69 (1H, m)

ESI-MS (m/e): 478, 480 [M+H]

1-(2-(6-(6-Methanesulfonyl-pyridin-3-yloxy)-2-pyridin-2-yl-3H-benzimidazol-5-yl)-pyrrolidin-1-yl)-ethanone $^1$HNMR (CDCl$_3$) δ: 1.57-2.59 (7H, m), 3.08-3.27 (3H, m), 3.57-3.89 (2H, m), 5.14-5.40 (1H, m), 6.94-7.64 (4H, m), 7.82-8.15 (2H, m), 8.33-8.75 (3H, m)

ESI-MS (m/e): 478 [M+H]

Example 127

1-(2-(2-Pyridin-2-yl-6-(quinolin-6-yloxy-3H-benzimidazol-5-yl)-pyrrolidin-1-yl)-ethanone The entitled compound was obtained as an oily substance in the same method as in Example 122 or in accordance with the method or by combining it with an ordinary method but using 6-bromo-quinoline.

$^1$HNMR (CDCl$_3$) δ: 1.67-2.69 (7H, m), 3.40-4.04 (2H, m), 5.25-5.63 (1H, m), 6.80-9.13 (12H, m), 10.22-11.44 (1H, br)

ESI-MS (m/e): 450 [M+H]

Example 128

4-(6-(1-Acetyl-pyrrolidin-2-yl)-2-pyridin-2-yl-1H-benzimidazol-5-yloxy)-2-methyl-benzonitrile The entitled compound was obtained as an oily substance in the same method as in Example 122 or in accordance with the method or by combining it with an ordinary method but using 4-bromo-2-methyl-benzonitrile.

$^1$HNMR (CDCl$_3$) δ: 1.48-2.54 (10H, m), 3.20-3.89 (2H, m), 5.06-5.41 (1H, m), 6.80-8.87 (10H, m)

ESI-MS (m/e): 438 [M+H]

Example 129

1-(2-(2-Pyridin-2-yl-6-(4-trifluoromethoxy-phenoxy)-3H-benzimidazol-5-yl)-pyrrolidin-1-yl)-ethanone The entitled compound was obtained as an oily substance in the same method as in Example 122 or in accordance with the method or by combining it with an ordinary method but using 1-bromo-4-trifluoromethoxy-benzene.

¹HNMR (CDCl₃) δ: 1.43-2.69 (7H, m), 3.32-3.91 (2H, m), 5.20-5.59 (1H, m), 6.23-8.97 (11H, m)

ESI-MS (m/e): 483 [M+H]

Example 130

1-(2-(2-pyridin-2-yl-6-(quinolin-3-yloxy)-3H-benz-imidazol-5-yl)-pyrrolidin-1-yl)-ethanone The entitled compound was obtained as a yellow oily substance in the same method as in Example 122 or in accordance with the method or by combining it with an ordinary method but using 3-bromo-quinoline.

¹HNMR (CDCl₃) δ: 1.00-2.47 (7H, m), 3.37-4.00 (2H, m), 5.26-5.54 (1H, m), 6.98-9.10 (12H, m), 10.44-10.73 (1H, m)

ESI-MS (m/e): 450 [M+H]

Example 131

1-(2-(6-(4-acetyl-phenoxy)-2-pyridin-2-yl-3H-benz-imidazol-5-yl)-pyrrolidin-1-yl)-ethanone The entitled compound was obtained in the same method as in Example 122 or in accordance with the method or by combining it with an ordinary method but using 1-(4-iodo-phenyl)-ethanone.

¹HNMR (CDCl₃) δ: 1.47-2.60 (10H, m), 3.52-3.88 (2H, m), 5.12-5.41 (1H, m), 6.97-7.74 (6H, m), 7.80-8.02 (3H, m), 8.30-8.44 (1H, m), 8.57-8.70 (1H, m)

ESI-MS (m/e): 441 [M+H]

Example 132

1-(2-(6-(Biphenyl-4-yloxy)-2-pyridin-2-yl-3H-benz-imidazol-5-yl)pyrrolidin-1-yl)-ethanone The entitled compound was obtained as a yellow oily substance in the same method as in Example 122 or in accordance with the method or by combining it with an ordinary method but using 4-bromo-biphenyl.

¹HNMR (CDCl₃) δ: 1.13-2.47 (7H, m), 3.40-3.91 (2H, m), 5.20-5.60 (1H, m), 6.72-7.89 (13H, m), 8.25-8.42 (1H, m), 8.42-8.67 (1H, m), 10.29-10.60 (1H, m)

ESI-MS (m/e): 475 [M+H]

Example 133

4-(6-(1-Acetyl-pyrrolidin-2-yl)-2-pyridin-2-yl-1H-benzimidazol-5-yloxy)-N,N-dimethyl-benzenesulfonamide The entitled compound was obtained as an oily substance in the same method as in Example 122 or in accordance with the method or by combining it with an ordinary method but using 4-iodo-N,N-dimethyl-benzenesulfonamide.

¹HNMR (CDCl₃) δ: 1.50-3.00 (13H, m), 3.40-3.92 (2H, m), 5.14-5.50 (1H, m), 6.40-8.80 (11H, m)

ESI-MS (m/e): 506 [M+H]

Example 134

1-(2-(6-Biphenyl-3-yloxy)-2-pyridin-2-yl-3H-benz-imidazol-5-yl)pyrrolidin-1-yl)-ethanone The entitled compound was obtained in the same method as in Example 122 or in accordance with the method or by combining it with an ordinary method but using 3-bromo-biphenyl.

¹HNMR (CDCl₃) δ: 0.80-2.50 (7H, m), 3.40-3.91 (2H, m), 5.20-5.60 (1H, m), 6.80-7.95 (13H, m), 8.25-8.45 (1H, m), 8.50-8.70 (1H, m)

ESI-MS (m/e): 475 [M+H]

Example 135

1-(2-(6-(4-Propane-2-sulfonyl)-phenoxy)-2-pyridin-2-yl-3H-benzimidazol-5-yl)-pyrrolidin-1-yl)-ethanone The entitled compound was obtained in the same method as in Example 122 or in accordance with the method or by combining it with an ordinary method but using 1-iodo-4-(propane-2-sulfonyl)-benzene.

¹HNMR (CDCl₃) δ: 1.10-2.50 (13H, m), 3.05-3.30 (1H, m), 3.50-3.95 (2H, m), 5.05-5.50 (1H, m), 7.00-7.95 (8H, m), 8.30-8.50 (1H, m), 8.58-8.75 (1H, m), 10.60-10.95 (1H, m)

ESI-MS (m/e): 505 [M+H]

Example 136

4-(6-(1-Acetyl-pyrrolidin-2-yl)-2-pyridin-2-yl-1H-benzimidazol-5-yloxy)-2-trifluoromethyl-benzonitrile The entitled compound was obtained in the same method as in Example 122 or in accordance with the method or by combining it with an ordinary method but using 4-bromo-2-trifluoromethyl-benzonitrile.

¹HNMR (CDCl₃) δ: 1.10-2.45 (7H, m), 3.50-3.95 (2H, m), 5.00-5.45 (1H, m), 6.60-7.95 (7H, m), 8.30-8.45 (1H, m), 8.55-8.75 (1H, m), 10.80-11.60 (1H, m)

ESI-MS (m/e): 492 [M+H]

Examples 137-1, 137-2

4-(6-(1-Acetyl-pyrrolidin-2-yl)-2-pyridin-2-yl-1H-benzimidazol-5-yloxy)-2-trifluoromethyl-benzamide monotrifluoroacetate 4-(6-(1-Acetyl-pyrrolidin-2-yl)-2-pyridin-2-yl-1H-benzimidazol-5-yloxy)-N-ethyl-2-trifluoromethyl-benzamide monotrifluoroacetate The entitled compounds were obtained in the same method as in Example 43 and Example 121 (step 12) or in accordance with the method or by combining it with an ordinary method but using 4-(6-(1-acetyl-pyrrolidin-2-yl)-2-pyridin-2-yl-1H-benzimidazol-5-yloxy)-2-trifluoromethyl-benzonitrile obtained in Example 136.

4-(6-(1-Acetyl-pyrrolidin-2-yl)-2-pyridin-2-yl-1H-benzimidazol-5-yloxy)-2-trifluoromethyl-benzamide monotrifluoroacetate ¹HNMR (CD₃OD) δ: 1.05-2.80 (7H, m), 3.50-4.20 (2H, m), 5.30-5.45 (1H, m), 7.30-7.80 (6H, m), 8.05-8.20 (1H, m), 8.20-8.38 (1H, m), 8.80-8.90 (1H, m)

ESI-MS (m/e): 510 [M+H]

4-(6-(1-Acetyl-pyrrolidin-2-yl)-2-pyridin-2-yl-1H-benzimidazol-5-yloxy)-N-ethyl-2-trifluoromethyl-benzamide monotrifluoroacetate $^1$HNMR (CD$_3$OD) δ: 1.05-2.80 (10H, m), 3.60-4.05 (2H, m), 4.80-5.00 (2H, m), 5.30-5.45 (1H, m), 7.30-7.80 (5H, m), 8.05-8.20 (1H, m), 8.20-8.38 (1H, m), 8.80-8.90 (1H, m), 9.10-9.30 (1H, m)
ESI-MS (m/e): 538 [M+H]

Example 138

1-(2-(6-(4-(2-Dimethylamino-ethoxy)-phenoxy)-2-pyridin-2-yl-3H-benzimidazol-5-yl)-pyrrolidin-1-yl)-ethanone The entitled compound was obtained in the same method as in Example 122 or in accordance with the method or by combining it with an ordinary method but using (2-(4-iodo-phenoxy)-ethyl)-dimethylamine.
$^1$HNMR (CDCl$_3$) δ: 1.05-2.90 (13H, m), 3.00-4.45 (6H, m), 5.20-5.45 (1H, m), 6.80-8.00 (8H, m), 8.25-8.40 (1H, m), 8.50-8.80 (1H, m)
ESI-MS (m/e): 486 [M+H]

Example 139

1-(2-(6-(4-Hydroxymethyl-phenoxy)-2-pyridin-2-yl-3H-benzimidazol-5-yl)-pyrrolidin-1-yl)-ethanone The entitled compound was obtained as a white solid in the same method as in Example 122 or in accordance with the method or by combining it with an ordinary method but using 4-bromo-benzyl alcohol.
$^1$HNMR (CDCl$_3$) δ: 1.68-2.40 (7H, m), 3.53-3.88 (2H, m), 4.62-4.72 (2H, m), 5.22-5.56 (1H, m), 6.82-7.62 (7H, m), 7.80-7.89 (1H, m), 8.32-8.40 (1H, m), 8.55-8.64 (1H, m)
ESI-MS (m/e): 429 [M+H]

Example 140

4-(6-(1-Acetyl-pyrrolidin-2-yl)-2-pyridin-2-yl-1H-benzimidazol-5-yloxy)-N,N-dimethyl-benzamide The entitled compound was obtained as a white solid in the same method as in Example 122 or in accordance with the method or by combining it with an ordinary method but using 4-bromobenzoic acid dimethylamide.
$^1$HNMR (CDCl$_3$) δ: 1.81-2.40 (7H, m), 2.98-3.17 (6H, m), 3.56-3.87 (2H, m), 5.20-5.53 (1H, m), 6.93-7.65 (7H, m), 7.81-7.89 (1H, m), 8.33-8.41 (1H, m), 8.60-8.67 (1H, m)
ESI-MS (m/e): 470 [M+H]

Example 141

4-(6-(1-Acetyl-pyrrolidin-2-yl)-2-pyridin-2-yl-1H-benzimidazol-5-yloxy)-N-methyl-benzamide The entitled compound was obtained as a white solid in the same method as in Example 122 or in accordance with the method or by combining it with an ordinary method but using 4-bromo-N-methylbenzamide.
$^1$HNMR (CDCl$_3$) δ: 1.80-2.39 (4H, m), 1.84 and 2.16 (total 13H, each s), 2.98-3.02 (3H, m), 3.58-3.74 (1H, m), 3.78-3.87 (1H, m), 5.16-5.43 (1H, m), 6.74-7.89 (8H, m), 8.36-8.39 (1H, m), 8.63-8.66 (1H, m)
ESI-MS (m/e): 456 [M+H]

Example 142

1-(2-(2-pyridin-2-yl-6-(4-(pyrrolidin-1-carbonyl)-phenoxy)-3H-benzimidazol-5-yl)-pyrrolidin-1-yl)-ethanone The entitled compound was obtained as a white solid in the same method as in Example 122 or in accordance with the method or by combining it with an ordinary method but using (4-bromo-phenyl)-pyrrolidin-1-yl-ethanone.
$^1$HNMR (CDCl$_3$) δ: 1.80-2.40 (8H, m), 1.87 and 2.21 (total 13H, each s), 3.43-3.52 (2H, m), 3.60-3.71 (3H, m), 3.81-3.90 (1H, m), 5.21-5.50 (1H, m), 6.84-7.02 (2H, m), 7.25-7.58 (5H, m), 7.83-7.93 (1H, m), 8.36-8.45 (1H, m), 8.62-8.67 (1H, m)
ESI-MS (m/e): 496 [M+H]

Example 143

1-(2-(6-(4-(morpholine-4-carbonyl)-phenoxy)-2-pyridin-2-yl-3H-benzimidazol-5-yl)-pyrrolidin-yl)-ethanone The entitled compound was obtained as a white solid in the same method as in Example 122 or in accordance with the method or by combining it with an ordinary method but using (4-bromo-phenyl)-morpholin-4-yl-methanone.
$^1$HNMR (CDCl$_3$) δ: 1.78-2.62 (7H, m), 3.40-3.90 (10H, m), 5.23-5.50 (1H, m), 6.82-7.54 (7H, m), 7.86-7.94 (1H, m), 8.38-8.46 (1H, m), 8.64-8.69 (1H, m)
ESI-MS (m/e): 512 [M+H]

Example 144

4-(6-(1-Acetyl-pyrrolidin-2-yl)-2-pyridin-2-yl-1H-benzimidazol-5-yloxy benzoic acid monotrifluoroacetate The entitled compound was obtained as a white solid in the same method as in Example 122 or in accordance with the method or by combining it with an ordinary method but using 4-bromo-benzoic acid.
$^1$HNMR (CDCl$_3$) δ: 1.86 and 2.10 (total 3H, each s), 1.92-2.48 (4H, m), 3.41-3.90 (2H, m), 5.36-5.39 (1H, m), 7.13-7.72 (5H, m), 8.00-8.07 (3H, m), 8.22-8.26 (1H, m), 8.73-8.80 (1H, m)
ESI-MS (m/e): 443 [M+H]

Example 145

1-(2-(6-(4-(Piperidine-1-carbonyl)-phenoxy)-2-pyridin-2-yl-3H-benzimidazol-5-yl)-pyrrolidin-1-yl)-ethanone The entitled compound was obtained as a white solid in the same method as in Example 122 or in accordance with the method or by combining it with an ordinary method but using (4-bromo-phenyl)-piperidin-1-yl-methanone.
$^1$HNMR (CDCl$_3$) δ: 1.45-2.40 (10H, m), 1.88 and 2.20 (total 3H, each s), 3.30-3.90 (6H, m), 5.23-5.53 (1H, m), 6.83-7.55 (7H, m), 7.84-7.94 (1H, m), 8.37-8.46 (1H, m), 8.63-8.68 (1H, m)
ESI-MS (m/e): 510 [M+H]

Example 146

1-(2-(6-(4-(4-Acetyl-piperazine-1-carbonyl)-phenoxy)-2-pyridin-2-yl-3H-benzimidazol-5-yl)-pyrrolidin 1-yl)-ethanone The entitled compound was obtained as a white solid in the same method as in Example 122 or in accordance with the method or by combining it with an ordinary method but using 1-(4-(4-bromo-benzoyl)-piperazin-1-yl)-ethanone.

$^1$HNMR (CDCl$_3$) δ: 1.84-2.40 (10H, m), 3.24-3.88 (10H, m), 5.22-5.48 (1H, m), 6.94-7.09 (2H, m), 7.22-7.48 (5H, m), 7.84-7.93 (1H, m), 8.37-8.43 (1H, m), 8.63-8.66 (1H, m)

ESI-MS (m/e): 553 [M+H]

Example 147

4-(6-(1-Acetyl-pyrrolidin-2-yl)-2-pyridin-2-yl-1H-benzimidazol-5-yloxy)-benzonitrile (Step 1) Production of 4-(6-(1-acetyl-pyrrolidin-2-yl)-2-pyridin-2-yl-1-(2-trimethylsilanyl-ethoxymethyl)-1H-benzimidazol-5-yloxy)-benzonitrile 5.8 mg of sodium hydride was added to an N-methylpyrrolidinone (1 ml) solution of 30 mg of 1-(2-(6-hydroxy-2-pyridin-2-yl-3-(2-trimethylsilanyl-ethoxymethyl)-3H-benzimidazol-5-yl)-pyrrolidin-1-yl)-ethanone obtained in Example 121 (step 10) and 20 mg of 4-fluorocyanobenzene, and the reaction liquid was stirred overnight in a sealed tube at 100° C. After cooled, aqueous saturated sodium bicarbonate was added to the reaction liquid, then this was extracted with ethyl acetate, the organic layer was washed with water, and dried with anhydrous magnesium sulfate. The solvent was evaporated away under reduced pressure, and the resulting residue was purified through partitioning thin-layer chromatography (Kieselgel™ 60F$_{254}$, Art 5744 (by Merck), chloroform/methanol=9/1) to obtain the entitled compound as a yellow oily substance.

(Step 2) Production of 4-(6-(1-acetyl-pyrrolidin-2-yl)-2-pyridin-2-yl-1H-benzimidazol-5-yloxy)-benzonitrile The entitled compound was obtained as an oily substance in the same method as in Example 121 (step 12) or in accordance with the method or by combining it with an ordinary method but using 4-(6-(1-acetyl-pyrrolidin-2-yl)-2-pyridin-2-yl-1-(2-trimethylsilanyl-ethoxymethyl)-1H-benzimidazol-5-yloxy)-benzonitrile.

$^1$HNMR (CDCl$_3$) δ: 1.52-2.42 (7H, m), 3.42-3.92 (2H, m), 5.02-5.40 (1H, m), 6.77-7.75 (7H, m), 7.75-7.94 (1H, m), 8.20-8.46 (1H, m), 8.50-8.69 (1H, m), 10.67-11.06 (1H, m)

ESI-MS (m/e): 424 [M+H]

Example 148

4-(6-(1-Acetyl-pyrrolidin-2-yl)-2-pyridin-2-yl-1H-benzimidazol-5-yloxy)-benzamide The entitled compound was obtained in the same method as in Example 43 or in accordance with the method or by combining it with an ordinary method but using 4-(6-(1-acetyl-pyrrolidin-2-yl)-2-pyridin-2-yl-1H-benzimidazol-5-yloxy)-benzonitrile obtained in Example 147.

$^1$HNMR (CDCl$_3$) δ: 1.05-2.40 (7H, m), 3.43-3.89 (2H, m), 5.10-6.32 (3H, m), 6.88-7.90 (8H, m), 8.27-8.42 (1H, m), 8.53-8.68 (1H, m), 10.47-11.80 (1H, m)

ESI-MS (m/e): 442 [M+H]

Example 149

2-(6-(1-Acetyl-pyrrolidin-2-yl)-2-pyridin-2-yl-1H-benzimidazol-5-yloxy)-benzonitrile The entitled compound was obtained as an oily substance in the same method as in Example 147 or in accordance with the method or by combining it with an ordinary method but using 2-fluoro-benzonitrile.

$^1$HNMR (CDCl$_3$) δ: 1.50-2.49 (7H, m), 3.43-3.89 (2H, m), 5.10-5.34 (1H, m), 6.83-7.92 (8H, m), 8.31-8.42 (1H, m), 8.53-8.68 (1H, m), 10.80-11.23 (1H, m)

ESI-MS (m/e): 424 [M+H]

Example 150

2-(6-(1-Acetyl-pyrrolidin-2-yl)-2-pyridin-2-yl-1H-benzimidazol-5-yloxy)-benzamide The entitled compound was obtained as an oily substance in the same method as in Example 43 or in accordance with the method or by combining it with an ordinary method but using 2-(6-(1-acetyl-pyrrolidin-2-yl)-2-pyridin-2-yl-1H-benzimidazol-5-yloxy)-benzonitrile obtained in Example 149.

$^1$HNMR (CDCl$_3$) δ: 1.52-2.46 (7H, m), 3.43-3.91 (2H, m), 5.10-5.51 (1H, m), 5.99 (1H, brs), 6.72-7.98 (8H, m), 8.26-8.43 (2H, m), 8.59-8.70 (1H, m), 10.58-10.94 (1H, m)

ESI-MS (m/e): 442 [M+H]

Example 151

1-(2-(6-(4-Nitro-phenoxy)-2-pyridin-2-yl-3H-benzimidazol-5-yl)-pyrrolidin-1-yl)-ethanone The entitled compound was obtained in the same method as in Example 147 or in accordance with the method or by combining it with an ordinary method but using 4-fluoro-nitrobenzene.

$^1$HNMR (CDCl$_3$) δ: 1.40-2.50 (7H, m), 3.50-3.95 (2H, m), 5.05-5.40 (1H, m), 7.00-7.80 (5H, m), 7.80-7.95 (1H, m), 8.15-8.30 (2H, m), 8.30-8.45 (1H, m), 8.60-8.70 (1H, m), 10.60-11.00 (1H, m)

ESI-MS (m/e): 444 [M+H]

Example 152

1-(2-(2-pyridin-2-yl-6-(4-(2H-tetrazol-5-yl)-phenoxy)-3H-benzimidazol-5-yl)-pyrrolidin-1-yl)-ethanone The entitled compound was obtained in the same method as in Example 60 and Example 121 (step 12) or in accordance with the method or by combining it with an ordinary method but using 4-(6-(1-acetyl-pyrrolidin-2-yl)-2-pyridin-2-yl-1-(2-trimethylsilanyl-ethoxymethyl)-1H-benzimidazol-5-yloxy)-benzonitrile obtained in Example 147 (step 1).

$^1$HNMR (CDCl$_3$) δ: 1.51-2.58 (7H, m), 3.43-3.90 (2H, M), 5.09-5.55 (1H, m), 6.73-7.60, 7.69-8.04, 8.29-8.69 (10H, each m)

ESI-MS (m/e): 467 [M+H]

Example 153

1-(2-(6-(4-(5-Methyl-[1,2,4]oxadiazol-3-yl)-phenoxy)-2-pyridin-2-yl-3H-benzimidazol-5-yl)pyrrolidin-1-yl)-ethanone The entitled compound was obtained in the same method as in Example 61, Example 64 and Example 121 (step 12) or in accordance with the method or by combining it with an ordinary method but using 4-(6-(1-acetyl-pyrrolidin-2-yl)-2-phenyl-1-(2-trimethylsilanyl-ethoxymethyl)-1H-benzimidazol-5-yloxy)-benzonitrile obtained in Example 147 (step 1).
$^1$HNMR (CDCl$_3$) δ: 1.49-2.7 (10H, m), 3.39-3.90 (2H, m), 5.17-5.52 (1H, m), 6.26-8.89 (11H, m)
ESI-MS (m/e): 481 [M+H]

Example 154

3-(4-(6-(1-Acetyl-pyrrolidin-2-yl)-2-pyridin-2-yl-1H-benzimidazol-5-yloxy)-phenyl)-4H-[1,2,4]oxadiazol-5-one The entitled compound was obtained in the same method as in Example 61, Example 62 and Example 121 (step 12) or in accordance with the method or by combining it with an ordinary method but using 4-(6-(1-acetyl-pyrrolidin-2-yl)-2-pyridin-2-yl-1-(2-trimethylsilanyl-ethoxymethyl)-1H-benzimidazol-5-yloxy)-benzonitrile obtained in Example 147 (step 1).
$^1$HNMR (CDCl$_3$) δ: 1.82-2.47 (7H, m), 3.60-3.3.94 (2H, m), 5.24-5.43 (1H, m), 7.15-8.05 (8H, m), 8.23-8.31 (1H, m), 8.71-8.78 (1H, m)
ESI-MS (m/e): 483 [M+H]

Example 155

5-(6-(1-Acetyl-pyrrolidin-2-yl)-2-pyridin-2-yl-1H-benzimidazol-5-yloxy)-1,3-dihydro-benzimidazol-2-one (Step 1) Production of 1-(2-(6-(3,4-dinitro-phenoxy)-2-pyridin-2-yl-3-(2-trimethylsilanyl-ethoxymethyl)-3H-benzimidazol-5-yl)-pyrrolidin-1-yl)-ethanone The entitled compound was obtained as a red oily substance in the same method as in Example 147 (step 1) or in accordance with the method or by combining it with an ordinary method but using 4-fluoro-1,2-dinitro-benzene.
$^1$HNMR (CD$_3$OD) δ: 1.80-2.57 (7H, m), 3.61-4.02 (2H, m), 5.27-5.60 (1H, m), 6.77-7.60 (6H, m), 7.91-8.06 (1H, m), 8.17-8.33 (1H, m), 8.72 (1H, brs)
ESI-MS (m/e): 455 [M+H]

(Step 2) Production of 1-(2-(6-(3,4-diamino-phenoxy)-2-pyridin-2-yl-3-(2-trimethylsilanyl-ethoxymethyl)-3H-benzimidazol-5-yl)-pyrrolidin-1-yl)-ethanone 0.030 ml of hydrazine monohydrate and 20 mg of developed Raney nickel catalyst were added to an ethanol (1 ml) solution of 72 mg of 1-(2-(6-(3,4-dinitro-phenoxy)-2-pyridin-2-yl-3-(2-trimethylsilanyl-ethoxymethyl)-3H-benzimidazol-5-yl)-pyrrolidin-1-yl)-ethanone, and the reaction liquid was stirred at room temperature for 2 hours. The catalyst was removed through filtration through Celite, and the solvent was evaporated away under reduced pressure. The resulting residue was purified through partitioning thin-layer chromatography (Kieselgel™ 60F$_{254}$, Art 5744 (by Merck), chloroform/methanol=9/1) to obtain the entitled compound as a brown oily substance.

(Step 3) Production of 5-(6-(1-acetyl-pyrrolidin-2-yl)-2-pyridin-2-yl-1-(2-trimethylsilanyl-ethoxymethyl)-1H-benzimidazol-5-yloxy)-1,3-dihydro-benzimidazol-2-one The entitled compound was obtained as a brown oily substance in the same method as in Example 62 or in accordance with the method or by combining it with an ordinary method but using 1-(2-(6-(3,4-diamino-phenoxy)-2-pyridin-2-yl-3-(2-trimethylsilanyl-ethoxymethyl)-3H-benzimidazol-5-yl)-pyrrolidin-1-yl)-ethanone.

(Step 4) Production of 5-(6-(1-acetyl-pyrrolidin-2-yl)-2-pyridin-2-yl-1H-benzimidazol-5-yloxy)-1,3-dihydro-benzimidazol-2-one The entitled compound was obtained as an amorphous substance in the same method as in Example 121 (step 12) or in accordance with the method or by combining it with an ordinary method but using 5-(6-(1-acetyl-pyrrolidin-2-yl)-2-pyridin-2-yl-1-(2-trimethylsilanyl-ethoxymethyl)-1H-benzimidazol-5-yloxy)-1,3-dihydro-benzimidazol-2-one.
$^1$HNMR (CDCl$_3$) δ: 1.80-2.57 (7H, m), 3.61-4.02 (2H, m), 5.27-5.60 (1H, m), 6.77-7.60 (6H, m), 7.91-8.06 (1H, m), 8.17-8.33 (1H, m), 8.72 (1H, brs)
ESI-MS (m/e): 455 [M+H]

Example 156

1-(2-(6-(3H-benzimidazol-5-yloxy)-2 pyridin-2-yl-3H-benzimidazol-5-yl)-pyrrolidin-1-yl)-ethanone 19 mg of 1-(2-(6-(3,4-diamino-phenoxy)-2-pyridin-2-yl-3-(2-trimethylsilanyl-ethoxymethyl)-3H-benzimidazol-5-yl)-pyrrolidin-1-yl)-ethanone obtained in Example 155 (step 2) was dissolved in 1 ml of formic acid, and the reaction liquid was stirred at 100° C. for 2 hours. The reaction liquid was concentrated under reduced pressure, and the resulting residue was purified through reversed-phase middle-pressure liquid chromatography [ODS-AS-360-CC (by YMC), mobile phase: water-acetonitrile-0.1% trifluoroacetic acid] to obtain the entitled compound.
$^1$HNMR (CD$_3$OD) δ: 1.80-2.2.55 (7H, m), 3.60-4.00 (2H, m), 5.33-5.69 (1H, m), 7.00-7.80, 7.91-8.04, 8.16-8.30, 8.67-8.80 (10H, each m)
ESI-MS (m/e): 439 [M+H]

Example 157

1-(2-(6-(2-Methyl-3H-benzimidazol-5-yloxy)-2-pyridin-2-yl-3H-benzimidazol-5-yl)-pyrrolidin-1-yl)-ethanone The entitled compound was obtained in the same method as in Example 156 or in accordance with the method or by combining it with an ordinary method but using acetic acid.

Example 158

5-(6-(1-Acetyl-pyrrolidin-2-yl)-2-pyridin-2-yl-1H-benzimidazol-5-yloxy)-pyrimidine-2-carbonitrile The entitled compound was obtained as a white solid in the same method as in Example 147 or in accordance with the method or by combining it with an ordinary method but using 5-bromo-pyrimidine-2-carbonitrile.
$^1$HNMR (CDCl$_3$) δ: 1.81-2.40 (7H, m), 3.56-3.88 (2H, m), 5.08-5.34 (1H, m), 6.75-7.70 (3H, m), 7.81-7.90 (1H, m), 8.33-8.63 (4H, m)
ESI-MS (m/e): 426 [M+H]

Example 159

5-(6-(1-Acetyl-pyrrolidin-2-yl)-2-pyridin-2-yl-1H-benzimidazol-5-yloxy)-pyrimidine-2-carboxamide The entitled compound was obtained as a white solid in the same method as in Example 43 or in accordance with the method or by combining it with an ordinary method but using 5-(6-(1-acetyl-pyrrolidin-2-yl)-2-pyridin-2-yl-1H-benzimidazol-5-yloxy)-pyrimidine-2-carbonitrile obtained in Example 158.
$^1$HNMR (CDCl$_3$) δ: 1.79-2.42 (7H, m), 3.60-3.90 (2H, m), 5.18-5.39 (1H, m), 6.99-7.71 (3H, m), 7.82-7.92 (1H, m), 8.34-8.42 (1H, m), 8.55-8.65 (3H, m)
ESI-MS (m/e): 444 [M+H]

Example 160

Ethyl 4-(6-(1-Acetyl-pyrrolidin-2-yl)-2-pyridin-2-yl-1H-benzimidazol-5-yloxy)benzoate The entitled compound was obtained as a white solid in the same method as in Example 147 or in accordance with the method or by combining it with an ordinary method but using ethyl 4-fluorobenzoate.
$^1$HNMR (CDCl$_3$) δ: 1.24-1.41 (3H, m), 1.70-2.38 (7H, m), 3.53-3.87 (2H, m), 4.32-4.41 (2H, m), 5.14-5.45 (1H, m), 6.96-7.67 (5H, m), 7.82-7.91 (1H, m), 7.98-8.06 (2H, m), 8.34-8.43 (1H, m), 8.61-8.68 (1H, m)
ESI-MS (m/e): 471 [M+H]

Example 161

1-(2-(6-Phenethyloxy-2-pyridin-2-yl-3H-benzimidazol-5-yl)-pyrrolidin 1-yl)-ethanone (Step 1) Production of 1-(2-(6-phenethyloxy-2-pyridin-2-yl-3-(2-trimethylsilanyl-ethoxymethyl)-3H-benzimidazol-5-yl)-pyrrolidin-1-yl)-ethanone 0.019 ml of diisopropylamine, 27.6 mg of triphenyl phosphine and 0.011 ml of 2-phenyl-ethanol were added in order to a tetrahydrofuran (1 ml) solution of 29.2 mg of 1-(2-(6-hydroxy-2-pyridin-2-yl-3-(2-trimethylsilanyl-ethoxymethyl)-3H-benzimidazol-5-yl)pyrrolidin-1-yl)-ethanone obtained in Example 121 (step 10), and the reaction liquid was stirred for 6 hours at room temperature. 0.040 ml of diisopropylamine, 53.2 mg of triphenyl phosphine and 0.023 ml of 2-phenyl-ethanol were added in order to the reaction liquid, and the reaction liquid was stirred overnight at room temperature. Aqueous saturated sodium bicarbonate was added to the reaction liquid, and this was extracted with ethyl acetate, and dried with anhydrous magnesium sulfate. The solvent was evaporated away under reduced pressure, and the resulting residue was purified through partitioning thin-layer chromatography (Kieselgel™ 60F$_{254}$, Art 5744 (by Merck), ethyl acetate) to obtain the entitled compound as a brown oily substance.

(Step 2) Production of 1-(2-(6-phenethyloxy-2-pyridin-2-yl-3H-benzimidazol-5-yl)-pyrrolidin-1-yl)-ethanone The entitled compound was obtained as an oily substance in the same method as in Example 121 (step 12) or in accordance with the method or by combining it with an ordinary method but using 1-(2-(6-phenethyloxy-2-pyridin-2-yl-3-(2-trimethylsilanyl-ethoxymethyl)-3H-benzimidazol-5-yl)-pyrrolidin-1-yl)-ethanone.
$^1$HNMR (CDCl$_3$) δ: 1.59-2.23 (7H, m), 2.87-3.10, 3.50-3.86, 3.96-4.35 (6H, each m), 5.04-5.13, 5.46-5.57 (1H, each m), 6.53-7.55 (8H, m), 7.77-7.89 (1H, m), 8.32-8.40 (1H, m), 8.54-8.65 (1H, m), 10.73-11.14 (1H, m)
ESI-MS (m/e): 427 [M+H]

Example 162

1-(2-(6-(4-Methanesulfonyl-phenoxy)-2-pyridin-2-yl-3H-benzimidazol-5-yl)-pyrrolidin 1-yl)-ethanone (Step 1) Production of t-butyl 2-(2-fluoro-5-nitro-phenyl)-pyrrole-1-carboxylate 1.1 g of tetrakis-triphenylphosphine palladium and 4.2 g of sodium carbonate were added to a solution of 4.3 g of 3-bromo-4-fluoro-nitrobenzene and 5.0 g of 1-(t-butoxycarbonyl)pyrrole-2-boronic acid in a mixture of 130 ml of dimethoxyethane and 22 ml of water, and the reaction liquid was heated overnight under reflux. Aqueous saturated sodium bicarbonate was added to the reaction liquid, and this was extracted with ethyl acetate. The organic layer was washed with water and saturated saline in order, and dried with anhydrous sodium sulfate. The solvent was evaporated away under reduced pressure, and the resulting residue was purified through silica gel column chromatography (developing solvent: hexane/ethyl acetate=20/1) to obtain the entitled compound as a yellow oily substance.

(Step 2) Production of t-butyl 2-((2-(4-methanesulfonyl-phenoxy)-5-nitro-phenyl)-pyrrole-1-carboxylate 3.38 g of potassium carbonate was added to a dimethylformamide (20 ml) solution of 2.5 g of t-butyl 2-(2-fluoro-5-nitro-phenyl)-pyrrole-1-carboxylate and 1.55 g of 4-methanesulfonyl-phenol, and the reaction liquid was stirred at 100° C. for 2 hours. After cooled, water was added to the reaction liquid, and this was extracted with ethyl acetate. The organic layer was washed with water and saturated saline, and dried with anhydrous sodium sulfate. The solvent was evaporated away under reduced pressure, and the resulting residue was purified through silica gel column chromatography (developing solvent: hexane/ethyl acetate=2/1) to obtain the entitled compound as a pale yellow solid.

---

$^1$HNMR (CD$_3$OD) δ: 1.69-2.63 (10H, m), 3.42-3.91 (2H, m), 5.20-5.64 (1H, m), 6.58-7.87 (9H, m), 8.22-8.66 (2H, m)
ESI-MS (m/e): 453 [M+H]

(Step 3) Production of t-butyl 2-(5-amino-2-(4-methanesulfonyl-phenoxy)-phenyl)-pyrrolidine-1-carboxylate 1.0 g of 5% platinum-carbon catalyst was added to 120 ml of an ethanol solution of 2.87 g of t-butyl 2-((2-(4-methanesulfonyl-phenoxy)-5-nitro-phenyl)-pyrrole-1-carboxylate, and the reaction liquid was stirred overnight in a hydrogen atmosphere. The catalyst was removed through filtration through Celite, and the solvent was evaporated away under reduced pressure. The resulting residue was purified through silica gel column chromatography (developing solvent: hexane/ethyl acetate=1/1 to ethyl acetate) to obtain the entitled compound as a white solid.

(Step 4) Production of 1-(2-(5-amino-2-(4-methanesulfonyl-phenoxy)-phenyl)-pyrrolidin-1-yl)-2,2,2-trifluoro-ethanone 342 mg of zinc powder and 650 mg of benzyl chloroformate were added to a benzene (25 ml) solution of 1.51 g of t-butyl 2-(5-amino-2-(4-methanesulfonyl-phenoxy)-phenyl)-pyrrolidine-1-carboxylate, and the reaction liquid was stirred overnight at room temperature. The reaction liquid was filtered through Celite, and aqueous saturated sodium bicarbonate was added to the filtrate. This was extracted with ethyl acetate, and the organic layer was washed with water and saturated saline in order, and dried with anhydrous sodium sulfate. The solvent was evaporated away under reduced pressure, and the resulting crude product was dissolved in 20 ml of 4 N hydrochloric acid/1,4-dioxane solution, and the reaction liquid was stirred at room temperature for 3 hours. The reaction liquid was distilled under reduced pressure, and the resulting crude product was dissolved in 30 ml of chloroform. With cooling with ice, 2 ml of pyridine and 0.5 ml of trifluoroacetic acid anhydride were added to it, and the reaction liquid was stirred for 2 hours at room temperature. 1 N hydrochloric acid was added to the reaction liquid, and this was extracted with ethyl acetate. The organic layer was washed with water, aqueous saturated sodium bicarbonate and saturated saline, and dried with anhydrous sodium sulfate. The solvent was evaporated away under reduced pressure, and 50 mg of 10% palladium-carbon catalyst was added to a methanol (100 ml) solution of the resulting crude product, and the reaction liquid was stirred overnight in a hydrogen atmosphere. The catalyst was removed through filtration through Celite, and the solvent was evaporated away under reduced pressure. The resulting residue was purified through silica gel column chromatography (developing solvent: hexane/ethyl acetate=1/1 to 1/3) to obtain the entitled compound as a white solid.

(Step 5) Production of 1-(2-(5-amino-2-(4-methanesulfonyl-phenoxy)-4-nitro-phenyl)-pyrrolidin-1-yl)-2,2,2-trifluoro-ethanone 153 mg of potassium nitrate was added to a trifluoroacetic acid (2 ml) solution of 588 mg of 1-(2-(5-amino-2-(4-methanesulfonyl-phenoxy)-phenyl)-pyrrolidin-1-yl)-2,2,2-trifluoro-ethanone, and the reaction liquid was stirred overnight at room temperature. Aqueous saturated sodium bicarbonate was added to the reaction liquid to neutralize it, and this was then extracted with ethyl acetate. The organic layer was washed with saturated saline, and dried with anhydrous sodium sulfate. The solvent was evaporated away under reduced pressure, and the resulting residue was purified through silica gel column chromatography (developing solvent: hexane/ethyl acetate=1/1) to obtain the entitled compound as a yellow solid.

(Step 6) Production of 2,2,2-trifluoro-1-(2-(6-(4-methanesulfonyl-phenoxy)-2-pyridin-2-yl-3H-benzimidazol-5-yl)-pyrrolidin-1-yl)-ethanone 100 mg of developed Raney nickel catalyst was added to an ethanol (10 ml) solution of 521 mg of 1-(2-(5-amino-2-(4-methanesulfonyl-phenoxy)-4-nitro-phenyl)-pyrrolidin-1-yl)-2,2,2-trifluoro-ethanone, and the reaction liquid was stirred overnight in a hydrogen atmosphere. The catalyst was removed through filtration through Celite, and the solvent was evaporated away under reduced pressure to obtain a crude product. 226 mg of pyridine-2-carboxaldehyde was added to a methanol (10 ml) solution of 448 mg of the resulting crude product, and the reaction liquid was stirred overnight at 50° C. Water was added to the reaction liquid, and extracted with ethyl acetate. The organic layer was washed with water and saturated saline, and dried with anhydrous sodium sulfate. The solvent was evaporated away under reduced pressure, and the resulting residue was purified through silica gel column chromatography (developing solvent: chloroform/methanol=20/1) to obtain the entitled compound as a pale yellow solid.

(Step 7) Production of 5-(4-methanesulfonyl-phenoxy)-2-pyridin-2-yl-6-pyrrolidin-2-yl-1H-benzimidazole 500 mg of potassium carbonate was added to a solution of 375 mg of 2,2,2-trifluoro-1-(2-(6-(4-methanesulfonyl-phenoxy)-2-pyridin-2-yl-3H-benzimidazol-5-yl)-pyrrolidin-1-yl)-ethanone in a mixture of 16 ml of methanol and 3 ml of water, and the reaction liquid was stirred overnight at room temperature. The reaction liquid was distilled under reduced pressure, diluted with aqueous saturated sodium bicarbonate added thereto, and then extracted with ethyl acetate. The organic layer was washed with saturated saline, and dried with anhydrous sodium sulfate. The solvent was evaporated away under reduced pressure, and the resulting residue was purified through silica gel column chromatography (developing solvent: chloroform/methanol/aqueous ammonia=10/1/0.1) to obtain the entitled compound as a pale yellow solid.

(Step 8) Production of 1-(2-(6-(4-methanesulfonyl-phenoxy)-2-pyridin-2-yl-3H-benzimidazol-5-yl)-pyrrolidin-1-yl)-ethanone 0.003 ml of acetic anhydride was added to a methylene chloride (1 ml) solution of 10 mg of 5-(4-methanesulfonyl-phenoxy)-2-pyridin-2-yl-6-pyrrolidin-2-yl-1H-benzimidazole, and the reaction liquid was stirred at room temperature for 1 hour. The reaction solvent was evaporated away under reduced pressure, and the resulting residue was purified through partitioning thin-layer chromatography (Kieselgel™ 60F$_{254}$, Art 5744 (by Merck), chloroform/methanol=10/1) to obtain the entitled compound as a white solid.

$^1$HNMR (CDCl$_3$) δ: 1.60-2.40 (7H, m), 3.05 and 3.08 (total 3H, each s), 3.52-3.90 (2H, m), 5.13-5.37 (1H, m), 7.08-7.69 (5H, m), 7.83-7.97 (3H, m), 8.32-8.40 (1H, m), 8.61-8.70 (1H, m)

ESI-MS (m/e): 477 [M+H]

Example 163

1-(2-(6-(4-Methanesulfonyl-phenoxy)-2-pyridin-2-yl-3H-benzimidazol-5-yl)-pyrrolidin-1-yl)-ethanone enantiomer A and enantiomer B 230 mg of 5-(4-methanesulfonyl-phenoxy)-2-pyridin-2-yl-6-pyrrolidin-2-yl-1H-benzimidazole obtained in Example 162 (step 7) was optically resolved, using an optical resolution column (CHIRALPAK AD 2 cmφ×25 cmL (by Daicel Chemical), mobile phase: hexane/2-propanol/diethylamine=20/80/0.1, flow rate: 10 ml/min), into an enantiomer A (retention time: 19.0 min) and an enantiomer B (retention time: 32.2 min) each as a yellow oily substance.

Example 164

1-(2-(6-(4-Methanesulfonyl-phenoxy)-2-pyridin-2-yl-3H-benzimidazol-5-yl)-pyrrolidin-1-yl)-ethanone A 0.003 ml of acetic anhydride was added to a methylene chloride (1 ml) solution of 12 mg of 1-(2-(6-(4-methanesulfonyl-phenoxy)-2-pyridin-2-yl-3H-benzimidazol-5-yl)-pyrrolidin-1-yl)-ethanone enantiomer A obtained in Example 163, and the reaction liquid was stirred at room temperature for 1 hour. The reaction solvent was evaporated away under reduced pressure, and the resulting residue was purified through partitioning thin-layer chromatography (Kieselgel™ 60F$_{254}$, Art 5744 (by Merck), chloroform/methanol=10/1) to obtain one chiral form of the entitled compound as a white solid.

$^1$H-NMR (CDCl$_3$) δ: 1.60-2.40 (7H, m), 3.05 and 3.08 (total 3H, each s), 3.52-3.90 (2H, m), 5.13-5.37 (1H, m), 7.08-7.69 (5H, m), 7.83-7.97 (3H, m), 8.35-8.43 (1H, m), 8.61-8.70 (1H, m)

ESI-MS (m/e): 477 [M+H]

Specific rotatory power: [α]$^{24}_D$ (c=0.100, ethanol) −46.9°

Example 165

1-(2-(6-(4-Methanesulfonyl-phenoxy)-2-pyridin-2-yl-3H-benzimidazol-5-yl)-pyrrolidin-1-yl)-ethanone B 0.011 ml of acetic anhydride was added to a methylene chloride (1 ml) solution of 44 mg of 1-(2-(6-(4-methanesulfonyl-phenoxy)-2-pyridin-2-yl-3H-benzimidazol-5-yl)-pyrrolidin-1-yl)-ethanone enantiomer B obtained in Example 163, and the reaction liquid was stirred at room temperature for 1 hour. The reaction solvent was evaporated away under reduced pressure, and the resulting residue was purified through partitioning thin-layer chromatography (Kieselgel™ 60F$_{254}$, Art 5744 (by Merck), chloroform/methanol=10/1) to obtain one chiral form of the entitled compound as a white solid.

ESI-MS (m/e): 477 [M+H]

Specific rotatory power: [α]$^{24}_D$ (c=0.100, ethanol) +47.7°

Example 166

2,2,2-Trifluoro-1-(2-(6-(4-fluoro-phenoxy)-2 pyridin-2-yl-3H-benzimidazol-5-yl)-pyrrolidin-1-yl)-ethanone The entitled compound was obtained as a white solid in the same method as in Example 162 (Step 2) to (Step 6) or in accordance with the method or by combining it with an ordinary method but using 4-fluorophenol.

$^1$HNMR (CDCl$_3$) δ: 1.96-2.21 (3H, m), 2.31-2.43 (1H, m), 3.77-4.08 (2H, m), 5.47-5.70 (1H, m), 6.88-6.91 (1H, m), 7.00-7.08 (4H, m), 7.26-7.50 (2H, m), 7.82-7.85 (1H, m), 8.31-8.35 (1H, m), 8.57-8.61 (1H, m)

ESI-MS (m/e): 471 [M+H]

Example 167

1-(2-(6-(4-Fluoro-phenoxy)-2-pyridin-2-yl-3H-benzimidazol-5-yl)-pyrrolidin-1-yl)-ethanone The entitled compound was obtained as a white solid in the same method as in Example 162 (Step 2) to (Step 8) or in accordance with the method or by combining it with an ordinary method but using 4-fluorophenol.

$^1$HNM (CDCl$_3$) δ: 1.83-2.03 (6H, m), 2.32-2.41 (1H, m), 3.58-3.86 (2H, m), 5.26-5.57 (1H, m), 6.96-7.06 (5H, m), 7.24-7.35 (2H, m), 7.80-7.88 (1H, m), 8.30-8.37 (1H, m), 8.56-8.62 (1H, m)

ESI-MS (m/e): 417 [M+H]

Example 168

1-(2-(6-(4-Fluoro-phenoxy-2-pyridin-2-yl-3H-benzimidazol-5-yl)pyrrolidin-1-yl-2-hydroxy-ethanone 4.5 mg of glycolic acid, 12.3 mg of N-hydroxybenzotriazole hydrate and 15.4 mg of 1-(3-dimethylaminopropyl)-3-ethylcarbodiimide hydrochloride were added in order to a chloroform (1 ml) solution of 20 mg of 5-(4-fluoro-phenoxy)-2-pyridin-2-yl-6-pyrrolidin-2-yl-1H-benzimidazole obtained in the same method as in Example 162 (Step 2) to (Step 7) but using 4-fluorophenol, and the reaction liquid was stirred overnight at room temperature. The reaction solvent was evaporated away, and the resulting residue was purified through partitioning thin-layer chromatography (Kieselgel™ 60F$_{254}$, Art 5744 (by Merck), chloroform/methanol=10/1) to obtain the entitled compound.

$^1$HNMR (CDCl$_3$) δ: 1.88-2.13 (3H, m), 2.20-2.43 (1H, m), 3.40-4.21 (4H, m), 5.14-5.60 (1H, m), 6.85-7.54 (7H, m), 7.78-7.86 (1H, m), 8.29-8.37 (1H, m), 8.56-8.61 (1H, m)

ESI-MS (m/e): 433 [M+H]

Example 169

1-(2-(6-(4-Fluoro-phenoxy)-2-pyridin-2-yl-3H-benzimidazol-5-yl)-pyrrolidin-1-yl)-2-methoxy-ethanone The entitled compound was obtained as a white solid in the same method as in Example 168 or in accordance with the method or by combining it with an ordinary method but using methoxyacetic acid.

$^1$HNMR (CDCl$_3$) δ: 1.80-2.41 (4H, m), 3.26-3.46 (3H, m), 3.52-4.16 (4H, m), 5.28-5.60 (1H, m), 6.79-7.57 (7H, m), 7.77-7.85 (1H, m), 8.28-8.38 (1H, m), 8.56-8.62 (1H, m)

ESI-MS (m/e): 447 [M+H]

Example 170

1-(2-(6-(4-Fluoro-phenoxy)-2-pyridin-2-yl-3H-benzimidazol-5-yl)-pyrrolidin-1-yl)-3-phenyl-propan-1-one The entitled compound was obtained as a white solid in the same method as in Example 168 or in accordance with the method or by combining it with an ordinary method but using 3-phenyl-propionic acid.

¹HNMR (CDCl₃) δ: 1.82-3.03 (8H, m), 3.48-3.93 (2H, m), 5.13-5.99 (1H, m), 6.82-7.60 (12H, m), 7.80-7.08 (1H, m), 8.09-8.39 (1H, m), 8.56-8.66 (1H, m)
ESI-MS (m/e): 507 [M+H]

Example 171

2-(6-(4-Fluoro-phenoxy)-2-pyridin-2-yl-3H-benzimidazol-5-yl)-pyrrolidin-1-yl)-(2R)-pyrrolidin-2-yl-methanone 13.8 mg of 1-t-butoxycarbonyl-D-proline, 12.3 mg of N-hydroxybenzotriazole hydrate and 15.4 mg of 1-(3-dimethylaminopropyl)-3-ethylcarbodiimide hydrochloride were added in order to a chloroform (1 ml) solution of 20 mg of 5-(4-fluoro-phenoxy)-2-pyridin-2-yl-6-pyrrolidin-2-yl-1H-benzimidazole obtained in Example 168, and the reaction liquid was stirred overnight at room temperature. The reaction solvent was evaporated away under reduced pressure, and the resulting residue was dissolved in 1 ml of 4 N hydrochloric acid-ethyl acetate solution, and the reaction liquid was stirred at room temperature for 1 hour. The solvent was evaporated away under reduced pressure, and the resulting residue was purified through thin-layer chromatography (NH TLC Plate (by Fuji Silysia Chemical), chloroform/methanol=30/1) to obtain the entitled compound as an oily substance.
¹HNMR (CDCl₃) δ: 0.82-4.00 (13H, m), 5.23-5.61 (1H, m), 6.82-7.59 (7H, m), 7.78-7.88 (1H, m), 8.32-8.39 (1H, m), 8.57-8.64 (1H, m)
ESI-MS (m/e): 472 [M+H]

Example 172

(2-(6-(4-Fluoro-phenoxy-2-pyridin-2-yl-3H-benzimidazol-5-yl)-pyrrolidin-1-yl)-(2S)-pyrrolidin-2-yl-methanone The entitled compound was obtained as an oily substance in the same method as in Example 171 or in accordance with the method or by combining it with an ordinary method but using 1-t-butoxycarbonyl-L-proline.
¹HNMR (CDCl₃) δ: 0.82-4.00 (13H, m), 5.23-5.61 (1H, m), 6.82-7.59 (7H, m), 7.78-7.88 (1H, m), 8.30-8.39 (1H, m), 8.57-8.64 (1H, m)
ESI-MS (m/e): 472 [M+H]

Example 173

2-Dimethylamino-1-(2-(6-(4-fluoro-phenoxy)-2-pyridin-2-yl-3H-benzimidazol-5-yl)-pyrrolidin-1-yl)-ethanone The entitled compound was obtained as an oily substance in the same method as in Example 168 or in accordance with the method or by combining it with an ordinary method but using N,N-dimethylglycine hydrochloride.
¹HNMR (CDCl₃) δ: 1.81-2.57 (10H, m), 2.76-3.96 (4H, m), 5.41-5.62 (1H, m), 6.94-7.37 (7H, m), 7.81-7.89 (1H, m), 8.33-8.38 (1H, m), 8.59-8.68 (1H, m)
ESI-MS (m/e): 460 [M+H]

Example 174

1-(2-(6-(4-Fluoro-phenoxy)-2-pyridin-2-yl-3H-benzimidazol-5-yl)-pyrrolidin-1-yl)-propan-1-one The entitled compound was obtained as an oily substance in the same method as in Example 168 or in accordance with the method or by combining it with an ordinary method but using propionic acid.
¹HNMR (CDCl₃) δ: 0.95-1.24 (3H, m), 1.70-2.60 (6H, m), 3.52-3.94 (2H, m), 5.24-5.62 (1H, m), 6.75-7.66 (7H, m), 7.77-7.92 (1H, m), 8.27-8.44 (1H, m), 8.52-8.68 (1H, m), 10.66-11.08 (1H, m)
ESI-MS (m/e): 431 [M+H]

Example 175

1-(2-(6-(4-Fluoro-phenoxy-2-pyridin-2-yl-3H-benzimidazol-5-yl)pyrrolidin-1-yl)-butan-1-one The entitled compound was obtained as an oily substance in the same method as in Example 168 or in accordance with the method or by combining it with an ordinary method but using n-butyric acid.
¹HNMR (CDCl₃) δ: 0.70-1.07 (3H, m), 1.40-2.44 (8H, m), 3.53-3.91 (2H, m), 5.25-5.60 (1H, m), 6.72-7.66 (7H, m), 7.80-7.93 (1H, m), 8.30-8.44 (1H, m), 8.53-8.68 (1H, m), 10.68-11.18 (1H, m)
ESI-MS (m/e): 445 [M+H]

Example 176

1-(2-(6-(4-Fluoro-phenoxy)-2-pyridin-2-yl-3H-benzimidazol-5-yl)-pyrrolidin-1-yl)-3-hydroxypropan-1-one The entitled compound was obtained as an oily substance in the same method as in Example 168 or in accordance with the method or by combining it with an ordinary method but using 3-hydroxypropionic acid.
¹HNMR (CDCl₃) δ: 1.43-2.73 (6H, m), 3.24-4.27 (5H, m), 5.24-5.60 (1H, m), 6.75-7.60 (7H, m), 7.76-7.88 (1H, m), 8.27-8.40 (1H, m), 8.53-8.66 (1H, m), 10.44-11.01 (1H, m)
ESI-MS (m/e): 447 [M+H]

Example 177

1-(2-(6-(4-Fluoro-phenoxy)-2-pyridin-2-yl-3H-benzimidazol-5-yl)-pyrrolidin-1-yl)-2-methylamino-ethanone The entitled compound was obtained in the same method as in Example 171 or in accordance with the method or by combining it with an ordinary method but using N-t-butoxycarbonyl-N-methylglycine.
¹HNMR (CDCl₃) δ: 1.82-2.01 (3H, m), 2.43-2.56 (4H, m), 3.25-4.15 (4H, m), 5.32-5.37 (1H, m), 7.00-7.31 (4H, m), 7.38-7.58 (2H, m), 8.03-8.08 (1H, m), 8.37-8.43 (1H, m), 8.69-8.79 (1H, m), 8.80-8.94 (1H, m)
ESI-MS (m/e): 446 [M+H]

Example 178

5-(4-Fluoro-phenoxy)-6-(1-methanesulfonyl-pyrrolidin-2-yl)-2-pyridin-2-yl-1H-benzimidazole 0.01 ml of triethylamine and 0.005 ml of methanesulfonyl chloride were added in order to an ethyl acetate (1 ml) solution of 20 mg of 5-(4-fluoro-phenoxy)-2-pyridin-2-yl-6-pyrrolidin-2-yl-1H-benzimidazole obtained in Example 168, and the reaction liquid was stirred overnight at room temperature. The reaction solvent was evaporated away under reduced pressure, and the resulting residue was purified through partitioning thin-layer chromatography (Kieselgel™ 60F₂₅₄, Art 5744 (by Merck), chloroform/methanol=10/1) to obtain the entitled compound as a white solid.

¹HNMR (CDCl₃) δ: 1.80-2.08 (3H, m), 2.28-2.42 (1H, m), 2.81 and 2.84 (total 13H, each s), 3.47-3.74 (2H, m), 5.17-5.37 (1H, m), 6.79-7.93 (8H, m), 8.30-8.37 (1H, m), 8.57-8.61 (1H, m)
ESI-MS (m/e): 453 [M+H]

Example 179

5-(4-Fluoro-phenoxy)-2-pyridin-2-yl-6-(1-pyrimidin-2-yl-pyrrolidin-2-yl)-1H-benzimidazole 0.013 ml of triethylamine and 6.3 mg of 2-chloro-pyrimidine were added in order to an ethanol (2 ml) solution of 17.1 mg of 5-(4-fluoro-phenoxy)-2-pyridin-2-yl-6-pyrrolidin-2-yl-1H-benzimidazole obtained in Example 168, and the reaction liquid was heated under reflux for 3 hours. The reaction solvent was evaporated away under reduced pressure, and the resulting residue was purified through reversed-phase middle-pressure liquid chromatography [ODS-AS-360-CC (by YMC), mobile phase: water-acetonitrile-0.1% trifluoroacetic acid], and the resulting fraction was diluted with ethyl acetate, washed with aqueous saturated sodium bicarbonate and saturated saline in order, and dried with anhydrous sodium sulfate. The solvent was evaporated away under reduced pressure to obtain the entitled compound as a white solid.
¹HNMR (CDCl₃) δ: 1.98-2.15 (3H, m), 2.34-2.42 (1H, m), 3.68-3.78 (1H, m), 3.90-4.07 (1H, m), 5.63 (1H, d, J=8.0 Hz), 6.43 (1H, brs), 6.87-7.55 (7H, m), 7.79-7.84 (1H, m), 8.15-8.34 (3H, m), 8.55-8.58 (1H, m)
ESI-MS (m/e): 453 [M+H]

Example 180

2-(2-(6-(4-Fluoro-phenoxy)-2-pyridin-2-yl-3H-benzimidazol-5-yl)-pyrrolidin-1-yl)-acetamide 11.4 mg of potassium carbonate and 11.1 mg of iodoacetamide were added in order to an acetonitrile (1 ml) solution of 20 mg of 5-(4-fluoro-phenoxy)-2-pyridin-2-yl-6-pyrrolidin-2-yl-1H-benzimidazole obtained in Example 168, and the reaction liquid was stirred overnight at room temperature. The reaction liquid was concentrated, and the resulting residue was purified through reversed-phase middle-pressure liquid chromatography [ODS-AS-360-CC (by YMC), mobile phase: water-acetonitrile-0.1% trifluoroacetic acid], and the resulting fraction was diluted with ethyl acetate, washed with aqueous saturated sodium bicarbonate and saturated saline in order, and dried with anhydrous sodium sulfate. The solvent was evaporated away under reduced pressure to obtain the entitled compound as a white solid.
¹HNMR (CDCl₃) δ: 1.60-2.04 (3H, m), 2.20-2.13 (1H, m), 2.80-2.85 (1H, m), 3.37-3.44 (2H, m), 3.96-4.03 (1H, m), 5.41-5.52 (1H, m), 6.90-7.34 (5H, m), 7.36-7.39 (1H, m), 7.65 and 8.00 (total 1H, each s), 7.83-7.87 (1H, m), 8.36-8.39 (1H, m), 8.59-8.64 (1H, m)
ESI-MS (m/e): 432 [M+H]

Example 181

Ethyl 2-(6-(4-fluoro-phenoxy)-2-pyridin-2-yl-3H-benzimidazol-5-yl)-pyrrolidine-1-carboxylate 5.2 mg of zinc powder and 0.006 ml of ethyl chloroformate were added in order to a benzene (1 ml) solution of 20 mg of 5-(4-fluoro-phenoxy)-2-pyridin-2-yl-6-pyrrolidin-2-yl-1H-benzimidazole obtained in Example 168, and the reaction liquid was stirred overnight at room temperature. The reaction solvent was evaporated away under reduced pressure, and the resulting residue was purified through partitioning thin-layer chromatography (Kieselgel™ 60F₂₅₄, Art 5744 (by Merck), chloroform/methanol=10/1) to obtain the entitled compound as a white solid.
¹HNMR (CDCl₃) δ: 1.23-1.31 (3H, m), 1.80-2.00 (3H, m), 2.20-2.39 (1H, m), 3.50-3.79 (2H, m), 3.91-4.17 (2H, m), 5.17-5.38 (1H, m), 6.81-7.63 (7H, m), 7.77-7.85 (1H, m), 8.28-8.39 (1H, m), 8.55-8.63 (1H, m)
ESI-MS (m/e): 447 [M+H]

Example 182

2-(6-(4-Methanesulfonyl-phenoxy)-2-pyridin-2-yl-3H-benzimidazol-5-yl)-pyrrolidine-1-carboxamide 5 mg of dimethylaminopyridine and 0.029 ml of trimethylsilyl isocyanate were added to a methylene chloride (1 ml) solution of 17.1 mg of 5-(4-methanesulfonyl-phenoxy)-2-pyridin-2-yl-6-pyrrolidin-2-yl-1H-benzimidazole obtained in Example 162 (step 7), and the reaction liquid was stirred overnight at room temperature. Water was added to the reaction liquid, and extracted with ethyl acetate, and then washed with saturated saline. After dried and concentrated, the resulting residue was purified through reversed-phase middle-pressure liquid chromatography [ODS-AS-360-CC (by YMC), mobile phase: water-acetonitrile-0.1% trifluoroacetic acid], and the resulting fraction was diluted with ethyl acetate, washed with aqueous saturated sodium bicarbonate and saturated saline in order, and dried with anhydrous sodium sulfate. The solvent was evaporated away under reduced pressure to obtain the entitled compound as a white solid.
¹HNMR (CDCl₃) δ: 1.83-2.09 (3H, m), 2.22-2.40 (1H, m), 3.07 (3H, s), 3.56-3.82 (2H, m), 4.35 and 4.62 (total 2H, each brs), 5.01-5.20 (1H, m), 7.08-7.95 (8H, m), 8.34-8.40 (1H, m), 8.62-8.64 (1H, m)
ESI-MS (m/e): 478 [M+H]

Examples 183-1, 183-2

2-(6-(4-Methanesulfonyl-phenoxy)-2-pyridin-2-yl-3H-benzimidazol-5-yl)-pyrrolidine-1-carboxamide enantiomer A and enantiomer B 10 mg of racemic 2-(6-(4-methanesulfonyl-phenoxy)-2-pyridin-2-yl-3H-benzimidazol-5-yl)-pyrrolidine-1-carboxamide obtained in Example 182 was optically resolved, using an optical resolution column (CHIRALPAK AD 2 cmφ×25 cmL (by Daicel Chemical), mobile phase: hexane/ethanol=20/80, flow rate: 10 ml/min), into an enantiomer A (retention time: 17.9 min) and an enantiomer B (retention time: 27.6 min) each as a white solid.

Enantiomer A:
ESI-MS (m/e): 478 [M+H]
Specific rotatory power: $[\alpha]^{24}_D$ (c=0.100, ethanol)–27.4°

Enantiomer B:
ESI-MS (m/e): 478 [M+H]
Specific rotatory power: $[\alpha]^{24}D$ (c=0.100, ethanol)+28.40

Example 184

2-(6-(4-fluoro-phenoxy)-2-pyridin-2-yl-3H-benzimidazol-5-yl)-pyrrolidine-1-carboxamide 2 mg of dimethylaminopyridine and 0.059 ml of trimethylsilyl isocyanate were added in order to a methylene chloride (1 ml) solution of 31.2 mg of 5-(4-fluoro-phenoxy)-2-pyridin-2-yl-6-pyrrolidin-2-yl-1H-benzimidazole obtained in Example 168, and the reaction liquid was stirred overnight at room temperature. Water was added to the reaction liquid, and extracted with ethyl acetate, and then washed with saturated saline. After dried and concentrated, the resulting residue was purified through reversed-phase middle-pressure liquid chromatography [ODS-AS-360-CC (by YMC), mobile phase: water-acetonitrile-0.1% trifluoroacetic acid] to obtain the entitled compound as a white solid.

$^1$HNMR (CDCl$_3$) δ: 1.88-2.08 (3H, m), 2.32-2.48 (1H, m), 3.62-3.87 (2H, m), 4.34 and 4.71 (total 2H, each brs), 5.15-5.30 (1H, m), 6.91-7.73 (7H, m), 7.81-7.87 (1H, m), 8.31-8.37 (1H, m), 8.59-8.61 (1H, m)

ESI-MS (m/e): 418 [M+H]

Examples 185-1, 185-2

2-(6-(4-Fluoro-phenoxy)-2-pyridin-2-yl-3H-benzimidazol-5-yl pyrrolidine-1-carboxamide enantiomer A and enantiomer B 9.0 mg of racemic 2-(6-(4-fluoro-phenoxy)-2-pyridin-2-yl-3H-benzimidazol-5-yl)-pyrrolidine-1-carboxamide obtained in Example 184 was optically resolved, using an optical resolution column (CHIRALPAK AD 2 cmϕ×25 cmL (by Daicel Chemical), mobile phase: hexane/2-propanol=50/50, flow rate: 10 ml/min), into an enantiomer A (retention time: 12.1 min) and an enantiomer B (retention time: 26.9 min) each as a white solid.

Enantiomer A:
ESI-MS (m/e): 418 [M+H]

Enantiomer B:
ESI-MS (m/e): 418 [M+H]

Example 186

2-(6-(4-Dimethylcarbamoyl-phenoxy)-2-pyridin-2-yl-3H-benzimidazol-5-yl)-pyrrolidine-1-carboxamide The entitled compound was obtained as a white solid in the same method as in Example 162 (step 2) to (step 7) and Example 182 or in accordance with the method or by combining it with an ordinary method but using 4-hydroxy-N,N-dimethyl-benzamide.

$^1$HNMR (CDCl$_3$) δ: 1.85-2.07 (3H, m), 2.28-2.43 (1H, m), 3.00-3.18 (6H, m), 3.60-3.80 (2H, m), 5.10-5.23 (1H, m), 7.01-7.76 (7H, m), 7.83-7.88 (1H, m), 8.33-8.39 (1H, m), 8.63-8.64 (1H, m)

ESI-MS (m/e): 471 [M+H]

Examples 187-1, 187-2

2-(6-(4-Dimethylcarbamoyl-phenoxy)-2-pyridin-2-yl-3H-benzimidazol-5-yl)-pyrrolidine-1-carboxamide enantiomer A and enantiomer B 72.2 mg of racemic 2-(6-(4-dimethylcarbamoyl-phenoxy)-2-pyridin-2-yl-3H-benzimidazol-5-yl)-pyrrolidine-1-carboxamide obtained in Example 186 was optically resolved, using an optical resolution column (CHIRALPAK AD 2 cmϕ×25 cmL (by Daicel Chemical), mobile phase: hexane/ethanol=40/60, flow rate: 10 ml/min), into an enantiomer A (retention time: 18.1 min) and an enantiomer B (retention time: 23.9 min) each as a white solid.

Enantiomer A:
ESI-MS (m/e): 471 [M+H]

Enantiomer B:
ESI-MS (m/e): 471 [M+H]

Example 188

2-(6-(4-Fluoro-phenoxy)-2-pyridin-2-yl-3H-benzimidazol-5-yl)-pyrrolidine-1-carboxylic acid ethyl amide The entitled compound was obtained as a white solid in the same method as in Example 184 or in accordance with the method or by combining it with an ordinary method but using ethyl isocyanate.

$^1$H-NMR (CDCl$_3$) δ: 0.94-1.07 (3H, m), 1.80-2.03 (3H, m), 2.25-2.41 (1H, m), 3.10-3.26 (2H, m), 3.57-3.74 (2H, m), 4.02-4.14 (1H, m), 5.07-5.23 (1H, m), 6.85-7.66 (7H, m), 7.78-7.85 (1H, m), 8.30-8.38 (1H, m), 8.54-8.63 (1H, m)

ESI-MS (m/e): 446 [M+H]

Example 189

1-(2-(6-(4-Fluoro-phenoxy)-2-pyrazin-2-yl-3H-benzimidazol-5-yl)-pyrrolidin-1-yl)-ethanone The entitled compound was obtained as a white solid in the same method as in Example 162 (step 6) to (step 8) or in accordance with the method or by combining it with an ordinary method but using pyrazine-2-carboxaldehyde.

$^1$HNMR (CDCl$_3$) δ: 1.86-2.08 (7H, m), 3.37-3.90 (2H, m), 5.27-5.55 (1H, m), 6.76-7.64 (6H, m), 8.32-8.62 (2H, m), 9.53-9.56 (1H, m)

ESI-MS (m/e): 418 [M+H]

Example 190

1-(2-(6-(4-Fluoro-phenoxy)-2-thiazol-2-yl-3H-benzimidazol-5-yl)-pyrrolidin-1-yl)-ethanone The entitled compound was obtained as a white solid in the same method as in Example 162 (step 6) to (step 8) or in accordance with the method or by combining it with an ordinary method but using thiazole-2-carboxaldehyde.

$^1$HNMR (CDCl$_3$) δ: 1.60-2.23 (6H, m), 2.24-2.43 (1H, m), 3.50-3.88 (2H, m), 5.28-5.57 (1H, m), 6.64-7.62 (7H, m), 7.89-7.94 (1H, m)

ESI-MS (m/e): 423 [M+H]

Example 191

(1-(6-(4-Methanesulfonyl-phenoxy-2-pyridin-2-yl-3H-benzimidazol-5-yl)-pyrrolidin-2-yl)-methanol The entitled compound was obtained as a white solid in the same method as in Example 15 or in accordance with the method or by combining it with an ordinary method but using D,L-prolinol.

$^1$HNMR (CDCl$_3$) δ: 1.64-1.92 (3H, m), 1.97-2.06 (1H, m), 3.00-3.12 (1H, m), 3.04 (3H, s), 3.38-3.46 (1H, m), 3.53-3.64 (2H, m), 3.84 (1H, brs), 6.98 (2H, d, J=8.6 Hz), 7.10 and 7.22 (total 1H, each s), 7.33-7.40 (1H, m), 7.50-7.57 (1H, m), 7.80-7.90 (3H, m), 8.34-8.41 (1H, m), 8.62-8.63 (1H, m)

ESI-MS (m/e): 465 [M+H]

Example 192

Methyl 1-(6-(4-methanesulfonyl-phenoxy)-2-pyridin-2-yl-3H-benzimidazol-5-yl)-pyrrolidine-2-carboxylate The entitled compound was obtained as a white solid in the same method as in Example 15 or in accordance with the method or by combining it with an ordinary method but using D,L-proline methyl ester hydrochloride.

$^1$HNMR (CDCl$_3$) δ: 1.83-2.03 (3H, m), 2.20-2.28 (1H, m), 3.05 (3H, s), 3.20-3.86 (2H, m), 3.54 (3H, s), 4.28-4.53 (1H, m), 6.91-7.37 (3H, m), 7.32-7.38 (2H, m), 7.81-7.87 (3H, m), 8.30-8.39 (1H, m), 8.61-8.62 (1H, m)

ESI-MS (m/e): 493 [M+H]

Example 193

1-(6-(4-Methanesulfonyl-phenoxy)-2-pyridin-2-yl-3H-benzimidazol-5-yl)-pyrrolidine-2-carboxylic acid methyl amide The entitled compound was obtained as a white solid in the same method as in Example 15 or in accordance with the method or by combining it with an ordinary method but using D,L-proline methyl amide hydrochloride.

$^1$HNMR (CDCl$_3$) δ: 1.80-2.03 (3H, m), 2.25-2.40 (1H, m), 2.46-2.53 (3H, m), 3.06 (3H, s), 3.20-3.26 (1H, m), 3.60-3.78 (1H, m), 4.18-4.24 (1H, m), 7.02-7.60 (3H, m), 7.03 (2H, d, J=9.0 Hz), 7.82-7.92 (1H, m), 7.89 (2H, d, J=9.0 Hz), 8.35 (1H, d, J=7.4 Hz), 8.63 (1H, d, J=4.7 Hz)

ESI-MS (m/e): 492 [M+H]

Example 194

1-(6-(4-Methanesulfonyl-phenoxy)-2-pyridin-2-yl-3H-benzimidazol-5-yl)-pyrrolidine-2-carboxamide The entitled compound was obtained as a white solid in the same method as in Example 15 or in accordance with the method or by combining it with an ordinary method but using D,L-proline amide hydrochloride.

$^1$HNMR (CDCl$_3$) δ: 1.91-2.03 (3H, m), 2.26-2.50 (1H, m), 3.02 and 3.06 (total 3H, each s), 3.18-3.28 (1H, m), 3.63-3.91 (1H, m), 4.13-4.29 (1H, m), 6.04-6.33 (1H, m), 6.86-7.28 (4H, m), 7.37-7.41 (1H, m), 7.48-7.54 (1H, m), 7.80-7.92 (3H, m), 8.34-8.38 (1H, m), 8.48-8.63 (1H, m)

ESI-MS (m/e): 478 [M+H]

Example 195

1-(2-(6-(4-Fluoro-phenoxy)-2-pyridin-2-yl-3H-benzimidazol-5-yl)-piperidin-1-yl)-ethanone (Step 1) Production of 2-(2-fluoro-5-nitro-phenyl)-pyridine 0.55 g of Tetrakis-triphenylphosphine palladium was added to a 1,4-dioxane (20 ml) solution of 2.1 g of 3-bromo-4-fluoro-nitrobenzene and 2.3 g of 2-trimethyltin-pyridine, and the reaction liquid was heated overnight under reflux. Aqueous saturated sodium bicarbonate was added to the reaction liquid, and extracted with ethyl acetate. The organic layer was washed with water and saturated saline, and dried with anhydrous sodium sulfate. The solvent was evaporated away under reduced pressure, and the resulting residue was purified through silica gel column chromatography (developing solvent: hexane/ethyl acetate=7/1) to obtain the entitled compound as a yellow solid.

(Step 2) Production of 2-(2-(4-fluoro-phenoxy)-5-nitro-phenyl)-pyridine 713 mg of potassium carbonate was added to a dimethylformamide (10 ml) solution of 600 mg of 4-fluoro-3-pyridylnitrobenzene and 347 mg of 4-fluoro-phenol, and the reaction liquid was stirred at 100° C. for 1 hour. After cooled, water was added to the reaction liquid, and extracted with ethyl acetate. The organic layer was washed with water and saturated saline in order, and dried with anhydrous sodium sulfate. The solvent was evaporated away under reduced pressure, and the resulting residue was purified through silica gel column chromatography (developing solvent: hexane/ethyl acetate=5/1) to obtain the entitled compound as a pale yellow solid.

(Step 3) Production of t-butyl (4-(4-fluoro-phenoxy)-3-pyridin-2-yl-phenyl)-carbamate 100 mg of 10% palladium-carbon catalyst was added to an ethyl acetate (10 ml) solution of 840 mg of 2-(2-(4-fluoro-phenoxy)-5-nitro-phenyl)-pyridine, and the reaction liquid was stirred overnight in a hydrogen atmosphere. The catalyst was removed through filtration through Celite, and the solvent was evaporated away under reduced pressure to obtain a crude product. 1.5 g of di-t-butyl dicarbonate was added to a tetrahydrofuran (10 ml) solution of the resulting crude product, and the reaction liquid was stirred overnight at 60° C. The reaction liquid was cooled, the solvent was evaporated away under reduced pressure, and the resulting residue was purified through silica gel column chromatography (developing solvent: hexane/ethyl acetate=10/1) to obtain the entitled compound as a white solid.

(Step 4) Production of 1-(2-(5-amino-2-(4-fluoro-phenoxy)-phenyl)-piperidin-1-yl)-ethanone 0.3 ml of acetic anhydride and 100 mg of 10% palladium-carbon catalyst were added to an ethanol (20 ml) solution of 300 mg of t-butyl (4-(4-fluoro-phenoxy)-3-pyridin-2-yl-phenyl)-carbamate, and the reaction liquid was stirred overnight in a hydrogen atmosphere. The catalyst was removed through filtration through Celite, and the filtrate was distilled under reduced pressure to obtain a crude product. The resulting crude product was dissolved in 5 ml of 4 N hydrochloric acid/1,4-dioxane solution, and the reaction liquid was stirred at room temperature for 1 hour. Aqueous saturated sodium bicarbonate was added to the reaction liquid, and extracted with ethyl acetate. The organic layer was washed with saturated saline, and dried with anhydrous sodium sulfate. The solvent was evaporated away under reduced pressure, and the resulting residue was purified through silica gel column chromatography (developing solvent: hexane/ethyl acetate=1/1 to ethyl acetate) to obtain the entitled compound as a pale yellow solid.

(Step 5) Production of 1-(2-(5-amino-2-(4-fluoro-phenoxy)-4-nitro-phenyl)-piperidin-1-yl)-ethanone 64 mg of potassium nitrate was added to a trifluoroacetic acid (1 ml) solution of 190 mg of 1-(2-(5-amino-2-(4-fluoro-phenoxy)-phenyl)-piperidin-1-yl)-ethanone, and the reaction liquid was stirred overnight at room temperature. Aqueous saturated sodium bicarbonate was added to the reaction liquid to neutralize it, and then extracted with ethyl acetate. The organic layer was washed with saturated saline, and dried with anhydrous sodium sulfate. The solvent was evaporated away under reduced pressure, and the resulting residue was purified through silica gel column chromatography (developing solvent: hexane/ethyl acetate=1/1) to obtain the entitled compound as a yellow solid.

(Step 6) Production of 1-(2-(6-(4-fluoro-phenoxy)-2-pyridin-2-yl-3H-benzimidazol-5-yl)-piperidin-1-yl)-ethanone 50 mg of developed Raney nickel catalyst was added to an ethanol (10 ml) solution of 180 mg of 1-(2-(5-amino-2-(4-fluoro-phenoxy)-4-nitro-phenyl)-piperidin-1-yl)-ethanone, and the reaction liquid was stirred overnight in a hydrogen atmosphere. The catalyst was removed through filtration through Celite, and the filtrate was distilled under reduced pressure to obtain 171 mg of a crude product. 50 mg of the resulting crude product was dissolved in 1 ml of N-methylpyrrolidone, and 16 mg of pyridine-2-carboxaldehyde was added to it, and the reaction liquid was stirred at room temperature for 3 days. Water was added to the reaction liquid, and extracted with ethyl acetate, and the organic layer was washed with water and saturated saline, and dried with anhydrous sodium sulfate. The solvent was evaporated away under reduced pressure, and the reaction mixture was purified through reversed-phase middle-pressure liquid chromatography [ODS-AS-360-CC (by YMC), mobile phase: water-acetonitrile-0.1% trifluoroacetic acid] to obtain the entitled compound as a pale yellow solid.
$^1$HNMR (CDCl$_3$) δ: 1.60-1.85 (3H, m), 1.92-2.09 (5H, m), 2.22-2.30 (1H, m), 3.50-3.78 (2H, m), 5.35-5.38 (1H, m), 6.94-7.08 (5H, m), 7.32-7.38 (2H, m), 7.84-7.89 (1H, m), 8.35-8.38 (1H, m), 8.62-8.67 (1H, m)
ESI-MS (m/e): 431 [M+H]

Example 196

5-(2-Cyano-phenoxy)-2-pyridin-2-yl-6-(6-methanesulfonyl-pyridin-3-yloxy)-1H-benzimidazole (Step 1) Production of tert-butyl (3-fluoro-4-hydroxy-phenyl)-carbamate 600 mg of 10% palladium-carbon catalyst was added to a methanol (100 ml) solution of 6.15 g of 3-fluoro-4-hydroxynitrobenzene and 930 mg of di-tert-butyl dicarbonate, and the reaction liquid was stirred overnight in a hydrogen atmosphere. The catalyst was removed through filtration, the solvent was evaporated away, and the residue was taken out through filtration with a mixed solvent of ethyl acetate/hexane to obtain the entitled compound.

(Step 2) Production of tert-butyl (3-fluoro-4-(6-methanesulfonyl-pyridin-3-yloxy)-phenyl)-carbamate 4.00 g of 5-chloro-2-methanesulfonyl-pyridine and 8.80 g of cesium carbonate were added to an N-methylpyrrolidinone (50 ml) solution of 4.74 g of tert-butyl (3-fluoro-4-hydroxyphenyl)-carbamate obtained in (step 1), and the reaction liquid was stirred at 100° C. for 2 hours. The reaction liquid was diluted with ethyl acetate, washed with water and saturated saline in order, and dried with anhydrous sodium sulfate. The solvent was evaporated away under reduced pressure, and the resulting residue was purified through silica gel column chromatography (developing solvent: hexane/ethyl acetate=1/1) to obtain the entitled compound.

(Step 3) Production of 5-fluoro-4-(6-methanesulfonyl-pyridin-3-yloxy)-2-nitro-phenylamine 0.98 g of potassium nitrate was added to a trifluoroacetic acid (35 ml) solution of 3.38 g of tert-butyl (3-fluoro-4-(6-methanesulfonyl-pyridin-3-yloxy)-phenyl)-carbamate obtained in (step 2), the reaction liquid was stirred at room temperature for 1 hour, and then the solvent was evaporated away under reduced pressure. The residue was diluted with ethyl acetate, washed with aqueous saturated sodium bicarbonate and saturated saline in order, and dried with anhydrous sodium sulfate. The solvent was evaporated away under reduced pressure, and the resulting residue was purified through silica gel column chromatography (developing solvent: hexane/ethyl acetate=1/2) to obtain the entitled compound.

(Step 4) Production of 5-(2-cyano-phenoxy)-4-(6-methanesulfonyl-pyridin-3-yloxy)-2-nitro-phenylamine 60 mg of 2-hydroxy-benzonitrile and 70 mg of potassium carbonate were added to an N-methylpyrrolidinone (2 ml) solution of 150 mg of 5-fluoro-4-(6-methanesulfonyl-pyridin-3-yloxy)-2-nitro-phenylamine obtained in (step 3), and the reaction liquid was stirred at 90° C. for 5 hours. Water was added to the reaction liquid, and the deposit was taken out through filtration to obtain the entitled compound.

(Step 5) Production of 4-(2-cyano-phenoxy)-5-(6-methanesulfonyl-pyridin-3-yloxy)-benzene-1,2-diamine 20 mg of developed Raney nickel catalyst was added to a methanol (5 ml) solution of 161 mg of 5-(2-cyano-phenoxy)-4-(6-methanesulfonyl-pyridin-3-yloxy)-2-nitro-phenylamine obtained in (step 4), and the reaction liquid was stirred overnight in a hydrogen atmosphere. The catalyst was removed through filtration, and the solvent was evaporated away under reduced pressure to obtain the entitled compound.

(Step 6) Production of 5-(2-cyano-phenoxy)-2-pyridin-2-yl-6-(6-methanesulfonyl-pyridin-3-yloxy)-1H-benzimidazole 0.007 ml of pyridine-2-carboxaldehyde and 0.5 ml of nitrobenzene were added to a methanol (1 ml) solution of 37 mg of 4-(2-cyano-phenoxy)-5-(6-methanesulfonyl-pyridin-3-yloxy)-benzene-1,2-diamine obtained in (step 5), and the reaction liquid was stirred overnight at 120° C. The solvent was evaporated away under reduced pressure, and the resulting residue was purified through silica gel column chromatography (developing solvent: chloroform/methanol=20/1) and through partitioning thin-layer chromatography (Kieselgel™ 60F$_{254}$, Art 5744 (by Merck), chloroform/methanol=15/1) to obtain the entitled compound as a brown solid.
$^1$HNMR (CD$_3$OD) δ: 3.20 (3H, s), 6.94 (1H, d, J=7.8 Hz), 7.22 (1H, t, J=7.8 Hz), 7.41-7.47 (1H, m), 7.47 (1H, t, J=7.8 Hz), 7.53 (1H, dd, J=7.8, 2.3 Hz), 7.56-7.61 (1H, m), 7.66 (1H, d, J=7.8 Hz), 7.72 (1H, s), 7.78 (1H, s), 8.04 (1H, d, J=7.8 Hz), 8.26 (1H, d, J=2.3 Hz), 8.35 (1H, d, J=7.8 Hz), 8.80 (1H, d, J=4.7 Hz)

ESI-MS (m/e): 484 [M+H]

Example 197

5-(2-Cyano-phenoxy)-2-pyrazin-2-yl-6-(6-methane-sulfonyl-pyridin-3-yloxy)-1H-benzimidazole 21 mg of pyrazine-2-carboxylic acid, 52 mg of hydroxy-benzotriazole and 52 mg of 1-(3-dimethylaminopropyl)-3-ethylcarbodiimide monohydride were added to a dimethylformamide (2 ml) solution of 72 mg of 4-(2-cyano-phenoxy)-5-(6-methanesulfonyl-pyridin-3-yloxy)-benzene-1,2-diamine obtained in Example 196 (step 5), and the reaction liquid was stirred at room temperature for 1 hour. The reaction liquid was diluted with ethyl acetate, washed with aqueous saturated sodium bicarbonate, water and saturated saline in order, and dried with anhydrous sodium sulfate. The solvent was evaporated away under reduced pressure, and the resulting residue was dissolved in 1 ml of N-methylpyrrolidinone, and 20 mg of ytterbium trifluoromethanesulfonate was added to it, and the reaction liquid was stirred at 160° C. for 2 h ours. The reaction liquid was diluted with ethyl acetate, washed with aqueous saturated sodium bicarbonate and saturated saline in order, and dried with anhydrous sodium sulfate. The solvent was evaporated away under reduced pressure, and the resulting residue was purified through silica gel column chromatography (developing solvent: chloroform/methanol=30/1) and through partitioning thin-layer chromatography (Kieselgel™ 60F$_{254}$, Art 5744 (by Merck), chloroform/methanol=10/1) to obtain the entitled compound as a brown solid.

$^1$HNMR (CD$_3$OD) δ: 3.20 (3H, s), 6.93 (1H, d, J=7.6 Hz), 7.21 (1H, t, J=7.6 Hz), 7.43 (1H, dd, J=8.6, 2.3 Hz), 7.58 (1H, t, J=7.6 Hz), 7.66 (1H, d, J=7.6 Hz), 7.67-7.90 (2H, m), 8.03 (1H, d, J=8.6 Hz), 8.25 (1H, d, J=2.3 Hz), 8.74 (1H, d, J=2.3 Hz), 8.81 (1H, d, J=2.3 Hz), 9.53 (1H, s)

ESI-MS (m/e): 485 [M+H]

Example 198

5-(2-Carbamoyl-phenoxy)-2-pyridin-2-yl-6-(6-methanesulfonyl-pyridin-3-yloxy)-1H-benzimidazole The entitled compound was obtained as a colorless solid in the same method as in Example 43 or in accordance with the method or by combining it with an ordinary method but using 5-(2-cyano-phenoxy)-2-pyridin-2-yl-6-(6-methanesulfonyl-pyridin-3-yloxy)-1H-benzimidazole obtained in Example 196.

$^1$HNMR (CD$_3$OD) δ: 3.23 (3H, s), 6.85-6.91 (1H, m), 7.17 (1H, t, J=7.8 Hz), 7.40-7.45 (2H, m), 7.53 (1H, dd, J=7.8, 4.3 Hz), 7.55-7.78 (1H, m), 7.88 (1H, dd, J=7.8, 2.3 Hz), 7.99 (1H, d, J=8.6 Hz), 8.02 (1H, td, J=7.8, 2.3 Hz), 8.27 (1H, d, J=2.3 Hz), 8.34 (1H, d, J=7.8 Hz), 8.78 (1H, d, J=4.3 Hz)

ESI-MS (m/e): 502 [M+H]

Example 199

5-(2-Carbamoyl-phenoxy)-2-pyrazin-2-yl-6-(6-methanesulfonyl-pyridin-3-yloxy)-1H-benzimidazole The entitled compound was obtained as a colorless solid in the same method as in Example 43 or in accordance with the method or by combining it with an ordinary method but using 5-(2-cyano-phenoxy)-2-pyrazin-2-yl-6-(6-methanesulfonyl-pyridin-3-yloxy)-1H-benzimidazole obtained in Example 197.

$^1$HNMR (CD$_3$OD) δ: 3.22 (3H, s), 6.87-6.91 (1H, m), 7.15-7.22 (1H, m), 7.41-7.46 (2H, m), 7.51-7.85 (2H, m), 7.87 (1H, dd, J=7.8, 2.3 Hz), 7.99 (1H, d, J=7.8 Hz), 8.25-8.28 (1H, m), 8.73-8.75 (1H, m), 8.80-8.82 (1H, m), 9.51-9.54 (1H, m)

ESI-MS (m/e): 503 [M+H]

Example 200

5-(2-Fluoro-phenoxy)-2-pyridin-2-yl-6-(6-methane-sulfonyl-pyridin-3-yloxy-1H-benzimidazole The entitled compound was obtained as a colorless solid in the same method as in Example 196 (step 4) to (step 6) or in accordance with the method or by combining it with an ordinary method but using 5-fluoro-4-(6-methanesulfonyl-pyridin-3-yloxy)-2-nitro-phenylamine obtained in Example 196 (step 3) and 2-fluorophenol.

$^1$HNMR (CDCl$_3$) δ: 3.20 (3H, s), 6.97-7.04 (1H, m), 7.05-7.15 (3H, m), 7.33 (½H, dd, J=8.8, 2.8 Hz), 7.34 (½H, dd, J=8.8, 2.8 Hz), 7.36-7.42 (1H, m), 7.42 (½H, s), 7.70 (½H, s), 7.86-7.91 (1H, m), 7.99 (½H, d, J=8.8 Hz), 8.00 (½H, d, J=8.8 Hz), 8.34-8.40 (1H, m), 8.44 (1H, d, J=2.8 Hz), 8.61-8.65 (1H, m), 10.85 (½H, brs), 10.96 (½H, brs)

ESI-MS (m/e): 477 [M+H]

Example 201

5-(2-Fluoro-phenoxy)-2-pyrazin-2-yl-6-(6-methane-sulfonyl-pyridin-3-oxy)-1H-benzimidazole The entitled compound was obtained as a colorless solid in the same method as in Example 197 or in accordance with the method or by combining it with an ordinary method but using 4-(2-fluoro-phenoxy)-5-(6-methanesulfonyl-pyridin-3-yloxy)-benzene-1,2-diamine obtained in Example 200 and pyrazine-2-carboxylic acid.

$^1$HNMR (CDCl$_3$) δ: 3.21 (3H, s), 7.02-7.08 (1H, m), 7.09-7.17 (3H, m), 7.11 (½H, s), 7.34 (½H, dd, J=8.6, 2.7 Hz), 7.36 (½H, dd, J=8.6, 2.7 Hz), 7.42 (½H, s), 7.43 (½H, s), 7.74 (½H, s), 8.01 (½H, d, J=8.6 Hz), 8.02 (½H, d, J=8.6 Hz), 8.46 (1H, d, J=2.7 Hz), 8.58 (½H, dd, J=2.7, 1.6 Hz), 8.60 (½H, dd, J=2.7, 1.6 Hz), 8.67 (½H, d, J=2.7 Hz), 8.68 (½H, d, J=2.7 Hz), 9.59 (½H, d, J=1.6 Hz), 9.62 (½H, d, J=1.6 Hz), 10.47 (½H, brs), 10.61 (½H, brs)

ESI-MS (m/e): 478 [M+H]

Example 202

5-(2-Fluoro-phenoxy)-2-(1H-pyrazol-3-yl)-6-(6-methanesulfonyl-pyridin-3-yloxy)-1H-benzimidazole 3.9 mg of 1H-pyrazole-3-carboxaldehyde was added to a dimethylformamide (0.5 ml) solution of 15 mg of 4-(2-fluoro-phenoxy)-5-(6-methanesulfonyl-pyridin-3-yloxy)-benzene-1,2-diamine obtained in Example 200, and the reaction liquid was stirred at 90° C. for 30 minutes. The solvent was evaporated away under reduced pressure, and the resulting residue was purified through partitioning thin-layer chromatography (Kieselgel™ 60F$_{254}$, Art 5744 (by Merck), chloroform/methanol=9/1) to obtain the entitled compound as a white solid.

¹HNMR (CDCl₃) δ: 3.20 (3H, s), 6.94-6.99 (1H, m), 7.01-7.15 (4H, m), 7.25-7.65 (2H, m), 7.31 (1H, dd, J=8.9, 2.7 Hz), 7.66 (1H, d, J=2.3 Hz), 7.98 (1H, d, J=8.9 Hz), 8.40 (1H, d, J=2.7 Hz)

ESI-MS (m/e): 466 [M+H]

Example 203

5-(2-Fluoro-phenoxy)-2-(1-methyl-1H-pyrazol-3-yl)-6-(6-methanesulfonyl-pyridin-3-yloxy)-1H-benzimidazole 4.3 mg of 1-methyl-1H-pyrazole-3-carboxylic acid, 6.0 mg of hydroxybenzotriazole and 8.5 mg of 1-(3-dimethylaminopropyl)-3-ethylcarbodiimide monohydrochloride were added to a dimethylformamide (0.5 ml) solution of 15 mg of 4-(2-fluoro-phenoxy)-5-(6-methanesulfonyl-pyridin-3-yloxy)-benzene-1,2-diamine obtained in Example 200, and the reaction liquid was stirred overnight at room temperature. The reaction liquid was diluted with chloroform, washed with water, and dried with anhydrous sodium sulfate. The solvent was evaporated away under reduced pressure, and 3 mg of p-toluenesulfonic acid was added to the resulting residue, and the reaction liquid was stirred at 120° C. for 2 hours. The reaction liquid was diluted with ethyl acetate, washed with water, and dried with anhydrous sodium sulfate. The solvent was evaporated away under reduced pressure, and the resulting residue was purified through partitioning thin-layer chromatography (Kieselgel™ 60F₂₅₄, Art 5744 (by Merck), chloroform/methanol=15/1) to obtain the entitled compound as a white solid.

¹HNMR (CDCl₃) δ: 3.19 (3H, s), 3.97 (3H, s), 6.94-7.00 (1H, m), 6.99 (½H, brs), 7.00-7.14 (4H, m), 7.27-7.33 (1H, m), 7.30 (½H, brs), 7.40 (½H, brs), 7.46 (1H, d, J=2.4 Hz), 7.65 (½H, brs), 7.98 (1H, d, J=8.8 Hz), 8.42 (1H, d, J=2.7 Hz)

ESI-MS (m/e): 480 [M+H]

Example 204

5-(2-Chloro-phenoxy)-2-pyridin-2-yl-6-(6-methanesulfonyl-pyridin-3-yloxy)-1H-benzimidazole (Step 1) Production of 4-(2-chlorophenoxy)-5-(6-methanesulfonyl-pyridin-3-yloxy)-benzene-1,2-diamine The entitled compound was obtained in the same method as in Example 196 (step 4) to (step 5) or in accordance with the method or by combining it with an ordinary method but using 5-fluoro-4-(6-methanesulfonyl-pyridin-3-yloxy)-2-nitro-phenylamine obtained in Example 196 (step 3) and 2-chlorophenol.

(Step 2) Production of 5-(2-chloro-phenoxy)-2-pyridin-2-yl-6-(6-methanesulfonyl-pyridin-3-yloxy)-1H-benzimidazole 0.26 ml of 1 M methanol solution of aniline and pyridine-2-carboxaldehyde (1/1) was added to a methanol (1 ml) solution of 35 mg of 4-(2-chlorophenoxy)-5-(6-methanesulfonyl-pyridin-3-yloxy)-benzene-1,2-diamine obtained in (step 1), and the reaction liquid was stirred overnight at 60° C. The solvent was evaporated away under reduced pressure, and the resulting residue was purified through reversed-phase middle-pressure liquid chromatography [ODS-AS-360-CC (by YMC), mobile phase: water-acetonitrile-0.1% trifluoroacetic acid]. The solvent of the resulting fraction was diluted with ethyl acetate, washed with aqueous saturated sodium bicarbonate, and then dried with anhydrous sodium sulfate. The solvent was evaporated away under reduced pressure to obtain the entitled compound as a pale yellow solid.

¹HNMR (CD₃OD) δ: 3.17 (3H, s), 6.92 (1H, d, J=8.0 Hz), 7.07 (1H, t, J=8.0 Hz), 7.22 (1H, t, J=8.0 Hz), 7.26-7.66 (4H, m), 7.66-7.80 (1H, brs), 7.90-8.08 (2H, m), 8.29 (1H, d, J=8.0 Hz), 8.31 (1H, d, J=2.4 Hz), 8.72 (1H, s)

ESI-MS (m/e): 493 [M+H]

Example 205

5-(2-Chloro-phenoxy)-2-pyrazin-2-yl-6-(6-methanesulfonyl-pyridin-3-yloxy)-1H-benzimidazole 15 mg of methylpyrazin-2-imidate (pyrazine-2-carboximidic acid methyl ester) and 0.0065 ml of methanesulfonic acid were added to an N-methylpyrrolidinone (0.5 ml) solution of 38 mg of 4-(2-chloro-phenoxy)-5-(6-methanesulfonyl-pyridin-3-yloxy)-benzene-1,2-diamine obtained in Example 204 (step 1), and the reaction liquid was stirred at 120° C. for 20 minutes. The reaction liquid was purified through reversed-phase middle-pressure liquid chromatography [ODS-AS-360-CC (by YMC), mobile phase: water-acetonitrile-0.1% trifluoroacetic acid]. The solvent of the resulting fraction was diluted with ethyl acetate, washed with aqueous saturated sodium bicarbonate, and then dried with anhydrous sodium sulfate. The solvent was evaporated away under reduced pressure to obtain the entitled compound as a yellow solid.

¹HNMR (CD₃OD) δ: 3.20 (3H, s), 6.97 (1H, d, J=7.8 Hz), 7.11 (1H, t, J=7.8 Hz), 7.26 (1H, t, J=7.8 Hz), 7.42 (1H, d, J=7.8 Hz), 7.48 (1H, dd, J=8.6, 2.3 Hz), 7.60-7.82 (2H, m), 8.02 (1H, d, J=8.6 Hz), 8.35 (1H, d, J=2.3 Hz), 8.71 (1H, s), 8.77 (1H, s), 9.48 (1H, s)

ESI-MS (m/e): 494 [M+H]

Example 206

5-(2-Trifluoromethyl-phenoxy)-2-pyridin-2-yl-6-(6-methanesulfonyl-pyridin-3-yloxy)-1H-benzimidazole The entitled compound was obtained as a colorless solid in the same method as in Example 196 (step 4) to (step 6) or in accordance with the method or by combining it with an ordinary method but using 5-fluoro-4-(6-methanesulfonyl-pyridin-3-yloxy)-2-nitro-phenylamine obtained in Example 196 (step 3) and 2-trifluoromethylphenol.

¹HNMR (CD₃OD) δ: 3.17 (3H, s), 6.93-6.98 (1H, m), 7.21 (1H, t, J=7.4 Hz), 7.40-7.81 (6H, m), 7.97-8.05 (2H, m), 8.24-8.39 (2H, m), 8.73-8.87 (1H, m)

ESI-MS (m/e): 527 [M+H]

Example 207

5-(2-Trifluoromethyl-phenoxy)-2-pyrazin-2-yl-6-(6-methanesulfonyl-pyridin-3-yloxy)-1H-benzimidazole The entitled compound was obtained as a yellow solid in the same method as in Example 205 or in accordance with the method or by combining it with an ordinary method but using 4-(2-trifluoromethyl-phenoxy)-5-(6-methanesulfonyl-pyridin-3-yloxy)-benzene-1,2-diamine obtained in Example 206, and methylpyrazin-2-imidate.

¹HNMR (CD₃OD) δ: 3.17 (3H, s), 6.97 (1H, d, J=7.8 Hz), 7.22 (1H, t, J=7.8 Hz), 7.46 (1H, dd, J=8.6, 2.3 Hz), 7.54 (1H, t, J=7.8 Hz), 7.44-7.60 (1H, m), 7.65 (1H, d, J=7.8 Hz), 7.84-7.86 (1H, m), 8.01 (1H, d, J=8.6 Hz), 8.31 (1H, d, J=2.3 Hz), 8.73 (1H, d, J=2.3 Hz), 8.80 (1H, d, J=2.3 Hz), 9.50 (1H, s)

ESI-MS (m/e): 528 [M+H]

Example 208

5-(3-Trifluoromethyl-phenoxy)-2-pyridin-2-yl-6-(6-methane-sulfonyl-pyridin-3-yloxy)-1H-benzimidazole The entitled compound was obtained as a white solid in the same method as in Example 196 (step 4) to (step 6) or in accordance with the method or by combining it with an ordinary method but using 5-fluoro-4-(6-methanesulfonyl-pyridin-3-yloxy)-2-nitro-phenylamine obtained in Example 196 (step 3) and 3-trifluoromethylphenol.

$^1$HNMR (CD$_3$OD) δ: 3.20 (3H, s), 7.00-7.15 (2H, m), 7.37 (1H, d, J=7.8 Hz), 7.45-7.55 (3H, m), 7.66 (1H, d, J=1.0 Hz), 7.76 (1H, brs), 7.99-8.04 (2H, m), 8.30-8.35 (2H, m), 8.77 (1H, d, J=2.7 Hz)

ESI-MS (m/e): 527 [M+H]

Example 209

5-(4-Trifluoromethyl-phenoxy)-2-pyridin-2-yl-6-(6-methanesulfonyl-pyridin-3-yloxy)-1H-benzimidazole The entitled compound was obtained as a white solid in the same method as in Example 196 (step 4) to (step 6) or in accordance with the method or by combining it with an ordinary method but using 5-fluoro-4-(6-methanesulfonyl-pyridin-3-yloxy)-2-nitro-phenylamine obtained in Example 196 (step 3) and 4-trifluoromethylphenol.

$^1$HNMR (CD$_3$OD) δ: 3.20 (3H, s), 6.98 (2H, d, J=8.6 Hz), 7.46-7.77 (4H, m), 7.60 (2H, d, J=8.6 Hz), 8.00-8.04 (2H, m), 8.31 (1H, d, J=3.1 Hz), 8.34 (1H, d, J=8.2 Hz), 8.78 (1H, d, J=4.7 Hz)

ESI-MS (m/e): 527 [M+H]

Example 210

5-(2-Difluoromethyl-phenoxy)-2-pyridin-2-yl-6-(6-methanesulfonyl-pyridin-3-yloxy)-1H-benzimidazole The entitled compound was obtained as a brown solid in the same method as in Example 196 (step 4) to (step 6) or in accordance with the method or by combining it with an ordinary method but using 5-fluoro-4-(6-methanesulfonyl-pyridin-3-yloxy)-2-nitro-phenylamine obtained in Example 196 (step 3) and 2-difluoromethylphenol.

$^1$HNMR (CD$_3$OD) δ: 3.17 (3H, s), 6.70 (1H, t, J=55.2 Hz), 6.87 (1H, d, J=7.4 Hz), 7.18 (1H, t, J=7.4 Hz), 7.40-7.46 (2H, m), 7.50-7.59 (3H, m), 7.59-7.82 (1H, m), 7.98-8.04 (2H, m), 8.27-8.35 (2H, m), 8.76 (1H, brs)

ESI-MS (m/e): 509 [M+H]

Example 211

5-(2-Fluoropyridin-3-yloxy)-6-(6-methanesulfonyl-pyridin-3-yloxy)-2-pyridin-2-yl-1H-benzimidazole The entitled compound was obtained as a colorless solid in the same method as in Example 196 (step 4) to (step 6) or in accordance with the method or by combining it with an ordinary method but using 5-fluoro-4-(6-methanesulfonyl-pyridin-3-yloxy)-2-nitro-phenylamine obtained in Example 196 (step 3) and 2-fluoro-pyridin-3-ol produced according to the method described in Journal of Medicinal Chemistry, 1999, Vol. 42, No. 12, pp. 2251-2259.

$^1$HNMR (CDCl$_3$) δ: 3.21 (3H, s), 7.11-7.17 (1H, m), 7.22 (½H, s), 7.29-7.36 (2H, m), 7.29-7.36 (½H, m), 7.40-7.43 (1H, s), 7.53 (½H, s), 7.72 (½H, s), 7.88-7.93 (1H, m), 7.93-7.96 (1H, m), 7.99-8.03 (1H, m), 8.37-8.41 (2H, m), 8.65-8.67 (1H, m), 10.78 (½H, brs), 10.82 (½H, brs)

ESI-MS (m/e): 478 [M+H]

Example 212

5-(2-Fluoropyridin-3-yloxy-6-(6-methanesulfonyl-pyridin-3-yloxy)-2-pyrazin-2-yl-1H-benzimidazole The entitled compound was obtained as a colorless solid in the same method as in Example 197 or in accordance with the method or by combining it with an ordinary method but using 4-(2-fluoro-pyridin-3-yloxy)-5-(6-methanesulfonyl-pyridin-3-yloxy)-benzene-1,2-diamine obtained in Example 211 and pyrazine-2-carboxylic acid.

$^1$HNMR (CDCl$_3$) δ: 3.21 (3H, s), 7.14-7.19 (1H, m), 7.23 (½H, s), 7.26-7.40 (2H, m), 7.46 (½H, s), 7.54 (½H, s), 7.56 (½H, s), 7.96-8.00 (1H, m), 8.03 (1H, dd, J=8.6, 3.9 Hz), 8.41 (1H, dd, J=2.7, 1.6 Hz), 8.62 (1H, ddd, J=4.7, 2.7, 1.6 Hz), 8.69-8.71 (1H, m), 9.62 (1H, dd, J=6.3, 1.6 Hz), 10.48 (½H, brs), 10.56 (½H, brs)

ESI-MS (m/e): 479 [M+H]

Example 213

5-(2-Fluoropyridin-3-yloxy)-2-(1H-pyrazol-3-yl)-6-(6-methanesulfonyl-pyridin-3-yloxy)-1H-benzimidazole The entitled compound was obtained as a colorless solid in the same method as in Example 202 or in accordance with the method or by combining it with an ordinary method but using 4-(2-fluoro-pyridin-3-yloxy)-5-(6-methanesulfonyl-pyridin-3-yloxy)-benzene-1,2-diamine obtained in Example 211 and 1H-pyrazole-3-carboxaldehyde.

$^1$HNMR (CDCl$_3$) δ: 3.21 (3H, s), 7.08 (1H, d, J=2.3 Hz), 7.09-7.19 (1H, m), 7.19-7.49 (4H, m), 7.71 (1H, d, J=2.3 Hz), 7.88-7.96 (1H, m), 7.97-8.03 (1H, m), 8.36 (1H, d, J=2.7 Hz)

ESI-MS (m/e): 467 [M+H]

Example 214

5-(2-Fluoropyridin-3-yloxy)-2-(1-methyl-1H-pyrazol-3-yl)-6-(6-methanesulfonyl-pyridin-3-yloxy)-1H-benzimidazole The entitled compound was obtained as a colorless solid in the same method as in Example 203 or in accordance with the method or by combining it with an ordinary method but using 4-(2-fluoro-pyridin-3-yloxy)-5-(6-methanesulfonyl-pyridin-3-yloxy)-benzene-1,2-diamine obtained in Example 211 and 1-methyl-1H-pyrazole-3-carboxylic acid.

$^1$HNMR (CDCl$_3$) δ: 3.20 (3H, s), 4.00 (3H, s), 7.00 (1H, d, J=2.4 Hz), 7.10-7.16 (1H, m), 7.19 (½H, brs), 7.26-7.33 (2H, m), 7.35 (½H, brs), 7.48 (1H, d, J=2.4 Hz), 7.52 (½H, brs), 7.67 (½H, brs), 7.91-7.94 (1H, m), 8.00 (1H, d, J=8.6 Hz), 8.37 (1H, d, J=2.5 Hz), 10.13 (1H, brs)
ESI-MS (m/e): 481 [M+H]

Example 215

5-(2-Difluoromethoxy-pyridin-3-yloxy)-6-(6-methanesulfonyl-pyridin-3-yloxy)-2-pyridin-2-yl-1H benzimidazole The entitled compound was obtained as a colorless solid in the same method as in Example 196 (step 4) to (step 6) or in accordance with the method or by combining it with an ordinary method but using 5-fluoro-4-(6-methanesulfonyl-pyridin-3-yloxy)-2-nitro-phenylamine obtained in Example 196 (step 3) and 2-difluoromethoxy-pyridin-3-ol obtained in Reference Example 2.
$^1$HNMR (DMSO-$d_6$) δ: 3.22 (3H, s), 7.19-7.27 (1H, m), 7.29-7.86 (6H, m), 7.95-8.07 (3H, m), 8.33-8.35 (1H, m), 8.45-8.48 (1H, m), 8.77 (1H, s).
ESI-MS (m/e): 526 [M+H]

Example 216

5-(2-Difluoromethoxy-pyridin-3-yloxy)-6-(6-methanesulfonyl-pyridin-3-yloxy)-2-pyrazin-2-1H-benzimidazole The entitled compound was obtained as a colorless solid in the same method as in Example 205 or in accordance with the method or by combining it with an ordinary method but using 4-(2-difluoromethoxy-pyridin-3-yloxy)-5-(6-methanesulfonyl-pyridin-3-yloxy)-benzene-1,2-diamine obtained in Example 215 and methylpyrazin-2-imidate.
$^1$HNMR (DMSO-$d_6$) δ: 3.20 (3H, s), 7.21 (1H, dd, J=7.8, 4.9 Hz), 7.30-7.90 (4H, m), 7.62 (1H, t, J=72.6 Hz), 7.94 (1H, d, J=8.8 Hz), 7.97 (1H, d, J=4.8 Hz), 8.45 (1H, d, J=2.7 Hz), 8.77-8.83 (2H, m), 9.48 (1H, s)
ESI-MS (m/e): 527 [M+H]

Example 217

5-(2-Difluoromethoxy-pyridin-3-yloxy-6-(6-methanesulfonyl-pyridin-3-yloxy)-2-(1-methyl-1H-pyrazol-3-yl)-1H-benzimidazole The entitled compound was obtained as a colorless solid in the same method as in Example 203 or in accordance with the method or by combining it with an ordinary method but using 4-(2-difluoromethoxy-pyridin-3-yloxy)-5-(6-methanesulfonyl-pyridin-3-yloxy)-benzene-1,2-diamine obtained in Example 215 and 1-methyl-1H-pyrazole-3-carboxylic acid.
$^1$HNMR (DMSO-$d_6$) δ: 3.22 (3H, s), 4.00 (3H, s), 6.88 (1H, d, J=2.2 Hz), 7.17-7.82 (6H, m), 7.90-7.99 (3H, m), 8.42-8.45 (1H, m)
ESI-MS (m/e): 529 [M+H]

Example 218

5-(2-Cyanopyridin-3-yloxy)-6-(6-methanesulfonyl-pyridin-3-yloxy)-2-pyridin-2-yl-1H-benzimidazole (Step 1) Production of 4-(6-methanesulfonyl-pyridin-3-yloxy)-2-nitro-5-(1-oxy-pyridin-3-yloxy)-phenylamine The entitled compound was obtained in the same method as in Example 196 (step 4) or in accordance with the method or by combining it with an ordinary method but using 5-fluoro-4-(6-methanesulfonyl-pyridin-3-yloxy)-2-nitro-phenylamine obtained in Example 196 (step 3) and 1-oxy-pyridin-3-ol.

(Step 2) Production of 4-(6-methanesulfonyl-pyridin-3-yloxy)-2-nitro-5-(2-cyano-pyridin-3-yloxy)-phenylamine 0.90 ml of trimethylsilylnitrile and 0.90 ml of triethylamine were added to an acetonitrile (6 ml) solution of 216 mg of 4-(6-methanesulfonyl-pyridin-3-yloxy)-2-nitro-5-(1-oxy-pyridin-3-yloxy)-phenylamine, and the reaction liquid was stirred overnight with heating under reflux. The solvent was evaporated away under reduced pressure, and 1,1,1,3,3,3-hexamethyldisilazane was added to it, and the reaction liquid was stirred for 1 hour with heating under reflux. The reaction liquid was purified through silica gel column chromatography (developing solvent: chloroform/methanol=30/1) to obtain the entitled compound.

(Step 3) Production of 5-(2-cyanopyridin-3-yloxy)-6-(6-methanesulfonyl-pyridin-3-yloxy)-2-pyridin-2-yl-1H-benzimidazole The entitled compound was obtained as a white solid in the same method as in Example 196 (step 5) and (step 6) or in accordance with the method or by combining it with an ordinary method but using 4-(6-methanesulfonyl-pyridin-3-yloxy)-2-nitro-5-(2-cyano-pyridin-3-yloxy)-phenylamine.
$^1$HNMR (CDCl$_3$) δ: 3.22 (3/2H, s), 3.23 (3/2H, s), 7.18-7.23 (2H, m), 7.40-7.48 (2H, m), 7.50 (1H, s), 7.76-7.78 (1H, m), 7.91-7.95 (1H, m), 8.03-8.06 (1H, m), 8.20-8.23 (1H, m), 8.37-8.44 (2H, m), 8.58-8.67 (1H, m), 11.04 (1H, brs)
ESI-MS (m/e): 485 [M+H]

Example 219

5-(2-Cyanopyridin-3-yloxy)-6-(6-methanesulfonyl-pyridin-3-yloxy)-2-pyrazin-2-yl-1H-benzimidazole The entitled compound was obtained as a colorless solid in the same method as in Example 197 or in accordance with the method or by combining it with an ordinary method but using 4-(2-cyanopyridin-3-yloxy)-5-(6-methanesulfonyl-pyridin-3-yloxy)-benzene-1,2-diamine obtained in Example 218 (step 3) and pyrazine-2-carboxylic acid.
$^1$HNMR (CDCl$_3$) δ: 3.23 (3/2H, s), 3.24 (3/2H, s), 7.21-7.26 (2H, m), 7.42-7.48 (1H, m), 7.55 (1H, d, J=1.2 Hz), 7.80 (½H, s), 7.82 (½H, s), 8.04 (½H, s), 8.06 (½H, s), 8.19-8.21 (1H, m), 8.41 (1H, dd, J=4.5, 1.2 Hz), 8.65 (1H, dd, J=3.9, 2.3 Hz), 8.73 (1H, d, J=2.3 Hz), 9.65 (1H, d, J=1.2 Hz), 10.99 (1H, brs)
ESI-MS (m/e): 486 [M+H]

Example 220

5-(2-Cyanopyridin-3-yloxy)-2-(1H-pyrazol-3-yl)-6-(6-methanesulfonyl-pyridin-3-yloxy)-1H-benzimidazole The entitled compound was obtained as a colorless solid in the same method as in Example 202 or in accordance with the method or by combining it with an ordinary method but using 4-(2-cyanopyridin-3-yloxy)-5-(6-methanesulfonyl-pyridin-3-yloxy)-benzene-1,2-diamine obtained in Example 218 (step 3) and 1H-pyrazole-3-carboxaldehyde.

¹HNMR (CDCl₃) δ: 3.22 (3H, s), 7.12 (1H, d, J=2.3 Hz), 7.17-7.25 (2H, m), 7.40-7.48 (2H, m), 7.71-7.74 (1H, m), 7.72 (1H, d, J=2.3 Hz), 8.00-8.03 (1H, m), 8.17-8.21 (1H, m), 8.38-8.41 (1H, m)

ESI-MS (m/e): 474 [M+H]

Example 221

5-(2-Cyano-phenoxy)-2-pyridin-2-yl-6-(6-ethane-sulfonyl-pyridin-3-yloxy)-1H-benzimidazole (Step 1) Production of 3-fluoro-4-(6-ethanesulfonyl-pyridin-3-yloxy)-phenylamine 10.9 g of 5-chloro-2-ethanesulfonyl-pyridine and 1.6 g of cesium carbonate were added to a dimethylformamide (150 ml) solution of 10.0 g of tert-butyl (3-fluoro-4-hydroxy-phenyl)-carbamate obtained in Example 196 (step 1), and the reaction liquid was stirred at 100° C. for 3 hours. The solvent was evaporated away under reduced pressure, diluted with chloroform, washed with aqueous saturated sodium bicarbonate, and dried with anhydrous sodium sulfate. The solvent was evaporated away under reduced pressure, and the resulting residue was purified through silica gel column chromatography (developing solvent: hexane/ethyl acetate=1/9) to obtain a crude product. The resulting crude product was dissolved in 4 N hydrochloric acid/dioxane, and stirred at room temperature for 1 hour. The solvent was evaporated away under reduced pressure, diluted with chloroform, washed with water, and dried with anhydrous sodium sulfate. The solvent was evaporated away under reduced pressure, and the resulting residue was purified through silica gel column chromatography (developing solvent: hexane/ethyl acetate=1/9) to obtain the entitled compound.

(Step 2) Production of 5-fluoro-4-(6-ethanesulfonyl-pyridin-3-yloxy)-2-nitro-phenylamine 3.8 g of potassium nitrate was added to a trifluoroacetic acid (100 ml) solution of 10.5 g of 3-fluoro-4-(6-ethanesulfo-nyl-pyridin-3-yloxy)-phenylamine, and the reaction liquid was stirred for 1 hour at room temperature, and the solvent was evaporated away under reduced pressure. The residue was diluted with ethyl acetate, washed with aqueous saturated sodium bicarbonate and saturated saline in order, and dried with anhydrous sodium sulfate. The solvent was evaporated away under reduced pressure, and the resulting residue was purified through silica gel column chromatography (developing solvent: hexane/ethyl acetate=1/2) to obtain the entitled compound.

(Step 3) Production of 5-(2-cyano-phenoxy)-2-pyridin-2-yl-6-(6-ethanesulfonyl-pyridin-3-yloxy)-1H-benzimidazole 60 mg of 2-hydroxy-benzonitrile and 70 mg of potassium carbonate were added to an N-methylpyrrolidinone (3 ml) solution of 150 mg of 5-fluoro-4-(6-ethanesulfonyl-pyridin-3-yloxy)-2-nitro-phenylamine, and the reaction liquid was stirred at 90° C. for 5 hours. Water was added to the reaction liquid, and the deposit was taken out through filtration to obtain a crude product. 10 mg of developed Raney nickel and 0.12 ml of hydrazine monohydrate were added to a methanol (5 ml) solution of the resulting crude product, and the reaction liquid was stirred for 1 hour. The catalyst was removed through filtration, and the solvent was evaporated away under reduced pressure to obtain 160 mg of a crude product. 0.20 ml of 1 M methanol solution of aniline and pyridine-2-carboxaldehyde (1/1) was added to a methanol (3 ml) solution of 35 mg of the resulting crude product, and the reaction liquid was stirred overnight at 80° C. The solvent was evaporated away under reduced pressure, and the resulting residue was purified through partitioning thin-layer chromatography (Kieselgel™ 60F₂₅₄, Art 5744 (by Merck), chloroform/methanol=15/1) to obtain the entitled compound as a yellow solid.

¹HNMR (CD₃OD) δ: 1.27 (3H, t, J=7.4 Hz), 3.37 (2H, q, J=7.4 Hz), 6.91 (1H, d, J=7.8 Hz), 7.19 (1H, t, J=7.8 Hz), 7.43 (1H, d, J=7.8 Hz), 7.50-7.60 (2H, m), 7.60-7.90 (3H, m), 7.99-8.04 (2H, m), 8.26 (1H, s), 8.34 (1H, d, J=7.8 Hz), 8.77 (1H, s)

ESI-MS (m/e): 498 [M+H]

Example 222

5-(2-Cyano-phenoxy)-2-pyrazin-2-yl-6-(6-ethane-sulfonyl-pyridin-3-yloxy)-1H-benzimidazole The entitled compound was obtained as a brown solid in the same method as in Example 205 or in accordance with the method or by combining it with an ordinary method but using 4-(2-cyano-phenoxy)-5-(6-ethanesulfonyl-pyridin-3-yloxy)-benzene-1,2-diamine obtained in Example 221 (step 3) and methylpyrazin-2-imidate.

¹HNMR (CD₃OD) δ: 1.28 (3H, t, J=7.6 Hz), 3.38 (2H, q, J=7.6 Hz), 6.94 (1H, d, J=7.6 Hz), 7.21 (1H, t, J=7.6 Hz), 7.45 (1H, dd, J=8.6, 2.7 Hz), 7.58 (1H, td, J=7.6, 1.8 Hz), 7.66 (1H, d, J=7.6 Hz), 7.68-7.90 (2H, m), 8.03 (1H, d, J=8.6 Hz), 8.28 (1H, d, J=2.7 Hz), 8.75 (1H, d, J=2.0 Hz), 8.82 (1H, dd, J=2.0, 1.2 Hz), 9.54 (1H, d=1.2 Hz)

ESI-MS (m/e): 499 [M+H]

Example 223

5-(2-Fluoro-phenoxy)-2-pyridin-2-yl-6-(6-ethane-sulfonyl-pyridin-3-yloxy)-1H-benzimidazole The entitled compound was obtained as a colorless solid in the same method as in Example 221 (step 3) or in accordance with the method or by combining it with an ordinary method but using 5-fluoro-4-(6-ethanesulfonyl-pyridin-3-yloxy)-2-nitro-phenylamine obtained in Example 221 (step 2) and 2-fluoro-phenol.

¹HNMR (CD₃OD) δ: 1.18-1.24 (3H, m), 3.02-3.41 (2H, m), 6.97-7.40 (5H, m), 7.47-7.77 (3H, m), 7.96-8.04 (2H, m), 8.30 (1H, d, J=7.8 Hz), 8.39-8.42 (1H, m), 8.73-8.78 (1H, m)

ESI-MS (m/e): 491 [M+H]

Example 224

5-(2-Fluoro-phenoxy)-2-pyrazin-2-yl-6-(6-ethane-sulfonyl-pyridin-3-yloxy)-1H-benzimidazole The entitled compound was obtained as a brown solid in the same method as in Example 205 or in accordance with the method or by combining it with an ordinary method but using 4-(2-fluoro-phenoxy)-5-(6-ethanesulfonyl-pyridin-3-yloxy)-benzene-1,2-diamine obtained in Example 223 and methylpyrazin-2-imidate.

¹HNMR (CD₃OD) δ: 1.22 (3H, t, J=7.4 Hz), 3.38 (2H, q, J=7.4 Hz), 7.52 (1H, dd, J=3.1, 8.6 Hz), 7.00-7.80 (6H, m), 8.04 (1H, d, J=8.6 Hz), 8.42 (1H, d, J=3.1 Hz), 8.72 (1H, s), 8.79 (1H, s), 9.49 (1H, s)

ESI-MS (m/e): 492 [M+H]

Example 225

5-(2-Fluoro-phenoxy)-2-(1H-pyrazol-3-yl)-6-(6-ethanesulfonyl-pyridin-3-yloxy)-1H-benzimidazole The entitled compound was obtained as a pale yellow solid in the same method as in Example 202 or in accordance with the method or by combining it with an ordinary method but using 4-(2-fluoro-phenoxy)-5-(6-ethanesulfonyl-pyridin-3-yloxy)-benzene-1,2-diamine obtained in Example 223 and 1H-pyrazole-3-carboxaldehyde.

$^1$HNMR (CD$_3$OD) δ: 1.22 (3H, t, J=7.4 Hz), 3.30-3.42 (2H, m), 6.88 (1H, d, J=1.6 Hz), 6.99-7.04 (1H, m), 7.07-7.20 (3H, m), 7.22-7.43 (1H, m), 7.49 (1H, dd, J=7.8, 3.11 Hz), 7.56-7.68 (1H, m), 7.83 (1H, d, J=1.6 Hz), 8.02 (1H, d, J=7.8 Hz), 8.39 (1H, d, J=3.1 Hz)

ESI-MS (m/e): 480 [M+H]

Example 226

5-(2,3-Difluoro-phenoxy)-2-pyridin-2-yl-6-(6-ethanesulfonyl-pyridin-3-yloxy)-1H-benzimidazole The entitled compound was obtained as a colorless solid in the same method as in Example 221 (step 3) or in accordance with the method or by combining it with an ordinary method but using 5-fluoro-4-(6-ethanesulfonyl-pyridin-3-yloxy)-2-nitro-phenylamine obtained in Example 221 (step 2) and 2,3-difluoro-phenol.

$^1$HNMR (CDCl$_3$) δ: 1.29 (3H, t, J=7.4 Hz), 3.38 (2H, q, J=7.4 Hz), 6.69-6.75 (1H, m), 6.91-7.02 (2H, m), 7.20 (½H, s), 7.27-7.34 (1H, m), 7.37-7.47 (1H, m), 7.41 (½H, s), 7.53 (½H, s), 7.72 (½H, s), 7.87-7.92 (1H, m), 8.00 (½H, d, J=8.7 Hz), 8.01 (½H, d, J=8.7 Hz), 8.36-8.41 (1H, m), 8.42 (1H, d, J=2.7 Hz), 8.63-8.67 (1H, m), 10.75 (½H, brs), 10.80 (½H, brs)

ESI-MS (m/e): 509 [M+H]

Example 227

5-(2,3-Difluoro-phenoxy)-2-pyrazin-2-yl-6-(6-ethanesulfonyl-pyridin-3-yloxy-1H-benzimidazole The entitled compound was obtained as a colorless solid in the same method as in Example 197 or in accordance with the method or by combining it with an ordinary method but using 4-(2,3-difluoro-phenoxy)-5-(6-ethanesulfonyl-pyridin-3-yloxy)-benzene-1,2-diamine obtained in Example 226 and pyrazine-2-carboxylic acid.

$^1$HNMR (CDCl$_3$) δ: 1.29 (3H, t, J=7.4 Hz), 3.38 (1H, q, J=7.4 Hz), 3.39 (1H, q, J=7.4 Hz), 6.72-6.78 (1H, m), 6.92-7.05 (2H, m), 7.22 (½H, s), 7.33 (½H, dd, J=8.8, 2.7 Hz), 7.34 (½H, dd, J=8.8, 2.7 Hz), 7.45 (½H, s), 7.53 (½H, s), 7.75 (½H, s), 01 (½H, d, J=8.8 Hz), 02 (½H, d, J=8.8 Hz), 43 (1H, d, J=2.7 Hz), 60 (½H, dd, J=2.5, 1.6 Hz), 62 (½H, dd, J=2.5, 1.6 Hz), 69 (½H, d, J=2.5 Hz), 70 (½H, d, J=2.5 Hz), 61 (½H, d, J=1.6 Hz), 63 (½H, d, J=1.6 Hz), 0.52 (½H, brs), 10.62 (½H, brs)

ESI-MS (m/e): 510 [M+H]

Example 228

5-(2,3-Difluoro-phenoxy)-2-(1-methyl-1H-pyrazol-3-yl)-6-(6-ethanesulfonyl-pyridin-3-yloxy)-1H-benzimidazole The entitled compound was obtained as a colorless solid in the same method as in Example 203 or in accordance with the method or by combining it with an ordinary method but using 4-(2,3-difluoro-phenoxy)-5-(6-ethanesulfonyl-pyridin-3-yloxy)-benzene-1,2-diamine obtained in Example 226 and 1-methyl-1H-pyrazole-3-carboxylic acid.

$^1$HNMR (CDCl$_3$) δ: 1.29 (3H, t, J=7.4 Hz), 3.37 (1H, q, J=7.4 Hz), 3.38 (1H, q, J=7.4 Hz), 3.97 (2H, s), 3.98 (1H, s), 6.65-6.75 (⅓H, m), 6.87 (½H, brs), 6.89-7.01 (3H, m), 7.10-7.19 (1H, m), 7.26-7.38 (1H, m), 7.30 (½H, s), 7.45 (⅔H, d, J=2.3 Hz), 7.47 (⅓H, d, J=2.3 Hz), 7.50-7.53 (⅙H, m), 7.62-7.67 (½H, m), 7.95-8.05 (1H, m), 8.39 (⅓H, d, J=2.5 Hz), 8.54 (⅔H, d, J=2.5 Hz), 10.00-10.25 (1H, m)

ESI-MS (m/e): 512 [M+H]

Example 229

5-(2,4-Difluoro-phenoxy)-2-pyridin-2-yl-6-(6-ethanesulfonyl-pyridin-3-yloxy)-1H-benzimidazole The entitled compound was obtained as a colorless solid in the same method as in Example 221 (step 3) or in accordance with the method or by combining it with an ordinary method but using 5-fluoro-4-(6-ethanesulfonyl-pyridin-3-yloxy)-2-nitro-phenylamine obtained in Example 221 (step 2) and 2,4-difluoro-phenol.

$^1$HNMR (CDCl$_3$) δ: 1.29 (3H, t, J=7.4 Hz), 3.37 (1H, q, J=7.4 Hz), 3.38 (1H, q, J=7.4 Hz), 6.81-6.95 (2H, m), 6.95-7.05 (1H, m), 7.06 (½H, s), 7.33 (½H, s), 7.32 (½H, dd, J=8.6, 2.7 Hz), 7.34 (½H, dd, J=8.6, 2.7 Hz), 7.37-7.41 (1H, m), 7.40 (½H, s), 7.70 (½H, s), 7.86-7.91 (1H, m), 8.00 (½H, d, J=8.6 Hz), 8.01 (½H, d, J=8.6 Hz), 8.34-8.39 (1H, m), 8.46 (1H, d, J=2.7 Hz), 8.62-8.67 (1H, m), 10.67 (½H, brs), 10.76 (½H, brs)

ESI-MS (m/e): 509 [M+H]

Example 230

5-(2,4-Difluoro-phenoxy)-2-pyrazin-2-yl-6-(6-ethanesulfonyl-pyridin-3-yloxy)-1H-benzimidazole The entitled compound was obtained as a colorless solid in the same method as in Example 197 or in accordance with the method or by combining it with an ordinary method but using 4-(2,4-difluoro-phenoxy)-5-(6-ethanesulfonyl-pyridin-3-yloxy)-benzene-1,2-diamine obtained in Example 229 and pyrazine-2-carboxylic acid.

$^1$HNMR (CDCl$_3$) δ: 1.30 (3H, t, J=7.4 Hz), 3.38 (1H, q, J=7.4 Hz), 3.39 (1H, q, J=7.4 Hz), 6.82-6.95 (2H, m), 6.98-7.05 (1H, m), 7.08 (½H, s), 7.34 (½H, dd, J=8.6, 2.7 Hz), 7.35 (½H, dd, J=8.6, 2.7 Hz), 7.38 (½H, s), 7.44 (½H, s), 7.74 (½H, s), 8.02 (½H, d, J=8.6 Hz), 8.03 (½H, d, J=8.6 Hz), 8.46 (½H, d, J=2.7 Hz), 8.47 (½H, d, J=2.7 Hz), 8.58 (½H, dd, J=2.7, 1.6 Hz), 8.60 (½H, dd, J=2.7, 1.6 Hz), 8.67 (½H, d, J=2.7 Hz), 8.68 (½H, d, J=2.7 Hz), 9.59 (½H, d, J=1.6 Hz), 9.61 (½H, d, J=1.6 Hz), 10.54 (½H, brs), 10.69 (½H, brs)

ESI-MS (m/e): 510 [M+H]

Example 231

5-(2,4-Difluoro-phenoxy)-2-(1-methyl-1H-pyrazol-3-yl)-6-(6-ethanesulfonyl-pyridin-3-yloxy)-1H-benzimidazole The entitled compound was obtained as a colorless solid in the same method as in Example 203 or in accordance with the method or by combining it with an ordinary method but using 4-(2,4-difluoro-phenoxy)-5-(6-ethanesulfonyl-pyridin-3-yloxy)-benzene-1,2-diamine obtained in Example 229 and 1-methyl-1H-pyrazole-3-carboxylic acid.

$^1$HNMR (CDCl$_3$) δ: 1.28 (3H, t, J=7.4 Hz), 3.38 (2H, q, J=7.4 Hz), 3.98 (3H, s), 6.78-6.85 (1H, m), 6.85-6.93 (1H, m), 6.93-6.98 (1H, m), 6.93-6.98 (½H, m), 6.99 (1H, d, J=2.3 Hz), 7.02 (½H, brs), 7.27-7.34 (1H, m), 7.36 (½H, brs), 7.46 (1H, d, J=2.3 Hz), 7.64 (½H, brs), 7.99 (1H, d, J=8.6 Hz), 8.43 (1H, d, J=2.7 Hz), 10.19 (½H, brs), 10.29 (½H, brs)

ESI-MS (m/e): 512 [M+H]

Example 232

5-(2,5-Difluoro-phenoxy)-2-pyridin-2-yl-6-(6-ethanesulfonyl-pyridin-3-yloxy)-1H-benzimidazole The entitled compound was obtained as a white solid in the same method as in Example 221 (step 3) or in accordance with the method or by combining it with an ordinary method but using 5-fluoro-4-(6-ethanesulfonyl-pyridin-3-yloxy)-2-nitro-phenylamine obtained in Example 221 (step 2) and 2,5-difluoro-phenol.

$^1$HNMR (CD$_3$OD) δ: 1.23 (3H, t, J=7.4 Hz), 3.38 (2H, q, J=7.4 Hz), 6.76-6.89 (2H, m), 7.15-7.24 (1H, m), 7.49-7.55 (3H, m), 7.71 (1H, s), 8.01 (1H, td, J=7.4, 2.3 Hz), 8.04 (1H, d, J=7.4 Hz), 8.32 (1H, d, J=7.4 Hz), 8.40 (1H, d, J=2.3 Hz), 8.77 (1H, d, J=4.3 Hz)

ESI-MS (m/e): 509 [M+H]

Example 233

5-(2,5-Difluoro-phenoxy)-2-pyridin-1-oxido-2-yl-6-(6-ethanesulfonyl-pyridin-3-yloxy)-1H-benzimidazole 7.5 mg of m-chloroperbenzoic acid was added to a chloroform (1.5 ml) solution of 7.5 mg of 5-(2,5-difluoro-phenoxy)-2-pyridin-2-yl-6-(6-ethanesulfonyl-pyridin-3-yloxy)-1H-benzimidazole obtained in Example 232, and the reaction liquid was stirred at 45° C. for 1 hour. The solvent was evaporated away under reduced pressure, and the resulting residue was purified through reversed-phase middle-pressure liquid chromatography [ODS-AS-360-CC (by YMC), mobile phase: water-acetonitrile-0.1% trifluoroacetic acid]. The solvent of the resulting fraction was diluted with ethyl acetate, washed with aqueous saturated sodium bicarbonate, and dried with anhydrous sodium sulfate. The solvent was evaporated away under reduced pressure to obtain the entitled compound as a pale yellow solid.

$^1$HNMR (CD$_3$OD) δ: 1.23 (3H, t, J=7.4 Hz), 3.38 (2H, q, J=7.4 Hz), 6.78-6.90 (2H, m), 7.20 (1H, td, J=9.8, 5.1 Hz), 7.52 (1H, dd, J=6.6, 3.1 Hz), 7.56 (1H, s), 7.62 (1H, t, J=8.2 Hz), 7.73 (1H, t, J=8.2 Hz), 7.78 (1H, s), 8.04 (1H, d, J=8.2 Hz), 8.41 (1H, d, J=3.1 Hz), 8.51 (1H, d, J=6.6 Hz), 8.64 (1H, d, J=8.2 Hz)

ESI-MS (m/e): 525 [M+H]

Example 234

5-(2,5-Difluoro phenoxy)-2-pyrazin-2-yl-6-(6-ethanesulfonyl-pyridin-3-yloxy)-1H-benzimidazole The entitled compound was obtained as a white solid in the same method as in Example 205 or in accordance with the method or by combining it with an ordinary method but using 4-(2,5-difluoro-phenoxy)-5-(6-ethanesulfonyl-pyridin-3-yloxy)-benzene-1,2-diamine obtained in Example 232 and methylpyrazin-2-imidate.

$^1$HNMR (CD$_3$OD) δ: 1.24 (3H, t, J=6.9 Hz), 3.38 (2H, q, J=6.9 Hz), 6.77-6.91 (2H, m), 7.17-7.24 (1H, m), 7.51 (1H, s), 7.52 (1H, dd, J=7.4, 4.3 Hz), 7.74 (1H, s), 8.04 (1H, d, J=7.4 Hz), 8.41 (1H, d, J=2.3 Hz), 8.74 (1H, d, J=4.3 Hz), 8.80 (1H, dd, J=2.3, 1.8 Hz), 9.51 (1H, d, J=1.8 Hz)

ESI-MS (m/e): 510 [M+H]

Example 235

5-(2,6-Difluoro-phenoxy)-2-pyridin-2-yl-6-(6-ethanesulfonyl-pyridin-3-yloxy)-1H-benzimidazole The entitled compound was obtained as a colorless solid in the same method as in Example 221 (step 3) or in accordance with the method or by combining it with an ordinary method but using 5-fluoro-4-(6-ethanesulfonyl-pyridin-3-yloxy)-2-nitro-phenylamine obtained in Example 221 (step 2) and 2,6-difluoro-phenol.

$^1$HNMR (CDCl$_3$) δ: 1.29 (3H, t, J=7.4 Hz), 3.38 (1H, q, J=7.4 Hz), 3.39 (1H, q, J=7.4 Hz), 6.68-6.75 (½H, m), 6.90-7.00 (2H, m), 7.12-7.26 (1H, m), 7.27-7.53 (3H, m), 7.68-7.72 (½H, m), 7.84-7.92 (1H, m), 7.98-8.04 (1H, m), 8.31-8.39 (1H, m), 8.41 (½H, d, J=2.3 Hz), 8.56 (½H, d, J=2.3 Hz), 8.57-8.63 (1H, m), 10.59-10.88 (1H, m)

ESI-MS (m/e): 509 [M+H]

Example 236

5-(2,6-Difluoro-phenoxy)-2-pyrazin-2-yl-6-(6-ethanesulfonyl-pyridin-3-yloxy)-1H-benzimidazole The entitled compound was obtained as a colorless solid in the same method as in Example 197 or in accordance with the method or by combining it with an ordinary method but using 4-(2,6-difluoro-phenoxy)-5-(6-ethanesulfonyl-pyridin-3-yloxy)-benzene-1,2-diamine obtained in Example 235 and pyrazine-2-carboxylic acid.

$^1$HNMR (CDCl$_3$) δ: 1.29 (3H, t, J=7.4 Hz), 3.38 (½H, q, J=7.4 Hz), 3.39 (1H, q, J=7.4 Hz), 3.40 (½H, q, J=7.4 Hz), 6.73-6.78 (½H, m), 6.93-7.04 (2H, m), 6.93-7.04 (½H, m), 7.14-7.20 (½H, m), 7.22 (¼H, s), 7.31-7.42 (1H, m), 7.44 (¼H, s), 7.45 (¼H, s), 7.53 (¼H, s), 7.74 (¼H, s), 7.75 (¼H, s), 8.00-8.05 (1H, m), 8.43 (½H, d, J=2.7 Hz), 8.56 (¼H, dd, J=2.5, 1.6 Hz), 8.57 (½H, d, J=2.7 Hz), 8.59 (¼H, dd, J=2.5, 1.6 Hz), 8.60 (¼H, dd, J=2.5, 1.6 Hz), 8.61 (¼H, dd, J=2.5, 1.6 Hz), 8.66 (¼H, d, J=2.5 Hz), 8.67 (¼H, d, J=2.5 Hz), 8.68 (¼H, d, J=2.5 Hz), 8.69 (¼H, d, J=2.5 Hz), 9.56 (¼H, d, J=1.6 Hz), 9.60 (¼H, d, J=1.6 Hz), 9.61 (¼H, d, J=1.6 Hz), 9.63 (¼H, d, J=1.6 Hz), 10.36 (¼H, brs), 10.48 (¼H, brs), 10.51 (¼H, brs), 10.57 (¼H, brs)

ESI-MS (m/e): 510 [M+H]

Example 237

5-(2,6-Difluoro-phenoxy)-2-(1-methyl-1H-pyrazol-3-yl)-6-(6-ethanesulfonyl-pyridin-3-yloxy)-1H-benzimidazole The entitled compound was obtained as a colorless solid in the same method as in Example 203 or in accordance with the method or by combining it with an ordinary method but using 4-(2,6-difluoro-phenoxy)-5-(6-ethanesulfonyl-pyridin-3-yloxy)-benzene-1,2-diamine obtained in Example 235 and 1-methyl-1H-pyrazole-3-carboxylic acid.

$^1$HNMR (CDCl$_3$) δ: 1.29 (3H, t, J=7.4 Hz), 3.38 (2H, q, J=7.4 Hz), 3.96 (3H, s), 6.87 (½H, brs), 6.93-7.00 (3H, m), 7.10-7.17 (1H, m), 7.18 (½H, s), 7.30 (½H, s), 7.32-7.40 (1H, m), 7.34 (1H, d, J=2.5 Hz), 7.63 (½H, brs), 7.98-8.03 (1H, m), 8.54 (1H, d, J=2.7 Hz), 10.18 (½H, brs), 10.35 (½H, brs)

ESI-MS (m/e): 512 [M+H]

Example 238

5-(2-Trifluoromethoxy-phenoxy)-2-pyrazin-2-yl-6-(6-ethanesulfonyl-pyridin-3-yloxy)-1H-benzimidazole The entitled compound was obtained as a colorless solid in the same method as in Example 196 (step 4), (step 5) and Example 205 or in accordance with the method or by combining it with an ordinary method but using 5-fluoro-4-(6-ethanesulfonyl-pyridin-3-yloxy)-2-nitro-phenylamine obtained in Example 221 (step 2) and 2-trifluoromethoxy-phenol.

$^1$HNMR (CDCl$_3$) δ: 1.27 (3H, t, J=7.4 Hz), 3.36 and 3.37 (total 2H, each q, J=7.4 Hz), 6.95-7.00 (1H, m), 7.12-7.46 (5H, m), 7.50 and 7.76 (total 1H, each s), 7.98 and 8.00 (total 1H, each d, J=8.8 Hz), 8.41 (1H, d, J=2.7 Hz), 8.59-8.62 (1H, m), 8.68 (1H, d, J=2.4 Hz), 9.61 and 9.63 (total 1H, each d, J=1.6 Hz)

ESI-MS (m/e): 558 [M+H]

Example 239

5-(2-Fluoropyridin-3-yloxy)-6-(6-ethanesulfonyl-pyridin-3-yloxy)-2-pyridin-2-yl-1H-benzimidazole The entitled compound was obtained as a colorless solid in the same method as in Example 221 (step 3) or in accordance with the method or by combining it with an ordinary method but using 5-fluoro-4-(6-ethanesulfonyl-pyridin-3-yloxy)-2-nitro-phenylamine obtained in Example 221 (step 2) and 2-fluoro-pyridin-3-ol.

$^1$HNMR (CDCl$_3$) δ: 1.29 (3H, t, J=7.4 Hz), 3.38 (2H, q, J=7.4 Hz), 7.11-7.16 (1H, m), 7.24 (½H, s), 7.26-7.35 (2H, m), 7.41-7.45 (1H, m), 7.43 (½H, s), 7.55 (½H, s), 7.72 (½H, s), 7.88-7.94 (2H, m), 7.99-8.03 (1H, m), 8.38-8.41 (2H, m), 8.65-8.67 (1H, m), 10.94 (½H, brs), 10.98 (½H, brs)

ESI-MS (m/e): 492 [M+H]

Example 240

5-(2-Fluoropyridin-3-yloxy)-6-(6-ethanesulfonyl-pyridin-3-yloxy)-2-pyrazin-2-1H-benzimidazole The entitled compound was obtained as a colorless solid in the same method as in Example 197 or in accordance with the method or by combining it with an ordinary method but using 4-(2-fluoropyridin-3-yloxy)-5-(6-ethanesulfonyl-pyridin-3-yloxy)-benzene-1,2-diamine obtained in Example 239, and pyrazine-2-carboxylic acid.

$^1$HNMR (CDCl$_3$) δ: 1.30 (3H, t, J=7.4 Hz), 3.38 (1H, q, J=7.4 Hz), 3.39 (1H, q, J=7.4 Hz), 7.13-7.24 (1H, m), 7.24 (½H, s), 7.26-7.39 (2H, m), 7.47 (½H, s), 7.56 (½H, s), 7.77 (½H, s), 7.95-8.05 (2H, m), 8.40 (1H, d, J=2.3 Hz), 7.62 (½H, dd, J=2.4, 1.6 Hz), 8.63 (½H, dd, J=2.4, 1.6 Hz), 8.70 (½H, d, J=2.4 Hz), 8.71 (½H, d, J=2.4 Hz), 9.62 (½H, d, J=1.6 Hz), 9.63 (½H, d, J=1.6 Hz), 10.45 (½H, brs), 10.51 (½H, brs)

ESI-MS (m/e): 493 [M+H]

Example 241

5-(2-Fluoropyridin-3-yloxy)-2-(1H-pyrazol-3-yl)-6-(6-ethanesulfonyl-pyridin-3-yloxy)-1H-benzimidazole The entitled compound was obtained as a colorless solid in the same method as in Example 202 or in accordance with the method or by combining it with an ordinary method but using 4-(2-fluoropyridin-3-yloxy)-5-(6-ethanesulfonyl-pyridin-3-yloxy)-benzene-1,2-diamine obtained in Example 239, and 1H-pyrazole-3-carboxaldehyde.

$^1$HNMR (CDCl$_3$) δ: 1.29 (3H, t, J=7.4 Hz), 3.37 (2H, q, J=7.4 Hz), 7.07 (1H, d, J=2.7 Hz), 7.08-7.13 (1H, m), 7.20 (½H, brs), 7.24-7.30 (2H, m), 7.34 (½H, brs), 7.52 (½H, brs), 7.65 (½H, brs), 7.71 (1H, d, J=2.7 Hz), 7.88-7.92 (1H, m), 7.99 (1H, d, J=8.6 Hz), 8.33 (1H, d, J=2.7 Hz)

ESI-MS (m/e): 481 [M+H]

Example 242

5-(2-Chloropyridin-3-yloxy)-6-(6-ethanesulfonyl-pyridin-3-yloxy)-2-pyridin-2-yl-1H-benzimidazole The entitled compound was obtained as a colorless solid in the same method as in Example 221 (step 3) or in accordance with the method or by combining it with an ordinary method but using 5-fluoro-4-(6-ethanesulfonyl-pyridin-3-yloxy)-2-nitro-phenylamine obtained in Example 221 (step 2) and 2-chloro-pyridin-3-ol.

$^1$HNMR (CDCl$_3$) δ: 1.29 (3H, t, J=7.4 Hz), 3.38 (2H, q, J=7.4 Hz), 7.14-7.20 (2H, m), 7.28 (½H, s), 7.20-7.31 (1H, m), 7.40-7.46 (1H, m), 7.46 (½H, s), 7.60 (½H, s), 7.76 (½H, s), 7.88-7.93 (1H, m), 8.00 (½H, d, J=8.6 Hz), 8.01 (½H, d, J=8.6 Hz), 8.11-8.16 (1H, m), 8.31-8.35 (1H, m), 8.38-8.42 (1H, m), 8.64-8.68 (1H, m), 10.82-10.95 (1H, m)

ESI-MS (m/e): 508 [M+H]

Example 243

5-(2-Chloropyridin-3-yloxy)-6-(6-ethanesulfonyl-pyridin-3-yloxy)-2-pyrazin-2-yl-1H-benzimidazole The entitled compound was obtained as a colorless solid in the same method as in Example 197 or in accordance with the method or by combining it with an ordinary method but using 4-(2-chloropyridin-3-yloxy)-5-(6-ethanesulfonyl-pyridin-3-yloxy)-benzene-1,2-diamine obtained in Example 242 and pyrazine-2-carboxylic acid.

$^1$HNMR (CDCl$_3$) δ: 1.29 (3H, t, J=7.4 Hz), 3.37 (2H, q, J=7.4 Hz), 7.18-7.24 (2H, m), 7.30 (½H, s), 7.31 (½H, dd, J=8.6, 2.7 Hz), 7.32 (½H, dd, J=8.6, 2.7 Hz), 7.51 (½H, s), 7.61 (½H, s), 7.81 (½H, s), 8.02 (½H, d, J=8.6 Hz), 8.04 (½H, d, J=8.6 Hz), 8.15-8.20 (1H, m), 8.35 (½H, d, J=2.7 Hz), 8.36 (½H, d, J=2.7 Hz), 8.63 (½H, dd, J=2.3, 1.6 Hz), 8.64 (½H, dd, J=2.3, 1.6 Hz), 8.72 (½H, d, J=2.3 Hz), 8.73 (½H, d, J=2.3 Hz), 9.64 (½H, d, J=1.6 Hz), 9.65 (½H, d, J=1.6 Hz), 10.60 (½H, brs), 10.68 (½H, brs)

ESI-MS (m/e): 509 [M+H]

Example 244

5-(2-Chloropyridin-3-yloxy)-2-(1-methyl-1H-pyrazol-3-yl)-6-(6-ethanesulfonyl-pyridin-3-yloxy)-1H-benzimidazole The entitled compound was obtained as a colorless solid in the same method as in Example 203 or in accordance with the method or by combining it with an ordinary method but using 4-(2-chloropyridin-3-yloxy)-5-(6-ethanesulfonyl-pyridin-3-yloxy)-benzene-1,2-diamine obtained in Example 242 and 1-methyl-1H-pyrazole-3-carboxylic acid.

$^1$HNMR (CDCl$_3$) δ: 1.29 (3H, t, J=7.4 Hz), 3.37 (2H, q, J=7.4 Hz), 4.01 (3H, s), 7.01 (1H, d, J=2.3 Hz), 7.12-7.17 (2H, m), 7.26 (1H, dd, J=8.8, 2.7 Hz), 7.39 (½H, brs), 7.48 (½H, brs), 7.49 (1H, d, J=2.3 Hz), 7.58 (½H, brs), 7.69 (½H, brs), 7.99 (1H, d, J=8.8 Hz), 8.10-8.15 (1H, m), 8.31 (1H, d, J=2.7 Hz), 10.28 (1H, brs)

ESI-MS (m/e): 511 [M+H]

Example 245

5-(2-Cyanopyridin-3-yloxy)-6-(6-ethanesulfonyl-pyridin-3-yloxy)-2-pyridin-2-yl-1H-benzimidazole The entitled compound was obtained as a colorless solid in the same method as in Example 218 or in accordance with the method or by combining it with an ordinary method but using 5-fluoro-4-(6-ethanesulfonyl-pyridin-3-yloxy)-2-nitro-phenylamine obtained in Example 221 (step 2) and 1-oxy-pyridin-3-ol.

$^1$HNMR (CDCl$_3$) δ: 1.30 (3H, t, J=7.4 Hz), 3.37 (2H, q, J=7.4 Hz), 7.12-7.26 (3H, m), 7.38-7.45 (2H, m), 7.45 (½H, s), 7.46 (½H, s), 7.75 (1H, s), 7.89-7.94 (1H, m), 7.99-8.05 (1H, m), 8.22-8.26 (1H, m), 8.39-8.43 (1H, m), 8.67-8.70 (1H, m), 10.88 (1H, brs)

ESI-MS (m/e): 499 [M+H]

Example 246

5-(2-Cyanopyridin-3-yloxy)-6-(6-ethanesulfonyl-pyridin-3-yloxy)-2-pyrazin-2-yl-1H-benzimidazole The entitled compound was obtained as a colorless solid in the same method as in Example 197 or in accordance with the method or by combining it with an ordinary method but using 4-(2-cyanopyridin-3-yloxy)-5-(6-ethanesulfonyl-pyridin-3-yloxy)-benzene-1,2-diamine obtained in Example 245 and pyrazine-2-carboxylic acid.

$^1$HNMR (CDCl$_3$) δ: 1.35 (3⁄2H, t, J=7.4 Hz), 1.37 (3⁄2H, t, J=7.4 Hz), 3.38 (1H, q, J=7.4 Hz), 3.39 (1H, q, J=7.4 Hz), 7.19-7.26 (2H, m), 7.42-7.47 (1H, m), 7.53 (½H, s), 7.54 (½H, s), 7.80 (½H, s), 7.81 (½H, s), 8.04 (½H, d, J=8.6 Hz), 8.05 (½H, d, J=8.6 Hz), 8.22-8.25 (1H, m), 8.40-8.43 (1H, m), 8.64-8.66 (1H, m), 8.73 (1H, d, J=2.5 Hz), 9.65 (1H, d, J=1.5 Hz), 10.87 (½H, brs), 10.90 (½H, brs)

ESI-MS (m/e): 500[M−H]

Example 247

5-(2-Difluoromethoxy-pyridin-3-yloxy)-6-(6-ethanesulfonyl-pyridin-3-yloxy)-2-pyridin-2-yl-1H-benzimidazole The entitled compound was obtained as a colorless solid in the same method as in Example 221 (step 3) or in accordance with the method or by combining it with an ordinary method but using 5-fluoro-4-(6-ethanesulfonyl-pyridin-3-yloxy)-2-nitro-phenylamine obtained in Example 221 (step 2) and 2-difluoromethoxy-pyridin-3-ol.

$^1$HNMR (DMSO-d$_6$) δ: 1.10 (3H, t, J=7.4 Hz), 3.36 (2H, q, J=7.4 Hz), 7.18-7.25 (1H, m), 7.31-7.87 (6H, m), 7.94-8.07 (3H, m), 8.32-8.36 (1H, m), 8.46-8.49 (1H, m), 8.77 (1H, s)

ESI-MS (m/e): 540 [M+H]

Example 248

5-(2-Difluoromethoxy-pyridin-3-yloxy)-6-(6-ethanesulfonyl-1-pyridin-3-yloxy)-2-pyrazin-2-yl-1H-benzimidazole The entitled compound was obtained as a colorless solid in the same method as in Example 205 or in accordance with the method or by combining it with an ordinary method but using 4-(2-difluoromethoxy-pyridin-3-yloxy)-5-(6-ethanesulfonyl-pyridin-3-yloxy)-benzene-1,2-diamine obtained in Example 247 and methylpyrazin-2-imidate.

$^1$HNMR (CDCl$_3$) δ: 1.30 (3H, t, J=7.4 Hz), 3.37 (2H, q, J=7.4 Hz), 7.07-7.11 (1H, m), 7.17 and 7.76 (total 1H, each s), 7.29-7.34 (2H, m), 7.37 (1H, t, J=72.8 Hz), 7.46 (1H, s), 7.96-8.03 (2H, m), 8.43 (1H, s), 8.60 and 8.62 (total 1H, each s), 8.69 (1H, s), 9.60 and 9.63 (total 1H, each d, J=1.5 Hz)

ESI-MS (m/e): 541 [M+H]

Example 249

5-(2-Difluoromethoxy-pyridin-3-yloxy)-6-(6-ethanesulfonyl-pyridin-3-yloxy)-2-(1-methyl-1H-pyrazol-3-yl)-1H-benzimidazole The entitled compound was obtained as a colorless solid in the same method as in Example 203 or in accordance with the method or by combining it with an ordinary method but using 4-(2-difluoromethoxy-pyridin-3-yloxy)-5-(6-ethanesulfonyl-pyridin-3-yloxy)-benzene-1,2-diamine obtained in Example 247 and 1-methyl-1H-pyrazole-3-carboxylic acid.

$^1$HNMR (DMSO-d$_6$) δ: 1.10 (3H, t, J=7.4 Hz), 3.36 (2H, q, J=7.4 Hz), 4.00 (3H, s), 6.88 (1H, d. J=2.3 Hz), 7.19 (1H, brs), 7.26-7.75 (4H, m), 7.63 (1H, t, J=72.4 Hz), 7.90-7.99 (3H, m), 8.45 (1H, d, J=2.7 Hz)

ESI-MS (m/e): 543 [M+H]

Example 250

6-Benzyloxy-5-(2-fluorophenoxy)-2-pyrazin-2-yl-1H-benzimidazole (Step 1) Production of 4-benzyloxy-3-fluoroaniline 2.91 ml of hydrazine monohydrate and about 1 g of developed Raney nickel catalyst were added to a methanol (60 ml) solution of 4.94 g of 4-benzyloxy-3-fluoronitrobenzene, and the reaction liquid was stirred at room temperature for 2 hours. The catalyst was removed through filtration through Celite, and the solvent was evaporated away under reduced pressure to obtain the entitled compound as a yellow oily substance.

(Step 2) Production of N-(4-benzyloxy-3-fluorophenyl)pyrazinecarboxamide 2.59 g of pyrazine-2-carboxylic acid and 4.73 g of 1-(3-dimethylaminopropyl)-3-ethylcarbodiimide monohydrochloride were added to a pyridine (60 ml) solution of 4.13 g of 4-benzyloxy-3-fluoroaniline, and the reaction liquid was stirred overnight at room temperature. Pyridine was evaporated away under reduced pressure, and then water was added to it. The resulting deposit was taken out through filtration to obtain the entitled compound as a brown solid.

(Step 3) Production of N-(4-benzyloxy-5-fluoro-2-nitrophenyl)pyrazinecarboxamide 40 ml of trifluoroacetic acid and 1.99 g of potassium nitrate were added to a chloroform (40 ml) suspension of 5.80 g of N-(4-benzyloxy-3-fluorophenyl)pyrazinecarboxamide, with cooling with ice, and the reaction liquid was stirred overnight at room temperature. The solvent was evaporated away under reduced pressure, and aqueous saturated sodium bicarbonate was added to it. The resulting solid was washed with a mixed solvent of ethyl acetate and hexane to obtain the entitled compound as a yellow solid.

(Step 4) Production of N-(4-benzyloxy-5-(2-fluorophenoxy)-2-nitrophenyl)pyrazinecarboxamide 0.54 ml of 2-fluorophenol and 2.53 g of potassium carbonate were added to a dimethylformamide (16 ml) solution of 2.14 g of N-(4-benzyloxy-5-fluoro-2-nitrophenyl)pyrazinecarboxamide, and the reaction liquid was stirred at 90° C. for 5 hours, and then water was added to it. The resulting deposit was taken out through filtration to obtain the entitled compound as a yellow solid.

(Step 5) Production of 5-benzyloxy-6-(2-fluorophenoxy)-2-pyrazin-2-yl-1H-benzimidazole 3.72 g of tin(II) chloride dihydrate was added to a dimethylformamide (16 ml) suspension of 1.52 g of N-(4-benzyloxy-5-(2-fluorophenoxy)-2-nitrophenyl)pyrazinecarboxamide, and the reaction liquid was stirred overnight at 80° C. The reaction liquid was diluted with ethyl acetate, washed with aqueous saturated sodium bicarbonate, water and saturated saline in order, and dried with anhydrous magnesium sulfate. The solvent was evaporated away under reduced pressure, and the resulting residue was washed with a mixed solvent of ethyl acetate and hexane to obtain the entitled compound as a yellow solid.

$^1$HNMR (DMSO-$d_6$) δ: 5.15 and 5.17 (total 2H, each s), 6.78-6.93 (1H, m), 7.06-7.40 (9H, m), 7.54 and 7.57 (total 1H, each s), 8.73 and 8.74 (total 1H, each s), 8.76-8.79 (1H, m), 9.43 and 9.44 (total 1H, each d, J=1.6 Hz)
ESI-MS (m/e): 413 [M+H]

Example 251

5-(2-Fluoro-phenoxy)-2-pyrazin-2-yl-6-(2-cyano-pyrimidin-5-yloxy)-1H-benzimidazole (Step 1) Production of 5-(2-fluorophenoxy)-6-hydroxy-2-pyrazin-2-yl-1H-benzimidazole 500 mg of 20% palladium hydroxide-carbon catalyst was added to a suspension of 697 mg of 5-benzyloxy-6-(2-fluorophenoxy)-2-pyrazin-2-yl-1H-benzimidazole obtained in Example 250, in 10 ml of methanol and 10 ml of tetrahydrofuran, and the reaction liquid was stirred in a hydrogen atmosphere at room temperature for 1 hour. The catalyst was removed through filtration through Celite, the solvent was evaporated away under reduced pressure, and the residue was purified through silica gel column chromatography (developing solvent: ethyl acetate) to obtain the entitled compound as a yellow solid.

(Step 2) Production of 5-(2-fluoro-phenoxy)-2-pyrazin-2-yl-6-(2-cyano-pyridin-5-yloxy)-1H-benzimidazole 7.0 mg of 5-bromo-2-cyano-pyrimidine and 15 mg of cesium carbonate were added to an N-methylpyrrolidinone (0.5 ml) solution of 7.0 mg of 5-(2-fluorophenoxy)-6-hydroxy-2-pyrazin-2-yl-1H-benzimidazole obtained in the step 1, and the reaction liquid was stirred at 90° C. for 15 minutes. The reaction mixture was purified through reversed-phase middle-pressure liquid chromatography [ODS-AS-360-CC (by YMC), mobile phase: water-acetonitrile-0.1% trifluoroacetic acid]. The resulting fraction was diluted with ethyl acetate, washed with aqueous saturated sodium bicarbonate, and dried with anhydrous sodium sulfate. The solvent was evaporated away under reduced pressure to obtain the entitled compound a colorless solid.

$^1$HNMR (CD$_3$OD) δ: 7.01-7.58 (5H, m), 7.64-7.82 (1H, m), 8.52 (2H, s), 8.67 (1H, s), 8.74 (1H, s), 9.44 (1H, s)
ESI-MS (m/e): 426 [M+H]

Example 252

5-(2-Fluoro-phenoxy)-2-pyrazin-2-yl-6-(6-cyano-pyridin-3-yloxy)-1H-benzimidazole The entitled compound was obtained as a yellow solid in the same method as in Example 251 (step 2) or in accordance with the method or by combining it with an ordinary method but using 5-(2-fluorophenoxy)-6-hydroxy-2-pyrazin-2-yl-1H-benzimidazole obtained in Example 251 (step 1) and 5-bromo-2-cyanopyridine.

$^1$HNMR (CD$_3$OD) δ: 7.01-7.30 (5H, m), 7.42 (1H, dd, J=8.6, 3.1 Hz), 7.55-7.77 (1H, m), 7.81 (1H, d, J=8.6 Hz), 8.39 (1H, d, J=3.1 Hz), 8.71 (1H, s), 8.77 (1H, s), 9.47 (1H, s)
ESI-MS (m/e): 425 [M+H]

Example 253

5-(2-Fluoro-phenoxy)-2-pyrazin-2-yl-6-(6-trifluoromethyl-pyridin-3-yloxy)-1H-benzimidazole 16 mg of 5-bromo-2-trifluoromethyl-pyridine, 50 mg of cesium carbonate and 10 mg of copper(II) oxide were added to an N-methylpyrrolidinone (1 ml) solution of 21 mg of 5-(2-fluorophenoxy)-6-hydroxy-2-pyrazin-2-yl-1H-benzimidazole obtained in Example 251 (step 1), and the reaction liquid was stirred at 130° C. for 5 hours. The deposit was separated through filtration, and the solution was purified through reversed-phase middle-pressure liquid chromatography [ODS-AS-360-CC (by YMC), mobile phase: water-acetonitrile-0.1% trifluoroacetic acid]. The resulting fraction was diluted with ethyl acetate, washed with aqueous saturated sodium bicarbonate, and dried with anhydrous sodium sulfate. The solvent was evaporated away under reduced pressure to obtain the entitled compound as a brown solid.

¹HNMR (CD₃OD) δ: 6.70-7.84 (6H, m), 7.49 (1H, dd, J=8.8 Hz, 2.8 Hz), 7.78 (1H, d, J=8.8 Hz), 8.39 (1H, d, J=2.8 Hz), 8.73 (1H, s), 8.80 (1H, s), 9.49 (1H, s)

ESI-MS (m/e): 468 [M+H]

Example 254

5-(2,6-Difluoro-phenoxy)-4-fluoro-2-pyrazin-2-yl-6-(6-methanesulfonyl pyridin-3-yloxy)-1H-benzimidazole (Step 1) Production of 2,3-difluoro-1-(6-methanesulfonyl-pyridin-3-yloxy)-4-nitro-benzene 112 mg of 6-methanesulfonyl-pyridin-3-ol and 100 mg of potassium carbonate were added to an N-methylpyrrolidinone (3 ml) solution of 135 mg of 2,3,4-trifluoro-nitrobenzene, and the reaction liquid was stirred at 50° C. for 1 hour. The reaction liquid was diluted with ethyl acetate, washed with water and saturated saline in order, and dried with anhydrous sodium sulfate. The solvent was evaporated away under reduced pressure, and the resulting residue was purified through silica gel column chromatography (developing solvent: hexane/ethyl acetate=1/1) to obtain the entitled compound.

(Step 2) Production of N-2,3-difluoro-4-(6-methanesulfonyl-pyridin-3-yloxy)-6-nitro-phenyl)pyrazinecarboxamide 0.2 ml of hydrazine monohydrate and about 0.01 g of developed Raney nickel were added to a methanol (3 ml) solution of 22 mg of 2,3-difluoro-1-(6-methanesulfonyl-pyridin-3-yloxy)-4-nitro-benzene, and the reaction liquid was stirred at room temperature for 15 minutes. The catalyst was removed through filtration through Celite, and the solvent was evaporated away under reduced pressure to obtain a crude product. 12 mg of pyrazine-2-carboxylic acid and 25 mg of 1-(3-dimethylaminopropyl)-3-ethylcarbodiimide monohydrochloride were added to a pyridine (1 ml) solution of the resulting crude product, and the reaction liquid was stirred overnight at room temperature. The reaction liquid was diluted with ethyl acetate, washed with water and saturated saline in order, and dried with anhydrous sodium sulfate. The solvent was evaporated away under reduced pressure to obtain a crude product. 0.1 ml of fuming nitric acid was added to a trifluoroacetic acid (2 ml) solution of the crude product, and the reaction liquid was stirred overnight at 45° C. The solvent was evaporated away under reduced pressure, and the resulting residue was purified through partitioning thin-layer chromatography (Kieselgel™ 60F₂₅₄, Art 5744 (by Merck), chloroform/methanol=20/1) to obtain the entitled compound.

(Step 3) Production of 5-(2,6-difluoro-phenoxy)-4-fluoro-2-pyrazin-2-yl-6-(6-methanesulfonyl-pyridin-3-yloxy)-1H-benzimidazole 8 mg of 2,6-difluorophenol and 8 mg of potassium carbonate were added to an N-methylpyrrolidinone (0.5 ml) solution of 8.6 mg of N-(2,3-difluoro-4-(6-methanesulfonyl-pyridin-3-yloxy)-6-nitro-phenyl)pyrazinecarboxamide, and the reaction liquid was stirred at 90° C. for 15 minutes. 75 mg of tin(II) chloride dihydrate was added to it, and the reaction liquid was stirred overnight at 90° C. Further, 3 mg of p-toluenesulfonic acid was added to it, and the reaction liquid was stirred at 90° C. for 2 hours. The deposit was taken out through filtration, and purified through reversed-phase middle-pressure liquid chromatography [ODS-AS-360-CC (by YMC), mobile phase: water-acetonitrile-0.1% trifluoroacetic acid]. The solvent of the resulting fraction was diluted with ethyl acetate, washed with aqueous saturated sodium bicarbonate, and dried with anhydrous sodium sulfate. The solvent was evaporated away under reduced pressure to obtain the entitled compound as a brown solid.

¹HNMR (CD₃OD) δ: 3.22 (3H, s), 6.93-6.99 (2H, m), 7.01-7.10 (1H, m), 7.30-7.45 (1H, m), 7.47-7.51 (1H, m), 8.02 (1H, d, J=8.6 Hz), 8.37 (1H, d, J=2.3 Hz), 8.75 (1H, d, J=2.3 Hz), 8.80 (1H, s), 9.56 (1H, s)

ESI-MS (m/e): 514 [M+H]

Example 255

5-(2,6-Difluoro-phenoxy)-7-fluoro-2-pyridin-2-yl-6-(6-ethanesulfonyl-1-pyridin-3-yloxy)-1H-benzimidazole (Step 1) Production of 2,3-difluoro-1-(2,6-difluoro-phenoxy)-4-nitro-benzene 470 mg of 2,6-difluoro-phenol and 1.5 g of tetrabutylammonium bromide were added to an N-methylpyrrolidinone (13 ml) solution of 500 mg of 2,3,4-trifluoro-nitrobenzene, and the reaction liquid was stirred overnight at 130° C. The reaction liquid was diluted with ethyl acetate, washed with water and saturated saline in order, and dried with anhydrous sodium sulfate. The solvent was evaporated away under reduced pressure, and the resulting residue was purified through silica gel column chromatography (developing solvent: hexane/ethyl acetate=4/1) to obtain the entitled compound.

(Step 2) Production of 5-(2,6-difluoro-phenoxy)-7-fluoro-2-pyridin-2-yl-6-(6-ethanesulfonyl-pyridin-3-yloxy)-1H-benzimidazole The entitled compound was obtained as a white solid in the same method as in Example 254 (step 2), (step 3) or in accordance with the method or by combining it with an ordinary method but using 2,3-difluoro-1-(2,6-difluoro-phenoxy)-4-nitro-benzene and 6-ethanesulfonyl-pyridin-3-ol obtained in Reference Example 4 in order.

¹HNMR (CD₃OD) δ: 1.25 (3H, t, J=7.4 Hz), 3.41 (2H, q, J=7.4 Hz), 6.91-6.96 (1H, m), 7.14 (2H, t, J=8.4 Hz), 7.27-7.34 (1H, m), 7.48-7.54 (1H, m), 7.63 (1H, dd, J=8.8, 2.7 Hz), 7.99 (1H, t, J=7.6 Hz), 8.10 (1H, d, J=8.8 Hz), 8.31-8.37 (1H, m), 8.59 (1H, d, J=2.7 Hz), 8.70-8.76 (1H, m)

ESI-MS (m/e): 527 [M+H]

Example 256

5-(Pyridin-2-yloxy)-2-pyridin-2-yl-6-(4-methanesulfonyl-phenoxy)-1H-benzimidazole The entitled compound was obtained as a brown solid in the same method as in Example 14 or in accordance with the method or by combining it with an ordinary method but using 5-fluoro-4-(4-methanesulfonyl-phenoxy)-2-nitro-phenylamine obtained in Example 14 and 2-hydroxypyridine.

¹HNMR (CD₃OD) δ: 3.09 (3H, s), 6.81 (1H, d, J=8.2 Hz), 7.02 (2H, d, J=8.6 Hz), 7.02-7.07 (1H, m), 7.49-7.54 (1H, m), 7.55 (1H, s), 7.63 (1H, s), 7.71-7.77 (1H, m), 7.83 (2H, d,

J=8.6 Hz), 7.98-8.03 (2H, m), 8.31 (1H, d, J=7.6 Hz), 8.76 (1H, d, J=4.3 Hz)

ESI-MS (m/e): 459 [M+H]

Example 257

5-(2-Difluoromethoxy-pyridin-3-yloxy)-6-(4-methanesulfonyl-phenoxy)-2-pyridin-2-yl-1H-benzimidazole The entitled compound was obtained as a pale yellow solid in the same method as in Example 14 or in accordance with the method or by combining it with an ordinary method but using 5-fluoro-4-(4-methanesulfonyl-phenoxy)-2-nitro-phenylamine obtained in Example 14 and 2-difluoromethoxy-pyridin-3-ol.

$^1$HNMR (CD$_3$OD) δ: 3.10 (3H, s), 7.05 (2H, d, J=8.4 Hz), 7.13-7.20 (1H, m), 7.33-7.70 (4H, m), 7.48 (1H, t, J=72.8 Hz), 7.87 (2H, d, J=8.4 Hz), 7.92 (1H, d, J=4.5 Hz), 8.01 (1H, t, J=7.4 Hz), 8.32 (1H, d, J=7.8 Hz), 8.77 (1H, brs)

ESI-MS (m/e): 525 [M+H]

Example 258

5-(1-Methyl-2-oxo-1,2-dihydro-pyridin-3-yloxy)-6-(4-methanesulfonyl-phenoxy)-2-pyridin-2-yl-1H-benzimidazole The entitled compound was obtained as a brown solid in the same method as in Example 14 or in accordance with the method or by combining it with an ordinary method but using 5-fluoro-4-(4-methanesulfonyl-phenoxy)-2-nitro-phenylamine obtained in Example 14 and 1-methyl-2-oxo-1,2-dihydro-pyridin-3-ol.

$^1$HNMR (CDCl$_3$) δ: 3.04 (3H, s), 3.56 (3H, s), 6.06 (1H, td, J=7.0, 2.7 Hz), 6.84 (½H, d, J=7.4 Hz), 6.88 (½H, dd, J=7.4, 1.8 Hz), 7.05-7.15 (3H, m), 7.20 (½H, s), 7.28 (½H, d, J=1.2 Hz), 7.38 (1H, dd, J=6.6, 4.7 Hz), 7.46 (½H, s), 7.60 (½H, s), 7.80-7.90 (3H, m), 8.36 (1H, t, J=7.2 Hz), 8.62 (1H, d, J=4.4 Hz)

ESI-MS (m/e): 489 [M+H]

Example 259

5-(2-Difluoromethoxy-pyridin-3-yloxy)-6-(4-ethanesulfonyl-phenoxy)-2-pyridin-2-yl-1H-benzimidazole (Step 1) Production of 5-fluoro-4-(4-ethanesulfonyl-phenoxy)-2-nitro-phenylamine The entitled compound was obtained in the same method as in Example 14 or in accordance with the method or by combining it with an ordinary method but using 6-ethanesulfonyl-pyridin-3-ol.

(Step 2) Production of 5-(2-difluoromethoxy-pyridin-3-yloxy)-6-(4-ethanesulfonyl-phenoxy)-2-pyridin-2-yl-1H-benzimidazole The entitled compound was obtained as a pale yellow solid in the same method as in Example 14 or in accordance with the method or by combining it with an ordinary method but using 5-fluoro-4-(4-ethanesulfonyl-phenoxy)-2-nitro-phenylamine and 2-difluoromethoxy-pyridin-3-ol.

$^1$HNMR (CD$_3$OD) δ: 1.20 (3H, t, J=7.4 Hz), 3.15 (2H, q, J=7.4 Hz), 7.04 (2H, d, J=8.4 Hz), 7.06-7.15 (1H, m), 7.30-7.70 (4H, m), 7.46 (1H, t, J=72.9 Hz), 7.80 (2H, d, J=8.4 Hz), 7.89 (1H, d, J=4.3 Hz), 7.99 (1H, t, J=7.7 Hz), 8.30 (1H, d, J=8.0 Hz), 8.74 (1H, brs)

ESI-MS (m/e): 539 [M+H]

Example 260

5-(2-Difluoromethoxy-pyridin-3-yloxy)-6-(4-ethanesulfonyl-henoxy)-2-pyrazin-2-yl-1H-benzimidazole The entitled compound was obtained as a pale yellow solid in the same method as in Example 197 or in accordance with the method or by combining it with an ordinary method but using 4-(2-difluoromethoxy-pyridin-3-yloxy)-5-(4-ethanesulfonyl-phenoxy)-benzene-1,2-diamine obtained in Example 259 (step 2).

$^1$HNMR (CDCl$_3$) δ: 1.27 and 1.28 (total 3H, each t, J=7.4 Hz), 3.09 and 3.10 (total 2H, each q, J=7.4 Hz), 6.98 and 6.99 (total 2H, each d, J=9.0 Hz), 7.04-7.10 (1H, m), 7.23 and 7.42 (total 1H, each s), 7.25-7.30 (1H, m), 7.36 and 7.37 (total 1H, each t, J=73.0 Hz), 7.52 and 7.73 (total 1H, each s), 7.80 and 7.81 (total 2H, each d, J=9.0 Hz), 7.90-7.96 (1H, m), 8.58-8.63 (1H, m), 8.68 and 8.69 (total 1H, each d, J=2.4 Hz), 9.61 and 9.63 (total 1H, each d, J=1.5 Hz)

ESI-MS (m/e): 540 [M+H]

Example 261

5-(2,4-Difluoro-phenoxy)-6-(4-ethanesulfonyl-phenoxy)-2-pyrazin-2-yl-1H-benzimidazole The entitled compound was obtained as a white solid in the same method as in Example 259 or in accordance with the method or by combining it with an ordinary method but using 4-fluoro-5-(4-ethanesulfonyl-phenoxy)-2-nitro-phenylamine obtained in Example 259 (step 1) and 2,4-difluorophenol.

$^1$HNMR (CD$_3$OD) δ: 1.21 (3H, t, J=7.4 Hz), 3.19 (2H, q, J=7.4 Hz), 6.89-6.95 (1H, m), 7.01-7.12 (2H, m), 7.11 (2H, d, J=8.4 Hz), 7.23-7.67 (3H, m), 7.84 (2H, d, J=8.4 Hz), 7.99 (1H, t, J=7.4 Hz), 8.29 (1H, d, J=8.2 Hz), 8.75 (1H, brs)

ESI-MS (m/e): 508 [M+H]

Example 262

4-(1-Methyl-1H-imidazol-2-ylsulfanyl)-6-(4-dimethylcarbamoyl-phenoxy)-2-pyridin-2-yl-1H benzimidazole The entitled compound was obtained as a pale brown solid in the same method as in Example 67 or in accordance with the method or by combining it with an ordinary method but using 1-methyl-1H-imidazol-2-thiol and 4-hydroxy-N,N-dimethylbenzamide in order.

$^1$HNMR (CDCl$_3$) δ: 3.09 (6H, s), 3.87 (3H, s), 6.69 (1H, s), 6.74 (1H, s), 6.79-6.89 (2H, m), 7.07 (2H, d, J=8.4 Hz), 7.16 (1H, d, J=2.0 Hz), 7.42 (2H, d, J=8.4 Hz), 7.53 (1H, t, J=7.6 Hz), 7.64 (1H, d, J=2.0 Hz), 8.17 (1H, d, J=7.4 Hz)

ESI-MS (m/e): 471 [M+H]

Example 263

4-(Pyridin-2-ylsulfanyl)-6-(4-dimethylcarbamoyl-phenoxy)-2-pyridin-2-yl-1H-benzimidazole The entitled compound was obtained as a pale brown solid in the same method as in Example 67 or in accordance with the method or by combining it with an ordinary method but using pyridine-2-thiol and 4-hydroxy-N,N-dimethylbenzamide in order.

$^1$HNMR (CDCl$_3$) δ: 3.05 (3H, s), 3.09 (3H, s), 6.90-7.08 (4H, m), 7.30-7.65 (6H, m), 7.85 (1H, t, J=7.5 Hz), 8.37 (1H, d, J=7.8 Hz), 8.45 (1H, d, J=3.9 Hz), 8.62 (1H, d, J=4.7 Hz)

ESI-MS (m/e): 468 [M+H]

Example 264

4-(2,6-Difluoro-phenoxy)-6-(4-methanesulfonyl-phenoxy)-2-pyridin-2-yl-1H-benzimidazole The entitled compound was obtained in the same method as in Example 67 or in accordance with the method or by combining it with an ordinary method but using 2,6-difluoro-phenol and 4-methanesulfonyl-phenol in order.

$^1$HNMR (CD$_3$OD) δ: 3.22 (3H, s), 6.25 (1H, s), 7.16-7.24 (3H, m), 7.49-7.54 (1H, m), 7.60-7.66 (1H, m), 7.70-7.78 (1H, m), 7.95 (2H, d, J=8.4 Hz), 8.02 (1H, m), 8.40 (1H, d, J=4.7 Hz), 8.70 (1H, d, J=2.3 Hz), 8.78 (1H, d, J=2.3 Hz)

ESI-MS (m/e): 494 [M+H]

Example 265

4-(1-Methyl-2-oxo-1,2-dihydro-pyridin-3-yloxy)-6-(4-methanesulfonyl-phenoxy)-2-pyridin-2-yl-1H-benzimidazole The entitled compound was obtained as a pale yellow solid in the same method as in Example 67 or in accordance with the method or by combining it with an ordinary method but using 3-hydroxy-1-methyl-1H-pyridin-2-one and 4-methanesulfonyl-phenol in order.

$^1$HNMR (CD$_3$OD) δ: 3.10 (3H, s), 3.63 (3H, s), 6.35 (1H, t, J=7.1 Hz), 6.39 (1H, s), 7.06 (1H, s), 7.16 (2H, d, J=8.0 Hz), 7.34 (1H, d, J=7.2 Hz), 7.42-7.52 (1H, m), 7.53 (1H, dd, J=6.8, 1.6 Hz), 7.90 (2H, d, J=8.0 Hz), 7.91-8.00 (1H, m), 8.28-8.38 (1H, m), 8.71 (1H, s)

ESI-MS (m/e): 489 [M+H]

Example 266

4-(2,6-Difluoro-phenoxy)-6-(6-methanesulfonyl-pyridin-3-yloxy)-2-pyrazin-2-yl-1H-benzimidazole The entitled compound was obtained in the same method as in Example 68 or in accordance with the method or by combining it with an ordinary method but using 2,6-difluoro-phenol and 6-methanesulfonyl-pyridin-3-ol obtained in Reference Example 3, in order.

$^1$HNMR (CD$_3$OD) δ: 3.22 (3H, s), 6.39 (1H, s), 7.16-7.24 (2H, m), 7.21 (1H, d, J=8.6 Hz), 7.32-7.40 (1H, m), 7.54-7.58 (1H, m), 8.06 (1H, d, J=8.6 Hz), 8.47 (1H, d, J=2.3 Hz), 8.72 (1H, d, J=2.3 Hz), 8.79 (1H, s), 9.56 (1H, s)

ESI-MS (m/e): 496 [M+H]

Example 267

4-(2,6-Difluoro-phenoxy)-6-(6-methanesulfonyl-pyridin-3-yloxy-2-pyrazin-2-yl-1H-benzimidazole The entitled compound was obtained in the same method as in Example 196 (step 6) or in accordance with the method or by combining it with an ordinary method but using 3-(2,6-difluoro-phenoxy)-5-(6-methanesulfonyl-pyridin-3-yloxy)-benzene-1,2-diamine obtained in Example 266.

$^1$HNMR (CD$_3$OD) δ: 3.32 (3H, s), 6.47 (1H, s), 7.19-7.26 (3H, m), 7.34-7.42 (1H, m), 7.56-7.63 (2H, m), 8.05-8.11 (2H, m), 8.41 (1H, d, J=8.6 Hz), 8.48 (1H, d, J=2.3 Hz), 8.83 (1H, d, J=4.7 Hz)

ESI-MS (m/e): 495 [M+H]

Example 268

4-(2,6-Difluoro-phenoxy)-6-(6-ethanesulfonyl-pyridin-3-yloxy-2-pyrazin-2-yl-1H-benzimidazole The entitled compound was obtained in the same method as in Example 68 or in accordance with the method or by combining it with an ordinary method but using 2,6-difluoro-phenol and 6-ethanesulfonyl-pyridin-3-ol obtained in Reference Example 4, in order.

$^1$HNMR (CD$_3$OD) δ: 1.25 (3H, t, J=7.4 Hz), 3.40 (2H, q, J=7.4 Hz), 6.38 (1H, s), 7.10-7.25 (3H, m), 7.32-7.40 (1H, m), 7.56 (1H, dd, J=8.6, 2.3 Hz), 8.06 (1H, d, J=9.0 Hz), 8.48 (1H, d, J=2.7 Hz), 8.72 (1H, d, J=2.7 Hz), 8.79 (1H, s), 9.56 (1H, s)

ESI-MS (m/e): 510 [M+H]

Example 269

4-(2,6-Difluoro-phenoxy)-6-(6-ethanesulfonyl-pyridin-3-yloxy)-2-pyridin-2-yl-1H-benzimidazole The entitled compound was obtained in the same method as in Example 196 (step 6) or in accordance with the method or by combining it with an ordinary method but using 3-(2,6-difluoro-phenoxy)-5-(6-ethanesulfonyl-pyridin-3-yloxy)-benzene-1,2-diamine obtained in Example 268.

$^1$HNMR (CD$_3$OD) δ: 1.24 (3H, t, J=7.4 Hz), 3.40 (2H, q, J=7.4 Hz), 6.44 (1H, s), 7.18-7.25 (3H, m), 7.32-7.41 (1H, m), 7.55-7.62 (2H, m), 8.03-8.09 (2H, m), 8.41 (1H, d, J=7.8 Hz), 8.49 (1H, d, J=2.3 Hz), 8.81 (1H, d, J=4.7 Hz)

ESI-MS (m/e): 509 [M+H]

Example 270

4-(2-Fluoro-pyridin-3-yloxy)-6-(6-methanesulfonyl-pyridin-3-yloxy)-2-pyrazin-2-yl-1H-benzimidazole The entitled compound was obtained in the same method as in Example 68 or in accordance with the method or by combining it with an ordinary method but using 2-fluoro-pyridin-3-ol and 6-methanesulfonyl-pyridin-3-ol in order.

$^1$HNMR (DMSO-d6) δ: 3.23 (3H, s), 6.09 (1H, d, J=2.3 Hz), 6.35 (1H, d, J=2.3 Hz), 7.28 (1H, dd, J=7.8, 5.5 Hz), 7.59-7.61 (1H, m), 7.66-7.67 (1H, m), 7.84-7.85 (1H, m), 8.06 (1H, d, J=8.6 Hz), 8.70-8.74 (1H, m), 8.87 (1H, d, J=2.3 Hz), 9.15 (1H, d, J=1.6 Hz), 9.86 (1H, s)

ESI-MS (m/e): 479 [M+H]

Examples 271, 272

4-(2-Fluoro-pyridin-3 yloxy)-6-(6-methanesulfonyl-pyridin-3-yloxy)-2-pyridin-2-yl-1H-benzimidazole and 4-(2-oxo-1,2-dihydro-pyridin-3-yloxy-6-(6-methanesulfonyl-pyridin-3-yloxy)-2-pyridin-2-yl-1H-benzimidazole The entitled compounds were obtained in the same method as in Examples 108-1 and 108-2 or in accordance with the method or by combining it with an ordinary method but using 2-fluoro-pyridin-3-ol and 6-methanesulfonyl-pyridin-3-ol in order.

4-(2-Fluoro-pyridin-3-yloxy-6-(6-methanesulfonyl-pyridin-3-yloxy)-2-pyridin-2-yl-1H-benzimidazole $^1$HNMR (CD$_3$OD) δ: 3.23 (3H, s), 6.19 (1H, d, J=2.3 Hz), 6.55 (1H, d, J=2.3 Hz), 7.23 (1H, dd, J=4.2, 2.1 Hz), 7.61-7.64 (2H, m), 7.67 (1H, dd, J=8.6, 2.7 Hz), 7.84-7.85 (1H, m), 8.02 (1H, td, J=7.8, 1.6 Hz), 8.09 (1H, d, J=8.6 Hz), 8.16 (1H, d, J=7.8 Hz), 8.51 (1H, d, J=2.3 Hz), 8.68 (1H, d, J=4.7 Hz)
ESI-MS (m/e): 478 [M+H]

6-(6-Methanesulfonyl-pyridin-3-yloxy)-4-(2-oxo-1,2-dihydro-pyridin-3-yloxy)-2-pyridin-2-yl-1H-benzimidazole $^1$HNMR (DMSO-d6) δ: 3.25 (3H, s), 6.61-6.62 (2H, m), 6.97-7.00 (2H, m), 7.63-7.67 (2H, m), 8.02-8.11 (4H, m), 8.56 (1H, d, J=2.3 Hz), 8.74 (1H, d, J=4.7 Hz), 10.33 (1H, s)
ESI-MS (m/e): 476 [M+H]

Example 273

4-(2-Fluoro-pyridin-3-yloxy)-6-(4-methanesulfonyl-phenoxy)-2-pyridin-2-yl-1H-benzimidazole The entitled compound was obtained in the same method as in Example 67 or in accordance with the method or by combining it with an ordinary method but using 2-fluoro-pyridin-3-ol and 4-methanesulfonyl-phenol in order.
$^1$HNMR (CD$_3$OD) δ: 3.13 (3H, s), 6.67 (1H, d, J=2.0 Hz), 7.21-7.25 (2H, m), 7.35-7.39 (2H, m), 7.60-7.63 (1H, m), 7.77-7.82 (1H, m), 7.95-7.97 (2H, m), 8.00-8.09 (2H, m), 8.36 (1H, d, J=8.2 Hz), 8.83 (1H, d, J=4.7 Hz)
ESI-MS (m/e): 477 [M+H]

Example 274

4-(1-Methyl-2-oxo-1,2-dihydro-pyridin-3-yloxy)-6-(4-ethanesulfonyl-phenoxy)-2-pyridin-2-yl-1H-benzimidazole (Step 1) Production of 5-(4-ethanesulfonyl-phenoxy)-3-(1-methyl-2-oxo-1,2-dihydro-pyridin-3-yloxy)-benzene-1,2-diamine The entitled compound was obtained as a brown oily substance in the same method as in Example 67 (step 1) to (step 4) or in accordance with the method or by combining it with an ordinary method but using 3-hydroxy-1-methyl-1H-pyridin-2-one and 4-ethanesulfonyl-phenol in order.

(Step 2) Production of 4-(1-methyl-2-oxo-1,2-dihydro-pyridin-3-yloxy)-6-(4-ethanesulfonyl-phenoxy)-2-pyridin-2-yl-1H-benzimidazole The entitled compound was obtained as a white solid in the same method as in Example 204 (step 2) or in accordance with the method or by combining it with an ordinary method but using 5-(4-ethanesulfonyl-phenoxy)-3-(1-methyl-2-oxo-1,2-dihydro-pyridin-3-yloxy)-benzene-1,2-diamine obtained in (step 1).
$^1$HNMR (CD$_3$OD) δ: 1.24 (3H, t, J=7.4 Hz), 3.21 (2H, q, J=7.4 Hz), 3.65 (3H, s), 6.37 (1H, t, J=7.2 Hz), 6.42 (1H, s), 7.09 (1H, s), 7.20 (2H, d, J=8.8 Hz), 7.37 (1H, d, J=6.6 Hz), 7.46-7.54 (1H, m), 7.55 (1H, d, J=6.0 Hz), 7.88 (2H, d, J=8.8 Hz), 7.94-8.02 (1H, m), 8.36 (1H, d, J=7.6 Hz), 8.73 (1H, s)
ESI-MS (m/e): 503 [M+H]

Example 275

4-(1-Methyl-2-oxo-1,2-dihydro-pyridin-3-yloxy)-6-(4-(propane-2-sulfonyl)-phenoxy)-2-pyridin-2-1H-benzimidazole The entitled compound was obtained as a white solid in the same method as in Example 274 or in accordance with the method or by combining it with an ordinary method but using 3-hydroxy-1-methyl-1H-pyridin-2-one and 4-(propane-2-sulfonyl)-phenol.
$^1$HNMR (CD$_3$OD) δ: 1.27 (6H, d, J=6.8 Hz), 3.27-3.38 (1H, m), 3.65 (3H, s), 6.37 (1H, t, J=7.4 Hz), 6.42 (1H, s), 7.10 (1H, s), 7.20 (2H, d, J=8.8 Hz), 7.35-7.45 (1H, m), 7.47-7.54 (1H, m), 7.55 (1H, d, J=6.8 Hz), 7.85 (2H, d, J=8.8 Hz), 7.27-8.03 (1H, m), 8.30-8.40 (1H, m), 8.74 (1H, s)
ESI-MS (m/e): 517 [M+H]

Example 276

4-(2,6-Difluoro-phenoxy)-6-(6-ethanesulfonyl-pyridin-3-yloxy)-2-(1H-pyrazol-3-yl)-1H-benzimidazole The entitled compound was obtained in the same method as in Example 202 or in accordance with the method or by combining it with an ordinary method but using 3-(2,6-difluoro-phenoxy)-5-(6-ethanesulfonyl-pyridin-3-yloxy)-benzene-1,2-diamine obtained in Example 268 and 1H-pyrazole-3-carboxaldehyde.
$^1$HNMR (CD$_3$OD) δ: 1.24 (3H, t, J=7.4 Hz), 3.37 (2H, q, J=7.4 Hz), 6.28-6.32 (1H, m), 7.09 (1H, s), 7.19 (2H, t, J=8.2 Hz), 7.34 (1H, s), 7.52 (1H, t, J=4.5 Hz), 7.83 (1H, s), 8.04 (1H, d, J=8.6 Hz), 8.46 (1H, d, J=2.7 Hz)
ESI-MS (m/e): 498 [M+H]

Example 277

4-(1-Methyl-2-oxo-1,2-dihydro-pyridin-3-yloxy)-6-(4-(N,N-dimethylaminosulfonyl)-phenoxy)-2-pyridin-2-yl-1H-benzimidazole The entitled compound was obtained as a pale yellow solid in the same method as in Example 274 or in accordance with the method or by combining it with an ordinary method but using 3-hydroxy-1-methyl-1H-pyridin-2-one and 4-(N,N-dimethylaminosulfonyl)-phenol in order.
$^1$HNMR (DMSO-d6) δ: 2.58 (6H, s), 3.48 (3H, s), 6.21 (1H, t, J=7.1 Hz), 6.31 (1H, s), 6.91 (1H, s), 7.16 (2H, d, J=8.8 Hz), 7.30 (1H, d, J=6.4 Hz), 7.52 (1H, dd, J=7.5, 5.7 Hz), 7.60 (1H, d, J=5.1 Hz), 7.71 (2H, d, J=8.8 Hz), 7.99 (1H, td, J=7.8, 1.6 Hz), 8.27 (1H, d, J=7.8 Hz), 8.73 (1H, d, J=4.6 Hz)
ESI-MS (m/e): 518 [M+H]

Example 278

4-(2-Chloro-phenoxy)-6-(6-ethanesulfonyl-pyridin-3-yloxy)-2-pyrazin-2-yl-1H-benzimidazole (Step 1) Production of 3-(2-chloro-phenoxy)-5-(6-ethanesulfonyl-pyridin-3-yloxy)-benzene-1,2-diamine The entitled compound was obtained as a brown oily substance in the same method as in Example 67 (step 1) to (step 4) or in accordance with the method or by combining it with an ordinary method but using 2-chloro-phenol and 6-ethanesulfonyl-pyridin-3-ol in order.

(Step 2) Production of 4-(2-chloro-phenoxy)-6-(6-ethanesulfonyl-pyridin-3-yloxy)-2-pyrazin-2-yl-1H-benzimidazole The entitled compound was obtained as a white solid in the same method as in Example 205 or in accordance with the method or by combining it with an ordinary method but using 3-(2-chloro-phenoxy)-5-(6-ethanesulfonyl-pyridin-3-yloxy)-benzene-1,2-diamine obtained in (step 1).
$^1$HNMR (CD$_3$OD) δ: 1.24 (3H, t, J=6.9 Hz), 3.39 (2H, q, J=6.9 Hz), 6.28 (1H, d, J=2.0 Hz), 7.10-7.20 (1H, m), 7.28-7.31 (2H, m), 7.39-7.43 (1H, m), 7.57 (2H, td, J=8.3, 4.2 Hz), 8.05 (1H, d, J=8.6 Hz), 8.48 (1H, d, J=2.7 Hz), 8.72 (1H, d, J=2.3 Hz), 8.79-8.80 (1H, m), 9.58 (1H, s)
ESI-MS (m/e): 508 [M+H]

Example 279

4-(2-Fluoro-phenoxy-6-(6-ethanesulfonyl-pyridin-3-yloxy)-2-pyrazin-2-yl-1H-benzimidazole The entitled compound was obtained in the same method as in Example 278 or in accordance with the method or by combining it with an ordinary method but using 2-fluoro-phenol and 6-ethanesulfonyl-pyridin-3-ol in order.
$^1$HNMR (CD$_3$OD) δ: 1.24 (3H, t, J=7.4 Hz), 3.39 (2H, q, J=7.4 Hz), 6.40 (1H, s), 7.10-7.20 (1H, m), 7.28-7.34 (4H, m), 7.57 (1H, dd, J=8.6, 2.7 Hz), 8.06 (1H, d, J=8.6 Hz), 8.48 (1H, d, J=2.7 Hz), 8.72 (1H, d, J=2.3 Hz), 8.79-8.80 (1H, m), 9.56 (1H, s)
ESI-MS (m/e): 492 [M+H]

Example 280

4-(2-Trifluoromethyl-phenoxy)-6-(6-ethanesulfonyl-pyridin-3-yloxy)-2-pyrazin-2-yl-1H-benzimidazole The entitled compound was obtained in the same method as in Example 278 or in accordance with the method or by combining it with an ordinary method but using 2-trifluoromethyl-phenol and 6-ethanesulfonyl-pyridin-3-ol in order.
$^1$HNMR (CD$_3$OD) δ: 1.25 (3H, t, J=7.4 Hz), 3.40 (2H, q, J=7.4 Hz), 6.50 (1H, d, J=2.0 Hz), 7.24 (2H, d, J=7.8 Hz), 7.38 (1H, t, J=7.8 Hz), 7.59 (1H, dd, J=8.6, 2.7 Hz), 7.64 (1H, t, J=7.6 Hz), 7.81 (1H, d, J=7.8 Hz), 8.06 (1H, d, J=8.6 Hz), 8.50 (1H, d, J=2.7 Hz), 8.71 (1H, d, J=2.3 Hz), 8.78-8.79 (1H, m), 9.54-9.55 (1H, m)
ESI-MS (m/e): 542 [M+H]

Example 281

4-(1-Methyl-2-oxo-1,2-dihydro pyridin-3-yloxy)-6-(4-cyclopropanesulfonyl-phenoxy)-2-pyridin-2-1H-benzimidazole The entitled compound was obtained as a pale yellow solid in the same method as in Example 274 or in accordance with the method or by combining it with an ordinary method but using 3-hydroxy-1-methyl-1H-pyridin-2-one and 4-cyclopropanesulfonyl-phenol in order.
$^1$HNMR (DMSO-d6) δ: 1.01-1.15 (4H, m), 2.81-2.90 (1H, m), 3.51 (3H, s), 6.24 (1H, t, J=7.0 Hz), 6.35 (1H, d, J=2.0 Hz), 6.95 (1H, d, J=2.0 Hz), 7.18 (2H, d, J=9.0 Hz), 7.33 (1H, dd, J=7.5, 1.8 Hz), 7.53-7.57 (1H, m), 7.63 (1H, dd, J=6.8, 1.8 Hz), 7.87 (2H, d, J=9.0 Hz), 8.02 (1H, td, J=7.8, 1.8 Hz), 8.31 (1H, d, J=8.0 Hz), 8.75 (1H, d, J=4.1 Hz)
ESI-MS (m/e): 515 [M+H]

Example 282

4-(2,6-Difluoro-phenoxy)-6-(6-ethanesulfonyl-pyridin-3-yloxy)-2-(1-methyl-pyrazol-3-yl)-1H-benzimidazole The entitled compound was obtained in the same method as in Example 203 or in accordance with the method or by combining it with an ordinary method but using 3-(2,6-difluoro-phenoxy)-5-(6-ethanesulfonyl-pyridin-3-yloxy)-benzene-1,2-diamine obtained in Example 268 and 1H-1-methyl-pyrazole-3-carboxylic acid.
$^1$HNMR (CD$_3$OD) δ: 1.24 (3H, t, J=7.4 Hz), 3.41 (2H, q, J=7.4 Hz), 4.12 (3H, s), 6.61 (1H, s), 7.19 (1H, d, J=2.3 Hz), 7.22 (1H, s), 7.25 (2H, dd, J=5.6, 2.3 Hz), 7.37-7.43 (1H, m), 7.62 (1H, dd, J=8.6, 2.7 Hz), 7.93 (1H, d, J=2.3 Hz), 8.08-8.09 (1H, m), 8.51 (1H, d, J=2.3 Hz)
ESI-MS (m/e): 512 [M+H]

Example 283

4-(3-Trifluoromethyl-phenoxy)-6-(6-ethanesulfonyl-pyridin-3-yloxy)-2-pyrazin-2-yl-1H-benzimidazole The entitled compound was obtained in the same method as in Example 278 or in accordance with the method or by combining it with an ordinary method but using 3-trifluoromethyl-phenol and 6-ethanesulfonyl-pyridin-3-ol in order.
$^1$HNMR (CD$_3$OD) δ: 1.25 (3H, t, J=7.4 Hz), 3.39 (2H, q, J=7.4 Hz), 6.39 (1H, s), 7.25-7.37 (5H, m), 7.57 (1H, dd, J=4.3, 2.2 Hz), 8.06 (1H, d, J=8.6 Hz), 8.48 (1H, d, J=2.7 Hz), 8.72 (1H, d, J=2.7 Hz), 8.79 (1H, s), 9.56 (1H, s)
ESI-MS (m/e): 542 [M+H]

Example 284

4-(4-Trifluoromethyl-phenoxy)-6-(6-ethanesulfonyl-pyridin-3-yloxy-2-pyrazin-2-yl-1H-benzimidazole The entitled compound was obtained in the same method as in Example 278 or in accordance with the method or by combining it with an ordinary method but using 4-trifluoromethyl-phenol and 6-ethanesulfonyl-pyridin-3-ol in order.
$^1$HNMR (CD$_3$OD) δ: 1.26 (3H, t, J=7.4 Hz), 3.40 (2H, q, J=7.4 Hz), 6.80 (1H, s), 7.32 (2H, d, J=8.6 Hz), 7.66-7.64 (1H, m), 7.72 (2H, d, J=8.6 Hz), 8.08 (1H, d, J=9.0 Hz), 8.54-8.56 (1H, m), 8.70-8.73 (1H, m), 8.78 (1H, s), 9.50 (1H, s)
ESI-MS (m/e): 542 [M+H]

Example 285

4-(2,3-Difluoro-phenoxy)-6-(6-ethanesulfonyl-pyridin-3-yloxy)-2-pyrazin-2-yl-1H-benzimidazole The entitled compound was obtained in the same method as in Example 278 or in accordance with the method or by combining it with an ordinary method but using 2,3-difluoro-phenol and 6-ethanesulfonyl-pyridin-3-ol in order.
$^1$HNMR (CD$_3$OD) δ: 1.24 (3H, t, J=7.3 Hz), 3.40 (2H, q, J=7.3 Hz), 6.59 (1H, d, J=1.6 Hz), 7.12-7.18 (4H, m), 7.60 (1H, dd, J=9.0, 2.7 Hz), 8.07 (1H, dd, J=8.6, 0.8 Hz), 8.51

(1H, d, J=2.3 Hz), 8.71 (1H, d, J=2.3 Hz), 8.79 (1H, dd, J=2.7, 1.4 Hz), 9.53 (1H, d, J=1.6 Hz)
ESI-MS (m/e): 510 [M+H]

Example 286

4-(2-Cyano-phenoxy)-6-(6-methanesulfonyl din-3-yloxy)-2-pyridin-2-yl-1H-benzimidazole The entitled compound was obtained in the same method as in Example 274 or in accordance with the method or by combining it with an ordinary method but using 2-cyano-phenol and 6-methanesulfonyl-pyridin-3-ol in order.
$^1$HNMR (CD$_3$OD) δ: 3.23 (3H, s), 6.86 (1H, d, J=2.0 Hz), 7.21 (1H, d, J=8.2 Hz), 7.33-7.37 (2H, m), 7.62-7.67 (3H, m), 7.84 (1H, d, J=7.8 Hz), 8.04-8.11 (2H, m), 8.36 (1H, d, J=7.8 Hz), 8.54 (1H, d, J=2.7 Hz), 8.82 (1H, d, J=4.7 Hz)
ESI-MS (m/e): 484 [M+H]

Example 287

4-(2,4-Difluoro-phenoxy)-6-(6-ethanesulfonyl-pyridin-3-yloxy)-2-pyridin-2-yl-1H-benzimidazole The entitled compound was obtained in the same method as in Example 274 or in accordance with the method or by combining it with an ordinary method but using 2,4-difluoro-phenol and 6-ethanesulfonyl-pyridin-3-ol in order.
$^1$HNMR (CD$_3$OD) δ: 1.11 (3H, t, J=7.4 Hz), 3.39 (2H, q, J=7.4 Hz), 6.51 (1H, d, J=2.0 Hz), 7.05-7.10 (2H, m), 7.37-7.39 (1H, m), 7.46-7.59 (3H, m), 7.98-8.02 (2H, m), 8.26 (1H, d, J=7.8 Hz), 8.56 (1H, d, J=2.7 Hz), 8.73 (1H, d, J=4.3 Hz)
ESI-MS (m/e): 509 [M+H]

Example 288

4-(Pyridin-2-ylsulfanyl)-6-(6-methanesulfonyl-pyridin-3-yloxy)-2-pyridin-2-yl-1H-benzimidazole The entitled compound was obtained as a yellow solid in the same method as in Example 274 or in accordance with the method or by combining it with an ordinary method but using pyridine-2-thiol and 6-methanesulfonyl-pyridin-3-ol in order.
$^1$HNMR (CDCl$_3$) δ: 3.22 (3H, s), 7.03 (1H, d, J=8.0 Hz), 7.06-7.10 (1H, m), 7.34 (1H, d, J=2.1 Hz), 7.37-7.41 (1H, m), 7.43 (1H, dd, J=8.8, 2.8 Hz), 7.52 (1H, td, J=7.8, 2.2 Hz), 7.64 (1H, d, J=2.1 Hz), 7.88 (1H, td, J=7.8, 1.8 Hz), 8.03 (1H, d, J=8.8 Hz), 8.39 (1H, d, J=7.8 Hz), 8.45 (1H, dd, J=4.9, 1.0 Hz), 8.51 (1H, d, J=2.3 Hz), 8.64 (1H, d, J=4.1 Hz)
ESI-MS (m/e): 476 [M+H]

Example 289

4-(2,6-Difluoro-phenoxy)-6-(6-ethanesulfonyl-pyridin-3-yloxy)-5-fluoro-2-pyrazin-2-yl-1H-benzimidazole The entitled compound was obtained as a pale yellow solid in the same method as in Example 119 or in accordance with the method or by combining it with an ordinary method but using 2,6-difluoro-phenol, 6-ethanesulfonyl-pyridin-3-ol and pyrazine-2-carboxylic acid in order.
$^1$HNMR (CDCl$_3$) δ: 1.30 and 1.32 (total 3H, each t, J=7.4 Hz), 3.38 and 3.40 (total 2H, each q, J=7.4 Hz), 6.96-7.03 (2H, m), 7.10-7.20 (1H, m), 7.14 and 7.52 (total 1H, each d, J=6.0 Hz), 7.34 and 7.38 (total 1H, each dd, J=8.6, 2.8 Hz), 8.03 and 8.06 (total 1H, each d, J=8.6 Hz), 8.48 and 8.52 (total 1H, each d, J=2.8 Hz), 8.55-8.72 (2H, m), 9.38 and 9.62 (total 1H, each d, J=1.5 Hz)
ESI-MS (m/e): 528 [M+H]

Example 290

4-(2,6-Difluoro-phenoxy)-6-(6-ethanesulfonyl-pyridin-3-yloxy)-5-fluoro-2-pyridin-2-yl-1H-benzimidazole The entitled compound was obtained as a brown solid in the same method as in Example 196 (step 6) or in accordance with the method or by combining it with an ordinary method but using 3-(2,6-difluoro-phenoxy)-4-fluoro-5-(6-ethanesulfonyl-pyridin-3-yloxy)-benzene-1,2-diamine obtained in Example 289.
$^1$HNMR (CDCl$_3$) δ: 1.30 (3H, t, J=7.4 Hz), 3.38 (2H, q, J=7.4 Hz), 6.94-7.01 (2H, m), 7.04-7.50 (4H, m), 7.79-7.95 (1H, m), 7.99-8.07 (1H, m), 8.23 and 8.37 (total 1H, each d, J=7.0 Hz), 8.48 (1H, s), 8.60-8.68 (1H, m)
ESI-MS (m/e): 527 [M+H]

Example 291

4-(2,6-Difluoro-henoxy)-6-(6-ethanesulfonyl-pyridin-3-yloxy)-5-fluoro-2-(1H-pyrazol-3-yl)-1H-benzimidazole The entitled compound was obtained as a pale yellow solid in the same method as in Example 203 or in accordance with the method or by combining it with an ordinary method but using 3-(2,6-difluoro-phenoxy)-4-fluoro-5-(6-ethanesulfonyl-pyridin-3-yloxy)-benzene-1,2-diamine obtained in Example 289 and 1H-1-methyl-pyrazole-3-carboxylic acid.
$^1$HNMR (CD$_3$OD) δ: 1.23 (3H, t, J=7.4 Hz), 3.38 (2H, q, J=7.4 Hz), 4.02 (3H, s), 6.94 (1H, s), 7.01-7.12 (2H, m), 7.14-7.23 (1H, m), 7.29 (1H, d, J=5.4 Hz), 7.51 (1H, d, J=8.0 Hz), 7.70 (1H, s), 8.06 (1H, d, J=8.6 Hz), 8.50 (1H, s)
ESI-MS (m/e): 530 [M+H]

Example 292

4-(2,6-Difluoro-phenoxy)-6-(6-methanesulfonyl-pyridin-3-yloxy)-5-fluoro-2-pyridin-2-1H-benzimidazole The entitled compound was obtained as a pale brown solid in the same method as in Example 290 or in accordance with the method or by combining it with an ordinary method but using 2,6-difluoro-phenol and 6-methanesulfonyl-pyridin-3-ol in order.
$^1$HNMR (CDCl$_3$) δ: 3.21 (3H, s), 6.98 (2H, t, J=8.0 Hz), 7.05-7.50 (4H, m), 7.80-7.93 (1H, m), 8.03 (1H, t, J=8.8 Hz), 8.23 and 8.37 (total 1H, each d, J=8.4 Hz), 8.47 (1H, s), 8.61 and 8.67 (total 1H, each s)
ESI-MS (m/e): 513 [M+H]

Example 293

1-(2-(6-(4-(2-Hydroxy-ethyl)-phenoxy)-2-pyridin-2-yl-3H-benzimidazol-5-yl)-pyrrolidin-1-yl)-ethanone The entitled compound was obtained as a white solid in the same method as in Example 122 or in accordance with the method or by combining it with an ordinary method but using 4-bromophenethyl-alcohol.

¹HNMR (CDCl₃) δ: 1.05-2.90 (10H, m), 3.00-4.45 (4H, m), 5.20-5.45 (1H, m), 6.80-7.70 (7H, m), 7.85-7.95 (1H, m), 8.20-8.45 (1H, m), 8.50-8.80 (1H, m)
ESI-MS (m/e): 443 [M+H]

Example 294

1-(2-(6-(4-(5-Methyl-[1,3,4]-oxadiazol-2-yl)-phenoxy)-2-pyridin-2-yl-3H-benzimidazol-5-yl)-pyrrolidin-1-yl)-ethanone The entitled compound was obtained as a colorless oily substance in the same method as in Example 122 or in accordance with the method or by combining it with an ordinary method but using 2-(4-bromo-phenyl)-5-methyl-[1,3,4]oxadiazole.
¹HNMR (CDCl₃) δ: 1.40-2.80 (10H, m), 3.50-3.95 (2H, m), 5.10-5.50 (1H, m), 6.90-7.60 (5H, m), 7.82-8.10 (3H, m), 8.35-8.45 (1H, m), 8.60-8.75 (1H, m)
ESI-MS (m/e): 481 [M+H]

Example 295

1-(2-(6-(4-(2-Methyl-oxazol-5-yl)-phenoxy)-2-pyridin-2-yl-3H-benzimidazol-5-yl)-pyrrolidin-1-yl)-ethanone The entitled compound was obtained in the same method as in Example 122 or in accordance with the method or by combining it with an ordinary method but using 5-(4-bromophenyl)-2-methyl-oxazole.
¹HNMR (CDCl₃) δ: 1.66-2.66 (10H, m), 3.53-3.94 (2H, m), 5.21-5.57 (1H, m), 6.93-7.92 (9H, m), 8.30-8.69 (2H, m), 10.61-10.97 (1H, m)
ESI-MS (m/e): 480 [M+H]

Example 296

2-Hydroxy-1-(2-(6-(4-methanesulfonyl-1-phenoxy)-2-pyridin-2-yl-3H-benzimidazol-5-yl)-pyrrolidin-1-yl)-ethanone The entitled compound was obtained as a white solid in the same method as in Example 168 or in accordance with the method or by combining it with an ordinary method but using 5-(4-methanesulfonyl-phenoxy)-2-pyridin-2-yl-6-pyrrolidin-2-yl-1H-benzimidazole enantiomer B obtained in Example 163.
¹HNMR (CD₃OD) δ: 1.84-2.16 (3H, m), 2.24-2.43 (1H, m), 3.12 and 3.14 (total 3H, each s), 3.49-4.24 (4H, m), 5.17-5.38 (1H, m), 7.20-7.58 (5H, m), 7.93-8.04 (3H, m), 8.26-8.30 (1H, m), 8.73 (1H, s)
ESI-MS (m/e): 493 [M+H]

Examples 297, 298

1-(2-(6-(6-Ethanesulfonyl-pyridin-3-yloxy)-2-pyridin-2-yl-3H-benzimidazol-5)-yl)-pyrrolidin-1-yl)-ethanone 1-(2-(6-(5-Chloro-pyridin-2-yloxy)-2-pyridin-2-yl-3H-benzimidazol-5-yl)-pyrrolidin-1-yl)-ethanone
The entitled compounds were obtained in the same method as in Example 122 or in accordance with the method or by combining it with an ordinary method but using 5-chloro-2-ethanesulfonyl-pyridine.

1-(2-(6-(6-Ethanesulfonyl-pyridin-3-yloxy)-2-pyridin-2-yl-3H-benzimidazol-5-yl)-pyrrolidin-1-yl)-ethanone ¹HNMR (CDCl₃) δ: 1.00-1.34 (3H, m), 1.44-2.41 (7H, m), 3.11-3.89 (4H, m), 5.05-5.47 (1H, m), 6.73-8.72 (9H, m), 10.89-11.47 (1H, m)
ESI-MS (m/e): 492 [M+H]

1-(2-(6-(5-Chloro-pyridin-2-yloxy)-2-pyridin-2-yl-3H-benzimidazol-5-yl)-pyrrolidin-1-yl)-ethanone ¹HNMR (CDCl₃) δ: 1.51-2.33 (7H, m), 3.41-3.90 (2H, m), 5.03-5.45 (1H, m), 6.79-8.67 (9H, m), 10.80-11.00 (1H, m)
ESI-MS (m/e): 434 [M+H]

Example 299

5-(4-Methanesulfonyl-phenoxy)-2-pyrazin-2-yl-6-pyrrolidin-2-yl-1H-benzimidazole enantiomer A and enantiomer B (Step 1) Production of 2,2,2-trifluoro-1-(2-(6-(4-methanesulfonyl-phenoxy)-2-pyrazin-2-yl-3H-benzimidazol-5-yl)-pyrrolidin-1-yl)-ethanone 14.5 mg of pyrazine-2-carboxylic acid and 27.0 mg of 1-(3-dimethylaminopropyl)-3-ethylcarbodiimide monohydrochloride were added in order to a pyridine (1 ml) solution of 53 mg of 1-(2-(4,5-diamino-2-(4-methanesulfonyl-phenoxy)-phenyl)-pyrrolidin-1-yl)-2,2,2-trifluoro-ethanone obtained in Example 162 (step 6), and the reaction liquid was stirred at room temperature for 3 hours. The reaction liquid was diluted with saturated saline, and extracted with ethyl acetate. The organic layers were combined, washed with aqueous saturated ammonium chloride and aqueous saturated sodium bicarbonate in order, and dried with anhydrous magnesium sulfate. The solvent was evaporated away under reduced pressure, and the resulting residue was dissolved in 1 ml of toluene. 9.9 mg of p-toluenesulfonic acid monohydrate was added to it, and the reaction liquid was stirred at 120° C. for 6 hours. After cooled, the reaction liquid was diluted with ethyl acetate, washed with aqueous saturated sodium bicarbonate and saturated saline in order, and dried with anhydrous magnesium sulfate. The solvent was evaporated away under reduced pressure, and the residue was purified through partitioning thin-layer chromatography (Kieselgel™ 60F₂₅₄, Art 5744 (by Merck), chloroform/methanol=9/1) to obtain the entitled compound as an oily substance.

(Step 2) Production of 5-(4-methanesulfonyl-phenoxy)-2-pyrazin-2-yl-6-pyrrolidin-2-yl-1H-benzimidazole 55 mg of potassium carbonate was added to a solution of 40 mg of 2,2,2-trifluoro-1-(2-(6-(4-methanesulfonyl-phenoxy)-2-pyrazin-2-yl-3H-benzimidazol-5-yl)-pyrrolidin-1-yl)-ethanone in a mixture of 1.6 ml of methanol and 0.4 ml of water, and the reaction liquid was stirred overnight at room temperature. The reaction liquid was concentrated under reduced pressure, and aqueous saturated ammonium chloride was added to the residue, then extracted with chloroform, and dried with anhydrous magnesium sulfate. The solvent was evaporated away under reduced pressure, and the resulting residue was purified through partitioning thin-layer chromatography (Kieselgel™ 60F₂₅₄, Art 5744 (by Merck), chloroform/methanol/aqueous ammonia=90/10/1) to obtain the entitled compound as an oily substance.

(Step 3) Production of 5-(4-methanesulfonyl-phenoxy)-2-pyrazin-2-yl-6-pyrrolidin-2-yl-1H-benzimidazole enantiomer A and enantiomer B 7.2 mg of 5-(4-methanesulfonyl-phenoxy)-2-pyrazin-2-yl-6-pyrrolidin-2-yl-1H-benzimidazole was optically resolved, using an optical resolution column (CHIRALPAK AD 2 cmφ×25 cmL (by Daicel Chemical), mobile phase: hexane/ethanol/diethylamine=20/80/0.1, flow rate: 10 ml/min), into an enantiomer A (retention time: 21.5 min) and an enantiomer B (retention time: 25.3 min) each as a yellow oily substance.

Example 300

1-(2-(6-(4-Methanesulfonyl-phenoxy)-2-pyrazin-2-yl-3H-benzimidazol-5-yl)-pyrrolidin-1-yl)-ethanone enantiomer A The entitled compound was obtained as an oily substance in the same method as in Example 164 or in accordance with the method or by combining it with an ordinary method but using 5-(4-methanesulfonyl-phenoxy)-2-pyrazin-2-yl-6-pyrrolidin-2-yl-1H-benzimidazole enantiomer A obtained in Example 299.
$^1$HNMR (CDCl$_3$) δ: 1.80-2.42 (7H, m), 3.00-3.09 (3H, m), 3.57-3.90 (2H, m), 5.10-5.43 (1H, m), 7.02-8.00 (6H, m), 8.57-8.73 (2H, m), 9.55-9.48 (1H, m)
ESI-MS (m/e): 478 [M+H]

Example 301

1-(2-(6-(4-Methanesulfonyl)-phenoxy)-2-pyrazin-2-yl-3H-benzimidazol-5-yl)-pyrrolidin-1-yl)-ethanone enantiomer B The entitled compound was obtained as an oily substance in the same method as in Example 164 or in accordance with the method or by combining it with an ordinary method but using 5-(4-methanesulfonyl-phenoxy)-2-pyrazin-2-yl-6-pyrrolidin-2-yl-1H-benzimidazole enantiomer B obtained in Example 299.
ESI-MS (m/e): 478 [M+H]

Example 302

1-(2-(6-(6-(Propane-2-sulfonyl)-pyridin-3-yloxy)-2-pyridin-2-yl-3H-benzimidazol-5-yl)-pyrrolidin-1-yl)-ethanone The entitled compound was obtained in the same method as in Example 122 or in accordance with the method or by combining it with an ordinary method but using 5-chloro-2-(propane-2-sulfonyl)-pyridine.
$^1$HNMR (CDCl$_3$) δ: 1.11-1.40 (6H, m), 1.55-2.43 (7H, m), 3.54-3.89 (3H, m), 5.11-5.48 (1H, m), 6.67-8.72 (9H, m), 11.00-11.69 (1H, m)
ESI-MS (m/e): 506 [M+H]

Example 303

1-(2-(6-(4-methanesulfonyl-phenoxy)-2-pyridin-2-yl-3H-benzimidazol-5-yl)-pyrrolidin-1-yl)-3-phenyl-propan-1-one The entitled compound was obtained as a colorless oily substance in the same method as in Example 296 or in accordance with the method or by combining it with an ordinary method but using 3-phenyl-propionic acid.
$^1$HNMR (CDCl$_3$) δ: 1.10-3.10 (11H, m), 3.40-4.00 (2H, m), 4.90-5.30 (1H, m), 6.80-8.00 (13H, m), 8.30-8.50 (1H, m), 8.60-8.75 (1H, m), 10.50-11.20 (1H, m)
ESI-MS (m/e): 567 [M+H]

Example 304

1-(2-(6-(4-methanesulfonyl-phenoxy)-2-pyridin-2-yl-3H-benzimidazol-yl)-pyrrolidin-1-yl)-ethanethione 0.010 ml of ethyl dithioacetate was added to a chloroform (1 ml) solution of 20 mg of 5-(4-methanesulfonyl-phenoxy)-2-pyridin-2-yl-6-pyrrolidin-2-yl-1H-benzimidazol enantiomer B obtained in Example 163, and the reaction liquid was stirred overnight at room temperature. The reaction liquid was diluted with chloroform, washed with aqueous saturated sodium bicarbonate and saturated saline in order, and dried with anhydrous magnesium sulfate. The solvent was evaporated away under reduced pressure, and the residue was purified through partitioning thin-layer chromatography (Kieselgel™ 60F$_{254}$, Art 5744 (by Merck), chloroform/methanol=9/1) to obtain the entitled compound as a white solid.
$^1$HNMR (CDCl$_3$) δ: 1.50-2.80 (7H, m), 3.00-3.20 (3H, m), 3.60-4.40 (2H, m), 5.30-5.50 (1H, m), 7.00-7.60 (5H, m), 7.80-8.00 (3H, m), 8.30-8.50 (1H, m), 8.60-8.75 (1H, m)
ESI-MS (m/e): 493 [M+H]

Example 305

2-Fluoro-1-(2-(6-(4-methanesulfonyl phenoxy-2-pyridin-2-yl-3H-benzimidazol-5-yl)-pyrrolidin-1-yl)-ethanone The entitled compound was obtained in the same method as in Example 168 or in accordance with the method or by combining it with an ordinary method but using sodium fluoroacetate.
$^1$HNMR (CDCl$_3$) δ: 1.67-2.40 (4H, m), 3.00-3.13 (3H, m), 3.51-4.00 (2H, m), 4.48-5.06 (2H, m), 5.18-5.46 (1H, m), 7.02-7.69 (5H, m), 7.80-7.98 (3H, m), 8.34-8.44 (1H, m), 8.53-8.70 (1H, m), 10.82-11.12 (1H, m)
ESI-MS (m/e): 495 [M+H]

Example 306

1-(2-(2-(5-Bromo-pyridin-2-yl)-6-(4-methanesulfonyl-phenoxy)-3H-benzimidazol-5-yl)-pyrrolidin-1-yl)-ethanone (Step 1) Production of 4-bromo-5-(4-methanesulfonyl-phenoxy)-2-nitro-phenylamine 5.2 g of 4-methanesulfonyl-phenol and 5.7 g of potassium carbonate were added in order to an N,N-dimethylformamide (50 ml) solution of 6.4 g of 4-bromo-5-fluoro-2-nitrophenylamine, and the reaction liquid was stirred at 120° C. for 3 hours. 200 ml of water was added to the reaction liquid, and the precipitated solid was taken out through filtration and dried to obtain the entitled compound as a brown solid.

(Step 2) Production of t-butyl 2-(4-amino-2-(4-methanesulfonyl-phenoxy)-5-nitro-phenyl)-pyrrole-1-carboxylate 7.9 g of 1-(t-butoxycarbonyl)pyrrole-2-boronic acid, 1.8 g of dichlorobistriphenylphosphine palladium, 50 ml of aqueous saturated sodium carbonate solution and 50 ml of water were added in order to a dimethoxyethane (100 ml) solution of 10.3 g of 4-bromo-5-(4-methanesulfonyl-phenoxy)-2-nitro-phenylamine, and the reaction liquid was stirred in a nitrogen atmosphere at 80° C. for 1 hour. After cooled, the reaction liquid was filtered through Celite, the filtrate was diluted with ethyl acetate, washed with water and saturated saline in order, and then dried with anhydrous magnesium sulfate. The solvent was evaporated away under reduced pressure, and the resulting residue was purified through silica gel column chromatography (developing solvent: hexane/ethyl acetate=1/1) to obtain the entitled compound as a brown oily substance.

(Step 3) Production of t-butyl 2-(4,5-diamino-2-(4-methanesulfonyl-phenoxy)phenyl)-pyrrolidine-1-carboxylate 20 ml of water and 4 g of 5% platinum-carbon catalyst were added to a 2-propanol (200 ml) solution of 12 g of t-butyl 2-(4-amino-2-(4-methanesulfonyl-phenoxy)-5-nitro-phenyl)-pyrrole-1-carboxylate, and the reaction liquid was stirred under a hydrogen atmosphere of 50 kgf/cm$^2$ at 70° C. for 2 days. The catalyst was removed through filtration through Celite, the solvent was evaporated away under reduced pressure, and the resulting residue was purified through silica gel column chromatography (developing solvent: chloroform/methanol=50/1) to obtain the entitled compound as a dark brown oily substance.

(Step 4) Production of 2-(5-bromo-pyridin-2-yl)-5-(4-methanesulfonyl-phenoxy)-6-pyrrolidin-2-yl-1H-benzimidazole 220 mg of 5-bromopyridine-2-carboxylic acid and 260 mg of 1-(3-dimethylaminopropyl)-3-ethylcarbodiimide monohydrochloride were added in order to a pyridine (10 ml) solution of 500 mg of t-butyl 2-(4,5-diamino-2-(4-methanesulfonyl-phenoxy)-phenyl)-pyrrolidine-1-carboxylate, and the reaction liquid was stirred at room temperature for 12 hours. The reaction liquid was diluted with chloroform, washed with water and saturated saline in order, and dried with anhydrous magnesium sulfate. The solvent was evaporated away under reduced pressure, the resulting residue was dissolved in 10 ml of trifluoroacetic acid, and the reaction liquid was heated under reflux for 3 hours. After cooled, the reaction liquid was distilled under reduced pressure, and the resulting residue was diluted with chloroform, and then made basic with aqueous saturated sodium bicarbonate added thereto. Then, the organic layer was washed with saturated saline and dried with anhydrous magnesium sulfate. The solvent was evaporated away under reduced pressure, and the resulting residue was purified through silica gel column chromatography (developing solvent: chloroform/methanol/aqueous ammonia=50/1/0.1) to obtain the entitled compound as a colorless oily substance.

(Step 5) Production of 1-(2-(2-(5-bromo-pyridin-2-yl)-6-(4-methanesulfonyl-phenoxy)-3H-benzimidazol-5-yl)-pyrrolidin-1-yl)-ethanone 0.050 ml of acetic anhydride was added to a pyridine (2 ml) solution of 220 mg of 2-(5-bromo-pyridin-2-yl)-5-(4-methanesulfonyl-phenoxy)-6-pyrrolidin-2-yl-1H-benzimidazole, and the reaction liquid was stirred at room temperature for 30 minutes. The reaction liquid was diluted with chloroform, washed with water and saturated saline in order, and dried with anhydrous magnesium sulfate. The solvent was evaporated away under reduced pressure, and the resulting residue was purified through silica gel column chromatography (developing solvent: chloroform/methanol/aqueous ammonia=50/1/0.1) to obtain the entitled compound as a pale brown solid.
$^1$HNMR (CDCl$_3$) δ: 1.60-2.40 (7H, m), 2.90-3.15 (3H, m), 3.50-3.90 (2H, m), 5.05-5.50 (1H, m), 6.80-7.80 (4H, m), 7.80-8.05 (3H, m), 8.20-8.35 (1H, m), 8.60-8.80 (1H, m), 10.50-11.05 (1H, m)
ESI-MS (m/e): 555,557 [M+H]

Example 307

1-(2-(2-(6-Fluoro-pyridin-2-yl)-6-(4-methanesulfonyl-phenoxy)-3H-benzimidazol-5-yl)-pyrrolidin-1-yl)-ethanone The entitled compound was obtained in the same method as in Example 306 (step 4), (step 5) or in accordance with the method or by combining it with an ordinary method but using t-butyl 2-(4,5-diamino-2-(4-methanesulfonyl-phenoxy)-phenyl)-pyrrolidin-1-carboxylate and 6-fluoro-pyridine-2-carboxylic acid.
$^1$HNMR (CDCl$_3$) δ: 1.70-2.40 (7H, m), 2.98-3.11 (3H, m), 3.57-3.90 (2H, m), 5.07-5.51 (1H, m), 6.81-8.32 (9H, m), 10.64-11.36 (1H, m)
ESI-MS (m/e): 495 [M+H]

Example 308

1-(2-(2-pyridin-2-yl-6-(6-trifluoromethyl-pyridin-3-yloxy)-3H-benzimidazol-5-yl)-pyrrolidin-1-yl)-ethanone The entitled compound was obtained as a pale yellow solid in the same method as in Example 122 or in accordance with the method or by combining it with an ordinary method but using 5-bromo-2-trifluoromethyl-pyridine.
$^1$HNMR (CD$_3$OD) δ: 1.89 and 2.14 (total 3H, each s), 1.90-2.20 (3H, m), 2.24-2.50 (1H, m), 3.63-3.99 (2H, m), 5.26-5.40 (1H, m), 7.34-7.63 (4H, m), 7.80-7.86 (1H, m), 7.94-8.02 (1H, m), 8.29-8.37 (1H, m), 8.58-8.59 (1H, m), 8.73-8.78 (1H, m)
ESI-MS (m/e): 468 [M+H]

Example 309

1-(2-(6-(6-Methanesulfonyl-pyridin-3-yloxy)-2-pyridin-2-yl-3H-benzimidazol-5-yl)-pyrrolidin-1-yl)-ethanone enantiomer A (Step 1) Production of 1-(2-(4,5-diamino-2-benzyloxy-phenyl)-pyrrolidin-1-yl)-ethanone enantiomer A and enantiomer B 2.2 g of 1-(2-(4,5-diamino-2-benzyloxy-phenyl)-pyrrolidin-1-yl)-ethanone obtained in Example 121 (step 8) was optically resolved, using an optical resolution column (CHIRALPAK AS 2 cmφ×25 cmL (by Daicel Chemical), mobile phase: hexane/ethanol=30/70, flow rate: 15 ml/min), into an enantiomer A (retention time: 11.43 min) and an enantiomer B (retention time: 16.32 min) each as a black solid.

(Step 2) Production of 1-(2-(6-(6-methanesulfonyl-pyridin-3-yloxy)-2-pyridin-2-yl-3H-benzimidazol-5-yl)-pyrrolidin-1-yl)-ethanone enantiomer A The entitled compound was obtained as an oily substance in the same method as in Example 121 (step 9) to (step 12) or in accordance with the method or by combining it with an ordinary method but using 1-(2-(4,5-diamino-2-benzyloxy-phenyl)-pyrrolidin-1-yl)-ethanone enantiomer A obtained in Example 309 (step 1) and 5-chloro-2-methanesulfonyl-pyridine.

$^1$HNMR (CDCl$_3$) δ: 1.80-2.42 (7H, m), 3.16-3.27 (3H, m), 3.57-3.91 (2H, m), 5.14-5.34 (1H, m), 7.04-8.10 (6H, m), 8.31-8.70 (3H, m), 10.59-10.94 (1H, m)
ESI-MS (m/e): 478 [M+H]

Example 310

1-(2-(6-(6-Methanesulfonyl-pyridin-3-yloxy)-2-pyridin-2-yl-3H-benzimidazol-5-yl)-pyrrolidin-1-yl)-ethanone enantiomer B The entitled compound was obtained as an oily substance in the same method as in Example 309 or in accordance with the method or by combining it with an ordinary method but using 1-(2-(4,5-diamino-2-benzyloxy-phenyl)-pyrrolidin-1-yl)-ethanone enantiomer B obtained in Example 309 (step 1).
ESI-MS (m/e): 478 [M+H]

Example 311

(2-(6-(4-Methanesulfonyl-phenoxy)-2-pyridin-2-yl-3H-benzimidazol-5-yl)-pyrrolidin-1-yl)-pyridin-2-yl-methanone The entitled compound was obtained in the same method as in Example 296 or in accordance with the method or by combining it with an ordinary method but using 5-(4-methanesulfonyl-phenoxy)-2-pyridin-2-yl-6-pyrrolidin-2-yl-1H-benzimidazole enantiomer B obtained in Example 163 and pyridine-2-carboxylic acid.

$^1$HNMR (CDCl$_3$) δ: 1.60-2.45 (4H, m), 2.91-3.09 (3H, m), 3.71-4.30 (2H, m), 5.44-5.60 and 5.91-6.03 (total 1H, each m), 6.77-7.93 (11H, m), 8.10-8.66 (3H, m), 10.82-11.00 (1H, m)
ESI-MS (m/e): 540 [M+H]

Example 312

(2-Fluoro-phenyl)-(2-(6-(4-methanesulfonyl-phenoxy)-2-pyridin-2-yl-3H-benzimidazol-5-yl)-pyrrolidin-1-yl)-methanone The entitled compound was obtained in the same method as in Example 296 or in accordance with the method or by combining it with an ordinary method but using 5-(4-methanesulfonyl-phenoxy)-2-pyridin-2-yl-6-pyrrolidin-2-yl-1H-benzimidazole enantiomer B obtained in Example 163 and 2-fluorobenzoic acid.

$^1$HNMR (CDCl$_3$) δ: 1.80-2.51 (4H, m), 2.90-3.08 (3H, m), 3.40-4.08 (2H, m), 4.91-5.02 and 5.46-5.60 (total 1H, each m), 6.55-8.69 (15H, m)
ESI-MS (m/e): 557 [M+H]

Example 313

6-(1-Acetylpyrrolidin-2-yl)-5-(4-fluorophenoxy)-2-isoxazol-3-yl-1H-benzimidazole The entitled compound was obtained in the same method as in Example 189 or in accordance with the method or by combining it with an ordinary method but using isoxazole-3-carbaldehyde.

$^1$HNMR (CDCl$_3$) δ: 1.80-2.46 (4H, m), 1.87 and 2.16 (total 3H, each s), 3.58-3.88 (2H, m), 5.13-5.17 and 5.52-5.55 (total 1H, each m), 6.85-7.40 (7H, m), 8.56 (1H, s)
ESI-MS (m/e): 407 [M+H]

Example 314

5-(6-(1-Acetyl-pyrrolidin-2-yl)-2-pyridin-2-yl-1H-benzimidazol-5-yloxy)-pyridine-2-carbonitrile The entitled compound was obtained as a white solid in the same method as in Example 309 or in accordance with the method or by combining it with an ordinary method but using 1-(2-(4,5-diamino-2-benzyloxy-phenyl)-pyrrolidin-1-yl)-ethanone enantiomer B obtained in Example 309 (step 1) and 2-cyano-5-bromo-pyridine.

$^1$HNMR (CDCl$_3$) δ: 1.53-2.42 (7H, m), 3.40-3.50 (2H, m), 5.07-5.29 (1H, m), 7.00-7.94 (6H, m), 8.28-8.68 (3H, m), 11.00-11.52 (1H, m)
ESI-MS (m/e): 425 [M+H]

Example 315

T-butyl (2-(2-(6-(4-methanesulfonyl-phenoxy)-2-pyridin-2-yl-3H-benzimidazol-5-yl)-pyrrolidin-1-yl)-2-oxo-ethyl)-methyl-carbamate The entitled compound was obtained in the same method as in Example 171 or in accordance with the method or by combining it with an ordinary method but using 5-(4-methanesulfonyl-phenoxy)-2-pyridin-2-yl-6-pyrrolidin-2-yl-1H-benzimidazole enantiomer B obtained in Example 163 and N-t-butoxycarbonyl-glycine.

$^1$HNMR (CDCl$_3$) δ: 1.20-1.69 (16H, m), 2.76-3.12 (7H, m), 5.15-5.26 (1H, m), 7.00-7.44 (5H, m), 7.76-8.00 (4H, m), 8.28-8.40 (1H, m), 8.58-8.73 (1H, m)
ESI-MS (m/e): 606 [M+H]

Example 316

1-(2-(6-(4-Methanesulfonyl-phenoxy)-2-pyridin-2-yl-3H-benzimidazol-5-yl)-pyrrolidin-1-yl)-2-methylamino-ethanone The entitled compound was obtained in the same method as in Example 171 or in accordance with the method or by combining it with an ordinary method but using t-butyl (2-(2-(6-(4-methanesulfonyl-phenoxy)-2-pyridin-2-yl-3H-benzimidazol-5-yl)-pyrrolidin-1-yl)-2-oxo-ethyl)-methyl-carbamate obtained in Example 315.

$^1$HNMR (CDCl$_3$) δ: 1.60-1.97 (4H, m), 2.20-2.46 (3H, m), 2.94-3.08 (5H, m), 3.19-3.90 (2H, m), 5.15-5.43 (1H, m), 7.08-7.65 (5H, m), 7.87-7.94 (3H, m), 8.36-8.38 (1H, m), 8.64 (1H, s)
ESI-MS (m/e): 506 [M+H]

Example 317

1-(2-(6-(4-Methanesulfonyl-phenoxy)-2-(1H-pyrazol-3-yl)-3H-benzimidazol-5-yl)-pyrrolidin-1-yl)-ethanone (Step 1) Production of t-butyl 2-(6-(4-methanesulfonyl-phenoxy)-2-(1H-pyrazol-3-yl)-3H-benzimidazol-5-yl)-pyrrolidin-1-carboxylate 10.0 mg of 1H-pyrazole-3-carboxaldehyde was added to an N,N-dimethylformamide (1 ml) solution of 49.0 mg of t-butyl 2-(4,5-diamino-2-(4-methanesulfonyl-phenoxy)-phenyl)-pyrrolidine-1-carboxylate obtained in Example 306 (step 3), and the reaction liquid was stirred overnight at 90° C.

After cooled, the reaction liquid was diluted with ethyl acetate, washed with saturated saline, and dried with anhydrous magnesium sulfate. The solvent was evaporated away under reduced pressure, and the resulting residue was purified through partitioning thin-layer chromatography (Kieselgel™ 60F$_{254}$, Art 5744 (by Merck), chloroform/methanol=9/1) to obtain the entitled compound as a brown solid.

(Step 2) Production of 1-(2-(6-(4-methanesulfonyl-phenoxy)-2-(1H-pyrazol-3-yl)-3H-benzimidazol-5-yl)-pyrrolidin-1-yl)-ethanone 49.2 mg of t-butyl 2-(6-(4-methanesulfonyl-phenoxy)-2-(1H-pyrazol-3-yl)-3H-benzimidazol-5-yl)-pyrrolidin-1-carboxylate was dissolved in 1 ml of 4 N hydrochloric acid-dioxane, and the reaction liquid was stirred at room temperature for 2 hours. The reaction solvent was evaporated away under reduced pressure, and 0.012 ml of acetic anhydride was added to 2 ml of a pyridine solution of the resulting residue, and stirred at room temperature for 30 minutes. The reaction solvent was evaporated away under reduced pressure, and the resulting residue was purified through partitioning thin-layer chromatography (Kieselgel™ 60F$_{254}$, Art 5744 (by Merck), chloroform/methanol=9/1) to obtain the entitled compound as a brown solid.

$^1$HNMR (CDCl$_3$) δ: 1.53-2.38 (7H, m), 2.97-3.10 (3H, s), 3.39-3.99 (2H, m), 5.06-5.31 (1H, m), 6.80-8.04 (8H, m)

ESI-MS (m/e): 466 [M+H]

Example 318

1-(2-(6-(4-Methanesulfonyl-phenoxy)-2-(1-methyl-1H-pyrazol-3-yl)-3H-benzimidazol-5-yl)-pyrrolidin-1-yl)-ethanone The entitled compound was obtained as a white solid in the same method as in Example 306 (step 4), (step 5) or in accordance with the method or by combining it with an ordinary method but using t-butyl 2-(4,5-diamino-2-(4-methanesulfonyl-phenoxy)-phenyl)-pyrrolidine-1-carboxylate obtained in Example 306 (step 3) and 1-methyl-1H-pyrazole-3-carboxylic acid.

$^1$HNMR (CDCl$_3$) δ: 1.70-2.37 (7H, m), 2.98-3.11 (3H, m), 3.52-4.02 (5H, m), 5.04-5.43 (1H, m), 6.74-7.67 (6H, m), 7.79-7.97 (2H, m), 10.38-11.00 (1H, m)

ESI-MS (m/e): 480 [M+H]

Example 319

1-(2-(2-(5-Fluoro-pyridin-2-yl-6-(4-methanesulfonyl-phenoxy)-3H-benzimidazol-5-yl)-pyrrolidin-1-yl)-ethanone The entitled compound was obtained as a white solid in the same method as in Example 318 or in accordance with the method or by combining it with an ordinary method but using 5-fluoro-pyridine-2-carboxylic acid.

$^1$HNMR (CDCl$_3$) δ: 1.60-2.50 (7H, m), 2.85-3.20 (3H, m), 3.50-4.00 (2H, m), 5.00-5.50 (1H, m), 6.80-8.10 (7H, m), 8.20-8.60 (2H, m), 10.50-11.20 (1H, m)

ESI-MS (m/e): 495 [M+H]

Example 320

(1-Amino-cyclopropyl)-(2-(6-(4-methanesulfonyl-phenoxy)-2-pyridin-2-yl-3H-benzimidazol-5-yl)-pyrrolidin-1-yl)-methanone The entitled compound was obtained as a white solid in the same method as in Example 168 or in accordance with the method or by combining it with an ordinary method but using 1-amino-cyclopropanecarboxylic acid.

$^1$HNMR (CD$_3$OD) δ: 0.80-1.10 (4H, m), 1.88-2.17 (3H, m), 2.32-2.40 (1H, m), 3.12 (3H, s), 4.06 (2H, brs), 5.21 (1H, brs), 7.18-7.54 (5H, m), 7.91-7.99 (3H, m), 8.27 (1H, d, J=8.0 Hz), 8.73 (1H, d, J=4.3 Hz)

ESI-MS (m/e): 518 [M+H]

Example 321

5-(6-(1-Acetyl-pyrrolidin-2-yl)-2-pyrazin-2-yl-1H-benzimidazol-5-yloxy)-pyridine-2-carbonitrile The entitled compound was obtained as an oily substance in the same method as in Example 121 (step 9) to (step 12) and Example 314 or in accordance with the method or by combining it with an ordinary method but using 1-(2-(4,5-di-amino-2-benzyloxy-phenyl)-pyrrolidin-1-yl)-ethanone enantiomer B obtained in Example 309 (step 1) and pyrazine-2-carboxaldehyde.

$^1$HNMR (CDCl$_3$) δ: 1.67-2.47 (7H, m), 3.60-3.92 (2H, m), 5.11-5.35 (1H, m), 7.00-7.77 (4H, m), 8.47-8.73 (3H, m), 9.52-9.68 (1H, m), 10.88-11.94 (1H, m)

ESI-MS (m/e): 426 [M+H]

Example 322

1-(2-(2-(5-Cyano-pyridin-2-yl)-6-(4-methanesulfonyl-phenoxy)-3H-benzimidazol-5-yl)-pyrrolidin-1-yl)-ethanone The entitled compound was obtained as a white solid in the same method as in Example 307 or in accordance with the method or by combining it with an ordinary method but using 5-cyano-pyridine-2-carboxylic acid.

$^1$HNMR (CDCl$_3$) δ: 1.05-2.40 (7H, m), 2.80-3.20 (3H, m), 3.60-4.00 (2H, m), 5.05-5.45 (1H, m), 6.90-7.80 (4H, m), 7.80-8.00 (2H, m), 8.05-8.20 (1H, m), 8.40-8.60 (1H, m), 8.80-9.00 (1H, m), 10.40-10.80 (1H, m)

ESI-MS (m/e): 502 [M+H]

Example 323

1-(2-(2-(4-Chloro-pyridin-2-yl)-6-(4-methanesulfonyl)phenoxy)-3H-benzimidazol-5-yl)-pyrrolidin-1-yl)-ethanone The entitled compound was obtained as a white solid in the same method as in Example 307 or in accordance with the method or by combining it with an ordinary method but using 4-chloro-pyridine-2-carboxylic acid.

$^1$HNMR (CDCl$_3$) δ: 1.67-2.40 (7H, m), 3.00-3.13 (3H, m), 3.54-3.91 (2H, m), 5.10-5.44 (1H, m), 6.79-7.52 (5H, m), 7.64-7.97 (2H, m), 8.36-8.57 (2H, m), 10.75-11.24 (1H, m)

ESI-MS (m/e): 511 [M+H]

Example 324

1-(2-(2-(5-Ethoxy-pyridin-2-yl)-6-(4-methanesulfonyl-phenoxy-3H-benzimidazol-5-yl)-pyrrolidin-1-yl)-ethanone The entitled compound was obtained as a yellow oily substance in the same method as in Example 307 or in accordance with the method or by combining it with an ordinary method but using 5-ethoxy-pyridine-2-carboxylic acid.

$^1$HNMR (CDCl$_3$) δ: 2.00-3.40 (10H, m), 3.60-4.00 (3H, m), 4.20-5.20 (4H, m), 5.80-6.40 (1H, m), 7.20-9.20 (9H, m), 11.50-12.00 (1H, m)
ESI-MS (m/e): 521 [M+H]

Example 325

Trans-1-(4-acetoxy-2-(6-(4-methanesulfonyl-phenoxy-2-pyridin-2-yl-3H-benzimidazol-5-yl)-pyrrolidin 1-yl)-ethanone (Step 1) Production of 1-(2-fluoro-4-nitro-phenyl)-3-buten-1-ol 0.65 ml of titanium tetrachloride was added to a chloroform (12 ml) solution of 2.00 g of 4-nitro-2-fluoro-benzaldehyde produced according to the method described in U.S. Pat. No. 6,239,152, and the reaction liquid was stirred at room temperature for 10 minutes, and then 2.4 ml of allyl-trimethyl-silane was added to it, and the reaction liquid was stirred at room temperature for 20 minutes. The reaction liquid was diluted with ethyl acetate, washed with water and saturated saline, and dried with anhydrous sodium sulfate. The solvent was evaporated away under reduced pressure, and the residue was purified through silica gel column chromatography (developing solvent: hexane/ethyl acetate=3/1) to obtain the entitled compound as an orange solid.

(Step 2) Production of N-(1-(2-fluoro-4-nitro-phenyl)-3-butenyl)-acetamide 0.29 ml of methanesulfonyl chloride and 0.63 ml of triethylamine were added to a chloroform (10 ml) solution of 480 mg of 1-(2-fluoro-4-nitro-phenyl)-3-buten-1-ol, and the reaction liquid was stirred at room temperature for 15 minutes. The reaction liquid was washed with water, and dried with anhydrous magnesium sulfate. The solvent was evaporated away under reduced pressure to obtain a crude product as a pale yellow oily substance. 310 mg of sodium azide was added to a dimethylformamide (10 ml) solution of the crude product, and the reaction liquid was stirred at 45° C. for 30 minutes. The reaction liquid was diluted with ethyl acetate, washed with water, and dried with anhydrous sodium sulfate. The solvent was evaporated away under reduced pressure to obtain a crude product as a brown oily substance. 1.0 g of triphenylphosphine and 2 ml of water were added to a tetrahydrofuran (10 ml) solution of the resulting crude product, and the reaction liquid was stirred for 12 hours with heating under reflux. 1 N hydrochloric acid was added to the reaction liquid, and the organic layer was removed. The aqueous layer was made basic with an aqueous 1 N sodium hydroxide solution added thereto. This was extracted with chloroform, and dried with anhydrous sodium sulfate, and the solvent was evaporated away under reduced pressure to obtain 380 mg of a crude product as a brown oily substance. 0.50 ml of triethylamine, 0.25 ml of acetic anhydride and 20 mg of 4-dimethylaminopyridine were added to a chloroform (10 ml) solution of 380 mg of the crude product, and the reaction liquid was stirred at room temperature for 30 minutes. The solvent was evaporated away under reduced pressure, and the residue was purified through silica gel column chromatography (developing solvent: chloroform/methanol=50/1) to obtain the entitled compound as a brown oily substance.

(Step 3) Production of 1-acetyl-2-(2-fluoro-4-nitro-phenyl)-4-hydroxy-pyrrolidine 1 ml of water and 600 mg of iodine were added to a tetrahydrofuran (4 ml) solution of 200 mg of N-(1-(2-fluoro-4-nitro-phenyl)-3-butenyl)-acetamide, and the reaction liquid was stirred overnight at room temperature. The reaction liquid was diluted with chloroform, washed with aqueous saturated sodium bicarbonate, aqueous saturated sodium thiosulfate and saturated saline in order, and dried with anhydrous sodium sulfate. The solvent was evaporated away under reduced pressure to obtain a crude product. 0.25 ml of triethylamine, 0.13 ml of acetic anhydride and 10 mg of 4-dimethylaminopyridine were added to a chloroform (5 ml) solution of the crude product, and the reaction liquid was stirred at room temperature for 15 minutes. The solvent was evaporated away under reduced pressure, 20 mg of potassium carbonate was added to a methanol (5 ml) solution of the resulting residue, and the reaction liquid was stirred at room temperature for 15 minutes. The solvent was evaporated away under reduced pressure, and the residue was purified through silica gel column chromatography (developing solvent: chloroform/methanol=30/1) to obtain the entitled compound as a colorless solid diastereomer mixture.

(Step 4) Production of 1-acetyl-2-(2-fluoro-4-((pyridin-2-carbonyl)-amino)-phenyl)-4-acetoxy-pyrrolidine 0.06 ml of acetic anhydride was added to a pyridine (2 ml) solution of 140 mg of 1-acetyl-2-(2-fluoro-4-nitro-phenyl)-4-hydroxy-pyrrolidine, and the reaction liquid was stirred overnight at 50° C. The solvent was evaporated away under reduced pressure, and the residue was purified through silica gel column chromatography (developing solvent: ethyl acetate) to obtain 150 mg of a product. About 50 mg of developed Raney nickel catalyst was added to a methanol (3 ml) solution of 57 mg of the product, and the reaction liquid was stirred in a hydrogen atmosphere for 30 minutes. Then, the catalyst was removed through filtration, and the solvent was evaporated away under reduced pressure. 30 mg of pyridine-2-carboxylic acid and 50 mg of 1-(3-dimethylaminopropyl)-3-ethylcarbodiimide monohydrochloride were added to a pyridine (2 ml) solution of the residue, and the reaction liquid was stirred overnight at room temperature. The reaction liquid was diluted with ethyl acetate, washed with aqueous saturated sodium bicarbonate and saturated saline, and dried with anhydrous sodium sulfate. The solvent was evaporated away under reduced pressure to obtain the entitled compound as a yellow oily substance.

(Step 5) Production of trans-1-acetyl-2-(5-nitro-2-fluoro-4-((pyridin-2-carbonyl)-amino)-phenyl)-4-acetoxy-pyrrolidine and cis-1-acetyl-2-(5-nitro-2-fluoro-4-((pyridin-2-carbonyl)-amino)-phenyl)-4-acetoxy-pyrrolidine 0.1 ml of fuming nitric acid was added to a trifluoroacetic acid (0.5 ml) solution of 36 mg of 1-acetyl-2-(2-fluoro-4-((pyridin-2-carbonyl)-amino)-phenyl)-4-acetoxy-pyrrolidine, and the reaction liquid was stirred at room temperature for 1 hour. The solvent was evaporated away under reduced pressure, and the residue was purified through silica gel column chromatography (developing solvent: chloroform/methanol=15/1) to obtain 30 mg of a diastereomer mixture of the entitled compound as a white solid. The resulting diastereomer mixture was purified through partitioning thin-layer chromatography (Kieselgel™ 60F$_{254}$, Art 5744 (by Merck), chloroform/methanol=15/1) to separate the mixture into the individual diastereomers of the entitled compounds, each as a yellow solid (Rf value: trans form >cis form.)

(Step 6) Production of trans-1-(4-acetoxy-2-(6-(4-methanesulfonyl-phenoxy)-2-pyridin-2-yl-3H-benzimidazol-5-yl)-pyrrolidin-1-yl)-ethanone 10 mg of 4-methanesulfonyl-phenol and 20 mg of cesium carbonate were added to a dimethylformamide (0.5 ml) solution of 21 mg of trans-1-acetyl-2-(5-nitro-2-fluoro-4-((pyridin-2-carbonyl)-amino)-phenyl)-4-acetoxy-pyrrolidine, and the reaction liquid was stirred at 90° C. for 1 hour. 100 mg of tin(II) chloride dihydrate was added to it, and the reaction liquid was stirred at 90° C. for 5 hours. The reaction liquid was diluted with ethyl acetate, washed with water and saturated saline in order, and dried with anhydrous sodium sulfate. The solvent was evaporated away under reduced pressure to obtain the entitled compound as a yellow oily substance.

$^1$HNMR (CD$_3$OD) δ: 1.50-1.90 (3H, m), 2.10-2.53 (2H, m), 2.98 (3H, s), 3.60-3.90 (2H, m), 5.13-5.26 (2H, m), 7.03-7.65 (5H, m), 7.78-7.87 (3H, m), 8.10-8.18 (1H, m), 8.59 (1H, s)

ESI-MS (m/e): 535 [M+H]

Example 326

Trans-1-(4-hydroxy-2-(6-(4-methanesulfonyl-phenoxy)-2-pyridin-2-yl-3H-benzimidazol-5-yl)-pyrrolidin-1-yl)-ethanone 0.015 ml of 25% sodium methoxide was added to a methanol (2 ml) solution of 40 mg of trans-1-(4-acetoxy-2-(6-(4-methanesulfonyl-phenoxy)-2-pyridin-2-yl-3H-benzimidazol-5-yl)-pyrrolidin-1-yl)-ethanone obtained in Example 325, and the reaction liquid was stirred at room temperature for 10 minutes. The solvent was evaporated away under reduced pressure, and the residue was purified through reversed-phase middle-pressure liquid chromatography [ODS-AS-360-CC (by YMC), mobile phase: water-acetonitrile-0.1% trifluoroacetic acid]. The solvent of the resulting fraction was diluted with ethyl acetate, washed with aqueous saturated sodium bicarbonate, and dried with anhydrous sodium sulfate. The solvent was evaporated away under reduced pressure to obtain the entitled compound as a white solid.

$^1$HNMR (CD$_3$OD) δ: 1.48-2.80 (5H, m), 2.99-3.10 (3H, m), 3.48-4.10 (2H, m), 4.40-4.60 (1H, m), 5.25-5.50 (1H, m), 7.00-7.50 (5H, m), 7.75-8.00 (3H, m), 8.24-8.48 (1H, m), 8.48-8.70 (1H, m), 10.70-11.20 (1H, m)

ESI-MS (m/e): 493 [M+H]

Example 327

Cis-1-(4-fluoro-2-(6-(4-methanesulfonyl-phenoxy-2-pyridin-2-yl-3H-benzimidazol-5-yl)-pyrrolidin-1-yl)-ethanone 0.02 ml of bis(2-methoxyethyl)aminosulfate trichloride was added to a chloroform (1 ml) solution of 10 mg of trans-1-(4-hydroxy-2-(6-(4-methanesulfonyl-phenoxy)-2-pyridin-2-yl-3H-benzimidazol-5-yl)-pyrrolidin-1-yl)-ethanone obtained in Example 326, and the reaction liquid was stirred at room temperature for 10 minutes. The solvent was evaporated away under reduced pressure, and the resulting residue was purified through partitioning thin-layer chromatography (Kieselgel™ 60F$_{254}$, Art 5744 (by Merck), chloroform/methanol=15/1) to obtain the entitled compound as a white solid.

$^1$HNMR (CD$_3$OD) δ: 1.92 (3H×½, s), 2.22 (3H×½, s), 2.22-2.80 (2H, m), 3.13 (3H×½, s), 3.15 (3H×½, s), 3.80-4.40 (2H, m), 5.20-5.50 (2H, m), 7.20-7.80 (5H, m), 7.90-8.10 (3H, m), 8.28 (1H, t, J=7.8 Hz), 8.74 (1H, brs)

ESI-MS (m/e): 495 [M+H]

Example 328

Cis-1-(4-acetoxy-2-(6-(4-methanesulfonyl-phenoxy)-2-pyridin-2-yl-3H-benzimidazol-5-pyrrolidin-1-yl)-ethanone The entitled compound was obtained as a colorless solid in the same method as in Example 325 (step 6) or in accordance with the method or by combining it with an ordinary method but using cis-1-acetyl-2-(5-nitro-2-fluoro-4-((pyridine-2-carbonyl)-amino)-phenyl)-4-acetoxy-pyrrolidine obtained in Example 325 (step 5).

$^1$HNMR (CD$_3$OD) δ: 1.40-1.90 (3H, m), 2.20-2.55 (2H, m), 3.00 (3H, s), 3.62-3.90 (2H, m), 5.12-5.28 (2H, m), 6.98-7.75 (5H, m), 7.78-7.88 (3H, m), 8.11-8.19 (1H, m), 8.60 (1H, s)

ESI-MS (m/e): 535 [M+H]

Example 329

Cis-1-(4-hydroxy-2-(6-(4-methanesulfonyl-phenoxy)-2-pyridin-2-yl-3H-benzimidazol-5-yl)-pyrrolidin-1-yl)-ethanone The entitled compound was obtained as a colorless solid in the same method as in Example 326 or in accordance with the method or by combining it with an ordinary method but using cis-1-(4-acetoxy-2-(6-(4-methanesulfonyl-phenoxy)-2-pyridin-2-yl-3H-benzimidazol-5-yl)-pyrrolidin-1-yl)-ethanone obtained in Example 328.

$^1$HNMR (CD$_3$OD) δ: 1.80-2.00 (3H, m), 2.04-2.75 (2H, m), 3.12-3.16 (3H, m), 3.40-4.00 (2H, m), 4.45-4.55 (1H, m), 5.25-5.43 (1H, m), 7.18-7.42 (3H, m), 7.50-7.59 (1H, m), 7.62-7.77 (1H, m), 7.90-8.08 (3H, m), 8.24-8.32 (1H, m), 8.75-8.81 (1H, m)

ESI-MS (m/e): 493 [M+H]

Example 330

Trans-1-(4-fluoro-2-(6-(4-methanesulfonyl-phenoxy)-2-pyridin-2-yl-3H-benzimidazol-5-yl)-pyrrolidin-1-yl)-ethanone The entitled compound was obtained as a pale yellow solid in the same method as in Example 327 or in accordance with the method or by combining it with an ordinary method but using cis-1-(4-hydroxy-2-(6-(4-methanesulfonyl-phenoxy)-2-pyridin-2-yl-3H-benzimidazol-5-yl)-pyrrolidin-1-yl)-ethanone.

$^1$HNMR (CD$_3$OD) δ: 1.70-2.73 (5H, m), 3.11-3.37 (3H, m), 3.62-4.51 (2H, m), 5.24-5.45 (2H, m), 7.13-7.76 (5H, m), 7.94-8.00 (3H, m), 8.28-8.33 (1H, m), 8.73-8.79 (1H, m)

ESI-MS (m/e): 495 [M+H]

Example 331

1-(4-Oxo-2-(6-(4-methanesulfonyl-phenoxy-2-pyridin-2-yl-3H-benzimidazol-5-yl)pyrrolidin-1-yl)-ethanone 0.003 ml of dimethylsulfoxide was added to a chloroform (1 ml) solution of 0.003 ml of oxalyl chloride at −50° C., and the reaction liquid was stirred at the same temperature for 5 minutes. A chloroform (1 ml) solution of 6.7 mg of trans-1-(4-hydroxy-2-(6-(4-methanesulfonyl-phenoxy)-2-pyridin-2-yl-3H-benzimidazol-5-yl)-pyrrolidin-1-yl)-ethanone obtained in Example 326 was added to the reaction liquid, and the reaction liquid stirred at −50° C. for 15 minutes. 0.02 ml of triethylamine was added to it, and the reaction liquid was stirred at room temperature for 5 minutes, and the reaction liquid was diluted with ethyl acetate, washed with aqueous saturated ammonium chloride and saturated saline in order, and dried with anhydrous sodium sulfate. The solvent was evaporated away under reduced pressure, and the residue was purified through reversed-phase middle-pressure liquid chromatography [ODS-AS-360-CC (by YMC), mobile phase: water-acetonitrile-0.1% trifluoroacetic acid]. The solvent of the resulting fraction was diluted with ethyl acetate, washed with aqueous saturated sodium bicarbonate, and dried with anhydrous sodium sulfate. The solvent was evaporated away under reduced pressure to obtain the entitled compound as a white solid.

$^1$HNMR (CD$_3$OD) δ: 2.03 (3H, s), 2.68 (2H, s), 3.16 (3H, s), 4.09-4.22 (2H, m), 5.70-5.77 (1H, m), 7.05-7.80 (5H, m), 7.94-8.01 (3H, m), 8.24-8.32 (1H, m), 8.72-8.77 (1H, m)

ESI-MS (m/e): 491 [M+H]

Example 332

1-(4,4-Difluoro-2-(6-(4-methanesulfonyl-phenoxy)-2 pyridin-2-yl-3H-benzimidazol-5-yl)-pyrrolidin-1-yl)-ethanone (Step 1) Production of 1-acetyl-2-(2-fluoro-4-nitro-phenyl)-4,4-difluoro-pyrrolidine 0.035 ml of dimethylsulfoxide was added to a chloroform (3 ml) solution of 0.035 ml of oxalyl chloride at −50° C., and the reaction liquid was stirred at the same temperature for 5 minutes. A chloroform (2 ml) solution of 40 mg of 1-acetyl-2-(2-fluoro-4-nitro-phenyl)-4-hydroxy-pyrrolidine obtained in Example 325 (step 3) was added to the reaction liquid, and the reaction liquid was stirred at −50° C. for 10 minutes. 0.10 ml of triethylamine was added to it, and the reaction liquid was stirred at room temperature for 5 minutes, then the reaction liquid was diluted with ethyl acetate, washed with aqueous saturated ammonium chloride and saturated saline in order, and dried with anhydrous sodium sulfate. The solvent was evaporated away under reduced pressure, and 0.06 ml of bis(2-methoxyethyl)aminosulfate trichloride was added to a chloroform (1 ml) solution of the resulting residue, and the reaction liquid was stirred overnight at 70° C. The solvent was evaporated away under reduced pressure, and the residue was purified through silica gel column chromatography (developing solvent: hexane/ethyl acetate=1/1) to obtain the entitled compound.

(Step 2) Production of 1-(4,4-difluoro-2-(6-(4-methanesulfonyl-phenoxy)-2-pyridin-2-yl-3H-benzimidazol-5-yl)-pyrrolidin-1-yl)-ethanone The entitled compound was obtained as a white solid in the same method as in Example 325 (step 4) to (step 6) or in accordance with the method or by combining it with an ordinary method but using 1-acetyl-2-(2-fluoro-4-nitro-phenyl)-4,4-difluoro-pyrrolidine obtained in (step 1).

$^1$HNMR (CD$_3$OD) δ: 2.03 (3H×½, s), 2.05 (3H×½, s), 2.50-2.63 (1H, m), 2.85-3.15 (1H, m), 3.14 (3H×½, s), 3.15 (3H×½, s), 3.95-4.25 (2H, m), 5.44-5.58 (1H, m), 7.22-7.29 (2H, m), 7.26-7.42 (1H, m), 7.48-7.54 (1H, m), 7.61-7.68 (1H, m), 7.94-8.04 (3H, m), 8.26-8.32 (1H, m), 8.72-8.77 (1H, m)

ESI-MS (m/e): 513 [M+H]

Example 333

Cis-1-(4-fluoro-2-(6-(4-methanesulfonyl-henoxy-2-pyridin-2-yl-3H-benzimidazol-5-yl-pyrrolidin-1-yl)-ethanone enantiomer A, and enantiomer B 45 mg of the racemic cis-1-(4-fluoro-2-(6-(4-methanesulfonyl-phenoxy)-2-pyridin-2-yl-3H-benzimidazol-5-yl)-pyrrolidin-1-yl)-ethanone obtained in Example 327 was optically resolved, using an optical resolution column (CHIRALPAK AD-H 2 cmφ×25 cmL (by Daicel Chemical), mobile phase: hexane/2-propanol=30/70, flow rate: 10 ml/min), into an enantiomer A (retention time: 18 min) and an enantiomer B (retention time: 22 min) each as a white solid.

Enantiomer A
ESI-MS (m/e): 495 [M+H]

Enantiomer B
ESI-MS (m/e): 495 [M+H]

Example 334

Methyl 6-(6-(1-acetyl-pyrrolidin-2-yl)-5-(4-methanesulfonyl-phenoxy)-1H-benzimidazol-2-yl)-nicotinate The entitled compound was obtained as a yellow solid in the same method as in Example 307 or in accordance with the method or by combining it with an ordinary method but using pyridine-2,5-dicarboxylic acid 5-methyl ester.

$^1$HNMR (CDCl$_3$) δ: 1.20-2.40 (7H, m), 2.80-3.20 (3H, m), 3.40-4.00 (2H, m), 3.99 (3H, s), 5.05-5.45 (1H, m), 6.80-7.80 (4H, m), 7.80-8.05 (2H, m), 8.35-8.60 (2H, m), 9.10-9.30 (1H, m), 10.60-11.30 (1H, m)

ESI-MS (m/e): 535 [M+H]

Example 335

6-(6-(1-Acetyl-pyrrolidin-2-yl)-5-(4-methanesulfonyl-phenoxy)-1H-benzimidazol-2-yl)-nicotinic acid The entitled compound was obtained as a pale yellow solid in the same method as in Example 121 (step 6) or in accordance with the method or by combining it with an ordinary method but using methyl 6-(6-(1-acetyl-pyrrolidin-2-yl)-5-(4-methanesulfonyl-phenoxy)-1H-benzimidazol-2-yl)-nicotinate obtained in Example 33-4.

$^1$HNMR (DMSO-d6) δ: 1.60-2.60 (7H, m), 3.21 (3H, s), 3.60-4.00 (2H, m), 5.00-5.20 (1H, m), 6.90-7.60 (4H, m), 7.80-8.00 (2H, m), 8.30-8.60 (2H, m), 9.20 (1H, s)

ESI-MS (m/e): 521 [M+H]

Example 336

2-(6-(4-Methanesulfonyl-phenoxy)-2-pyridin-2-yl-3H-benzimidazol-5-yl)-pyrrolidin-1-carboxylic acid dimethylamide (Step 1) Production of 4-nitrophenyl 2-(6-(4-methanesulfonyl-phenoxy)-2-pyridin-2-yl-2,3-dihydro-1H-benzimidazol-5-yl)-pyrrolidin-1-carboxylate 0.060 ml of triethylamine and 21 mg of 4-nitrobenzoyl chloride were added in order to a tetrahydrofuran (1 ml) solution of 37 mg of 5-(4-methanesulfonyl-phenoxy)-2-pyridin-2-yl-6-pyrrolidin-2-yl-1H-benzimidazole enantiomer B obtained in Example 163, and the reaction liquid was stirred overnight at room temperature. The reaction solvent was evaporated away under reduced pressure, and the resulting residue was purified through partitioning thin-layer chromatography (Kieselgel™ 60F$_{254}$, Art 5744 (by Merck), chloroform/methanol=10/1) to obtain the entitled compound as a white solid.

(Step 2) Production of 2-(6-(4-methanesulfonyl-phenoxy)-2-pyridin-2-yl-3H-benzimidazol-5-yl)-pyrrolidine-1-carboxylic acid dimethylamide 1 ml of dimethylamine (2.0 M tetrahydrofuran solution) was added to a tetrahydrofuran (1 ml) solution of 20 mg of 4-nitrophenyl 2-(6-(4-methanesulfonyl-phenoxy)-2-pyridin-2-yl-2,3-dihydro-1H-benzimidazol-5-yl)-pyrrolidin-1-carboxylate, and the reaction liquid was stirred overnight in a sealed tube at 100° C. The reaction solvent was evaporated away under reduced pressure, and the resulting residue was purified through reversed-phase middle-pressure liquid chromatography [ODS-AS-360-CC (by YMC), mobile phase: water-acetonitrile-0.1% trifluoroacetic acid]. The solvent of the resulting fraction was diluted with ethyl acetate, washed with aqueous saturated sodium bicarbonate, and dried with anhydrous sodium sulfate. The solvent was evaporated away under reduced pressure to obtain the entitled compound as a white solid.
$^1$HNMR (CD$_3$OD) δ: 1.80-1.92 (2H, m), 1.94-2.07 (1H, m), 2.33-2.42 (1H, m), 2.80 and 2.85 (total 6H, each brs), 3.12 (3H, s), 3.52-3.58 (1H, m), 3.62-3.78 (1H, m), 5.19-5.26 (1H, m), 7.16-7.80 (5H, m), 7.91-7.99 (3H, m), 8.27 (1H, d, J=7.6 Hz), 8.73 (1H, brs)
ESI-MS (m/e): 506 [M+H]

Example 337

1-(2-(2-(6-Hydroxy-pyridin-2-yl-6-(4-methanesulfonyl-phenoxy)-3H-benzimidazol-5-yl)-pyrrolidin-1-yl)-ethanone The entitled compound was obtained as a yellow solid in the same method as in Example 307 or in accordance with the method or by combining it with an ordinary method but using 6-hydroxy-pyridine-2-carboxylic acid.
$^1$HNMR (CD$_3$OD) δ: 1.75-2.47 (7H, m), 2.97-3.26 (4H, m), 3.44-3.96 (2H, m), 5.20-5.40 (1H, m), 6.60-8.05 (10H, m)
ESI-MS (m/e): 493 [M+H]

Example 338

1-(2-(6-(4-Fluoro-phenylsulfanyl-2-pyridin-2-yl-3H-benzimidazol-5-yl)-pyrrolidin-1-yl)-ethanone (Step 1) Production of t-butyl 2-(4-amino-2-fluoro-phenyl)-pyrrole-1-carboxylate 1.6 g of 1-(t-butoxycarbonyl)pyrrole-2-boronic acid, 200 mg of tetrakistriphenylphosphine palladium, 5 ml of aqueous saturated sodium carbonate solution and 5 ml of water were added in order to a dimethoxyethane (10 ml) solution of 1 g of 4-bromo-3-fluoro-phenylamine, and the reaction liquid was stirred in a nitrogen atmosphere at 70° C. for 3 hours. After cooled, the reaction liquid was filtered through Celite, and the filtrate was diluted with ethyl acetate, washed with water and saturated saline in order, and dried with anhydrous magnesium sulfate. The solvent was evaporated away under reduced pressure, and the resulting residue was purified through silica gel column chromatography (developing solvent: hexane/ethyl acetate=2/1) to obtain the entitled compound as a pale brown solid.

(Step 2) Production of t-butyl 2-(4-amino-2-fluoro-phenyl)-pyrrolidine-1-carboxylate 5 ml of water and 660 mg of 5% platinum-carbon catalyst were added to a 2-propanol (50 ml) solution of 2.2 g of t-butyl 2-(4-amino-2-fluoro-phenyl)-pyrrole-1-carboxylate, and stirred in a hydrogen atmosphere under a pressure of 50 kgf/cm$^2$ at 50° C. for 1 day. The catalyst was removed through filtration through Celite, the solvent was evaporated away under reduced pressure, and the residue was purified through silica gel column chromatography (developing solvent: hexane/ethyl acetate=1/1) to obtain the entitled compound as a brown oily substance.

(Step 3) Production of pyridine-2-carboxylic acid-(4-(1-acetyl-pyrrolidin-2-yl)-3-fluoro-phenyl)-amide 90 mg of pyridine-2-carboxylic acid and 190 mg of 1-(3-dimethylaminopropyl)-3-ethylcarbodiimide monohydrochloride were added in order to a pyridine (2 ml) solution of 181 mg of t-butyl 2-(4-amino-2-fluoro-phenyl)-pyrrolidine-1-carboxylate, and the reaction liquid was stirred at room temperature for 3 hours. The reaction liquid was diluted with chloroform, washed with water and saturated saline, and dried with anhydrous magnesium sulfate. The solvent was evaporated away under reduced pressure, and 2 ml of 4 N hydrochloric acid-dioxane solution was added to 300 mg of the resulting residue, and the reaction liquid was stirred at room temperature for 1 hour. The reaction liquid was diluted with chloroform, and made basic with aqueous saturated sodium bicarbonate solution added thereto, and the organic layer was washed with saturated saline and dried with anhydrous magnesium sulfate. The solvent was evaporated away under reduced pressure, and 0.020 ml of acetic anhydride was added to a pyridine (1 ml) solution of the resulting residue, and the reaction liquid was stirred at room temperature for 20 minutes. The reaction liquid was diluted with chloroform, washed with water and saturated saline in order, and dried with anhydrous magnesium sulfate. The solvent was evaporated away under reduced pressure, and the resulting residue was purified through silica gel column chromatography (developing solvent: chloroform/methanol=50/1) to obtain the entitled compound as a yellow solid.

(Step 4) Production of pyridine-2-carboxylic acid-(4-(1-acetyl-pyrrolidin-2-yl)-5-fluoro-2-nitro-phenyl)-amide 94 mg of potassium nitrate was added to a trifluoroacetic acid (3 ml) solution of pyridine-2-carboxylic acid-(4-(1-acetyl-pyrrolidin-2-yl)-3-fluoro-phenyl)-amide, and the reaction liquid was stirred at room temperature for 2 days. The reaction liquid was distilled under reduced pressure, diluted with chloroform, and made basic with aqueous saturated sodium bicarbonate solution, and then extracted with chloroform. The organic layers were combined, washed with saturated saline, and dried with anhydrous magnesium sulfate. The solvent was evaporated away under reduced pressure, and the resulting residue was purified through silica gel column chromatography (developing solvent: chloroform/methanol=50/1) to obtain the entitled compound as a pale yellow solid.

(Step 5) Production of 1-(2-(6-(4-fluoro-phenylsulfanyl)-2-pyridin-2-yl-3H-benzimidazol-5-yl)-pyrrolidin-1-yl)-ethanone 20 mg of 4-fluoro-benzenethiol and 30 mg of potassium carbonate were added in order to an N,N-dimethylformamide (1 ml) solution of 50 mg of pyridine-2-carboxylic acid-(4-(1-acetyl-pyrrolidin-2-yl)-5-fluoro-2-nitro-phenyl)-amide, and the reaction liquid was stirred at 100° C. for 2 hours. 30 mg of tin(II) chloride dihydrate was added to the reaction liquid, and the reaction liquid was stirred at 100° C. for 3 hours. After cooled, the reaction liquid was diluted with aqueous saturated sodium bicarbonate and extracted with chloroform, and the organic layer was dried with anhydrous magnesium sulfate, and the solvent was evaporated away under reduced pressure. The resulting residue was purified through partitioning thin-layer chromatography (Kieselgel™ 60F$_{254}$, Art 5744 (by Merck), chloroform/methanol=10/1) to obtain the entitled compound as a white solid.

$^1$HNMR (CDCl$_3$) δ: 1.60-2.50 (7H, m), 3.60-4.00 (2H, m), 5.20-5.80 (1H, m), 6.90-7.10 (2H, m), 7.15-7.80 (5H, m), 7.80-8.00 (1H, m), 8.30-8.45 (1H, m), 8.55-8.70 (1H, m), 10.60-11.20 (1H, m)

ESI-MS (m/e): 433 [M+H]

Example 339

1-(2-(6-(4-methanesulfonyl-phenylsulfanyl)-2-pyridin-2-yl-3H-benzimidazol-5-yl)-pyrrolidin-1-yl)-ethanone The entitled compound was obtained as a white solid in the same method as in Example 338 (step 5) or in accordance with the method or by combining it with an ordinary method but using 4-methanesulfonyl-benzenethiol.

$^1$HNMR (CDCl$_3$) δ: 1.40-2.45 (7H, m), 2.80-3.20 (3H, m), 3.50-4.00 (2H, m), 5.20-5.65 (1H, m), 7.10-8.25 (8H, m), 8.30-8.50 (1H, m), 8.50-8.80 (1H, m), 10.60-11.40 (1H, m)

ESI-MS (m/e): 493 [M+H]

Example 340

N-(5-(6-(1-Acetyl-pyrrolidin-2-yl)-2-pyridin-2-yl-1H-benzimidazol-5-yloxy)-pyridin-2-yl)-acetamide

(Step 1) Production of 1-(2-(6-(6-amino-pyridin-3-yloxy)-2-pyridin-2-yl-3H-benzimidazol-5-yl)-pyrrolidin-1-yl)-ethanone 53.5 mg of 5-bromo-2-nitro-pyridine, 84.2 mg of cesium carbonate and 25 mg of copper(II) oxide were added to a pyridine (1 ml) solution of 55.0 mg of 1-(2-(6-hydroxy-2-pyridin-2-yl-3-(2-trimethylsilanyl-ethoxymethyl)-3H-benzimidazol-5-yl)-pyrrolidin-1-yl)-ethanone obtained in Example 121 (step 10), and the reaction liquid was stirred overnight in a sealed tube at 120° C. After cooled, aqueous saturated ammonium chloride and saturated saline were added in order to the reaction liquid, extracted with ethyl acetate and dried with anhydrous magnesium sulfate. The solvent was evaporated away under reduced pressure, and 0.016 ml of hydrazine monohydrate and 20 mg of developed Raney nickel catalyst were added to an ethanol (2 ml) solution of the resulting residue, and the reaction liquid was stirred at room temperature for 30 minutes. The catalyst was removed through filtration through Celite, and the solvent was evaporated away under reduced pressure. The resulting residue was purified through partitioning thin-layer chromatography (Kieselgel™ 60F$_{254}$, Art 5744 (by Merck), chloroform/methanol=9/1) to obtain the entitled compound as a yellow oily substance.

(Step 2) Production of N-(5-(6-(1-acetyl-pyrrolidin-2-yl)-2-pyridin-2-yl-1H-benzimidazol-5-yloxy)-pyridin-2-yl)-acetamide 0.005 ml of acetic anhydride was added to a pyridine (1 ml) solution of 13.7 mg of 1-(2-(6-(6-amino-pyridin-3-yloxy)-2-pyridin-2-yl-3H-benzimidazol-5-yl)-pyrrolidin-1-yl)-ethanone, and the reaction liquid was stirred at room temperature for 3 hours. The reaction liquid was evaporated away under reduced pressure, the resulting residue was dissolved in 1 ml of trifluoroacetic acid, and the reaction liquid was stirred at room temperature for 3 hours. The reaction liquid was distilled under reduced pressure, and the resulting residue was purified through reversed-phase middle-pressure liquid chromatography [ODS-AS-360-CC (by YMC), mobile phase: water-acetonitrile-0.1% trifluoroacetic acid] and through silica gel column chromatography (developing solvent: chloroform/methanol=9/1) to obtain the entitled compound as an oily substance.

$^1$HNMR (CDCl$_3$) δ: 1.64-2.44 (10H, m), 3.57-3.91 (2H, m), 5.26-5.62 (1H, m), 6.76-8.74 (10H, m), 10.59-11.31 (1H, m)

ESI-MS (m/e): 457 [M+H]

Example 341

1-(2-(6-(6-Acetyl-pyridin-3-yloxy)-2-pyridin-2-yl-3H-benzimidazol-5-yl)-pyrrolidin-1-yl)-ethanone The entitled compound was obtained as an oily substance in the same method as in Example 122 or in accordance with the method or by combining it with an ordinary method but using 1-(5-bromo-pyridin-2-yl)-ethanone.

$^1$HNMR (CDCl$_3$) δ: 1.66-2.42 (7H, m), 2.59-2.74 (3H, m), 3.51-3.90 (2H, m), 5.12-5.45 (1H, m), 6.85-8.10 (6H, m), 8.30-8.70 (3H, m), 10.86-11.24 (1H, m)

ESI-MS (m/e): 442 [M+H]

Example 342

2-(5-Bromo-pyridin-2l1)-5-(4-methanesulfonyl-phenoxy-6-pyrrolidin-2-yl-1H-benzimidazol enantiomer A and enantiomer B 100 mg of the racemic 2-(5-bromo-pyridin-2-yl)-5-(4-methanesulfonyl-phenoxy)-6-pyrrolidin-2-yl-1H-benzimidazol obtained in Example 306 was optically resolved, using an optical resolution column (CHIRALPAK AD 2 cmφ×25 cmL (by Daicel Chemical), mobile phase: hexane/isopropanol/diethylamine=20/80/0.1, flow rate: 10 ml/min), into an enantiomer A (retention time: 24 min) and an enantiomer B (retention time: 27 min) each as an oily substance.

Example 343

1-(2-(2-(5-Bromo-pyridin-2-yl-6-(4-methanesulfonyl-phenoxy)-3H-benzimidazol-5-yl)-pyrrolidin-1-yl)-ethanone enantiomer A 0.020 ml of acetic anhydride was added to a pyridine (1 ml) solution of 43 mg of 2-(5-bromo-pyridin-2-yl)-5-(4-methanesulfonyl-phenoxy)-6-pyrrolidin-2-yl-1H-benzimidazol enantiomer A obtained in Example 342, and the reaction liquid was stirred at room temperature for 10 minutes. Aqueous saturated sodium bicarbonate solution was added to the reaction liquid, and extracted with chloroform, and the organic layer was dried with anhydrous magnesium sulfate, and the solvent was evaporated away under reduced pressure. The resulting residue was purified through partitioning thin-layer chromatography (Kieselgel™ 60F$_{254}$, Art 5744 (by Merck), chloroform/methanol=10/1) to obtain the entitled compound as a white solid.

$^1$HNMR (CDCl$_3$) δ: 1.60-2.40 (7H, m), 2.80-3.20 (3H, m), 3.50-3.95 (2H, m), 5.05-5.45 (1H, m), 6.90-7.80 (5H, m), 7.80-8.00 (2H, m), 8.10-8.30 (1H, m), 8.60-8.80 (1H, m)

ESI-MS (m/e): 555, 557 [M+H]

Example 344

1-(2-(2-(5-Bromo-pyridin-2-yl)-6-(4-methanesulfonyl-phenoxy)-3H-benzimidazol-5-yl)-pyrrolidin-1-yl)-ethanone enantiomer B The entitled compound was obtained as a white solid in the same method as in Example 343 or in accordance with the method or by combining it with an ordinary method but using 2-(5-bromo-pyridin-2-yl)-5-(4-methanesulfonyl-phenoxy)-6-pyrrolidin-2-yl-1H-benzimidazol enantiomer B obtained in Example 342.

Example 345

1-(2-(6-(4-Methanesulfonyl)phenoxy)-2-(5-vinyl-pyridin-2-yl)-3H-benzimidazol-5-yl)-pyrrolidin-1-yl)-ethanone The entitled compound was obtained as a yellow solid in the same method as in Example 307 or in accordance with the method or by combining it with an ordinary method but using 5-vinyl-pyridine-2-carboxylic acid.

$^1$HNMR (CDCl$_3$) δ: 1.20-2.40 (7H, m), 2.90-3.15 (3H, m), 3.50-3.90 (2H, m), 5.00-5.45 (1H, m), 5.48 (1H, dd, J=5.6, 11.2 Hz), 5.94 (1H, dd, J=5.6, 17.6 Hz), 6.70-6.85 (1H, m), 7.00-7.25 (2H, m), 7.25-7.80 (2H, m), 7.80-8.00 (3H, m), 8.30-8.40 (1H, m), 8.55-8.70 (1H, m), 10.50-10.80 (1H, m)

ESI-MS (m/e): 503 [M+H]

Example 346

1-(2-(6-(6-(1-Hydroxy-1-methyl-ethyl)-pyridin-3-yloxy)-2-pyridin-2-yl-3H-benzimidazol-5-yl)-pyrrolidin-1-yl)-ethanone 0.1 ml of methyl lithium (1.0 M diethyl ether solution) was added to a tetrahydrofuran (1.5 ml) solution of 15.0 mg of 1-(2-(6-(6-acetyl-pyridin-3-yloxy)-2-pyridin-2-yl-3H-benzimidazol-5-yl)-pyrrolidin-1-yl)-ethanone obtained in Example 341, at −78° C., and the reaction liquid was stirred at −78° C. for 30 minutes. The reaction liquid was poured into aqueous saturated ammonium chloride solution, extracted with chloroform, and dried with anhydrous magnesium sulfate. The solvent was evaporated away under reduced pressure, and the resulting residue was purified through silica gel column chromatography (developing solvent: chloroform/methanol=7.5/1) to obtain the entitled compound as a yellow solid.

$^1$HNMR (CDCl$_3$) δ: 1.46-1.63 (6H, m), 1.63-2.47 (7H, m), 2.87-2.99 and 3.34-3.91 (total 3H, each m), 5.18-5.51 (1H, m), 6.72-7.91 (6H, m), 8.17-8.68 (3H, m), 10.54-10.94 (1H, br)

ESI-MS (m/e): 458 [M+H]

Example 347

Ethyl(5-(6-(1-acetyl-pyrrolidin-2-yl)-2-pyridin-2-yl-1H-benzimidazol-5-yloxy)-pyridin-2-yl)-carbamate 0.003 ml of ethyl chloroformate was added to a pyridine (1 ml) solution of 14.4 mg of 1-(2-(6-(6-amino-pyridin-3-yloxy)-2-pyridin-2-yl-3H-benzimidazol-5-yl)-pyrrolidin-1-yl)-ethanone obtained in Example 340 (step 1), and the reaction liquid was stirred at room temperature for 30 minutes. The reaction liquid was distilled under reduced pressure, and the resulting residue was dissolved in 1 ml of trifluoroacetic acid, and the reaction liquid was stirred at room temperature for 1 hour. The reaction liquid was distilled under reduced pressure, and the resulting residue was purified through reversed-phase middle-pressure liquid chromatography [ODS-AS-360-CC (by YMC), mobile phase: water-acetonitrile-0.1% trifluoroacetic acid] and through silica gel column chromatography (developing solvent: chloroform/methanol=9/1) to obtain the entitled compound as a yellow oily substance.

$^1$HNMR (CDCl$_3$) δ: 1.14-1.51 (3H, m), 1.52-2.46 (7H, m), 2.78-2.93 and 3.51-3.88 (total 3H, each m), 4.16-4.26 (2H, m), 5.27-5.63 (1H, m), 6.80-8.69 (10H, m)

ESI-MS (m/e): 487 [M+H]

Example 348

1-(2-(6-(6-(5-Methyl-[1,2,4]oxadiazol-3-yl)-pyridin-3-yloxy)-2-pyridin-2-yl-3H-benzimidazol-5-pyrrolidin-1-yl)-ethanone The entitled compound was obtained as a white solid in the same method as in Example 153 or in accordance with the method or by combining it with an ordinary method but using 5-bromo-2-cyano-pyridine.

$^1$HNMR (CDCl$_3$) δ: 1.49-2.42 (7H, m), 2.54-2.71 (3H, m), 3.50-3.88 (2H, m), 5.04-5.48 (1H, m), 7.00-8.67 (10H, m)

ESI-MS (m/e): 482 [M+H]

Example 349

3-(2-(6-(4-Methanesulfonyl-phenoxy-2-pyridin-2-yl-3H-benzimidazol-5-yl)-pyrrolidin-1-yl)-3-oxo-propionitrile The entitled compound was obtained as a white solid in the same method as in Example 296 or in accordance with the method or by combining it with an ordinary method but using cyanoacetic acid.

$^1$HNMR (CDCl$_3$) δ: 1.80-2.05 (4H, m), 3.05-3.25 (4H, m), 3.47-3.93 (3H, m), 5.19-5.41 (1H, m), 7.00-7.59 (5H, m), 7.82-7.99 (3H, m), 8.35-8.41 (1H, m), 8.62-8.68 (1H, m)

ESI-MS (m/e): 502 [M+H]

Example 350

Cyclopropyl-(2-(6-(4-methanesulfonyl-phenoxy)-2-pyridin-2-yl-3H-benzimidazol-5-yl)-pyrrolidin-1-yl) methanone The entitled compound was obtained as a white solid in the same method as in Example 296 or in accordance with the method or by combining it with an ordinary method but using cyclopropanecarboxylic acid.

$^1$HNMR (CDCl$_3$) δ: 0.92-1.08 (4H, m), 1.60-1.66 (2H, m), 1.85-1.99 (2H, m), 2.20-2.38 (1H, m), 3.05-3.08 (3H, m), 3.63-4.00 (2H, m), 5.33-5.41 (1H, m), 7.12-7.44 (5H, m), 7.86-7.92 (3H, m), 8.40-8.44 (1H, m), 8.60-8.68 (1H, m)
ESI-MS (m/e): 503 [M+H]

Example 351

3,3,3-Trifluoro-1-(2-(6-(4-methanesulfonyl phenoxy)-2-pyridin-2-yl-3H-benzimidazol-5-yl)-pyrrolidin-1-yl)-propan-1-one The entitled compound was obtained as a white solid in the same method as in Example 296 or in accordance with the method or by combining it with an ordinary method but using 3,3,3-trifluoro-propionic acid.

$^1$HNMR (CDCl$_3$) δ: 1.85-2.40 (4H, m), 2.90-3.27 (5H, m), 3.65-3.90 (2H, m), 5.15-5.43 (1H, m), 6.97-7.63 (5H, m), 7.84-7.96 (3H, m), 8.38-8.43 (1H, m), 8.60-8.68 (1H, m)
ESI-MS (m/e): 545 [M+H]

Example 352

(2-(6-(4-Methanesulfonyl-phenoxy)-2-pyridin-2-yl-3H-benzimidazol-5)-yl)-pyrrolidin-1-yl)-(tetrahydro-furan-2-yl)-methanone The entitled compound was obtained as a white solid in the same method as in Example 296 or in accordance with the method or by combining it with an ordinary method but using tetrahydrofuran-2-carboxylic acid.

$^1$HNMR (CDCl$_3$) δ: 1.85-2.33 (7H, m), 3.05-3.10 (3H, m), 3.63-4.08 (5H, m), 4.15-4.62 (1H, m), 5.33-5.62 (1H, m), 7.11-7.55 (5H, m), 7.84-7.95 (3H, m), 8.37-8.42 (1H, m), 8.60-8.67 (1H, m)
ESI-MS (m/e): 533 [M+H]

Example 353

N-(2-(2-(6-(4-Methanesulfonyl-phenoxy)-2-pyridin-2-yl-3H-benzimidazol-5-yl)-pyrrolidin-1-yl)-2-oxo-ethyl)-acetamide The entitled compound was obtained as a white solid in the same method as in Example 296 or in accordance with the method or by combining it with an ordinary method but using acetylamino-acetic acid.

$^1$HNMR (CDCl$_3$) δ: 1.90-2.05 (8H, m), 3.07-3.09 (3H, m), 3.47-4.01 (3H, m), 5.16-5.40 (1H, m), 6.52-6.70 (1H, m), 7.04-7.20 (2H, m), 7.33-7.57 (2H, m), 7.84-7.98 (3H, m), 8.35-8.38 (1H, m), 8.61-8.67 (1H, m)
ESI-MS (m/e): 534 [M+H]

Examples 354 (Diastereomer A), 355 (Diastereomer B)

1-(1-(6-(4-Methanesulfonyl-phenoxy)-2-pyridin-2-yl-3H-benzimidazol-5-yl)-pyrrolidin-2-yl)-ethanol diastereomer A and diastereomer B The entitled compound was obtained as a pale yellow solid, diastereomer mixture, in the same method as in Example 15 or in accordance with the method or by combining it with an ordinary method but using 5-fluoro-4-(4-methanesulfonyl-phenoxy)-2-nitro-phenylamine obtained in Example 14 and 1-pyrrolidin-2-yl-ethanol. The resulting diastereomer mixture was purified through partitioning thin-layer chromatography (Kieselgel™ 60F$_{254}$, Art 5744 (by Merck), chloroform/methanol=10/1) into the individual diastereomers A and B each as a pale yellow solid.

1-(1-(6-(4-Methanesulfonyl-phenoxy)-2-pyridin-2-yl-3H-benzimidazol-5-yl)-pyrrolidin-2-yl)-ethanol diastereomer A $^1$HNMR (CD$_3$OD) δ: 1.09 (3H, d, J=6.7 Hz), 1.66-1.78 (1H, m), 1.80-1.99 (3H, m), 3.06-3.18 (1H, m), 3.12 (3H, s), 3.61-3.69 (1H, m), 3.78-3.83 (1H, m), 3.90-3.99 (1H, m), 6.97-7.81 (5H, m), 7.89-8.00 (3H, m), 8.26 (1H, d, J=8.2 Hz), 8.74 (1H, d, J=4.7 Hz)
ESI-MS (m/e): 479 [M+H]

1-(1-(6-(4-Methanesulfonyl-phenoxy)-2-pyridin-2-yl-3H-benzimidazol-5-yl)-pyrrolidin-2-yl)-ethanol diastereomer B $^1$HNMR (CD$_3$OD) δ: 0.76 (3H, d, J=6.3 Hz), 1.70-1.82 (3H, m), 1.92-2.00 (1H, m), 3.06-3.13 (1H, m), 3.10 (3H, s), 3.61-3.69 (1H, m), 3.83-3.90 (1H, m), 3.95-4.03 (1H, m), 7.04 (2H, d, J=8.9 Hz), 7.37-7.44 (2H, m), 7.46-7.49 (1H, m), 7.89 (2H, d, J=8.9 Hz), 7.93-7.99 (1H, m), 8.27 (1H, d, J=7.8 Hz), 8.74 (1H, d, J=4.7 Hz)
ESI-MS (m/e): 479 [M+H]

Example 356

5-(2-(1-Fluoro-ethyl)-pyrrolidin-1-yl)-6-(4-methane-sulfonyl-phenoxy)-2-pyridin-2-yl-1H-benzimidazole 0.007 ml of diethylaminosulfur trifluoride was added to a chloroform (1 ml) solution of 21 mg of 1-(1-(6-(4-methanesulfonyl-phenoxy)-2-pyridin-2-yl-3H-benzimidazol-5-yl)-pyrrolidin-2-yl)-ethanol diastereomer A obtained in Example 354, at −78° C., and the reaction liquid was stirred at −78° C. for 1 hour. The reaction liquid was heated up to room temperature, and aqueous saturated sodium bicarbonate was added to the reaction liquid, and then extracted with ethyl acetate, and dried with anhydrous magnesium sulfate. The solvent was evaporated away, and the resulting residue was purified through partitioning thin-layer chromatography (Kieselgel™ 60F$_{254}$, Art 5744 (by Merck), chloroform/methanol=10/1) to obtain the entitled compound as a pale yellow solid.

$^1$HNMR (CD$_3$OD) δ: 1.18 and 1.24 (total 3H, each d, J=6.3, 6.7 Hz), 1.53-1.78 (1H, m), 1.83-2.00 (3H, m), 3.11 (3H, s), 3.11-3.20 (1H, m), 3.52-3.61 (1H, m), 3.89-4.01 (1H, m), 4.63-4.87 (1H, m), 7.04 (2H, d, J=9.0 Hz), 7.21-7.53 (3H, m), 7.89 (2H, d, J=9.0 Hz), 7.96-8.02 (1H, m), 8.27 (1H, d, J=7.8 Hz), 8.74 (1H, d, J=4.7 Hz)
ESI-MS (m/e): 481 [M+H]

Example 357

5-(2-(1-Fluoro-ethyl)-pyrrolidin-1-yl)-6-(4-methane-sulfonyl-phenoxy)-2-pyridin-2-yl-1H-benzimidazole The entitled compound was obtained as a pale yellow solid in the same method as in Example 356 or in accordance with the method or by combining it with an ordinary method but using 1-(1-(6-(4-methanesulfonyl-phenoxy)-2-pyridin-2-yl-3H-benzimidazol-5-yl)-pyrrolidin-2-yl)-ethanol diastereomer B obtained in Example 355.

¹HNMR (CD₃OD) δ: 0.99 and 1.09 (total 3H, each d, J=6.5, 6.2 Hz), 1.59-1.83 (3H, m), 1.93-2.03 (1H, m), 3.00-3.10 (1H, m), 3.09 (3H, s), 3.54-3.67 (1H, m), 4.10-4.19 (1H, m), 4.37-4.54 (1H, m), 7.04 (2H, d, J=8.9 Hz), 7.36-7.48 (3H, m), 7.86 (2H, d, J=8.9 Hz), 7.94-7.98 (1H, m), 8.25 (1H, d, J=7.8 Hz), 8.72 (1H, d, J=4.7 Hz)

ESI-MS (m/e): 481 [M+H]

Example 358

1-(1-(6-(4-Methanesulfonyl-phenoxy)-2-pyridin-2-yl-3H-benzimidazol-5-yl)-pyrrolidin-2-yl)-ethanone 0.080 ml of oxalyl chloride and 0.087 ml of dimethylsulfoxide were added in order to 3 ml of methylene chloride at −78° C., and the reaction liquid was stirred at −78° C. for 10 minutes, and then a methylene chloride (2 ml) solution of 146 mg of the diastereomer mixture of 1-(1-(6-(4-methanesulfonyl-phenoxy)-2-pyridin-2-yl-3H-benzimidazol-5-yl)-pyrrolidin-2-yl)-ethanol obtained in Examples 354 and 355, at −78° C. The reaction liquid was stirred at −78° C. for 30 minutes, and 0.42 ml of triethylamine was added to it, and the reaction mixture was stirred at −78° C. for 10 minutes, and then heated up to room temperature. Aqueous saturated ammonium chloride was added to the reaction liquid, extracted with ethyl acetate, and dried with anhydrous magnesium sulfate. The solvent was evaporated away under reduced pressure, and the resulting residue was purified through partitioning thin-layer chromatography (Kieselgel™ 60F₂₅₄, Art 5744 (by Merck), chloroform/methanol=10/1) to obtain the entitled compound as a pale yellow solid.

¹HNMR (CD₃OD) δ: 1.78-2.07 (3H, m), 1.94 (3H, s), 2.20-2.29 (1H, m), 3.06 (3H, s), 3.37-3.45 (1H, m), 3.64-3.77 (1H, m), 4.27-4.30 (1H, m), 6.80-7.44 (5H, m), 7.80-7.88 (3H, m), 8.27-8.40 (1H, m), 8.61-8.62 (1H, m)

ESI-MS (m/e): 477 [M+H]

Examples 359 (Enantiomer A), 360 (Enantiomer B)

1-(1-(6-(4-Methanesulfonyl-phenoxy-2-pyridin-2-yl-3H-benzimidazol-5-yl)-pyrrolidin-2-yl)-ethanone enantiomer A, and enantiomer B 27 mg of the racemic 1-(1-(6-(4-methanesulfonyl-phenoxy)-2-pyridin-2-yl-3H-benzimidazol-5-yl)-pyrrolidin-2-yl)-ethanone obtained in Example 358 was optically resolved, using an optical resolution column (CHIRALPAK AD-H 2 cmφ×25 cmL (by Daicel Chemical), mobile phase: ethanol, flow rate: 10 ml/min), into an enantiomer A (retention time: 20.8 min) and an enantiomer B (retention time: 46.9 min) each as a pale yellow solid.

1-(1-(6-(4-Methanesulfonyl-phenoxy)-2-pyridin-2-yl-3H-benzimidazol-5-yl)-pyrrolidin-2-yl)-ethanone enantiomer A ESI-MS (m/e): 477 [M+H]

1-(1-(6-(4-Methanesulfonyl-phenoxy)-2-pyridin-2-yl-3H-benzimidazol-5-yl)-pyrrolidin-2-yl)-ethanone enantiomer B ESI-MS (m/e): 477 [M+H]

Example 361

1-(1-(6-(6-Methanesulfonyl-pyridin-3-yloxy)-2-pyridin-2-yl-3H-benzimidazol-5-yl)-pyrrolidin-2-yl)-ethanone The entitled compound was obtained as a pale yellow solid in the same method as in Examples 354, 355 and 358 or in accordance with the method or by combining it with an ordinary method but using 5-fluoro-4-(6-methanesulfonyl-pyridin-3-yloxy)-2-nitro-phenylamine obtained in Example 196 (step 3) and 1-methyl-1-(2-pyrrolidinyl)ethanol.

¹HNMR (CD₃OD) δ: 1.80-2.10 (3H, m), 2.08 (3H, s), 2.28-2.39 (1H, m), 3.24 (3H, s), 3.40-3.47 (1H, m), 3.66-3.73 (1H, m), 4.46 (1H, t, J=7.4 Hz), 7.17 (1H, s), 7.40 (1H, s), 7.48 (1H, dd, J=2.7, 8.8 Hz), 7.54 (1H, dd, J=4.9, 7.6 Hz), 8.02 (1H, dt, J=0.8, 7.8 Hz), 8.07 (1H, dd, J=0.6, 8.8 Hz), 8.24 (1H, d, J=7.8 Hz), 8.46 (1H, dd, J=0.6, 2.7 Hz), 7.78 (1H, dt, J=0.8, 4.9 Hz)

ESI-MS (m/e): 478 [M+H]

Examples 362 (Enantiomer A), 363 (Enantiomer B)

1-(1-(6-(6-Methanesulfonyl-pyridin-3-yloxy-2-pyridin-2-yl-3H-benzimidazol-5-yl)-pyrrolidin-2-yl)-ethanone enantiomer A, and enantiomer B 34 mg of the racemic 1-(1-(6-(6-methanesulfonyl-pyridin-3-yloxy)-2-pyridin-2-yl-3H-benzimidazol-5-yl)-pyrrolidin-2-yl)-ethanone obtained in Example 361 was optically resolved, using an optical resolution column (CHIRALPAK AD-H 2 cmφ×25 cmL (by Daicel Chemical), mobile phase: ethanol, flow rate: 10 ml/min), into an enantiomer A (retention time: 28.8 min) and an enantiomer B (retention time: 48.2 min) each as a pale yellow solid.

1-(1-(6-(6-Methanesulfonyl-pyridin-3-yloxy-2-pyridin-2-yl-3H-benzimidazol-5-yl)-pyrrolidin-2-ethanone enantiomer A ESI-MS (m/e): 478 [M+H]

1-(1-(6-(6-Methanesulfonyl-pyridin-3-yloxy-2-pyridin-2-yl-3H-benzimidazol-5-yl)-pyrrolidin-2-yl)-ethanone enantiomer B ESI-MS (m/e): 478 [M+H]

Example 364

(2S)-1-(6-(4-methanesulfonyl-phenoxy)-2-pyridin-2-yl-3H-benzimidazol-5-yl)-pyrrolidine-2-carboxamide The entitled compound was obtained as a pale yellow solid in the same method as in Example 15 or in accordance with the method or by combining it with an ordinary method but using 5-fluoro-4-(4-methanesulfonyl-phenoxy)-2-nitro-phenylamine obtained in Example 14, and L-prolinamide hydrochloride.

¹HNMR (CDCl₃) δ: 1.91-2.03 (3H, m), 2.26-2.50 (1H, m), 3.02 and 3.06 (total 3H, each s), 3.18-3.28 (1H, m), 3.63-3.91 (1H, m), 4.19-4.23 (1H, m), 6.04-6.13 (1H, m), 6.86-7.28 (4H, m), 7.37-7.41 (1H, m), 7.48-7.54 (1H, m), 7.80-7.92 (3H, m), 8.34-8.38 (1H, m), 8.48-8.63 (1H, m)

ESI-MS (m/e): 478 [M+H]

Example 365

(2R)-1-(6-(4-methanesulfonyl-phenoxy)-2-pyridin-2-yl-3H-benzimidazol-5-yl)-pyrrolidine-2-carboxamide The entitled compound was obtained as a pale yellow solid in the same method as in Example 15 or in accordance with the method or by combining it with an ordinary method but using 5-fluoro-4-(4-methanesulfonyl-phenoxy)-2-nitro-phenylamine obtained in Example 14, and D-prolinamide.

$^1$HNMR (CDCl$_3$) δ: 1.91-2.03 (3H, m), 2.26-2.50 (1H, m), 3.02 and 3.06 (total 3H, each s), 3.18-3.28 (1H, m), 3.63-3.91 (1H, m), 4.19-4.23 (1H, m), 6.04-6.13 (1H, m), 6.86-7.28 (4H, m), 7.37-7.41 (1H, m), 7.48-7.54 (1H, m), 7.80-7.92 (3H, m), 8.34-8.38 (1H, m), 8.48-8.63 (1H, m)

ESI-MS (m/e): 478 [M+H]

Example 366

6-((3R)-3-fluoro-pyrrolidin-1-yl)-5-(4-methanesulfonyl-phenoxy)-2-pyridin-2-yl-1H-benzimidazole The entitled compound was obtained as a yellow oily substance in the same method as in Example 15 or in accordance with the method or by combining it with an ordinary method but using 5-fluoro-4-(4-methanesulfonyl-phenoxy)-2-nitro-phenylamine obtained in Example 14, and (R)-3-fluoropyrrolidine.

$^1$HNMR (CD$_3$OD) δ: 1.95-2.40 (2H, m), 3.10 (3H, s), 3.25-3.73 (4H, m), 5.14-5.40 (1H, m), 7.06 (2H, d, J=8.9 Hz), 7.07-7.20 (1H, m), 7.32-7.40 (1H, m), 7.42-7.48 (1H, m), 7.89 (2H, d, J=8.9 Hz), 7.93-7.99 (1H, m), 8.23 (1H, d, J=8.2 Hz), 8.71 (1H, d, J=5.1 Hz)

ESI-MS (m/e): 453 [M+H]

Example 367

1-(6-(4-Methanesulfonyl-phenol)-2-pyridin-2-yl-3H-benzimidazol-5-yl)-pyrrolidine-3-carboxamide The entitled compound was obtained in the same method as in Example 15 or in accordance with the method or by combining it with an ordinary method but using 5-fluoro-4-(4-methanesulfonyl-phenoxy)-2-nitro-phenylamine obtained in Example 14, and pyrrolidine-3-carboxamide.

$^1$HNMR (CDCl$_3$) δ: 2.03-2.30 (2H, m), 2.89-2.99 (1H, m), 3.06 (3H, s), 3.24-3.60 (4H, m), 5.70-5.86 (2H, m), 7.00-7.48 (5H, m), 7.80-7.90 (3H, m), 8.34-8.40 (1H, m), 8.57-8.64 (1H, m)

ESI-MS (m/e): 478 [M+H]

Example 368

(2R)-1-(6-(4-Methanesulfonyl-phenoxy)-2-pyridin-2-yl-3H-benzimidazol-5-yl)-pyrrolidine-2-carboxylic acid methoxy-methyl-amide The entitled compound was obtained in the same method as in Example 15 or in accordance with the method or by combining it with an ordinary method but using 5-fluoro-4-(4-methanesulfonyl-phenoxy)-2-nitro-phenylamine obtained in Example 14, and (R)—N-methoxy-N-methylprolinamide.

$^1$HNMR (CD$_3$OD) δ: 1.83-2.05 (3H, m), 2.25-2.40 (1H, m), 3.09 (3H, brs), 3.13 (3H, s), 3.40-3.47 (1H, m), 3.68-3.78 (1H, m), 3.84 (3H, brs), 4.90-5.09 (1H, m), 7.06-7.30 (4H, m), 7.42-7.50 (1H, m), 7.87-8.00 (3H, m), 8.19-8.28 (1H, m), 8.70-8.76 (1H, m)

ESI-MS (m/e): 522 [M+H]

Example 369

(2R)-1-(1-(6-(6-ethanesulfonyl-pyridin-3-yloxy)-2-pyridin-2-yl-3H-benzimidazol-5-yl)-pyrrolidin-2-yl)-ethanone The entitled compound was obtained as a pale yellow solid in the same method as in Examples 354, 355 and 358 or in accordance with the method or by combining it with an ordinary method but using 4-(6-ethanesulfonyl-pyridin-3-yloxy)-5-fluoro-2-nitro-phenylamine obtained in Example 221 (step 2) and 1-(R)-pyrrolidin-2-yl-ethanol.

$^1$HNMR (CD$_3$OD) δ: 1.24 (3H, t, J=7.4 Hz), 1.78-2.03 (3H, m), 2.03 (3H, s), 2.22-2.35 (1H, m), 3.30-3.43 (1H, m), 3.39 (2H, q, J=7.4 Hz), 3.64-3.75 (1H, m), 4.35-4.42 (1H, m), 7.03-7.48 (4H, m), 7.90-7.99 (1H, m), 8.03 (1H, d, J=8.6 Hz), 8.17-8.28 (1H, m), 8.43-8.46 (1H, m), 8.70-8.75 (1H, m)

ESI-MS (m/e): 492 [M+H]

Example 370

(2R)-1-(1-(6-(6-ethanesulfonyl-pyridin-3-yloxy)-2-pyrazin-2-yl-3H-benzimidazol-5-yl)-pyrrolidin-2-yl) ethanone The entitled compound was obtained as a pale yellow solid in the same method as in Examples 205 and 358 or in accordance with the method or by combining it with an ordinary method but using 4-(6-ethanesulfonyl-pyridin-3-yloxy)-5-fluoro-2-nitro-phenylamine obtained in Example 225 (step 2) and 1-(R)-pyrrolidin-2-yl-ethanol.

$^1$HNMR (CD$_3$OD) δ: 1.24 (3H, t, J=7.4 Hz), 1.80-2.03 (3H, m), 2.04 (3H, s), 2.24-2.34 (1H, m), 3.30-3.45 (1H, m), 3.39 (2H, q, J=7.4 Hz), 3.63-3.74 (1H, m), 4.37-4.44 (1H, m), 7.07 (1H, brs), 7.22-7.50 (2H, m), 8.03-8.05 (1H, m), 8.42-8.46 (1H, m), 8.63-8.66 (1H, m), 8.73 (1H, d, J=1.6 Hz), 9.37-9.43 (1H, m)

ESI-MS (m/e): 493 [M+H]

Example 371

(2R)-1-(1-(6-(4-ethanesulfonyl-phenoxy)-2-pyridin-2-yl-3H-benzimidazol-5-yl)-pyrrolidin-2-yl)-ethanone The entitled compound was obtained as a pale yellow solid in the same method as in Example 369 or in accordance with the method or by combining it with an ordinary method but using 4-(4-ethanesulfonyl-phenoxy)-5-fluoro-2-nitro-phenylamine obtained in Example 259 (step 1) and 1-(R)-pyrrolidin-2-yl-ethanol.

$^1$HNMR (CD$_3$OD) δ: 1.25 (3H, t, J=7.4 Hz), 1.81-2.03 (3H, m), 2.02 (3H, s), 2.24-2.33 (1H, m), 3.22 (2H, q, J=7.4 Hz), 3.38-3.46 (1H, m), 3.72-3.79 (1H, m), 4.40 (1H, t, J=7.5 Hz), 7.10-7.12 (3H, m), 7.29 (1H, s), 7.45-7.48 (1H, m), 7.87-7.90 (2H, m), 7.90-7.98 (1H, m), 8.24 (1H, d, J=7.6 Hz), 8.72 (1H, d, J=4.9 Hz)

ESI-MS (m/e): 491 [M+H]

Example 372

(2R)-1-(1-(6-(4-ethanesulfonyl-phenoxy)-2-pyrrolidin-2-yl-3H-benzimidazol-5-yl)-pyrrolidin-2-yl)-ethanone The entitled compound was obtained as a pale yellow solid in the same method as in Example 369 or in accordance with the method or by combining it with an ordinary method but using 4-(4-ethanesulfonyl-phenoxy)-5-fluoro-2-nitro-phenylamine obtained in Example 259 (step 1) and 1-(R)-pyrrolidin-2-yl-ethanol.
$^1$HNMR (CD$_3$OD) δ: 1.25 (3H, t, J=7.4 Hz), 1.82-2.04 (3H, m), 2.04 (3H, s), 2.24-2.34 (1H, m), 3.22 (2H, q, J=7.4 Hz), 3.34-3.50 (1H, m), 3.70-3.79 (1H, m), 4.38-4.48 (1H, m), 7.00-7.38 (4H, m), 7.89 (2H, d, J=9.0 Hz), 8.66 (1H, brs), 8.75 (1H, dd, J=1.6, 2.5 Hz), 9.38-9.48 (1H, m)
ESI-MS (m/e): 492 [M+H]

Example 373

(2R)-1-(1-(6-(6-ethanesulfonyl-pyridin-3-yloxy)-2-pyridin-2-yl-3H-benzimidazol-5-yl)-pyrrolidin-2-yl)-propan-1-ol The entitled compound was obtained as a pale yellow solid in the same method as in Example 369 or in accordance with the method or by combining it with an ordinary method but using 5-fluoro-4-(6-ethanesulfonyl-pyridin-3-yloxy)-2-nitro-phenylamine obtained in Example 221 (step 2) and 1-(R)-pyrrolidin-2-yl-propanol.
$^1$HNMR (CD$_3$OD) δ: 0.93 (3H, t, J=7.2 Hz), 1.25-1.27 (3H, m), 1.75-2.00 (3H, m), 2.23-2.53 (3H, m), 3.33-3.44 (3H, m), 3.71 (2H, q, J=7.3 Hz), 4.43 (1H, t, J=7.6 Hz), 7.14 (1H, s), 7.38 (1H, s), 7.45-7.50 (2H, m), 7.93-8.00 (1H, m), 8.06 (1H, d, J=8.8 Hz), 8.25 (1H, d, J=8.0 Hz), 8.45 (1H, d, J=2.9 Hz), 8.73 (1H, d, J=4.9 Hz)
ESI-MS (m/e): 506 [M+H]

Example 374

(2R)-2-(1-(6-(6-ethanesulfonyl-pyridin-3-yloxy-2-pyridin-2-yl-3H-benzimidazol-5-yl)-pyrrolidin-2-yl)-ol-2-ol The entitled compound was obtained in the same method as in Example 369 or in accordance with the method or by combining it with an ordinary method but using 5-fluoro-4-(6-ethanesulfonyl-pyridin-3-yloxy)-2-nitro-phenylamine obtained in Example 221 (step 2) and (R)-1-methyl-1-(2-pyrrolidinyl)ethanol.
$^1$HNMR (CD$_3$OD) δ: 0.85 and 0.87 (total 6H, each s), 1.22 (3H, t, J=7.3 Hz), 1.59-1.84 (3H, m), 1.93-2.05 (1H, m), 3.08-3.17 (1H, m), 3.31-3.40 (2H, m), 3.53-3.61 (1H, m), 4.00-4.03 (1H, m), 7.43-7.64 (4H, m), 7.91-7.98 (1H, m), 8.02 (1H, d, J=8.8 Hz), 8.25 (1H, d, J=7.8 Hz), 8.45 (1H, d, J=2.7 Hz), 8.71-8.73 (1H, m)
ESI-MS (m/e): 508 [M+H]

Example 375

(2R,4R)-4-hydroxy-1-(6-(4-methanesulfonyl-phenoxy)-2-pyridin-2-yl-3H-benzimidazol-5-yl)-pyrrolidine-2-carboxamide The entitled compound was obtained as a pale yellow solid in the same method as in Example 15 or in accordance with the method or by combining it with an ordinary method but using cis-4-hydroxy-D-prolinamide.
$^1$HNMR (CD$_3$OD) δ: 1.94-2.00 (1H, m), 2.50-2.59 (1H, m), 3.11 (3H, s), 3.38-3.44 (1H, m), 3.73-3.77 (1H, m), 4.23-4.28 (1H, m), 4.36-4.42 (1H, m), 7.12 (2H, d, J=9.0 Hz), 7.24 (1H, s), 7.33 (1H, s), 7.44-7.47 (1H, m), 7.89-7.97 (3H, m), 8.21-8.24 (1H, m), 8.70-8.72 (1H, m)
ESI-MS (m/e): 494 [M+H]

Example 376

(2R,4S)-4-fluoro-1-(6-(4-methanesulfonyl-phenoxy)-2-pyridin-2-yl-3H-benzimidazol-5-yl)-pyrrolidine-2-carboxamide The entitled compound was obtained as a pale yellow solid in the same method as in Example 356 or in accordance with the method or by combining it with an ordinary method but using (2R,4R)-4-hydroxy-1-(6-(4-methanesulfonyl-phenoxy)-2-pyridin-2-yl-3H-benzimidazol-5-yl)-pyrrolidine-2-carboxamide obtained in Example 375.
$^1$HNMR (CD$_3$OD) δ: 2.01-2.21 (1H, m), 2.54-2.67 (1H, m), 3.13 (3H, s), 3.48 (1H, dd, J=12.8, 27.2 Hz), 4.09 (1H, ddd, J=3.6, 12.8, 39.7 Hz), 4.48 (1H, dd, J=6.4, 10.0 Hz), 5.20-5.34 (1H, m), 7.15 (2H, d, J=8.8 Hz), 7.25 (1H, brs), 7.41 (1H, brs), 7.46-7.49 (1H, m), 7.92-7.99 (3H, m), 8.26 (1H, d, J=8.0 Hz), 8.73 (1H, d, J=4.7 Hz)
ESI-MS (m/e): 496 [M+H]

Example 377

(2R,4S)-4-hydroxy-1-(6-(4-methanesulfonyl-phenoxy-2-pyridin-2-yl-3H-benzimidazol-5-yl)-pyrrolidine-2-carboxamide The entitled compound was obtained as a pale yellow solid in the same method as in Example 15 or in accordance with the method or by combining it with an ordinary method but using trans-4-hydroxy-D-prolinamide.
$^1$HNMR (CD$_3$OD) δ: 2.00-2.07 (1H, m), 2.33-2.39 (1H, m), 3.13 (3H, s), 3.25 (1H, d, J=10.8 Hz), 4.00 (1H, dd, J=4.1, 10.8 Hz), 4.44-4.50 (2H, m), 7.14 (2H, d, J=9.0 Hz), 7.23 (1H, brs), 7.37 (1H, brs), 7.46-7.49 (1H, m), 7.92-7.99 (3H, m), 8.25 (1H, d, J=8.0 Hz), 8.73 (1H, d, J=4.7 Hz)
ESI-MS (m/e): 494 [M+H]

Example 378

1-((2R,4R)-1-(6-(6-ethanesulfonyl-pyridin-3-yloxy)-2-pyridin-2-yl-3H-benzimidazol-5-yl)-4-hydroxy-pyrrolidin-2-yl)-ethanone (Step 1) Production of (2R,4R)-1-(6-(6-ethanesulfonyl-pyridin-3-yloxy)-2-pyridin-2-yl-3H-benzimidazol-5-yl)-4-hydroxy-pyrrolidin-2-carboxylic acid methoxy-methyl-amide The entitled compound was obtained as a pale yellow solid in the same method as in Example 369 or in accordance with the method or by combining it with an ordinary method but using (2R,4R)-4-hydroxy-pyrrolidine-2-carboxylic acid methoxy-methylamide obtained in Reference Example 5.

(Step 2) Production of 1-((2R,4R)-1-(6-(6-ethanesulfonyl-pyridin-3-yloxy)-2-pyridin-2-yl-3H-benzimidazol-5-yl)-4-hydroxy-pyrrolidin-2-yl)-ethanone 0.360 ml of methyl lithium (1.0 M diethyl ether solution was added to a tetrahydrofuran (1 ml) solution of 20 mg of (2R,4R)-1-(6-(6-ethanesulfonyl-pyridin-3-yloxy)-2-pyridin- 2-yl-3H-benzimidazol-5-yl)-4-hydroxy-pyrrolidin-2-carboxylic acid methoxy-methyl-amide obtained in (step 1), at −78° C. The reaction liquid was stirred at −78° C. for 1 hour, heated up to 0° C. and stirred for 1 hour. Aqueous saturated ammonium chloride solution was added to the reaction liquid, extracted with ethyl acetate, and dried with anhydrous magnesium sulfate. The solvent was evaporated away under reduced pressure, and the resulting residue was purified through partitioning thin-layer chromatography (Kieselgel™ 60F$_{254}$, Art 5744 (by Merck), chloroform/methanol=10/1) to obtain the entitled compound as a pale yellow solid.

$^1$HNMR (CD$_3$OD) δ: 1.24 (3H, t, J=7.4 Hz), 1.79-1.88 (1H, m), 2.08 (3H, s), 2.43-2.54 (1H, m), 3.33 (2H, q, J=7.4 Hz), 3.46-3.63 (2H, m), 4.34-4.43 (2H, m), 7.10 (1H, brs), 7.39 (1H, brs), 7.43-7.50 (2H, m), 7.93-7.97 (1H, m), 8.04 (1H, d, J=8.8 Hz), 8.23 (1H, d, J=8.0 Hz), 8.46 (1H, d, J=2.7 Hz), 8.71 (1H, d, J=4.3 Hz)

ESI-MS (m/e): 508 [M+H]

Example 379

1-((2R,4S)-1-(6-(6-ethanesulfonyl-pyridin-3-yloxy)-2-pyridin-2-yl-3H-benzimidazol-5-yl)-4-fluoro-pyrrolidin-2-yl)-ethanone The entitled compound was obtained as a pale yellow solid in the same method as in Example 356 or in accordance with the method or by combining it with an ordinary method but using 1-((2R,4R)-1-(6-(6-ethanesulfonyl-pyridin-3-yloxy)-2-pyridin-2-yl-3H-benzimidazol-5-yl)-4-hydroxy-pyrrolidin-2-yl)-ethanone obtained in Example 378.

$^1$HNMR (CDCl$_3$) δ: 1.31 (3H, t, J=7.4 Hz), 1.80-2.05 (1H, m), 1.96 and 2.02 (total 3H, each s), 2.26-2.60 (1H, m), 3.30-3.43 (2H, m), 3.43-3.66 (1H, m), 3.70-4.04 (1H, m), 4.50-4.64 (1H, m), 5.12-5.37 (1H, m), 6.90-7.56 (4H, m), 7.80-7.91 (1H, m), 7.93-8.02 (1H, m), 8.30-8.68 (3H, m)

ESI-MS (m/e): 510 [M+H]

Example 380

1-((2R,4S)-1-(6-(6-ethanesulfonyl-pyridin-3-yloxy)-2-pyrazin-2-yl-3H-benzimidazol-5-yl)-4-fluoro-pyrrolidin-2-yl)-ethanone The entitled compound was obtained as a pale yellow solid in the same method as in Example 370, Example 378 (step 2) and Example 356 or in accordance with the method or by combining it with an ordinary method but using (2R,4R)-4-hydroxy-pyrrolidine-2-carboxylic acid methoxy-methylamide obtained in Reference Example 5.

$^1$HNMR (CD$_3$OD) δ: 1.25 (3H, t, J=7.4 Hz), 1.98-2.20 (1H, m), 2.05 (3H, s), 2.48-2.61 (1H, m), 3.41 (2H, q, J=7.4 Hz), 3.56 (1H, dd, J=11.9, 24.5 Hz), 3.99 (1H, ddd, J=3.1, 11.9, 39.1 Hz), 4.65 (1H, dd, J=6.6, 10.3 Hz), 5.22-5.36 (1H, m), 7.13 (1H, brs), 7.48-7.50 (2H, m), 8.05 (1H, dd, J=0.6, 8.8 Hz), 8.52 (1H, d, J=2.8 Hz), 8.67 (1H, d, J=2.5 Hz), 8.76 (1H, dd, J=1.4, 2.5 Hz), 9.43 (1H, d, J=1.4 Hz)

ESI-MS (m/e): 511 [M+H]

Example 381

5-(2-Fluoro-phenoxy)-2-pyridin-2-yl-6-(4-methanesulfonyl-phenoxy)-1H-benzimidazole The entitled compound was obtained as a colorless solid in the same method as in Example 196 (step 4) to (step 6) or in accordance with the method or by combining it with an ordinary method but using 5-fluoro-4-(4-methanesulfonyl-phenoxy)-2-nitro-phenylamine obtained in Example 14 and 2-fluorophenol.

$^1$HNMR (CD$_3$OD) δ: 3.10 (3H, s), 6.98-7.05 (1H, m), 7.07-7.21 (5H, m), 7.21-7.66 (3H, m), 7.88 (2H, d, J=9.0 Hz), 7.98 (1H, t, J=7.6 Hz), 8.28 (1H, d, J=8.2 Hz), 8.74 (1H, s)

ESI-MS (m/e): 476 [M+H]

Example 382

5-(2-Fluoro-phenoxy)-2-pyrazin-2-yl-6-(4-methanesulfonyl-phenoxy)-1H-benzimidazole The entitled compound was obtained as a brown solid in the same method as in Example 205 or in accordance with the method or by combining it with an ordinary method but using 5-(4-methanesulfonyl-phenoxy)-4-(2-fluoro-phenoxy)-benzene-1,2-diamine obtained in Example 381.

$^1$HNMR (CD$_3$OD) δ: 3.11 (3H, s), 7.00-7.08 (1H, m), 7.08-7.70 (5H, m), 7.11 (2H, d, J=8.8 Hz), 7.90 (2H, d, J=8.8 Hz), 8.71 (1H, s), 8.78 (1H, s), 9.47 (1H, s)

ESI-MS (m/e): 477 [M+H]

Example 383

5-(2,3-Difluoro-phenoxy)-2-pyridin-2-yl-6-(6-methanesulfonyl-pyridin-3-yloxy-1H-benzimidazole The entitled compound was obtained as a pale yellow solid in the same method as in Example 196 (step 4) to (step 6) or in accordance with the method or by combining it with an ordinary method but using 2,3-difluorophenol.

$^1$HNMR (CD$_3$OD) δ: 3.20 (3H, s), 6.79-6.83 (1H, m), 6.98-7.12 (2H, m), 7.17-7.80 (4H, m), 7.98-8.05 (2H, m), 8.27-8.35 (1H, m), 8.39 (1H, d, J=2.7 Hz), 8.64-8.79 (1H, m)

ESI-MS (m/e): 495 [M+H]

Example 384

5-(2,4-Difluoro-phenoxy)-2-pyridin-2-yl-6-(6-methanesulfonyl-pyridin-3-yloxy)-1H-benzimidazole The entitled compound was obtained as a pale yellow solid in the same method as in Example 196 (step 4) to (step 6) or in accordance with the method or by combining it with an ordinary method but using 2,4-difluorophenol.

$^1$HNMR (CD$_3$OD) δ: 3.21 (3H, s), 6.91-7.41 (4H, m), 7.47-7.75 (3H, m), 7.98-8.06 (2H, m), 8.27-8.33 (1H, m), 8.40-8.45 (1H, m), 8.66-8.76 (1H, m)

ESI-MS (m/e): 495 [M+H]

Example 385

5-(2,5-Difluoro-phenoxy)-2-pyridin-2-yl-6-(6-methanesulfonyl-pyridin-3-yloxy-1H-benzimidazole The entitled compound was obtained as a pale yellow solid in the same method as in Example 196 (step 4) to (step 6) or in accordance with the method or by combining it with an ordinary method but using 2,5-difluorophenol.

$^1$HNMR (CD$_3$OD) δ: 3.20 (3H, s), 6.85-6.95 (2H, m), 7.24 (1H, td, J=9.6, 5.1 Hz), 7.53 (1H, s), 7.56 (1H, dd, J=8.6, 2.7 Hz), 7.64 (1H, dd, J=7.8, 4.7 Hz), 7.81 (1H, s), 8.05 (1H, d, J=8.6 Hz), 8.10 (1H, t, J=7.8 Hz), 8.33 (1H, d, J=7.8 Hz), 8.43 (1H, d, J=2.7 Hz), 8.84 (1H, d, J=4.7 Hz)

ESI-MS (m/e): 495 [M+H]

Example 386

5-(2,6-Difluoro-phenoxy)-2-pyridin-2-yl-6-(6-methanesulfonyl-pyridin-3-yloxy)-1H-benzimidazole The entitled compound was obtained as a pale yellow solid in the same method as in Example 196 (step 4) to (step 6) or in accordance with the method or by combining it with an ordinary method but using 2,6-difluorophenol.

1HNMR (CD$_3$OD) δ: 3.22 (3H, s), 7.09-7.17 (2H, m), 7.14 (2H, t, J=8.2 Hz), 7.26-7.32 (1H, m), 7.47-7.52 (1H, m), 7.55 (1H, dd, J=9.0, 2.3 Hz), 7.98 (1H, t, J=7.8 Hz), 8.07 (1H, d, J=9.0 Hz), 8.27 (1H, d, J=7.8 Hz), 8.51 (1H, d, J=2.3 Hz), 8.72-8.74 (1H, m)

ESI-MS (m/e): 495 [M+H]

Example 387

5-(2,5-Difluoro-phenoxy)-2-pyrazin-2-yl-6-(6-methanesulfonyl-pyridin-3-yloxy)-1H-benzimidazole The entitled compound was obtained as a pale yellow solid in the same method as in Example 205 or in accordance with the method or by combining it with an ordinary method but using 4-(2,5-difluoro-phenoxy)-5-(6-methanesulfonyl-pyridin-3-yloxy)-benzene-1,2-diamine obtained in Example 385.

1HNMR (CD$_3$OD) δ:
3.21 (3H, s), 6.75-6.92 (2H, m), 7.17-7.24 (1H, m), 7.35-7.85 (2H, m), 7.52 (1H, dd, J=8.6, 2.7 Hz), 8.04 (1H, d, J=8.6 Hz), 8.41 (1H, d, J=2.7 Hz), 8.73 (1H, s), 8.79 (1H, s), 9.50 (1H, s)

ESI-MS (m/e): 496 [M+H]

Example 388

5-(3,4-Difluoro-phenoxy)-2-pyrazin-2-yl-6-(6-methanesulfonyl-pyridin-3-yloxy)-1H-benzimidazole The entitled compound was obtained as a pale yellow solid in the same method as in Example 383 and Example 387 or in accordance with the method or by combining it with an ordinary method but using 3,4-difluorophenol.

1HNMR (CD$_3$OD) δ: 3.18 (3H, s), 6.65 (1H, brs), 6.80 (1H, brs), 7.17 (1H, q, J=9.4 Hz), 7.46 (1H, dd, J=8.6, 2.7 Hz), 7.49-7.80 (2H, m), 8.00 (1H, d, J=8.6 Hz), 8.33 (1H, d, J=2.7 Hz), 8.69 (1H, s), 8.76 (1H, s), 9.46 (1H, s)

ESI-MS (m/e): 496 [M+H]

Example 389

5-(3,5-Difluoro-phenoxy)-2-pyrazin-2-yl-6-(6-methanesulfonyl-pyridin-3-yloxy)-1H-benzimidazole The entitled compound was obtained as a pale yellow solid in the same method as in Example 388 or in accordance with the method or by combining it with an ordinary method but using 3,5-difluorophenol.

1HNMR (CD$_3$OD) δ: 3.22 (3H, s), 6.41-6.49 (2H, m), 6.60-6.69 (1H, m), 7.50 (1H, dd, J=8.6, 2.7 Hz), 7.54-7.82 (2H, m), 8.04 (1H, d, J=8.6 Hz), 8.36 (1H, d, J=2.7 Hz), 8.74 (1H, brs), 8.80 (1H, brs), 9.52 (1H, s)

ESI-MS (m/e): 496 [M+H]

Example 390

5-(2-Difluoromethoxypyridin-3-yloxy)-6-(6-methanesulfonyl-pyridin-3-yloxy)-2-(5-methyl-pyrazin-2-yl)-1H-benzimidazole The entitled compound was obtained as a pale yellow solid in the same method as in Example 38 or in accordance with the method or by combining it with an ordinary method but using 4-(2-difluoromethoxy-pyridin-3-yloxy)-5-(6-methanesulfonyl-pyridin-3-yloxy)-benzene-1,2-diamine obtained in Example 215 and 5-methyl-pyrazine-2-carboxylic acid.

1HNMR (CD$_3$OD) δ: 2.65 (3H, s), 3.18 (3H, s), 7.15 (1H, dd, J=8.0, 4.9 Hz), 7.32-7.80 (2H, m), 7.40 (1H, d, J=7.4 Hz), 7.45 (1H, dd, J=8.8, 2.7 Hz), 7.46 (1H, t, J=72.6 Hz), 7.93 (1H, dd, J=4.9, 1.4 Hz), 8.01 (1H, dd, J=8.8, 0.6 Hz), 8.35 (1H, dd, J=2.7, 0.6 Hz), 8.67 (1H, d, J=1.0 Hz), 9.32 (1H, d, J=1.3 Hz)

ESI-MS (m/e): 541 [M+H]

Example 391

5-Phenoxy-2-pyrazin-2-yl-6-(6-ethanesulfonyl-pyridin-3-yloxy)-1H-benzimidazole (Step 1) Production of pyrazine-2-carboxylic acid (5-fluoro-4-(6-methanesulfonyl-pyridin-3-yloxy)-2-nitro-phenyl)-amide 3.8 g of pyrazine-2-carboxylic acid, 4.1 g of 1-hydroxybenzotriazole and 5.8 g of 1-(3-dimethylaminopropyl)-3-ethylcarbodiimide monohydrochloride were added to a dimethylformamide (75 ml) solution of 7.5 g of 3-fluoro-4-(6-methanesulfonyl-pyridin-3-yloxy)-phenylamine obtained in Example 221 (step 1), and the reaction liquid was stirred overnight at room temperature. Water was added to the reaction liquid, and the precipitated deposit was taken out through filtration to obtain 8.0 g of a crude product. 0.44 ml of fuming nitric acid was added to a trifluoroacetic acid (35 ml) solution of 3.6 g of the resulting crude product, and the reaction liquid was stirred overnight at room temperature, and the solvent was evaporated away under reduced pressure. Water was added to the residue, and the precipitated deposit was taken out through filtration to obtain the entitled compound.

(Step 2) Production of 5-(2,5-difluoro-phenoxy)-2-pyrazin-2-yl-6-(6-methanesulfonyl-pyridin-3-yloxy)-1H-benzimidazole 15 mg of 2,5-difluoro-phenol and 28 mg of cesium carbonate were added to an N-methylpyrrolidinone (0.5 ml) solution of 26 mg of pyrazine-2-carboxylic acid (5-fluoro-4-(6-methanesulfonyl-pyridin-3-yloxy)-2-nitro-phenyl)-amide obtained in (step 1), and the reaction liquid was stirred at 90° C. for 15 minutes, and 100 mg of tin(II) chloride dihydrate was added to the reaction liquid. The reaction liquid was stirred at 90° C. for 1 hour, and ethyl acetate and aqueous saturated sodium bicarbonate were added to it. The deposit was removed through filtration, the solvent was evaporated away under reduced pressure, and the residue was purified through reversed-phase middle-pressure liquid chromatography [ODS-AS-360-CC (by YMC), mobile phase: water-acetonitrile-0.1% trifluoroacetic acid]. The solvent of the resulting fraction was diluted with ethyl acetate, washed with aqueous saturated sodium bicarbonate, and dried with anhydrous sodium sulfate. The solvent was evaporated away under reduced pressure to obtain the entitled compound as a pale yellow solid.

1HNMR (CD$_3$OD) δ: 1.23 (3H, t, J=7.2 Hz), 3.24-3.44 (2H, m), 6.82-6.92 (2H, m), 7.04-7.18 (1H, m), 7.26-7.38 (3H, m), 7.48-7.56 (2H, m), 8.03 (1H, d, J=8.4 Hz), 8.38 (1H, s), 8.74 (1H, s), 8.81 (1H, s), 9.51 (1H, s)

ESI-MS (m/e): 474 [M+H]

Example 392

5-(Naphthalen-1-yloxy)-2-pyrazin-2-yl-6-(6-ethanesulfonyl-pyridin-3-yloxy)-1H-benzimidazole The entitled compound was obtained as a brown solid in the same method as in Example 391 (step 2) or in accordance with the method or by combining it with an ordinary method but using pyrazine-2-carboxylic acid (5-fluoro-4-(6-ethanesulfonyl-pyridin-3-yloxy)-2-nitro-phenyl)-amide obtained in Example 391 and naphthalen-1-ol.

1HNMR (CD$_3$OD) δ: 1.17 (3H, t, J=7.4 Hz), 3.29 (2H, q, J=7.4 Hz), 6.81 (1H, d, J=7.6 Hz), 7.29-7.40 (3H, m), 7.45-7.49 (1H, m), 7.55 (1H, d, J=7.6 Hz), 7.56 (1H, s), 7.72 (1H, d, J=8.6 Hz), 7.75 (1H, s), 7.83 (1H, d, J=8.2 Hz), 7.89 (1H, d, J=8.6 Hz), 8.17 (1H, d, J=3.0 Hz), 8.70 (1H, dd, J=2.3, 1.2 Hz), 8.77 (1H, d, J=2.3 Hz), 9.48 (1H, d, J=1.2 Hz)

ESI-MS (m/e): 524 [M+H]

Example 393

5-(Naphthalen-2-yloxy-2-pyrazin-2-yl-6-(6-ethanesulfonyl-pyridin-3-yloxy)-1H-benzimidazole The entitled compound was obtained as a brown solid in the same method as in Example 391 (step 2) or in accordance with the method or by combining it with an ordinary method but using pyrazine-2-carboxylic acid (5-fluoro-4-(6-ethanesulfonyl-pyridin-3-yloxy)-2-nitro-phenyl)-amide obtained in Example 391 and naphthalen-2-ol.

1HNMR (CD$_3$OD) δ: 1.11 (3H, t, J=7.6 Hz), 3.24 (2H, q, J=7.6 Hz), 7.10 (1H, dd, J=8.8, 2.5 Hz), 7.16 (1H, brs), 7.35-7.46 (3H, m), 7.50 (1H, d, J=3.1 Hz), 7.52 (1H, d, J=2.5 Hz), 7.67 (1H, d, J=8.2 Hz), 7.81 (1H, s), 7.83 (1H, s), 7.95 (1H, d, J=6.3 Hz), 8.34 (1H, d, J=2.3 Hz), 8.73 (1H, d, J=2.7 Hz), 8.80 (1H, dd, J=2.7, 1.6 Hz), 9.52 (1H, d, J=1.6 Hz)

ESI-MS (m/e): 524 [M+H]

Example 394

5-(2-Difluoromethyl-phenoxymethyl-2-pyridin-2-yl-6-(6-ethanesulfonyl-pyridin-3-yloxy)-1H-benzimidazole The entitled compound was obtained as a colorless solid in the same method as in Example 221 (step 3) or in accordance with the method or by combining it with an ordinary method but using 2-difluoromethyl-phenol.

1HNMR (CD$_3$OD) δ: 1.21 (3H, t, J=8.4 Hz), 3.37 (2H, q, J=8.4 Hz), 6.72 (1H, t, J=59.8 Hz), 6.85-6.90 (1H, m), 7.17 (1H, t, J=8.6 Hz), 7.39-7.46 (3H, m), 7.51-7.84 (3H, m), 7.98-8.05 (2H, m), 8.31-8.39 (2H, m), 8.65-8.85 (1H, m)

ESI-MS (m/e): 523 [M+H]

Example 395

5-(2-Carbamoyl-phenoxy)-2-pyridin-2-yl-6-(6-ethanesulfonyl-pyridin-3-yloxy)-1H-benzimidazole The entitled compound was obtained as a colorless solid in the same method as in Example 43 or in accordance with the method or by combining it with an ordinary method but using 5-(2-cyano-phenoxy)-2-pyridin-2-yl-6-(6-ethanesulfonyl-pyridin-3-yloxy)-1H-benzimidazole obtained in Example 196.

1HNMR (CD$_3$OD) δ: 1.25 (3H, t, J=7.3 Hz), 3.37 (2H, q, J=7.3 Hz), 6.88 (1H, d, J=8.2 Hz), 7.16 (1H, t, J=7.4 Hz), 7.40-7.46 (2H, m), 7.51-7.54 (1H, m), 7.64 (1H, brs), 7.70 (1H, brs), 7.87 (1H, d, J=7.8 Hz), 7.98 (1H, d, J=8.6 Hz), 8.01 (1H, t, J=8.6 Hz), 8.30 (1H, d, J=2.7 Hz), 8.33 (1H, d, J=7.8 Hz), 8.76 (1H, brs)

ESI-MS (m/e): 516 [M+H]

Example 396

5-Benzyloxy-2-pyridin-2-yl-6-(6-ethanesulfonyl-pyridin-3-yloxy)-1H-benzimidazole The entitled compound was obtained as a brown solid in the same method as in Example 250 or in accordance with the method or by combining it with an ordinary method but using 4-benzyloxy-3-fluoroaniline obtained in Example 250 (step 1), picolinic acid and 6-ethanesulfonyl-pyridin-3-ol.

1HNMR (CDCl$_3$) δ: 1.26 (3H, t, J=7.6 Hz), 3.35 (2H, q, J=7.6 Hz), 5.07 (2H, s), 7.10-7.13 (2H, m), 7.15 (1H, s), 7.26-7.27 (4H, m), 7.34-7.39 (1H, m), 7.51 (1H×½, s), 7.64 (1H×½, s), 7.83-7.86 (1H, m), 7.95-7.96 (1H, m), 8.33-8.35 (1H, m), 8.45-8.46 (1H, m), 8.60-8.63 (1H, m), 10.43-10.46 (1H, m)

ESI-MS (m/e): 487 [M+H]

Example 397

5-(2-Methanesulfonyl-6-fluoro-phenoxy)-2-pyridin-2-yl-6-(6-ethanesulfonyl-pyridin-3-yloxy)-1H-benzimidazole (Step 1) Production of 5-hydroxy-2-pyridin-2-yl-6-(6-ethanesulfonyl-pyridin-3-yloxy)-1H-benzimidazole The entitled compound was obtained as a pale green solid in the same method as in Example 251 (step 1) or in accordance with the method or by combining it with an ordinary method but using 5-benzyloxy-2-pyridin-2-yl-6-(6-ethanesulfonyl-pyridin-3-yloxy)-1H-benzimidazole obtained in Example 396.

(Step 2) Production of 5-(2-methanesulfonyl-6-fluoro-phenoxy)-2-pyridin-2-yl-6-(6-ethanesulfonyl-pyridin-3-yloxy)-1H-benzimidazole The entitled compound was obtained as a pale green solid in the same method as in Example 251 or in accordance with the method or by combining it with an ordinary method but using 5-hydroxy-2-pyridin-2-yl-6-(6-ethanesulfonyl-pyridin-3-yloxy)-1H-benzimidazole obtained in (step 1) and 1,2-difluoro-3-methanesulfonyl-benzene.

1HNMR (CD$_3$OD) δ: 1.25 (3H, t, J=7.4 Hz), 2.97 (3H, s), 3.41 (2H, q, J=7.4 Hz), 7.11 (1H, s), 7.50-7.57 (2H, m), 7.61-7.70 (2H, m), 7.70 (1H, s), 7.87 (1H, d, J=8.0 Hz), 7.99 (1H, t, J=8.0 Hz), 8.10 (1H, d, J=8.6 Hz), 8.27 (1H, d, J=7.0 Hz), 8.57 (1H, d, J=2.7 Hz), 8.74 (1H, d, J=4.3 Hz)

ESI-MS (m/e): 569 [M+H]

Example 398

5-(2-Fluoro-6-cyanophenoxy)-2-pyridin-2-yl-6-(6-ethanesulfonyl-pyridin-3-yloxy)-1H-benzimidazole The entitled compound was obtained as a pale green solid in the same method as in Example 251 or in accordance with the method or by combining it with an ordinary method but using 5-hydroxy-2-pyridin-2-yl-6-(6-ethanesulfonyl-pyridin-3-yloxy)-1H-benzimidazole obtained in Example 397 and 1,2-difluoro-3-cyano-benzene.

1HNMR (CD$_3$OD) δ: 1.26 (3H, t, J=7.4 Hz), 3.39 (2H, q, J=7.4 Hz), 7.27-7.43 (1H, m), 7.40 (1H, td, J=8.0, 4.6 Hz), 7.49-7.55 (2H, m), 7.56-7.76 (3H, m), 7.99 (1H, t, J=7.6 Hz), 8.06 (1H, d, J=9.0 Hz), 8.30 (1H, d, J=7.6 Hz), 8.46 (1H, d, J=2.7 Hz), 8.75 (1H, d, J=4.3 Hz)

ESI-MS (m/e): 516 [M+H]

Example 399

5-(2-Fluoro-6-carbamoyl-phenoxy)-2-pyridin-2-yl-6-(6-ethanesulfonyl-pyridin-3-yloxy)-1H-benzimidazole The entitled compound was obtained as a colorless solid in the same method as in Example 43 or in accordance with the method or by combining it with an ordinary method but using 5-(2-fluoro-6-cyano-phenoxy)-2-pyridin-2-yl-6-(6-ethanesulfonyl-pyridin-3-yloxy)-1H-benzimidazole obtained in Example 397.

1HNMR (CD$_3$OD) δ: 1.25 (3H, t, J=7.4 Hz), 3.40 (2H, q, J=7.4 Hz), 7.00-7.18 (1H, m), 7.34-7.43 (2H, m), 7.49 (1H, brs), 7.54-7.56 (2H, m), 7.66 (1H, brs), 7.97 (1H, t, J=8.0 Hz), 8.07 (1H, d, J=8.6 Hz), 8.20-8.30 (1H, m), 8.53 (1H, d, J=2.7 Hz), 8.70-8.77 (1H, m)

ESI-MS (m/e): 534 [M+H]

Example 400

5-(2-Fluoro-6-cyano-phenoxy)-2-pyrazin-2-yl-6-(4-ethanesulfonyl-phenoxy-1H-benzimidazole (Step 1) Production of 3-fluoro-4-(2-fluoro-6-cyano-phenoxy)-phenylamine The entitled compound was obtained in the same method as in Example 221 (step 1) or in accordance with the method or by combining it with an ordinary method but using tert-butyl (3-fluoro-4-hydroxy-phenyl)-carbamate obtained in Example 196 (step 1) and 1,2-difluoro-3-cyano-benzene.

(Step 2) Production of pyrazine-2-carboxylic acid (5-fluoro-4-(2-fluoro-6-cyano-phenoxy)-2-nitro-phenyl)-amide The entitled compound was obtained in the same method as in Example 391 (step 1) or in accordance with the method or by combining it with an ordinary method but using 5-fluoro-4-(2-fluoro-6-cyano-phenoxy)-phenylamine obtained in (step 1) and pyrazine-2-carboxylic acid.

(Step 3) Production of 5-(2-fluoro-6-cyano-phenoxy)-2-pyrazin-2-yl-6-(4-ethanesulfonyl-phenoxy)-1H-benzimidazole The entitled compound was obtained as a brown solid in the same method as in Example 391 (step 2) or in accordance with the method or by combining it with an ordinary method but using pyrazine-2-carboxylic acid (5-fluoro-4-(2-fluoro-6-cyano-phenoxy)-2-nitro-phenyl)-amide obtained in (step 2) and 4-ethanesulfonyl-phenol.

1HNMR (CD$_3$OD) δ: 1.24 (3H, t, J=7.4 Hz), 3.20 (2H, q, J=7.4 Hz), 7.12 (2H, d, J=9.0 Hz), 7.33-7.40 (2H, m), 7.55-7.62 (3H, m), 7.86 (2H, d, J=9.0 Hz), 8.72 (1H, s), 8.78 (1H, s), 9.48 (1H, s)

ESI-MS (m/e): 516 [M+H]

Example 401

5-(2-Fluoro-6-carbamoyl phenoxy)-2-pyrazin-2-yl-6-(4-ethanesulfonyl-phenoxy)-1H-benzimidazole, and 5-(2-fluoro-6-isopropylcarbamoyl-phenoxy)-2-pyrazin-2-yl-6-(4-ethanesulfonyl-phenoxy)-1H-benzimidazole The entitled compounds were obtained as a brown solid and a pale yellow solid, respectively, in the same method as in Example 43 or in accordance with the method or by combining it with an ordinary method but using 5-(2-fluoro-6-cyano-phenoxy)-2-pyrazin-2-yl-6-(4-ethanesulfonyl-phenoxy)-1H-benzimidazole obtained in Example 400.

5-(2-Fluoro-6-carbamoyl-phenoxy)-2-pyrazin-2-yl-6-(4-ethanesulfonyl-phenoxy)-1H-benzimidazole 1HNMR (CD$_3$OD) δ: 1.25 (3H, t, J=7.4 Hz), 3.22 (2H, q, J=7.4 Hz), 7.00-7.34 (1H, m), 7.23 (2H, d, J=8.8 Hz), 7.34-7.70 (4H, m), 7.91 (2H, d, J=8.8 Hz), 8.71 (1H, s), 8.77 (1H, s), 9.46 (1H, s)

ESI-MS (m/e): 534 [M+H]

5-(2-Fluoro-6-isopropylcarbamoyl-phenoxy)-2-pyrazin-2-yl-6-(4-ethanesulfonyl-phenoxy)-1H-benzimidazole 1HNMR (CDCl$_3$) δ: 1.10 (6H, d, J=9.6 Hz), 1.24 (3H, t, J=7.4 Hz), 3.01-3.11 (2H, m), 4.06-4.16 (1H, m), 6.80-7.87 (9H, m), 8.52-8.60 (2H, m), 9.51-9.54 (1H, m), 10.78-10.80 (1H, m)

ESI-MS (m/e): 576 [M+H]

Example 402

5-(2-Fluoro-6-cyano-phenoxy)-2-pyrazin-2-yl-6-(6-ethanesulfonyl-pyridin-3-yloxy)-1H-benzimidazole The entitled compound was obtained as a white solid in the same method as in Example 400 (step 3) or in accordance with the method or by combining it with an ordinary method but using pyrazine-2-carboxylic acid (5-fluoro-4-(2-cyano-6-fluoro-phenoxy)-2-nitro-phenyl)-amide obtained in Example 400 (step 2) and 6-ethanesulfonyl-pyridin-3-ol.

1HNMR (DMSO-d6) δ: 1.10 (3H, t, J=7.4 Hz), 3.27-3.36 (2H, m), 7.22-7.35 (1H, m), 7.38-7.50 (2H, m), 7.72-7.77 (3H, m), 7.98 (1H, d, J=9.0 Hz), 8.50 (1H, d, J=2.7 Hz), 8.76 (1H, s), 8.79 (1H, s), 9.45 (1H, s).

ESI-MS (m/e): 517 [M+H]

Example 403

5-(2-Fluoro-6-carbamoyl-phenoxy)-2-pyrazin-2-yl-6-(6-ethanesulfonyl-pyridin-3-yloxy)-1H-benzimidazole and 5-(2-fluoro-6-isopropylcarbamoyl-phenoxy)-2-pyrazin-2-yl-6-(6-ethanesulfonyl-pyridin-3-yloxy)-1H-benzimidazole The entitled compounds were obtained each as a colorless solid in the same method as in Example 43 or in accordance with the method or by combining it with an ordinary method but using 5-(2-fluoro-6-cyano-phenoxy)-2-pyrazin-2-yl-6-(6-ethanesulfonyl-pyridin-3-yloxy)-1H-benzimidazole obtained in Example 402.

5-(2-Fluoro-6-carbamoyl-phenoxy)-2-pyrazin-2-yl-6-(6-ethanesulfonyl-pyridin-3-yloxy)-1H-benzimidazole 1HNMR (CD$_3$OD) δ: 1.27 (3H, t, J=7.4 Hz), 3.43 (2H, q, J=7.4 Hz), 7.08-7.11 (1H, m), 7.38-7.46 (2H, m), 7.46-7.80 (3H, m), 8.10 (1H, d, J=4.7 Hz), 8.55 (1H, d, J=2.7 Hz), 8.71 (1H, s), 8.78 (1H, s), 9.47 (1H, s)

ESI-MS (m/e): 535 [M+H]

5-(2-Fluoro-6-isopropylcarbamoyl-phenoxy)-2-pyrazin-2-yl-6-(6-ethanesulfonyl-pyridin-3-yloxy)-1H-benzimidazole 1HNMR (CD$_3$OD) δ: 1.08 (6H, d, J=6.6 Hz), 1.25 (3H, t, J=7.4 Hz), 3.40 (2H, q, J=7.4 Hz), 3.94-4.02 (1H, m), 7.10 (1H, s), 7.36-7.46 (3H, m), 7.59 (1H, d, J=9.0 Hz), 7.74 (1H, s), 8.08 (1H, d, J=9.0 Hz), 8.56 (1H, s), 8.75 (1H, s), 8.80 (1H, s), 9.44 (1H, s)

ESI-MS (m/e): 577 [M+H]

Example 404

5-(2-Fluoro-6-(tetrazol-5-yl)-phenoxy)-2-pyrazin-2-yl-6-(6-ethanesulfonyl-pyridin-3-yloxy)-1H-benzimidazole The entitled compound was obtained as a colorless solid in the same method as in Example 60 or in accordance with the method or by combining it with an ordinary method but using 5-(2-fluoro-6-cyano-phenoxy)-2-pyrazin-2-yl-6-(6-ethanesulfonyl-pyridin-3-yloxy)-1H-benzimidazole obtained in Example 402.

1HNMR (CD$_3$OD) δ: 1.27 (3H, t, J=7.4 Hz), 3.39 (2H, q, J=7.4 Hz), 7.37-7.46 (4H, m), 7.60 (1H, s), 7.84 (1H, d, J=5.9 Hz), 7.94 (1H, d, J=9.0 Hz), 8.32 (1H, d, J=2.0 Hz), 8.71 (1H, s), 8.77 (1H, s), 9.47 (1H, s)

ESI-MS (m/e): 560 [M+H]

Example 405

5-(2-Methylsulfanyl-phenoxy)-2-pyridin-2-yl-6-(6-ethanesulfonyl-pyridin-3-yloxy)-1H-benzimidazole The entitled compound was obtained as a pale yellow solid in the same method as in Example 221 (step 3) or in accordance with the method or by combining it with an ordinary method but using 2-methylsulfanyl-phenol.

1HNMR (CDCl$_3$) δ: 1.28 (3H, t, J=7.4 Hz), 3.38 (2H, q, J=7.4 Hz), 6.78 (1H, ddd, J=7.6, 7.6, 1.5 Hz), 7.03-7.12 (2H, m), 7.08 (½H, s), 7.16 (1H, d, J=7.6 Hz), 7.30 (1H, dd, J=8.7, 2.5 Hz), 7.36 (½H, s), 7.37-7.41 (1H, m), 7.47 (½H, s), 7.72 (½H, s), 7.86-7.90 (1H, m), 7.97 (1H, d, J=8.7 Hz), 8.38 (1H, d, J=2.5 Hz), 8.38-8.41 (1H, m), 8.61-8.63 (1H, m), 11.16 (½H, brs), 11.28 (½H, brs)

ESI-MS (m/e): 519 [M+H]

Example 406

5-(2-Methanesulfinyl-phenoxy)-2-pyridin-2-yl-6-(6-ethanesulfonyl-pyridin-3-yloxy)-1H-benzimidazole, and 5-(2-methanesulfonyl-phenoxy)-2-pyridin-2-yl-6-(6-ethanesulfonyl-pyridin-3-yloxy)-1H-benzimidazole 2 ml of water and 89 mg of Oxone were added to a methanol (3 ml) solution of 46 mg of 5-(2-methylsulfanyl-phenoxy)-2-pyridin-2-yl-6-(6-ethanesulfonyl-pyridin-3-yloxy)-1H-benzimidazole obtained in Example 405, and the reaction liquid was stirred at room temperature for 5 hours. The solvent was evaporated away under reduced pressure, and the resulting residue was purified through partitioning thin-layer chromatography (Kieselgel™ 60F$_{254}$, Art 5744 (by Merck), chloroform/methanol=15/1) to obtain the entitled compounds each as a pale yellow solid.

5-(2-Methanesulfinyl-phenoxy)-2-pyridin-2-yl-6-(6-ethanesulfonyl-pyridin-3-yloxy-1H-benzimidazole 1HNMR (CDCl$_3$) δ: 1.30 (3H, t, J=7.6 Hz), 2.59 (³⁄₂H, s), 2.63 (³⁄₂H, s), 3.38 (2H, q, J=7.6 Hz), 6.78-6.81 (1H, m), 7.25-7.33 (2H, m), 7.35-7.43 (1H, m), 7.08 (½H, s), 7.16 (1H, d, J=7.6 Hz), 7.30 (1H, dd, J=8.7, 2.5 Hz), 7.36 (½H, s), 7.37-7.41 (1H, m), 7.47 (½H, s), 7.72 (½H, s), 7.86-7.90 (1H, m), 7.97 (1H, d, J=8.7 Hz), 8.38 (1H, d, J=2.5 Hz), 8.38-8.41 (1H, m), 8.61-8.63 (1H, m), 11.16 (½H, brs), 11.28 (½H, brs)

ESI-MS (m/e): 535 [M+H]

5-(2-Methanesulfonyl-phenoxy)-2-pyridin-2-yl-6-(6-ethanesulfonyl-pyridin-3-yloxy)-1H-benzimidazole 1HNMR (CDCl$_3$) δ: 1.29 (3H, t, J=7.4 Hz), 2.95 (³⁄₂H, s), 3.02 (³⁄₂H, s), 3.36 (2H, q, J=7.4 Hz), 6.92-6.97 (1H, d), 7.20-7.27 (1H, m), 7.31-7.35 (³⁄₂H, m), 7.41-7.45 (³⁄₂H, m), 7.51-7.57 (1H, m), 7.65 (½H, s), 7.72 (½H, s), 7.87-7.92 (1H, m), 7.97-8.04 (2H, m), 8.34-8.42 (2H, m), 8.65-8.67 (1H, m), 10.72 (1H, brs)

ESI-MS (m/e): 551 [M+H]

Example 407

5-(2-Bromopyridin-3-yloxy)-2-pyrazin-2-yl-6-(6-ethanesulfonyl-pyridin-3-yloxy)-1H-benzimidazole The entitled compound was obtained as a pale yellow solid in the same method as in Example 391 or in accordance with the method or by combining it with an ordinary method but using pyrazine-2-carboxylic acid (5-fluoro-4-(6-ethanesulfonyl-pyridin-3-yloxy)-2-nitro-phenyl)-amide obtained in Example 391, and 2-bromo-pyridin-3-ol.

1HNMR (CDCl$_3$) δ: 1.30 (3H, t, J=7.4 Hz), 3.39 (2H, q, J=7.4 Hz), 7.03 (1H, dd, J=8.0, 1.6 z), 7.19-7.22 (1H, m), 7.28-7.32 (1H, m), 7.34 (½H, brs), 7.51 (½H, brs), 7.62 (½H, brs), 7.93 (½H, brs), 8.00 (1H, d, J=8.6 Hz), 8.14 (1H, brs), 8.31-8.32 (1H, m), 8.62 (1H, brs), 8.70 (1H, d, J=2.4 Hz), 9.64 (1H, brs), 10.91 (½H, brs), 10.98 (½H, brs)

ESI-MS (m/e): 553 [M+H]

Example 408

5-(2-Vinylpyridin-3-yloxy)-2-pyrazin-2-yl-6-(6-ethanesulfonyl-pyridin-3-yloxy)-1H-benzimidazole The entitled compound was obtained as a pale yellow solid in the same method as in Example 407 or in accordance with the method or by combining it with an ordinary method but using 2-vinyl-pyridin-3-ol.

1HNMR (CDCl$_3$) δ: 1.27 (3H, t, J=7.5 Hz), 3.37 (2H, q, J=7.5 Hz), 5.34 (1H, dd, J=10.9, 1.9 Hz), 6.30 (1H, dd, J=17.4, 1.9 Hz), 6.72 (1H, dd, J=17.4, 10.9 Hz), 7.09 (1H, dd, J=8.2, 1.5 Hz), 7.12 (1H, dd, J=8.2, 4.3 Hz), 7.27 (1H, dd, J=8.7, 2.9 Hz), 8.00 (1H, d, J=8.7 Hz), 8.31 (1H, d, J=2.9 Hz), 8.33 (1H, dd, J=4.3, 1.5 Hz), 8.61 (1H, dd, J=2.6, 1.6 Hz), 8.69 (1H, d, J=2.6 Hz), 10.60 (½H, brs), 10.68 (½H, brs)

ESI-MS (m/e): 501 [M+H]

Example 409

5-(2-Cyclopropyl-pyridin-3-yloxy)-2-pyrazin-2-yl-6-(6-ethanesulfonyl-pyridin-3-yloxy)-1H-benzimidazole The entitled compound was obtained as a pale yellow solid in the same method as in Example 407 or in accordance with the method or by combining it with an ordinary method but using 2-cyclopropyl-pyridin-3-ol.

1HNMR (CDCl$_3$) δ: 0.77-1.02 (2H, m), 1.24-1.31 (2H, m), 1.29 (3H, t, J=7.4 Hz), 3.37 (2H, q, J=7.4 Hz), 6.96 (⅖H, dd, J=8.2, 4.6 Hz), 6.98 (⅗H, dd, J=8.2, 4.6 Hz), 7.03 (⅖H, dd, J=8.2, 1.5 Hz), 7.04 (⅗H, dd, J=8.2, 1.5 Hz), 7.16 (½H, s), 7.33 (1H, dd, J=8.8, 3.0 Hz), 7.48 (½H, s), 7.53 (½H, s), 7.78 (½H, s), 8.00 (1H, d, J=8.8 Hz), 8.20 (⅖H, dd, J=4.6, 1.5 Hz), 8.22 (⅗H, dd, J=4.6, 1.5 Hz), 8.39 (⅖H, d, J=3.0 Hz), 8.40 (⅗H, d, J=3.0 Hz), 8.59-8.62 (1H, m), 8.68-8.70 (1H, m), 9.62-9.64 (1H, m), 10.60 (⅗H, brs), 10.66 (⅖H, brs)

ESI-MS (m/e): 515 [M+H]

Example 410

5-(2-Difluoromethoxypyridin-3-yloxy)-2-pyridin-2-yl-6-(4-dimethylsulfamoyl-phenoxy-1H-benzimidazole The entitled compound was obtained as a pale yellow solid in the same method as in Example 221 (step 1) to (step 3) or in accordance with the method or by combining it with an ordinary method but using 4-(N,N-dimethylaminosulfonyl)-phenol and 2-difluoromethoxy-pyridin-3-ol in order.

1HNMR (CD$_3$OD) δ: 2.66 (6H, s), 7.05 (2H, d, J=8.6 Hz), 7.10-7.19 (1H, m), 7.32-7.62 (4H, m), 7.49 (1H, t, J=72.8 Hz), 7.71 (2H, d, J=8.6 Hz), 7.91 (1H, d, J=4.1 Hz), 8.01 (1H, t, J=7.8 Hz), 8.32 (1H, d, J=7.6 Hz), 8.77 (1H, s)

ESI-MS (m/e): 554 [M+H]

Example 411

5-(2-Difluoromethoxypyridin-3-yloxy)-6-(3-chloro-4-methanesulfonyl-phenoxy)-2-pyridin-2-yl-1H-benzimidazole The entitled compound was obtained as a pale yellow solid in the same method as in Example 221 (step 1) to (step 3) or in accordance with the method or by combining it with an ordinary method but using 4-methanesulfonyl-3-chloro-phenol and 2-difluoromethoxy-pyridin-3-ol in order.

1HNMR (CD$_3$OD) δ: 3.25 (3H, s), 6.98 (1H, dd, J=8.6, 2.3 Hz), 7.09 (1H, d, J=2.3 Hz), 7.15 (1H, dd, J=7.8, 4.9 Hz), 7.35-7.46 (2H, m), 7.46-7.74 (3H, m), 7.48 (1H, t, J=74.0 Hz), 7.91-7.94 (1H, m), 8.02 (1H, d, J=8.6 Hz), 8.32 (1H, d, J=7.8 Hz), 8.75-8.77 (1H, m)

ESI-MS (m/e): 552[M−H]

Example 412

5-(2-Fluoro-phenoxy)-2-pyrazin-2-yl-6-(4-(N-hydroxycarbamimidoyl)-phenoxy)-1H-benzimidazole 0.5 ml of hydroxyamine (50% aqueous solution) was added to an ethanol (0.5 ml) solution of 6.0 mg of 5-(2-fluoro-phenoxy)-2-pyrazin-2-yl-6-(6-cyano-pyridin-3-yloxy)-1H-benzimidazole obtained in Example 252, and the reaction liquid was stirred at room temperature for 3 hours. Then, the solvent was evaporated away under reduced pressure to obtain the entitled compound as a pale yellow solid.

1HNMR (CD$_3$OD) δ: 7.01-7.04 (1H, m), 7.10-7.22 (3H, m), 7.29-7.35 (2H, m), 7.60 (1H, s), 7.82 (1H, d, J=9.0 Hz), 8.24 (1H, d, J=2.3 Hz), 8.70 (1H, d, J=1.6 Hz), 8.77 (1H, d, J=1.6 Hz), 9.48 (1H, s)

ESI-MS (m/e): 458 [M+H]

Example 413

5-(2-Fluoro-phenoxy)-2-pyrazin-2-yl-6-(6-(5-methyl-[1,2,4]oxadiazol)-3-yloxy)-1H-benzimidazole An acetic anhydride (1 ml) solution of 3.6 mg of 5-(2-fluoro-phenoxy)-2-pyrazin-2-yl-6-(4-(N-hydroxycarbamimidoyl)-phenoxy)-1H-benzimidazole obtained in Example 412 was stirred overnight at 60° C. The solvent was evaporated away under reduced pressure, and the residue was purified through reversed-phase middle-pressure liquid chromatography [ODS-AS-360-CC (by YMC), mobile phase: water-acetonitrile-0.1% trifluoroacetic acid]. The solvent of the resulting fraction was diluted with ethyl acetate, washed with aqueous saturated sodium bicarbonate, and dried with anhydrous sodium sulfate. The solvent was evaporated away under reduced pressure to obtain the entitled compound as a colorless solid.

1HNMR (CD$_3$OD) δ: 2.69 (3H, s), 7.00-7.40 (5H, m), 7.48 (1H, dd, J=7.8, 2.3 Hz), 7.52-7.85 (1H, m), 8.10 (1H, d, J=7.8 Hz), 8.37 (1H, d, J=2.3 Hz), 8.71 (1H, s), 8.78 (1H, s), 9.48 (1H, s)

ESI-MS (m/e): 482 [M+H]

Example 414

5-(2-Fluoro-phenoxy)-2-pyrazin-2-yl-6-(6-(5-trifluoromethyl-[1,2,4]oxadiazol)-3-yloxy)-1H-benzimidazole A trifluoroacetic anhydride (1 ml) solution of 2.0 mg of 5-(2-fluoro-phenoxy)-2-pyrazin-2-yl-6-(4-(N-hydroxycarbamimidoyl)-phenoxy)-1H-benzimidazole obtained in Example 412 was stirred at 60° C. for 1 hour. The solvent was evaporated away under reduced pressure, and the residue was purified through partitioning thin-layer chromatography (Kieselgel™ 60F$_{254}$, Art 5744 (by Merck), chloroform/methanol=15/1) to obtain the entitled compound as a colorless solid.

1HNMR (CD$_3$OD) δ: 7.00-7.50 (5H, m), 7.55 (1H, dd, J=7.8 Hz, 2.3 Hz), 7.60-7.80 (1H, m), 8.22 (1H, d, J=7.8 Hz), 8.45 (1H, d, J=2.3 Hz), 8.73 (1H, s), 8.80 (1H, s), 9.50 (1H, s)

ESI-MS (m/e): 536 [M+H]

Example 415

5-(2-Fluoro-phenoxy)-2-pyrazin-2-yl-6-(imidazo[1,2-a]pyridin-6-yloxy)-1H-benzimidazole Step (1) Production of 5-(2-fluoro-phenoxy)-2-pyrazin-2-yl-6-(6-nitro-pyridin-3-yloxy)-1H-benzimidazole The entitled compound was obtained in the same method as in Example 251 (step 2) or in accordance with the method or by combining it with an ordinary method but using 2-nitro-5-pyridine.

(Step 2) Production of 5-(2-fluoro-phenoxy)-2-pyrazin-2-yl-6-(imidazo[1,2-a]pyridin-6-yloxy)-1H-benzimidazole Developed Raney nickel catalyst was added to a methanol (0.5 ml) solution of 12 mg of 5-(2-fluoro-phenoxy)-2-pyrazin-2-yl-6-(6-nitro-pyridin-3-yloxy)-1H-benzimidazole obtained in (step 1), and the reaction liquid was stirred in a hydrogen atmosphere for 1 hour. The catalyst was removed through filtration, and the solvent was evaporated away under reduced pressure. 0.02 ml of chloroacetaldehyde (40% aqueous solution) was added to an ethanol (0.3 ml) solution of the resulting residue, and the reaction liquid was stirred overnight at room temperature. The solvent was evaporated away under reduced pressure, and the residue was purified through partitioning thin-layer chromatography (Kieselgel™ 60F$_{254}$, Art 5744 (by Merck), chloroform/methanol=15/1) to obtain the entitled compound as a pale yellow solid.

1HNMR (CDCl$_3$) δ: 1.25 (3H, t, J=7.0 Hz), 3.73 (2H, q, J=7.0 Hz), 7.00-7.22 (6H, m), 7.31-7.65 (4H, m), 7.82 (½H, s), 7.88 (½H, s), 8.57 (1H, dd, J=2.5, 1.5 Hz), 8.64 (1H, s), 9.59 (1H, s), 10.57 (½H, brs), 10.97 (½H, brs)

ESI-MS (m/e): 439 [M+H]

Example 416

5-(Pyridin-2-ylsulfanyl)-2-pyrazin-2-yl-6-(6-ethanesulfonyl-pyridin-3-yloxy)-1H-benzimidazole The entitled compound was obtained as a yellow solid in the same method as in Example 391 (step 2) or in accordance with the method or by combining it with an ordinary method but using pyridine-2-thiol.

1HNMR (CD$_3$OD) δ: 1.23 (3H, t, J=7.4 Hz), 3.36 (2H, q, J=7.4 Hz), 7.07 (1H, d, J=8.2 Hz), 7.11 (1H, dd, J=7.4, 4.9 Hz), 7.41 (1H, d, J=7.6 Hz), 7.58-7.80 (1H, m), 7.60 (1H, td, J=7.6, 1.8 Hz), 7.95 (1H, dd, J=8.6, 0.6 Hz), 8.00-8.25 (1H, m), 8.28 (1H, dd, J=5.1, 1.0 Hz), 8.33 (1H, d, J=0.6 Hz), 8.75 (1H, d, J=2.5 Hz), 8.82 (1H, dd, J=2.5, 1.5 Hz), 9.53 (1H, d, J=1.5 Hz)

ESI-MS (m/e): 491 [M+H]

Example 417

5-(3-Cyano-pyridin-2-ylsulfanyl)-2-pyrazin-2-yl-6-(6-ethanesulfonyl-pyridin-3-yloxy)-1H-benzimidazole The entitled compound was obtained as a yellow solid in the same method as in Example 391 (step 2) or in accordance with the method or by combining it with an ordinary method but using 3-cyano-pyridine-2-thiol.

1HNMR (CDCl$_3$) δ: 1.29 (3H, t, J=7.4 Hz), 3.36 (2H, q, J=7.4 Hz), 7.08 (1H, dd, J=7.8, 4.9 Hz), 7.35 (1H, dd, J=8.6, 2.8 Hz), 7.35 and 7.65 (total 1H, each s), 7.80 (1H, dd, J=7.8, 1.8 Hz), 7.93 (1H, d, J=8.4 Hz), 7.95 and 8.22 (total 1H, each s), 8.36 (2H, d, J=2.5 Hz), 8.63 (1H, s), 8.71 (1H, s), 9.65 (1H, d, J=1.4 Hz)

ESI-MS (m/e): 516 [M+H]

Example 418

5-(2-Chlorophenyl-sulfanyl)-2-pyridin-2-yl-6-(6-methanesulfonyl-pyridin-3-yloxy)-1H-benzimidazole The entitled compound was obtained as a pale yellow solid in the same method as in Example 196 (step 4) to (step 6) or in accordance with the method or by combining it with an ordinary method but using 2-chloro-thiophenol.

1HNMR (CD$_3$OD) δ: 3.20 (3H, s), 7.03-7.10 (1H, m), 7.13-7.20 (2H, m), 7.34-7.39 (2H, m), 7.50-7.86 (3H, m), 7.94 (1H, d, J=8.6 Hz), 8.01 (1H, t, J=7.8 Hz), 8.29-8.35 (2H, m), 8.77 (1H, d, J=4.7 Hz)

ESI-MS (m/e): 509 [M+H]

Example 419

4-(2-Cyano-phenoxy)-6-(6-ethanesulfonyl-pyridin-3-yloxy)-2-pyridin-2-yl-1H-benzimidazole The entitled compound was obtained in the same method as in Example 274 or in accordance with the method or by combining it with an ordinary method but using 2-cyano-phenol and 6-ethanesulfonyl-pyridin-3-yl in order.

1HNMR (CD$_3$OD) δ: 1.25 (3H, t, J=7.4 Hz), 3.40 (2H, q, J=7.4 Hz), 6.78 (1H, s), 7.12 (1H, d, J=8.6 Hz), 7.29-7.31 (2H, m), 7.50-7.51 (1H, m), 7.63-7.65 (2H, m), 7.82 (1H, d, J=7.4 Hz), 7.95-7.97 (1H, m), 8.08 (1H, d, J=8.6 Hz), 8.32 (1H, d, J=8.2 Hz), 8.55 (1H, d, J=2.7 Hz), 8.75 (1H, d, J=4.3 Hz)

ESI-MS (m/e): 498 [M+H]

Example 420

4-(2-Cyano-phenoxy)-6-(6-ethanesulfonyl-pyridin-3-yloxy)-2-pyrazin-2-yl-1H-benzimidazole The entitled compound was obtained as a white solid in the same method as in Example 205 or in accordance with the method or by combining it with an ordinary method but using 3-(2-cyano-phenoxy)-5-(6-ethanesulfonyl-pyridin-3-yloxy)-benzene-1,2-diamine obtained in Example 419.

$^1$HNMR (CD$_3$OD) δ: 1.27 (3H, t, J=8.0 Hz), 3.42 (2H, q, J=8.0 Hz), 6.79-6.84 (1H, m), 7.14-7.17 (1H, m), 7.31-7.35 (1H, m), 7.61-7.68 (2H, m), 7.80-7.85 (2H, m), 8.08 (1H, d, J=8.4 Hz), 8.54-8.59 (1H, m), 8.70-8.73 (1H, m), 8.77-8.79 (1H, m), 9.48-9.50 (1H, m)

ESI-MS (m/e): 499 [M+H]

Example 421

4-(2-Cyano-phenoxy)-6-(6-methanesulfonyl-pyridin-3-yloxy)-2-pyrazin-2-yl-1H-benzimidazole The entitled compound was obtained as a white solid in the same method as in Example 205 or in accordance with the method or by combining it with an ordinary method but using 3-(2-cyano-phenoxy)-5-(6-methanesulfonyl-pyridin-3-yloxy)-benzene-1,2-diamine obtained in Example 286.

$^1$HNMR (CD$_3$OD) δ: 3.24 (3H, s), 6.80-6.83 (1H, m), 7.72 (1H, d, J=8.6 Hz), 7.30-7.50 (2H, m), 7.60-7.80 (2H, m), 7.88 (1H, d, J=7.8 Hz), 8.11 (1H, d, J=9.0 Hz), 8.56 (1H, s), 8.73 (1H, s), 8.79 (1H, s), 9.50 (1H, s)

ESI-MS (m/e): 485 [M+H]

Example 422

4-(2,3-Difluoro-phenoxy)-6-(6-methanesulfonyl-pyridin-3-yloxy)-2-pyridin-2-yl-1H-benzimidazole The entitled compound was obtained in the same method as in Example 274 or in accordance with the method or by combining it with an ordinary method but using 2,3-difluoro-phenol and 6-methanesulfonyl-pyridin-3-ol in order.

213

¹HNMR (CD₃OD) δ: 3.23 (3H, s), 6.70 (1H, d, J=2.3 Hz), 7.12-7.25 (3H, m), 7.29 (1H, d, J=2.3 Hz), 7.60-7.65 (2H, m), 8.07-8.10 (2H, m), 8.39 (1H, d, J=7.9 Hz), 8.50 (1H, d, J=3.4 Hz), 8.83-8.85 (1H, m)

ESI-MS (m/e): 495 [M+H]

Example 423

4-(2,3-Difluoro-phenoxy)-6-(6-ethanesulfonyl-pyridin-3-yloxy)-2-pyridin-2-1H-benzimidazole The entitled compound was obtained in the same method as in Example 204 (step 2) or in accordance with the method or by combining it with an ordinary method but using 3-(2,3-difluoro-phenoxy)-5-(6-ethanesulfonyl-pyridin-3-yloxy)-benzene-1,2-diamine obtained in Example 285.

¹HNMR (CD₃OD) δ: 1.25 (3H, t, J=7.6 Hz), 3.40 (2H, q, J=7.6 Hz), 6.71 (1H, d, J=2.0 Hz), 7.12-7.26 (3H, m), 7.30 (1H, d, J=2.0 Hz), 7.60-7.68 (2H, m), 8.06-8.13 (2H, m), 8.40 (1H, d, J=7.4 Hz), 8.52 (1H, d, J=2.7 Hz), 8.86 (1H, d, J=5.1 Hz)

ESI-MS (m/e): 509 [M+H]

Example 424

4-(2,5-Difluoro-phenoxy)-6-(6-ethanesulfonyl-pyridin-3-yloxy)-2-pyrazin-2-yl-1H-benzimidazole The entitled compound was obtained as a white solid in the same method as in Example 278 or in accordance with the method or by combining it with an ordinary method but using 2,5-difluoro-phenol and 6-ethanesulfonyl-pyridin-3-ol.

¹HNMR (CD₃OD) δ: 1.25 (3H, t, J=8.2 Hz), 3.41 (2H, q, J=8.2 Hz), 6.59 (1H, s), 6.99-7.05 (1H, m), 7.06-7.14 (1H, m), 7.22 (1H, brs), 7.34 (1H, td, J=9.8, 4.9 Hz), 7.61 (1H, dd, J=8.6, 4.3 Hz), 8.07 (1H, d, J=8.6 Hz), 8.52 (1H, d, J=4.3 Hz), 8.72 (1H, d, J=1.2 Hz), 8.79 (1H, s), 9.54 (1H, d, J=1.2 Hz)

ESI-MS (m/e): 510 [M+H]

Example 425

4-(2,5-Difluoro-phenoxy)-6-(6-ethanesulfonyl-pyridin-3-yloxy)-2-pyridin-2-yl-1H-benzimidazole The entitled compound was obtained as a white solid in the same method as in Example 204 (step 2) or in accordance with the method or by combining it with an ordinary method but using 3-(2,5-difluoro-phenoxy)-5-(6-ethanesulfonyl-pyridin-3-yloxy)-benzene-1,2-diamine obtained in Example 42-4.

¹HNMR (CD₃OD) δ: 1.25 (3H, t, J=7.5 Hz), 3.40 (2H, q, J=7.5 Hz), 6.55 (1H, s), 6.96-7.05 (1H, m), 7.05-7.14 (1H, m), 7.21 (1H, s), 7.28-7.38 (1H, m), 7.50-7.56 (1H, m), 7.56-7.63 (1H, m), 7.97-8.03 (1H, m), 8.07 (1H, d, J=8.2 Hz), 8.38 (1H, d, J=7.0 Hz), 8.51 (1H, s), 8.76 (1H, s)

ESI-MS (m/e): 509 [M+H]

Example 426

4-(2,6-Difluoro-phenoxy)-6-(4-ethanesulfonyl-phenoxy)-2-pyrazin-2-yl-1H-benzimidazole The entitled compound was obtained in the same method as in Example 278 or in accordance with the method or by combining it with an ordinary method but using 2,6-difluoro-phenol and 4-ethanesulfonyl-phenol in order.

¹HNMR (CD₃OD) δ: 1.26 (3H, t, J=7.4 Hz), 3.21 (2H, q, J=7.4 Hz), 6.37 (1H, brs), 7.13-7.25 (5H, m), 7.34-7.39 (1H, m), 7.89 (2H, d, J=8.8 Hz), 8.78 (1H, d, J=2.7 Hz), 8.84 (1H, dd, J=1.6, 2.7 Hz), 9.56 (1H, d, J=1.6 Hz)

ESI-MS (m/e): 509 [M+H]

Example 427

4-(2,6-Difluoro-phenoxy)-6-(4-ethanesulfonyl-phenoxy)-2-pyridin-2-yl-1H-benzimidazole The entitled compound was obtained in the same method as in Example 204 (step 2) or in accordance with the method or by combining it with an ordinary method but using 3-(2,6-difluoro-phenoxy)-5-(4-ethanesulfonyl-phenoxy)-benzene-1,2-diamine obtained in Example 426.

¹HNMR (CD₃OD) δ: 1.24 (3H, t, J=7.4 Hz), 3.21 (2H, q, J=7.4 Hz), 6.23 (1H, brs), 7.08 (1H, brs), 7.15-7.22 (4H, m), 7.28-7.38 (1H, m), 7.51 (1H, t, J=5.9 Hz), 7.87 (2H, d, J=9.0 Hz), 8.00 (1H, t, J=7.4 Hz), 8.41 (1H, d, J=7.4 Hz), 8.76 (1H, brs)

ESI-MS (m/e): 508 [M+H]

Example 428

4-(2-Difluoromethyl-phenoxy)-6-(6-ethanesulfonyl-pyridin-3-yloxy)-2-pyridin-2-yl-1H-benzimidazole The entitled compound was obtained as a colorless solid in the same method as in Example 274 or in accordance with the method or by combining it with an ordinary method but using 2-difluoromethyl-phenol and 6-ethanesulfonyl-pyridin-3-ol.

¹HNMR (CD₃OD) δ: 1.24 (3H, t, J=7.4 Hz), 3.39 (2H, q, J=7.4 Hz), 6.50 (1H, s), 7.15 (1H, d, J=7.4 Hz), 7.22 (1H, t, J=55.5 Hz), 7.34 (1H, t, J=7.4 Hz), 7.49-7.62 (4H, m), 7.74 (1H, d, J=7.4 Hz), 7.98 (1H, t, J=7.4 Hz), 8.05 (1H, d, J=8.6 Hz), 8.37 (1H, d, J=7.4 Hz), 8.49 (1H, d, J=2.3 Hz), 8.74-8.77 (1H, m)

ESI-MS (m/e): 523 [M+H]

Example 429

4-(2-Difluoromethyl-phenoxy)-6-(6-ethanesulfonyl-pyridin-3-yloxy)-2-pyrazin-2-yl-1H-benzimidazole The entitled compound was obtained as a yellow solid in the same method as in Example 205 or in accordance with the method or by combining it with an ordinary method but using 3-(2-difluoromethyl-phenoxy)-5-(6-ethanesulfonyl-pyridin-3-yloxy)-benzene-1,2-diamine obtained in Example 428.

¹HNMR (CD₃OD) δ: 1.25 (3H, t, J=7.8 Hz), 3.40 (2H, q, J=7.8 Hz), 6.54 (1H, s), 7.17 (1H, d, J=7.4 Hz), 7.21 (1H, t, J=55.8 Hz), 7.36 (1H, t, J=7.4 Hz), 7.50-7.65 (2H, m), 7.75 (1H, d, J=7.4 Hz), 8.06 (1H, d, J=8.6 Hz), 8.51 (1H, d, J=2.7 Hz), 8.72 (1H, s), 8.79 (1H, s), 9.54 (1H, s)

ESI-MS (m/e): 524 [M+H]

Example 430

4-(2-Difluoromethoxy-pyridin-3-yloxy)-6-(4-ethanesulfonyl-phenoxy-2-pyridin-2-yl-1H-benzimidazole The entitled compound was obtained in the same method as in Example 274 or in accordance with the method or by combining it with an ordinary method but using 2-difluoromethoxy-pyridin-3-ol and 4-ethanesulfonyl-phenol in order.

¹HNMR (CD₃OD) δ: 1.25 (3H, t, J=7.3 Hz), 3.40 (2H, q, J=7.3 Hz), 6.60 (1H, d, J=2.0 Hz), 7.27-7.30 (2H, m), 7.57-7.61 (2H, m), 7.64 (1H, t, J=72.1 Hz), 7.73 (1H, dd, J=7.8, 1.6 Hz), 8.05-8.08 (2H, m), 8.10 (1H, dd, J=4.9, 1.6 Hz), 8.37 (1H, d, J=8.2 Hz), 8.51 (1H, d, J=2.7 Hz), 8.81 (1H, d, J=4.9 Hz)

ESI-MS (m/e): 540 [M+H]

Example 431

4-(1-Methyl-2-oxo-1,2-dihydro-pyridin-3-yloxy-6-(4-ethanesulfonyl-phenoxy)-2-pyrazin-2-yl-1H-benzimidazole The entitled compound was obtained as a pale yellow solid in the same method as in Example 205 or in accordance with the method or by combining it with an ordinary method but using 3-(1-methyl-2-oxo-1,2-dihydro-pyridin-3-yloxy)-5-(4-ethanesulfonyl-phenoxy)-benzene-1,2-diamine obtained in Example 274 (step 1).

¹HNMR (CD₃OD) δ: 1.24 (3H, t, J=7.4 Hz), 3.21 (2H, q, J=7.4 Hz), 3.65 (3H, s), 6.38 (1H, t, J=7.2 Hz), 6.44 (1H, s), 7.07 (1H, s), 7.15-7.22 (2H, m), 7.40 (1H, d, J=7.0 Hz), 7.57 (1H, dd, J=7.0, 1.8 Hz), 7.84-7.90 (2H, m), 8.70 (1H, s), 8.76 (1H, s), 9.52 (1H, s)

ESI-MS (m/e): 504 [M+H]

Example 432

4-(1-Methyl-2-oxo-1,2-dihydro-pyridin-3-yloxy)-6-(6-ethanesulfonyl-pyridin-3-yloxy)-2-pyridin-2-yl-1H-benzimidazole The entitled compound was obtained as a pale brown solid in the same method as in Example 274 or in accordance with the method or by combining it with an ordinary method but using 1-methyl-2-oxo-1,2-dihydro-pyridin-3-ol and 6-ethanesulfonyl-pyridin-3-ol in order.

¹HNMR (CD₃OD) δ: 1.26 (3H, t, J=7.4 Hz), 3.40 (2H, q, J=7.4 Hz), 3.65 (3H, s), 6.36 (1H, t, J=6.7 Hz), 6.46 (1H, s), 7.13 (1H, s), 7.38-7.60 (4H, m), 7.95-8.08 (2H, m), 8.35 (1H, s), 8.49 (1H, s), 8.73 (1H, s)

ESI-MS (m/e): 504 [M+H]

Example 433

4-(1-Methyl-2-oxo-1,2-dihydro-pyridin-3-yloxy)-6-(6-ethanesulfonyl-pyridin-3-yloxy)-2-pyrazin-2-yl-1H-benzimidazole The entitled compound was obtained as a pale yellow solid in the same method as in Example 205 or in accordance with the method or by combining it with an ordinary method but using 3-(1-methyl-2-oxo-1,2-dihydro-pyridin-3-yloxy)-5-(6-ethanesulfonyl-pyridin-3-yloxy)-benzene-1,2-diamine obtained in Example 432.

¹HNMR (DMSO-d6) δ: 1.13 (3H, t, J=7.4 Hz), 3.40 (2H, q, J=7.4 Hz), 3.50 (3H, s), 6.24 (1H, t, J=6.8 Hz), 6.46 (1H, s), 7.05 (1H, br s), 7.32-7.40 (1H, m), 7.58 (1H, dd, J=8.8, 2.5 Hz), 7.74 (1H, dd, J=6.8, 2.0 Hz), 8.01 (1H, d, J=8.6 Hz), 8.57 (1H, d, J=2.5 Hz), 8.79 (1H, d, J=2.2 Hz), 8.82 (1H, dd, J=2.5, 1.5 Hz), 9.47 (1H, d, J=1.4 Hz)

ESI-MS (m/e): 505 [M+H]

Example 434

4-(2-Cyano-pyridin-3-yloxy-6-(4-methanesulfonyl-phenoxy)-2-pyridin-2-yl-1H-benzimidazole (Step 1) Production of 5-(4-methanesulfonyl-phenoxy)-2-nitro-3-(1-oxy-pyridin-3-yloxy)-phenylamine The entitled compound was obtained in the same method as in Example 67 (step 1) and (step 2) or in accordance with the method or by combining it with an ordinary method but using 1-oxy-pyridin-3-ol and 6-methanesulfonyl-pyridin-3-ol.

(Step 2) Production of 5-(4-methanesulfonyl-phenoxy)-2-nitro-3-(2-cyano-pyridin-3-yloxy)-phenylamine The entitled compound was obtained in the same method as in Example 218 (step 2) or in accordance with the method or by combining it with an ordinary method but using 5-(4-methanesulfonyl-phenoxy)-2-nitro-3-(1-oxy-pyridin-3-yloxy)-phenylamine.

(Step 3) Production of 4-(2-cyano-pyridin-3-yloxy)-6-(4-methanesulfonyl-phenoxy)-2-pyridin-2-yl-1H-benzimidazole The entitled compound was obtained in the same method as in Examples 196 (step 5) and 204 (step 1) or in accordance with the method or by combining it with an ordinary method but using 5-(4-methanesulfonyl-phenoxy)-2-nitro-3-(2-cyano-pyridin-3-yloxy)-phenylamine.

¹HNMR (CD₃OD) δ: 3.23 (3H, s), 7.07 (1H, brs), 7.44 (1H, brs), 7.56-7.69 (4H, m), 8.02 (1H, t, J=7.8 Hz), 8.09 (1H, d, J=8.6 Hz), 8.29 (1H, d, J=7.8 Hz), 8.46-8.48 (1H, m), 8.55-8.57 (1H, m), 8.78-8.80 (1H, m)

ESI-MS (m/e): 485 [M+H]

Example 435

4-(2-Cyano-pyridin-3-yloxy)-6-(4-ethanesulfonyl-phenoxy)-2-pyridin-2-yl-1H-benzimidazole The entitled compound was obtained in the same method as in Example 434 or in accordance with the method or by combining it with an ordinary method but using 4-ethanesulfonyl-phenol.

¹HNMR (CD₃OD) δ: 1.25 (3H, t, J=7.3 Hz), 3.22 (2H, q, J=7.3 Hz), 6.94 (1H, brs), 7.27 (2H, d, J=8.6 Hz), 7.33 (1H, brs), 7.49 (2H, d, J=8.6 Hz), 7.59-7.62 (1H, m), 7.91-7.98 (3H, m), 8.24 (1H, d, J=8.6 Hz), 8.45 (1H, d, J=5.1 Hz), 8.74 (1H, d, J=5.5 Hz)

ESI-MS (m/e): 498 [M+H]

Example 436

4-Benzyloxy-6-(6-ethanesulfonyl-pyridin-3-yloxy)-2-pyridin-2-yl-1H-benzimidazole The entitled compound was obtained in the same method as in Example 274 or in accordance with the method or by combining it with an ordinary method but using benzyl alcohol and 6-ethanesulfonyl-pyridin-3-ol in order.

¹HNMR (CD₃OD) δ: 1.24 (3H, t, J=7.6 Hz), 3.45 (2H, q, J=7.6 Hz), 5.41 (2H, s), 7.02-7.05 (1H, m), 7.15-7.17 (1H, m), 7.39-7.45 (3H, m), 7.53-7.59 (4H, m), 8.07 (1H, d, J=8.6 Hz), 8.11-8.14 (1H, m), 8.39 (1H, d, J=7.0 Hz), 8.53 (1H, d, J=2.7 Hz), 8.87-8.90 (1H, m)
ESI-MS (m/e): 487 [M+H]

Example 437

4-Benzyloxy-6-(6-ethanesulfonyl-pyridin-3-yloxy)-2-pyrazin-2-yl-1H-benzimidazole The entitled compound was obtained in the same method as in Example 205 or in accordance with the method or by combining it with an ordinary method but using 3-benzyl-5-(6-ethanesulfonyl-pyridin-3-yloxy)-benzene-1,2-diamine obtained in Example 436.
¹HNMR (CD₃OD) δ: 1.27 (3H, t, J=7.4 Hz), 3.42 (2H, q, J=7.4 Hz), 5.38 (2H, s), 6.80 (1H, d, J=2.0 Hz), 7.06 (1H, d, J=2.0 Hz), 7.36-7.42 (3H, m), 7.49 (1H, dd, J=8.8, 2.9 Hz), 7.54 (2H, d, J=6.7 Hz), 8.03 (1H, d, J=8.8 Hz), 8.49 (1H, d, J=2.7 Hz), 8.72 (1H, d, J=2.7 Hz), 8.78-8.80 (1H, m), 9.54-9.56 (1H, m)
ESI-MS (m/e): 488 [M+H]

Example 438

4-(2-Cano-6-fluoro-phenoxy-6-(6-ethanesulfonyl pyridin-3-yloxy-2-pyridin-2-yl-1H-benzimidazole (Step 1) Production of 4-hydroxy-6-(6-ethanesulfonyl-pyridin-3-yloxy)-2-pyridin-2-yl-1H-benzimidazole The entitled compound was obtained in the same method as in Example 251 (step 1) or in accordance with the method or by combining it with an ordinary method but using 4-benzyloxy-6-(6-ethanesulfonyl-pyridin-3-yloxy)-2-pyridin-2-yl-1H-benzimidazole obtained in Example 436.

(Step 2) Production of 4-(2-cyano-6-fluoro-phenoxy)-6-(6-ethanesulfonyl-pyridin-3-yloxy)-2-pyridin-2-yl-1H-benzimidazole The entitled compound was obtained in the same method as in Example 251 (step 2) or in accordance with the method or by combining it with an ordinary method but using 4-hydroxy-6-(6-ethanesulfonyl-pyridin-3-yloxy)-2-pyridin-2-yl-1H-benzimidazole and 2,3-difluorobenzonitrile.
¹HNMR (CD₃OD) δ: 1.26 (3H, t, J=7.4 Hz), 3.40 (2H, q, J=7.4 Hz), 6.61 (1H, d, J=2.0 Hz), 7.28 (1H, d, J=2.0 Hz), 7.36-7.42 (1H, m), 7.48-7.54 (1H, m), 7.58-7.63 (2H, m), 7.65-7.69 (1H, m), 8.07 (2H, d, J=8.2 Hz), 8.38 (1H, d, J=7.8 Hz), 8.51 (1H, d, J=2.7 Hz), 8.82 (1H, d, J=4.7 Hz)
ESI-MS (m/e): 516 [M+H]

Example 439

4-(6-Cyano-pyridin-2-yloxy)-6-(4-ethanesulfonyl-phenoxy)-2-pyridin-2-yl-1H-benzimidazole The entitled compound was obtained in the same method as in Example 438 (step 2) or in accordance with the method or by combining it with an ordinary method but using 4-hydroxy-6-(6-ethanesulfonyl-pyridin-3-yloxy)-2-pyridin-2-yl-1H-benzimidazole obtained in Example 438 (step 1) and 2-chloro-3-cyanopyridine.

¹HNMR (CD₃OD) δ: 1.26 (3H, t, J=7.4 Hz), 3.42 (2H, q, J=7.4 Hz), 7.21 (1H, d, J=2.0 Hz), 7.30 (1H, dd, J=7.4, 5.1 Hz), 7.48 (1H, d, J=2.0 Hz), 7.58 (1H, dd, J=5.1, 7.8 Hz), 7.71 (1H, dd, J=8.8, 2.9 Hz), 8.00-8.05 (1H, m), 8.11 (1H, d, J=8.6 Hz), 8.26-8.33 (3H, m), 8.60 (1H, d, J=2.7 Hz), 8.78 (1H, d, J=5.1 Hz)
ESI-MS (m/e): 499 [M+H]

Example 440

4-(2-Cyano-3-fluoro-phenoxy)-6-(6-ethanesulfonyl-pyridin-3-yloxy)-2-pyridin-2-yl-1H-benzimidazole The entitled compound was obtained in the same method as in Example 439 or in accordance with the method or by combining it with an ordinary method but using 2,6-difluorobenzonitrile.
¹HNMR (CD₃OD) δ: 1.26 (3H, t, J=7.4 Hz), 3.41 (2H, q, J=7.4 Hz), 6.91 (1H, d, J=8.6 Hz), 7.04 (1H, d, J=1.8 Hz), 7.13 (1H, t, J=8.6 Hz), 7.44 (1H, d, J=1.8 Hz), 7.55-7.64 (2H, m), 7.67 (1H, dd, J=8.6, 3.2 Hz), 8.00-8.06 (1H, m), 8.10 (1H, d, J=8.6 Hz), 8.33 (1H, d, J=7.8 Hz), 8.57 (1H, d, J=2.3 Hz), 8.78-8.81 (1H, m)
ESI-MS (m/e): 516 [M+H]

Example 441

4-(2-Carbamoyl-6-fluoro-phenoxy)-6-(6-ethane-sulfonyl-pyridin-3-yloxy-2-pyridin-2-yl-1H-benzimidazole The entitled compound was obtained in the same method as in Example 43 or in accordance with the method or by combining it with an ordinary method but using 4-(2-cyano-6-fluoro-phenoxy)-6-(6-ethanesulfonyl-pyridin-3-yloxy)-2-pyridin-2-yl-1H-benzimidazole obtained in Example 438.
¹HNMR (CD₃OD) δ: 1.24 (3H, t, J=7.4 Hz), 3.40 (2H, q, J=7.4 Hz), 6.53 (1H, brs), 7.26 (1H, brs), 7.42-7.53 (2H, m), 7.57-7.62 (2H, m), 7.68 (1H, dd, J=8.2, 3.9 Hz), 8.07 (1H, d, J=8.6 Hz), 8.11-8.16 (1H, m), 8.41 (1H, d, J=8.2 Hz), 8.49 (1H, d, J=2.7 Hz), 8.88 (1H, d, J=3.9 Hz)
ESI-MS (m/e): 534 [M+H]

Example 442

4-(2-Cyano-6-fluoro-phenoxy)-6-(6-ethanesulfonyl-pyridin-3-yloxy)-2-pyrazin-2-yl-1H-benzimidazole The entitled compound was obtained in the same method as in Example 438 or in accordance with the method or by combining it with an ordinary method but using 4-benzyloxy-6-(6-ethanesulfonyl-pyridin-3-yloxy)-2-pyrazin-2-yl-1H-benzimidazole obtained in Example 437.
¹HNMR (CD₃OD) δ: 1.25 (3H, t, J=7.4 Hz), 3.40 (2H, q, J=7.4 Hz), 6.57 (1H, brs), 7.23 (1H, brs), 7.46-7.51 (1H, m), 7.57-7.61 (1H, m), 7.64-7.71 (2H, m), 8.06 (1H, d, J=9.0 Hz), 8.51 (1H, d, J=2.3 Hz), 8.71 (1H, d, J=2.3 Hz), 8.78 (1H, s), 9.48 (1H, s)
ESI-MS (m/e): 517 [M+H]

Example 443

4-(2-Cyano-5-fluoro-phenoxy)-6-(6-ethanesulfonyl-pyridin-3-yloxy)-2-pyrazin-2-yl-1H-benzimidazole The entitled compound was obtained in the same method as in Example 438 (step 2) or in accordance with the method or by combining it with an ordinary method but using 4-hydroxy-6-(6-ethanesulfonyl-pyridin-3-yloxy)-2-pyrazin-2-yl-1H-benzimidazole obtained in Example 442 and 2,4-difluoro-benzonitrile.

$^1$HNMR (CD$_3$OD) δ: 1.20 (3H, t, J=7.4 Hz), 3.41 (2H, q, J=7.4 Hz), 6.88 (1H, d, J=10.2 Hz), 6.98 (1H, d, J=2.0 Hz), 7.05-7.11 (1H, m), 7.39-7.44 (1H, m), 7.68 (1H, dd, J=3.1, 8.0 Hz), 7.89 (1H, dd, J=8.8, 6.1 Hz), 8.08-8.12 (1H, m), 8.57-8.60 (1H, m), 8.71 (1H, d, J=2.3 Hz), 8.77-8.79 (1H, m), 9.46-9.48 (1H, m)

ESI-MS (m/e): 517 [M+H]

Example 444

4-(2-Cyano-4-fluoro-phenoxy)-6-(6-ethanesulfonyl-pyridin-3-yloxy)-2-pyrazin-2-yl-1H-benzimidazole The entitled compound was obtained in the same method as in Example 443 or in accordance with the method or by combining it with an ordinary method but using 2,5-difluoro-benzonitrile.

$^1$HNMR (CD$_3$OD) δ: 1.26 (3H, t, J=7.4 Hz), 3.41 (2H, q, J=7.4 Hz), 6.81 (1H, d, J=2.3 Hz), 7.22 (1H, dd, J=4.6, 9.0 Hz), 7.35 (1H, d, J=2.3 Hz), 7.45 (1H, ddd, J=8.6, 4.6, 7.4 Hz), 7.63-7.69 (2H, m), 7.72-7.75 (1H, m), 8.09 (1H, d, J=8.6 Hz), 8.55 (1H, d, J=3.1 Hz), 8.72 (1H, d, J=2.3 Hz), 8.79 (1H, dd, J=2.0, 3.1 Hz), 9.49 (1H, d, J=2.0 Hz)

ESI-MS (m/e): 517 [M+H]

Example 445

4-(2-Carbamoyl-6-fluoro-phenoxy)-6-(6-ethane-sulfonyl-pyridin-3-yloxy)-2-pyrazin-2-yl-1H-benzimidazole The entitled compound was obtained in the same method as in Example 43 or in accordance with the method or by combining it with an ordinary method but using 4-(2-cyano-6-fluoro-phenoxy)-6-(6-ethanesulfonyl-pyridin-3-yloxy)-2-pyrazin-2-yl-1H-benzimidazole obtained in Example 442.

$^1$HNMR (CD$_3$OD) δ: 1.25 (3H, t, J=7.4 Hz), 3.39 (2H, q, J=7.4 Hz), 6.39 (1H, s), 7.21 (1H, s), 7.42-7.51 (2H, m), 7.55 (1H, dd, J=8.6, 2.7 Hz), 7.64 (1H, d, J=7.4 Hz), 8.06 (1H, d, J=8.6 Hz), 8.47 (1H, d, J=2.7 Hz), 8.75-8.78 (1H, m), 8.82-8.84 (1H, m), 9.54 (1H, brs)

ESI-MS (m/e): 535 [M+H]

Example 446

4-(6-Cyano-pyridin-2-yloxy)-6-(4-ethanesulfonyl-phenoxy)-2-pyrazin-2-yl-1H-benzimidazole The entitled compound was obtained in the same method as in Example 443 or in accordance with the method or by combining it with an ordinary method but using 2-chloro-3-cyanopyridine.

$^1$HNMR (CD$_3$OD) δ: 1.25 (3H, t, J=7.4 Hz), 3.41 (2H, q, J=7.4 Hz), 7.14 (1H, d, J=2.0 Hz), 7.30 (1H, dd, J=7.4, 5.1 Hz), 7.45 (1H, d, J=2.0 Hz), 7.69 (1H, dd, J=9.0, 2.7 Hz), 8.10 (1H, d, J=9.0 Hz), 8.27-8.33 (2H, m), 8.59 (1H, d, J=2.7 Hz), 8.70-8.72 (1H, m), 8.76-8.79 (1H, m), 9.41-9.43 (1H, m)

ESI-MS (m/e): 500 [M+H]

Example 447

4-(2-Cyano-6-fluoro-phenoxy)-6-(6-methanesulfonyl-pyridin-3-yloxy)-2-pyridin-2-yl-1H-benzimidazole The entitled compound was obtained as a pale yellow solid in the same method as in Example 438 or in accordance with the method or by combining it with an ordinary method but using 6-methanesulfonyl-pyridin-3-ol.

$^1$HNMR (CD$_3$OD) δ: 3.23 (3H, s), 6.50 (1H, s), 7.22 (1H, s), 7.45-7.62 (3H, m), 7.62-7.78 (2H, m), 7.95-8.05 (1H, m), 8.08 (1H, d, J=8.8 Hz), 8.37 (1H, d, J=8.0 Hz), 8.49 (1H, s), 8.77 (1H, s)

ESI-MS (m/e): 502 [M+H]

Example 448

4-(2-Fluoro-6-methanesulfonyl-phenoxy)-6-(6-methanesulfonyl-pyridin-3-yloxy)-2-pyridin-2-yl-1H-benzimidazole The entitled compound was obtained as a pale yellow solid in the same method as in Example 438 (step 2) or in accordance with the method or by combining it with an ordinary method but using 4-hydroxy-6-(6-methanesulfonyl-pyridin-3-yloxy)-2-pyridin-2-yl-1H-benzimidazole obtained in Example 447 and 2,3-difluoro-methanesulfonylbenzene.

$^1$HNMR (CD$_3$OD) δ: 3.21 (3H, s), 3.46 (3H, s), 6.54 (1H, d, J=2.0 Hz), 7.27 (1H, d, J=2.0 Hz), 7.54-7.67 (3H, m), 7.70-7.74 (1H, m), 7.93 (1H, d, J=7.8 Hz), 8.04 (1H, d, J=8.6 Hz), 8.11 (1H, ddd, J=7.8, 8.6, 2.7 Hz), 8.40 (1H, d, J=7.8 Hz), 8.46 (1H, d, J=2.7 Hz), 8.86 (1H, d, J=5.1 Hz)

ESI-MS (m/e): 555 [M+H]

Example 449

4-(2-Carbamoyl-6-fluoro-phenoxy)-6-(6-methane-sulfonyl-pyridin-3-yloxy)-2-pyridin-2-1H-benzimidazole The entitled compound was obtained in the same method as in Example 43 or in accordance with the method or by combining it with an ordinary method but using 4-(2-cyano-6-fluoro-phenoxy)-6-(6-methanesulfonyl-pyridin-3-yloxy)-2-pyridin-2-yl-1H-benzimidazole obtained in Example 447.

$^1$HNMR (CD$_3$OD) δ: 3.22 (3H, s), 6.53 (1H, d, J=1.6 Hz), 7.25 (1H, d, J=1.6 Hz), 7.42-7.53 (2H, m), 7.57 (1H, dd, J=8.6, 2.7 Hz), 7.61 (1H, d, J=7.4 Hz), 7.68 (1H, dd, J=7.6, 4.3 Hz), 8.06 (1H, d, J=9.0 Hz), 8.10-8.16 (1H, m), 8.41 (1H, d, J=8.2 Hz), 8.47 (1H, d, J=2.7 Hz), 8.87 (1H, d, J=4.3 Hz)

ESI-MS (m/e): 520 [M+H]

Example 450

4-(2-Cyano-6-fluoro-phenoxy)-6-(6-methanesulfonyl-pyridin-3-yloxy)-2-pyrazin-2-yl-1H-benzimidazole The entitled compound was obtained in the same method as in Example 442 or in accordance with the method or by combining it with an ordinary method but using 6-methanesulfonyl-pyridin-3-ol.

$^1$HNMR (CD$_3$OD) δ: 3.23 (3H, s), 6.57 (1H, brs), 7.23 (1H, brs), 7.49 (1H, td, J=8.0, 4.6 Hz), 7.59 (1H, dd, J=9.0, 3.2 Hz), 7.65-7.71 (2H, m), 8.07 (1H, d, J=9.0 Hz), 8.50 (1H, d, J=2.3 Hz), 8.71 (1H, d, J=2.3 Hz), 8.78 (1H, brs), 9.48 (1H, brs)

ESI-MS (m/e): 503 [M+H]

Example 451

4-(Pyridin-2-ylsulfanyl-6-(6-ethanesulfonyl-pyridin-3-yloxy)-2-pyridin-2-yl-1H-benzimidazole The entitled compound was obtained as a pale brown solid in the same method as in Example 288 or in accordance with the method or by combining it with an ordinary method but using 6-ethanesulfonyl-pyridin-3-ol.

$^1$HNMR (CDCl$_3$) δ: 1.31 (3H, t, J=7.4 Hz), 3.39 (2H, q, J=7.4 Hz), 7.03 (1H, d, J=8.0 Hz), 7.08 (1H, ddd, J=7.4, 4.7, 1.0 Hz), 7.35 (1H, d, J=2.2 Hz), 7.38-7.44 (2H, m), 7.52 (1H, td, J=7.8, 2.0 Hz), 7.64 (1H, d, J=2.1 Hz), 7.88 (1H, td, J=7.8, 1.8 Hz), 8.03 (1H, d, J=8.8 Hz), 8.38 (1H, d, J=7.8 Hz), 8.45 (1H, dd, J=4.9, 1.0 Hz), 8.53 (1H, d, J=2.7 Hz), 8.64 (1H, d, J=4.9 Hz)

ESI-MS (m/e): 490 [M+H]

Example 452

4-(Pyridin-2-ylsulfanyl)-6-(6-ethanesulfonyl-pyridin-3-yloxy)-2-pyrazin-2-yl-1H-benzimidazole The entitled compound was obtained as a yellow solid in the same method as in Example 68 or in accordance with the method or by combining it with an ordinary method but using 3-(pyridin-2-ylsulfanyl)-5-(6-ethanesulfonyl-pyridin-3-yloxy)-benzene-1,2-diamine obtained in Example 451.

$^1$HNMR (CDCl$_3$) δ: 1.32 (3H, t, J=7.4 Hz), 3.39 (2H, q, J=7.4 Hz), 7.08-7.19 (2H, m), 7.38 (1H, d, J=2.2 Hz), 7.43 (1H, dd, J=8.6, 2.8 Hz), 7.57 (1H, td, J=7.8, 1.8 Hz), 7.66 (1H, d, J=2.2 Hz), 8.04 (1H, d, J=8.6 Hz), 8.48 (1H, d, J=4.7 Hz), 8.53 (1H, d, J=2.7 Hz), 8.63 (1H, t, J=2.0 Hz), 8.69 (1H, d, J=2.5 Hz), 9.63 (1H, d, J=1.4 Hz)

ESI-MS (m/e): 491 [M+H]

Example 453

4-(1-Methyl-1H-imidazol-2-ylsulfanyl)-6-(6-ethanesulfonyl-pyridin-3-yloxy)-2-pyrazin-2-yl-1H-benzimidazole The entitled compound was obtained as a yellow solid in the same method as in Example 452 or in accordance with the method or by combining it with an ordinary method but using 1-methyl-1H-imidazole-2-thiol.

$^1$HNMR (CDCl$_3$) δ: 1.33 (3H, t, J=7.4 Hz), 3.41 (2H, q, J=7.4 Hz), 3.94 (3H, s), 6.65-6.69 (1H, m), 6.77 (1H, d, J=1.4 Hz), 6.87 (1H, d, J=1.6 Hz), 7.23 (1H, d, J=2.4 Hz), 7.48 (1H, dd, J=8.6, 2.8 Hz), 7.72 (1H, d, J=2.2 Hz), 8.05 (1H, dd, J=8.6, 0.6 Hz), 8.16 (1H, d, J=2.6 Hz), 8.54 (1H, dd, J=2.8, 0.6 Hz), 9.42 (1H, d, J=1.6 Hz)

ESI-MS (m/e): 494 [M+H]

Example 454

4-(4-Methoxybenzyl-sulfanyl)-6-(6-ethanesulfonyl-pyridin-3-yloxy)-2-pyrazin-2-yl-1H-benzimidazole The entitled compound was obtained as a brown solid in the same method as in Example 452 or in accordance with the method or by combining it with an ordinary method but using (4-methoxyphenyl)methanethiol.

$^1$HNMR (CDCl$_3$) δ: 1.32 (3H, t, J=7.4 Hz), 3.40 (2H, q, J=7.4 Hz), 3.61 and 3.79 (total 3H, each s), 4.05 and 4.40 (total 2H, each s), 6.69 and 6.79 (total 2H, each d, J=8.6 Hz), 6.88-7.52 (5H, m), 7.98 and 8.01 (total 1H, each d, J=8.6 Hz), 8.44 and 8.46 (total 1H, each d, J=2.9 Hz), 8.58-8.65 (1H, m), 8.68 and 8.70 (total 1H, each d, J=2.5 Hz), 9.58 and 9.74 (total 1H, each d, J=1.4 Hz), 10.05 and 10.46 (total 1H, each brs)

ESI-MS (m/e): 534 [M+H]

Example 455

4-(6-Cyano-pyridin-2-ylsulfanyl)-6-(6-ethanesulfonyl-pyridin-3-yloxy)-2-pyrazin-2-yl-1H-benzimidazole The entitled compound was obtained as a pale yellow solid in the same method as in Example 446 or in accordance with the method or by combining it with an ordinary method but using 2-chloro-3-cyanopyridine.

$^1$HNMR (CDCl$_3$) δ: 1.32 (3H, t, J=7.4 Hz), 3.39 (2H, q, J=7.4 Hz), 7.20 (1H, dd, J=7.8, 4.9 Hz), 7.41 (1H, d, J=2.2 Hz), 7.45 (1H, dd, J=8.8, 2.8 Hz), 7.72 (1H, d, J=2.2 Hz), 7.93 (1H, dd, J=7.8, 1.8 Hz), 8.04 (1H, d, J=8.6 Hz), 8.44 (1H, dd, J=4.9, 2.0 Hz), 8.54 (1H, d, J=2.8 Hz), 8.62 (1H, dd, J=2.5, 1.5 Hz), 8.70 (1H, d, J=2.5 Hz), 9.64 (1H, d, J=1.5 Hz)

ESI-MS (m/e): 516 [M+H]

Example 456

4-(2-Cyano-pyridin-3-ylsulfanyl)-6-(6-ethanesulfonyl-pyridin-3-yloxy)-2-yl-benzimidazole The entitled compound was obtained as a pale yellow solid in the same method as in Example 438 (step 2) or in accordance with the method or by combining it with an ordinary method but using 4-mercapto-6-(6-ethanesulfonyl-pyridin-3-yloxy)-2-pyrazin-2-yl-1H-benzimidazole obtained in Example 455 and 2-cyano-3-fluoropyridine.

$^1$HNMR (DMSO-d6) δ: 1.13 (3H, t, J=7.4 Hz), 3.40 (2H, q, J=7.4 Hz), 7.22 (1H, s), 7.41 (1H, s), 7.64 (2H, dd, J=8.6, 2.7 Hz), 7.96-8.04 (2H, m), 8.59-8.66 (2H, m), 8.77-8.83 (2H, m), 9.32 (1H, s)

ESI-MS (m/e): 516 [M+H]

Example 457

4-(Pyridin-2-ylsulfanyl)-5-chloro-6-(6-ethanesulfonyl-pyridin-3-yloxy)-2-pyridin-2-yl-1H-benzimidazole The entitled compound was obtained as a pale yellow solid in the same method as in Example 117 and Example 290 or in accordance with the method or by combining it with an ordinary method but using pyridine-2-thiol.

$^1$HNMR (CDCl$_3$) δ: 1.31 (3H, t, J=7.4 Hz), 3.40 (2H, q, J=7.4 Hz), 7.02 (1H, d, J=7.5 Hz), 7.05-7.10 (1H, m), 7.31 (1H, dd, J=8.6, 2.7 Hz), 7.41 (1H, t, J=6.0 Hz), 7.53 (1H, t, J=7.4 Hz), 7.75 (1H, s), 7.88 (1H, t, J=7.8 Hz), 8.03 (1H, d, J=8.8 Hz), 8.37 (1H, d, J=8.0 Hz), 8.41 (1H, d, J=4.1 Hz), 8.50 (1H, d, J=2.5 Hz), 8.63 (1H, s)

ESI-MS (m/e): 524, 526 [M+H]

Examples 458-1, 458-2

4-(Pyridin-2-ylsulfinyl)-6-(6-ethanesulfonyl-pyridin-3-yloxy)-2-pyridin-2-yl-1H-benzimidazole and 4-(pyridin-2-ylsulfonyl)-6-(6-ethanesulfonyl-pyridin-3-yloxy)-2-pyridin-2-yl-1H-benzimidazole 50 mg of Oxone and 0.5 ml of water were added to a methanol (3 ml) solution of 20 mg of 4-(pyridin-2-ylsulfanyl)-6-(6-ethanesulfonyl-pyridin-3-yloxy)-2-pyridin-2-yl-1H-benzimidazole obtained in Example 451, and the reaction liquid was stirred at room temperature for 3 hours. The solvent was evaporated away under reduced pressure, and the resulting residue was diluted with ethyl acetate, washed with water, and dried with anhydrous magnesium sulfate. The solvent was evaporated away under reduced pressure, and the resulting residue was purified through reversed-phase middle-pressure liquid chromatography [ODS-AS-360-CC (by YMC), mobile phase: water-acetonitrile-0.1% trifluoroacetic acid]. Aqueous saturated sodium hydrogencarbonate was added to the resulting fraction, extracted with ethyl acetate, and dried with anhydrous magnesium sulfate. The solvent was evaporated away under reduced pressure to obtain the entitled compound.

4-(Pyridin-2-ylsulfinyl)-6-(6-ethanesulfonyl-pyridin-3-yloxy)-2-pyridin-2-yl-1H-benzimidazole $^1$HNMR (CDCl$_3$) δ: 1.33 (3H, t, J=7.4 Hz), 3.40 (2H, q, J=7.4 Hz), 7.35 (1H, dd, J=8.8, 2.7 Hz), 7.37-7.45 (2H, m), 7.55 (1H, d, J=2.1 Hz), 7.61 (1H, d, J=2.1 Hz), 7.89 (1H, t, J=7.8 Hz), 7.96 (1H, t, J=7.8 Hz), 8.02 (1H, d, J=8.6 Hz), 8.15 (1H, d, J=8.2 Hz), 8.37 (1H, d, J=7.8 Hz), 8.49 (1H, d, J=2.7 Hz), 8.65 (1H, d, J=3.7 Hz), 8.76 (1H, d, J=4.5 Hz)
ESI-MS (m/e): 506 [M+H]

4-(pyridin-2-ylsulfonyl)-6-(6-ethanesulfonyl din-3-yloxy)-2-pyridin-2-yl-1H-benzimidazole $^1$HNMR (CDCl$_3$) δ: 1.33 (3H, t, J=7.4 Hz), 3.40 (2H, q, J=7.4 Hz), 7.37 (1H, dd, J=8.6, 2.8 Hz), 7.44-7.49 (1H, m), 7.55 (1H, dd, J=7.4, 4.5 Hz), 7.70 (1H, d, J=1.8 Hz), 7.80 (1H, d, J=2.2 Hz), 7.88-7.94 (1H, m), 7.96-8.02 (1H, m), 8.04 (1H, d, J=8.6 Hz), 8.26 (1H, d, J=7.4 Hz), 8.40 (1H, d, J=8.0 Hz), 8.49 (1H, d, J=2.7 Hz), 8.73 (1H, d, J=4.7 Hz), 8.77 (1H, d, J=4.9 Hz)
ESI-MS (m/e): 522 [M+H]

Example 459

6-(1-Acetylpyrrolidin-2-yl)-5-((2'-fluorobiphenyl-4-yl)oxy)-2-pyridin-2-yl-1H-benzimidazole The entitled compound was obtained as a white solid in the same method as in Example 338 (step 5) or in accordance with the method or by combining it with an ordinary method but using 2'-fluorobiphenyl-4-ol.
$^1$HNMR (CDCl$_3$) δ: 1.00-2.60 (7H, m), 3.40-4.00 (2H, m), 5.20-5.65 (1H, m), 7.00-7.70 (11H, m), 7.80-8.00 (1H, m), 8.25-8.45 (1H, m), 8.50-8.70 (1H, m)
ESI-MS (m/e): 493 [M+H]

Example 460

6-(1-yl-2-yl)-5-(4-(difluoromethyl)phenoxy)-2-pyridin-2-yl-1H-benzimidazole monotrifluoroacetate (Step 1) Production of 4-(6-(1-acetylpyrrolidin-2-yl)-2-pyridin-2-yl-1-((2-(trimethylsilyl)ethoxy)methyl)-1H-benzimidazol-5-yl)oxy)benzaldehyde 143 mg of cesium carbonate and 0.048 ml of p-fluorobenzaldehyde were added in order to an N-methyl-2-pyrrolidinone (1 ml) solution of 100 mg of 1-(2-(6-hydroxy-2-pyridin-2-yl-3-(2-trimethylsilanyl-ethoxymethyl)-3H-benzimidazol-5-yl)-pyrrolidin-1-yl)-ethanone obtained in Example 121 (step 11), and the reaction liquid was stirred under heat at 80° C. for 3 hours. The reaction liquid was cooled to room temperature, and aqueous saturated ammonium chloride was added to it, and extracted with ethyl acetate, and the organic layer was washed with saturated saline. After dried, the solvent was evaporated away, and the residue was purified through silica gel column chromatography (developing solvent: chloroform/methanol=100/1) to obtain the entitled compound as an orange oily substance.

(Step 2) Production of 6-(1-acetylpyrrolidin-2-yl)-5-(4-(difluoromethyl)phenoxy)-2-pyridin-2-yl-1H-benzimidazole 0.036 ml of bis(2-methoxyethyl)aminosulfur trifluoride was added to a chloroform (0.2 ml) solution pf 22 mg of 4-(6-(1-acetylpyrrolidin-2-yl)-2-pyridin-2-yl-1-((2-(trimethylsilyl)ethoxy)methyl)-1H-benzimidazol-5-yl)oxy)benzaldehyde, and the reaction liquid was stirred under heat at 80° C. for 8 hours. The solvent was evaporated away under reduced pressure, and the residue was purified through partitioning thin-layer chromatography (Kieselgel™ 60F$_{254}$, Art 5744 (by Merck), hexane/ethyl acetate=1/1) to obtain the entitled compound as a yellow solid.

(Step 3) Production of 6-(1-acetylpyrrolidin-2-yl)-5-(4-(difluoromethyl)phenoxy)-2-pyridin-2-yl-1H-benzimidazole monotrifluoroacetate 0.5 ml of trifluoroacetic acid was added to 12 mg of 6-(1-acetylpyrrolidin-2-yl)-5-(4-(difluoromethyl)phenoxy)-2-pyridin-2-yl-1H-benzimidazole, and the reaction liquid was stirred at room temperature for 1 hour. Trifluoroacetic acid was evaporated away under reduced pressure, and the residue was purified through reversed-phase middle-pressure liquid chromatography [ODS-AS-360-CC (by YMC), mobile phase: water-acetonitrile-0.1% trifluoroacetic acid], and the solvent of the resulting fraction was evaporated away under reduced pressure to obtain the entitled compound as a red oily substance.
$^1$HNMR (CD$_3$OD) δ: 0.78-0.95 (4H, m), 1.91-2.15 (2H, m), 2.69 (3H, s), 5.38-5.43 (1H, m), 7.21-7.34 (4H, m), 7.52-7.63 (6H, m), 8.27-8.29 (1H, m)
ESI-MS (m/e): 449 [M+H]

Example 461

1-(2-(6-(3-Chloro-4-methanesulfonyl-henoxy)-2-pyridin-2-yl-3H-benzimidazol-5-yl)-pyrrolidin-1-yl)-ethanone The entitled compound was obtained as a white solid in the same method as in Example 338 (step 5) or in accordance with the method or by combining it with an ordinary method but using (3-chloro-4-methanesulfonyl)phenol.
$^1$HNMR (CDCl$_3$) δ: 1.85-2.40 (4H, m), 2.90-3.27 (5H, m), 3.65-3.90 (2H, m), 5.15-5.43 (1H, m), 6.90-7.45 (5H, m), 7.84-8.15 (2H, m), 8.35-8.42 (1H, m), 8.60-8.68 (1H, m)
ESI-MS (m/e): 511 [M+H]

Example 462

2-(6-(1-Acetylpyrrolidin-2-yl)-5-(4-(methanesulfonyl)phenoxy)-1H-benzimidazol-2-yl)(1,3)thiazolo(5,4-b)pyridine monotrifluoroacetate The entitled compound was obtained as a yellow oily substance in the same method as in Example 306 (step 4) and (step 5) or in accordance with the method or by combining it with an ordinary method but using t-butyl 2-(4,5-diamino-2-

(4-methanesulfonyl-phenoxy)-phenyl)-pyrrolidine-1-carboxylate obtained in Example 306 (step 3) and (1,3)thiazolo(5,4-b)pyridine-2-carboxylic acid.

¹HNMR (CD₃OD) δ: 1.60-2.40 (7H, m), 3.00-3.80 (5H, m), 5.00-5.60 (1H, m), 7.20-7.40 (2H, m), 7.25-7.80 (3H, m), 7.90-8.10 (2H, m), 8.40-8.80 (2H, m)

ESI-MS (m/e): 534 [M+H]

Example 463

5-(1-Acetylpyrrolidin-2-yl)-6-(4-(methanesulfonyl)phenoxy)-2-(5-(trifluoromethyl-pyridin-2-yl)-1H-benzimidazole The entitled compound was obtained as a white solid in the same method as in Example 462 or in accordance with the method or by combining it with an ordinary method but using 5-(trifluoromethyl)pyridine-2-carboxylic acid.

¹HNMR (CDCl₃) δ: 0.89 (1H, m), 1.22 (2H, m), 1.88-2.11 (3H, m), 2.27 (1H, m), 3.08 (3H, m), 3.63-3.76 (1H, m), 3.84 (1H, s), 5.38 (1H, dd, J=25.8, 8.6 Hz), 7.11-7.20 (2H, m), 7.39 (1H, m), 7.54 (1H, m), 7.93 (2H, m), 8.11 (1H, m), 8.51 (1H, m), 8.93 (1H, m), 10.58-10.88 (1H, m)

ESI-MS (m/e): 545 [M+H]

Example 464

6-(1-Acetylpyrrolidin-2-yl)-2-(5-(difluoromethyl-pyridin-2-yl-5-(4-methanesulfonyl)phenoxy)-1H-benzimidazole monotrifluoroacetate The entitled compound was obtained as a yellow oily substance in the same method as in Example 462 or in accordance with the method or by combining it with an ordinary method but using 5-(difluoromethyl)pyridine-2-carboxylic acid.

¹HNMR (CD₃OD) δ: 0.92 (1H, m), 1.32 (2H, m), 1.89 (1H, m), 1.97-2.08 (2H, m), 2.13-2.14 (1H, m), 2.69 (3H, s), 3.16-3.17 (3H, s), 5.35 (1H, m), 7.30-7.32 (1H, m), 7.41-7.58 (1H, m), 7.60-7.62 (1H, m), 8.00-8.02 (3H, m), 8.04-8.22 (2H, m), 9.04 (1H, m)

ESI-MS (m/e): 527 [M+H]

Example 465

6-(1-Acetylpyrrolidin-2-yl)-5-(4-(methoxymethyl)phenoxy)-2-pyridin-2-yl-1H-benzimidazole monotrifluoroacetate 7 mg of sodium borohydroxide was added to a methanol (0.5 ml) solution of 50 mg of 4-(6-(1-acetylpyrrolidin-2-yl)-2-pyridin-2-yl-1-((2-(trimethylsilyl)ethoxy)methyl)-1H-benzimidazol-5-yl)oxy)benzaldehyde obtained in Example 460 (step 1), with cooling with ice, and the reaction liquid was stirred for 1 hour. Aqueous saturated ammonium chloride solution was added to the reaction liquid, and extracted with ethyl acetate. The organic layer was washed with saturated saline, dried with anhydrous sodium sulfate, and the solvent was evaporated away under reduced pressure to obtain a crude product. 10 mg of sodium hydride and 0.030 ml of methyl iodide were added in order to a dimethylformamide (1 ml) solution of the resulting crude product, and stirred at room temperature for 30 minutes. Aqueous saturated ammonium chloride solution was added to the reaction liquid, and extracted with ethyl acetate. The organic layer was washed with saturated saline, and dried with anhydrous sodium sulfate, and the solvent was evaporated away under reduced pressure to obtain a crude product. 0.5 ml of trifluoroacetic acid was added to the resulting crude product, and the reaction liquid was stirred at room temperature for 2 hours. Trifluoroacetic acid was evaporated away under reduced pressure, and the residue was purified through reversed-phase middle-pressure liquid chromatography [ODS-AS-360-CC (by YMC), mobile phase: water-acetonitrile-0.1% trifluoroacetic acid], and the solvent of the resulting fraction was evaporated away under reduced pressure to obtain the entitled compound as a yellow oily substance.

¹HNMR (CD₃OD) δ: 1.93 (1H, m), 2.07-2.11 (3H, m), 2.18 (2H, m), 2.45 (1H, m), 3.43 (3H, d, J=3.1 Hz), 3.75-3.95 (2H, m), 4.50 (d, 2H, J=4.3 Hz), 5.49-5.56 (1H, m), 7.16 (3H, m), 7.44-7.49 (2H, m), 7.57 (1H, m), 7.70-7.73 (1H, m), 8.15 (1H, m), 8.27-8.30 (1H, m), 8.89 (1H, m)

ESI-MS (m/e): 443 [M+H]

Example 466

1-(4-(6-(1-Acetylpyrrolidin-2-yl)-2-pyridin-2-yl-1H-benzimidazol-5-yl)oxy)phenyl)ethanol monotrifluoroacetate 0.4 ml of methyl lithium (1.0 M diethyl ether solution) was added to a tetrahydrofuran (1.3 ml) solution of 70 mg of 4-(6-(1-(acetylpyrrolidin-2-yl)-2-pyridin-2-yl-1-(2-(trimethylsilyl)ethoxy)methyl)-1H-benzimidazol-5-yl)oxy)benzaldehyde obtained in Example 460 (step 1), at −78° C., and the reaction liquid was stirred at −78° C. for 30 minutes. Saturated ammonium chloride solution was added to the reaction liquid, and extracted with ethyl acetate. The organic layer was washed with saturated saline, and dried with anhydrous sodium sulfate, and the solvent was evaporated away under reduced pressure to obtain a crude product. 0.5 ml of trifluoroacetic acid was added to the resulting crude product, and stirred at room temperature for 90 minutes, and then trifluoroacetic acid was evaporated away, and the residue was purified through reversed-phase middle-pressure liquid chromatography [ODS-AS-360-CC (by YMC), mobile phase: water-acetonitrile-0.1% trifluoroacetic acid], and the solvent of the resulting fraction was evaporated away under reduced pressure to obtain the entitled compound as a yellow oily substance.

¹HNMR (CD₃OD) δ: 0.90-0.96 (1H, m), 1.31 (4H, m), 1.25-1.90 (3H, m), 2.42 (1H, m), 2.68 (3H, s), 3.89-3.91 (1H, m), 5.50 (1H, m), 7.02-7.33 (4H, m), 7.42-7.52 (2H, m), 7.59-7.67 (1H, m), 8.10-8.14 (1H, m), 8.22-8.26 (1H, m), 8.80-8.87 (1H, m)

ESI-MS (m/e): 443 [M+H]

Example 467

6-(1-Acetylpyrrolidin-2-yl)-5-(4-(3-methyl-[1,2,4]-oxadiazol-5-yl)phenoxy)-2-pyridin-2-yl-1H-benzimidazole The entitled compound was obtained as a dark brown oily substance in the same method as in Example 122 or in accordance with the method or by combining it with an ordinary method but using 5-(4-iodophenyl)-3-methyl-[1,2,4]-oxadiazole.

¹HNMR (CDCl₃) δ: 1.39-2.49 (10H, m), 3.42-3.88 (2H, m), 5.14-5.4 (1H, m), 6.70-8.69 (10H, m)

ESI-MS (m/e): 481 [M+H]

Example 468

(1-Acetyl-2-(5-(4-(methanesulfonyl)phenoxy)-2-pyridin-2-yl-1H-benzimidazol-6-yl)pyrrolidin-3-yl acetate diastereomer A

(Step 1) Production of 3-((t-butyl(dimethyl)silyl)oxy)dihydrofuran-2 (3H)-one 9.0 g of imidazole and 15.9 g of t-butyldimethylsilyl chloride were added in order to a dimethylformamide (180 ml) solution of 9.0 g of 3-hydroxydihydrofuran-2-(3H)-one, and the reaction liquid was stirred for 1 hour at room temperature. The reaction liquid was diluted with ethyl acetate, washed with water, and dried with anhydrous sodium sulfate. The solvent was evaporated away under reduced pressure, and the resulting residue was purified through silica gel column chromatography (developing solvent: hexane/ethyl acetate=5/1) to obtain the entitled compound as a colorless oily substance.

(Step 2) Production of N-(4-(2-((t-butyl(dimethyl)silyl)oxy)-4-hydroxybutanoyl)-3-fluorophenyl)pyridine-2-carboxamide 3.1 ml of n-butyl lithium (2.66 M hexane solution) was dropwise added to a tetrahydrofuran (100 ml) solution of 1.1 g of N-(4-bromo-3-fluorophenyl)pyridine-2-carboxamide at −78° C., and the reaction liquid was stirred at the same temperature for 15 minutes. 1.21 g of 3-((t-butyl(dimethyl)silyl)oxy)dihydrofuran-2 (3H)-one was added to the reaction liquid, and the reaction liquid was stirred at the same temperature for 1 hour. Aqueous saturated sodium bicarbonate solution was added to the reaction liquid at the same temperature, then heated up to room temperature and extracted with ethyl acetate. The organic layer was dried with anhydrous sodium sulfate, the solvent was evaporated away under reduced pressure, and the resulting residue was purified through silica gel column chromatography (developing solvent: chloroform/methanol=100/1) to obtain the entitled compound as a colorless oily substance.

(Step 3) Production of N-(4-(2-((t-butyl(dimethyl)silyl)oxy)-1,4-dihydroxybutyl)-3-fluorophenyl)pyridine-2-carboxamide 114 mg of sodium borohydride was added to a methanol (20 ml) solution of 860 mg of N-(4-(2-((t-butyl(dimethyl)silyl)oxy)-4-hydroxybutanoyl)-3-fluorophenyl)pyridine-2-carboxamide, with cooling with ice, and the reaction liquid was stirred at room temperature for 30 minutes. Aqueous saturated sodium bicarbonate solution was added to the reaction liquid, extracted with chloroform, and dried with anhydrous sodium sulfate. The solvent was evaporated away under reduced pressure, and the resulting residue was purified through silica gel column chromatography (developing solvent: chloroform/methanol=100/1) to obtain the entitled compound as a white solid.

(Step 4) Production of N-(4-(3-((t-butyl(dimethyl)silyl)oxy)pyrrolidin-2-yl)-3-fluorophenyl)pyridine-2-carboxamide 155 mg of triethylamine and 130 mg of methanesulfonyl chloride were added in order to a chloroform (8 ml) solution of 165 mg of N-(4-(2-((t-butyl(dimethyl)silyl)oxy)-1,4-dihydroxybutyl)-3-fluorophenyl)pyridine-2-carboxamide, with cooling with ice, and the reaction liquid was stirred at room temperature for 30 minutes. The reaction liquid was diluted with chloroform, washed with aqueous saturated sodium bicarbonate, and dried with anhydrous sodium sulfate. The solvent was evaporated away under reduced pressure, and 25 mg of sodium azide was added to a dimethylformamide (5 ml) solution of the resulting residue, and the reaction liquid was stirred at 40° C. for 2 hours. The reaction liquid was cooled, water was added to it, extracted with ethyl acetate, and dried with anhydrous sodium sulfate. The solvent was evaporated away under reduced pressure, and 50 mg of sodium borohydride and 5 mg of copper sulfate pentahydrate were added in order to a methanol (10 ml) solution of the resulting residue, and the reaction liquid was stirred at 40° C. for 2 hours. The reaction liquid was cooled, aqueous saturated sodium bicarbonate was added to it, extracted with chloroform, and dried with anhydrous sodium sulfate. The solvent was evaporated away under reduced pressure, and the resulting residue was purified through silica gel column chromatography (developing solvent: chloroform/methanol=50/1) to obtain the entitled compound as a colorless oily substance.

(Step 5) Production of 1-acetyl-2-(2-fluoro-4-((pyridin-2-ylcarbonyl)amino)phenyl)pyrrolidin-3-yl acetate 2 ml of 4 N hydrochloric acid-dioxane was added to a methanol (1 ml) solution of 59 mg of N-(4-(3-((t-butyl(dimethyl)silyl)oxy)pyrrolidin-2-yl)-3-fluorophenyl)pyridine-2-carboxamide, and the reaction liquid was stirred at room temperature for 1 hour. The solvent was evaporated away under reduced pressure, and 100 mg of triethylamine, 90 mg of acetic anhydride and 5 mg of N,N-4-dimethylaminopyridine were added in order to a chloroform (5 ml) solution of the resulting residue, and the reaction liquid was stirred at room temperature for 15 minutes. The solvent was evaporated away under reduced pressure, and the resulting residue was purified through silica gel column chromatography (developing solvent: chloroform/methanol=200/1) to obtain the entitled compound as a colorless oily substance.

(Step 6) Production of 1-acetyl-2-(2-fluoro-5-nitro-4-((pyridin-2-ylcarbonyl)amino)phenyl)pyrrolidin-3-yl acetate diastereomer A and diastereomer B 1 ml of fuming nitric acid was added to 57 mg of N-(4-(3-((t-butyl(dimethyl)silyl)oxy)pyrrolidin-2-yl)-3-fluorophenyl)pyridine-2-carboxamide, and the reaction liquid was stirred at room temperature for 40 minutes. The reaction liquid was poured into a mixed solution of ice-aqueous saturated sodium bicarbonate, extracted with chloroform, and dried with anhydrous sodium sulfate. The solvent was evaporated away under reduced pressure, and the resulting residue was purified through partitioning thin-layer chromatography (Kieselgel™ 60F$_{254}$, Art 5744 (by Merck), chloroform/methanol=20/1) to obtain diastereomer A and diastereomer B of the entitled compound each as a yellow oily substance.

(Step 7) Production of 1-acetyl-2-(5-(4-(methanesulfonyl)phenoxy)-2-pyridin-2-yl-1H-benzimidazol-6-yl)pyrrolidin-3-yl acetate diastereomer A The entitled compound was obtained as a white solid in the same method as in Example 338 (step 5) or in accordance with the method or by combining it with an ordinary method but using 4-(methanesulfonyl)phenol and (1-acetyl-2-(2-fluoro-5-nitro-4-((pyridin-2-ylcarbonyl)amino)phenyl)pyrrolidin-3-yl acetate diastereomer A.

¹HNMR (CDCl₃) δ: 1.86-2.42 (8H, m), 3.04-3.10 (3H, m), 3.72-4.02 (2H, m), 5.06-5.38 (2H, m), 7.08-7.70 (5H, m), 7.83-7.97 (3H, m), 8.34-8.42 (1H, m), 8.61-8.68 (1H, m), 10.54-10.65 (1H, m)
ESI-MS (m/e): 535 [M+H]

Example 469

1-Acetyl-2-(5-(4-(methanesulfonyl)phenoxy)-2-pyridin-2-yl-1H-benzimidazol-6-yl)pyrrolidin-3-ol diastereomer A 5 mg of potassium carbonate was added to a methanol (2 ml) solution of 14 mg of (1-acetyl-2-(5-(4-(methanesulfonyl)phenoxy)-2-pyridin-2-yl-1H-benzimidazol-6-yl)pyrrolidin-3-yl acetate diastereomer A obtained in Example 468, and the reaction liquid was stirred overnight at room temperature. The solvent was evaporated away, and the resulting residue was purified through partitioning thin-layer chromatography (Kieselgel™ 60F₂₅₄, Art 5744 (by Merck), chloroform/methanol=15/1) to obtain the entitled compound as a white solid.
¹HNMR (CDCl₃) δ: 1.82-2.47 (5H, m), 3.05&3.08 (3H, s), 3.70-3.97 (2H, m), 4.29-4.45 (1H, m), 5.00-5.32 (1H, m), 7.00-7.67 (5H, m), 7.81-7.96 (2H, m), 8.00-8.42 (1H, m), 8.60-8.69 (1H, m), 10.62-10.85 (1H, m)
ESI-MS (m/e): 493 [M+H]

Example 470

6-(1-Acetyl-4,5-dihydro-1H-pyrrol-2-yl)-5-(4-(methanesulfonyl)phenoxy)-2-pyridin-2-yl-1H-benzimidazole 2 mg of bis(2-methoxyethyl)aminosulfur trifluoride was added to a chloroform (1 ml) solution of 2 mg of 1-acetyl-2-(5-(4-(methanesulfonyl)phenoxy)-2-pyridin-2-yl-1H-benzimidazol-6-yl)pyrrolidin-3-ol diastereomer A obtained in Example 469, and the reaction liquid was stirred at room temperature for 15 minutes. The solvent was evaporated away under reduced pressure, and the resulting residue was purified through partitioning thin-layer chromatography (Kieselgel™ 60F₂₅₄, Art 5744 (by Merck), chloroform/methanol=15/1) to obtain the entitled compound as a colorless oily substance.
¹HNMR (CDCl₃) δ: 1.40-4.43 (10H, m), 7.03-7.80 (6H, m), 7.82-7.95 (3H, m), 8.32-8.46 (1H, m), 8.60-8.71 (1H, m), 10.38-10.60 (1H, m)
ESI-MS (m/e): 475 [M+H]

Example 471

1-Acetyl-2-(5-(4-(methanesulfonyl)phenoxy)-2-pyridin-2-yl-1H-benzimidazol-6-yl)pyrrolidin-3-yl acetate diastereomer B The entitled compound was obtained in the same method as in Example 468 (step 7) or in accordance with the method or by combining it with an ordinary method but using (1-acetyl-2-(2-fluoro-5-nitro-4-((pyridin-2-ylcarbonyl)amino)phenyl)pyrrolidin-3-yl acetate diastereomer B obtained in Example 468 (step 6).

¹HNMR (CDCl₃) δ: 1.72-2.30 (8H, m), 3.02-3.08 (3H, m), 3.64-3.99 (2H, m), 5.26-5.47 (1H, m), 5.58-5.72 (1H, m), 7.09-7.73 (5H, m), 7.82-7.94 (3H, m), 8.33-8.43 (1H, m), 8.60-8.70 (1H, m), 10.47-10.68 (1H, m)
ESI-MS (m/e): 535 [M+H]

Example 472

1-Acetyl-2-(5-(4-(methanesulfonyl)phenoxy)-2-pyridin-2-yl-1H-benzimidazol-6-yl)pyrrolidin-3-ol diastereomer B The entitled compound was obtained in the same method as in Example 469 or in accordance with the method or by combining it with an ordinary method but using (1-acetyl-2-(5-(4-(methanesulfonyl)phenoxy)-2-pyridin-2-yl-1H-benzimidazol-6-yl)pyrrolidin-3-yl acetate diastereomer B obtained in Example 471.
¹HNMR (CDCl₃) δ: 1.78-2.25 (5H, m), 3.03-3.10 (3H, m), 3.60-4.00 (2H, m), 4.50-4.68 (1H, m), 5.27-5.45 (1H, m), 7.03-7.73 (5H, m), 7.81-7.96 (3H, m), 8.32-8.45 (1H, m), 8.60-8.69 (1H, m), 10.51-10.82 (1H, m)
ESI-MS (m/e): 493 [M+H]

Example 473

1-(4-((6-(1-Acetylpyrrolidin-2-yl)-2-pyridin-2-yl-1H-benzimidazol-5-yloxy)phenyl)piperidin-2-one The entitled compound was obtained as an oily substance in the same method as in Example 338 (step 5) or in accordance with the method or by combining it with an ordinary method but using 1-(4-hydroxyphenyl)piperidin-2-one.
¹HNMR (CDCl₃) δ: 1.74-2.62 (13H, m), 3.52-3.87 (4H, m), 5.18-5.36 (1H, m), 6.71-7.64 (7H, m), 7.76-7.90 (1H, m), 8.26-8.41 (1H, m), 8.56-8.68 (1H, m), 10.98-11.33 (1H, m)
ESI-MS (m/e): 496 [M+H]

Example 474

6-(1-Acetylpyrrolidin-2-yl)-5-((6-phenylpyridin-3-yl)oxy)-2-pyridin-2-yl-1H-benzimidazole The entitled compound was obtained as a yellow solid in the same method as in Example 338 (step 5) or in accordance with the method or by combining it with an ordinary method but using 6-phenylpyridin-3-ol.
¹HNMR (CDCl₃) δ: 1.40-2.50 (7H, m), 3.40-4.00 (2H, m), 5.20-5.60 (1H, m), 6.90-8.00 (1H, m), 8.20-8.45 (1H, m), 8.50-8.70 (2H, m), 10.60-10.90 (1H, m)
ESI-MS (m/e): 476 [M+H]

Example 475

6-(1-Acetylpyrolidin-2-yl)-5-((6-(2-flurophenyl)pyridin-3-yl)oxy-2-pyridin-2-yl-1H-benzimidazole The entitled compound was obtained as a yellow solid in the same method as in Example 338 (step 5) or in accordance with the method or by combining it with an ordinary method but using 6-(2-fluorophenyl)pyridin-3-ol.
¹HNMR (CDCl₃) δ: 1.60-2.50 (7H, m), 3.45-4.00 (2H, m), 5.20-5.60 (1H, m), 6.80-8.05 (10H, m), 8.30-8.45 (1H, m), 8.50-8.70 (2H, m), 10.80-11.20 (1H, m)
ESI-MS (m/e): 494 [M+H]

Example 476

1-(2-(6-(3-Fluoro-4-methanesulfonyl-phenoxy)-2-pyridin-2-yl-3H-benzimidazol-5-yl)-pyrrolidin-1-yl)-ethanone The entitled compound was obtained as a yellow solid in the same method as in Example 338 (step 5) or in accordance with the method or by combining it with an ordinary method but using (3-fluoro-4-methanesulfonyl)phenol.

¹HNMR (CDCl₃) δ: 1.87-2.38 (4H, m), 2.85-3.27 (5H, m), 3.60-3.95 (2H, m), 5.20-5.41 (1H, m), 6.83-7.00 (1H, m), 7.28-7.40 (4H, m), 7.81-7.98 (2H, m), 8.35-8.42 (1H, m), 8.60-8.68 (1H, m)
ESI-MS (m/e): 495 [M+H]

Example 477

1-(4-{[6-(1-Acetylpyrrolidin-2-yl)-2-pyridine-2-pyridin-2-yl-1H-benzimidazol-5-yl]oxy}phenyl)pyrrolidin-2-one The entitled compound was obtained as a yellow solid in the same method as in Example 338 (step 5) or in accordance with the method or by combining it with an ordinary method but using 1-(4-hydroxyphenyl)pyrrolidin-2-one.
¹HNMR (CDCl₃) δ: 1.80-2.40 (6H, m), 2.62 (2H, m), 3.55-3.95 (4H+½H, m), 5.28 (½H, m), 6.90-7.10 (3H, m), 7.35 (1H+½H, m), 7.45-7.65 (2H+½H, m), 7.85 (1H, m), 8.34 (1H, m), 8.61 (1H, m), 10.4-10.8 (1H, br)
ESI-MS (m/e): 482 [M+H]

Example 478

1-(4-((6-(1-Acetylpyrrolidin-2-yl)-2-pyridin-2-yl-1H-benzimidazol-5-yl)oxy)phenyl)pyridin-2 (11H)-one The entitled compound was obtained as an oily substance in the same method as in Example 338 (step 5) or in accordance with the method or by combining it with an ordinary method but using 1-(4-hydroxyphenyl)pyridin-2 (1H)-one.
¹HNMR (CDCl₃) δ: 1.72-2.42 (7H, m), 3.48-3.86 (2H, m), 5.15-5.52 (1H, m), 6.19-6.32 (1H, m), 6.61-6.73 (1H, m), 6.80-7.66 (9H, m), 7.77-7.89 (1H, m), 8.32-8.41 (1H, m), 8.52-8.65 (1H, m), 11.07-11.48 (1H, m)
ESI-MS (m/e): 492 [M+H]

Example 479

5-((6-(1-Acetylpyrrolidin-2-yl)-2-pyridin-2-yl-1H-benzimidazol-5-yl)oxy)-2,2'-bipyridine monotrifluoroacetate The entitled compound was obtained as a yellow substance in the same method as in Example 338 (step 5) or in accordance with the method or by combining it with an ordinary method but using 2,2'-bipyridin-5-ol.
¹HNMR (CD₃OD) δ: 1.80-2.80 (7H, m), 3.60-4.05 (2H, m), 5.20-5.60 (1H, m), 7.50-7.90 (4H, m), 8.00-8.15 (1H, m), 8.15-8.25 (1H, m), 8.30-8.40 (1H, m), 8.45-8.60 (1H, m), 8.60-9.00 (5H, m)
ESI-MS (m/e): 477 [M+H]

Example 480

N-(2-(2-(6-(4-Methanesulfonyl-phenoxy)-2-pyridin-2-yl-3H-benzimidazol-5-yl)-pyrrolidin-1-yl)-2-oxo-ethyl)-methanesulfonamide The entitled compound was obtained in the same method as in Example 171 and 178 or in accordance with the method or by combining it with an ordinary method but using 5-(4-methanesulfonyl-phenoxy)-2-pyridin-2-yl-6-pyrrolidin-2-yl-1H-benzimidazole obtained in Example 162 (step 7) and N-t-butoxycarbonyl-glycine.

¹HNMR (CD₃OD) δ: 1.93-2.14 (3H, m), 2.06-2.27 (1H, m), 2.86 and 2.95 (total 3H, each s), 3.13 (3H, s), 3.43-4.08 (4H, m), 5.20-5.38 (1H, m), 7.20-7.60 (5H, m), 7.93-8.02 (3H, m), 8.23-8.30 (1H, m), 8.74 (1H, brs)
ESI-MS (m/e): 570 [M+H]

Example 481

Ethyl (2-(2-(6-(4-methanesulfonyl-phenoxy)-2-pyridin-2-yl-3H-benzimidazol-5-yl)-pyrrolidin-1-yl)-2-oxo-ethyl)-carbamate The entitled compound was obtained in the same method as in Example 171 and 181 or in accordance with the method or by combining it with an ordinary method but using 5-(4-methanesulfonyl-phenoxy)-2-pyridin-2-yl-6-pyrrolidin-2-yl-1H-benzimidazole obtained in Example 162 (step 7) and N-t-butoxycarbonyl-glycine.
¹HNMR (CD₃OD) δ: 1.18 and 1.23 (total 3H, each t, J=each 7.1 Hz), 1.93-2.14 (3H, m), 2.22-2.44 (1H, m), 3.12 and 3.13 (total 3H, each s), 3.30-4.13 (6H, m), 5.24-5.33 (1H, m), 7.20-7.60 (5H, m), 7.93-8.01 (3H, m), 8.28 (1H, t, J=8.2 Hz), 8.73 (1H, brs)
ESI-MS (m/e): 564 [M+H]

Example 482

6-(1-Acetylpyrrolidin-2-yl)-5-(4-bromophenoxy)-2-pyridin-2-yl-1H-benzimidazole enantiomer A (Step 1) Production of N-(4-(1-acetylpyrrolidin-2-yl)-5-fluoro-2-nitrophenyl)pyridine-2-carboxamide enantiomer A and enantiomer B 100 mg of N-(4-(1-acetylpyrrolidin-2-yl)-5-fluoro-2-nitrophenyl)pyridine-2-carboxamide obtained in Example 338 (step 4) was optically resolved, using an optical resolution column (CHIRAL CEL OD 2 cmφ×25 cmL (by Daicel Chemical), mobile phase: hexane/ethanol/diethylamine=60/40/0.1, flow rate: 10 ml/min), into an enantiomer A (retention time: 17.8 min) and an enantiomer B (retention time: 21.0 min) each as a pale yellow solid.

(Step 2) Production of 6-(1-acetylpyrrolidin-2-yl)-5-(4-bromophenoxy)-2-pyridin-2-yl-1H-benzimidazole enantiomer A The entitled compound was obtained as an oily substance in the same method as in Example 338 (step 5) or in accordance with the method or by combining it with an ordinary method but using N-(4-(1-acetylpyrrolidin-2-yl)-5-fluoro-2-nitrophenyl)pyridine-2-carboxamide enantiomer A obtained in Example 482 (step 1), and 4-bromophenol.
¹HNMR (CDCl₃) δ: 1.56-2.41 (7H, m), 3.42-3.90 (2H, m), 5.16-5.51 (1H, m), 6.78-7.66 (7H, m), 7.80-7.93 (1H, m), 8.32-8.44 (1H, m), 8.54-8.67 (1H, m), 11.14-11.65 (1H, m)
ESI-MS (m/e): 479 [M+H]

Example 483

6-(1-Acetylpyrrolidin-2-yl)-5-(4-bromophenoxy)-2-pyridin-2-yl-1H-benzimidazole enantiomer B The entitled compound was obtained as an oily substance in the same method as in Example 338 (step 5) or in accordance with the method or by combining it with an ordinary method but using N-(4-(1-acetylpyrrolidin-2-yl)-5-fluoro-2- nitrophenyl)pyridine-2-carboxamide enantiomer B obtained in Example 482 (step 1), and 4-bromophenol.
ESI-MS (m/e): 479 [M+H]

Example 484

6-(1-Acetylpyrrolidin-2-yl)-5-((6-(5-methyl-[1,2,4]-oxadiazol-3-yl)pyridin-3-yl)oxy)-2-pyridin-2-yl-1H-benzimidazole The entitled compound was obtained as a white solid in the same method as in Example 483 or in accordance with the method or by combining it with an ordinary method but using 6-(5-methyl-[1,2,4]-oxadiazol-3-yl)pyridin-3-ol.
$^1$HNMR (CDCl$_3$) δ: 1.51-2.43 (7H, m), 2.59-2.74 (3H, m), 3.50-3.93 (2H, m), 5.17-5.46 (1H, m), 7.00-7.72 (4H, m), 7.82-8.13 (2H, m), 8.34-8.44 (1H, m), 8.57-8.69 (2H, m), 10.75-11.14 (1H, m)
ESI-MS (m/e): 482 [M+H]

Example 485

5-(1-Acetyl-3-methylpyrrolidin-2-yl)-6-(4-(methylsulfonyl)phenoxy)-2-pyridin-2-yl-1H-benzimidazole (Step 1) Production of N-(3-fluoro-4-(2-(2-hydroxyethyl)acryloyl)phenyl)pyridine-2-carboxamide 136 mg of 60% sodium hydride was added to a tetrahydrofuran (20 ml) solution of 1.0 g of N-(4-bromo-3-fluorophenyl)pyridine-2-carboxamide with cooling with ice, and the reaction liquid was stirred at the same temperature for 15 minutes. The reaction liquid was cooled to −78° C., and 1.53 ml of n-butyllithium (2.66 M hexane solution) was dropwise added to it, and the reaction liquid was stirred at the same temperature for 30 minutes. 0.36 ml of 3-methylenedihydrofuran-2 (3H)-one was added to the reaction liquid at the same temperature, and the reaction liquid was stirred at the same temperature for 2 hours, and then heated up to 0° C., and stirred for 30 minutes. Aqueous saturated sodium bicarbonate was added to the reaction temperature at the same temperature, extracted with ethyl acetate, and the organic layer was washed with saturated saline, and dried with anhydrous sodium sulfate. The solvent was evaporated away under reduced pressure, and the resulting residue was purified through silica gel column chromatography (developing solvent: hexane/ethyl acetate=3/1) to obtain the entitled compound as a colorless oily substance.

(Step 2) Production of N-(4-(1,4-dihydroxy-2-methylbutyl)-3-fluorophenyl)pyridine-2-carboxamide 150 mg of sodium borohydride was added to a methanol (8 ml) solution of 320 mg of N-(3-fluoro-4-(2-(2-hydroxyethyl)acryloyl)phenyl)pyridine-2-carboxamide, and the reaction liquid was stirred at room temperature for 1 hour. Aqueous saturated sodium bicarbonate was added to the reaction liquid, extracted with chloroform, and dried with anhydrous sodium sulfate. The solvent was evaporated away under reduced pressure, and the resulting residue was purified through silica gel column chromatography (developing solvent: chloroform/methanol=100/1) to obtain the entitled compound as a colorless oily substance.

(Step 3) Production of N-(4-(1-acetyl-3-methylpyrrolidin-2-yl)-3-fluorophenyl)pyridine-2-carboxamide 0.18 ml of triethylamine and 0.07 ml of methanesulfonyl chloride were added in order to a chloroform (5 ml) solution of 100 mg of N-(4-(1,4-dihydroxy-2-methylbutyl)-3-fluorophenyl)pyridine-2-carboxamide, and the reaction liquid was stirred at room temperature for 30 minutes. Aqueous saturated sodium bicarbonate was added to the reaction liquid, extracted with chloroform, and dried with anhydrous sodium sulfate. The solvent was evaporated away under reduced pressure, and 23 mg of sodium azide was added to a dimethylformamide (4 ml) solution of the resulting residue, and the reaction liquid was stirred at 40° C. for 2 hours. The reaction liquid was cooled to room temperature, water was added to it, extracted with ethyl acetate, and dried with anhydrous sodium sulfate. The solvent was evaporated away under reduced pressure, and 50 mg of sodium borohydride and 5 mg of copper sulfate pentahydrate were added in order to a methanol (5 ml) solution of the resulting residue, and the reaction liquid was stirred at 40° C. for 15 minutes. The reaction liquid was cooled to room temperature, and then aqueous saturated sodium bicarbonate was added to it, extracted with chloroform and dried with anhydrous sodium sulfate. The solvent was evaporated away under reduced pressure, and 0.08 ml of triethylamine, 0.07 ml of acetic anhydride and 5 mg of N,N-4-dimethylaminopyridine were added in order to a chloroform (4 ml) solution of the resulting residue, and the reaction liquid was stirred at room temperature for 30 minutes. Aqueous saturated sodium bicarbonate was added to the reaction liquid, extracted with chloroform, and dried with anhydrous sodium sulfate. The solvent was evaporated away under reduced pressure, and the resulting residue was purified through silica gel column chromatography (developing solvent: chloroform/methanol=100/1) to obtain the entitled compound as a colorless oily substance.

(Step 4) Production of N-(4-(1-acetyl-3-methylpyrrolidin-2-yl)-5-fluoro-2-nitrophenyl)pyridine-2-carboxamide 1 ml of fuming nitric acid was added to 70 mg of N-(4-(1-acetyl-3-methylpyrrolidin-2-yl)-3-fluorophenyl)pyridine-2-carboxamide, and the reaction liquid was stirred at room temperature for 2 hours. The reaction liquid was poured into a mixture of ice-aqueous saturated sodium bicarbonate, extracted with chloroform, and dried with anhydrous sodium carbonate. The solvent was evaporated away under reduced pressure, and the resulting residue was purified through partitioning thin-layer chromatography (Kieselgel™ 60F$_{254}$, Art 5744 (by Merck), chloroform/methanol=20/1) to obtain the entitled compound as a yellow solid.

(Step 5) Production of 5-(1-acetyl-3-methylpyrrolidin-2-yl)-6-(4-(methanesulfonyl)phenoxy)-2-pyridin-2-yl-1H-benzimidazole The entitled compound was obtained as a white solid in the same method as in Example 338 (step 5) or in accordance with the method or by combining it with an ordinary method but using N-(4-(1-acetyl-3-methylpyrrolidin-2-yl)-5-fluoro-2-nitrophenyl)pyridine-2-carboxamide and 4-(methanesulfonyl)phenol.
$^1$HNMR (CDCl$_3$) δ: 0.81-2.73 (9H, m), 3.03-3.11 (3H, m), 3.36-3.99 (2H, m), 4.65-5.43 (1H, m), 7.00-7.75 (5H,), 7.81-7.79 (3H, m), 8.32-8.45 (1H, m), 8.60-8.68 (1H, m), 10.51-10.82 (1H, br)
ESI-MS (m/e): 491 [M+H]

Example 486

6-((6-(1-Acetylpyrrolidin-2-yl)-2-pyridin-2-yl-1H-benzimidazol-5-yl)oxy)-3,4-dihydronaphthalen-1 (2H)-one The entitled compound was obtained as a yellow solid in the same method as in Example 338 (step 5) or in accordance with the method or by combining it with an ordinary method but using 6-hydroxy-3,4-dihydronaphthalen-1 (2H)-one.

$^1$HNMR (CDCl$_3$) δ: 1.00-3.00 (13H, m), 3.40-3.95 (2H, m), 5.00-5.50 (1H, m), 6.60-7.80 (5H, m), 7.80-8.20 (2H, m), 8.30-8.50 (1H, m), 8.50-8.80 (1H, m), 10.80-11.20 (1H, m)

ESI-MS (m/e): 467 [M+H]

Example 487

6-(1-Acetylpyrrolidin-2-yl)-5-(4-(1H-imidazol-1-yl) phenoxy)-2-pyridin-2-yl-1H-benzimidazole The entitled compound was obtained as a yellow solid in the same method as in Example 338 (step 5) or in accordance with the method or by combining it with an ordinary method but using 4-(1H-imidazol-1-yl)phenol.

$^1$HNMR (CDCl$_3$) δ: 1.00-2.50 (7H, m), 3.50-4.50 (2H, m), 5.20-6.00 (1H, m), 6.80-8.80 (13H, m)

ESI-MS (m/e): 465 [M+H]

Example 488

6-((6-(1-Acetylpyrrolidin-2-yl)-2-pyridin-2-yl-1H-benzimidazol-5-yl)oxy)-1-methyl-[1,2,3,4]-tetrahydronaphthalen-1-ol 0.050 ml of methylmagnesium bromide (5.0 M tetrahydrofuran solution) was added to a tetrahydrofuran (0.5 ml) solution of 7 mg of 6-((6-(1-acetylpyrrolidin-2-yl)-2-pyridin-2-yl-1H-benzimidazol-5-yl)oxy)-3,4-dihydronaphthalen-1 (2H)-one obtained in Example 486, with cooling with ice, and the reaction liquid was stirred at 0° C. for 30 minutes. The reaction liquid was diluted with chloroform, washed with aqueous saturated ammonium chloride, and dried with anhydrous sodium sulfate. The solvent was evaporated away under reduced pressure, and the resulting residue was purified through partitioning thin-layer chromatography (Kieselgel™ 60F$_{254}$, Art 5744 (by Merck), chloroform/methanol=10/1) to obtain the entitled compound as a colorless oily substance.

$^1$HNMR (CDCl$_3$) δ: 1.10-2.80 (16H, m), 3.50-4.00 (2H, m), 5.10-5.50 (1H, m), 6.60-7.90 (7H, m), 8.30-8.50 (1H, m), 8.50-70 (1H, m)

ESI-MS (m/e): 465 [M+H]

Example 489

6-((6-(1-Acetylpyrrolidin-2-yl)-2-pyridin-2-yl-1H-benzimidazol-5-yl)oxy)-[1,2,3,4]-tetrahydronaphthalen-1-ol 5 mg of sodium borohydride was added to a tetrahydrofuran (0.5 ml) solution of 7 mg of 6-((6-(1-acetylpyrrolidin-2-yl)-2-pyridin-2-yl-1H-benzimidazol-5-yl)oxy)-3,4-dihydronaphthalen-1 (2H)-one obtained in Example 486, with cooling with ice, and the reaction liquid was stirred at room temperature for 30 minutes. The reaction liquid was diluted with chloroform, washed with aqueous saturated ammonium chloride, and dried with anhydrous sodium sulfate. The solvent was evaporated away, and the resulting residue was purified through partitioning thin-layer chromatography (Kieselgel™ 60F$_{254}$, Art 5744 (by Merck), chloroform/methanol=10/1) to obtain the entitled compound as a colorless oily substance.

$^1$HNMR (CDCl$_3$) δ: 1.00-2.50 (14H, m), 4.00-6.00 (3H, m), 6.80-8.50 (9H, m)

ESI-MS (m/e): 469 [M+H]

Example 490

5-(1-Acetyl-3-fluoropyrrolidin-2-yl)-6-(4-(methanesulfonyl)phenoxy)-2-pyridin-2-yl-1H-benzimidazole diastereomer A (Step 1) Production of ethyl (2Z)-4-((t-butyl(dimethyl)silyl)oxy)-2-fluorobut-2-anoate A tetrahydrofuran (40 ml) solution of 2.0 g of ethyl(diethoxyphosphoryl)(fluoro)acetate was cooled at −78° C., and then 3.4 ml of n-butyllithium (2.66 M hexane solution) was dropwise added to it, and the reaction liquid was stirred at the same temperature for 15 minutes. 2.1 ml of ((t-butyl)dimethyl)silyl)oxy)acetaldehyde was added to the reaction liquid, and the reaction liquid was stirred at the same temperature for 2 hours. At the same temperature, aqueous saturated sodium bicarbonate was added to the reaction liquid, and heated up to room temperature, and then extracted with ethyl acetate. This was dried with anhydrous sodium sulfate, the solvent was evaporated away under reduced pressure, and the resulting residue was purified through silica gel column chromatography (developing solvent: hexane/ethyl acetate=50/1) to obtain the entitled compound as a colorless oily substance.

(Step 2) Production of N-(4-((2Z)-4-((t-butyl(dimethyl)silyl)oxy)-2-fluorobut-2-anonyl)-3-fluorophenyl)pyridine-2-carboxamide 136 mg of 60% sodium hydride was added to a tetrahydrofuran (40 ml) solution of 1.0 g of N-(4-bromo-3-fluorophenyl)pyridine-2-carboxamide with cooling with ice, and the reaction liquid was stirred at the same temperature for 20 minutes. The reaction liquid was cooled to −78° C., and 1.53 ml of n-butyllithium (2.66 M hexane solution) was dropwise added to it, and the reaction liquid was stirred at the same temperature for 20 minutes. At the same temperature, 1.07 g of ethyl (2Z)-4-((t-butyl(dimethyl)silyl)oxy)-2-fluorobut-2-anoate was added to the reaction liquid, and the reaction liquid was stirred at the same temperature for 4 hours. Aqueous saturated sodium bicarbonate was added to the reaction liquid at the same temperature, heated up to room temperature, and extracted with ethyl acetate. The organic layer was washed with saturated saline, and dried with anhydrous sodium sulfate. The solvent was evaporated away under reduced pressure, and the resulting residue was purified through silica gel column chromatography (developing solvent: hexane/ethyl acetate=3/1) to obtain the entitled compound as a colorless oily substance.

(Step 3) N-(4-(4-((t-butyl(dimethyl)silyl)oxy)-2-fluoro-1-hydroxybutyl)-3-fluorophenyl)pyridine-2-carboxamide 100 mg of 10% palladium-carbon catalyst was added to a methanol (20 ml) solution of 300 mg of N-(4-((2Z)-4-((t-butyl(dimethyl)silyl)oxy)-2-fluorobut-2-anonyl)-3-fluorophenyl)pyridine-2-carboxamide, and in a hydrogen atmosphere, the reaction liquid was stirred at room temperature for 4 hours. The catalyst was removed through filtration, the solvent was evaporated away under reduced pressure, and 50 mg of sodium borohydride was added to a methanol (4 ml) solution of the resulting residue, and the reaction liquid was stirred at room temperature for 1 hour. Aqueous saturated sodium bicarbonate was added to the reaction liquid, extracted with ethyl acetate, and dried with anhydrous sodium sulfate. The solvent was evaporated away, and the resulting residue was purified through silica gel column chromatography (developing solvent: chloroform/methanol=100/1) to obtain the entitled compound as a colorless oily substance.

(Step 4) Production of N-(4-(1-acetyl-3-fluoropyrrolidin-2-yl)-3-fluorophenyl)pyridin-2-carboxamide diastereomer A and diastereomer B 46 mg of triethylamine and 39 mg of methanesulfonyl chloride were added to a chloroform (5 ml) solution of 100 mg of N-(4-(4-((t-butyl(dimethyl)silyl)oxy)-2-fluoro-1-hydroxybutyl)-3-fluorophenyl)pyridine-2-carboxamide, and the reaction liquid was stirred at room temperature for 30 minutes. Aqueous saturated sodium bicarbonate was added to the reaction liquid, extracted with chloroform, and dried with anhydrous sodium sulfate. The solvent was evaporated away under reduced pressure, and 22 mg of sodium azide was added to a dimethylformamide (4 ml) solution of the resulting residue, and the reaction liquid was stirred at 40° C. for 2 hours. The reaction liquid was cooled, water was added to it, extracted with ethyl acetate, and dried with anhydrous sodium sulfate. The solvent was evaporated away under reduced pressure, and 0.3 ml of tetrabutylammonium fluoride (1.0 M tetrahydrofuran solution) was added to a tetrahydrofuran (4 ml) solution of the resulting residue, and the reaction liquid was stirred at room temperature for 1 hour. Water was added to the reaction liquid, extracted with ethyl acetate, and dried with anhydrous sodium sulfate. The solvent was evaporated away under reduced pressure, and 46 mg of triethylamine and 39 mg of methanesulfonyl chloride were added in order to a chloroform (5 ml) solution of the resulting residue, and the reaction liquid was stirred at room temperature for 30 minutes. Aqueous saturated sodium bicarbonate was added to the reaction liquid, extracted with ethyl acetate, and dried with anhydrous sodium sulfate. The solvent was evaporated away under reduced pressure, and 10 mg of copper sulfate pentahydrate and 50 mg of sodium borohydride were added in order to a methanol (4 ml) solution of the resulting residue, and the reaction liquid was stirred at 40° C. for 1 hour. The reaction liquid was cooled, aqueous saturated sodium bicarbonate was added to it, extracted with chloroform, and dried with anhydrous sodium sulfate. The solvent was evaporated away under reduced pressure, and 46 mg of triethylamine, 35 mg of acetic anhydride and 5 mg of N,N-4-dimethylaminopyridine were added in order to a chloroform (4 ml) solution of the resulting residue, and the reaction liquid was stirred at room temperature for 30 minutes. The solvent was evaporated away under reduced pressure, and the resulting residue was purified through partitioning thin-layer chromatography (chloroform/methanol=30/1) to obtain a diastereomer A and a diastereomer B of the entitled compound each as a colorless oily substance.

(Step 5) Production of 5-(1-acetyl-3-fluoropyrrolidin-2-yl)-6-(4-(methanesulfonyl)phenoxy)-2-pyridin-2-yl-1H-benzimidazole diastereomer A 0.5 ml of fuming nitric acid was added to 18 mg of N-(4-(1-acetyl-3-fluoropyrrolidin-2-yl)-3-fluorophenyl)pyridin-2-carboxamide diastereomer A, and the reaction liquid was stirred at room temperature for 10 minutes. The reaction liquid was poured into a mixture of ice-aqueous saturated sodium bicarbonate, extracted with chloroform, and then dried with anhydrous sodium sulfate. The solvent was evaporated away under reduced pressure to obtain a crude product. The entitled compound was obtained as a pale yellow solid in the same method as in Example 338 (step 5) or in accordance with the method or by combining it with an ordinary method but using the resulting crude product and 4-(methanesulfonyl)phenol.

$^1$HNMR (CDCl$_3$) δ: 1.85-2.40 (5H, m), 3.06 and 3.09 (3H, s), 3.79-4.08 (2H, m), 4.96-5.62 (2H, m), 7.05-7.70 (5H, m), 7.83-7.99 (3H, m), 8.34-8.43 (1H, m), 8.61-8.69 (1H, m), 10.58-10.84 (1H, m)

ESI-MS (m/e): 495 [M+H]

Example 491

6-(1-Acetylpyrrolidin-2-yl)-2-pyridin-2-yl-5-(4-(2-thienyl)phenoxy)-1H-benzimidazole The entitled compound was obtained as a yellow solid in the same method as in Example 338 (step 5) or in accordance with the method or by combining it with an ordinary method but using 4-(2-thienyl)phenol.

$^1$HNMR (CDCl$_3$) δ: 1.05-2.45 (7H, m), 3.40-4.00 (2H, m), 5.10-5.60 (1H, m), 6.80-8.00 (11H, m), 8.30-8.50 (1H, m), 8.50-8.80 (1H, m)

ESI-MS (m/e): 481 [M+H]

Example 492

2-(4-((6-(1-Acetylpyrrolidin-2-yl)-2-pyridin-2-yl-1H-benzimidazol-5-yl)oxy)phenyl)-1H-isoindole-1,3(2H)-dione The entitled compound was obtained as a white solid in the same method as in Example 338 (step 5) or in accordance with the method or by combining it with an ordinary method but using 2-(4-hydroxyphenyl)-1H-isoindole-1,3-(2H)-dione.

$^1$HNMR (CDCl$_3$) δ: 1.05-2.40 (7H, m), 3.40-4.05 (2H, m), 5.05-5.60 (1H, m), 6.80-8.20 (12H, m), 8.30-8.70 (2H, m)

ESI-MS (m/e): 544 [M+H]

Example 493

5-(1-Acetyl-3-fluoropyrrolidin-2-yl)-6-(4-(methanesulfonyl)phenol)-2-pyridin-2-yl-1H-benzimidazole diastereomer B The entitled compound was obtained as a pale yellow solid in the same method as in Example 490 (step 5) or in accordance with the method or by combining it with an ordinary method but using N-(4-(1-acetyl-3-fluoropyrrolidin-2-yl)-3-fluorophenyl)pyridine-2-carboxamide diastereomer B obtained in Example 490 (step 4).

$^1$HNMR (CDCl$_3$) δ: 1.80-2.45 (5H, m), 3.05 and 3.08 (3H, s), 3.61-4.31 (2H, m), 5.08-5.54 (2H, m), 7.03-7.80 (5H, m), 7.81-7.97 (3H, m), 8.33-8.43 (1H, m), 8.60-8.68 (1H, m), 10.52-10.75 (1H, m)

ESI-MS (m/e): 495 [M+H]

Example 494

6-(1-Acetylpyrrolidin-2-yl)-5-(4-(5-methyl-1H-tetrazol-1-yl)phenoxy)-2-pyridin-2-yl-1H-benzimidazole The entitled compound was obtained as a white solid in the same method as in Example 338 (step 5) or in accordance with the method or by combining it with an ordinary method but using 4-(5-methyl-1H-tetrazol-1-yl)phenol.

¹HNMR (CD₃OD) δ: 1.91 and 2.15 (total 3H, each s), 1.97-2.20 (3H, m), 2.22-2.58 (1H, m), 2.63 and 2.64 (total 3H, each s), 3.62-4.00 (2H, m), 5.34-5.42 (1H, m), 7.22-7.68 (7H, m), 7.94-8.05 (1H, m), 8.30 (1H, t, J=7.8 Hz), 8.76 (1H, brs)
ESI-MS (m/e): 481 [M+H]

Example 495

Ethyl 5-((6-(1-Acetylpyrrolidin-2-yl)-2-pyridin-2-yl-1H-benzimidazol-5-yl)oxy)pyridine-2-carboxylate The entitled compound was obtained as a yellow solid in the same method as in Example 338 (step 5) or in accordance with the method or by combining it with an ordinary method but using ethyl 5-hydroxypyridine-2-carboxylate.
¹HNMR (CDCl₃) δ: 1.30-1.50 (3H, m), 1.50-2.50 (7H, m), 3.50-3.90 (2H, m), 4.35-4.60 (2H, m), 5.10-5.45 (1H, m), 6.90-7.70 (4H, m), 7.80-7.95 (1H, m), 8.00-8.20 (1H, m), 8.30-8.80 (3H, m), 10.60-11.20 (1H, m)
ESI-MS (m/e): 472 [M+H]

Example 496

6-(1-Acetylpyrrolidin-2-yl)-5-(4-pyrazin-2-ylphenoxy)-2-pyridin-2-yl-1H-benzimidazole The entitled compound was obtained as a yellow solid in the same method as in Example 338 (step 5) or in accordance with the method or by combining it with an ordinary method but using 4-pyrazin-2-ylphenol.
¹HNMR (CDCl₃) δ: 0.80-2.40 (7H, m), 3.60-3.90 (2H, m), 5.20-5.60 (1H, m), 6.80-8.05 (8H, m), 8.30-8.80 (4H, m), 8.90-9.10 (1H, m), 10.40-10.80 (1H, m)
ESI-MS (m/e): 477 [M+H]

Example 497

6-(1-Acetylpyrrolidin-2-yl)-5-(1H-indol-5-yloxy)-2-pyridin-2-yl-1H-benzimidazole The entitled compound was obtained as a yellow solid in the same method as in Example 338 (step 5) or in accordance with the method or by combining it with an ordinary method but using 1H-indol-5-ol.
¹HNMR (CDCl₃) δ: 1.20-2.40 (7H, m), 3.60-4.00 (2H, m), 5.20-5.60 (1H, m), 6.40-6.60 (1H, m), 6.80-8.00 (7H, m), 8.20-8.50 (2H, m), 8.50-8.80 (1H, m)
ESI-MS (m/e): 438 [M+H]

Example 498

(2-(2-(5-((2'-Fluorobiphenyl-4-41)oxy)-2-pyridin-2-yl-1H-benzimidazol-6-yl)pyrrolidin-1-yl)-2-oxoethyl)methylamine (Step 1) Production of (3-fluoro-4-pyrrolidin-2-ylphenyl)amine dihydrochloride 100 ml of 4 N hydrochloric acid-dioxane solution was added to a solution of 19 g of t-butyl 2-(4-amino-2-fluorophenyl)-pyrrolidine-1-carboxylate obtained in Example 338 (step 2) in a mixture of 50 ml of ethyl acetate and 50 ml of methanol, with cooling with ice, and the reaction liquid was stirred overnight at room temperature. The solvent was evaporated away under educed pressure to obtain the entitled compound as a white solid.

(Step 2) Production of 2,2,2-trifluoro-N-(3-fluoro-4-(1-(trifluoroacetyl)pyrrolidin-2-yl)phenyl)acetamide 39 ml of pyridine and 24 ml of trifluoroacetic acid anhydride were added in order to a chloroform (200 ml) solution of 20 g of (3-fluoro-4-pyrrolidin-2-ylphenyl)amine dihydrochloride with cooling with ice, and the reaction liquid was stirred at room temperature for 30 minutes. The reaction liquid was diluted with ethyl acetate, washed with water and saturated saline in order, and dried with anhydrous magnesium sulfate. The solvent was evaporated away under reduced pressure to obtain the entitled compound as a brown oily substance.

(Step 3) Production of 2,2,2-trifluoro-N-(5-fluoro-2-nitro-4-(1-(trifluoroacetyl)pyrrolidin-2-yl)phenyl) acetamide 100 ml of fuming nitric acid was added to 28 g of 2,2,2-trifluoro-N-(3-fluoro-4-(1-(trifluoroacetyl)pyrrolidin-2-yl)phenyl)acetamide with cooling with ice, and the reaction liquid was stirred at room temperature for 1 hour. Water with ice was added to the reaction liquid to dilute it, then extracted with ethyl acetate, washed with saturated saline, and dried with anhydrous magnesium sulfate. The solvent was evaporated away under reduced pressure, and the resulting residue was purified through silica gel column chromatography (developing solvent: hexane/ethyl acetate=10/1) to obtain the entitled compound as a yellow oily substance.

(Step 4) Production of t-butyl 2-(4-amino-2-fluoro-5-nitrophenyl)pyrrolidin-1-yl carboxylate 150 ml of aqueous 1 N sodium hydroxide solution was added to a tetrahydrofuran (150 ml) solution of 29 g of 2,2,2-trifluoro-N-(5-fluoro-2-nitro-4-(1-(trifluoroacetyl)pyrrolidin-2-yl)phenyl)acetamide with cooling with ice, and the reaction liquid was stirred at room temperature for 5 hours. 23 ml of di-t-butyl dicarbonate was added to the reaction liquid, and the reaction liquid was stirred for 30 minutes. The reaction liquid was diluted with ethyl acetate, washed with water and saturated saline in order, and dried with anhydrous magnesium sulfate. The solvent was evaporated away under reduced pressure, and the resulting residue was purified through silica gel column chromatography (developing solvent: hexane/ethyl acetate=5/1) to obtain the entitled compound as a yellow solid.

(Step 5) Production of t-butyl 2-(4-amino-2-((2'-fluorobiphenyl-4-yl)oxy)-5-nitrophenyl)pyrrolidine-1-carboxylate 200 mg of 2'-fluorobiphenyl-4-ol and 184 mg of potassium carbonate were added to an N,N-dimethylformamide (3 ml) solution of 288 mg of t-butyl 2-(4-amino-2-fluoro-5-nitrophenyl)pyrrolidine-1-carboxylate, and the reaction liquid was stirred overnight at 80° C. The reaction liquid was diluted with ethyl acetate, washed with water and saturated saline in order, and dried with anhydrous magnesium sulfate. The solvent was evaporated away, and the resulting residue was purified through silica gel column chromatography (developing solvent: hexane/ethyl acetate=5/1) to obtain the entitled compound as a yellow solid.

(Step 6) Production of t-butyl 2-(4,5-diamino-2-((2'-fluorobiphenyl-4-yl)oxy)phenyl)pyrrolidine 1-carboxylate 1 ml of developed Raney nickel was added to a methanol (5 ml) solution of 410 mg of t-butyl 2-(4-amino-2-((2'-fluorobiphenyl-4-yl)oxy)-5-nitrophenyl)pyrrolidine-1-carboxylate, and the reaction liquid was stirred in a hydrogen atmosphere at room temperature for 1 day. The catalyst was removed through filtration through Celite, and the solvent was evaporated away under reduced pressure, and the residue was purified through silica gel column chromatography (developing solvent: hexane/ethyl acetate=1/1) to obtain the entitled compound as a brown oily substance.

(Step 7) Production of 5-((2'-fluorobiphenyl-4-yl)oxy)-2-pyridin-2-yl-6-pyrrolidin-2-yl-1H-benzimidazole 1.6 ml of N-((1E)-pyridin-2-ylmethylene)aniline (1 M methanol solution) was added to a methanol (5 ml) solution of 255 mg of t-butyl 2-(4,5-diamino-2-((2'-fluorobiphenyl-4-yl)oxy)phenyl)pyrrolidine-1-carboxylate, and the reaction liquid was stirred at 90° C. for 1 day. The reaction liquid was diluted with ethyl acetate, washed with water and saturated saline in order, and dried with anhydrous magnesium sulfate. The solvent was evaporated away under reduced pressure, and 5 ml of 4 N hydrochloric acid-dioxane solution was added to 332 mg of the resulting residue, and the reaction liquid was stirred at room temperature for 3 hours. The solvent was evaporated away under reduced pressure, diluted with aqueous saturated sodium bicarbonate, and extracted with chloroform. The organic layer was washed with saturated saline, and dried with anhydrous magnesium sulfate. The solvent was evaporated away under reduced pressure, and the resulting residue was purified through silica gel column chromatography (developing solvent: chloroform/methanol/aqueous ammonia=20/1/0.1) to obtain the entitled compound as a pale yellow substance.

(Step 8) Production of (2-(2-(5-((2'-fluorobiphenyl-4-yl)oxy)-2-pyridin-2-yl-1H-benzimidazol-6-yl)pyrrolidin-1-yl)-2-oxoethyl)methylamine 19 mg of N-(t-butoxycarbonyl)-N-methylglycine and 24 mg of 1-(3-dimethylaminopropyl)-3-ethylcarbodiimide monohydrochloride were added in order to a pyridin (1 ml) solution of 37 mg of 5-((2'-fluorobiphenyl-4-yl)oxy)-2-pyridin-2-yl-6-pyrrolidin-2-yl-1H-benzimidazole, and the reaction liquid was stirred at room temperature for 3 hours. 2 ml of 4 N hydrochloric acid-dioxane solution was added to the reaction liquid, and the reaction liquid was stirred at room temperature for 1 hour. The reaction liquid was diluted with chloroform, and made basic with aqueous saturated sodium carbonate added thereto, and the organic layer was washed with saturated saline and dried with anhydrous magnesium sulfate. The solvent was evaporated away under reduced pressure, and the resulting residue was purified through silica gel column chromatography (developing solvent: chloroform/methanol=10/1) to obtain the entitled compound as a pale yellow solid.

$^1$HNMR (CDCl$_3$) δ: 1.60-2.60 (6H, m), 2.80-3.05 (1H, m), 3.10-4.00 (4H, m), 5.20-5.60 (1H, m), 6.95-7.70 (11H, m), 7.75-7.95 (1H, m), 8.30-8.50 (1H, m), 8.50-8.70 (1H, m)

ESI-MS (m/e): 522 [M+H]

Example 499

6-(1-Acetylpyrrolidin-2-yl)-5-((6-(5-methyl-[1,3,4]-oxadiazol-2-yl)pyridin-3-yl)oxy)-2-pyridin-2-yl-1H-benzimidazole The entitled compound was obtained as a yellow oily substance in the same method as in Example 338 (step 5) or in accordance with the method or by combining it with an ordinary method but using 6-(5-methyl-[1,3,4]-oxadiazol-2-yl)pyridin-3-ol.

$^1$HNMR (CDCl$_3$) δ: 1.40-2.40 (7H, m), 2.50-2.80 (3H, m), 3.50-3.95 (2H, m), 5.05-5.50 (1H, m), 6.80-7.80 (4H, m), 7.80-8.00 (1H, m), 8.05-8.30 (1H, m), 8.30-8.50 (1H, m), 8.50-8.80 (2H, m), 10.50-11.00 (1H, m)

ESI-MS (m/e): 482 [M+H]

Example 500

6-(1-Acetylpyrrolidin-2-yl)-5-((6-([1,3,4]oxadiazol-2-yl)pyridin-3-yl)oxy)-2-pyridin-2-yl-1H-benzimidazole The entitled compound was obtained as a yellow oily substance in the same method as in Example 338 (step 5) or in accordance with the method or by combining it with an ordinary method but using 6-([1,3,4]-oxadiazol-2-yl)pyridin-3-ol.

$^1$HNMR (CDCl$_3$) δ: 1.40-2.40 (7H, m), 3.50-3.95 (2H, m), 5.05-5.50 (1H, m), 6.80-7.80 (4H, m), 7.80-8.00 (1H, m), 8.05-8.80 (5H, m), 10.50-11.00 (1H, m)

ESI-MS (m/e): 468 [M+H]

Example 501

6-(1-Acetylpyrrolidin-2-yl)-2-pyridin-2-yl-5-(4-pyrimidin-2-ylphenoxy)-1H-benzimidazole The entitled compound was obtained as a white solid in the same method as in Example 338 (step 5) or in accordance with the method or by combining it with an ordinary method but using 4-pyrimidin-2-ylphenol.

$^1$HNMR (CD$_3$OD) δ: 1.90 and 2.13 (total 3H, each s), 1.94-2.53 (4H, m), 3.62-3.80 (1H, m), 3.80-4.00 (1H, m), 5.38-5.46 (1H, m), 7.16-7.56 (6H, m), 7.95-8.04 (1H, m), 8.24-8.33 (1H, m), 8.46 (2H, d, J=9.0 Hz), 8.70-8.79 (1H, m), 8.83-8.85 (2H, m)

ESI-MS (m/e): 477 [M+H]

Example 502

1-((5-((6-(1-Acetylpyrrolidin-2-yl)-2-pyridin-2-yl-1H-benzimidazol-5-yl)oxy)pyridin-2-yl)methyl)pyrrolidine-2,5-dione The entitled compound was obtained as a white solid in the same method as in Example 338 (step 5) or in accordance with the method or by combining it with an ordinary method but using 1-((5-hydroxypyridin-2-yl)methyl)pyrrolidine-2,5-dione.

$^1$HNMR (CDCl$_3$) δ: 1.80-2.46 (7H, m), 2.74-2.86 (4H, m), 3.53-3.90 (2H, m), 4.76-4.87 (2H, m), 5.18-5.48 (1H, m), 6.76-7.67 (5H, m), 7.80-7.91 (1H, m), 8.28-8.44 (2H, m), 8.57-8.67 (1H, m), 11.07-11.41 (1H, m)

ESI-MS (m/e): 511 [M+H]

Example 503

6-(1-Acetylpyrrolidin-2-yl)-2-pyridin-2-yl-5-((6-(5-(trifluoromethyl)-[1,2,4]-oxadiazol-3-yl)pyridin-3-yl)oxy)-1H-benzimidazole The entitled compound was obtained as a white solid in the same method as in Example 338 (step 5) or in accordance with the method or by combining it with an ordinary method but using 6-(5-(trifluoromethyl)-[1,2,4]-oxadiazol-3-yl)pyridin-3-ol.

$^1$HNMR (CD$_3$OD) δ: 1.89-2.54 (7H, m), 3.84-4.01 (2H, m), 5.32-5.42 (1H, m), 7.20-7.80 (4H, m), 7.98-8.03 (1H, m), 8.24-8.37 (2H, m), 8.60-8.65 (1H, m), 8.73-8.80 (1H, m)

ESI-MS (m/e): 536 [M+H]

Example 504

6-(1-Acetylpyrrolidin-2-yl)-5-((6-chloropyridin-3-yl)oxy)-2-pyridin-2-yl-1H-benzimidazole The entitled compound was obtained as a white solid in the same method as in Example 338 (step 5) or in accordance with the method or by combining it with an ordinary method but using 6-chloropyridin-3-ol.

$^1$HNMR (CDCl$_3$) δ: 1.60-2.60 (7H, m), 3.50-3.95 (2H, m), 5.10-5.60 (1H, m), 6.80-7.70 (5H, m), 7.80-8.50 (3H, m), 8.50-8.70 (1H, m), 10.60-11.00 (1H, m)

ESI-MS (m/e): 434 [M+H]

Example 505

6-(1-Acetylpyrrolidin-2-yl)-5-((6-bromopyridin-3-yl)oxy)-2-pyridin-2-yl-1H-benzimidazole The entitled compound was obtained as a white solid in the same method as in Example 338 (step 5) or in accordance with the method or by combining it with an ordinary method but using 6-bromopyridin-3-ol.

$^1$HNMR (CDCl$_3$) δ: 1.60-2.60 (7H, m), 3.50-3.95 (2H, m), 5.10-5.60 (1H, m), 6.80-7.70 (5H, m), 7.70-8.00 (1H, m), 8.05-8.50 (2H, m), 8.50-8.70 (1H, m), 10.60-11.00 (1H, m)

ESI-MS (m/e): 478,480 [M+H].

Example 506

6-(1-Acetylpyrrolidin-2-yl)-5-((6-methoxypyridin-3-yl)oxy)-2-pyridin-2-yl-1H-benzimidazole The entitled compound was obtained as a yellow solid in the same method as in Example 338 (step 5) or in accordance with the method or by combining it with an ordinary method but using 6-methoxypyridin-3-ol.

$^1$HNMR (CDCl$_3$) δ: 1.60-2.60 (7H, m), 3.50-4.10 (5H, m), 5.10-5.70 (1H, m), 6.60-7.70 (5H, m), 7.70-7.95 (1H, m), 7.95-8.10 (1H, m), 8.25-8.45 (1H, m), 8.50-8.70 (1H, m), 10.60-11.00 (1H, m)

ESI-MS (m/e): 430 [M+H]

Example 507

5-((2'-Fluorobiphenyl-4-yl)oxy)-6-(1-(methanesulfonyl)pyrrolidin-2-yl)-2-pyridin-2-yl-1H-benzimidazole The entitled compound was obtained as a colorless oily substance in the same method as in Example 178 or in accordance with the method or by combining it with an ordinary method but using 5-((2'-fluorobiphenyl-4-yl)oxy)-2-pyridin-2-yl-6-pyrrolidin-2-yl-1H-benzimidazole obtained in Example 498 (step 7).

$^1$HNMR (CDCl$_3$) δ: 1.80-2.20 (3H, m), 2.20-2.50 (1H, m), 2.70-3.00 (3H, m), 3.40-3.80 (2H, m), 5.10-5.40 (1H, m), 6.90-8.10 (12H, m), 8.30-8.50 (1H, m), 8.50-8.70 (1H, m), 10.50-10.80 (1H, m)

ESI-MS (m/e): 529 [M+H]

Example 508

Methyl 2-(5-((2'-fluorobiphenyl-4-yl)oxy)-2-pyridin-2-yl-1H-benzimidazol-6-yl)pyrrolidine-1-carboxylate The entitled compound was obtained as a colorless oily substance in the same method as in Example 181 or in accordance with the method or by combining it with an ordinary method but using 5-((2'-fluorobiphenyl-4-yl)oxy)-2-pyridin-2-yl-6-pyrrolidin-2-yl-1H-benzimidazole obtained in Example 498 (step 7).

$^1$HNMR (CDCl$_3$) δ: 1.80-2.20 (3H, m), 2.20-2.50 (1H, m), 3.40-3.80 (5H, m), 5.10-5.40 (1H, m), 6.90-8.10 (12H, m), 8.30-8.50 (1H, m), 8.50-8.70 (1H, m), 10.50-10.80 (1H, m)

ESI-MS (m/e): 509 [M+H]

Example 509

2-(5-((2'-Fluorobiphenyl-4-yl)oxy)-2-pyridin-2-yl-1H-benzimidazol-6-yl)-N,N-dimethylpyrrolidine-1-carboxamide The entitled compound was obtained as a white solid in the same method as in Example 336 (step 1) and (step 2) or in accordance with the method or by combining it with an ordinary method but using 5-((2'-fluorobiphenyl-4-yl)oxy)-2-pyridin-2-yl-6-pyrrolidin-2-yl-1H-benzimidazole obtained in Example 498 (step 7).

$^1$HNMR (CDCl$_3$) δ: 1.60-2.20 (3H, m), 2.20-2.50 (1H, m), 2.72 (3H, s), 2.84 (3H, s), 3.40-3.80 (2H, m), 5.10-5.40 (1H, m), 6.90-8.10 (12H, m), 8.30-8.50 (1H, m), 8.50-8.70 (1H, m), 10.50-10.80 (1H, m)

ESI-MS (m/e): 522 [M+H]

Example 510

1-((5-(6-(1-Acetylpyrrolidin-2-yl)-2-pyridin-2-yl-1H-benzimidazol-5-yl)oxy)pyridin-2-yl)methyl)pyrrolidin-2-one The entitled compound was obtained as an oily substance in the same method as in Example 338 (step 5) or in accordance with the method or by combining it with an ordinary method but using 1-((5-hydroxypyridin-2-yl)methyl)pyrrolidin-2-one.

$^1$HNMR (CDCl$_3$) δ: 1.80-2.57 (11H, m), 3.33-3.89 (4H, m), 4.48-4.64 (2H, m), 5.20-5.51 (1H, m), 6.77-7.67 (5H, m), 7.77-7.90 (1H, m), 8.27-8.42 (2H, m), 8.56-8.66 (1H, m), 11.16-11.53 (1H, m)

ESI-MS (m/e): 497 [M+H]

Example 511

6-(1-Acetylpyrrolidin-2-yl)-5-(4-(3-methyl-1H-[1,2,4]-triazol-5-yl)phenoxy)-2-pyridin-2-yl-1H-benzimidazole The entitled compound was obtained as an oily substance in the same method as in Example 338 (step 5) or in accordance with the method or by combining it with an ordinary method but using 4-(3-methyl-1H-[1,2,4]-triazol-5-yl)phenol.

$^1$HNMR (CDCl$_3$) δ: 1.76-2.82 (10H, m), 3.50-3.90 (2H, m), 5.13-5.59 (1H, m), 6.64-8.04 (8H, m), 8.23-8.64 (2H, m)

ESI-MS (m/e): 480 [M+H]

Example 512

6-(1-(Difluoroacetyl)pyrrolidin-2-yl)-5-((2'-fluorobiphenyl-4-yl)oxy)-2-pyridin-2-yl-1H-benzimidazole The entitled compound was obtained as a white solid in the same method as in Example 498 (step 8) or in accordance with the method or by combining it with an ordinary method but using difluoroacetic acid.

$^1$HNMR (CDCl$_3$) δ: 1.80-2.50 (4H, m), 3.60-4.20 (2H, m), 5.20-6.20 (2H, m), 6.90-8.10 (12H, m), 8.30-8.50 (1H, m), 8.50-8.70 (1H, m), 10.50-10.80 (1H, m)

ESI-MS (m/e): 529 [M+H]

Example 513

2-(2-(5-((2'-Fluorobiphenyl-4-yl)oxy)-2-pyridin-2-yl-1H-benzimidazol-6-yl)pyrrolidin-1-yl)-2-oxoethyl acetate The entitled compound was obtained as a yellow oily substance in the same method as in Example 498 (step 8) or in accordance with the method or by combining it with an ordinary method but using acetoxyacetic acid.

$^1$HNMR (CDCl$_3$) δ: 1.60-2.40 (7H, m), 3.40-4.00 (2H, m), 4.05-4.80 (2H, m), 5.10-5.60 (1H, m), 6.90-8.10 (12H, m), 8.30-8.50 (1H, m), 8.50-8.70 (1H, m), 10.50-10.80 (1H, m)

ESI-MS (m/e): 551 [M+H]

Example 514

(5-((6-(1-Acetylpyrrolidin-2-yl)-2-pyridin-2-yl-1H-benzimidazol-5-yl)oxy)pyridin-2-yl)methanol 20 mg of lithiumaluminium hydride was added to a tetrahydrofuran (2 ml) solution of 90 mg of ethyl 5-((6-(1-acetylpyrrolidin-2-yl)-2-pyridin-2-yl-1H-benzimidazol-5-yl)oxy)pyridine-2-carboxylate obtained in Example 495 with cooling with ice, and the reaction liquid was stirred at 0° C. for 30 minutes. The reaction liquid was diluted with chloroform, washed with aqueous saturated ammonium chloride, aqueous saturated sodium bicarbonate and saturated saline in order, and dried with anhydrous sodium sulfate. The solvent was evaporated away under reduced pressure, and the resulting residue was purified through partitioning thin-layer chromatography (Kieselgel™ 60F$_{254}$, Art 5744 (by Merck), chloroform/methanol=10/1) to obtain the entitled compound as a white solid.

$^1$HNMR (CDCl$_3$) δ: 1.60-2.60 (7H, m), 3.50-4.00 (2H, m), 4.70-4.85 (2H, m), 5.10-5.60 (1H, m), 6.80-7.70 (5H, m), 7.70-7.95 (1H, m), 8.30-8.50 (2H, m), 8.50-8.70 (1H, m)

ESI-MS (m/e): 430 [M+H]

Example 515

2-(2-(5-((2'-Fluorobiphenyl-4-yl)oxy)-2-pyridin-2-yl-1H-benzimidazol-6-yl)pyrrolidin-1-yl)-2-oxoethanol 10 mg of potassium carbonate was added to a methanol (0.5 ml) solution of 11 mg of 2-(2-(5-((2'-fluorobiphenyl-4-yl)oxy)-2-pyridin-2-yl-1H-benzimidazol-6-yl)pyrrolidin-1-yl)-2-oxoethyl acetate obtained in Example 513, and the reaction liquid was stirred at room temperature for 1 day. The reaction liquid was diluted with chloroform, washed with water and saturated saline in order, and dried with anhydrous sodium sulfate. The solvent was evaporated away under reduced pressure, and the resulting residue was purified through partitioning thin-layer chromatography (Kieselgel™ 60F$_{254}$, Art 5744 (by Merck), chloroform/methanol=10/1) to obtain the entitled compound as a white solid.

$^1$HNMR (CDCl$_3$) δ: 1.40-2.50 (4H, m), 3.40-4.20 (4H, m), 5.05-5.70 (1H, m), 6.90-8.10 (12H, m), 8.30-8.50 (1H, m), 8.50-8.70 (1H, m), 10.50-10.80 (1H, m)

ESI-MS (m/e): 509 [M+H]

Example 516

6-(1-Acetylpyrrolidin-2-yl)-5-((6-(fluoromethyl)pyridin-3-yl)oxy)-2-pyridin-2-yl-1H-benzimidazole 0.050 ml of bis(2-methoxyethyl)aminosulfur trichloride was added to a chloroform (1 ml) solution of 17 mg of (5-((6-(1-acetylpyrrolidin-2-yl)-2-pyridin-2-yl-1H-benzimidazol-5-yl)oxy)pyridin-2-yl)methanol obtained in Example 514 with cooling with ice, and the reaction liquid was stirred at 0° C. for 2 hours. The reaction liquid was diluted with chloroform, washed with aqueous saturated sodium bicarbonate and saturated saline in order, and dried with anhydrous sodium sulfate. The solvent was evaporated away under reduced pressure, and the resulting residue was purified through partitioning thin-layer chromatography (Kieselgel™ 60F$_{254}$, Art 5744 (by Merck), chloroform/methanol=10/1) to obtain the entitled compound as a pale yellow solid.

$^1$HNMR (CDCl$_3$) δ: 1.60-2.60 (7H, m), 3.50-4.00 (2H, m), 5.05-5.60 (3H, m), 6.80-7.70 (5H, m), 7.70-7.95 (1H, m), 8.30-8.50 (2H, m), 8.50-8.70 (1H, m), 10.60-11.00 (1H, m)

ESI-MS (m/e): 432 [M+H]

Example 517

6-(1-Acetylpyrrolidin-2-yl)-5-((6-(3-methyl-[1,2,4]-oxadiazol-5-yl)pyridin-3-yl)oxy)-2-pyridin-2-yl-1H-benzimidazole The entitled compound was obtained as an oily substance in the same method as in Example 338 (step 5) or in accordance with the method or by combining it with an ordinary method but using 6-(3-methyl [1,2,4]-oxadiazol-5-yl)pyridin-3-ol.

$^1$HNMR (CDCl$_3$) δ: 1.65-2.57 (10H, m), 3.48-3.93 (5H, m), 5.17-5.52 (1H, m), 6.82-7.67 (7H, m), 7.80-7.91 (1H, m), 8.34-8.44 (1H, m), 8.57-8.67 (1H, m), 11.32-11.68 (1H, m)

ESI-MS (m/e): 482 [M+H]

Example 518

6-(1-Acetylpyrrolidin-2-yl)-5-(4-(1-methyl-1H-tetrazol-5-yl)phenoxy)-2-pyridin-2-yl-1H-benzimidazole The entitled compound was obtained as a white solid in the same method as in Example 338 (step 5) or in accordance with the method or by combining it with an ordinary method but using 4-(1-methyl-1H-tetrazol-5-yl)phenol.
$^1$HNMR (CDCl$_3$) δ: 1.83-2.40 (7H, m), 3.58-3.90 (2H, m), 4.15 and 4.19 (total 3H, each s), 5.16-5.48 (1H, m), 6.93-7.78 (7H, m), 7.80-7.91 (1H, m), 8.34-8.42 (1H, m), 8.56-8.65 (1H, m)
ESI-MS (m/e): 481 [M+H]

Example 519

6-((6-(1-Acetylpyrrolidin-2-yl)-2-pyridin-2-yl-1H-benzimidazol-5-yl)oxy-N-methylpyridine-2-carboxamide The entitled compound was obtained as a pale yellow solid in the same method as in Example 338 (step 5) or in accordance with the method or by combining it with an ordinary method but using 5-hydroxy-N-methylpyridine-2-carboxamide.
$^1$HNMR (CDCl$_3$) δ: 1.60-2.50 (7H, m), 2.90-3.10 (3H, m), 3.50-4.00 (2H, m), 5.05-5.50 (1H, m), 6.80-7.70 (3H, m), 7.70-8.00 (2H, m), 8.10-8.50 (3H, m), 8.50-8.70 (1H, m)
ESI-MS (m/e): 457 [M+H]

Example 520

3-(5-((6-(1-Acetylpyrrolidin-2-yl)-2-pyridin-2-yl-1H-benzimidazol-5-yl)oxy)pyridin-2-yl)-1,3-oxazolidin-2-one The entitled compound was obtained as a pale yellow solid in the same method as in Example 338 (step 5) or in accordance with the method or by combining it with an ordinary method but using 3-(5-hydroxypyridin-2-yl)-1,3-oxazolidin-2-one.
$^1$HNMR (CDCl$_3$) δ: 1.60-2.50 (7H, m), 3.50-4.00 (2H, m), 4.10-4.35 (2H, m), 4.40-4.60 (2H, m), 5.20-5.60 (1H, m), 6.80-7.70 (4H, m), 7.70-8.00 (1H, m), 8.10-8.50 (3H, m), 8.50-8.70 (1H, m), 10.70-11.10 (1H, m)
ESI-MS (m/e): 485 [M+H]

Example 521

6-(1-Acetylpyrrolidin-2-yl)-5-(6-methylpyridin-3-ylsulfanyl)-2-pyridin-2-yl-1H-benzimidazole The entitled compound was obtained as a pale yellow solid in the same method as in Example 338 (step 5) or in accordance with the method or by combining it with an ordinary method but using 6-methylpyridine-3-thiol.
$^1$HNMR (CDCl$_3$) δ: 1.20-2.50 (10H, m), 3.50-4.00 (2H, m), 5.20-5.60 (1H, m), 6.80-8.00 (6H, m), 8.20-8.70 (3H, m)
ESI-MS (m/e): 430 [M+H]

Example 522

Methyl 5-((6-(1-acetylpyrrolidin-2-yl)-2-pyridin-2-yl-1H-benzimidazol-5-yl)oxy)nicotinate The entitled compound was obtained as a white solid in the same method as in Example 338 (step 5) or in accordance with the method or by combining it with an ordinary method but using methyl 5-hydroxynicotinate.
$^1$HNMR (CD$_3$OD) δ: 1.89 and 2.14 (total 3H, each s), 1.96-2.20 (3H, m), 2.32-2.54 (1H, m), 3.63-3.90 (2H, m), 3.93 (3H, s), 5.37-5.41 (1H, m), 7.20-7.57 (3H, m), 7.92-8.03 (2H, m), 8.30 (1H, t, J=8.4 Hz), 8.65-8.67 (1H, m), 8.74-8.78 (1H, m), 8.89-8.92 (1H, m)
ESI-MS (m/e): 458 [M+H]

Example 523

6-(1-Acetylpyrrolidin-2-yl)-5-((6-methylthio)pyridin-3-yl)oxy-2-pyridin-2-yl-1H-benzimidazole The entitled compound was obtained as a pale yellow solid in the same method as in Example 338 (step 5) or in accordance with the method or by combining it with an ordinary method but using 6-methylthiopyridin-3-ol.
$^1$HNMR (CDCl$_3$) δ: 1.60-2.70 (10H, m), 3.50-4.00 (2H, m), 5.20-5.60 (1H, m), 6.80-8.10 (6H, m), 8.20-8.50 (2H, m), 8.50-8.70 (1H, m), 10.70-11.10 (1H, m)
ESI-MS (m/e): 446 [M+H]

Example 524

6-(1-Acetylpyrrolidin-2-yl)-5-(4-(1,3-dimethyl-1H-[1,2,4]-triazol-5-yl)phenoxy)-2-pyridin-2-yl-1H-benzimidazole The entitled compound was obtained as an oily substance in the same method as in Example 338 (step 5) or in accordance with the method or by combining it with an ordinary method but using 4-(1,3-dimethyl-1H-[1,2,4]-triazol-5-yl)phenol.
$^1$HNMR (CDCl$_3$) δ: 1.79-2.2.53 (10H, m), 3.50-3.90 (5H, m), 5.19-5.30 (1H, m), 6.87-7.66 (5H, m), 7.77-7.91 (1H, m), 7.96-8.10 (2H, m), 8.33-8.43 (1H, m), 8.56-8.67 (1H, m), 10.82-11.08 (1H, m)
ESI-MS (m/e): 494 [M+H]

Example 525

6-(1-Acetylpyrrolidin-2-yl)-5-(4-(1,5-dimethyl-1H-[1,2,4]-triazol-3-yl)phenoxy)-2-pyridin-2-yl-1H-benzimidazole The entitled compound was obtained as an oily substance in the same method as in Example 338 (step 5) or in accordance with the method or by combining it with an ordinary method but using 4-(1,5-dimethyl-1H-[1,2,4]-triazol-3-yl)phenol.
$^1$HNMR (CDCl$_3$) δ: 1.79-2.53 (10H, m), 3.50-3.90 (5H, m), 5.19-5.30 (1H, m), 6.87-7.66 (5H, m), 7.77-7.91 (1H, m), 7.96-8.10 (2H, m), 8.33-8.43 (1H, m), 8.56-8.67 (1H, m), 10.82-11.08 (1H, m)
ESI-MS (m/e): 494 [M+H]

Example 526

6-(1-Acetylpyrrolidin-2-yl)-5-((2'-fluorobiphenyl-4-yl)oxy)-2-pyrazin-2-yl-1H-benzimidazole The entitled compound was obtained as a white solid in the same method as in Example 338 (step 3) to (step 5) or in accordance with the method or by combining it with an ordinary method but using t-butyl 2-(4-amino-2-fluoro-phenyl)-pyrrolidin-1-carboxylate obtained in Example 338 (step 2) and pyrazine-2-carboxylic acid and 2'-fluorobiphenyl-4-ol.

¹HNMR (CDCl₃) δ: 1.20-2.50 (7H, m), 3.50-3.95 (2H, m), 5.10-5.60 (1H, m), 6.80-7.80 (10H, m), 8.50-8.90 (2H, m), 9.40-10.00 (1H, m), 10.50-11.20 (1H, m)
ESI-MS (m/e): 494 [M+H]

Example 527

6-(1-Acetylpyrrolidin-2-yl)-5-((5-chloropyridin-3-yl)oxy)-2-pyridin-2-yl-1H-benzimidazole The entitled compound was obtained as a white solid in the same method as in Example 338 (step 5) or in accordance with the method or by combining it with an ordinary method but using 5-chloro-3-pyridinoyl.
¹HNMR (CD₃OD) δ: 1.89 and 2.15 (total 3H, each s), 1.94-2.20 (3H, m), 2.29-2.49 (1H, m), 3.62-3.97 (2H, m), 5.32-5.40 (1H, m), 7.17-7.63 (4H, m), 7.94-8.04 (1H, m), 8.26-8.41 (3H, m), 8.73-8.79 (1H, m)
ESI-MS (m/e): 434 [M+H]

Example 528

1-(5-(6-(1-Acetylpyrrolidin-2-yl)-2-pyridin-2-yl-1H-benzimidazol-5-yl)oxy)pyridin-2-yl)pyrrolidin-2-one The entitled compound was obtained as an oily substance in the same method as in Example 338 (step 5) or in accordance with the method or by combining it with an ordinary method but using 1-(5-hydroxypyridin-2-yl)pyrrolidin-2-one.
¹HNMR (CDCl₃) δ: 1.79-2.43 (9H, m), 2.58-2.71 (2H, m), 3.53-3.89 (2H, m), 3.98-4.17 (2H, m), 5.21-5.57 (1H, m), 6.77-7.57 (4H, m), 7.74-8.66 (5H, m)
ESI-MS (m/e): 483 [M+H]

Example 529

6-(1-Acetylpyrrolidin-2-yl)-5-((6-methylpyridin-3-yl)oxy)-2-pyrazin-2-yl-1H-benzimidazole The entitled compound was obtained as a white solid in the same method as in Example 526 or in accordance with the method or by combining it with an ordinary method but using 6-methylpyridin-3-ol.
¹HNMR (CDCl₃) δ: 1.60-2.60 (10H, m), 3.50-3.95 (2H, m), 5.20-5.60 (1H, m), 6.65-7.80 (4H, m), 8.20-8.40 (1H, m), 8.50-8.70 (2H, m), 9.50-9.70 (1H, m), 10.60-11.40 (1H, m)
ESI-MS (m/e): 415 [M+H]

Example 530

6-(1-Acetylpyrrolidin-2-yl)-5-((6-([1,2,4]-oxadiazol-3-yl)pyridin-3-yl)oxy)-2-pyridin-2-yl-1H-benzimidazole The entitled compound was obtained as an oily substance in the same method as in Example 338 (step 5) or in accordance with the method or by combining it with an ordinary method but using 6-([1,2,4]-oxadiazol-3-yl)pyridin-3-ol.
¹HNMR (CDCl₃) δ: 1.80-2.43 (7H, m), 3.57-3.92 (2H, m), 5.19-5.46 (1H, m), 6.98-8.43 (7H, m), 8.55-8.87 (3H, m), 10.53-10.74 (1H, m)
ESI-MS (m/e): 468 [M+H]

Example 531

6-(1-Acetylpyrrolidin-2-yl)-5-(4-(1,3-oxazol-4-yl)phenoxy)-2-pyridin-2-yl-1H-benzimidazole The entitled compound was obtained as a white solid in the same method as in Example 338 (step 5) or in accordance with the method or by combining it with an ordinary method but using 4-(1,3-oxazol-4-yl)phenol.
¹HNMR (CD₃OD) δ: 1.89-2.20 (6H, m), 2.28-2.50 (1H, m), 3.62-4.00 (2H, m), 5.39-5.50 (1H, m), 7.12-7.53 (5H, m), 7.80-7.89 (2H, m), 7.93-8.04 (1H, m), 8.24-8.33 (3H, m), 8.70-8.79 (1H, m)
ESI-MS (m/e): 466 [M+H]

Example 532

6-(1-Acetylpyrrolidin-2-yl)-5-((6-chloropyridin-3-yl)oxy)-2-pyrazin-2-yl-1H-benzimidazole The entitled compound was obtained as a white solid in the same method as in Example 526 or in accordance with the method or by combining it with an ordinary method but using 6-chloropyridin-3-ol.
¹HNMR (CDCl₃) δ: 1.60-2.60 (7H, m), 3.50-3.95 (2H, m), 5.20-5.60 (1H, m), 6.65-8.30 (5H, m), 8.40-8.70 (2H, m), 9.50-9.70 (1H, m), 10.60-11.60 (1H, m)
ESI-MS (m/e): 435 [M+H]

Example 533

6-(1-Acetylpyrrolidin-2-yl)-5-(4-(2-methyl-2H-tetrazol-5-yl)phenoxy)-2-pyrazin-2-yl-1H-benzimidazole The entitled compound was obtained as a white solid in the same method as in Example 526 or in accordance with the method or by combining it with an ordinary method but using 4-(2-methyl-2H-tetrazol-5-yl)phenol.
¹HNMR (CD₃OD) δ: 1.90-2.19 (6H, m), 2.27-2.51 (1H, m), 3.61-4.00 (2H, m), 4.43 and 4.44 (total 3H, each s), 5.38-5.46 (1H, m), 7.23 (2H, d, J=8.6 Hz), 7.24-7.60 (2H, m), 8.11-8.19 (2H, m), 8.67-8.70 (1H, m), 8.77 (1H, brs), 9.46 (1H, d, J=8.6 Hz)
ESI-MS (m/e): 482 [M+H]

Example 534

6-(1-Acetylpyrrolidin-2-yl)-5-((6-bromopyridin-3-yl)oxy)-2-pyrazin-2-yl-1H-benzimidazole The entitled compound was obtained as a white solid in the same method as in Example 526 or in accordance with the method or by combining it with an ordinary method but using 6-bromopyridin-3-ol.
¹HNMR (CDCl₃) δ: 1.60-2.50 (7H, m), 3.60-3.95 (2H, m), 5.20-5.50 (1H, m), 6.80-8.40 (5H, m), 8.50-8.80 (2H, m), 9.50-9.70 (1H, m), 10.40-11.10 (1H, m)
ESI-MS (m/e): 479, 481 [M+H]

Example 535

5-(1-Acetyl-3-fluoropyrrolidin-2-yl)-6-(4-(methanesulfonyl)phenoxy-2-pyridin-2-yl-1H-benzimidazole enantiomer A and enantiomer B 10 mg of 5-(1-acetyl-3-fluoropyrrolidin-2-yl)-6-(4-(methanesulfonyl)phenoxy)-2-pyridin-2-yl-1H-benzimidazole diastereomer B obtained in Example 493 was optically resolved, using an optical resolution column (CHIRALPAK AD 2 cmφ×25 cmL (by Daicel Chemical), mobile phase: hexane/ethanol/diethylamine=40/60/0.1, flow rate: 10 ml/min), into an enantiomer A (retention time: 10.5 min) and an enantiomer B (retention time: 19.0 min) each as a white solid.

Enantiomer A:
ESI-MS (m/e): 495 [M+H]

Enantiomer B:
ESI-MS (m/e): 495 [M+H]

Example 536

6-(1-Acetylpyrrolidin-2-yl)-5-((6-(1-methyl-1H-tetrazol-5-yl)pyridin-3-yl)oxy)-2-pyridin-2-yl-1H-benzimidazole The entitled compound was obtained as a white solid in the same method as in Example 338 (step 5) or in accordance with the method or by combining it with an ordinary method but using 6-(1-methyl-1H-tetrazol-5-yl)pyridin-3-ol.

$^1$HNMR (CD$_3$OD) δ: 1.88 and 2.02 (total 3H, each s), 1.93-2.20 (3H, m), 2.28-2.50 (1H, m), 3.60-4.00 (2H, m), 4.47 and 4.48 (total 3H, each s), 5.32-5.42 (1H, m), 7.22-7.70 (4H, m), 7.95-8.02 (1H, m), 8.25-8.32 (2H, m), 8.61-8.64 (1H, m), 8.73 (1H, brs)
ESI-MS (m/e): 482 [M+H]

Example 537

6-(1-Acetylpyrrolidin-2-yl)-5-((6-(1-methyl-1H-tetrazol-5-yl)pyridin-3-yl)oxy)-2-pyrazin-2-yl-1H-benzimidazole The entitled compound was obtained as a white solid in the same method as in Example 526 or in accordance with the method or by combining it with an ordinary method but using 6-(1-methyl-1H-tetrazol-5-yl)pyridin-3-ol.

$^1$HNMR (CD$_3$OD) δ: 1.91 and 2.16 (total 3H, each s), 2.00-2.20 (3H, m), 2.38-2.55 (1H, m), 3.63-4.01 (2H, m), 4.50 and 4.51 (total 3H, each s), 5.35-5.44 (1H, m), 7.33-7.60 (2H, m), 7.66-7.73 (1H, m), 8.27-8.34 (1H, m), 8.65-8.67 (1H, m), 8.71-8.73 (1H, m), 8.78-8.80 (1H, m), 9.48-9.50 (1H, m)
ESI-MS (m/e): 483 [M+H]

Example 538

6-(1-Acetylpyrrolidin-2-yl)-5-((6-(2-methyl-2H-tetrazol-5-yl)-pyridin-3-yloxy)-2-pyridin-2-yl-1H-benzimidazole The entitled compound was obtained as a white solid in the same method as in Example 338 (step 5) or in accordance with the method or by combining it with an ordinary method but using 6-(2-methyl-2H-tetrazol-5-yl)pyridin-3-ol.

$^1$HNMR (CD$_3$OD) δ: 1.91-2.20 (6H, m), 2.33-2.52 (1H, m), 3.60-4.00 (2H, m), 4.48-4.90 (3H, m), 5.37-5.44 (1H, m), 7.22-7.68 (4H, m), 7.97-8.04 (1H, m), 8.19-8.23 (1H, m), 8.25-8.31 (1H, m), 8.55-8.59 (1H, m), 8.74 (1H, brs)
ESI-MS (m/e): 482 [M+H]

Example 539

6-(1-Acetylpyrrolidin-2-yl)-5-(4-(5-methyl-1H-tetrazol-1-yl)phenoxy)-2-pyrazin-2-yl-1H-benzimidazole The entitled compound was obtained as a white solid in the same method as in Example 526 or in accordance with the method or by combining it with an ordinary method but using 4-(5-methyl-1H-tetrazol-1-yl)phenol.

$^1$HNMR (CD$_3$OD) δ: 1.91 and 2.16 (total 3H, each s), 1.96-2.20 (3H, m), 2.33-2.54 (1H, m), 2.63 and 2.64 (total 3H, each s), 3.64-4.00 (2H, m), 5.38-5.43 (1H, m), 7.32-7.57 (4H, m), 7.61-7.68 (2H, m), 8.70-8.73 (1H, m), 8.78-8.80 (1H, m), 9.47-9.49 (1H, m)
ESI-MS (m/e): 482 [M+H]

Example 540

6-(1-Acetylpyrrolidin-2-yl)-5-((6-(1H-pyrazol-1-yl)pyridin-3-yl)oxy)-2-pyridin-2-yl-1H-benzimidazole The entitled compound was obtained as an oily substance in the same method as in Example 338 (step 5) or in accordance with the method or by combining it with an ordinary method but using 6-(1H-pyrazol-1-yl)pyridin-3-ol.

$^1$HNMR (CDCl$_3$) δ: 1.67-2.48 (7H, m), 3.50-3.92 (2H, m), 5.14-5.57 (1H, m), 6.41-6.50 (1H, m), 6.80-8.03 (7H, m), 8.17-8.67 (4H, m), 11.00-11.11.27 (1H, m)
ESI-MS (m/e): 466 [M+H]

Example 541

6-(1-Acetylpyrrolidin-2-yl)-2-pyridin-2-yl-5-((6-(1H-[1,2,4]-triazol-1-yl)pyridin-3-yl)oxy-1H-benzimidazole The entitled compound was obtained as an oily substance in the same method as in Example 338 (step 5) or in accordance with the method or by combining it with an ordinary method but using 6-(1H-[1,2,4]-triazol-1-yl)pyridin-3-ol.

$^1$HNMR (CDCl$_3$) δ: 1.62-2.45 (7H, m), 3.52-3.90 (2H, m), 5.20-5.55 (1H, m), 6.79-8.68 (10H, m), 9.02-9.13 (1H, m), 11.17-11.52 (1H, m)
ESI-MS (m/e): 467 [M+H]

Example 542

5-(4-(2-Methyl-2H-tetrazol-5-yl)phenoxy-2-pyridin-2-yl-6-pyrrolidin-2-yl-1H-benzimidazole enantiomer A and enantiomer B 59.0 mg of 5-(4-(2-methyl-2H-tetrazol-5-yl)phenoxy)-2-pyridin-2-yl-6-pyrrolidin-2-yl-1H-benzimidazole obtained in the same method as in Example 162 (step 2) to (step 7) using 4-(2-methyl-2H-tetrazol-5-yl)phenol was optically resolved, using an optical resolution column (CHIRALPAK AD 2 cmφ×25 cmL (by Daicel Chemical), mobile phase: ethanol/2-propanol/diethylamine=25/75/0.1, flow rate: 12 to 18 ml/min), into an enantiomer A and an enantiomer B. (Retention time: enantiomer A 13.5 min; enantiomer B 30.8 min, CHIRALPAK AD 4.6 mmφ×250 mL (by Daicel Chemical), mobile phase: ethanol/2-propanol/diethylamine=25/75/0.1, flow rate: 1 ml/min).

Example 543

6-(1-Acetylpyrrolidin-2-yl)-5-(4-(2-methyl-2H-tetrazol-5-yl)phenoxy)-2-pyridin-2-yl-1H-benzimidazole enantiomer A 0.006 ml of acetic anhydride was added to a chloroform (1 ml) solution of 24.7 mg of 5-(4-(2-methyl-2H-tetrazol-5-yl)phenoxy)-2-pyridin-2-yl-6-pyrrolidin-2-yl-1H-benzimidazole enantiomer A obtained in Example 542, and the reaction liquid was stirred at room temperature for 10 minutes. The reaction solvent was evaporated away under reduced pressure, and the resulting residue was purified through partitioning thin-layer chromatography (Kieselgel™ 60F$_{254}$, Art 5744 (by Merck), chloroform/methanol=10/1) to obtain one chiral form of the entitled compound as a white solid.
$^1$HNMR (CD$_3$OD) δ: 1.90-2.20 (6H, m), 2.24-2.49 (1H, m), 3.66-4.00 (2H, m), 5.37-5.46 (1H, m), 7.12-7.60 (5H, m), 7.94-8.04 (1H, m), 8.04-8.20 (2H, m), 8.29 (1H, t, J=8.2 Hz), 8.68-8.78 (1H, m)
ESI-MS (m/e): 481 [M+H]

Example 544

6-(Acetylpyrrolidin-2-yl)-5-(4-(2-methyl-2H-tetrazol-5-yl)phenoxy)-2-pyridin-2-yl-1H-benzimidazole enantiomer B 0.007 ml of acetic anhydride was added to a chloroform (1 ml) solution of 30.9 mg of 5-(4-(2-methyl-2H-tetrazol-5-yl)phenoxy)-2-pyridin-2-yl-6-pyrrolidin-2-yl-1H-benzimidazole enantiomer B obtained in Example 542, and the reaction liquid was stirred at room temperature for 10 minutes. The reaction solvent was evaporated away under reduced pressure, and the resulting residue was purified through partitioning thin-layer chromatography (Kieselgel™ 60F$_{254}$, Art 5744 (by Merck), chloroform/methanol=10/1) to obtain one chiral form of the entitled compound as a white solid.
ESI-MS (m/e): 481 [M+H]

Example 545

5-(1-Acetyl-5-methylpyrrolidin-2-yl)-6-(4-(methanesulfonyl)phenoxy-2-pyridin-2-yl-1H-benzimidazole enantiomers A, B, C and D A mixture of the four components of the entitled compound was obtained in the same method as in Example 485 or in accordance with the method or by combining it with an ordinary method but using 5-methyldihydrofuran-2 (3H)-one. 15 mg of the resulting mixture of the four components was optically resolved, using an optical resolution column (CHIRAL-CEL OD-H 2 cmφ×25 cmL (by Daicel Chemical), mobile phase: hexane/ethanol/diethylamine=80/20/0.1), into an enantiomer A (retention time; 13.67 min), an enantiomer B (retention time: 15.24 min), enantiomer C (retention time: 18.96 min) and enantiomer D (retention time: 22.90 min) each as a pale yellow solid.

Enantiomer A:
$^1$HNMR (CDCl$_3$) δ: 1.23-1.38 (3H, m), 1.50-2.57 (7H, m), 3.04 and 3.08 (3H, s), 4.24-4.60 (1H, m), 5.18-5.43 (1H, m), 6.92-7.83 (5H, m), 7.83-7.98 (3H, m), 8.34-8.43 (1H, m), 8.60-8.67 (1H, m), 10.84-11.33 (1H, m)
ESI-MS (m/e): 491 [M+H]

Enantiomer B:
$^1$HNMR (CDCl$_3$) δ: 1.22-2.20 (9H, m), 2.23-2.45 (1H, m), 3.04 and 3.08 (3H, s), 4.10-4.22 (1H, m), 5.09-5.23 (1H, m), 7.04-7.70 (5H, m), 7.83-7.97 (3H, m), 8.34-8.48 (1H, m), 8.61-8.69 (1H, m), 10.73-11.16 (1H, m)
ESI-MS (m/e): 491 [M+H]

Enantiomer C:
ESI-MS (m/e): 491 [M+H]

Enantiomer D:
ESI-MS (m/e): 491 [M+H]

Example 546

(6-(1-Acetylpyrrolidin-2-yl)-5-((6-(2-methyl-2H-tetrazol-5-yl)pyridin-3-yloxy)-2-pyrazin-2-yl-1H-benzimidazole The entitled compound was obtained as a white solid in the same method as in Example 526 or in accordance with the method or by combining it with an ordinary method but using 6-(2-methyl-2H-tetrazol-5-yl)pyridin-3-ol.
$^1$HNMR (CD$_3$OD) δ: 1.88-2.20 (6H, m), 2.21-2.31 (1H, m), 3.61-4.00 (2H, m), 4.46 and 4.47 (total 3H, each s), 5.34-5.44 (1H, m), 7.22-7.71 (3H, m), 8.18-8.25 (1H, m), 8.50-8.60 (1H, m), 8.65-8.70 (1H, m), 8.72-8.80 (1H, m), 9.44-9.47 (1H, m)
ESI-MS (m/e): 483 [M+H]

Example 547

6-(Acetylpyrrolidin-2-yl)-5-(4-(2-(methoxymethyl)-2H-tetrazol-5-yl)phenoxy)-2-pyridin-2-yl-1H-benzimidazole The entitled compound was obtained as a white solid in the same method as in Example 338 (step 5) or in accordance with the method or by combining it with an ordinary method but using 4-(2-(methoxymethyl)-2H-tetrazol-5-yl)phenol.
$^1$HNMR (CD$_3$OD) δ: 1.90-2.20 (6H, m), 2.22-2.71 (1H, m), 3.53 (3H, s), 5.38-5.46 (1H, m), 5.96 and 5.97 (total 3H, each s), 7.20-7.56 (5H, m), 7.95-8.03 (1H, m), 8.17-8.22 (2H, m), 8.29 (1H, t, J=8.0 Hz), 8.73-8.79 (1H, m)
ESI-MS (m/e): 511 [M+H]

Example 548

6-(1-Acetylpyrrolidin-2-yl)-5-((6-(methoxymethyl)pyridin-3-yl)oxy)-2-pyridin-2-yl-1H-benzimidazole The entitled compound was obtained as an oily substance in the same method as in Example 483 or in accordance with the method or by combining it with an ordinary method but using 6-(methoxymethyl)pyridin-3-ol.
$^1$HNMR (CDCl$_3$) δ: 1.60-2.43 (7H, m), 3.34-3.91 (5H, m), 4.45-4.59 (2H, m), 5.20-5.52 (1H, m), 6.86-7.67 (5H, m), 7.80-7.90 (1H, m), 8.29-8.48 (2H, m), 8.55-8.67 (1H, m), 10.87-11.27 (1H, m)
ESI-MS (m/e): 444 [M+H]

Example 549

2-(2-(5-(4-(2-Methyl-2H-tetrazol-5-yl)phenoxy)-2-pyridin-2-yl-1H-benzimidazol-6-yl)pyrrolidin-1-yl)-2-oxoethanol The entitled compound was obtained as a white solid in the same method as in Example 168 or in accordance with the method or by combining it with an ordinary method but using 5-(4-(2-methyl-2H-tetrazol-5-yl)phenoxy)-2-pyridin-2-yl-6-pyrrolidin-2-yl-1H-benzimidazole obtained in the same method as in Example 162 (step 2) to (step 7) but using 4-(2-methyl-2H-tetrazol-5-yl)phenol.

$^1$HNMR (CD$_3$OD) δ: 1.94-2.16 (3H, m), 2.23-2.48 (1H, m), 3.57-4.34 (4H, m), 4.43 and 4.44 (total 3H, each s), 5.27-5.52 (1H, m), 7.17-7.57 (5H, m), 7.94-8.04 (1H, m), 8.09-8.20 (2H, m), 8.24-8.32 (1H, m), 8.69-8.81 (1H, m)

ESI-MS (m/e): 497 [M+H]

Example 550

6-(1-Acetyl-3-fluoropyrrolidin-2-yl)-5-((6-(5-methyl-[1,2,4]-oxadiazol-3-yl)pyridin-3-yl)oxy)-2-pyridin-2-yl-1H-benzimidazole The entitled compound was obtained in the same method as in Example 338 (step 5) or in accordance with the method or by combining it with an ordinary method but using N-(4-(1-acetyl-3-fluoropyrrolidin-2-yl)-5-fluoro-2-nitrophenyl)pyridin-2-carboxamide diastereomer B obtained in Example 493 and 6-(5-methyl-[1,2,4]-oxadiazol-3-yl)pyridin-3-ol.

$^1$HNMR (CDCl$_3$) δ: 1.82-2.43 (5H, m), 2.68 and 2.70 (3H, s), 3.64-4.40 (2H, m), 5.19-5.40 (1H, m), 5.42-5.64 (1H, m), 7.02-7.79 (4H, m), 7.80-7.92 (1H, m), 8.00-8.12 (1H, m), 8.35-8.42 (1H, m), 8.60-8.75 (2H, m), 10.50-10.68 (1H, m)

ESI-MS (m/e): 500 [M+H]

Example 551

6-(1-Acetylpyrrolidin-2-yl)-5-(4-(2-ethyl-2H-tetrazol-5-yl)phenoxy-2-pyridin-2-1H-benzimidazole The entitled compound was obtained as a white solid in the same method as in Example 338 (step 5) or in accordance with the method or by combining it with an ordinary method but using 4-(2-ethyl-2H-tetrazol-5-yl)phenol.

$^1$HNMR (CD$_3$OD) δ: 1.68 (3H, t, J=7.2 Hz), 1.90 and 2.13 (total 3H, each s), 1.97-2.20 (3H, m), 2.29-2.53 (1H, m), 3.62-4.00 (2H, m), 4.73-7.79 (2H, m), 5.37-5.47 (1H, m), 7.19-7.60 (5H, m), 7.93-8.03 (1H, m), 8.10-8.20 (2H, m), 8.23-8.33 (1H, m), 8.74 (1H, brs)

ESI-MS (m/e): 495 [M+H]

Example 552

2-(5-(4-(2-Methyl-2H-tetrazol-5-yl)phenoxy)-2-pyridin-2-yl-1H-benzimidazol-6-yl)pyrrolidine-1-carboxamide The entitled compound was obtained as a white solid in the same method as in Example 184 or in accordance with the method or by combining it with an ordinary method but using 5-(4-(2-methyl-2H-tetrazol-5-yl)phenoxy)-2-pyridin-2-yl-6-pyrrolidin-2-yl-1H-benzimidazole obtained in the same method as in Example 162 (step 2) to (step 7) but using 4-(2-methyl-2H-tetrazol-5-yl)phenol.

$^1$HNMR (CD$_3$OD) δ: 1.97-2.10 (3H, m), 2.28-2.41 (1H, m), 3.52-3.63 (1H, m), 3.74-3.62 (1H, m), 5.26-5.41 (1H, m), 7.10-7.33 (1H, m), 7.23 (2H, d, J=8.8 Hz), 7.44-7.61 (2H, m), 7.95-7.99 (1H, m), 8.12 (2H, d, J=8.8 Hz), 8.27 (1H, d, J=8.2 Hz), 8.72-8.73 (1H, m)

ESI-MS (m/e): 482 [M+H]

Example 553

6-(1-Acetyl-3-fluoropyrrolidin-2-yl)-5-(4-(2-methyl-2H-tetrazol-5-yl)phenoxy)-2-pyridin-2-yl H-benzimidazole The entitled compound was obtained as a white solid in the same method as in Example 550 or in accordance with the method or by combining it with an ordinary method but using 4-(2-methyl-2H-tetrazol-5-yl)phenol.

$^1$HNMR (CD$_3$OD) δ: 1.83-2.17 (total 3H, each s), 2.10-2.40 (2H, m), 3.62-4.21 (2H, m), 4.41 and 4.42 (total 3H, each s), 5.23-5.43 (1H, m), 5.46-5.73 (1H, m), 7.10-7.65 (5H, m), 7.94-8.02 (1H, m), 8.03-8.17 (2H, m), 8.27 (1H, t, J=8.8 Hz), 8.72 (1H, brs)

ESI-MS (m/e): 499 [M+H]

Example 554

5'-((2-Pyridin-2-yl-6-pyrrolidin-2-yl-1H-benzimidazol-5-yl)oxy)-2H-1,2'-bipyridin-2-one enantiomer A and enantiomer B 15.0 mg of 5'-((2-pyridin-2-yl-6-pyrrolidin-2-yl-1H-benzimidazol-5-yl)oxy)-2H-1,2'-bipyridin-2-one obtained in the same method as in Example 162 (step 2) to (step 7) but using 5'-hydroxy-2H-1,2'-bipyridin-2-one was optically resolved, using an optical resolution column (CHIRALPAK AD 2 cmφ×25 cmL (by Daicel Chemical), mobile phase: 2-propanol, flow rate: 10 ml/min), into an enantiomer A (retention time: 23.6 min) and an enantiomer B (retention time: 50.7 min) each as a pale yellow solid.

Example 555

5'-((6-(1-Acetylpyrrolidin-2-yl)-2-pyridin-2-yl-1H-benzimidazol-5-yl)oxy)-2H-1,2'-bipyridin-2-one enantiomer A 0.003 ml of acetic anhydride was added to a chloroform (1 ml) solution of 6.5 mg of 5'-((2-pyridin-2-yl-6-pyrrolidin-2-yl-1H-benzimidazol-5-yl)oxy)-2H-1,2'-bipyridin-2-one enantiomer A obtained in Example 554, and the reaction liquid was stirred at room temperature for 30 minutes. The reaction solvent was evaporated away, and the resulting residue was purified through partitioning thin-layer chromatography (Kieselgel™ 60F$_{254}$, Art 5744 (by Merck), chloroform/methanol=10/1) to obtain one chiral form of the entitled compound as a white solid.

$^1$HNMR (CD$_3$OD) δ: 1.91 and 2.16 (total 3H, each s), 1.94-2.20 (3H, m), 2.32-2.52 (1H, m), 3.63-3.98 (2H, m), 5.38-5.44 (1H, m), 6.49-6.54 (1H, m), 6.63-6.68 (1H, m), 7.23-7.58 (3H, m), 7.60-7.67 (2H, m), 7.77 (1H, dd, J=8.8, 15.8 Hz), 7.87-7.93 (1H, m), 7.95-8.01 (1H, m), 8.27-8.31 (1H, m), 8.41 (1H, d, J=2.9 Hz), 8.73 (1H, t, J=4.7 Hz)

ESI-MS (m/e): 493 [M+H]

Example 556

5'-((6-(1-Acetylpyrrolidin-2-yl)-2-pyridin-2-yl-1H-benzimidazol-5-yl)oxy)-2H-1,2'-bipyridin-2-one enantiomer B 0.003 ml of acetic anhydride was added to a chloroform (1 ml) solution of 5.8 mg of 5'-((2-pyridin-2-yl-6-pyrrolidin-2-yl-1H-benzimidazol-5-yl)oxy)-2H-1,2'-bipyridin-2-one enantiomer B obtained in Example 554, and the reaction liquid was stirred at room temperature for 30 minutes. The reaction solvent was evaporated away, and the resulting residue was purified through partitioning thin-layer chromatography (Kieselgel™ 60F$_{254}$, Art 5744 (by Merck), chloroform/methanol=10/1) to obtain one chiral form of the entitled compound as a white solid.
ESI-MS (m/e): 493 [M+H]

Example 557

6-(Cis-1-acetyl-4-fluoropyrrolidin-2-yl)-5-(4-(2-methyl-2H-tetrazol-5-yl)phenoxy)-2-pyridin-2-yl-1H-benzimidazole The entitled compound was obtained as a white solid in the same method as in Example 325 (step 6) or in accordance with the method or by combining it with an ordinary method but using cis-1-acetyl-2-(5-nitro-2-fluoro-4-((pyridin-2-carbonyl)-amino)-phenyl)-4-acetoxy-pyrrolidine obtained in Example 325 (step 5) and 4-(2-methyl-2H-tetrazol-5-yl)phenol.
$^1$HNMR (CD$_3$OD) δ: 1.80-2.84 (2H, m), 1.94 and 2.25 (total 3H, each s), 3.90-4.30 (2H, m), 4.43 (3H, s), 5.28-5.50 (1H, m), 5.51-5.59 (1H, m), 7.18-7.64 (5H, m), 7.94-8.01 (1H, m), 8.12-8.18 (2H, m), 8.25-8.29 (1H, m), 8.70-8.77 (1H, m)
ESI-MS (m/e): 499 [M+H]

Example 558

3-(4-((6-(1-Acetylpyrrolidin-2-yl)-2-pyridin-2-yl-1H-benzimidazol-5-yl)oxy)phenyl)-1,3-oxazolidin-2-one The entitled compound was obtained as a yellow oily substance in the same method as in Example 483 or in accordance with the method or by combining it with an ordinary method but using 3-(4-hydroxyphenyl)-1,3-oxazolidin-2-one.
$^1$HNMR (CDCl$_3$) δ: 1.20-2.50 (7H, m), 3.50-4.00 (2H, m), 3.90-4.25 (2H, m), 4.40-4.60 (2H, m), 5.20-5.60 (1H, m), 6.80-7.70 (7H, m), 7.80-8.00 (1H, m), 8.25-8.50 (1H, m), 8.50-8.80 (1H, m), 10.50-10.80 (1H, m)
ESI-MS (m/e): 484 [M+H]

Example 559

6-(1-Acetylpyrrolidin-2-yl)-5-((6-methylpyridin-3-yl)oxy)-2-pyridin-2-yl-1H-benzimidazole The entitled compound was obtained as an oily substance in the same method as in Example 483 or in accordance with the method or by combining it with an ordinary method but using 6-methylpyridin-3-ol.
$^1$HNMR (CDCl$_3$) δ: 1.72-2.59 (10H, m), 3.53-3.90 (2H, m), 5.20-5.55 (1H, m), 6.81-7.66 (5H, m), 7.78-7.92 (1H, m), 8.28-8.43 (2H, m), 8.55-8.66 (1H, m), 11.07-11.55 (1H, m)
ESI-MS (m/e): 414 [M+H]

Example 560

6-(1-Acetylpyrrolidin-2-yl)-5-((6-pyrazin-2-ylpyridin-3-yloxy)-2-pyridin-2-yl-1H-benzimidazole The entitled compound was obtained as a yellow oily substance in the same method as in Example 483 or in accordance with the method or by combining it with an ordinary method but using 6-pyrazin-2-ylpyridin-3-ol.
$^1$HNMR (CDCl$_3$) δ: 0.80-2.40 (7H, m), 3.60-3.90 (2H, m), 5.20-5.60 (1H, m), 7.00-7.80 (4H, m), 7.80-8.00 (1H, m), 8.30-8.50 (2H, m), 8.50-8.80 (4H, m), 9.50-9.70 (1H, m), 10.40-10.80 (1H, m)
ESI-MS (m/e): 478 [M+H]

Example 561

6-(Cis-1-acetyl-4-fluoropyrrolidin-2-yl)-5-((2'-fluorobiphenyl-4-yl)oxy)-2-pyridin-2-yl-1H-benzimidazole The entitled compound was obtained as a yellow oily substance in the same method as in Example 325 (step 6) or in accordance with the method or by combining it with an ordinary method but using cis-1-acetyl-2-(5-nitro-2-fluoro-4-((pyridin-2-carbonyl)-amino)-phenyl)-4-acetoxy-pyrrolidine obtained in Example 325 (step 5) and 2'-fluorobiphenyl-4-ol.
$^1$HNMR (CDCl$_3$) δ: 0.80-2.80 (6H, m), 3.80-4.40 (2H, m), 5.05-5.50 (1H, m), 7.00-7.70 (11H, m), 7.75-7.95 (1H, m), 8.30-8.50 (1H, m), 8.50-8.75 (1H, m), 10.60-10.80 (1H, m)
ESI-MS (m/e): 511 [M+H]

Example 562

6-(Cis-1-acetyl-4-fluoropyrrolidin-2-yl)-5-(4-pyrazin-2-ylphenoxy)-2-pyridin-2-yl-1H-benzimidazole The entitled compound was obtained as a yellow oily substance in the same method as in Example 325 (step 6) or in accordance with the method or by combining it with an ordinary method but using cis-1-acetyl-2-(5-nitro-2-fluoro-4-((pyridin-2-carbonyl)-amino)-phenyl)-4-acetoxy-pyrrolidine obtained in Example 325 (step 5) and 4-pyrazin-2-ylphenol.
$^1$HNMR (CDCl$_3$) δ: 1.20-2.80 (6H, m), 3.80-4.40 (2H, m), 5.20-5.50 (1H, m), 7.00-7.70 (5H, m), 7.80-7.95 (1H, m), 7.95-8.20 (2H, m), 8.30-8.50 (2H, m), 8.50-8.80 (2H, m), 8.95-9.20 (1H, m), 10.60-10.80 (1H, m)
ESI-MS (m/e): 495 [M+H]

Example 563

N-((5-((6-(1-Acetylpyrrolidin-2-yl)-2-pyridin-2-yl-1H-benzimidazol-5-yl)oxy)pyridin-2-yl)methyl)acetamide The entitled compound was obtained as an oily substance in the same method as in Example 483 or in accordance with the method or by combining it with an ordinary method but using N-((5-hydroxypyridin-2-yl)methyl)acetamide.
$^1$HNMR (CDCl$_3$) δ: 1.83-2.47 (10H, m), 3.54-3.90 (2H, m), 4.48-4.59 (2H, m), 5.21-5.50 (1H, m), 6.66-7.69 (6H, m), 7.79-7.91 (1H, m), 8.30-8.44 (2H, m), 8.54-8.69 (1H, m), 10.96-11.29 (1H, m)
ESI-MS (m/e): 471 [M+H]

Example 564

6-(1-Acetylpyrrolidin-2-yl)-5-((6-fluoropyridin-3-yl)oxy)-2-pyridin-2-yl-1H-benzimidazole The entitled compound was obtained as a yellow oily substance in the same method as in Example 338 (step 5) or in accordance with the method or by combining it with an ordinary method but using 6-fluoropyridin-3-ol.

$^1$HNMR (CDCl$_3$) δ: 1.40-2.50 (7H, m), 3.50-4.00 (2H, m), 5.00-5.60 (1H, m), 6.80-7.70 (5H, m), 7.80-7.95 (1H, m), 8.00-8.15 (1H, m), 8.25-8.50 (1H, m), 8.50-8.70 (1H, m), 10.60-10.80 (1H, m)

ESI-MS (m/e): 418 [M+H]

Example 565

Cis-1-(4-fluoro-2-(6-(6-cyano din-3-yloxy)-2-pyridin-2-yl)-3H-benzimidazol-5-yl)-pyrrolidin-1-yl)-ethanone enantiomer A and enantiomer B (Step 1) Production of cis-1-(4-fluoro-2-(6-(6-cyano-pyridin-3-yloxy)-2-pyridin-2-yl-3H-benzimidazol-5-yl)-pyrrolidin-1-yl)-ethanone The entitled compound was obtained in the same method as in Example 325 (step 6) or in accordance with the method or by combining it with an ordinary method but using cis-1-acetyl-2-(5-nitro-2-fluoro-4-((pyridin-2-carbonyl)-amino)-phenyl)-4-acetoxy-pyrrolidine obtained in Example 325 (step 5) and 6-cyano-pyridin-3-ol.

(Step 2) Production of cis-1-(4-fluoro-2-(6-(6-cyano-pyridin-3-yloxy)-2-pyridin-2-yl-3H-benzimidazol-5-yl)-pyrrolidin-1-yl)-ethanone enantiomer A and enantiomer B The entitled compound was obtained in the same method as in Example 333 or in accordance with the method or by combining it with an ordinary method but using the racemic cis-1-(4-fluoro-2-(6-(6-cyano-pyridin-3-yloxy)-2-pyridin-2-yl-3H-benzimidazol-5-yl)-pyrrolidin-1-yl)-ethanone obtained in (step 1).

Enantiomer A $^1$HNMR (CD$_3$OD) δ: 1.91 (3H×½, s), 2.22 (3H×½, s), 2.32-2.67 (2H, m), 3.95-4.30 (2H, m), 5.27-5.47 (2H, m), 7.35-7.64 (3H, m), 7.85-7.92 (1H, m), 7.97-7.99 (1H, m), 8.29 (1H, t, J=7.6 Hz), 8.60 (1H, d, J=3.1 Hz), 8.74 (1H, s).

ESI-MS (m/e): 443 [M+H]

Enantiomer B

ESI-MS (m/e): 443 [M+H]

Example 566

6-(1-Acetyl-3-fluoropyrrolidin-2-yl)-5-((2'-fluorobiphenyl-4-yl)oxy)-2-pyridin-2-yl-1H-benzimidazole enantiomer A (Step 1) Production of N-(4-(1-acetyl-3-fluoropyrrolidin-2-yl)-5-fluoro-2-nitrophenyl)pyridin-2-carboxamide enantiomer A and enantiomer B 300 mg of N-(4-(1-acetyl-3-fluoropyrrolidin-2-yl)-5-fluoro-2-nitrophenyl)pyridin-2-carboxamide diastereomer B obtained in Example 493 was optically resolved, using an optical resolution column (CHIRALCEL OD 2 cmφ×25 cmL (by Daicel Chemical), mobile phase: hexane/ethanol/diethylamine=50/50/0.1, flow rate: 10 ml/min), into an enantiomer A and an enantiomer B each as a yellow solid.

(Step 2) Production of 6-(1-acetyl-3-fluoropyrrolidin-2-yl)-5-((2'-fluorobiphenyl-4-yl)oxy)-2-pyridin-2-yl-1H-benzimidazole enantiomer A The entitled compound was obtained in the same method as in Example 338 (step 5) or in accordance with the method or by combining it with an ordinary method but using N-(4-(1-acetyl-3-fluoropyrrolidin-2-yl)-5-fluoro-2-nitrophenyl)pyridin-2-carboxamide enantiomer A and 2'-fluorobiphenyl-4-ol.

$^1$HNMR (CDCl$_3$) δ: 1.82-2.43 (5H, m), 3.63-4.36 (2H, m), 5.25-5.70 (2H, m), 7.07-7.58 (11H, m), 7.74-7.90 (1H, m), 8.35-8.43 (1H, m), 8.58-8.68 (1H, m), 10.37-10.60 (1H, m)

ESI-MS (m/e): 511 [M+H]

Example 567

6-(1-Acetyl-3-fluoropyrrolidin-2-yl)-5-((2'-fluorobiphenyl-4-yl)oxy)-2-pyridin-2-yl-1H-benzimidazole enantiomer B The entitled compound was obtained in the same method as in Example 566 (step 2) or in accordance with the method or by combining it with an ordinary method but using N-(4-(1-acetyl-3-fluoropyrrolidin-2-yl)-5-fluoro-2-nitrophenyl)pyridin-2-carboxamide enantiomer B obtained in Example 566 (step 1).

ESI-MS (m/e): 511 [M+H]

Example 568

Cis-1-(4-fluoro-2-(6-(4-ethanesulfonyl-phenoxy)-2-pyridin-2-yl-3H-benzimidazol-5-yl)pyrrolidin-1-yl)-ethanone The entitled compound was obtained in the same method as in Example 565 (step 1) or in accordance with the method or by combining it with an ordinary method but using 4-ethanesulfonyl-phenol.

$^1$HNMR (CD$_3$OD) δ: 1.90 (3H×0.5, s), 2.22 (3H×0.5, s), 2.25-2.75 (2H, m), 3.88-4.39 (2H, m), 5.24-5.48 (2H, m), 7.23-7.75 (5H, m), 7.90-8.02 (3H, m), 8.27-8.30 (1H, m), 8.73-8.75 (1H, m).

ESI-MS (m/e): 509 [M+H]

Example 569

3-(4-(((6-(1-Acetylpyrrolidin-2-yl)-2-pyrazin-2-yl-1H-benzimidazol-5-yl)oxy)phenyl)-1,3-oxazolidin-2-one enantiomer A (Step 1) Production of t-butyl 2-(2-fluoro-4-((pyrazin-2-ylcarbonyl)amino)phenyl)pyrrolidine-1-carboxylate 1.5 g of pyrazine-2-carboxylic acid and 3.1 g of 1-(3-dimethylaminopropyl)-3-ethylcarbodiimide monohydrochloride were added to a pyridine (50 ml) solution of 3 g of t-butyl 2-(4-amino-2-fluoro-phenyl)-pyrrolidine-1-carboxylate obtained in Example 338 (step 2), and the reaction liquid was stirred at room temperature for 3 hours. The reaction liquid was diluted with chloroform, washed with water and saturated saline in order, and dried with anhydrous magnesium sulfate. The solvent was evaporated away under reduced pressure, and the resulting residue was purified through silica gel column chromatography (developing solvent: chloroform/methanol=50/1) to obtain the entitled compound as a yellow oily substance.

(Step 2) Production of N-(3-fluoro-4-pyrrolidin-2-ylphenyl)pyrazine-2-carboxamide dihydrochloride 50 ml of 4 N hydrochloric acid-dioxane solution was added to a methanol (50 ml) solution of 4.4 g of t-butyl 2-(2-fluoro-4-((pyrazin-2-ylcarbonyl)amino)phenyl)pyrrolidine-1-carboxylate, and the reaction liquid was stirred at room temperature for 1 hour. The solvent was evaporated away under reduced pressure to obtain the entitled compound as a yellow solid.

(Step 3) Production of N-(4-(1-acetylpyrrolidin-2-yl)-3-fluorophenyl)pyrazine-2-carboxamide 1.5 ml of acetic anhydride was added to a pyridine (50 ml) solution of 4.3 g of N-(3-fluoro-4-pyrrolidin-2-ylphenyl) pyrazine-2-carboxamide dihydrochloride, and the reaction liquid was stirred at room temperature for 20 minutes. The reaction liquid was diluted with chloroform, washed with water and saturated saline in order, and dried with anhydrous magnesium sulfate. The solvent was evaporated away under reduced pressure, and the resulting residue was purified through silica gel column chromatography (developing solvent: chloroform/methanol=50/1) to obtain the entitled compound as a yellow solid.

(Step 4) Production of N-(4-(1-acetylpyrrolidin-2-yl)-5-fluoro-2-nitrophenyl)pyrazin-2-carboxamide 40 ml of fuming nitric acid was added to 3.9 g of N-(4-(1-acetylpyrrolidin-2-yl)-3-fluorophenyl)pyrazine-2-carboxamide with cooling with ice, and the reaction liquid was stirred at room temperature for 2 hours. The reaction liquid was diluted with water with ice, made basic with aqueous saturated sodium bicarbonate, and then extracted with chloroform. The organic layer was washed with saturated saline, and dried with anhydrous magnesium sulfate. The solvent was evaporated away under reduced pressure, and the resulting residue was purified through silica gel column chromatography (developing solvent: chloroform/methanol=50/1) to obtain the entitled compound as a yellow oily substance.

(Step 5) Production of N-(4-(1-acetylpyrrolidin-2-yl)-5-fluoro-2-nitrophenyl)pyrazin-2-carboxamide enantiomer A and enantiomer B 500 mg of N-(4-(1-acetylpyrrolidin-2-yl)-5-fluoro-2-nitrophenyl)pyrazin-2-carboxamide was optically resolved, using an optical resolution column (CHIRALPAK OD-H 2 cmφ×25 cmL (by Daicel Chemical), mobile phase: hexane/2-propanol=1/1, flow rate: 15 ml/min), into an enantiomer A (retention time: 18 min) and an enantiomer B (retention time: 25 min) each as a pale yellow oily substance.

(Step 6) Production of 3-(4-((6-(1-acetylpyrrolidin-2-yl)-2-pyrazin-2-yl-1H-benzimidazol-5-yl)oxy) phenyl)-1,3-oxazolidin-2-one enantiomer A One chiral form of the entitled compound was obtained as a yellow oily substance in the same method as in Example 338 (step 5) or in accordance with the method or by combining it with an ordinary method but using 3-(4-hydroxyphenyl)-1,3-oxazolidin-2-one and N-(4-(1-acetylpyrrolidin-2-yl)-5-fluoro-2-nitrophenyl)pyrazin-2-carboxamide enantiomer A.

$^1$HNMR (CDCl$_3$) δ: 1.00-2.40 (7H, m), 3.50-3.90 (2H, m), 3.90-4.20 (2H, m), 4.40-4.60 (2H, m), 5.20-5.60 (1H, m), 6.80-7.70 (6H, m), 8.50-8.75 (2H, m), 9.50-9.70 (1H, m), 10.30-10.60 (1H, m)
ESI-MS (m/e): 485 [M+H]

Example 570

3-(4-((6-(1-Acetylpyrrolidin-2-yl)-2-pyrazin-2-yl-1H-benzimidazol-5-yl)oxy)phenyl)-1,3-oxazolidin-2-one enantiomer B The entitled compound was obtained as a yellow oily substance in the same method as in Example 338 (step 5) or in accordance with the method or by combining it with an ordinary method but using 3-(4-hydroxyphenyl)-1,3-oxazolidin-2-one and N-(4-(1-acetylpyrrolidin-2-yl)-5-fluoro-2-nitrophenyl)pyrazin-2-carboxamide enantiomer B obtained in Example 569 (step 5).
ESI-MS (m/e): 485 [M+H]

Example 571

6-(1-Acetylpyrrolidin-2-yl)-5-(4-(cyclopropylsulfonyl)phenoxy)-2-pyridin-2-yl-1H-benzimidazole The entitled compound was obtained as a pale yellow solid in the same method as in Example 483 or in accordance with the method or by combining it with an ordinary method but using 4-(cyclopropylsulfonyl)phenol.
$^1$HNMR (CDCl$_3$) δ: 0.90-1.20 (2H, m), 1.20-1.40 (3H, m), 1.60-2.60 (7H, m), 3.50-4.00 (2H, m), 5.05-5.50 (1H, m), 7.00-8.20 (8H, m), 8.30-8.50 (1H, m), 8.55-8.80 (1H, m), 10.70-11.20 (1H, m)
ESI-MS (m/e): 503 [M+H]

Example 572

6-(1-Acetylpyrrolidin-2-yl)-5-(4-(ethanesulfonyl)phenoxy)-2-pyridin-2-yl-1H-benzimidazole The entitled compound was obtained as a white solid in the same method as in Example 483 or in accordance with the method or by combining it with an ordinary method but using 4-(ethanesulfonyl)phenol.
$^1$HNMR (CDCl$_3$) δ: 1.20-1.40 (3H, m), 1.60-2.50 (7H, m), 3.00-3.20 (2H, m), 3.50-4.00 (2H, m), 5.10-5.50 (1H, m), 6.90-7.80 (5H, m), 7.80-8.00 (3H, m), 8.30-8.50 (1H, m), 8.50-8.75 (1H, m), 10.60-11.20 (1H, m)
ESI-MS (m/e): 491 [M+H]

Example 573

Cis-1-(4-fluoro-2-(6-(6-ethanesulfonyl-pyridin-3-yloxy)-2-pyridin-2-yl-3H-benzimidazol-5-yl)-pyrrolidin-1-yl)-ethanone The entitled compound was obtained in the same method as in Example 565 (step 1) or in accordance with the method or by combining it with an ordinary method but using 6-ethanesulfonyl-pyridin-3-ol.
$^1$HNMR (CD$_3$OD) δ: 1.20-1.40 (3H, m), 1.90-2.30 (3H, m), 2.00-2.80 (2H, m), 3.20-3.50 (2H, m), 3.84-4.25 (2H, m), 5.27-5.45 (2H, m), 7.40-7.80 (4H, m), 8.00-8.20 (2H, m), 8.24-8.40 (1H, m), 8.66 (1H, s), 8.80 (1H, brs)
ESI-MS (m/e): 510 [M+H]

Example 574

Cis-1-(4-fluoro-2-(6-(6-(5-methyl-[1,2,4]-oxadiazol-3-yl)pyridin-3-yloxy)-2-pyridin-2-yl-3H-benzimidazol-5-yl)-pyrrolidin-1-yl)-ethanone The entitled compound was obtained in the same method as in Example 565 (step 1) or in accordance with the method or by combining it with an ordinary method but using 6-(5-methyl-[1,2,4]-oxadiazol-3-yl)pyridin-3-ol.

$^1$HNMR (CD$_3$OD) δ: 1.90-2.30 (3H, m), 2.00-2.80 (2H, m), 2.75 (3H, s), 3.84-4.40 (2H, m), 5.30-5.45 (2H, m), 7.25-7.80 (4H, m), 7.90-8.40 (3H, m), 8.55-8.68 (1H, m), 8.75 (1H, s)

ESI-MS (m/e): 500 [M+H]

Example 575

5-((6-(1-Acetyl-3-fluoropyrrolidin-2-yl)-2-pyridin-2-yl-1H-benzimidazol-5-yl)oxy)pyridine-2-carbonitrile The entitled compound was obtained as an oily substance in the same method as in Example 338 (step 5) or in accordance with the method or by combining it with an ordinary method but using N-(4-(1-acetyl-3-fluoropyrrolidin-2-yl)-5-fluoro-2-nitrophenyl)pyridine-2-carboxamide enantiomer B obtained in Example 566 (step 1) and 5-hydroxypyridine-2-carbonitrile.

$^1$HNMR (CDCl$_3$) δ: 1.54-2.45 (5H, m), 3.61-4.34 (2H, m), 5.09-5.54 (2H, m), 7.01-7.95 (6H, m), 8.34-8.47 (1H, m), 8.54-8.73 (2H, m), 10.66-10.79 (1H, m)

ESI-MS (m/e): 443 [M+H]

Example 576

6-(1-Acetyl-3-fluoropyrrolidin-2-yl)-5-((6-(5-methyl-[1,2,4]-oxadiazol-3-yl)pyridin-3-yl)oxy)-2-pyridin-2-yl-1H-benzimidazole The entitled compound was obtained as an oily substance in the same method as in Example 575 or in accordance with the method or by combining it with an ordinary method but using 6-(5-methyl-[1,2,4]-oxadiazol-3-yl)pyridin-3-ol.

$^1$HNMR (CDCl$_3$) δ: 1.54-2.45 (5H, m), 3.61-4.34 (2H, m), 5.09-5.54 (2H, m), 7.01-7.95 (6H, m), 8.34-8.47 (1H, m), 8.54-8.73 (2H, m), 10.66-10.79 (1H, m)

ESI-MS (m/e): 443 [M+H]

Example 577

6-(1-Acetylpyrrolidin-2-yl)-2-pyrazin-2-yl-5-((6-pyrazin-2-ylpyridin-3-yl)oxy)-1H-benzimidazole The entitled compound was obtained as a pale yellow oily substance in the same method as in Example 570 or in accordance with the method or by combining it with an ordinary method but using 6-pyrazin-2-ylpyridin-3-ol.

$^1$HNMR (CDCl$_3$) δ: 1.05-2.50 (7H, m), 3.50-4.00 (2H, m), 5.20-5.60 (1H, m), 7.00-7.80 (3H, m), 8.20-8.45 (1H, m), 8.45-8.80 (5H, m), 9.50-9.70 (2H, m), 10.40-11.30 (1H, m)

ESI-MS (m/e): 479 [M+H]

Example 578

6-(1-Acetyl-5-methylpyrrolidin-2-yl)-5-((6-methylpyridin-3-yl)oxy)-2-pyridin-2-yl-1H-benzimidazole The entitled compound was obtained as a pale yellow solid in the same method as in Example 338 (step 5) or in accordance with the method or by combining it with an ordinary method but using N-(4-(1-acetyl-5-methylpyrrolidin-2-yl)-5-fluoro-2-nitrophenyl)pyridine-2-carboxamide obtained in Example 545 and 6-methylpyridin-3-ol.

$^1$HNMR (CDCl$_3$) δ: 1.20-2.30 (7H, m), 2.30-2.70 (6H, m), 4.05-4.60 (1H, m), 5.20-5.60 (1H, m), 6.80-7.50 (4H, m), 7.70-7.90 (1H, m), 8.15-8.20 (1H, m), 8.25-8.40 (2H, m), 8.50-8.80 (1H, m)

ESI-MS (m/e): 428 [M+H]

Example 579

6-(1-Acetyl-5-methylpyrrolidin-2-yl)-5-((6-chloropyridin-3-yloxy)-2-pyridin-2-yl-1H-benzimidazole The entitled compound was obtained as a pale yellow solid in the same method as in Example 578 or in accordance with the method or by combining it with an ordinary method but using 6-chloropyridin-3-ol.

$^1$HNMR (CDCl$_3$) δ: 1.20-2.60 (10H, m), 4.05-4.65 (1H, m), 5.10-5.50 (1H, m), 6.80-7.70 (4H, m), 7.80-8.10 (2H, m), 8.15-8.50 (2H, m), 8.60-8.80 (1H, m), 10.80-11.30 (1H, m)

ESI-MS (m/e): 448 [M+H]

Example 580

2-(5-((6-(1-Acetylpyrrolidin-2-yl)-2-pyridin-2-yl-1H-benzimidazol-5-yl)oxy)pyridin-2-ylsulfanyl)ethanol 20 mg of 2-mercaptoethanol and 10 mg of potassium carbonate were added in order to an N,N-dimethylformamide (1 ml) solution of 20 mg of 6-(1-acetylpyrrolidin-2-yl)-5-(6-chloropyridin-3-yl)oxy-2-pyridin-2-yl-1H-benzimidazole obtained in Example 504, and the reaction liquid was stirred at 120° C. for 5 hours. After cooled, the reaction liquid was diluted with aqueous saturated sodium bicarbonate, extracted with chloroform, and the organic layer was dried with anhydrous magnesium sulfate, and the solvent was evaporated away under reduced pressure. The resulting residue was purified through partitioning thin-layer chromatography (Kieselgel™ 60F$_{254}$, Art 5744 (by Merck), chloroform/methanol=10/1) to obtain the entitled compound as a white solid.

$^1$HNMR (CDCl$_3$) δ: 1.10-2.50 (7H, m), 3.20-3.40 (2H, m), 3.50-4.00 (4H, m), 5.20-5.50 (1H, m), 6.80-7.70 (5H, m), 7.80-7.95 (1H, m), 8.10-8.50 (2H, m), 8.50-8.70 (1H, m), 10.60-10.80 (1H, m)

ESI-MS (m/e): 476 [M+H]

Example 581

3-(5-((6-(1-Acetylpyrrolidin-2-yl)-2-pyridin-2-yl-1H-benzimidazol-5-yl)oxy)pyridin-2-ylsulfanyl)ol-1-ol The entitled compound was obtained as a white solid in the same method as in Example 580 or in accordance with the method or by combining it with an ordinary method but using 3-mercaptopropan-1-ol.

$^1$HNMR (CDCl$_3$) δ: 1.60-2.50 (7H, m), 3.20-3.40 (2H, m), 3.50-4.40 (6H, m), 5.20-5.60 (1H, m), 6.80-7.70 (5H, m), 7.80-7.95 (1H, m), 8.20-8.50 (2H, m), 8.50-8.70 (1H, m), 10.80-11.20 (1H, m)

ESI-MS (m/e): 490 [M+H]

Example 582

6-(1-Acetylpyrrolidin-2-yl)-2-(5-methylpyridin-2-yl)-5-(4-methanesulfonyl-phenoxy)-1H-benzimidazole The entitled compound was obtained as a pale yellow solid in the same method as in Example 462 or in accordance with the method or by combining it with an ordinary method but using 5-methylpicolinic acid.

$^1$HNMR (CD$_3$OD) δ: 1.86 and 2.10 (total 3H, each s), 1.92-2.43 (4H, m), 2.65 and 2.66 (total 3H, each s), 3.14 and 3.16 (total 3H, each s), 3.62-3.96 (2H, m), 5.25-5.32 (1H, m), 7.23 and 7.25 (total 2H, each d, J=8.8 Hz), 7.20-7.58 (3H, m), 7.95 and 7.99 (total 2H, each d, J=8.8 Hz), 8.38-8.42 (1H, m), 9.12-9.16 (1H, m)

ESI-MS (m/e): 491 [M+H]

Example 583

6-(1-Acetylpyrrolidin-2-yl)-2-(5-methylpyrazin-2-yl)-5-(4-methanesulfonyl-phenoxy)-1H-benzimidazole The entitled compound was obtained as a pale yellow solid in the same method as in Example 462 or in accordance with the method or by combining it with an ordinary method but using 5-methylpyrazine-2-carboxylic acid.

$^1$HNMR (CD$_3$OD) δ: 1.87-2.45 (7H, m), 2.66 and 2.67 (total 3H, each s), 3.14 and 3.16 (total 3H, each s), 3.63-4.00 (2H, m), 5.26-5.34 (1H, m), 7.20-7.61 (4H, m), 7.96 and 7.99 (total 2H, each d, J=8.8 Hz), 8.69 (1H, s), 9.32 and 9.34 (total 1H, each s)

ESI-MS (m/e): 492 [M+H]

Example 584

1-(4-((6-(1-Acetyl-3-fluoropyridin-2-yl)-2-pyridin-2-yl-1H-benzimidazol-5-yl)oxy)phenyl)ethanone The entitled compound was obtained as an oily substance in the same method as in Example 575 or in accordance with the method or by combining it with an ordinary method but using 1-(4-hydroxyphenyl)ethanone.

$^1$HNMR (CDCl$_3$) δ: 1.62-2.60 (8H, m), 3.60-3.98, 4.04-4.33 (total 2H, each m), 5.11-5.56 (2H, m), 7.00-8.02 (8H, m), 8.33-8.48 (1H, m), 8.57-8.71 (1H, m), 10.76-11.09 (1H, m)

ESI-MS (m/e): 459 [M+H]

Example 585

6-(1-Acetyl-3-fluoropyridin-2-yl)-5-((6-chloropyridin-3-yl)oxy)-2-pyridin-2-yl-1H-benzimidazole The entitled compound was obtained as an oily substance in the same method as in Example 575 or in accordance with the method or by combining it with an ordinary method but using 6-chloropyridin-3-ol.

$^1$HNMR (CDCl$_3$) δ: 1.54-2.45 (5H, m), 3.60-4.35 (2H, m), 5.20-5.60 (2H, m), 6.90-7.00, 7.21-7.43, 7.60-7.93 (total 6H, each m), 8.22-8.45 (2H, m), 8.58-8.70 (1H, m), 10.63-10.90 (1H, m)

ESI-MS (m/e): 452 [M+H]

Example 586

6-(1-Acetylpyrrolidin-2-yl)-5-((6-(5-methyl-[1,2,4]-oxadiazol-3-yl)pyridin-3-yl)oxy)-2-pyrazin-2-yl-1H-benzimidazole The entitled compound was obtained as an oily substance in the same method as in Example 570 or in accordance with the method or by combining it with an ordinary method but using 6-(5-methyl-[1,2,4]-oxadiazol-3-yl)pyridin-3-ol.

$^1$HNMR (CDCl$_3$) δ: 1.60-2.47 (7H, m), 2.57-2.73 (3H, m), 3.57-3.93 (2H, m), 5.21-5.48 (1H, m), 7.00-7.76 (3H, m), 7.96-8.14 (1H, m), 8.52-8.68 (3H, m), 9.54-9.65 (1H, m), 10.70-11.02, 11.53-10.66 (total 1H, each m)

ESI-MS (m/e): 483 [M+H]

Example 587

6-(1-Acetylpyrrolidin-2-yl)-5-((6-(methanesulfonyl)pyridin-3-yl)oxy)-2-pyrazin-2-yl-1H-benzimidazole The entitled compound was obtained as an oily substance in the same method as in Example 570 or in accordance with the method or by combining it with an ordinary method but using 6-(methanesulfonyl)pyridin-3-ol.

$^1$HNMR (CDCl$_3$) δ: 1.51-2.47 (7H, m), 3.14-3.27 (3H, m), 3.58-3.92 (2H, m), 5.14-5.40 (1H, m), 7.03-7.79 (4H, m), 7.95-8.11 (1H, m), 8.48-8.71 (2H, m), 9.56-9.66 (1H, m), 10.65-10.94, 11.34-11.49 (total 1H, each m)

ESI-MS (m/e): 479 [M+H]

Example 588

1-(4-((6-(1-Acetylpyrrolidin-2-yl)-2-pyrazin-2-yl-1H-benzimidazol-5-yl)oxy)phenyl)ethanone The entitled compound was obtained as an oily substance in the same method as in Example 570 or in accordance with the method or by combining it with an ordinary method but using 1-(4-hydroxyphenyl)ethanone.

$^1$HNMR (CDCl$_3$) δ: 1.53-2.61 (10H, m), 3.51-3.93 (2H, m), 5.14-5.47 (1H, m), 6.95-7.74 (4H, m), 7.88-8.02 (2H, m), 8.53-8.68 (2H, m), 9.54-9.66 (1H, m), 10.60-10.88, 11.43-11.54 (total 1H, each m)

ESI-MS (m/e): 442 [M+H]

Example 589

6-(Acetylpyrrolidin-2-yl)-5-((6-(difluoromethoxy)pyridin-3-yloxy)-2-pyridin-2-yl-1H-benzimidazole The entitled compound was obtained as a pale yellow solid in the same method as in Example 338 (step 5) or in accordance with the method or by combining it with an ordinary method but using 6-(difluoromethoxy)pyridin-3-ol.

$^1$HNMR (CD$_3$OD) δ: 1.92 and 2.18 (total 3H, each s), 1.98-2.57 (4H, m), 3.65-4.00 (2H, m), 5.41-5.48 (1H, m), 7.03 and 7.07 (total 1H, each d, J=8.8 Hz), 7.00-7.72 (5H, m), 7.94-8.00 (1H, m), 8.08 (1H, s), 8.25 (1H, t, J=7.4 Hz), 8.73 (1H, s)

ESI-MS (m/e): 466 [M+H]

Example 590

6-(1-Acetylpyrrolidin-2-yl)-2-pyrazin-2-yl-5-(4-pyrazin-2-ylphenoxy)-1H-benzimidazole The entitled compound was obtained as a white solid in the same method as in Example 526 or in accordance with the method or by combining it with an ordinary method but using 4-pyrazin-2-ylphenol.

$^1$HNMR (CDCl$_3$) δ: 1.10-2.60 (7H, m), 3.50-4.00 (2H, m), 5.20-5.60 (1H, m), 6.70-7.80 (4H, m), 7.90-8.20 (2H, m), 8.50-8.80 (4H, m), 8.95-9.20 (1H, m), 9.50-9.75 (1H, m), 10.60-11.40 (1H, m)
ESI-MS (m/e): 478 [M+H]

Example 591

4-((6-(1-Acetylpyrrolidin-2-yl)-2-pyrazin-2-yl-1H-benzimidazol-5-yl)oxy)benzonitrile The entitled compound was obtained as a yellow oily substance in the same method as in Example 526 or in accordance with the method or by combining it with an ordinary method but using 4-cyanophenol.

$^1$HNMR (CDCl$_3$) δ: 1.50-2.50 (7H, m), 3.50-3.90 (2H, m), 5.05-5.50 (1H, m), 6.65-7.80 (6H, m), 8.50-8.80 (2H, m), 9.50-9.70 (1H, m), 10.40-11.20 (1H, m)
ESI-MS (m/e): 425 [M+H]

Example 592

Methyl 4-((6-(1-acetylpyrrolidin-2-yl)-2-pyrazin-2-yl-1H-benzimidazol-5-yl)oxy)benzoate The entitled compound was obtained as a yellow oily substance in the same method as in Example 526 or in accordance with the method or by combining it with an ordinary method but using methyl 4-hydroxybenzoate.

$^1$HNMR (CDCl$_3$) δ: 1.60-2.50 (7H, m), 3.50-4.00 (5H, m), 5.10-5.60 (1H, m), 6.70-7.80 (4H, m), 7.90-8.20 (2H, m), 8.50-8.70 (2H, m), 9.50-9.70 (1H, m), 10.60-11.60 (1H, m)
ESI-MS (m/e): 458 [M+H]

Example 593

2-(5-((2'-Fluorobiphenyl-4-yl)oxy)-2-pyridin-2-yl-1H-benzimidazol-6-yl)pyrrolidine-1-carboxamide The entitled compound was obtained as a pale yellow solid in the same method as in Example 182 or in accordance with the method or by combining it with an ordinary method but using 2'-fluorobiphenyl-4-ol.

$^1$HNMR (DMSO-d$_6$) δ: 1.60-2.60 (4H, m), 3.20-4.20 (2H, m), 5.10-5.30 (1H, m), 5.60-5.90 (2H, m), 6.90-7.70 (11H, m), 7.90-8.10 (1H, m), 8.20-8.40 (1H, m), 8.60-8.80 (1H, m)
ESI-MS (m/e): 494 [M+H]

Example 594

6-(1-Acetylpyrrolidin-2-yl)-5-(4-(5-methyl-[1,2,4]-oxadiazol-3-yl)phenoxy-2-pyrazin-2-yl-1H-benzimidazole The entitled compound was obtained as a white solid in the same method as in Example 526 or in accordance with the method or by combining it with an ordinary method but using 4-(5-methyl-[1,2,4]-oxadiazol-3-yl)phenol.

$^1$HNMR (CDCl$_3$) δ: 1.60-2.80 (10H, m), 3.50-4.00 (2H, m), 5.15-5.60 (1H, m), 6.70-7.80 (5H, m), 7.90-8.20 (2H, m), 8.50-8.70 (1H, m), 9.50-9.70 (1H, m), 10.60-11.50 (1H, m)
ESI-MS (m/e): 482 [M+H]

Example 595

6-((2R,5S)-1-acetyl-5-methylpyrrolidin-2-yl)-5-(4-methanesulfonyl-phenoxy)-2-pyrazin-2-yl-1H-benzimidazole (Step 1) Production of 2-fluoro-N-methoxy-N-methylbenzamide 5.79 g of N-methoxy-N-methylamine hydrochloride and 12.4 g of 1-ethyl-3-(3'-dimethylaminopropyl)-carbodiimide hydrochloride were added to a pyridine (80 ml) suspension of 10 g of 2-fluoro-4-nitrobenzoic acid, and the reaction liquid was stirred overnight at room temperature. Pyridine was evaporated away under reduced pressure, and water was added to it. The resulting deposit was taken out through filtration, washed with water, and dried to obtain the entitled compound as a pale yellow solid.

(Step 2) Production of 4-amino-2-fluoro-N-methoxy-N-methylbenzamide 15.2 g of ammonium chloride and 8 g of iron powder were added to a suspension of 10.84 g of 2-fluoro-N-methoxy-N-methylbenzamide in 60 ml of methanol and 30 ml of water, and the reaction liquid was heated under reflux for 3 hours. The reaction liquid was filtered through Celite, and the solvent was evaporated away under reduced pressure. The resulting residue was diluted with ethyl acetate, washed with water, and dried with anhydrous magnesium sulfate. The solvent was evaporated away under reduced pressure, and the resulting residue was purified through silica gel column chromatography (developing solvent: hexane/ethyl acetate=9/1 to 1/2 to obtain the entitled compound as a brown oily substance.

(Step 3) Production of N-(3-fluoro-4-((N-methoxy-N-methylamino)carbonyl)phenyl)pyrazine-2-carboxamide 2.56 g of pyrazine-2-carboxylic acid and 4.66 g of 1-ethyl-3-(3'-dimethylaminopropyl)-carbodiimide hydrochloride were added to a pyridine (20 ml) solution of 3.7 g of 4-amino-2-fluoro-N-methoxy-N-methylbenzamide, and the reaction liquid was stirred at room temperature for 1 hour. Pyridine was evaporated away under reduced pressure, and the residue was diluted with ethyl acetate, washed with water, and dried with anhydrous magnesium sulfate. The solvent was evaporated away under reduced pressure, and the resulting solid was washed with a mixed solvent of ethyl acetate and hexane to obtain the entitled compound as a pale yellow solid.

(Step 4) Production of N-(4-((4R)-4-((tert-butyl(dimethyl)silyl)oxy)-2-pentynoyl)-3-fluorophenyl)pyrazine-2-carboxamide 10.8 ml of n-butyllithium (2.46 M hexane solution was added to a tetrahydrofuran (80 ml) solution of 4.92 g of (3R)-3-(tert-butyl(dimethyl)silyl)oxy-1-butyne at −78° C., and the reaction liquid was stirred at the same temperature for 1 hour. A tetrahydrofuran (60 ml) solution of 2.7 g of N-(3-fluoro-4-((N-methoxy-N-methylamino)carbonyl)phenyl) pyrazine-2-carboxamide was added to it at −78° C., and the reaction liquid was heated up to room temperature and stirred for 2 hours. Water was added to the reaction liquid, extracted with ethyl acetate, and dried with anhydrous magnesium sulfate. The solvent was evaporated away under reduced pressure, and the resulting residue was purified through silica gel column chromatography (developing solvent: hexane/ethyl acetate=9/1 to 1/1) to obtain the entitled compound as a yellow solid.

(Step 5) Production of N-(4-((4R)-4-((tert-butyl(dimethyl)silyl)oxy)-pentanoyl)-3-fluorophenyl)pyrazine-2-carboxamide 100 mg of 10% palladium-carbon catalyst was added to a solution of 513 mg of N-(4-((4R)-4-((tert-butyl(dimethyl)silyl)oxy)-2-pentynoyl)-3-fluorophenyl)pyrazine-2-carboxamide in 5 ml of tetrahydrofuran and 20 ml of ethanol, and the reaction liquid was stirred in a hydrogen atmosphere for 1.5 hours. The catalyst was removed through filtration, the solvent was evaporated away under reduced pressure, and the resulting residue was purified through silica gel column chromatography (developing solvent: hexane/ethyl acetate=9/1 to 1/1) to obtain the entitled compound as a pale yellow solid.

(Step 6) Production of N-(4-((4R)-1,4-dihydropentyl)-3-fluorophenyl)pyrazine-2-carboxamide 89 mg of sodium borohydride was added to a solution of 340 mg of N-(4-((4R)-4-((tert-butyl(dimethyl)silyl)oxy)-pentanoyl)-3-fluorophenyl)pyrazine-2-carboxamide in a mixture of 10 ml of methanol and 5 ml of tetrahydrofuran, and the reaction liquid was stirred at room temperature for 30 minutes. The reaction liquid was distilled under reduced pressure, and the residue was diluted with ethyl acetate, washed with aqueous saturated ammonium chloride, and dried with anhydrous magnesium sulfate. The solvent was evaporated away under reduced pressure to obtain a crude product. 1.18 ml of tetrabutylammonium fluoride (1 M tetrahydrofuran solution) was added to a tetrahydrofuran (6 ml) solution of the resulting crude product with cooling with ice, and the reaction liquid was stirred at room temperature for 2 hours. The solvent was evaporated away under reduced pressure, and the resulting residue was purified through silica gel column chromatography (developing solvent: hexane/ethyl acetate=1/1 to ethyl acetate) to obtain the entitled compound as a pale yellow solid.

(Step 7) Production of N-(4-((5S)-1-acetyl-5-methylpyrrolidin-2-yl)-3-fluorophenyl)pyrazine-2-carboxamide 0.26 ml of triethylamine and 0.11 ml of methanesulfonyl chloride were added to a chloroform (6 ml) suspension of 147 mg of N-(4-((4R)-1,4-dihydropentyl)-3-fluorophenyl)pyrazine-2-carboxamide, and the reaction liquid was stirred at room temperature for 2 hours. The reaction liquid was diluted with chloroform, washed with aqueous saturated sodium bicarbonate, and dried with anhydrous magnesium sulfate. The solvent was evaporated away under reduced pressure to obtain a crude product. 30 mg of sodium azide was added to a dimethylformamide (4 ml) solution of the resulting crude product with cooling with ice, and the reaction liquid was stirred overnight at room temperature. The reaction liquid was diluted with ethyl acetate, washed with water and saturated saline, and dried with anhydrous magnesium sulfate. The solvent was evaporated away under reduced pressure to obtain a crude product. 15 mg of copper sulfate pentahydrate and 52 mg of sodium borohydride were added to a methanol (5 ml) solution of the resulting crude product, and the reaction liquid was stirred at room temperature for 2 hours. 35 mg of sodium borohydride was added to it, and the reaction liquid was stirred for 30 minutes. Further, 35 mg of sodium borohydride was added to it, and the reaction liquid was stirred for 30 minutes. The solvent was evaporated away, and the residue was diluted with chloroform, washed with aqueous saturated sodium bicarbonate, and dried with anhydrous magnesium sulfate. The solvent was evaporated away under reduced pressure to obtain a crude product. 0.043 ml of acetic anhydride was added to a chloroform (4 ml) solution of the resulting crude product, and the solvent was evaporated away under reduced pressure and purified through partitioning thin-layer chromatography (Kieselgel™ 60F$_{254}$, Art 5744 (by Merck), ethyl acetate/methanol=10/1) to obtain the entitled compound as a pale yellow oily substance.

(Step 8) Production of N-(4-((2R,5S)-1-acetyl-5-methylpyrrolidin-2-yl)-5-fluoro-2-nitrophenyl)pyrazine-2-carboxamide 1 ml of fuming nitric acid was added to 59 mg of N-(4-((5S)-1-acetyl-5-methylpyrrolidin-2-yl)-3-fluorophenyl)pyrazine-2-carboxamide at room temperature, and the reaction liquid was stirred at the same temperature for 30 minutes. The reaction liquid was diluted with chloroform, washed with aqueous saturated sodium bicarbonate, and dried with anhydrous magnesium sulfate. The solvent was evaporated away under reduce pressure, and purified through partitioning thin-layer chromatography (Kieselgel™ 60F$_{254}$, Art 5744 (by Merck), ethyl acetate) to obtain the entitled compound as a pale yellow oily substance. (Rf: trans form>cis form.)

(Step 9) Production of 6-((2R,5S)-1-acetyl-5-methylpyrrolidin-2-yl)-5-(4-methanesulfonyl-phenoxy)-2-pyrazin-2-yl-1H-benzimidazole 9.2 mg of 4-methanesulfonyl-phenol and 26.2 mg of cesium carbonate were added to an N-methylpyrrolidinone (1 ml) solution of 10.4 mg of N-(4-((2R,5S)-1-acetyl-5-methylpyrrolidin-2-yl)-5-fluoro-2-nitrophenyl)pyrazine-2-carboxamide, and the reaction liquid was stirred at 90° C. for 1 hour. 60 mg of tin(II) chloride dihydrate was added to it, and the reaction liquid was stirred at 90° C. for 1 hour and at 100° C. for 2 hours. Ethyl acetate and aqueous saturated sodium bicarbonate were added to the reaction liquid, the resulting deposit was removed through filtration, extracted with ethyl acetate, and the organic layer was washed with water and saturated saline, and dried with anhydrous magnesium sulfate. The solvent was evaporated away under reduced pressure, and purified through partitioning thin-layer chromatography (Kieselgel™ 60F$_{254}$, Art 5744 (by Merck), chloroform/methanol=10/1) to obtain the entitled compound as a pale yellow oily substance.

$^1$HNMR (CDCl$_3$) δ: 1.31 and 1.33 (total 3H, each d, J=6.0 Hz), 1.55-2.60 (7H, m), 3.03-3.10 (3H, m), 4.25-4.62 (1H, m), 5.20-5.44 (1H, m), 7.01-7.68 (4H, m), 7.85-7.97 (2H, m), 8.57-8.69 (2H, m), 9.56-9.63 (1H, m)

ESI-MS (m/e): 492 [M+H]

Example 596

N-methyl-2-(2-(5-(4-(2-methyl-2H-tetrazol-5-yl)phenoxy)-2-pyridin-2-yl-1H-benzimidazol-6-yl)pyrrolidin-1-yl)-2-oxoethanamine The entitled compound was obtained as a yellow oily substance in the same method as in Example 498 (step 5) to (step 8) or in accordance with the method or by combining it with an ordinary method but using 2-methyl-2H-tetrazol-5-ylphenol.

¹HNMR (CDCl₃) δ: 1.80-2.50 (7H, m), 2.90-4.00 (4H, m), 4.30-4.50 (3H, m), 5.10-5.65 (1H, m), 7.10 (2H, m), 7.20-7.85 (3H, m), 7.80-7.95 (1H, m), 8.05-8.20 (2H, m), 8.30-8.50 (1H, m), 8.50-8.70 (1H, m)

ESI-MS (m/e): 510 [M+H]

Example 597

6-(1-Acetylpyrrolidin-2-yl)-5-((4'-fluorobiphenyl-4-yl)oxy)-2-pyridin-2-yl-1H-benzimidazole The entitled compound was obtained as a pale yellow solid in the same method as in Example 483 or in accordance with the method or by combining it with an ordinary method but using 4'-fluorophenyl-4-ol.

¹HNMR (CDCl₃) δ: 1.66-2.43 (7H, m), 3.44-3.92 (2H, m), 5.21-5.60 (1H, m), 6.80-7.67 (11H, m), 7.77-7.91 (1H, m), 8.30-8.43 (1H, m), 8.53-8.67 (1H, m), 10.89-11.43 (1H, m)

ESI-MS (m/e): 493 [M+H]

Example 598

6-(1-Acetylpyrrolidin-2-yl)-5-((3'-fluorobiphenyl-4-yl)oxy)-2-pyridin-2-yl-1H-benzimidazole The entitled compound was obtained as a pale yellow solid in the same method as in Example 483 or in accordance with the method or by combining it with an ordinary method but using 3'-fluorophenyl-4-ol.

¹HNMR (CDCl₃) δ: 1.67-2.44 (7H, m), 3.44-3.92 (2H, m), 5.22-5.58 (1H, m), 6.92-7.68 (11H, m), 7.78-7.93 (1H, m), 8.33-8.45 (1H, m), 8.56-8.68 (1H, m), 10.88-11.38 (1H, m)

ESI-MS (m/e): 493 [M+H]

Example 599

2-(5-((6-Cyanopyridin-3-yl)oxy)-2-pyridin-2-yl-1H-benzimidazol-6-yl)pyrrolidine-1-carboxamide The entitled compound was obtained as a white solid in the same method as in Example 162 and Example 182 or in accordance with the method or by combining it with an ordinary method but using 6-cyanopyridin-3-ol.

¹HNMR (CD₃OD) δ: 1.80-2.20 (3H, m), 2.20-2.50 (1H, m), 3.40-3.60 (1H, m), 3.70-3.80 (1H, m), 4.80-5.30 (1H, m), 6.60-6.75 (2H, m), 7.20-7.70 (3H, m), 7.80-8.20 (3H, m), 8.20-8.30 (1H, m), 8.50-8.65 (1H, m), 8.70-8.80 (1H, m)

ESI-MS (m/e): 426 [M+H]

Example 600

6-((2R,5S)-1-acetyl-5-methylpyrrolidin-2-yl)-5-((6-(5-methyl-[1,2,4]-oxadiazol-3-yl)pyridin-3-yl)oxy)-2-pyrazin-2-yl-1H-benzimidazole The entitled compound was obtained as a pale yellow solid in the same method as in Example 595 (step 9) or in accordance with the method or by combining it with an ordinary method but using N-(4-((2R,5S)-1-acetyl-5-methylpyrrolidin-2-yl)-5-fluoro-2-nitrophenyl)pyrazine-2-carboxamide obtained in Example 595 (step 8) and 4-(5-methyl-[1,2,4]-oxadiazol-3-yl)phenol.

¹HNMR (CDCl₃) δ: 1.33 and 1.34 (total 3H, each d, J=6.0 Hz), 1.55-2.60 (7H, m), 2.68 and 2.70 (total 3H, each s), 4.26-4.62 (1H, m), 5.28-5.49 (1H, m), 7.03-8.12 (4H, m), 8.40-8.69 (3H, m), 9.57-9.63 (1H, m)

ESI-MS (m/e): 497 [M+H]

Example 601

6-(Acetylpyrrolidin-2-yl)-2-(5-methylpyrazin-2-yl)-5-(4-(2-methyl-2H-tetrazol-5-yl)-phenoxy)-1H-benzimidazole The entitled compound was obtained as a pale yellow solid in the same method as in Example 306 or in accordance with the method or by combining it with an ordinary method but using 4-(2-methyl-2H-tetrazol-5-yl)phenol and 5-methylpyrazine-2-carboxylic acid.

¹HNMR (CD₃OD) δ: 1.88-2.48 (7H, m), 2.63 and 2.64 (total 3H, each s), 3.61-3.99 (2H, m), 4.41 and 4.42 (total 3H, each s), 5.37-5.4 (1H, m), 7.15-7.55 (2H, m), 7.17 (2H, d, J=8.8 Hz), 8.08 and 8.11 (total 2H, each d, J=8.8 Hz), 8.64 (1H, s), 9.27 and 9.29 (total 11H, each s)

ESI-MS (m/e): 496 [M+H]

Example 602

6-(1-Acetyl-4-methylpyrrolidin-2-yl)-5-(4-(methanesulfonyl)phenoxy-2-pyridin-2-yl-1H-benzimidazole (Step 1) Production of N-(3-fluoro-4-(3-methyl-3-butenoyl)phenyl)pyridine-2-carboxamide 9.89 ml of (2-methyl-2-propen-1-yl)magnesium chloride (0.50 M tetrahydrofuran solution) was added to a tetrahydrofuran (10 ml) solution of 500 mg of N-(3-fluoro-4-((methoxy (methyl)amino)carbonyl)phenyl)pyridine-2-carboxamide obtained in the same method as in Example 145 (step 3) or in accordance with the method or by combining it with an ordinary method but using pyridine-2-carboxylic acid, with cooling with ice. The reaction liquid was stirred for 3 hours with cooling with ice, and then water was poured into the reaction solution, extracted with ethyl acetate and dried with anhydrous sodium sulfate. The solvent was evaporated away under reduced pressure, and the resulting residue was purified through silica gel column chromatography (developing solvent: hexane/ethyl acetate=3/1) to obtain the entitled compound.

(Step 2) Production of N-(3-fluoro-4-(1-hydroxy-3-methyl-3-buten-1-yl)phenyl)pyridine-2-carboxamide 88.8 mg of sodium borohydride was added to a methanol (5 ml) solution of 280 mg of N-(3-fluoro-4-(3-methyl-3-butenoyl)phenyl)pyridine-2-carboxamide. The reaction liquid was stirred at room temperature for 3 hours, and then poured into an aqueous saturated ammonium chloride solution, extracted with ethyl acetate, and dried with anhydrous sodium sulfate. The solvent was evaporated away under reduced pressure, and the resulting residue was purified through silica gel column chromatography (developing solvent: hexane/ethyl acetate=2/1) to obtain the entitled compound.

(Step 3) Production of N-(4-(1,4-dihydroxy-3-methylbutyl)-3-fluorophenyl)pyridine-2-carboxamide 1.20 ml of borane-methyl sulfide complex (1 M dichloromethane solution) was added to a tetrahydrofuran (5 ml) solution of 0.082 ml of cyclohexene with cooling with ice. The reaction liquid was stirred for 10 minutes with cooling with ice, and a tetrahydrofuran (3 ml) solution of 301 mg of N-(3-fluoro-4-(1-hydroxy-3-methyl-3-buten-1-yl)phenyl) pyridine-2-carboxamide was added to it, and the reaction liquid was stirred at room temperature for 1 hour. 0.50 ml of aqueous 5 N sodium hydroxide solution and aqueous 35% hydrogen peroxide solution were added in order to the reaction liquid, and stirred at room temperature for 10 minutes. The reaction liquid was poured into an aqueous saturated ammonium chloride solution, extracted with ethyl acetate, and dried with anhydrous sodium sulfate. The solvent was evaporated away under reduced pressure, and the resulting residue was purified through silica gel column chromatography (developing solvent: chloroform/methanol=9/1) to obtain the entitled compound.

(Step 4) Production of N-(3-fluoro-4-(4-methylpyrrolidin-2-yl)phenyl)pyridine-2-carboxamide 0.62 ml of triethylamine and 0.23 ml of methanesulfonyl chloride were added in order to a chloroform (5 ml) solution of 236 mg of N-(4-(1,4-dihydroxy-3-methylbutyl)-3-fluorophenyl)pyridine-2-carboxamide, with cooling with ice, and the reaction liquid was stirred at room temperature for 3 hours. The reaction liquid was poured into aqueous saturated sodium bicarbonate, extracted with chloroform, and dried with anhydrous sodium sulfate. The solvent was evaporated away under reduced pressure to obtain a crude product. 53.0 mg of sodium azide was added to a dimethylformamide (3 ml) solution of the resulting crude product, with cooling with ice. The reaction liquid was stirred for 30 minutes with cooling with ice, and stirred at room temperature for 3 hours. The reaction liquid was diluted with ethyl acetate, washed with water, and dried with anhydrous sodium sulfate. The solvent was evaporated away under reduced pressure to obtain a crude product. 20 mg of copper sulfate pentahydrate and 168 mg of sodium borohydride were added in order to a methanol (4 ml) solution of the resulting crude product. The reaction liquid was stirred at room temperature for 4 hours, and then poured into aqueous saturated sodium bicarbonate, extracted with chloroform, and dried with anhydrous sodium sulfate. The solvent was evaporated away under reduced pressure to obtain a crude product. 0.050 ml of acetic anhydride was added to a chloroform (3 ml) solution of the resulting crude product, and the reaction liquid was stirred at room temperature for 30 minutes. The solvent was evaporated away under reduced pressure, and the residue was purified through silica gel column chromatography (developing solvent: hexane/ethyl acetate=1/3) to obtain the entitled compound.

(Step 5) Production of N-(4-(1-acetyl-4-methylpyrrolidin-2-yl)-5-fluoro-2-nitrophenyl)pyridine-2-carboxamide 1 ml of fuming nitric acid was added to 70.7 mg of N-(3-fluoro-4-(4-methylpyrrolidin-2-yl)phenyl)pyridine-2-carboxamide, and the reaction liquid was stirred at room temperature for 10 minutes. The reaction liquid was poured into aqueous saturated sodium bicarbonate, extracted with ethyl acetate, and dried with anhydrous sodium sulfate. The solvent was evaporated away under reduced pressure, and the resulting residue was purified through silica gel column chromatography (developing solvent: hexane/ethyl acetate=1/2) to obtain the entitled compound.

(Step 6) Production of 6-(1-acetyl-4-methylpyrrolidin-2-yl)-5-(4-(methanesulfonyl)phenoxy)-2-pyridin-2-yl-1H-benzimidazole 13.4 mg of 4-(methanesulfonyl)phenol and 44.9 mg of cesium carbonate were added in order to an N-methyl-pyrrolidinone (2 ml) solution of 15 mg of N-(4-(1-acetyl-4-methylpyrrolidin-2-yl)-5-fluoro-2-nitrophenyl)pyridine-2-carboxamide, and the reaction liquid was stirred at 90° C. for 1 hour. 43.8 mg of tin chloride dihydrate was added to the reaction liquid, then heated up to 100° C. and stirred for 2 hours. The reaction liquid was dissolved in ethyl acetate, washed with aqueous saturated sodium bicarbonate, and dried with anhydrous sodium sulfate. The solvent was evaporated away under reduced pressure, and the resulting residue was purified through partitioning thin-layer chromatography (Kieselgel™ 60F$_{254}$, Art 5744 (by Merck), chloroform/methanol=9/1) to obtain the entitled compound as a white solid.

$^1$HNMR (CDCl$_3$) δ: 0.80-2.63 (9H, m), 3.00-4.40 (2H, m), 3.05 and 3.08 (total 3H, each s), 5.03-5.43 (1H, m), 7.00-7.73 (5H, m), 7.83-7.98 (3H, m), 8.33-8.43 (1H, m), 8.62-8.70 (1H, m), 10.62-10.80 (1H, m)

ESI-MS (m/e): 491 [M+H]

Example 603

6-((2R,5S)-1-acetyl-5-methylpyrrolidin-2-yl)-5-((6-(methoxymethyl)pyridin-3-yl)oxy)-2-pyrazin-2-yl-1H-benzimidazole The entitled compound was obtained as a pale yellow oily substance in the same method as in Example 595 (step 9) or in accordance with the method or by combining it with an ordinary method but using N-(4-((2R,5S)-1-acetyl-5-methylpyrrolidin-2-yl)-5-fluoro-2-nitrophenyl)pyrazine-2-carboxamide obtained in Example 595 (step 8) and 6-(methoxymethyl)pyridin-3-ol.

$^1$HNMR (CDCl$_3$) δ: 1.10-2.22 (10H, m), 3.48 and 3.50 (total 3H, each s), 4.26-4.62 (1H, m), 4.57 and 4.59 (total 2H, each s), 5.33-5.52 (1H, m), 7.20-7.50 (4H, m), 8.40-8.70 (3H, m), 9.57-9.63 (1H, m)

ESI-MS (m/e): 459 [M+H]

Reference Example 1

[1,2,4]Thiadiazole-5-carboxylic acid 2 ml of N,N-dimethylformamide dimethylacetal was added to a chloroform (10 ml) solution of 1 g of ethyl thioxamate, and the reaction liquid was stirred at room temperature for 4 hours. The solvent was evaporated away under reduced pressure, and the resulting residue was purified through silica gel column chromatography (developing solvent: hexane/ethyl acetate=9/1 to 1/2) to obtain 1.1 g of an amidine compound as a red oily substance.

An ethanol (20 ml) solution of 721 mg of hydroxylamine-O-sulfonic acid was added to an ethanol (18 ml) solution of 1.09 g of the amidine compound and 0.95 ml of pyridine, and the reaction liquid was stirred overnight at room temperature. The solvent was evaporated away under reduced pressure, and the residue was diluted with ethyl acetate, washed with aqueous saturated sodium bicarbonate, and dried with anhydrous magnesium sulfate. The solvent was evaporated away under reduced pressure, and the resulting residue was purified through silica gel column chromatography (developing solvent: hexane/ethyl acetate=9/1) to obtain ethyl [1,2,4]thiadiazole-5-carboxylate as a pale yellow oily substance. 5.7 ml of aqueous 1 N sodium hydroxide solution was added to a methanol (8 ml) solution of 300 mg of the resulting ethyl [1,2,4]thiadiazole-5-carboxylate, and the reaction liquid was stirred overnight at room temperature. The reaction liquid was distilled under reduced pressure, and the residue was neutralized with 2 N hydrochloric acid. The reaction liquid was distilled under reduced pressure, and the residue was washed with chloroform/methanol=10/1, and the resulting organic layer was distilled under reduced pressure to obtain the entitled compound as a white solid.

Reference Example 2

2-Difluoromethoxy-pyridin-3-ol 2.1 g of sodium carbonate and 1.24 ml of difluorofluorosulfonylacetic acid was added to an acetonitrile (40 ml) suspension of 2 g of 3-benzyloxy-2-hydroxypyridine, and the reaction liquid was stirred at room temperature for 1 hour, and then the solvent was evaporated away under reduced pressure. The residue was diluted with ethyl acetate, washed with water, and dried with anhydrous magnesium sulfate. The solvent was evaporated away under reduced pressure, and the resulting residue was purified through silica gel column chromatography (developing solvent: hexane/ethyl acetate=9/1 to 4/1) to obtain a difluoromethoxy compound as a pale yellow oily substance. 500 mg of 10% palladium-carbon catalyst was added to a methanol (25 ml) solution of 2.38 g of the difluoromethoxy compound, and the reaction liquid was stirred in a hydrogen atmosphere at room temperature for 1 hour. The catalyst was removed through filtration through Celite, and the solvent was evaporated away under reduced pressure to obtain the entitled compound as a pale purple oily substance.

Reference Example 3

6-Methanesulfonyl-pyridin-3-ol 6.6 g of bis(pinacolate)diboron, 5.9 g of potassium acetate and 980 mg of (1,1'-bis(diphenylphosphino)ferrocene)dichloropalladium(II) dichloromethane complex were added to a dimethylsulfoxide (80 ml) solution of 4.72 g of 3-bromo-6-methanesulfonyl-pyridine, and the reaction liquid was stirred at 80° C. for 2 hours. Ethyl acetate and water were added to the reaction liquid, the insoluble substance was removed through filtration through Celite, and the organic layer was separated. The organic layer was washed with water and saturated saline, and dried with anhydrous magnesium sulfate, and the solvent was evaporated away under reduced pressure. 60 ml of aqueous 5 N sodium hydroxide solution and 30 ml of aqueous 30% hydrogen peroxide solution were added to a tetrahydrofuran (200 ml) solution of the resulting residue at 0° C., and the reaction liquid was stirred overnight at room temperature. The reaction liquid was diluted with diethyl ether, and washed with water. The aqueous layer was made acidic with 5 N hydrochloric acid, and extracted with ethyl acetate. The organic layer was dried with anhydrous magnesium sulfate, and the solvent was evaporated away under reduced pressure. The resulting residue was washed with a mixed solvent of chloroform and hexane to obtain the entitled compound as a brown solid.

Reference Example 4

6-Ethanesulfonyl-pyridin-3-ol

The entitled compound was obtained in the same method as in Reference Example 3 or in accordance with the method or by combining it with an ordinary method but using 3-chloro-6-ethanesulfonyl-pyridine.

Reference Example 5

(2R,4R)-4-hydroxy-pyrrolidine-2-carboxylic acid methoxy-methylamide (Step 1) Production of (2R,4R)-4-(tert-butyl-diphenyl-silanyloxy)-pyrrolidine-1,2-dicarboxylic acid 1-benzyl ester 2.32 g of tert-butyldiphenylsilyl chloride and 2.32 g of imidazole were added in order to a dimethylformamide (60 ml) solution of 3.61 g of (2R,4R)-4-hydroxy-pyrrolidine-1,2-dicarboxylic acid 1-benzyl ester, and the reaction liquid was stirred overnight at room temperature. The reaction liquid was diluted with ethyl acetate, washed with aqueous saturated ammonium chloride and saturated saline in order, and dried with anhydrous sodium sulfate. The solvent was evaporated away under reduced pressure, and the resulting residue was purified through silica gel column chromatography (developing solvent: hexane/ethyl acetate=1/2) to obtain the entitled compound.

(Step 2) Production of benzyl (2R,4R)-4-(tert-butyl-diphenyl-silanyloxy)-2-(methoxy-methyl-carbamoyl)-pyrrolidine-1-carboxylate 1.50 g of 1-(3-dimethylaminopropyl)-3-ethylcarbodiimide hydrochloride and 761 mg of O,N-dimethylhydroxylamine hydrochloride were added in order to a pyridine (30 ml) solution of 2.62 g of (2R,4R)-4-(tert-butyl-diphenyl-silanyloxy)-pyrrolidine-1,2-dicarboxylic acid 1-benzyl ester obtained in (step 1), and the reaction liquid was stirred overnight at room temperature. The solvent of the reaction liquid was evaporated away under reduced pressure, and the resulting residue was purified through silica gel column chromatography (developing solvent: hexane/ethyl acetate=1/1) to obtain the entitled compound.

(Step 3) Production of benzyl (2R,4R)-4-hydroxy-2-methoxy-methyl-carbamoyl-pyrrolidine-1-carboxylate 7.46 ml of tetrabutylammonium fluoride (1 M tetrahydrofuran solution) was added to a tetrahydrofuran (30 ml) solution of 2.04 g of benzyl (2R,4R)-4-(tert-butyl-diphenyl-silanyloxy)-2-(methoxy-methyl-carbamoyl)-pyrrolidine-1-carboxylate obtained in (step 2), and the reaction liquid was stirred at room temperature for 20 minutes. The solvent of the reaction liquid was evaporated away under reduced pressure, and the resulting residue was purified through silica gel column chromatography (developing solvent: hexane/ethyl acetate=1/3) to obtain the entitled compound.

(Step 4) Production of (2R,4R)-4-hydroxy-pyrrolidine-2-carboxylic acid methoxy-methylamide 100 mg of 10% palladium-carbon catalyst was added to an ethanol (20 ml) solution of 600 mg of benzyl (2R,4R)-4-hydroxy-2-methoxy-methyl-carbamoyl-pyrrolidine-1-carboxylate obtained in (step 3), and the reaction liquid was stirred overnight in a hydrogen atmosphere. The catalyst was removed through filtration through Celite, and the solvent was evaporated away under reduced pressure to obtain the entitled compound.

INDUSTRIAL APPLICABILITY

The substituted benzimidazole derivatives of formula (I-0) of the invention have an excellent glucokinase activity, and are useful in the field of medicines for remedy and/or prevention of diabetes, complications of diabetes or obesity.

The invention claimed is:
1. A compound of a formula (I-0):

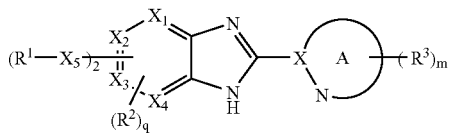

(I-0)

or a pharmaceutically acceptable salt thereof, wherein:
X represents a carbon atom or a nitrogen atom;
$X_1$, $X_2$, $X_3$ and $X_4$ each independently represent a carbon atom;
one $X_5$ represents a member selected from the group consisting of O, S, S(O) and $SO_2$ and the other $X_5$ represents a direct bond;
ring A represents a member selected from the group consisting of thiazolyl, imidazolyl, isothiazolyl, triazolyl, oxazolyl, oxadiazolyl, pyrazinyl, pyridyl, pyrazolyl and pyrimidinyl;
one $R^1$ represents phenyl optionally substituted with one to three $R^4$ groups, or a 5-6 membered nitrogen-containing aromatic hetero ring having from 1-4 heteroatoms selected from nitrogen, sulfur and oxygen,
and the other $R^1$ is a 5-7 membered nitrogen containing aliphatic hetero ring, having as the heteroatom a nitrogen atom and optionally having 1-2 additional heteroatoms selected from N, O and S;
each $R^2$ independently represents hydroxy, formyl, $—CH_{3-a}F_a$, $—OCH_{3-a}F_a$, $NH_2$, CN, halo, $C_{1-6}$ alkyl or $—(CH_2)_{1-4}OH$;
each $R^3$ independently represents a member selected from the group consisting of:
$—C_{1-6}$ alkyl, $—(CH_2)_{1-6}—OH$, $—C(O)—OC_{1-6}$ alkyl, $—(CH_2)_{1-6}—OC_{1-6}$ alkyl, $—(CH_2)_{1-6}—NH_2$, CN, $—C(O)—C_{1-6}$ alkyl, halo, $—C_{2-6}$ alkenyl, $—OC_{1-6}$ alkyl, $—COOH$, $—OH$ and oxo;
each $R^4$ independently represents a member selected from the group consisting of:
$—C_{1-6}$ alkyl and the alkyl may be substituted with the same or different, from 1 to 3 hydroxyl groups, halo atoms or $—OC(O)—C_{1-6}$ alkyl groups, the alkyl portion thereof being optionally substituted with from 1 to 3 halo atoms or $—OC_{1-6}$ alkyl groups;
$—C_{3-7}$ cycloalkyl;
$—C_{2-6}$ alkenyl;
$—C(O)—N(R^{51})R^{52}$;
$—S(O)_2—N(R^{51})R^{52}$;
$—O—C_{1-6}$ alkyl and the $C_{1-6}$ alkyl may be substituted with a halogen or $N(R^{51})R^{52}$;
$—S(O)_{0-2}—C_{1-6}$ alkyl;
$—C(O)—C_{1-6}$ alkyl and the $C_{1-6}$ alkyl may be substituted with a halo atom, amino group, CN, hydroxy group, $—O—C_{1-6}$ alkyl, $—CH_{3-a}F_a$, $—OC(O)—C_{1-6}$ alkyl, $—N(C_{1-6}$ alkyl)$C(O)O—C_{1-6}$ alkyl, $—NH—C(O)O—C_{1-6}$ alkyl, phenyl, $—N(R^{51})R^{52}$, $—NH—C(O)—C_{1-6}$ alkyl, $—N(C_{1-6}$ alkyl)$-C(O)—C_{1-6}$ alkyl or $—NH—S(O)_{0-2}—C_{1-6}$ alkyl;
$—C(S)—C_{3-7}$ cycloalkyl;
$—C(S)—C_{1-6}$ alkyl;
$—C(O)—O—C_{1-6}$ alkyl;
$—(CH_2)_{0-4}—N(R^{53})—C(O)—R^{54}$;
$—N(R^{53})—C(O)—O—R^{54}$;
—C(O)-aryl optionally substituted with a halogen;
—C(O)-aromatic hetero ring;
—C(O)-aliphatic hetero ring;
a hetero ring optionally substituted with a halo atom or $—OC_{1-6}$ alkyl group, which is optionally substituted with a halo atom or an $—O—C_{1-6}$ alkyl group; and
a phenyl ring optionally substituted with a halo atom, $—C_{1-6}$ alkyl or $—O—C_{1-6}$ alkyl, the alkyl portions of which are optionally substituted with a halogen, CN, formyl, COOH, $NH_2$, oxo, hydroxy, hydroxyamidino or nitro group;
each $R^{51}$ and $R^{52}$ independently represents a hydrogen atom or $—C_{1-6}$ alkyl; or taken together with the nitrogen atom to which they are attached, $R^{51}$ and $R^{52}$ together form a 4- to 7-membered hetero ring;
each $R^{53}$ represents a hydrogen atom or a $—C_{1-6}$ alkyl group;
each $R^{54}$ represents $—C_{1-6}$ alkyl, or when $R^{53}$ and $R^{54}$ each represent alkyl groups, $R^{53}$, $R^{54}$ and $—N—C(O)—$ together form a 4- to 7-membered nitrogen-containing aliphatic hetero ring, or
$R^{53}$, $R^{54}$ and $—N—C(O)—O—$ together form a 4- to 7-membered nitrogen-containing aliphatic hetero ring and the aliphatic hetero ring may be substituted with an oxo, or the aliphatic hetero ring may have 1 or 2 double bonds in the ring;
a represents an integer selected from 1, 2 and 3;
q indicates an integer of from 0 to 2; and
m indicates an integer of from 0 to 2.

2. A compound represented by formula (I-2):

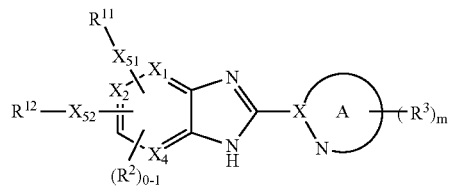

(I-2)

or a pharmaceutically acceptable salt thereof, wherein:
$X^1$, $X^2$ and $X^4$ represent carbon atoms;
X in ring A represents a carbon or nitrogen atom;
ring A represents a member selected from the group consisting of:
thiazolyl, imidazolyl, isothiazolyl, thiadiazolyl, triazolyl, pyrazinyl, pyridyl, pyridazinyl, pyrazolyl and pyrimidinyl;
$R^{11}$ represents phenyl optionally substituted with from 1 to 3 $R^4$ groups, or represents a 5- or 6-membered nitrogen-containing aromatic hetero ring having from 1 to 4 hetero atoms selected from the group consisting of nitrogen, sulfur and oxygen, and said hetero ring being optionally substituted with from 1 to 3 $R^4$ groups;
$R^{12}$ represents a non-aromatic 4- to 7-membered nitrogen-containing hetero ring having, as the hetero atom constituting the heterocyclic ring, at least one nitrogen atom and optionally having, as the other hetero atoms, from 1 to 4 hetero atoms selected from the group consisting of nitrogen, sulfur, and oxygen, said ring being optionally substituted with from 1 to 3 $R^4$ groups, and when the hetero ring is an aliphatic hetero ring, then it may have 1 or 2 double bonds;
one of $X_{51}$ and $X_{52}$ represents $—O—$, $—S—$, $—S(O)—$ or $—S(O)_2—$, and the other represents a direct bond;

if present, R² represents a member selected from the group consisting of: OH; formyl, —CH$_{3-a}$F$_a$, —OCH$_{3-a}$F$_a$, NH$_2$, CN, halo, C$_{1-6}$ alkyl and (CH$_2$)$_{1-4}$OH;

m is 0, 1 or 2 and when present, each R³ is independently selected from the group consisting of: —C$_{1-6}$ alkyl, —(CH$_2$)$_{1-6}$OH, —C(O)—OC$_{1-6}$ alkyl, —(CH$_2$)$_{1-6}$—OC$_{1-6}$ alkyl, —(CH$_2$)$_{1-6}$—NH$_2$, CN, —C(O)—C$_{1-6}$ alkyl, halo, —C$_{2-6}$ alkenyl, —OC$_{1-6}$ alkyl, —COOH, —OH and oxo.

3. A compound in accordance with claim 2, or a pharmaceutically acceptable salt thereof, wherein R¹² represents a 4- to 7-membered saturated nitrogen-containing aliphatic hetero ring having one nitrogen atom and optionally having 1 or 2 hetero atoms selected from the group consisting of nitrogen, sulfur and oxygen, said heterocyclic ring being optionally substituted with from 1 to 3 R⁴ groups, and X$_{52}$ is a single bond; or R¹² represents a 5- to 7-membered nitrogen-containing aliphatic hetero ring having, at least one nitrogen atom and optionally having 1 or 2 additional hetero atoms selected from a group consisting of nitrogen, sulfur and oxygen, and optionally having in the ring, 1 or 2 double bonds, said 5- to 7-membered hetero ring being optionally substituted with from 1 to 3 R⁴ groups.

4. A compound in accordance with claim 2, or a pharmaceutically acceptable salt thereof, wherein R¹² represents a 5- to 7-membered nitrogen-containing aliphatic hetero ring having, at least one nitrogen atom and optionally having, 1 or 2 hetero atoms selected from the group consisting of nitrogen, sulfur and oxygen and having, in the ring, 1 or 2 additional double bonds and the 5- to 7-membered hetero ring may be substituted with from 1 to 3 R⁴ groups.

5. A compound represented by formula (I-11), or a pharmaceutically acceptable salt thereof:

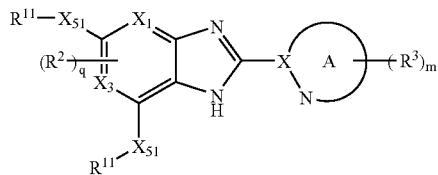

(I-11)

wherein:
X$_1$ and X$_3$ represent carbon atoms;
X represents a carbon or nitrogen atom;
ring A represents a member selected from the group consisting of thiazolyl, imidazolyl, isothiazolyl, triazolyl, oxazolyl, oxadiazolyl, pyrazinyl, pyridyl, pyrazolyl and pyrimidinyl;
one X$_{51}$ represents —O—, —S—, —S(O)— or —S(O)$_2$— and the other represents a direct bond;
q represents 0, 1 or 2;
each R² independently represents a member selected from the group consisting of: hydroxy, formyl, —CH$_{3-a}$F$_a$, —OCH$_{3-a}$F$_a$, NH$_2$, CN, halo, C$_{1-6}$ alkyl and —(CH$_2$)$_{1-4}$OH;
R¹¹ represents a phenyl optionally substituted with from 1 to 3 R⁴'s, or represents a 5- or 6-membered nitrogen-containing aromatic hetero ring having from 1 to 4 hetero atoms selected from the group consisting of a nitrogen atom, a sulfur atom and an oxygen atom and the nitrogen-containing aromatic hetero ring optionally substituted with from 1 to 3 R⁴ groups;
m represents 0, 1 or 2, and;
each R³ represents a member selected from the group consisting of: —C$_{1-6}$ alkyl, —(CH$_2$)$_{1-6}$—OH, —C(O)—OC$_{1-6}$ alkyl, —(CH$_2$)$_{1-6}$—OC$_{1-6}$ alkyl, —(CH$_2$)$_{1-6}$—NH$_2$, CN, —C(O)—C$_{1-6}$ alkyl, halo, —C$_{2-6}$ alkenyl, —OC$_{1-6}$ alkyl, —COOH, —OH and oxo.

6. A compound selected from the group consisting of:
1-(2-(6-(5-bromo-pyridin-2-yloxy)-2-pyridin-2-yl-3H-benzimidazol-5-yl)-pyrrolidin-1-yl)-ethanone,
1-(2-(6-(6-methanesulfonyl-pyridin-3-yloxy)-2-pyridin-2-yl-3H-benzimidazol-5-yl)-pyrrolidin-1-yl)-ethanone,
1-(2-(6-(4-hydroxymethyl-phenoxy)-2-pyridin-2-yl-3H-benzimidazol-5-yl)-pyrrolidin-1-yl)-ethanone,
1-(2-(6-(4-methanesulfonyl-phenoxy)-2-pyridin-2-yl-3H-benzimidazol-5-yl)-pyrrolidin-1-yl)-ethanone,
2-(6-(4-methanesulfonyl-phenoxy)-2-pyridin-2-yl-3H-benzimidazol-5-yl)-pyrrolidine-1-carboxamide,
2-hydroxy-1-(2-(6-(4-methanesulfonyl-1-phenoxy)-2-pyridin-2-yl-3H-benzimidazol-5-yl)-pyrrolidin-1-yl)-ethanone,
1-(2-(6-(6-ethanesulfonyl-pyridin-3-yloxy)-2-pyridin-2-yl-3H-benzimidazol-5-yl)-pyrrolidin-1-yl)-ethanone,
1-(2-(6-(4-methanesulfonyl-phenoxy)-2-pyrazin-2-yl-3H-benzimidazol-5-yl)-pyrrolidin-1-yl)-ethanone,
2-fluoro-1-(2-(6-(4-methanesulfonyl-phenoxy)-2-pyridin-2-yl-3H-benzimidazol-5-yl)-pyrrolidin-1-yl)-ethanone,
5-(6-(1-acetyl-pyrrolidin-2-yl)-2-pyridin-2-yl-1H-benzimidazole-5-yloxy)pyridine-2-carbonitrile,
1-(2-(6-(4-methanesulfonyl-phenoxy)-2-pyridin-2-yl-3H-benzimidazol-5-yl)-pyrrolidin-1-yl)-2-methylamino-ethanone,
1-(2-(6-(4-methanesulfonyl-phenoxy)-2-(1H-pyrazol-3-yl)-3H-benzimidazol-5-yl)-pyrrolidin-1-yl)-ethanone,
1-(4-fluoro-2-(6-(4-methanesulfonyl-phenoxy)-2-pyridin-2-yl-3H-benzimidazol-5-yl)-pyrrolidin-1-yl)-ethanone,
N-(5-(6-(1-acetyl-pyrrolidin-2-yl)-2-pyridin-2-yl-1H-benzimidazol-5-yloxy)-pyridin-2-yl)-acetamide,
1-(2-(2-(5-bromo-pyridin-2-yl)-6-(4-methanesulfonyl-phenoxy)-3H-benzimidazol-5-yl)-pyrrolidin-1-yl)-ethanone,
N-(2-(2-(6-(4-methanesulfonyl-phenoxy)-2-pyridin-2-yl-3H-benzimidazol-5-yl)pyrrolidin-1-yl)-2-oxo-ethyl)-acetamide,
6-(1-acetylpyrrolidin-2-yl)-5-(4-(methoxymethyl)phenoxy)-2-pyridin-2-yl-1H-benzimidazol monotrifluoroacetate,
1-(4-((6-(1-acetylpyrrolidin-2-yl)-2-pyridin-2-yl-1H-benzimidazol-5-yl)oxy)phenyl)pyridin-2(1H)-one,
6-(1-acetylpyrrolidin-2-yl)-5-((6-(5-methyl-[1,2,4]-oxadiazol-3-yl)pyridin-3-yl)oxy)-2-pyridin-2-yl-1H-benzimidazole,
(2-(2-(5-((2'-fluorobiphenyl-4-yl)oxy)-2-pyridin-2-yl-1H-benzimidazol-6-yl)pyrrolidin-1-yl)-2-oxoethyl)methylamine,
6-(1-acetylpyrrolidin-2-yl)-5-((6-([1,2,4]-oxadiazol-3-yl)pyridin-3-yl)oxy)-2-pyridin-2-yl-1H-benzimidazole,
6-(1-acetylpyrrolidin-2-yl)-5-(4-(2-methyl-2H-tetrazol-5-yl)phenoxy)-2-pyrazin-2-yl-1H-benzimidazole,
5-(1-acetyl-3-fluoropyrrolidin-2-yl)-6-(4-(methanesulfonyl)phenoxy)-2-pyridin-2-yl-1H-benzimidazole,
6-(1-acetylpyrrolidin-2-yl)-5-((6-(2-methyl-2H-tetrazol-5-yl)pyridin-3-yl)oxy)-2-pyridin-2-yl-1H-benzimidazole,
6-(1-acetylpyrrolidin-2-yl)-5-(4-(2-methyl-2H-tetrazol-5-yl)phenoxy)-2-pyridin-2-yl-1H-benzimidazole,
5-(1-acetyl-5-methylpyrrolidin-2-yl)-6-(4-(methanesulfonyl)phenoxy)-2-pyridin-2-yl-1H-benzimidazole, 6-(1-acetylpyrrolidin-2-yl)-5-((6-(2-methyl-2H-tetrazol-5-yl)pyridin-3-yl)oxy)-2-pyrazin-2-yl-1H-benzimidazole, 6-(1-acetylpyrrolidin-2-yl)-5-(6-methoxymethylpyridin-3-yl)oxy)-2-pyridin-2-yl-1H-benzimidazole, 2-(2-(5-(4-(2-methyl-2H-tetrazol-5-yl)phenoxy)-2-pyridin-2-yl-1H-benzimidazol-6-yl)pyrrolidin-1-yl)-2-oxoethanol, 2-(5-(4-(2-methyl-2H-tetrazol-5-yl)phenoxy)-2-pyridin-2-yl-1H-benzimidazol-6-yl)pyrrolidine-1-carboxamide, 5'-((6-(1-acetylpyrrolidin-2-yl)-2-pyridin-2-yl-1H-benzimidazol-5-yl)oxy)-2H-1,2'-bipyridin-2-one, 3-(4-((6-(1-acetylpyrrolidin-2-yl)-2-pyridin-2-yl-1H-benzimidazol-5-yl)oxy)phenyl)-1,3-oxazolidin-2-one, 6-(1-acetylpyrrolidin-2-yl)-5-((6-methylpyridin-3-yl)oxy)-2-pyridin-2-yl-1H-benzimidazole, 6-(1-acetylpyrrolidin-2-yl)-5-((6-pyrazin-2-ylpyridin-3-yl)oxy)-2-pyridin-2-yl-1H-benzimidazole, 6-(1-acetyl-3-fluoropyrrolidin-2-yl)-5-((2'-fluorobiphenyl-4-yl)oxy)-2-pyridin-2-yl-1H-benzimidazole, 3-(4-((6-(1-acetylpyrrolidin-2-yl)-2-pyrazin-2-yl-1H-benzimidazol-5-yl)oxy)phenyl)-1,3-oxazolidine-2-one, 6-(1-acetylpyrrolidin-2-yl)-2-pyrazin-2-yl-5-((6-pyrazin-2-ylpyridin-3-yl)oxy)-1H-benzimidazole, 6-(1-acetylpyrrolidin-2-yl)-5-((6-(5-methyl-[1,2,4]-oxadiazol-3-yl)pyridin-3-yl)oxy)-2-pyrazin-2-yl-1H-benzimidazole, 1-(4-((6-(1-acetylpyrrolidin-2-yl)-2-pyrazin-2-yl-1H-benzimidazol-5-yl)oxy)phenyl)ethanone, 6-(1-acetylpyrrolidin-2-yl)-5-(4-(5-methyl-[1,2,4]-oxadiazol-3-yl)phenoxy)-2-pyrazin-2-yl-1H-benzimidazole, 6-(1-acetyl-5-methylpyrrolidin-2-yl)-5-(4-methanesulfonyl-phenoxy)-2-pyrazin-2-yl-1H-benzimidazole, N-methyl-2-(2-(5-(4-(2-methyl-2H-tetrazol-5-yl)phenoxy)-2-pyridin-2-yl-1H-benzimidazol-6-yl)pyrrolidin-1-yl)-2-oxoethanamine, 6-(1-acetyl-5-methylpyrrolidin-2-yl)-5-((6-(methoxymethyl)pyridin-3-yl)oxy)-2-pyrazin-2-yl-1H-benzimidazole, 1-(1-(6-(4-methanesulfonyl-phenoxy)-2-pyridin-2-yl-3H-benzimidazol-5-yl)-pyrrolidin-2-yl)-ethanone, 1-(1-(6-(6-methanesulfonyl-pyridin-3-yloxy)-2-pyridin-2-yl-3H-benzimidazol-5-yl)pyrrolidin-2-yl)-ethanone, 1-(1-(6-(6-ethanesulfonyl-pyridin-3-yloxy)-2-pyrazin-2-yl-3H-benzimidazol-5-yl)pyrrolidin-2-yl)ethanone, or 1-(1-(6-(6-ethanesulfonyl-pyridin-3-yloxy)-2-pyrazin-2-yl-3H-benzimidazol-5-yl)-4-fluoro-pyrrolidin-2-yl)-ethanone, or a pharmaceutically acceptable salt thereof.

7. A pharmaceutical composition comprising a compound in accordance with claim 1 in combination with a pharmaceutically acceptable carrier.

8. A method of treating type 2 diabetes in a mammalian patient in need of such treatment comprising administering to the patient a compound in accordance with claim 1 in an amount that is effective to treat type 2 diabetes.

9. A method of treating obesity in a mammalian patient in need of such treatment comprising administering to the patient a compound in accordance with claim 1 in an amount that is effective to treat obesity.

10. A compound having the name 6-(1-acetylpyrrolidin-2-yl)-5-(6-methoxymethylpyridin-3-yl)oxy-2-pyridin-2-yl-1H-benzimidazole, or a pharmaceutically acceptable salt thereof.

11. A pharmaceutical composition comprised of a compound in accordance with claim 10, or a pharmaceutically acceptable salt thereof, in combination with a pharmaceutically acceptable carrier.

* * * * *

UNITED STATES PATENT AND TRADEMARK OFFICE
CERTIFICATE OF CORRECTION

PATENT NO.           : 7,728,025 B2
APPLICATION NO.      : 10/582564
DATED                : June 1, 2010
INVENTOR(S)          : Katsumasa Nonoshita et al.

It is certified that error appears in the above-identified patent and that said Letters Patent is hereby corrected as shown below:

On the cover of the patent in the field (75) Inventors, insert --; Jun-Ichi Eiki, Ibaraki (JP)-- after "Teruyuki Nishimura, Ibaraki (JP)".

Signed and Sealed this
Thirteenth Day of March, 2012

David J. Kappos
*Director of the United States Patent and Trademark Office*